(12) United States Patent
Xu et al.

(10) Patent No.: US 8,912,387 B2
(45) Date of Patent: Dec. 16, 2014

(54) GENETIC LOCI ASSOCIATED WITH HEAD SMUT RESISTANCE IN MAIZE

(75) Inventors: Mingliang Xu, Beijing (CN); Bailin Li, Hockessin, DE (US); Kevin Fengler, Wilmington, DE (US); Qing Chao, Beijing (CN); Yongsheng Chen, Beijing (CN); Xianrong Zhao, Beijing (CN); Jing Zhao, Beijing (CN)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1160 days.

(21) Appl. No.: 12/545,226

(22) Filed: Aug. 21, 2009

(65) Prior Publication Data

US 2010/0050291 A1    Feb. 25, 2010

Related U.S. Application Data

(60) Provisional application No. 61/090,704, filed on Aug. 21, 2008.

(51) Int. Cl.
*A01H 1/04* (2006.01)
*A01H 3/00* (2006.01)

(52) U.S. Cl.
USPC .......................................... 800/267; 800/275

(58) Field of Classification Search
None
See application file for complete search history.

(56) References Cited

PUBLICATIONS

Negrotto et al (Plant Cell Reports 19: 798-803, 2000).*
Xu et al (Plant Disease 83(4): 390-395, 1999).*
Bernardo et al (Agronomie 12: 303-306, 1992).*
Wu XL, Pang ZC, Tian LM, Hu JS (1981) On the environmental factors affecting infection and cultural measures of controlling corn head smut (in Chinese, English abstract). Acta Phytophlacica Sinica 8:41-46.
Krüger W (1962) *Sphacelotheca reiliana* on maize, I-Infection and control studies. South Afr J Agric Sci 5:43-56.
Mytac CA, Kommedahl T (1985a) Factors affecting the developmen of head smut caused by *Sphacelotheca reiliana* on corn. Phytopathology 75: 577-581.
Frederiksen RA (1977) Head smuts of corn and *Sorghum*. Proc Corn *Soghum* Res Conf 32:89-104.
Jin QM, Li JP, Zhang XW, Wang GX, Song SY, Liu YC, Wang LX (2000) Establishment IPM of system of corn diseases and pest insects in the spring corn belt (in Chinese, English abstract). Journal of maize science 8: 84-88.
Bai JK, Song ZH, Chen J, Liang JY, Liu GZ, Zhao TC, Zhou YL (1994) A review of the pathogenic variation of corn diseases and breeding of resistant cultivars (in Chinese, English abstract). Journal of Maize Sciences 2:67-72.
Xu ML, Melchinger AE, Lübberstedt T (1999) Species-Specific detection of the maize pathogens *Sporisorium reiliana* and *Ustilago maydis* by Dot Blot Hybridization and PCR-Based Assays. Plant Dis 83: 390-395.
Lu XW, Brewbaker JL (1999) Molecular mapping of QTLs conferring resistance to *Sphacelotheca reiliana* (Kühn) Clint. Maize Genetics Cooperation Newsletter (MNL) 73:36.
Ma BY, Li YL, Duan SK (1983) Study on the resistance to head smut corn varieties and its inheritance (in Chinese, English abstract) Scientia Agrcultura Sinica 4: 12-17.
Stromberg EL, Stienstra WC, Kommmendahl T, Matyac CA, Windels CE, Geadelmann JL (1984) Smut expression and resistance of corn to *Sphacelotheca reiliana* in Minnesota. Plant Dis 68:880-884.
Ali A, Baggett JR (1990) Inheritance of resistance to head smut corn disease in corn. J Am Soc Hortic Sci 115: 668-672.
Bernardo R, Bourner M, Olivier JL (1992) Generation means analysis of resistance to head smut in Maize. Agronomie 12: 303-306.
Shi HL, Jiang YX, Wang ZH, Li XH, Li MS, Zhang (2005) QTL identification of resistance to head smut in maize (in Chinese, English abstract). Acta Agronomica Sinica 31:1449-1454.
Lander and Botstein (1989), Mapping mendelian factors underlying quantitative traits using RFLP linage maos genetics. 121:185-199.
Lebowitz et al. (1987) Trait-based Analyses for the detection of linkage between marker loci and quantitative trait loci in crosses between inbred lined. Theor. Appl. Genet. 73:556-562.
Yongsheng Chen et al., Identification and fine-mapping of a major QTL conferring resistance against head smut in maize, Theor. Appl. Genet, 2008, pp. 1241-1252, vol. 117.
X.H. Li et al., Analysis of QTL for resistance to head smut (*Sporisorium reiliana*) in maize, Elsevier-Field Crops Research, 2008, pp. 148-155, vol. 106.
T. Lubberstedt et al., QTL mapping of resistance to *Sporisorium reiliana* in maize, Theor Appl Genet, 1999, pp. 593-596, vol. 99.
Wenkai Xiao et al., Mapping of genome-wide resistance gene analogs (RGAs)in maize (*Zea mays* L.), Theor Apl Genet, 2007, pp. 501-508, vol. 115.
Internation Search Report, 2009.

* cited by examiner

*Primary Examiner* — Shubo (Joe) Zhou
*Assistant Examiner* — Keith Robinson

(57) ABSTRACT

Head smut is one of the most devastating diseases in maize, causing severe yield loss worldwide. The present invention describes the fine-mapping of a major QTL conferring resistance to head smut. Markers useful for breeding, and methods for conferring head smut resistance are described. Nucleic acid sequence from the genetic locus conferring head smut resistance is disclosed. Genes encoding proteins conferring head smut resistance are disclosed.

4 Claims, 4 Drawing Sheets

Figure 1:

Mo17 MPSRMWNLNKALVTSLLCISALSSSPWPCTAAGQLGGKPLVTAVTKDASTSLYTAPLKDGHPLVLDLTSPVISLATCASSSKNNNGTLTA
B73  MPSRMWNLNKALVTSLLCISALSSSPWPCTAAGQLGGKPLVTAVTKDASTSLYTAPLKDGHPLVLDLTSPVISLATCASSSKNNNGTLTA
                              *                                                               ++

Mo17 TLSANATDGQNPLFPVSFSAVATCAPSSRLPAGA--VGVAGLAPSSSSQQSLPAQVARTQKVADKVALCLPSDGRSTSGDSVGVAIFGGG
B73  TLSANATDGQNPLFPVSFSAVATCAPSSKLPAGAGAVGVAGLAPSSSSQQSLPAQVARTQKVADKVALCLPSDGRSTSGDSVGVAIFGGG
                                 *

Mo17 PLFFVPPDRGDFTTMLAGTAPLHAGAGAGAPGYYVSSTGIAVEQARVGGPAGALVVALSSTVPYTALRPDVYAPFVKAFDAAAAGPNFPW
B73  PLFFVPPDRGDFTTMLAGTAPLHAGAGAGAPGYYVSSTGIAVEQARVGGPRGALVVALSSTVPYTALRPDVYAPFVKAFDAAAAGPNFPW
                                                      *

Mo17 MSRVAAVAPFDR------LLGYAVPQIDVMLEGGQNFTVLGGNSMVQVNANTACLGFVQAPGQAPAAVIGGFQLENHLLLDVDKK
B73  MSRVAAVAPFDRCYDSTKLPQSLLGYAVPQIDVMLEGGQNFTVLGGNSMVQVNANTACLGFVQAPGQAPAAVIGGFQLENHLLLDVDKK
                 ++++++++

Mo17 QLGFTTFLNAIGLSCSSENFTLAS
B73  QLGFTTFLNAIGLSCSSENFTLAS

FIG. 3

SEQUENCE LISTING

<160> NUMBER OF SEQ ID NOS: 117

<210> SEQ ID NO 1
<211> LENGTH: 20
<212> TYPE: DNA
<213> ORGANISM: Artificial Sequence
<220> FEATURE:
<223> OTHER INFORMATION: primer CAPS25082-L

<400> SEQUENCE: 1
aagtccttca cggtctacca        20

```
<210> SEQ ID NO 2
<211> LENGTH: 20
<212> TYPE: DNA
<213> ORGANISM: Artificial Sequence
<220> FEATURE:
<223> OTHER INFORMATION: primer CAPS25082-R

<400> SEQUENCE: 2
cggttaggac gatgtcagaa                                                  20

<210> SEQ ID NO 3
<211> LENGTH: 20
<212> TYPE: DNA
<213> ORGANISM: Artificial Sequence
<220> FEATURE:
<223> OTHER INFORMATION: primer SNP140313-L

<400> SEQUENCE: 3
cagaggcatt gaacaggaag                                                  20

<210> SEQ ID NO 4
<211> LENGTH: 20
<212> TYPE: DNA
<213> ORGANISM: Artificial Sequence
<220> FEATURE:
<223> OTHER INFORMATION: primer SNP140313-R

<400> SEQUENCE: 4
ctgctattcc acgaagtgct                                                  20

<210> SEQ ID NO 5
<211> LENGTH: 20
<212> TYPE: DNA
<213> ORGANISM: Artificial Sequence
<220> FEATURE:
<223> OTHER INFORMATION: primer SNP140313-snpL

<400> SEQUENCE: 5
ctcttccacc gagaatagcg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer SNP140313-snpR

<400> SEQUENCE: 6
ctgctattcc acgaagtgct                                                  20

<210> SEQ ID NO 7
<211> LENGTH: 20
<212> TYPE: DNA
<213> ORGANISM: Artificial Sequence
<220> FEATURE:
<223> OTHER INFORMATION: primer SNP661-L

<400> SEQUENCE: 7
cttctgttct gtgccaggta                                                  20

<210> SEQ ID NO 8
<211> LENGTH: 20
<212> TYPE: DNA
<213> ORGANISM: Artificial Sequence
<220> FEATURE:
<223> OTHER INFORMATION: primer SNP661-R
```

```
<400> SEQUENCE: 8
caagaacgta gcaactcagc                                               20

<210> SEQ ID NO 9
<211> LENGTH: 20
<212> TYPE: DNA
<213> ORGANISM: Artificial Sequence
<220> FEATURE:
<223> OTHER INFORMATION: primer SNP661-snpL

<400> SEQUENCE: 9
attgtccctg agatgattcg                                               20

<210> SEQ ID NO 10
<211> LENGTH: 20
<212> TYPE: DNA
<213> ORGANISM: Artificial Sequence
<220> FEATURE:
<223> OTHER INFORMATION: primer SNP661-snpR

<400> SEQUENCE: 10
caagaacgta gcaactcagc                                               20

<210> SEQ ID NO 11
<211> LENGTH: 20
<212> TYPE: DNA
<213> ORGANISM: Artificial Sequence
<220> FEATURE:
<223> OTHER INFORMATION: primer STS1944-L

<400> SEQUENCE: 11
cattggcaac aggacaagtg                                               20

<210> SEQ ID NO 12
<211> LENGTH: 20
<212> TYPE: DNA
<213> ORGANISM: Artificial Sequence
<220> FEATURE:
<223> OTHER INFORMATION: primer STS1944-R

<400> SEQUENCE: 12
gacatcagcc tcaacattgg                                               20

<210> SEQ ID NO 13
<211> LENGTH: 20
<212> TYPE: DNA
<213> ORGANISM: Artificial Sequence
<220> FEATURE:
<223> OTHER INFORMATION: primer STS171-L

<400> SEQUENCE: 13
ccagagactt gcgtgaagat                                               20

<210> SEQ ID NO 14
<211> LENGTH: 20
<212> TYPE: DNA
<213> ORGANISM: Artificial Sequence
<220> FEATURE:
<223> OTHER INFORMATION: primer STS171-R

<400> SEQUENCE: 14
aacagactgg ttgtacgtgc                                               20

<210> SEQ ID NO 15
<211> LENGTH: 20
```

```
<212> TYPE: DNA
<213> ORGANISM: Artificial Sequence
<220> FEATURE:
<223> OTHER INFORMATION: primer SSR148152-L

<400> SEQUENCE: 15
gtaggaagac tgccggagac                                             20

<210> SEQ ID NO 16
<211> LENGTH: 20
<212> TYPE: DNA
<213> ORGANISM: Artificial Sequence
<220> FEATURE:
<223> OTHER INFORMATION: primer SSR148152-R

<400> SEQUENCE: 16
gacgctagaa tgactgaacc                                             20

<210> SEQ ID NO 17
<211> LENGTH: 22
<212> TYPE: DNA
<213> ORGANISM: Artificial Sequence
<220> FEATURE:
<223> OTHER INFORMATION: primer STSrga3195-L

<400> SEQUENCE: 17
ctagaggttc aggcatatgg cg                                          22

<210> SEQ ID NO 18
<211> LENGTH: 22
<212> TYPE: DNA
<213> ORGANISM: Artificial Sequence
<220> FEATURE:
<223> OTHER INFORMATION: primer STSrga3195-R

<400> SEQUENCE: 18
agctccacag gaattcgttg ag                                          22

<210> SEQ ID NO 19
<211> LENGTH: 20
<212> TYPE: DNA
<213> ORGANISM: Artificial Sequence
<220> FEATURE:
<223> OTHER INFORMATION: primer STSrga840810-L

<400> SEQUENCE: 19
gcgtcaggca gttcaacttc                                             20

<210> SEQ ID NO 20
<211> LENGTH: 20
<212> TYPE: DNA
<213> ORGANISM: Artificial Sequence
<220> FEATURE:
<223> OTHER INFORMATION: primer STSrga840810-R

<400> SEQUENCE: 20
tgttcttgca ctcgcacttg                                             20

<210> SEQ ID NO 21
<211> LENGTH: 20
<212> TYPE: DNA
<213> ORGANISM: Artificial Sequence
<220> FEATURE:
<223> OTHER INFORMATION: primer STSsyn1-L

<400> SEQUENCE: 21
```

```
ggcacatgga cgtacaagat                                                    20
```

<210> SEQ ID NO 22
<211> LENGTH: 20
<212> TYPE: DNA
<213> ORGANISM: Artificial Sequence
<220> FEATURE:
<223> OTHER INFORMATION: primer STSsyn1-R

<400> SEQUENCE: 22

```
gcacagagga agctaggaga                                                    20
```

<210> SEQ ID NO 23
<211> LENGTH: 412
<212> TYPE: DNA
<213> ORGANISM: Zea mays

<400> SEQUENCE: 23

```
gtatttctac cagcgtggcc ttcaccgatg ttggacggcc gacggaggca aaaccttgag        60
cacatgaact gcccttttaac atcttcatga gacactgccc tttaaccgat gttggacggc      120
cgacggagtc ttgccaaaacc ttcctgacct aggatagaca gttagacacc accttcagct     180
ccttttgccc gtccatcatg agctctctaa cttcagactt gggaacctcg agaccgacgg      240
ggacgacgat ctcctccggg agcagcccac gacgaccggc gccaacgatt tctccacata     300
cagcagcatc agcagaacaa aattccagta cttgcttgga aagctcgtac ctttcacagc      360
ggcgcatagc ttcctggatc cgctccttga attcttcgat ctgcagcttg tc             412
```

<210> SEQ ID NO 24
<211> LENGTH: 176
<212> TYPE: DNA
<213> ORGANISM: Zea mays

<400> SEQUENCE: 24

```
cttccatcgg tactccattc aagcagaaac aaacaggtta caggcataca ttatactgtt       60
cgccaacagt tccctcgggt cgctccattt ctttactgac acgtgaaatt ggcaaacaat     120
ggagaaaaaa actaagtgca ggaaattaat tatactgatt tctcacacct ggagaa         176
```

<210> SEQ ID NO 25
<211> LENGTH: 270439
<212> TYPE: DNA
<213> ORGANISM: Zea mays
<220> FEATURE:
<221> NAME/KEY: misc_feature
<222> LOCATION: (25001)..(25020)
<223> OTHER INFORMATION: n is a, c, g, or t
<220> FEATURE:
<221> NAME/KEY: misc_feature
<222> LOCATION: (66226)..(66245)
<223> OTHER INFORMATION: n is a, c, g, or t
<220> FEATURE:
<221> NAME/KEY: misc_feature
<222> LOCATION: (81020)..(81039)
<223> OTHER INFORMATION: n is a, c, g, or t
<220> FEATURE:
<221> NAME/KEY: misc_feature
<222> LOCATION: (100923)..(100942)
<223> OTHER INFORMATION: n is a, c, g, or t
<220> FEATURE:
<221> NAME/KEY: misc_feature
<222> LOCATION: (105186)..(105205)
<223> OTHER INFORMATION: n is a, c, g, or t
<220> FEATURE:
<221> NAME/KEY: misc_feature
<222> LOCATION: (112496)..(112515)
<223> OTHER INFORMATION: n is a, c, g, or t

```
<220> FEATURE:
<221> NAME/KEY: misc_feature
<222> LOCATION: (115136)..(115155)
<223> OTHER INFORMATION: n is a, c, g, or t
<220> FEATURE:
<221> NAME/KEY: misc_feature
<222> LOCATION: (128466)..(128485)
<223> OTHER INFORMATION: n is a, c, g, or t

<400> SEQUENCE: 25
```

| | | | | | |
|---|---|---|---|---|---|
| agtgatgatt | tcactggttt | gtttctccaa | taagctggct | tcctcatgat | catctgcctc     60 |
| cggcttcact | tgccggagta | tttctaccag | cgtggccttc | accgatgttg | gacggccgac    120 |
| ggaggcaaaa | ccttgagcac | atgaactgcc | ctttaacatc | ttcatgagac | actgcccttt    180 |
| aaccgatgtt | ggacggccga | cggagtcttg | ccaaaccttc | ctgacctagg | atagacagtt    240 |
| agacaccacc | ttcagctcct | tttgcccgtc | catcatgagc | tctctaactt | cagacttggg    300 |
| aacctcgaga | ccgacgggga | cgacgatctc | ctccgggagc | agcccacgac | gaccggcgcc    360 |
| aacgatttct | ccacatacag | cagcatcagc | agaacaaaat | tccagtactt | gcttggaaag    420 |
| ctcgtacctt | tcacagcggc | gcatagcttc | ctggatccgc | tccttgaatt | cttcgatctg    480 |
| cagcttgtcc | tcctcgtcac | tgaaatcatc | gcccgtcgcg | ccacctcctg | cttcagatcg    540 |
| atccagtttt | ccatgtcgta | cacatttggt | tggagagaaa | tcgtcgagtg | ttccaagggc    600 |
| agcaaagaga | cattgagcag | gttgccttct | caatcaagga | agtatttaaa | agcagagcat    660 |
| ctctcccgca | ctcatttgga | ggctagtggt | ctgaacgcat | caatggattt | aaataggaca    720 |
| ggaggagtgg | agttttttttt | ttgataatgg | aaacatgagt | tccggcttta | gcatggtaat    780 |
| gcgtacagcc | aacacaagac | aattattaca | tccgagaaac | gttgcacaga | aatgaaact    840 |
| aacttaaaga | agcaaaatca | cgagaatgta | ggtaactcta | gccatcctca | attcttgcat    900 |
| ttgagcgcca | tccatgattt | gcaaagactt | ccatcgacac | cacttccaac | gcttgacaga    960 |
| catcgaggat | ttgttgatgt | gattcctcct | tctgtagaag | tctccagaat | ctgaaccagt   1020 |
| aagtacctct | gaaaatgacc | tgcagaattg | atggtattgg | tttatgatta | aaagcaactt   1080 |
| catttcgact | aagccaaata | gatcaaaata | aagctgagat | tccagagagt | aataattttt   1140 |
| tgtaacctgg | actcatattg | cttccccaag | acccaataat | gtgattaatg | ctaacgggcc   1200 |
| tgtctatctt | taaggcatag | taaattaatc | tccatatgtt | gctggccata | tagcagtcaa   1260 |
| aaaagagatg | atgaatactc | tcattttggt | tgcaaaagct | acagtcaag | ctgccttcc   1320 |
| agcgtctttt | ggctaggtta | tctttagtaa | ggatcgctcc | ccgacataaa | ttccacaaaa   1380 |
| aaacttttat | tttcaagggg | agcttaagtt | tccagagctt | tttattccgt | tcgtcgttag   1440 |
| gattattcat | caaacaatgg | tacatagatt | ggactgagaa | aattccaagg | aggagtggag   1500 |
| ttagttgatg | ggggttacat | ttagttgtag | cttgttttttg | taaataatgg | ggatgcagtg   1560 |
| gttttggagg | ctttgctgtt | atcttgtgta | atgcagagtt | tgtatttttc | actcttctaa   1620 |
| tatatttgcg | tggcaaagct | tttgccacat | atttcaaaaa | aaaagcttcc | ggacctgctt   1680 |
| catccacacc | ttggcttgtt | cacccaccac | cttttgctcgg | gcaaatcgat | ctgttcatga   1740 |
| tatcctctct | gagccttttg | agatcttgta | gcaaacccte | caacaaggga | tggtttgcca   1800 |
| tcatttgggt | gatctcgtcc | acaagggagt | tgatcgcccc | catcgaatag | cacaccattg   1860 |
| ctccacactc | catgctagct | atatctctaa | caacaagcag | agatacatcg | gagcagtcac   1920 |
| tacatctctg | cgcgctggta | tatatagcag | aggaagaaaa | aaaagaacaa | taatcaaagt   1980 |
| acacctacct | tttaggacga | gtaaaatac | gtagttggca | tgcaatgcca | cttggatctc   2040 |

```
caaacttttta taagtatgct caaaaatgac acgccatgtt gcgaacacaa ggtggacttg   2100
ttttttgtgg ttcggattgt gatgagggat tgttttttt gaaagggagg ggcaaaagat    2160
ttgccggtcc aatatattag agatgagaaa cacttacaag acactcatgg agacaaaaaa   2220 ggggggggaag aaagaagaag ggcaaaactc aaccacctac taaccaccta ctgaggctaa  2280
atacaactcc gagactacca ggcccaaact aacccaatag agcaccaact agctctttca   2340
ctaaagaagc gacctgatct ggattcttct gttgattcct gaagatcatg ttgtttcttt   2400
ctaaccataa gctccaccaa aaatagatta gaaggtcgtc gaattttttt cctagattgc   2460
ctattacaga gacctcttag attcctccac caatcatact gcgactcgga tgtccggttt   2520
cctcccagga aagaacagtt cccccatatc aatatttat tccacacctc tctactaaaa    2580
gggcaatctt tgcataaatg agttaccgtc tctagcactg agctacagag acagcaaact   2640
gggttacact gccaatgtct tttctgaagg ttgtcagcag tcagcacttt attatgcaaa   2700
agagtccacg caaaaaaacg acgtttaggt tcagttttg ctttccaaat ggggtcaatt    2760
ttcattgtgc aataatttgt tgcaaattga atcttatatg cgctacttgc actatactca   2820
ccatcttccg tccatctcca agaaatggag tcttctagat cattgagccc atgtgtacta   2880
ttgatggcct gccaaaggga ggccaattcc ttgatttctt ctgcaccacc gtagggagcg   2940
cataactgga tccaacggct gtttctcagg gaatggaaag tcgaaatgtt cttcctttt    3000 gcttttttga aaagacttgg tgcaatgttt tttggtgctt gaccatggat ccaactagat   3060
ttccagaata ttgcagtttt cccattaccc accttcacac aagtggaagc gttgaaaaga   3120
tcttcatctg tcttatcaca tggcagctgc agatccaccc atgctttgtc tttggccttc   3180
catcgcgacc acaaccatct tagtcttaaa gccctcgcaa aacgattcag gtctaggatg   3240
cccaatcccc ctttgcactt tggcaggcaa gtagtagacc aattgatcaa acagtgaccc   3300
ccgttgcatg actctggatt acttcctttc tagaggaagt ttcttcttat cttatcaatt   3360
tttttcaata gccattttg agccgggaag accgtcaggt gataaatagg ttgtgcggat    3420
aacacagatt taactaatgt ctctctacct gcctttgaga gaagccttcc tttccatcct   3480
gcgagtcttt tattgatttt tttcaactaa aggttgcagc tcaatacttt taacggttct   3540
aaagtgaagg gggaatccta ggtatttccc gggtaactta gcgaatttac tagggaaggc   3600
ttctacaaga tttggccaca gggcatccgc gtaacggatc ggaaaaattt ctgttttatc   3660
gaagtttatc ttcagccctg aacacccttc gaaagtctat agaatcgatt ttagaacttt   3720
gagacctgct ttatccgctc taataaacac ccgtgcatcg tctgcgtata gggaacagcg   3780
aagctttgcc cctcttggca ggacccgccc cagtaaccca gcctcagccg ccctctcgat   3840
catcctctgc agaggatcca ttgctaatat gaagagaaaa ggggaaaggg gatcccctg    3900 ccgcacacca cgcatgtggt taattttgtc tgattgttga ccattgatga taactctaga   3960
ggtagatgaa ccaagaattg tggcgatcca attcgccac cttaggggga atccccgggc    4020
ttttagcaca tcgagaaggt aagcccaatt tagggaatca aaagctttgg atatatcaag   4080
cttaacaaac agagcaggct ggccgttttt atgaagttcc agatcaccct tgaacatat    4140 aggaagttat cgtgaattga ccgtttctgg atgaaggcgt tctgagcagt ggatacgatc   4200
tcattcattc tcagtgcaag tctgttagcc agaattttgg atatgatttt catgaagcta   4260
tttataagac tgattggtct aaatttgtct attgtgtcag agatctctct ttggggtagc   4320
agaatgatgt ttgcctcatt aactaggtgt aagctcctgc attttaggtg ataaaagtcg   4380
ttaattgctt tggagaggtc gtctttaacc acgtcgaagc agcatctata gaacaaccca   4440
```

```
atgaagccgt ccggacctgg cgccttttca gcttgtaacc ccataaccac tttcttgatc    4500
tcattatcct ctatcgcatt gtctaactcg ggtaattcaa atggcaagta acccaaatta    4560
tcccaacgaa cagccctctg tctcactcca cttgttccaa gcactgcatt aaaatgatgg    4620
tgagcctcgt gcagtttatc tcgttggctg gtcaatattg attcaccatg aactagagat    4680
ctgatatagt ttttcttct tctgttgttg gccatcaaat ggaagaattt attattagcg     4740 cccccagac gcatccagat gagcctggaa tgttgtcttg caattgtctt ttgaatgcaa     4800
gctaggccaa gaattttgga tttaagccat ttcctgaatt ccaattcgtc actggtgagc    4860
tgcctagctt cctgagcctt ctccagtagg gttagcacta tctgaatgat tgccaattgc    4920
acattgacac tactaactgt ttttcttctc cacgcgctta gttccttggt tgtgcgttgc    4980
atcttcacat ggagcacaag aattgcatca gcaaaattga caccagtctt ccaagcgtgc    5040
tgcactacct ccttaaatcc atcgattttt gtccagaacg actcaaatct aaaacccta    5100 aagaaggaga aggaagaacg accttgcata attagcggac agtgatccga ggtcattgtg    5160
ccaatggcct gaaggtctgc cgaggggaat agttgatgcc actctgttgt cgcaagaaat    5220
atgtcaatcc tcgtcattgt aggttcattc tgttcatttg accatgtgaa agctctacca    5280
ttgagaccaa gttctaatag ctgcagatca tcaattgtct tattgaattg actcattatt    5340
cttctgttaa ttatcccttt atttttttcc cgtgctctcc ttatcatatt gaagtcccct    5400
aaaatgatcc attccggtcg caccaaattg tgaatattat gaagttcatt aagaaaatcc    5460
attttctcat tttcttgctg aggaccataa actccagtga ggtcccacac ctcgtcctcc    5520
aatttcgagc tgattctaac cgaacgagtg attgtcaata gatagcgtct tgggttgaat    5580
cgtgtagact aaccagggtg tgaattatgt gttgtgcaat tatgtctctt ggattgtggt    5640
gtgcaagtgt gcaacacagg gacgacagtc gacggtgaat gtgaaaacca tgtgggctcg    5700
tgccgatggg ccaggagcga cgaaggacga atgcatgacc tttgatcgag ggactggaga    5760
agtcgggtga ctagctgcag cggctgacat ttgcgacaca cactggcatg aggacggaga    5820
gcggatcgtg ttgttagcgc ggtcaaggac tggtgggaca cgtgaccagg acgcgaggga    5880
cgtgtatgga gtacgccact cttggagttt cggtggttga gcctcaaaac cacctagcgc    5940
catggatgtc agttttactg agtttgggct tcaaaactgg gtggtatggt tctgacggac    6000
tgaccaactc cgcgtcgagc aactcaacaa gaaggatgga ccgaccaact ccgagtctag    6060
caactctgcg agatggactg accaaccaac tcctgccgag caactcggcg aggcgaacag    6120
accaaccaac tccggcctag caactaggcg aggtggtgcg ctcctggcgg gaatcggagg    6180
cggcacatgg tgtcatcgcg aagggtgttt cgagacgaat caacttcgtg aggagcgtaa    6240
ggtcgtctta tgaaaaatct taggagttgg tctattttac cctcagctaa atggataggt    6300
tctatgtatc tacgagtaga ataggaagta gaaataaccc cctataaata ggtggtatgg    6360
ctgttgtgtg cagtagctat ctccttgagc atttgtgtag aggacacata gtttccatttt   6420 cctagtcgct agctctagcc gagatccgca ggcgattttg tttcccatcg tctatgtctg    6480
tgtacttcag atactgagag gaagggtggc cgtaaccacc cgcagtgcag catttgtcaa    6540
atcaatgtgc tcagtttgtg tgtgctgcag ttttttattt gattttgttt tcactctcga    6600
tacctctctt ctctcttaca tttttgaag atccatcgat ttcttgagtt gcggtttgtg     6660
ttggagatgc cttggggtga agatcacttc ttagaccatt gcaaacttta gaatctgtca    6720
atgaaatttt gttacatgag agggggaaac aatacctcga ataaggatga gcggctatag    6780
```

```
agaaatgtca agggtaacat agaatctgtc aatgcatttt tgttacatga aaggacaaaa    6840
caatatctga tgagcggcta tggtgaaatg tcaaggagta acatagaatc tgttaatgca    6900
ttcctgtcac atgacagggt gtaaagcaat tcaatgagcg gattaatttg gtgaaatgtc    6960
cgtgaagtct aswgtctaga ccatgtcaag gaaatcagac ctaccgtatc gaattctgag    7020
cttcaatatg ggccatttgc cgaccagcat cgtaagaacg ggcagcagca cggacagaac    7080
gcagatcgca atggccagcc aaggaaggcg atcttccaga accgtgtaca gaccagtcgc    7140
aaatgcaagg gtggttgcca tgtacgcgaa ccacatgagc ttcgtcgtga cggacctgta    7200
gtgcagcaag aactcaaagt ccatccacct tgctatgacg catatgaagg caacgacgag    7260
ggaggcgcac atcgccgagg tgtcgaagat caagaacgcc tggaacgcga ccttcctagc    7320
catgattggg agcccctcgc ttccagcatc actgctgtac cctcctggca atgtgaaagc    7380
tgcagcgaag gtaatcgtcg ctatgaggat agccactaag gacgtgttgc ttgtgtatgt    7440
ttggatcaga gacttggcat ctttccttgt tgtatcgatt actttgttcc tgatctcctc    7500
ttggaaattg tagatgtcag tttcagctct acgatccgca ttcagtatga ggcagcagat    7560
tttgttctgc atatatgcat ggattcaatc aaaaaaagtt aggcaccatc tgaattaatg    7620
aagcaatctc atacattaca tacagaaata catacatacc cagtttatag tcttgacgta    7680
gtccccatca tggtacagat tccagatcgc tgtgcaatta cgctggttga caacggtgat    7740
gtcgatgtca gggtgatcca gcaaagcacg gaccatcctc gggttgttct tctgaaccgc    7800
gagatgcaga gcactgtcat caacgctatc tagcatgttg acaagtttcc ggagcttgga    7860
gttgtcgtca aggatgaact caacaaactc cgcccggtcc ttgtctacag cttcgtggag    7920
acatgtcctg ccctgctcgt cgtggtaggg cgcatctgga cagtgctcca gaagcgctcg    7980
agcaaaagct acgtggcctc ggtctgcggc gatggaaaga gaggcgtgg agtgttcctc     8040
gtgcagcacg taccccaagg accgatcaca tctcagcatc agcgttagaa tcctatccct    8100
gttgaaatgc gcagtgagat gcattggagt gtccctttta ctgtccgctt gtctcgccag    8160
cactttggcc ttctcgggat gcttgtccac aagttgttca cgaaatctg aaaaaacaag     8220
ttagtttcgc ggttttggct tttaagcaag agacgaagag ggaaaaaaaa tgcatgaaga    8280
gcaagcatct gcagcaggta ccttggtgtc cgtacttgac agcagcgtgc aaggcgttgg    8340
agccattggc cccgctgtat tccgacctct cgttgctcag cagcgccatg tagacgctcc    8400
tgaaaccttt gagaaccgcg atgaacatgg gcgactcgcc gcgcccgctg cgggactccg    8460
agagcgcagg ctgccggccg atcagtcgca gcgcgaggcc ctcgtcgtag ccgttgcgga    8520
tggcgtggtg caggacgttg catccgtgcc tgtctcgctt cagaaggtgc tcgtccagca    8580
gctcgtgcct cgagtgctgc tcgagcaggt caagggccag ggagacgcgg ccgctcttca    8640
cagcgacgag cagcggcgtc tccccgtcgt cgttggcggt ggagagcaga gacgacggga    8700
gactcggctc ctgcgtcagg cggagggcga ggaccttgct gcagaaatcc ccgtggccgc    8760
agagagcggc gatgtggagg caggtgttcc ctgcttcagt tgtttggtat agcacctcag    8820
gcttgtcttg caccagctgc tccagttctt gggctctgcc tttgatggcc gcctgcagta    8880
gcatctcgaa ttcgtccatc tagctacact ttgaacactg ccacagagag actagagaaa    8940
tgaaacctag acgctcactt attcaaataa tactatgaag gaaaattaag attgtaacgg    9000
tgaatctggt gacccaactg aaagatggat gtttctcctg caactctggg gagagagttt    9060
caaaaccacc ccaaccggtc cggccgttcc ccttgtgcgc attaaaaaat acacaagctt    9120
acgaggtttc gctagtgagc ctttggtttt agtaatgatt actcccttt g agtgtactat   9180
```

```
tagttgtcgt ttagaacagc gatatggtct caaaaatata aatttaacca atatttttta    9240
aatataaata aactcttaat atatttatac ttttgtaaaa gaacttgtta agataaatcg    9300
gtgtatataa acattatgtt ttaaaactac ataataaaat agttattat  aataaagagt    9360 ttataacttt gatttaaatc ttatccaaaa tgacaacaaa cgggacacgt gagggagtag    9420
agttgagcac gggacgggac taatgtaagc atttgacttg ggtccaacgg ctagttagag    9480
tgaagaaccg gtggagaggg gtaaatggga gcctgcagtt cttgggctct gcctttgatg    9540
gccgcctgca ggctgcagta gcctctcgaa ttcgtcgtcc atctatccac aaaggaaatg    9600
ctacttgaac accaataaaa ctctcatata tacatgccaa acactaagc  atgctgaacc    9660 tgggcatctc cttccaaaat aaacaaatga aatctagaaa cggaattcaa atatgccaag    9720
gaaaatttaa ctggcacacta ctgattgtaa taactagtga ctggcgcgcg ttgcacgcgt    9780
acgaaacatt tcgtaattta agtattatga ataccatttt attgtaagtt agttatttgc    9840
atgtgtagta atttatttat ttacagtaaa tatatgaccg ctggctagat taattagttt    9900
tttttagcat ggaactgatt caaaagaaca tgaaatctag tgttatttga aaatttgggt    9960
aaccaatttg aagtatcgaa gatacctgca acatcaagaa tttaaaaatg aaggtcagct   10020
gtgtatatat atatatatat atatatatat aaacaggaaa gtaaagttat gtatgtaatt   10080
tataatctga caggcaacat ttaaaatatt tctttcttta agtgtatac  gaattgaaaa   10140 aagagacttt cagattgtgc atagttgctt tcgttaaaaa ttagcagcaa aatatatcgg   10200
ttcatgcatt agtagttgtt ggttgtgcat tagtagctat acccgtttgt acttgcagat   10260
agaattatta aattgttgtt ctctggttgt ttgcgaaccg ttgcgagatg aagagttttg   10320
gtaattgatg gttatcgtg  catagcaaaa ggctcttgtg agaaactaat gtatagagaa   10380
gctggcagtg gtgaggtagg ttaaatagaa aaaacaataa agggacaaaa agggtctggt   10440
gatgtattgt tacctctctt ttttcgtggt ggtcacattt tcgttgcagc atgtatagtc   10500
aagcagaaaa tacgttagta agtgcataat aatgtatcgg taaataaacc gcgcgatgtt   10560
aatgtgagga ggcaatgtat agataaagtg gtagtattaa ggtaaatcaa ataagaaaaa   10620
caatgaacga atagaggtgt tatactggag tattgtcgtt atactttttt ttttttttgga   10680 atatttgaga tgtatcaaag taatgtgtgt gcgttcgtac acattttta  gtatgtacat   10740 gttttccaaa tacaaacgtg caggagtatg catcctagct gtacacgtca gtgcaataac   10800
aaatttgaca tattgtacat agaaaaatag gatatgaaca aattgaggat gtaggtgcga   10860
agtgcttcag taaccaaaga aaaaactgtg catcgtagat gaagagctgg ttgcaggtgt   10920
catcagtgaa aagaaagaca tacatgattg atttgaaagt cacagccgtt tgaatttgct   10980
ttaagggtat caggaaatag ttgattggtt aaatagatat aactggttat gttgcgtatt   11040
taggtaggaa aaaatagtta tttaaaaggg ttgttgacat aaacatatca gtgaatgagt   11100
tggttatttg tatcaagatt gaagaaatat ctatgtcaaa aggttgtaaa tgtttgaaaa   11160
ataaagtagt ctatcatttt cttactcctt actttcttga ttagcccagt cacgctaggg   11220
gataaggtcc tccatcgtcg ttatcgtcgt ctcgccgatg ctgttgacct cctccctctg   11280
gcaggaaaga tgtgaacctc cgctacatag actggaagcc tccagacgct tcacggcggg   11340
gttgtgtctt ttttaaggtt gcactttagt tctcctagac aactgcgttc cgcttgccgt   11400
cgataaaata ttgaacggcg gatgatttaa acactaacgt ggatggccta gcttgccagg   11460
gatgctccct gctttaatat atagaaattc ataaaagaac tcttgggaga agtttccag    11520
```

-continued

```
accacccgtc cccaaccggc ccattaaaaa acccacaagc ttcagctttc actagtcggt    11580
tcttggtttc agcattgacg agaataatat ataagcatta ttaagtcttg cattccaacg    11640
gctagtgcgg cagaccgcag acggacacgt atgagtttcg gttggacact aaaaaaaagc    11700
catccagtca tttgaagccc tttgtttatt gcactcgggt gaaagagttc atgtccattc    11760
ttgcctcgac attttttttgt gaagagttta tttcaccatt catttgtgac catatttcaa    11820
atagagcata tgagttcatg ttcatggcta gtatagctcc ttttctgctg gtttataaat    11880
agagaaattc gtggtcctta aaaactagta aatgccgcgt acgtgccctg catgcgtgcg    11940
ttatcaaaat tcgtttgtga ccataaatat aagtatgttt ttttttagtg taatgataat    12000
atgactcttg cagaactgta gtaacggtca aaaaaaaata agagtgttga cacctttttta    12060 gggcgtcaag cactcaacac gaaccagcga tggtgctctc tgcacaggga cagatggtcc    12120
gcgcgcaagg gccggacggt ctgcggcctg gtgcgaggct agagttcatg ccggacggtc    12180
cgcgccctga ggccggacgg tccgcgcgtg cgcggggggcg gcagaagatc accggcggcg    12240
cctggatctc actcccggga gggaccccgt cgggaaggag agatcctagg agttgtctag    12300
gaccgtccgc cggctcaaag tggtgctcaa catatgcccc ctgccttttg gtggagctga    12360
gcaaaccaaa agcaactaac tcgatgtgat tacatcggtt ctcttagtca tcttgccaca    12420
tactaggatg gtactgtttg aggaaacgtc cattcaaagc cttgtgtaaa tccttgtctt    12480
gtaatgtttg tagtaaatat gtgttaccgg atattacctg ttttacttta taaggaccct    12540
cccagcttgg cgatcatttc ccaaacttcc ggtctttatt tcttagaggc aggatggtct    12600
tccacaccaa gttccctaat tgaaatgact ttgctctgac cttcttgttg tatgccctgg    12660
ctactatgat tttgtccttt tctattgctc ccaaagctat cacccttttg tcggtcacct    12720
catcaatatt atccatcatt gaattataat aatccatgac ggttagatca ttttgtctgg    12780
cgaacctgac agcattcaaa cttatttcca caggcaacac tgcttcctgc ccatagacaa    12840
gctcaaaagg agatacttta gtagcactat gtttagatat tctgtgagct cataaagctt    12900
cggacaaaat cttatgccaa tgcttaggat tatcggatat cttcttttt atcaagttaa    12960 tcaatgtcct attactagac tcggcatgtc cattggcctg agcataatat ggagatgaat    13020
taagcaactt aattctatat aattcagcaa attcacgtac atcctttgac ataaaataag    13080
tctcttaatc tgtagtcaag gtctgaggaa tgccgaatct atgaataata tgctcagtta    13140
tgaactcaat tacctccttg tgtgtcatgt tcttcagagc aacgacttca gtccatttgg    13200
taaagtagtc agtggcaact aacacgaacc gatgcccctt tgatgatgaa ggatgaattt    13260
ccccaataaa gtctaatccc catcctctga aaggccaagg cttgatgata gaatgtaatt    13320
cggctgcagg gaccaactgt aggtcgccaa attttttaca cacttggcaa cccttgtagt    13380
acttaaaacc atcagctatc atattaggcc aataaaaact agaccttcgc aacagccact    13440
tcatctttgg agccgattga tgggtaccac aaattcctttc atgtacttcg gccatggcta    13500
atatagcatc atctgggccg aagcacttaa gcaggacgtc gttgactgtt cggaggtaga    13560
gttcatcact catcaaaaca tacttgaaag ttgtacgccg aatgttctta tctgtcctga    13620
cattgggatt tcataaataa ttagttatgg acgtcctcca atcacttgca tcggcttcat    13680
tatcagacga atcgattagg agaactttcc tggtaacccc ggacggtccg gcgtcttcac    13740
gcggacggtc cgcgacctgg ggatttggcc ctgcactggt tatcagattt tcagtattgt    13800
gaaatttccc tcgctttatc cgataacctg atgcatcttg tgccaaattg ttagctctat    13860
gattctcaac tctagagata tgtcgaatac tgaattcgtc aaaagaatgg attatgctcc    13920
```

```
aacattttc  aaggtagcta  tttagagtac  catcaaaaca  ttgatattct  tctaacacat   13980
gttggacgac  cagctgagaa  tcaccaaatg  cctttacatg  ttttactccc  atacaattta   14040
aaagttccaa  gccgaacaaa  agggcttcgt  acttggcttg  attgttagtg  cagtaagttt   14100
tcaatcggct  agagaagtcg  aaggagacat  tacttggtga  aacaagcaca  atgccaatcc   14160
cttgcccttc  attgcaaacc  gatccatcaa  aatataaagt  ccaaggagta  atagtgaggt   14220
atgacatgtc  tagtttatga  gtatcattaa  tccgatgttc  tacagtaaaa  tccgctacga   14280
cctggcttct  cacagatttc  aatggttcat  aggccaagtc  atattctatg  agtgcataag   14340
cccacttacc  aattctacca  ctcataattg  agttatgcaa  catatattta  attacatcgg   14400
cttgaccaga  aacagtgcaa  tgactagaca  gtaaataaca  tctacacttg  gtgcatgcat   14460
aaaacaagca  taagcataac  ttctcaataa  aagtgtacct  cgtttcagca  tccaccaacc   14520
aacgacttag  atacgtcacc  acatgctcct  ttccttcagt  ttcttgtgtc  agaacaacac   14580
caatgacctt  atcttcagct  gcaatgtata  atcggaatgg  tactcctgct  catggtgctt   14640
ttaatacgag  agctgaagac  aagtattttt  taatgagatc  aaatgcatcc  tgctgctctg   14700
cccccaagca  aattcagcat  cattattaag  ccgaaggata  ggggtgaagg  catcaatctt   14760
cccggctagg  ttagaaataa  accttcgtaa  ataattcacc  ttgccaagaa  acttctgcac   14820
ttcgacctta  caggtcggag  gccccacatt  ccgaatagac  ttgattcggt  cagggtctat   14880
ctctatgcca  tgttcatgga  tgacaaatcc  taaaaactta  ccagccgaca  ccccaaaagc   14940
acatttacgt  gagttcattt  tcaaagcata  ccgacacatt  ttatcaaagg  ctttgcgtaa   15000
atcagctata  tgagaactaa  actcagccga  tttgactaca  atatcatcaa  tgtagacttc   15060
cacagtgttt  cctaacaact  catggaagat  caaattcata  gccctctgat  aagtagcacc   15120
agcatttta  agaccaaatg  tcatgacaac  ccattcaaat  aaaccaatga  agcctggaca   15180
tataaaggcc  attttagacg  catcctcttc  ggccatgaag  atctggttat  atccggcatt   15240
accatcaaga  aagctaataa  ttctatttcc  tgatgcatta  ttaataatgt  gtcggctatg   15300
ggcatgggat  actcatcttt  aggagttgct  ctatttaaat  tacgaaaatc  aatgcatact   15360
ctaagcttac  ctgactcctt  ctccaccgac  acaatattgg  agaccattc  tgcgtatctg   15420
caaggtctaa  taaaatcaac  ttctagcagc  cggtggagtt  cgtccttgat  tcgtgggaga   15480
agatctagac  gaaatgttct  agctttctac  ttgaaaggtc  tgaaatcgga  cttaataggc   15540
agccgatgca  cttcgatctc  tcggcttaat  ccaggcatct  cagtgtaatt  ccaagcaaag   15600
caatctgaat  attccttcaa  tagaccgaac  atctcatttc  taggatcgat  ctccagggtc   15660
ttgtttacaa  aagtcggcct  tgaaatttta  ccatctccta  tgtcaatctc  ctccaaatga   15720
tcagccgatg  taaccccta  tcctagttta  tcaaaatatc  tgaattcctc  tatcacgtcc   15780
cctacagagg  aaccagatga  tctttgtgtg  atggcgggct  ttccggtctc  ggggaccgga   15840
tcatccgtaa  cactgtcttt  actctgcggt  agatgttcgg  tcttaaagtc  cgaactgttt   15900
tgcggaagac  cataccatcc  ggccttagaa  gtcgaactgt  ccgtaaccaa  agactcatga   15960
actttgtgtg  tactcatcat  ttaaactttt  tttaggattt  agccgattct  ccatcggctc   16020
tagcattaca  ggaatgaaac  ccttcctatc  tatacttatg  aactgataat  cagaaaaatc   16080
tactcctgtg  agacatgtag  cagtctcata  agtccaaagt  acagggcat  cggccacatc   16140
gatacaggcc  gatacatcag  catgtacttg  ttctacatca  tcgcctaccc  attgtattaa   16200
catttgatgt  aatgtagatg  gtatacattg  attggcatga  atccaatctc  ttcctaggat   16260
```

```
taaactgtaa ttttcttcta catcagcgac gaagaatgca gcagcaaggg tcttagtctc    16320
gatggttaat tcaacggacg tgactcccct ggctttgatc gaactattag tttcaacacc    16380
actgagggtc atgttggtct tgacaagttc atcatcttgt ttacctaatt ttctgtataa    16440
tgaataacgc attagattta caaccgcccc tccatctacc aacattttag aaatcggtat    16500
cccatcaatg tgaccgcgca cgaagagcgg ctttaaatga tgtaccgatt cctttggttt    16560
agtaaatgtg gcttctttag gaccaaaatc aaactgggca acaacaggtt catcgtcgcc    16620
gacaatagta caatcgacga aaaatgtaat aacatttacg tacatacatg ggcgctctag    16680
agaagcctcg tagtcgacca ggtcttctcc cagtaggtca tcttcttcca ttgatgttgg    16740
catgtcattg gaggcttcct ggtgtggtgc ggacggtccg gactccgagg gcggacggtc    16800
cgcgcctggt gcagaatgtc cgaccttgtt ggccaagcta tctgccatac ctgcaggtg     16860 ctgcacaagt gttgttttat ttctatttt cgtggccgtt tgttttcttt caacggcctt    16920
tggtctccat ttcttttgtg gtggcgtgta ttgtggatgt gtgtcattga atatcttttc    16980
cgcctccttc tcctggctct cctttgctct taggcgctaa atttccgct tttaggaccg     17040 tgtcaatccc gctgggcacc atcgaggcat ggagtatttt ggatcgactg ttttgatggt    17100
agccgtatct tcttttttgg ttgtgttggc cgattcacca aaaatcatcg gcccttttat    17160
atcttcctgt atgacaacat ctgtagtacc tattttgatg atgtcctttt ttgtgttctt    17220
tcagttgctg caggcatatg ccccctgcc agattggtcg gccttggagg ccgagtagtc     17280
cggcaatctt gttgggtctg tgcctggtgc ccggattgag cggcgctcaa tcggccttgt    17340
actagtggtg ccaacctgtt gaatacgaat gtttggggtg ccccaagcg gggtactgtg     17400 gcatcccaaa cgaatatggt ggcatgcccc acatttgatt tggaacatat ggtggaggca    17460
tgtatgtgta tggatatggc ataggtggat atggaggtgg aggtgtccat gtaggtatgt    17520
taggtctcaa ttgcaaagta tgacctttca tttcttctga ttggtgaggt ggtccaatcg    17580
gccttacctg acgttgctca tgaacaggtg agcggggtcg cttttgctggc cggtccctgg    17640 ggctggcctt cttttttcacg tacttagaca ataattgatc gaaggtcggg acagttttga    17700
ccaaccgacc agctgccttg aatgtatttg ttttccacgt acctatctct ggtcgtcgtg    17760
gtttgaaggt acgtggccgt tgcgagtctt gagtggggct ggaccgtctg ctggaattct    17820
ccggaccgtc cggcgtggtc ccggaccgtc cgcatctgtg tgtcggaccg tcctggatgc    17880
gcagcatggg ttcctgctcc ttggtttgtg cctgccctcc agtgccggag gtcgtgatgg    17940
tcaccttaag agtttcccct ccatcgggag tcttctctgc caccactttc ctgcaagaaa    18000
ttttatgatt ctcatcggcc tctcttgcat tgtcgatgac tatctccttg cctttgtctt    18060
tattggttgt gtttggccga accaggactt tcttgccctc gaagtcgatc atgttcattg    18120
gaaagggctc tgtatccacc tgcatttctt gaaatttcaa tcgtccctcg ttaatggccg    18180
attgaatctg tcgacggaat acattacaat cattagttgc atgagaaaat gagttatgcc    18240
acttgcagta tgcccgacgt tttagctcgt tggcggatgg aacagtgtga tttatttaa     18300 tgttgtcatt tttgagtaat tcatcaaata ttctatcaca tttaccaaca ttaaatgtaa    18360
acttaacttc ctcttgccgt ttcttctgaa ccggctgcaa ggaggaacaa gccgaagatt    18420
tggcctgctt aggccaaacc atttcagcag tataaacttc tgttgattcg tcgtccgagc    18480
tactttggtc gcattctact atatggacat tgtgacgaat ggttttggta gtttctttgc    18540
ttcggctttc acaggccaaa gctctttggt gtaactgtgc tagtatgaaa aattggatgt    18600
cttctagtgt ttcttttaaa taatattgta gaccattaaa ggctaatcct gctagctgtt    18660
```

```
tttctgctaa atgaatttgg aagcatcgat ttcttgtatc tcggaatctt cggatgtaat   18720
cattaaccga ttcatctttc gcttgacgca aggacactaa atctaccaaa tctaactcat   18780
agtcaccaga gaaaaagtgg tcatgaaatt tttgttctaa atcccccat gacaaaatag    18840 aattaggagg taaagtggcg taccatgcaa acgtggttcc tgttaaagat aatgaaaata   18900
aacgcacacg aaatgcttct gtgtcggcca attcccctaa ctgtgctaaa aactggcata   18960
tgtgttcgcg cgtgtttttt ccttggtcac ccaaaaattt tgcgaatttg gtatcttgg    19020 ttccctgtgg gtatgggtgg tgatcaaatc ggctgtcata cgggttccga tatgattgcc   19080
ccccaggaac catgcttact ccgagcttat ctcggaacgc cccggctatt tcctcccta    19140 ctatatcaat ggcagccggt gcaagaccac cggctctctg gtcaaacata ggtggggttg   19200
gctggaaatt agcatgttgt cttcccccca ctggttatgt ggtgcattgc cacttgccct   19260
atatggttca taggtttgat cgttcctttt cggccttcta ggtggggccg aaagctttc    19320 ctggctctgg atcttgaatt aacgagctga tgcattgcat agtgtgaagg gaagtgtggc   19380
tgggacgggt gaggattcag gtaataatcc tcctcaaaaa ggtcatgcgc ggactgtctg   19440
gacattggcc cggactgtcc gtgattatat gcggaccgtc tgttgttgta tgcggacggt   19500
ccggctgggt agtttaaatg atgtgtcgta tgttgtggct cgggtgcatg tcggggtaac   19560
tcattaaaaa tgggcccggc cgtggctggc gcggactgtc cgctctcacg tgcggacggt   19620
ccgggcatgt gtagatcggc tgatttactg ccgatttgcg attgctcagg gtatgtgtcc   19680
atcggcatcc tataaagggg ttgtgactgg tcgtgacaac ctatagccga tgtattacgc   19740
atgttatccc ctaattcaac ctcgtgcgaa ggaaaatttg caatactaga tttatcaaat   19800
gcacgtacta gtctcctata atcgttttgc ataccccta taatattttg catttgttct    19860
cgctgttcat ctacataatt cttaagagat tgcacctcgt ttgtattact tacgttgggg   19920
atatctggtg tgggtcgaag cgaagccgga tccgtcgccc gttgtcggac gaccttgttg   19980
ttcctgtcca ctttgaagtt ggccaagaac tttgcttttg cctcctggat cagctgctcc   20040
ttgtgctcct cgaactggag ctgttcgtcg gccgacaagg tttcccaagt cggcactata   20100
atgttgctgg gggagacttc agagctatcc cttgaaccga ccattgaggg ccgatttgat   20160
gagtctagat gtgttttccc cagcagagtc gtcaaaaagt atgttgacac cttttaggg    20220 cgccaaacac tcaacacgaa ccagcggcgg tgctctctgc acaggggcgg acggtccgcg   20280
cgcaggggcc ggacggtccg cggtctggtg cgagggctag ggttcctgcc tgacggccgg   20340
atcgtccgcg ccctggggcc ggacggtccg cgcgtgcgca ggggcggcgg aagatcgccg   20400
gtggcgcata gatctcgctc ttgggaggga ccccgtcggg aggagagatc ctaggagttg   20460
tctaggctcg gcaggccga cctagactcc tctaatcgac gtagagtcga agagaagcga    20520
agaatttggg gatcggaagg ctaaactaga actactccta ggaaataaat gcgaaataga   20580
agtgttatta attcgattga taattacaaa tcggtcgtat atctctctat ttatagagga   20640
gggggctgga tcctttacaa actaatttcc gagttatttc cgcgaatcta gctaacaacc   20700
gtagcacaaa actcggaacc ctaaactgct ctgcgcacgc gcggaccgtc cggtccaaag   20760
tggtgctcaa caaagagcat ataaaattat gataacaatg ttcgtaagca tttatgtgtc   20820
ttcattaaat cgtttgtttt aactcttgca gaactccagc ataaatcgtt tgttttagta   20880
gtctaaaaga ttgacctata tatacaaata aagagggtc gttcatgctt acatgtgtct    20940
aaggtgcata tgacatctaa aagcggaaca cagcaaaaga aatgtaacgc cctagttttt   21000
```

```
aaatcaaaaa aatttatcaa gatctagttt aattattcgg tgagatttga gtagtttaga    21060
atcacgaatt atagttttaa gtattttctt tctataaatc aattgacaaa atgagttata    21120
aagttagatg aaaaggccct tatgtgagta aaatcatttc tttgttgaat aatatattta    21180
gaacattctc taaatatga aaaaactaga atttgggttt ttgaaatgaa tagaaagatt     21240
ctcccttctt taattaaggt aactgttctt tttatgaatt acgtgtttag aagcattcat    21300
ctaaacgaat aaaataataa ataaatataa ttaaccttac atctgatgct gaagttttat    21360
ttgcttgagc atttcaaatt gtgtgaatga atttcaaacc aaattcgaat ttaatcggaa    21420
aactgaaatt agaaaaaaaa caagatttat gctggagttt tatctagaaa catgcatgtg    21480
catatgtacg ttgcgctacg cttgaaaatg gggctatttt taagagtagt taatatacat    21540
ttaacattgt aaaataaga gcttgaatac cgcatatggt gatgcatacg tgtgtgtgga     21600
atgaataaaa tacttatcct agtactcatg aatatgtcta ctcgtacaca ggtatgtaat    21660
gtgtctgttg acgccgattt gggcagcgcc aatcactagg ggtgtaccgc ctggtggtac    21720
tctctgtgga ggcgtggaca gtccgcggct ctgggccgga cggtccgtga cctgagtgca    21780
gaagcgacgc cttgcccagt gttgcaccga atggtccgcg cacagggtcg acggtccgc     21840 gatggcgcag ggtcatcttg cacctcgctg gaatctagat ctcgcacctt ggggagagat    21900
cttagggcgc tctgggtcga taggtcacct ggggcgtcca cagacgacgt ggagtcgcct    21960
aagaattaag aggtagtcga gatatagtat tttgaatgaa caactagatc ttgccctcgg    22020
gtagggtcgt cttcggatcg gcaggccata caagacggat ctagacgaca tagagtcgaa    22080
tatgagtggg ggtggatatg cggaaggcta caaactagaa ctacgctaca tctactctta    22140
agataagaaa gataaataaa gtagatagat tcgattggaa tatgttcgga ggttcttaat    22200
cggtcgtgag ttgatctgat cacaaagata tacttattta tatttatagg ggaggatgtc    22260
tggacttgtt cctagaatat agctaacaac tcccacgtga ttagatgaat aaccacgcac    22320
gagataagga tgatcaccta agttgatctg atcacggggc cgcggaccgt tcgggcccta    22380
gggccggacc gtccgtcact tttggtgctc aacagtgtca attatttgta tggacataca    22440
tcaaattaag aagtataaag cgaagcaatt catgcgaatt actatgttta cagatagaca    22500
ttgctgtttt attggaagag aataaatcat gtatatttat ttgagttgag gaacccttat    22560
tattgcttgt atcagtaccg ccgccatgtt cagcgcttca catgagctca ctaccggaat    22620
cgacggcttt gccgagtgcc tgaagcactc gacaaagcct taaaaacact cggcaaagtc    22680
tttgccgagt gtcgcactcg gcaaagaggg ctcgacacac agtgcatcgg taaagccttc    22740
tttgctgagt acttttttctc gggcactcgg caaagttgtt tgccgagtgc cagagagcac    22800
tcggcaaaga aaagcagccg ttacagcgct gggtgacgaa gacggcgttt ttgccgagtg    22860
tcccaggtga cactcggcaa aggagttacc tttgccgagt gtctgcctga cagcactcgg    22920
caaagaattc gtcagagggg tccccatgtc aggtactttg ccgagtgctt ggtacggtac    22980
tcagcaaagc gtgcttcttt gtcgagtgcc agagccattg cactcggcaa agaacctata    23040
ccggtgccca ggtggttctt tgccgagtgc tatggttctg acactcgtca agaggtgct    23100 ttggcgagtg ttacactcgg caaagtgatc agtacacacc ttttttatttt gttttttccta    23160 ttccatccaa ataaacaaaa gatatttcac aaatatcaca tatatgcatc acagatcatc    23220
acagacatat atagccaaca caacaatat taacacaaat tctgacataa gtattcaaca    23280
taagttgaga ggttctcaac acaaatagta ttaacagaaa ttcagaagta tcaacacaag    23340
ttcacaagct ctgacaagta ttcaacataa gttttgtgtt caaaacacta aaaacataac    23400
```

```
tctcatagag gtgggcagtt ggactggtgc tgcgttgggt tgtacccttc atcagggttg   23460
ttggatgccg ccccagattg gccctgcaca gagaagagat tgcatgtgtt ataccagatg   23520
tattaccaac atgtaactac aattttgata ttcacaggag tatggaacag agcagggtca   23580
actgcaagga acaatggagg tggcagagcg aaaccatgtg cgacgccaag gctctacatg   23640
tactggaaca tctccgccgt cctctgatca gccgccaggc gagcctcccg ctccgccatt   23700
atcctcgcct ccatctgttg acgttccctc ctctcttctt ctagttgggt ctgtaatatt   23760
acaagccaac attatagtaa ctcaaagaga aggtatataa ctcaaggaag gacgaattac   23820
agaagcacta acctcgagtt gttgtatgtg atgctgtgag ctgtcgtgct gagggtcgta   23880
tggctggact cgagcccatg ctccttgctc gcacctgaga cagagtggga gtggaggacg   23940
agtcgattgc ctcgtcggca atctagtacc gcccatgtct cttgcctcat ccgaccctca   24000
tgagcacatc gaggtcgatt tgctcggtgc tcggatcata ttctgggcca tggacctcct   24060
gcgccatggc ggtgtagtca tgaaggcggc tgtagatggc ggggttggtg taggcctcgg   24120
gcccgtcatc cggggttgtag gtgacgtcgg gacgtcgcct tgcccttatg ggccatagca   24180
taggccgaga agatggagca aggccggcca ccatgtgacg ccgactgcaa caaaaccaac   24240
gagatagtta gaaatactat ctaatccagt gctatatacc taaataaaaa agagggctta   24300
cccatgcttc tgcatattag cccaggctcc ggctgccttg gtggtgggag ggaccttgca   24360
tcatcatacg tcgtttccgg ctagcgttgt gcgcctcgtc ccactcagcc gaacaccacc   24420
tatccaccat ctgctcccag cacagaggat gtgcggcgca cccaatgtga aatcatctac   24480
aaagtaaaca cataaagtgc atatcagaag ataaaataaa attcatgcat ggagtactgg   24540
taccaaacat gcatgacttt acctgcaggt actggtccct ggtcaacgat atggttcggg   24600
cttgctgctt ggtcagcttc tctgcacggg gaggtttcga aaatttccat cctctaacag   24660
aagcctagca atagaaaatt tcggcagcac ctcccctgc acggggaggt ttcaaaatcc   24720
tgcaaataaa actatcagca cgatggctga catacacgca taattcaatg gcacgatggc   24780
cgacaatcac acacacacac acacacacac atatatatat attcaatcca tgcatgtttt   24840
agagtttggc attcttttat taatctacta gaaaaaggtt atccatacaa tacaaattct   24900
aagtacctag tggctagaga taatataact ctaactatcc atcacattat caatcacatg   24960
ctcaacaaaa ataaagaatg atttaccaaa cgatggcgtg nnnnnnnnnn nnnnnnnnnn   25020
caaagagggc tttgccgagt gtcaactgac aggtactcgg caaagatcta ttctaggttc   25080
tttgccgagt gccaagggga tggcactagg caaagcagat tctttgccga gtgtcaaata   25140
tctggcactc ggcaaaggag gtctttaccg agtgtcatct cggacactcg acaaagtaca   25200 tttttattt ttttaatttt ggcaaccaaa cttttgtgg tatgttgcta cactatgtag   25260
acttacatgt accattttgg gacaattaga aaagtgtttt ttatagctag tagatttagt   25320
tcgtttattt gaatttcttt ggaaaattca catttgaact gcaagtcact cgaaacttag   25380
aaaaccgtgc gtgcaaacat aatatccatg ctatttagca caagttacga ccgacttcag   25440
gagcggaccg gaaacttcga gcaccatgct cactcaacat ggccgtgaac ttgccatcca   25500
gttgtttaaa aattgtataa aacacaaaca aagtcaaaaa attatgaaac ttgtccacgt   25560
gtcatgatat catatgtaga ggctgtggta aaaatttgag aatgtttcga gaaagttgtg   25620
acgtactatg tgtagaaacc taggagaact atattgaaac ttgtccactt gctcctcgct   25680
ggaatctaga tctcgcacct gtgggagata tcttaggacg ctccaggtcg acaggtcacc   25740
```

```
cggggcgtca ccagacgacg tggagtctcc taggaattaa gaggcagtcg agatatagta    25800
ttttgaacga acaactagat cttgccccccc gagaggggta agatcctagg gtcgtcttgt   25860
ggtcggcagg ctacccaagt cggatataga cgacgtagag tcgaataagg gtggaggtgg   25920
atatacagaa ggctataaac tagaactacg ctacatctac tcttaagaca agaaaggtaa    25980
ataaagtaga tagattcgat tgaaatgtgt tcgagagttc tcaatcggcc gtgagttgat    26040
ctgatcgtgg agatatatat tttttttatat ttataggggga ggaggtctgt acctgttcaa    26100
gatagctaac aactcgcacg tgattagatg gataaccaca cacgagataa ggatgatcac    26160
ctgagttgat ctgatcgctg ggccgtggac cgttcgggcc ctagagccgg agtgtctgct    26220
acttttggtg ttcaacaatg tcaattattt gtatggacat acatcaaatt aagaagtata    26280
aagcgaagca attcatgcga attactatgt ttacagatag acattgctgt tttattattg    26340
ccgccatgtt cagcgcttca catgtgccga ccgaccattc ttattgcttg cttcgcttcc    26400
attcatctgc gtgcttcgaa ctcgcttgag agctgcagag gccattattt tatatatgtg    26460
tacccagcag tagtaccttc actcgcttaa gctcctcgac aacctctgcc atggttggcc    26520
tctccctctt gtcttccttg aggcatcgga cggccaacat gccaatcatg tcgaggcaac    26580
gcttgttgca tcgagattga gtatcctcgc ctgagaaatc aagtctgcta tcatacatcg    26640
cacatccgct accgtggtcc ttgaagcact tgacgaactc gatggggagg atcttgttcc    26700
cttgctgatc ttgttcatac cagctggccc ttctcctcgt gatgagctcc agaagcacca    26760
cgccgaagct gtagacatcg cactccaatg tgaagtgctc ggtcttcata tataatgggt    26820
ccatgtagcc tatatctgca gccactgccc taacgtagta gctatggatt gccaggagct    26880
tggaggaacc aaagtcagag acttttggat tgaggtcatc gtcaaggagg atgttggaag    26940
gcttgatgtc tccatggaca cgcttttgat tgtcaaggga gtgcatgtag gcgatagctt    27000
ccgcggagcc aatggcgatg tccagccgct ccggcagcga gagggtacat ggtttcttgg    27060
cactatgaag tatgtcctcc aggcttccat tggcgacaaa ctcgaagact aggatcggaa    27120
tgtcggtctc taggcagcat cccaggagct ggaccaagtt cttgtgacga ctgacttcga    27180
actggaacct gatctcgttc atgaacgacc catcttcctc cacccctctgt tgcggtagcg    27240 gtacacggcg aggtcgaatc aaattcttcc aatggcagcg gtgcgacgac acccttgtcc    27300
gcaaaggaca tttgacggcg accttttctgc cgtcgacgat ggtgccctcg taaacattgc    27360
caaagtgccc tcctccaagg cgtttgctgt agccattagt tatcttcttc agctccctttt   27420 tggtgtaggt ggttatgccc tgggcattca gtagtttacc tccatttctg ttgaatcttt    27480
tcctgttgtt tagagtctga agcaaaacaa ttgcgacaca tccaaggacg acggcagcaa    27540
atgttgctgc agacagaatt caagaaagat acatgcatgt tcaaccattc aactaacaga    27600
acatagcatg aatcttattg catatctatc cccgtgaatc tatatttgag ttttttcaaat    27660 tttgatctag tcggttgctg ctatcttttt ttttgctaac tcaaaatcat aatgcttctt    27720
gtttctttta ttcattttta gaattttta aggcctaggc aacgctctta gttcttctat    27780
ttgtgtaatt gaatgtttaa gaaattatca gaacactaca caaaagactt ttacctacgg    27840
tagaaaactg atctttaggg ctagtttgga aacctaattt tcccaatgga ttttcatttt    27900
tccaagaaaa attagttcat tttacaatgg aaaaatagaa attccatgag aaaatggagt    27960
tctcaaacta gcccttattg atggtttctt taaccgcccg tacgtgtgca aggccagaca    28020
ttggttaaaa accgccacta taaatattta cattctcaga cactaggttt acaataatag    28080
cagttttatt aataaaacta ccactataaa tgatttttt aaattataaa ccaggctaac    28140
```

```
atcaccaaaa aattcatgga gaaacctcgc taagtcgcta gataggctca cgcccgtgtt    28200
gtcgcaaatc acaactcaag gcgactcata gccttacatt tttctccctt ggccactttta   28260 tcccggtagc taaaggtcca agtacaaaga gctaaaaatg actaaaatgg tgcaaaagtt    28320
ttgtcgtttt agtcactttt aggacgaaac agaaacatga attaaggat caacaagcta     28380 agtgcaaatt aaagagaatg atgtaatgta acaaggtgtt aatagaattt tgtgcttact    28440
taacagtgca acggcagcca taggaattaa gggatcacat tgctgccctc ttcggaagaa    28500
attgcattga caataatagc ctccgtctgt gtcaatgcat ttgctgccac ttgaacaatt    28560
atgtgacttt ggatcttggc actcgttgat atctgtatat aattaattat taattttgtg   28620
agcattcaaa tagtcacaaa agagagtcag tcgtttgcca ataatttatg aaagcaagga    28680
gcgatctttt gagatgtgag aactcaaaag aatccaacac acggttcgga aaattaatct    28740
taataaacag attcctgctc ttttgttttt tttaaaggca cccttttta aaaggttgaa     28800 gtcattgcta ctttgtcgct tttgtgcgtt tggatatata ccttcatttt agtggaacta    28860
gaattcagtc aataaagtaa cccatttacc ttggaattta acattctacc acttttaag    28920 gttcagatat aagtctatct caaattcatg agatggaaga ttggaaatga ttttatgaat    28980
caatataatt tgtttcgact ctctaactta caagacgatt ttcaactcac ttctcgatag    29040
taaaaatgta gcacataaat atctccgata ccttgttaat aacagtatac aaatatattt    29100
tacataaaat cgaattagtt aattagtata tacctaatta ctgttattag aatggaattc    29160
aattccaatg atctaaacgg gacataacaa taatgcgagt gctatcacaa tttcttgtca    29220
acgaatagga agtagacaaa ggaatctgta tggatgtgat gtgtggccat acaaatttgt    29280
cgttgataat aattccatga tcatatggat ttctggacag tgacatcaga ccaactatct    29340
ccgttattat caacgacact agtccgacaa cttgtgccct ctcacggact ggatggctta    29400
gcccatttcc aaaccactat ttcttgtcaa agtattcaaa gttgtcgtct catatgttat    29460
tattgaagat tctatatagt tatcccgtgt atattaccat acgttgtttc atagtccaca    29520
ctaccggact cacgttcttt gccgagtgtc taaaacactc ggctcggcaa aggccatttt    29580
acacttgaca aatattttat cggtaaaggg ttttgtcga gtatattttt tcggatactc     29640
aacaaagact ttgtcaagtg tcgaaaaaca ctcggtaaat taggaatcgc aaaaaaaaac    29700
cctaaaaaat agcaaaacat tttctaaatt atatgaacaa ctctccaacc actacccaat    29760 accataccc attatcctat catttttcac tattattttg aataaaattt acatgtttta     29820
tgaatagtga gattcgaact tgcaacctct ctcgcgcact acactactac atcaattatg    29880
tctatattac gttttcattc ccatatacta taacaacccg agagtaattt gattatttga    29940
gacactaaat gaattcattt gaaaatgtga acaactataa agttgtataa cttttcaaga    30000
tctacaagtt ctattttgat agtttctaca tacgagattg tttacaaaac ttcaatttca    30060
aattttaaaa cttcacacga aattttaaat ggtaagatga tttaaaataa aaatttgtc    30120 aattacaaag ttttattaca tttcaagacc tacaactttt attttggtgg tttttccatt    30180
cgaggtagtt ttaaaaattc aaattttaaa atttaatcat agtttttgcat gacaagatga   30240 tttcaaacca aaatattgtc aactataaag tttcataacc cttcaatacc tacaattttc    30300
atgttggtgg ttttttttcga ggtcgttttc aaaattcaaa ttttaaattt ttaaaattca   30360
gacgtagttt tagttgacaa gatgacttca aatgaaaaag ttgtcaacta taacttcta    30420 taacttctca agatctacaa agtttatttc ggtggtttgg tcatttgttc atctcacatg    30480
```

```
atggttctaa caatatgcac aaatctaata catctctctc gtagttttat aaactacgag    30540
agagatatag attttataaa taaatttact tatattttgt catatgaaga aatgttcaaa    30600
atataaattg tacatcatga tgagtgatac aaatttgtag ttgaaatttt tttatttgaa    30660
ttaatttact gctttaaaat gtgatttaaa attgtctttg ccgagtgtaa aaaataaaac    30720
actcggcaaa gatcttgttt gccgagtgtt ttatttaccg aggcttttt gtctggcact    30780 tggtaaaaaa cttctttgac gagtgcctga aagaaaacac tcggcaaaat atttggcacc    30840
cggcaaaaag ccgaattccg atagtgccac acataagaca atttaacgat aattgtgtat    30900
gagagaatga attgtggtca tttagttgtt ttaggtttca atgcctatga tcccgtgtct    30960
aagtggcatc tccctcaaga tattgtttta ttttcttcct tctttactca aatgtcacat    31020
cagctttcta tcctacatgg tatatattaa ataatgagta tagtatggca ccgtgccttg    31080
agaatataca ccagtcctgc tccaaattat gccaatttag tttttctaga tgcattacta    31140
gatatataga gaaaattcta cgtatgtcac cgcaattttg tccagtacat cctaaactct    31200
tctatgtcac tcggatgcaa tttcttacct tttcatgctc tcgtcagtga cgtaaaaggg    31260
taagaaaatc acatgtactt atccttttgt gccactgacg atagcatgaa aggatagaaa    31320
aattacatct gaaagacata tagaagtgat taggacattt gccatcacaa acaaggtacg    31380
ggcaaaattg caatgaggta gatatatata tatcgggata catatagtta ataataaaag    31440
tgatgtattt aaaataacca aataaaacca cttatagatt gagaagaagg gaattatact    31500
acttactcgt gcattcacca tcactctgga catagggggtt tccgtcgtag ccatgggcac    31560
acttgcagaa gtagccaggg ccattggttg aattagtgca ctcgctatgc ttgctgcggc    31620
agccatagtc aggttcgttg ggtgcctggg cgcaggagat ggaagtcatg gagtcgccgt    31680
tgttgtcgcg gatgggccag tcgagacgca gtggcatggt ccaccagtcc aaaggcagac    31740
ggttgtcggg tgtgtgcgac acaaggtcgg atgccttgaa ggtgtagttg cccttctcca    31800
cgatgaaggc gtagtcgcag gggcagaagg tctggttggc acgcgtccag gtagacgaga    31860
aggtcatgct ggtgtccgtg atgcctggcg ggatgtcgac gcggcagcag ccgaggcccg    31920
cgcaggcacc gtcgcgcggg tccttctcgt ctacactgac ggtgatacac cccgtgaagt    31980
atctgtaagg gaagcgtgcg ttaacgttgt gcaccctcac gcctttggtg aacgcatagg    32040
tgtcgcagcc gaggacgaag agctcgttct gtgtgttgga gatgcggtat acgccctctg    32100
ggttgaagtc cacatctccc gagtagatcc cagtgacgcc cccggcggcg ttgaagcact    32160
gccatgccac cggaagaagc actcgagcct ccggcaacgg cgacacggac aggttcagca    32220
cccggatgtt ctggtagcgc gtagtaggta gcagcactgg aatctcctcg cccgcgctgc    32280
cgttgatgca cttgatccgg aacccttgc gggagcagtt ggtgccgacg ccgaatggat    32340
agggtatctc tacgcctcca cattgcgtta ggcagcctgg aatcgcggcg gagaggcact    32400
ccactgctgc aagctggatg agcagcactc gcaacaggag tgatgacatc ggtggcttta    32460
tttgctcagt agtatagtgt gttcgctgga ttattaattt gctactagtt tgatgcgtga    32520
tatatatgta cgccccccag ggagggttta tatagaaaaa actagctagg gtttgaagga    32580
caagatggtc ctttcactat aactttaatt tcttattagg tatgtgttcg tacgatgcca    32640
cagaatataa attgacgagc ctccaacgac tcagggccct atcgacgggc gacgtgactc    32700
gtgagtacat caaaatacat gattaaacat agacacagaa ccatataaat acgtaataaa    32760
aaatgatgtt ttgttctctt atgtgttgtg catagaatac aaagattttt tttgaagaa    32820 ctttgttatc aatctgttaa gttatcagga taattcttgt tgatatgcta tccttgcaaa    32880
```

```
catacattaa agacttatcc attcacattt gaacaatata tttgagatgc atttgaaaca    32940
acaaatttag caaaactaaa atatgtacag aaaatatgta caatatattt aaacaatata    33000
tttgagatgc atttgaaaca acaaatttag caaaactaaa atatgtacaa tatatttgag    33060
atgcatttga gagtatgaaa aatatgtatg tacagaaaat aaaagtaaaa cgtgtctaat    33120
ataggtattt acttataaag gacgaaattt agaggacgct gcagaagaga gattagatat    33180
acaggaggaa atattttata taagaccgta aaggatgaat atagataatg gatataaagg    33240
atattgctgg agatagtatt agcagactgt gaagttggac tgtggatgag aacgatggaa    33300
gtggtctgtt cactgtagtt ttagcccata tacttgctat tttttttaca gtatatttaa    33360
tgtatatata tatgaaacaa aaaatttagg tggggccatg gccctcttta ccccactatt    33420
ggatccgcct ctgtttacaa taatagcctc tgttaatgca tttgctgcta tgactttgga    33480
tcttagcact cgttgatatc tgtatataat taatttgtga acattcaaat agtcacaaaa    33540
gagagtcagt cgtttgccaa taattatgaa agcacgaagc gatttaaagg ttggagtagt    33600
cgttgctact ttctcgcttt tcgctaacgc ccggtttgga ttgttgaaat tgaattccat    33660
tttaataata gtaatttagt cacatgtcaa ttaagttaat tggattttat acaaaatgta    33720
tttgtatact atattattaa gaatatgtcg aagatattta tgtgctacat ttttattata    33780
gaggagtgag ccgaagatcg ttctataagt tgtagagtag aaacaaattc tactgataca    33840
taaaattatt tccattatcc acccatgaat tcgagataga catatatatg aactttagag    33900
aagtgaaagt taaattccaa actaaataga tactttatta agtaaatttt aatttttttc    33960
aaaatgaata atggatgcaa acgccccgta acagtaatgc gagcgctatc acaatttcta    34020
gtcaccttat agcatgagta ggaagtagac aaggaaatct gtatggatat gatgtgacca    34080
tacaaatttg tccttcttaa taattccatg atcatatgga tttctggaca ataaccagct    34140
ccattattat cagctagtcc gtcaacttat gctctctcac gttctggtat cttaggctat    34200
tcacaactaa ttgtttatta tcacattatt taaagttatc atctcatata ttactataaa    34260
aaatatagtt gtccaatgta tattatcatg cgttgtttta tagtcccaca agacaattaa    34320
atactaaata tatataagag tatatgaatt atgggtcatt tagacaactt aagtttcaga    34380
agttatatct ccctcaagat aatgctttat taaatgctaa atattctttt acctctttac    34440
tcacatgtca catcagcttt gtatcctaaa tggcatataa taaatgagta tgattatagg    34500
ccaatttatt tttctaggtg gatatataac tagatataaa gacaattcta cttatgtcat    34560
tgcaattttg tctagtacgt cctaattagg gatggcaatg ggtacgcatt tgggtatata    34620
actgcagata attatctatt ggacatgggt atggtggaat ttgctatcca cgggtactat    34680
ggatataata tggtatctgt tgaacagcaa aagtggcgga cggtccggcc ctagggcacg    34740
gacggtctgc acccctgtga tcagattaac tcgagtgatt atctttatct cgtgtgtggt    34800
tatccatcta attatgttgg atttgttagc tatcgcccag taacgggtcc agatcttccc    34860
ctatatatat gaaggggtat gaccgattgc gaaccccga acatatttgt cggcgtttcg    34920
agaccggggg gtccctaagc cgacgagtga aatgtcgctg cgtgcctcag cccagatggg    34980
tcggcgcgag gccgagcgcg aagggggaa gtgaagtggc cggagtcggg cgtgagagag    35040
gtggaaatcc cgcggccttc gtgttcgtcc cgcgcccagg tcgggtgcgc ttgcagtagg    35100
gggttacaag cgtccacacg ggagagggag cgagcggcct cgcgcgagcg cctgtctcgt    35160
cctcgtcccc gcgcggccaa ccctctctaa gagggccctg gtccttcctt ttataggcgt    35220
```

| | |
|---|---|
| aaggagagga tccaggtgta caatgggggg tgtagcagag tgctacgtgt ctagcggagg | 35280 |
| agagctagcg ccctaagtac acgccatcgt ggcggccgga gagattttgg cgcccggttt | 35340 |
| gcgtgatgtc gtggccgtcg gaggagcgct ggagcctggc ggagggacag ctgtcggggc | 35400 |
| tgtcgagtcc ttgctgacgt cctcttgctt ccgtaagggg accgagagcc gccatcgtca | 35460 |
| gggagcgtgc ggggcaccat cattgcctat ctggcggagc gagctagatg ggatgccggt | 35520 |
| cttgttcccc gtagcctgag tcggcttgga gtagggtaat gatggcgcct cccgttgacg | 35580 |
| tggcccggcc cgcgccctag gttgggcgat gtggaggctc ctccgaggtc gaggtcgagt | 35640 |
| ccatcttccg tgaccgaggt tgagtccgtc ttccgtgacc gaggtcgagt ccgagcccct | 35700 |
| aggtcgggcg aggcggagtt tgtcgtcttc tggggctgag cccaagtccg agccctgggt | 35760 |
| cgggcggagc ggaattcgtc gtcttctggg gctgagccca gtccgagcc ctgggtcggg | 35820 |
| cggaaccgag ttcgccgtct tccggggctt agcccgagtc cgagccctgg gtcgggcgga | 35880 |
| gcggagttcg ccgtcttccg gggctgagcc caagtccgag ccctgggtcg gcggaacgg | 35940 |
| agttcgccgt cttccggggc ttagcccgag tccgagccct gggtcgggcg gagcggagtt | 36000 |
| cgccgtcttc tggggcttag cccgagtccg agccctgggt cgggcggact gcctatggtg | 36060 |
| cctgcggccg ggcctgactg cctgtcagcc tcactctgtc aagtggcacc gcagtcggag | 36120 |
| cggcgcaggc ggcgctgtct ttctggcaga ccggtcaatg gagcggcgaa gtgacggcgg | 36180 |
| tcactttggc tctgtcggct gaggggcgcg cgtcaggata aaggtgtcag gccacctttg | 36240 |
| cattaaatgc tcctgcgatt tggtcggtcg gcgcggcgat ttggtcaggg ttgcttcttg | 36300 |
| gcgaagacag ggcctcgggc gagccggaaa tatgttcgcc gctggagggg ggcctcgggc | 36360 |
| gaggcggaga tccttcgggg tcggctgccc ttgtccgagg ctaggcttgg gcgaggcgtg | 36420 |
| atcgagtccc tcgaatggac tgatccctga cttaatcgca cccatcaggc ctttgcagct | 36480 |
| ttatgctgat gggggttacc agctaagaat taggagcctt gagggtaccc ctaattatgg | 36540 |
| tccccgacag tagccctcga gcctcgaagg gagtgttagc actcgcttgg aggctttcgt | 36600 |
| cgcacttttt tgcaaggggg ccagccttc tcggttgcgt tttgttccgg tgggtgcgcg | 36660 |
| cgagcgcacc cgccgggtgt agcccacgag gcctcggagg agtggtttga ctcctccgag | 36720 |
| gtcttaatgc ctcgcgcaat gcctcggctg gtctggtcgt tcccttatgc gagctggccg | 36780 |
| tagcccgggt gtatggtcgg gtcccaagtt ctcgggctgg tatgttgacg ctgtcaacgg | 36840 |
| tttggccgga gccgggtttg cgagagcagc ccccgagcct ctgcacaggg cgagagggtg | 36900 |
| atcagggaca gactcgactt ttttacatac gcccctgcgt cgccttttcca caaggaggag | 36960 |
| gggggagagc gccatgttgc cctcggtggg cgccaaacat ggtgtctccg gtgagctgca | 37020 |
| ggcgggtgat ccgagcggac gtccgtgccc cgttcgttag gggtcggcta gaggcccaga | 37080 |
| ggcgcgccca aaagtacctg cgggtgatct gccggacccg gtccctggc gacggagtcc | 37140 |
| gagggctcga tgcctccctc tgatgggatt ccgttacaag atcgttcccg ctggtcttgg | 37200 |
| aaatgtccta gggtaccttg ggagcgcagc ccgagccttg gttatgtatc gaacgtaccc | 37260 |
| atggtcatcc ctcgctctgt gtctaaggcg gctgtgaacc cttcggggc cagccttcga | 37320 |
| acccctgatc agtagtgggc gcggagcccg agtagcctga ggcggccgtt gaacccttcc | 37380 |
| gaggggccgg ccttcgaacc tctgaccagt agtgggtgtg gagcccacgt gctctgaggc | 37440 |
| ggctgttgaa cccttccgag gggccagcct tcgaacctct gatcagtagg gaggctcgga | 37500 |
| gcctggttcc ttcacgggga aggatccttt tcggggtatc ccccttttccc ggtccctgtt | 37560 |
| gcaagagaga gaaagaggaa aaaaggaaaa ggatacgaaa tcgaacgacg cggtgtacct | 37620 |

```
tttttgacgc ggtcattatg gcgaaggcga agcgtcgctc gcttctcctg ccagaggcgc   37680
cgcctgtccc gccgcggagt taatgcgacg gggcgagtgg ttcgcggggc ggccgttgcg   37740
cgtgtgcgag ccgttcgagg aatggctgtt tcgcttcgtg tttttgaatc ccgcggctgg   37800
tccgggcgga acgttgaacc ggtctcgcct tggtctttat atactcgggg gagggtctgg   37860
cgatggttct ttgcttcgct tcctgcctct ctcttaggtt ttcgcaaccc gagagactta   37920
gccagagaaa aggaaaccac ccaccctgtc ctttgcgccg ccaccccttc tgctcggtga   37980
tggccgaccg ggtgaccatc atctcgccgc gcgacccatg gcctttctcc acagtgacgg   38040
cgggtgatct ggaggatctt gttgctgagg gtttacttcg ccctctctct gatgagaggc   38100
ggccggaatg gattcccccc gtgagcggag ccgctccgtc cccaccgccg gggtacatcg   38160
tgagcttcgt ctccttccac gagcggggat ttggtgtgcc ggcgagccgc tttatgcggg   38220
cgattctgca ccactacggg gtggagttgc acaacctcag ccccaactcc atctcgcagg   38280
ccgccatctt cgtagcggtg tgcgaggggt acttggggat cgctcccac tgggacttgt    38340 ggactcatct ctttttcgcg gagcttttca cttcgccgac ggggagaga aggtccgcg      38400 cggcagtgcg ggccggcggc tgcatccttc agctaaggca gtcgcgggcg tcgctgtata   38460
ttcctgccat ccttgcgtct tcgaacaaag ggtggcagcg ccggtggttc tacctccgga   38520
atgacgggcg agttgctcct gtcgtttcc cagcgagtag tcaccgtcgc cgccgatgct      38580
tggcgcccac gggaccacgc acgaaagaca gaagaacctc gaaccccttc tcaaggcctt   38640
ggaggcgttg cggaaagggg gactcaccgc cgcgggagtg attgccgcca tccaccgctg   38700
gagggtgctt cccttggcgg agcgacggtt gccgctctgg gagatgacac cggaggctga   38760
cttggagggc tcgtggatgt cctcggatcc tcttcccttc gacgttctcc acgggcgggt   38820
ggccgtcgcg ttggggaaac cggaccccag cgccttctcc aagcctttga tgcgccctga   38880
ccaagggtgc gtgactctgg tgagtgtccg ctccttcctt cctcttgcat cgggttgccc   38940
ctggttctta cggtcgggat ttccatccgt cttcaggagg tagggtggca caagccttcc   39000
ctgccacggg tcccgcagga tgcggtggac cgagcagcgc ggcgggttgc cgaggaggag   39060
aagaagaaaa agaaggacgc ggagaaggcc tgggcccgcg agcggatgcg ggctcgagac   39120
gccttggaaa agctctgtcg tcggcaggag agggagggggc tcccgaggga gccgtcgccg   39180
gaaacgcctg atgacgacga cgatgatgaa gatgatgacg aggaagatga catggctgcc   39240
cgcctcggct tcagccctgg cttgaggtta ggccaggagc cgtcaagcca tcccccgagt   39300
gggctgatgc cgtcagtccc tggagtcggg acgccgaggt cccagcccga agagcggggg   39360
cagaccgaga gggtacttga ccctcagct gggggagttg aggcgacccc ggggagccag    39420
gccgaggcgt ctgttcccg agagccgtcg cccacgccgg cagcgcagga gagcgaccct   39480
caggtcgccg tggcggtgcc tgggcagtcc gcctcccggg cgtccaaagc acccaaagca   39540
agggtggtgc cgaagctgcc ggcgaagcgg acctcggcgg cggcttcggg ggtcgagatc   39600
cgagagacct ccccctcaggc acggttgatc atggcccgga gcgggtaagt atcttggaac   39660
gtcttcgtcc tggcttttca ttcgtatgtc ccgaccgtga ttttctttc ctcctcagca    39720 agcgaagcca tggcctgacc gatctggctc cccgaaaggc ccttaagacg cgtcggctt    39780 ccgcagccgg cgccgcttcg ggccttgccg ttcagctgac cttctcgcaa ggcgctccac   39840
aatagggggc tcaggcggca ccagtcgccg tggagcgatt tcccgaggcc ggctcttctg   39900
ccgaggcggc catcgtgcta ggggaggcgg ctgacgcgga cgtggcccg gccccaccgg    39960
```

```
acgtgtcggc ggtgctggca ccggttgcta ttgaagtcgc tgccgtccca gtcggggagc   40020
gacctgtcgc tgccgacgct gagacggccg aggcgtcggc gcttggtgcc tcgaaggagg   40080
ggggcgtgga gacgcgatcc gtcccgccga gcggcagcct tgtcattgtg cggcggagct   40140
ccgagggtcg gcgccagttg ctctggttct ggaccgcgga ggcctcggat cccttcttcg   40200
ttctcgatga tgagtgggag gagcagtcct gggacgagct ccgcgagtgt gccgaagcaa   40260
cggtgggggtc gctccagttg tcgctggagg ttttctgcag ggacgtcccc aaaattctcc   40320
aggtaacggt ttcaggcata cctcttcttt tttgtgacca aggcgtcttt cgtgacgccc   40380
cgcttccttc cctcaggatc tgacggatct aagcgccgcc aagtcgtcgt tcatccgcca   40440
cgaggtcgac atctggggct cgctgcgatc cctgaggacc tcgctcgccg gggctactgc   40500
gcgcctctct cagtagggcg ccgaggcggc ggaccttcgg ttgctctgca ccgatctgag   40560
agccgaggcg gcagcggcac acgcggaggc ggcagcggcg cgcgcagaag tgcaacgaca   40620
gtagtcggag ttcgtccgga tcgtcggtga gtgggaccaa tctcggggcc gggctaccga   40680
ggccgaaagc cgggctggag cccttgcagc cgacctagcc gtagcccagg tcacagcctc   40740
ggagcagcgt gcccgagctg gagatacgcc ttgtccatt tcggttttcg tttcagcttg   40800
tttcctccgc ttgtgtttga gatctttcgt tctggctgtt cgcagagctc gagttcgccc   40860
ttgatgagtc cgccaaggcg cttgccgagg cgcttgccgg ggcggccgag cagagggagg   40920
ccgaccatgc ggccatgtct gaggccgtct cggacttctg ccgggtcctt ggctccggca   40980
acgtccccctt aggaagctcc cctcaaagtc gcctgcaggc cttgggcgac cgtgtgcgcg   41040
gcagactccg cgaggcgcta caccacgcg tcaggcgggc cttcgccgtg ctcgcttccc   41100
actacgttgt gaacctggag cgagtaagcg aggggtattg ccttcctgac gaagacgaag   41160
ccgccctggc agaagtttag aggctcgatg cggccgccgc gggtccgagc gcagtgctgg   41220
cgaccacctt cgaggcagag atcctcccgc ctatgccgtc gtccgaagcc gggatgaact   41280
ttgccgaggg cagggacgag gccgaaggcg cggctccttc ccaggggcgac gcctaactct   41340
gtcggagcag tttctgttgg atgcacgtgt gtctttctgc ggccgctgag gcctgaacac   41400
tttattaccg ttgcataaag tcgtgctcct ttccctttca ttttgtgtgt ccggcccccgc   41460
ctgtcagtag cagggtggct tccccaagta ggggtcactt ttcgtggcgg gtgacgagtg   41520
aggtgtccgt aacccagagg cgtaggagtc cctcggctca gtcagccttg ccacttacat   41580
gcacccgcgt tcgctccttg gggtcctgct tccgacatag ccggggggaac gcaaaagcct   41640
tttcgattga aaattttgac gcagagggggt tcccccttttt ttagccccccg agggagggtc   41700
aggctctgcc gaggcaaggc tgacccttcc ttgatgacta aaacttgcgt gggggcaagg   41760
taagcgaaca acttgaaagc atcttcaggg tagaggcgac gtagctgtta gacgttcgaa   41820
gtgttggtgc agacctcgcc ttgactgtcg gccagttcgt ttgttccggg cttcagaact   41880
ttggcagtga caagcggccc ttcccagggg tgtgtgtagc cccgggtgt ctccaacaag   41940
ggctcggggg tgcggtggtg gagctccttc ccatccctca gcaagacgaa cgacttggcg   42000
cgccgcgcca accgccgagc tttggctcgg tcgagggta gctctccttg gtggagatat   42060
tgcaggtacg gggtctgtta gcttcgatta ggcgtgaccc cgcttcgctc ctcctcgacg   42120
cgtagtgcct cgccctcggg tgccgagggt gcctcgggcc gagctgaggg tgcctctggc   42180
cgtgccgagg gtgcttcggg ctcggcgctg tcgtcgattt tgacggaggg ttgatgcagg   42240
tctcgggagc aggcttccgg gggaaacgtt attcgccccg aggcggtaca gaggcaggcc   42300
ccttttgccg aggtgcggga tgaaaaggct gagggccgca agacatccca tgactctcag   42360
```

```
tacgcctttc aagtcgcccc atgctggtga tggccgcgat cttctccggg ttggcttcga   42420
tgccccgctc ggagacgatg taccccaaga gcatgcctcg gggcacccca aagacacact   42480
tttcgggatt gagcttgacg cctttcgcct tgagacatca gaatgccact tcaaggtcgg   42540
aaaggaggtc ggaggctttc ctcgtcttga ctacgatgtc atcgacgtag gcctcgacca   42600
tgcggccaat gtgttcaccg aacacatggt tcatgcaccg ctggtacgtc gcgcccgcat   42660
tcctcaagcc gaacggcatg gtgacatagc agtacatgcc gaagggtgtg atgaaagaag   42720
tcgcgagctg gtcggactct ttcatcctga tttggtgata ccctctttga tgaactctgc   42780
cgccattagc ttgtggatct cctcgcctat ggctctgcgc ttctcctcgt cgaatcggcg   42840
cagaggctgc ttgacgggtc gggctccggc tcggatgtcc agcgagtgct cggcgacatc   42900
cctcggtatg tcgggcatgt ccgagggact ccacgcgaag acgtcggcgt tcgtgcggag   42960
aaagttgacg agcactgctt cctatttggg atcgagcccg gagccgatcc agatttgctt   43020
ggaggcatcg ctgctggggt cgaggggac ggacttaact gtctccgctg gctcgaagtt   43080
gccggcatga cgcttcacgt ctggcacctc cttagagagg ctttccaggt cggcgatgag   43140
ggcctcggcg tactccacgc actccacgtc gcattcgaac gcgtgtttgt acgtggggcc   43200
gacggtgatg accccgttgg ggcccgacat tttgagcttg aggtaggtgt agttggggac   43260
aaccatgaac ttcgcgtagc atggcctccc cagtaccgcg tggtaggttc ctcggaaccc   43320
gaccacctcg aacgtcaggg tctcccttcg gaagttggag ggtgttccga agcagacggg   43380
aagatcgagt tgtccgaggg gctggacgcg cttcccgggg atgatcccat ggaaaggcgc   43440
agcgcccgcc cggaccgagg acagatcgat acgcagaagc ccgagggtct cggcgtagat   43500
gatgttgagg ctactgcctc cgtccatgag gaccttggtg agcctgacgt cgccgatgac   43560
ggggtcgacg acgagcgggt atttccccgg gctccgcaca tggtcggggt ggtcggcttg   43620
gtcgaaggtg atgggcttgt cggaccagtc taggtagact ggcgccgcca ccttcaccga   43680
acagacctcc cggcgctctt gcttgcggtg ccgagccaag gcgttcgccg cttgcccacc   43740
gtagatcatg aagcagtcgc ggacctcggg gaactctcct gcctggtgat cttccttttt   43800
gtcgtcgtcg cgggccctgc caccctccgc gggtggcccg gccctatgga agtggcgccg   43860
aagcaagacg cactcctcaa gggtgtgctt gacgggcccc tggtggtagg ggcatgactc   43920
cttgagcatc ttgtcgaaga ggttggcgcc tccgggggggt ttctgagggt tcttgtactc   43980
ggcggcggcg acaaggtccg cgtcggcggt gtcgcgtttc gcttgcgact tcttcttgcc   44040
cttcttcttg gcgccgcgct gagttgacgc cttgggggca tcttccgatg gcggccctg   44100 gggctgcttg tccttccgga agatagcctc gaccgcctcc tggccggagg cgaacttggt   44160
ggcgatgtcc atcagctcgc tcgccctggt ggggtcttg cgacccagct tgctcaccaa   44220
gtcgcggcag gtggtgtcgg cgaggaacgc gccgatgaca tccgagtcag tgatgttggg   44280
cagctcggtg cgctgcttcg agaatcgccg gatgtagtcc ggagagact ctcccggctg   44340 ctgtcggcag cttttggaggt cccaggaatt ccccggcgc acgaacgtgc cctggaaatt   44400
gccggcgaaa gcttggacta ggtcgtccca gttggagatc tgccccggag gcaggtgctc   44460
caaccaggcg cgagcggtgt cggagaggaa caggggggagg ttacgatga tgaggttgtc   44520 gtcgtccgtt ccacccagtt ggcaggccag acggtagtcc gcgagccaca gttccggtct   44580
cgtctccccc gagtactttg tgatagtagt cggggggtcgg aaccgggtta ggaacggcgc   44640
ccgtcgtatg ccaggtggtt caggcgaagg actccgatcc tccccgctgt cgtagcgtcc   44700
```

```
cccacgcctg gggtggtagc ctcggcgcac cctctcgtcg aggtgggccc gacggtcgcg    44760
gtgatggtgc tcgttgccga ggcgacccgg ggccgcaggc gctgtgttgc gcgtgcgttc    44820
ggtgtagacc gaggcttccc gcatgaatcc ggaagtcgcg gcatgatgtt ccgaggggta    44880
cccctgcctt cgggaggcgg agctctcggc ccgccggacc gcggcgcctt ccaggagatt    44940
cttgagctgt ccctggattc gccacccctc ggtggttgat ggctctggca tcgcgcggag    45000
gagcattgct gctgcagcca ggttctggcc gaccccactg gacgcgggtg gcggcctgac    45060
cctgacatcg tcggcgatgc ggtgctggag gccctggggt agatgacgca tttctccggc    45120
tggaggttgg cccgcccatg cctgcccgac gtcccggcgg attgcctcaa gcgctcctgc    45180
tccctcgtcg agcctggcct gcaccccgcg gatttgctcg agctgtgggt cgtgaccccc    45240
cgccggaacg gggaccacag ctagctcccg tgggatgtca acgcgaggca ccggcctaga    45300
gagatcaccg tcctccggca tgccgagatg gttgccttcg gagggacccc ctagatcgac    45360
gtggaaacat tcgcggcttg ggccgcagcc ctcgtcgtcg aggctacggc taccgtcgga    45420
acagtcggaa aggcagtagt cgcatgcggt catgaagtcc cgcatggcac tggggttgcc    45480
aagtccggag aaatcccaac agaagctggg ctcgtcgtct tcctcggacc cagagggccc    45540
gtaggtcgag acgtccatca gccggtccca aggtgaccgc atacgaaacc ccagagggtt    45600
cggactcgcc tctacgagag cgtccgccaa agcgaagccg ctaggcgggt cgagactgaa    45660
tccgaaaggc gtgggatggg aatcggtcgg tacctcttgg tcgacgggcg gtgatgaagt    45720
cacgtcgggg actgactgca ccgtcgtctc aggtacgagg gtgacaccca gcaagccttt    45780
cgcgagcgtg ctggcgtcgt ccgtttgctc gggattggtg tgtcgtgggg agacagcgct    45840
cgtcttcgtc tcaagcgcga ggtcgatgcc cggcgcgccc ccgttgggg tgctggcgtt    45900
gtcgactcgc tcgacagccg acgaggcgct gcctcctgct tggccttggt tgccccgcct    45960
cctcccccgt cggcggggaa gaggacgggg cgagctcgaa ggttgttctt ccaccacgcg    46020
gggaagacgt cgtcgattcc gccgccgcg gggcgggctg tcggccgcca ttgtcgctgc    46080
cgcccggcgg tggaaggtgt atcatgtcgt agctgccgtc gagggacatg aacccaagac    46140
tcccaaaacg gagcaccgtc ccgggccgga gaggttgctg gagactgccc atctggagct    46200
tgacgggaag ctgttcgtca acacgcagca ggcccctacc tggcgtgcca actgtcggcg    46260
tttcgagacc aggggtccc taagccgacg agtgaaatgt cgccgcgtgc cccagcccag    46320
atgggtcggc gcgaggccga gcgcgaaggg gggaagtgag gtggccggag tcgggcatga    46380
gagaggtgga aatcccgcga ccttcgtgtt cgtcccgcgc ccaggtcggg tgcgcctgca    46440
ttaggggggtt acaagcgtcc acacgggaga gggagcgagc ggcctcgcgc gagcgcctgt    46500
ctcgtcctcg tccccgcgcg gccaaccctc tctaagaggg ccctggtcct tccttttata    46560
ggcgtaagga gaggatccag gtgtacaatg gggggtgtag cagagtgcta cgtgtctagc    46620
ggaggagagc tagcgcccta agtacacgcc atcgtagcgg ccggagagat tttggcgccc    46680
ggtttgtgtg atgtcgtggc cgtcggagga gcgctggagc ctggcggagg acagctgtc    46740
ggggctgtcg agtccttgtt gacgtcctct tgcttccgta aggggggccga gagccgccat    46800
cgtcagagag cgtgcgggc gccatcattg cctatctggc ggagcgagcc agatgggatg    46860
ccggtcttgt tccccccgtag cctgagtcag cttggagtag ggtaatgatg gagcctcccg    46920
ttgacgtggc cggtccgcgc cctaggttgg gcgatgtgaa ggctcctccg aggtcgaggt    46980
cgagtccgtc ttccgtgacc gaggtcgagt ccgagcccct aggtcgggtg aggcggagtt    47040
tgtcgtcttc tagggctgag cccaagtccg agccctgggt cgggcggagc ggaattcgtc    47100
```

```
gtcttctggg gctgagccca agtccgagcc ctggatcggg cggaacggag ttcgccgtct   47160
tccggggctt agcccgagtc cgagccctgg gtcgggcgga gcggagttcg ccgtcttccg   47220
gggctgagcc caagtccgag ccctgggtcg gcggaacgg  agttcgccgt cttccggggc   47280
ttagcccaag tccgagccct gggtcgggcg gagcggagtt cgccgtcttc cggggcttag   47340
cccgagtccg agccctgggt cgggcggagc ggagcttcct atggtgcctg cggcccggcc   47400
tgactgcctg tcagcctcac tctgtcaagt ggcaccgcag tcgagcggc  gcaggcggcg   47460 ctgtctttct ggcagaccgg tcagtggaga ggcgaagtga cggcggtcac tttggctcta   47520
tcggctgagg ggcgcgcgtc aggataaagg tgtcaggcca cctttgcatt aaatgctcct   47580
gcgatttggt cggtcggcgc ggcgatttgg tcagggttgc ttcttggcga agacagggcc   47640
tcgggcgagc cggaaatatg ttcgccgctg gagggggggcc tcgggcgagg cggagatcct   47700
ccagggtcgg ctgcccttgt ccgaggctag gctcgggcga ggcgtgatcg agtccctcga   47760
atggactgat ccctgactta atcgcaccca tcaggccttt gcagctttat gctgatgggg   47820
ttaccagctg agaattagga gccttgaggg taccctaat  tatggtcccc gacaatattc   47880
caattgaacc aattactttc tttataattc cttccctagg agtagatgta gcgtagttct   47940
agttatagct ttcctcatat ccacctccac ccctattcgg ctctacgtcg tttagatccg   48000
tcttgggtga cctaccgacc caagacgac  catacgatct taccccttat ggggaaaga   48060 tctagttgtt cattcaagat actttacctc gactgtctct taattcttag gcgactccgc   48120
gtcgtctagg gacgcctcgg gtgacctctc aacccgaagc accataagat ctcccccagt   48180
gggcgagatc tagattccag cgaggaggaa gacgaccctg tgtcatcatg gatcgtctgc   48240
ccttatgcgt gtaccgtctg gcacggcaca gggaaggcac cgctcctact cccaggttgc   48300
gaaccatccg acctagagct gcggaccgtc cacaccgccg cagagggcac caccagacga   48360 tacacccta  gtgattggcg ttgcccgatt ccgctgtgga acaaggttgc agatttacaa   48420
aatcaagctt acatggccga ttctaaagat ctcaacggtg cttctccaaa caacgacaca   48480
agactgacta attttccggc tgctgagtat aaaaaattag aaaatgacat gaagaagagg   48540
gacgaggaga tccagtgaca ataagatcag gtcctcaagg tggcgaagaa gtggttactc   48600
tcacacttca gggtagatta ccactagaag gtcgttcggg atcgggaaat aagcgttgat   48660
tacatggcaa tcgtacgtgc tgcagcagct ccccacgcta tgtgatgcta gttcagccga   48720
tgaaattcaa actattaaaa tttattttga taatcggatt aaaagtatca cagaggatat   48780
agagaagatg tgtgtatgcgt taggaaaaac agacatgcct aattttttat cacataaatt   48840
aggcaccaaa acaatttccc caaacatatc gacgacaaat ggttttcccc agccatattc   48900
tggtatgcca atggactcat atccaggaag accatcaccg ccatctccgc taaatggtgg   48960
gtcaactctg agcacgaccg gaccgtccac acatgatctc ggaccatacg gcccttggtc   49020
aaaccgtacg acaccctacg tcggacagtc cggagtcaca cagagcccat gacaagggtc   49080
acaggcgttg cccaacgtga ccaagaatag taccggacag tccggtccac tcgcagaccg   49140
tctgactgca taggtcggac cgtttggagc accaaaagtg acatgtgatc cgcctagtgc   49200
agaagatcga cataaagata gtcggccact caagccccaa gagtcgaaaa agtcacctgt   49260
cgctgagctt gtttggcccg ctaaggccaa atcttttgtt cgctctcatc cacacttgac   49320
gcaaaaggag aaacttaagt tcacatttaa tattgctaag tgtgataaat atttgatgag   49380
ttacttaagc atggtaatat taaattgtca cttataattc ctccgattga agaattaaaa   49440
```

| | |
|---|---|
| atggcatggc tcttttcttc ataacaccga tgattgtgtt gtcttctatt agcaaataca | 49500 |
| atcgattata aatgaaggct ggttgggatt tcaaaaagag gtgaagattc acaggccacc | 49560 |
| tgaccttatc accacattag agccgacgag caaaaaagtc ttagttcggc catgtgcgac | 49620 |
| cgataaaagc aaagataaaa atatcgtcat tggtgatcct cacacgccaa atatgtcacg | 49680 |
| tagagtggtg actctgaagg ctccggacaa aggaaagacc agagacacta gaggacaagc | 49740 |
| acgatcagac acacgatcac ggtcatcaat cctatggacg caggacgatc caggtactaa | 49800 |
| ggtcacacag tacgggatag gcgcgaatag ttcgtttata aaggccggac ggtcagtaga | 49860 |
| cgaccaaaag cagcagcaac ctgagaccgt cggaccacat cattctaaaa taggtattag | 49920 |
| aaagaaaaac acctccaaga cgtctggccg actcagcata gtcggcccta cttttaatca | 49980 |
| actgcttgct aaatatatga agaaggtcgt tccacacaat cggccaataa aacaaacgaa | 50040 |
| gtaaaaaaaa cgatctgtgc gaaagcaaag tccaactaaa ccgcccaaa aggtagcaca | 50100 |
| gtcaagatcg cctggtcatc ctcctccagg gatggcatgg tgcttccctg tatatccatc | 50160 |
| gccgatgtgt tgtcctactc aagtgtgggg tggtacggcg atgagtccgt attgctggct | 50220 |
| caatttgttt gcttattcag gctcgggca ccacatgatg gtcaggcaga catggcccaa | 50280 |
| gaggatgcaa tccgaaacgg cctttgtgca tcaaagttct atgaattatt tatattatct | 50340 |
| gatcacaaga gtcgatgact tgcatcgaga tgagtcctta cttcgggaac aaaacaactc | 50400 |
| atgagatcaa ttgtttttga agttcgctgg tgcttttggt ttgccaagct ccatcaaaag | 50460 |
| gcagggggca tgtgttgaac accaaaagtg gcaaacggtc tagccctagg gcacggacgg | 50520 |
| tccgcacccc tgcgatcaaa ttaacttagg cgattatcct tatcttgtgt gtggttatcc | 50580 |
| atctaatcat gtgggatttg ttatctatcg cttagaaatg ggtccaggct ttcccctata | 50640 |
| tatatgaagg ggtacaacca attgacaacc cctaaacaca ttccaatcaa accaattact | 50700 |
| ttgtttatca ttccagtcct aggagtagat gtagcgtagt tctagttata gctttccgca | 50760 |
| tatccacctc caccctttctt cgactctacg tcgttttgat ctatcttggg tggcctaccg | 50820 |
| actccaagac gaccatagga tcttaccccct cctaagggca agatctagtt gtccattcaa | 50880 |
| gatactctac ctcgactatt tcttaatttc caggtgactc cacatcgttt gaggacgccc | 50940 |
| tgggtgacct gtcgactcag agcacgctaa gatctcccct agtaggcgag atctagattc | 51000 |
| cagcaaggag gaagacgacc atgcgccatc acagaacgtc tggccctgtg tgcggacctt | 51060 |
| ctagtgcgat gcagggaagg caccgctcat gcacccacct aggttgcgga ccgtccggcc | 51120 |
| cagaggcgcg gaccgtttgc gccgccgcag agggcaccgc aggcaataca cccctagtga | 51180 |
| taggtgctgc ccagattggc accaacagta tccacggaaa aaaatttcgt gggtatggat | 51240 |
| atccagtatc tgtacctgtt acccgatggg tatatgcata tggaccatac gaattcaata | 51300 |
| cattatccta aattcccatt tttcaatttt caaccataac atgttgtttg gtgctaaaat | 51360 |
| tatcgtttga tgccactaga atgataaaat tcttcaaatg tgatagaact gttgtttggt | 51420 |
| gttgaatgct aaaattatag tgggcagacg tgtaatgggt atccaccgga tccagcgggt | 51480 |
| atggggtac agatccatac ccacgaacgt atttgggtat gtgtttagtt tttgcctcgt | 51540 |
| ggctatgtgt ttgcgaacta tatattcatg tcctacccac ccgattgcca tccctagtcc | 51600 |
| taatcccttc tatgtcaccc ggatgcaatt tcttattatc ctttcatgcc ctcgccagtg | 51660 |
| gcgtagaagg gtaagaaaat cacatgtcct tctttatcct tttatgacag tggtgaaagt | 51720 |
| cgcctagagg gggggtgaa tagggcgaat atgaaattta taaacttaag cacaactaca | 51780 |
| agccgggtta gcgttagaaa tataaacgag tccgagagag agggtgaaaa acaaatcgca | 51840 |

```
agcaaataaa gagtgagaca caagatttgt tttaccgagg ttcggttctt gcaaacctac   51900
tccccgttga ggtggtcaca aagaccgggt ctctttcaac cctttccctc tctcaaacgg   51960
tcacttagac cgagtgagct tctcttctca atcaaacggg acacaaagtc cccgtaagga   52020
ccaccacaca attggtgtct cttgcctcgg ttacaattga gtttatcaca agaaagaatg   52080
agaaaaagaa gcaatccaag cgcaagagct caaatgaaca caagtcactc tctcactagt   52140
cactatttga tttggaatga actatggact tgggagagaa tttgatctct ttggtgtgtc   52200
ttgtattgaa tgctatagct cttgtaaggt gtaggaagtt ggaaaacttg gatacaatga   52260
atggtgggtg gttgggggta tttataaccc caaccaccaa aagtggccgt tgggggttgt   52320
ctgtcgcatg gcgcaccgga cagtccgatg cgccaccgga cactgtccga tgcgccagcc   52380
acgtcagccg gcagttgggt tctgaccgtt ggagctctga ctggtggggc ctctgggctg   52440
tccggtggtg caccggacag gtcctgtaga ctgtccggtg ccccttctgc gcgtgctctg   52500
actctggcgc gcactgtagc acatttaatg cggttgcagt cgaccgttgg cgcgaagtag   52560
tcgttgctcc gctggcacac cggacagtcc ggtgtgacac cggacactgt ccggtgcttc   52620
actggacagt ccggtgaatt atagcggagc ggcctcccat tttcccgaag gtagcgagtt   52680
cagcgtcaag ttccctggtg caccggacac tgtccggtgg cacaccggac agtccagtgc   52740
gccagaccag ggtgcctttg ggatgtcttt agctcttttt atttgaaccc atctttggtc   52800
tttttattgg cttgttgtga acctttggca cctgtaaaac ttatagacta gagcaaacta   52860
gttagtccaa ttatttgtgt tgggcaattc aaccaccaaa atcaatttag gaaaaggtgt   52920
aagcctattt cccttttcaat ctccccccttt ttggtgattg atgccaacgc aaaccaaagc   52980
aaatatagaa atgcataaat gaactagttt gcataattgt aagtgacaag gttgcttgga   53040
atgaaaccaa tatgttctca taagatatgc atgtattgtt tctttatatt tttaacattt   53100
ttgaccacgc ttgcaccaca tgttttttg caaatccttt tgtaaattct ttttaaagtc   53160
tttttgcaaa tagtcaaagg taaatgaata agattttgag aagcattttc aagatttgaa   53220
tttttctccc cctgtttcaa atgcttttcc tttgactaaa cataactccc cctcaataaa   53280
atcctcctct tagtgttcaa gagggtttta gatattagtt tttgaagagg gtgatccaat   53340
ttgaaattct atcaaaaaat aggataccaa ttgaaaaaat tcatcatttc aaaacctttt   53400
cttaactcaa attttgaaaa ttggtggtgg tgcggtcctt ttgctttggg ctaatgcttt   53460 ctccccctttt ggcatgaatc gccaaaaatg gatacttgag tgaaatataa gcccttttaa   53520
ctactttctc cccctttgt gaacaaaata tgagtgaaga ttataccaaa gttggagagt   53580
tgctcggagc gacggcgaag gatgagtaat ttgatggagt ggagtggaag cctttgtctt   53640
cgccgaagac tccaattccc tttcaatcta tgacttggtt tgaaatacac ttgaaaacac   53700
attagtcata gcatataaaa gagacacgat caaaggtata ttaatgaact atgtgtgcaa   53760
gacatcaaaa aaaattccga gaatcaagaa tatttagctc atgcctaagt ttgttaaatg   53820
tttgttcatc tagtggcttg gtaaagatat cagctaattg ttctttggtg ttaatatatg   53880
caatctcgat atcccccttt tgttggtgat cccttagaaa atgataccga atggctatgt   53940
gtttagtgcg gctatgctca acgggattat ccgccatgcg gattgcactc tcattatcac   54000
atagaagagg aactttggtt aatttgtaac catagtccct aagggtttgc ctcatccaaa   54060
gcaattgcgc gcaacaatgg cctgcgacaa tatactcggc ttcggcggta gaaaaagcta   54120
cagaattttg cttctttgaa gcccaagaca ccagagacct ttccaagaac tggcaagtcc   54180
```

```
ccgatgtgct ctttctatta attttacacc ctgcccaatc ggcatccgaa taaccaatta   54240
aatcgaatgt ggatccctta ggataccaaa gcccaaactt aggagtataa actaaatatc   54300
tcaagattcg ttttacggcc ctaaggtgag cttccttagg atcggcttgg aattttgcac   54360
acatgcatac ggaaagcata atatccggtc gtgaagcaca taaatatagc aaggaaccta   54420
tcatcgaccg atatcccttt tgatctacgg atttacctcc catgtcgagg tcgagatgtc   54480
cattggttcc catgggtgtc ttgatgggct tggcatcctt catcccaaac ttgtttagaa   54540
tgtcttgaat atacttcgtt tggctaatga aagtgccctc ttggagttgc ttcacttgaa   54600
atcctaagaa gtacttcaac tcccccatca tagacatctc gaattttttgt gtcatgatcc   54660 tactaaactc ttcacatgta gatttgttag tagacccaaa tatgatatca tcaacataaa   54720
tttggcatac aaacaaatcg ttagtaagtg ttttagtaaa taaagtagga tcgacctttc   54780
cgactttgaa gccattagcg ataagaaaat ctcttaggca ttcataccat gctcttgggg   54840
cttgcttgag cccataaagc gccttagaga gtttatatac gtgattagga tactcactat   54900
cttcaaagcc gggaggttgc tcaacataga cctcttcctt aattggtcca ttgaggaagg   54960
cacttttcac gtccatttga taaagcttga agccatggta agtagcatag gcaagtaaaa   55020
ttcgaattga ttctagccta gctacgggtg cataggtttc accgaaatcc aaactttcga   55080
cttgtgaata cccgttggcc acaagtcggg cttttgttcct tgtcaccaca ccatgctcgt   55140
cttgcttgtt gcggaagacc cacttggttc ctatagcatt ttgattagga cgtggaacta   55200
aatgccatac atcattccta gtgaagttgt tgagctcctc ttgcatcgcc accacccaat   55260
ccgaatcttg aagtgcttcc tctaccttgt gtggctcaat agagcaaaca aaagagtaat   55320
gttcacaaaa atgagcaaca cgagatcgag tagttacccc ctttttgaata tcaccgagga   55380 tggtgttcac ggggtgatct cgttgaattg cttggtggac tcttgggtgt ggcggccttg   55440
gaacttgttc atcttcctca tcttgatcat gggcatctcc cccttgataa ttgctctcct   55500
cttgaggtgg ctcaacttct tgatcttctc cttcatcatt ttgagcctca tcctcgtctt   55560
gagttggtgg agatgcttgc atggaggaag atggttgatc ttgtgcttgt ggtggctctt   55620
cggattcctt aggacacaca tccccaatgg acatgttcct tagcgcgacg cacgaagcct   55680
cttcgtcatc tagctcatca agatcaactt gctctacttg agagccgtta gtctcatcaa   55740
acacaatgtc acaagaaact tcaactagta cagaggactt gttaaagact ctatatgccc   55800
ttgtgtttga atcatatcct agtaaaaagc cttctatata tatccttagg agaaaattta   55860 gatttttctac ctcttttaac aagaataaag catttgctat caaagactct aaaatatgaa   55920
acattgggct tttactggtt aggagttcgt atgatgtctt cttgaggatt cggtgtagat   55980
ataaacagtt gatggcgtat catgcggtgt tgaccgcctc ggcccaaaac cgatccgaag   56040
tcttgtattc atcaagcatg gttcttgcca tgtccaatag agttctattc ttcctctcca   56100
ctacaccatt ttgttgtggc gtgtagggac aagagaactc atgcttgatg ccctcctcct   56160
caagaaagcc ttcaatttga gagttcttga actccgtcct gttgtcgctt ctaatttttct   56220 tgatccttaa gccaaactcg ttttgagccc gtctcaagaa tcgctttaag gtttcttggg   56280
tatgagattt ttcctgcaaa aagaatccca agtgaagcg agaatagtca tccacaataa   56340
ctagacagta cttactcccg ccgatgctta tataagcaat caggccgaat agatccatgt   56400
gtaggagctc aagtggcctg tcagttgtca tgatgttctt gtgtggatga tgcacaccaa   56460
cttgcttccc tgcctgacat gcgctacaaa ccctgtcttt ctcaaaatga acatttgtta   56520
gtcccaaaat gtgttctccc tttagaagct tgtgaagatt cttcattcca acatgtgcta   56580
```

```
gtcggcgatg ccagagccag cccatgttag tcttagcaat taagcaagtg tcgagttcag    56640
ctctatcaaa atctactagg tatagctgac cctctaacac tcccttaaat gctattgaat    56700
catcacttct tctaaagaca gtgacaccta tatctgtaaa agacagttg tagcccattt     56760 tacataattg cgaaactgaa agcaagttat aatctaaaga atctacaaga aaaacattgg    56820
aaatggagtg gtcaggagat ataacaattt tacccagtcc tttgaccaaa ccttgatttc    56880
catccccgaa tgtgatagca cgttggggat attggttttt ctcataggag gagaacatct    56940
tcttctcccc tgtcatatga tttgtgcacc cgctatcaat gatccaactt gagccccgg    57000 atgcataaac ctacaaaaca aatttagttc ttgattttag gtacccaaac ggttttgggt    57060
tctttgacat tagatacaag aactttgggt acccaaacac aagtatttga tcccttgtgt    57120
ttgcccccaa catacttggc aactaccttg ccagatttat tagtcaaaac ataagatgca    57180
tcaaagtttt taaatgaaat gttagaatca tttgatgcac taggagtttt cttcttaggc    57240
aatttagcac gggttgatta tctagagcta gatgtctcac ccttatacat aaaagcatga    57300
ttagggccag agtgagattt cctagagtga attctcctaa tcttttgctc gggataaccg    57360
acagggtaca aaatgtaacc ctcgttatcc tgaggcatgg gagccttgcc cttaacaaag    57420
tttgacaatt tcttaggagg ggcattaagt ttgacattgt ccccctttg gaagccaatg    57480 ccatccttga tgccagggcg tctcccacta tagagcatgc ttctagcaaa tttaaatttt    57540
tcattttcta agtcatgctc attaattttg gcattaagtt gagctatgtg atcatttttgt    57600 ttcttaatta aagctaggtg atcatgaata gcatcaacat taatgtctct acatctagtg    57660
caaatggaaa catgctcaac ggtagatgta gagggtttgc aagattttag ttcaacaatc    57720
ttagcatgta aaatgtcatt ttcacttcta agattggaaa tggtaacatt gcaaacatct    57780
aagtctttag ccttagcaat taattttttca ttctcatttt taaggctagc aagagagaca    57840
ttcaattctt caatcttagc aagtaaaacta acattatcat ctctaagatt gggaattgaa    57900
acatcacaaa catttaagtc aaccttagca attatttag cattttcatt tctaaggttg    57960
gcaataatat catggcaagt gcatagctca ctagatagtt tttcacattt ttctacttct    58020
agagcgtaag cattttttaac cttaacatgc ttccttatttt ccttaattag gaagtcctct    58080
tgggagtcca agagttcatc cttctcatga atagcactaa ttaattcatt caatttttct    58140
ttttattgca tgtttaggtt ggcaaaaagg gtgcgcaagt tatcctcctc atcactagaa    58200 ttatttttcat cgctagagga tgcatatta gtggaggatt ttgattttac cttcttcctt    58260
ttgccgtcct ttgccatgag gcacttgtgg ccgacgttgg ggaagaggag gcccttggtg    58320
acggcgatgt tggcggcgtc ctcgtcggag gaggagtcgg aggagctctc gtcggagttc    58380
cactcgcggc acacatgggc atcgccgccc ttcttcttgt agtatctctt cttttctctc    58440
ctctttccct tcttgtcgtc gccctgtca ctatcactag ataatggaca tttagcaatg    58500
aaatgaccgg gcttaccaca cttgtagcac accttcttgg aacggggctt gtaatctttc    58560
cccttccttt gtttgagaat ttgacggaag ctcttgatga tgagcgccat ctcctcattg    58620
tcgagcttgg aggcgtcgat ggggattcta cttggagtag aatcttcttt cttctcctcc    58680
gttgctttga atgcaacggg ttgtgcttcg ggtgtggagg agttcccttg ctcgatgatc    58740
tttttggagc ctttgatcat tagctcaaag ctcacaaatt tacctatgac ctccttggga    58800
gacattagcg tgtatctagg atcacctcga attaattgaa cttgcatagg gttaaggaaa    58860
acgagggatc ttagaataac cttgaccatc tcatggtcat cccatttggt gctcccgagg    58920
```

```
ttgcgcactt gattcatcaa ggtcttcaag cggttgtata tggcttgtgg gtccttgcct    58980
tggttgagtc ggaaccgacc gagctccccc tcgatcgtct cccgcttggt gattttagtc    59040
acctcatctc cttcgtgcgc ggtcttgagc acgtcccaaa tctccttggc gcttttagt     59100 ccttgcacct tgttatactc ctctcgactt agagaggcaa ggagtatagt ggtggcttga    59160
gagttgaagt gtcggatttg ggcgaccttg tccgaatcat agtcttcatc ccccggtgat    59220
ggtacctgta ctccaatctc aacaacatcc caaatgctag tgtggagtga ggttagatga    59280
tgcctcattt tatcactcca catattataa tcttcaccat caaacatagg tggtttgcct    59340
aatgggacgg aaagtaatgg agtacgtttg gaaatgcgag ggtagcgtaa ggggatctta    59400
ctaaacttct tacgctcatg gcgcttagaa gttacggacg gcgtgtcgga gccggaggtg    59460
gatggcgacg aatagtcggt ctcgtagtag accaccttct tcatcttctt cttcttgtca    59520
ccgctccgac gcgacttgtc gtgtgaaggg ggtcccttca ccttgttggc ggactccccg    59580
gatggagcct tcccatggct tgtggcgggc ttctcgccgg tcccgatccc cctcttggcg    59640
gatgctcccg acatcacttc gagtggttag gctctaatga agcaccgggc tctgatacca    59700
attgaaagtc gcctagaggg gggtgaatag ggtaaatctg aaatttataa acttaagcac    59760
aactacaagc cgggttagcg ttagaaatat aaacgagtcc gagagagagg gtgaaaaaca    59820
aatcgcaagc aaataaagag tgagacacaa ggatttgttt taccgaggtt cggttcttgc    59880
aaacctactc cccattgagg tggtcacaaa gacccgggtc ctttcaaccc tttccctctc    59940
tcaaacgatc acttagaccg agtgagcttc tcttctcaat caaacgggac acaaagtccc    60000
cgcaaggacc accacacaat tggtgtctct tgcctcggtt acaattgagt tgatcacaag    60060
aaagaatgag aaaaagaagc aatccaagcg caagagctca aatgaacaca agtcactctc    60120
tcactagtca ctatttgatt tggaatgaac tatggacttg ggagaggatt tgatctcttt    60180
ggtgtgtctt gtattgaatg ttatagctct tgtaaggtgt agaaagttgg aaaacatgga    60240
tactatgaat ggtgggtggt tggggggtatt tataaccccca accaccaaaa gtggctgttg    60300
ggaggctgtc tgtcgcatgg cgcaccggac agtccggtgc gccaccggac actgtccgat    60360
gcgccagcca cgtcagccgg cagttgggtt ctgaccattg gagctctgac tggtggggcc    60420
tctgggctgt ccggtggtgc accggacagg tcctgtagac tgtccggtgc cccttctgcg    60480
cgtgctctga ctctggcgcg cactgtagca catttaatgc ggttgccagt cgaccgttgg    60540
cgcgaagtag tcgttgctcc gctggcacac cggacagtcc ggtgtgacac cggacactgt    60600
cccggtgctt cactgacag  tccggtgaat tatagcggag cgacctccca ttttcccgaa     60660
ggtagcgagt tcagcgtcaa gttccctggt gcaccggaca ctgtccggtg gcacaccgga    60720
cagtccggtg cgccagacca gggttccttt gggatgtctt tagctctttt tatttgaacc    60780
catctttggt ctttttattg gcttgttgtg aacctttggc acctgtaaaa cttatagact    60840
agagcaaact agttagtcca attttttgtg ttgaacaatt caaccaccaa aattaattta    60900
ggaaaagatg taagcctatt tcccttcaa atggcgattg catgaaagga taaaaagttg    60960
gatccgaaag acagaagcaa ttaggacatt tgtgatggca agcaaggtac gggcaaaatt    61020
gcaatgacat aggacctatt tgaatccatg gtggtaaagt ttagtactac acttttagat    61080
aaactttagt acttagatat ttagataaga gtgctaaaag gtgctaaaag agaagcagta    61140
aactctagca ctcaatagca atttagctcc tcaaggtata ctaaacttta gcatctacta    61200
aagtttagaa catggaatcc aaacagtccc atgcattcat agagcgaatt gccccctagc    61260
tagataagta gacataggat atgtctagat acataattaa taaaagttat gtgtttaaaa    61320
```

```
tatagaggca aataaaaacc actttataga ttgagacgga gcggattcac ctaagtagac   61380
tacttactcg tgcatccacc gtcaccatcg gcgtgtaggg gtttcctcgt ataagttcga   61440
atttacttgt gtatctgaat ttgttcttaa attcatatgt gatagaaagt tgatatcttt   61500
gacaataagc tctcgtttgg tttgagagac taaagattag tctcttcatt ttagtttcat   61560
ttaatcccta aattgccaaa agataggact aaattagaga ctaaactgtg ttagtctcta   61620
atcacttaag gggtaactaa aagtgactag actatataaa ttatacccttt tgtcactcct   61680 ttatttcagt tgcattaatg ataggagaat gctaagggat attttagttc tgttatgatt   61740
catttaatat gttttgaata gttttaatat ctaaaaccaa ataggataga gactaatctt   61800
taggccatgt ttggtttctt tagtctatgg actaaagttt agttatggga ctaaagttta   61860
gtccctaaca tgtttggttt taggggctaa aaatagtaag aatatactaa atgactcata   61920
agaagactaa aatgaccttt aacattctcc tgctattagt acaattgaac taaatgaggg   61980
gtaaatgtgg aattaatatg gtttcgtcca ttttagcaca tatgtgaagg actaaggggg   62040
tgtttggttt ctagggacta atgtttagtc ccttcatttt attccttttt agtgtataaa   62100
ttgataaata tagaaactaa aataaagttt tagtttctat atttagtaat tttggaacta   62160
aaatggaata aaatctaggg actaaacatt agtccctaga aaccaaacag cccctaaaga   62220
ctaaatcatt ttagtccata ttttagtcct agtgtttgat aaaaaaggga ctaaatgaga   62280
ctaaaaacta gagactaatc tttagtccct ctaaccaaac ccccttagt ctcataacta   62340 aacttttagt ccctgaacta aagtaaccaa actagatcta agttattggt ttccatttaa   62400
ctagctactc tggccacctg ctccttttac taagcaacaa tcaaacatgg gacctctaaa   62460
tgccattaaa tatcattaga tattatacat attccttgtg ttgcattaaa tatcatttaa   62520
gaaatatttt tgcgtgtgat atataggccc agtaatatat aaggaattag tataatttt   62580 tatgacatac aagaaattgt cccaaatatt ctgcggctgt tcgtccatgc aatgcttcgc   62640
ttctcttttt gtcggtgatc acaagaaagg agtgtttggt tttatagact aactaggtgg   62700
atgcccgtgc gttgccacga gagttaaaat ttagtataaa acatagatac agaaagataa   62760
acatcactat gatatgttaa atccatgtgg taagaccgtt ccaaattata gatgttttag   62820
tatttctaaa gaatcagtat tgaagcacac attgacgacg tcgtccgtgg cgcccatgac   62880
gccgcagtga cacagcacgt cgcagaggcg cgtgtcgcac tgcatggacg tggagatggc   62940
actgaggcca gttcaagccc acttttcggc acaccatgtt atgctccttg tgtcggttgg   63000
ccacgcatac cagcgtcacg gggagttcca aggcctcgaa ctccgtcacc agttgctcca   63060
tggtcagctt ggcgggggcg tctcacgagt cacgagcccc accaccacgt atgtcggtta   63120
agtatgtcgg taagccgata ttcttaacat aagaacgtcg atctattaga gtaagaacgt   63180
cggtttctag ccgacatttt tccagtagtg gtagtggtgc ggtgccgggg tgatgaagtc   63240
gtgcgccatc agccacgaca ccaaaggctc taagttgaag gggtgcttgc ccgtgagccg   63300
gacgagcgtc gggtggcgcc gcacccacgc gtcagatgtg gcctcgccgc gtgagtcgca   63360 gacggggtggc tccacctcga ggcacaggag gtacggtgat cgccagtcca gcgggatgt   63420 tgtattttc cttggaatca aaatcggat gggtgcgacg cttgcctcct gggccaccgg   63480
agcagaacat gttgaagctc ttgggaggcg caatggccga ccacgggtgg gggcgggggg   63540
caggtgccgc tcaacagagg tcgccattgt cggcgcgagc tacgagaacg attttttaatt   63600 gtgatgtcca gagctcgaga ttaatcggaa gctcgaggaa tataatcatg catgccctca   63660
```

```
gaaagaaaac acagaataaa aaaggaaaca caataaatta ggcaagggaa acagtcagtc    63720
acgattttct gatacaatca ggcggtatat taatagatat tacgcgacat tatatatgaa    63780
gcaagtatta acacaacatt atatcaatag atcgggaaag tatattagac ggcaattata    63840
agggaaacac aataaatcag gcaagtatat tacacgacat tgcatagaat acaatcagga    63900
gcaaattcag atactatgct gatctaaact gctgtattcg gtagattatg tttgcaaatc    63960
tacgattcta gggacaactc acgtaaacaa aacttaagat ttcaaaaaag aagccaggtt    64020
aggtaagact tccacaagac tgttactgca agcaagctgg cataaagctg cattcgagat    64080
cacgttttcc ttcatcttgg tcagcgcgcc ttcatgctga ttttgtatt tgccaaaaaa    64140 gtgttgggct gtaatatagt tgagaaaaga atcccccaag tgtctctaat gattcctgcg    64200
aaaagtcctc tcggcaattc tttgctgtaa gtgcttccag aatctgcaag tcaatgaaca    64260
tgggttaaaa ataagaacta tgttcgtgta atgccacatc aatctgaaag tgactatggc    64320
attaggtatg aacatatggg aatcatcaaa ctacttccaa cgaaaagaac aatagacaaa    64380
tgcatgtgta atgtattgac tgtttgatgg aatgcaaaat ttctacagaa ctctagattt    64440
caccagaaac aagtacattt tgatagcggg gagttctaca cactttcctg cttagacttg    64500
tcagatctct atcacaacag ctacaaaacg atcagaagcc taagcatgta aggagagaac    64560
atgagtgatg atcatttaca tcatgatggg cgaacaaatc aggagcaact acaccactgt    64620
tgggaagtag cgacgaacat tttacattac aaaatagtat agtaataact aaaaacaacc    64680
ctacgtattt accagtctcc atatcctaca ttcttacctt aattactctg gaccaacatg    64740
cgccagttta ctggcttaac actggcggta ctccatcact aattttagt ccctctattt    64800 tatttcattt tagttactaa atttctaaat atggaaacta aatagagtt ttatttcca    64860 tatttaatat tttagggact aaaatataat aaaattgatg gacaaaaaa ttagtcccta    64920 taaccaaac acccccttaa ataatttaca tagtttagc tctctcagat actgctgagc    64980
ccctcctctc tagatgtttc aatatcacct tcgcttgcat cggccctgca catgaggag    65040 ccaaaaccaa aaaattgacc atggcagacg cctggcgccc ctgctctcta gatgctctac    65100
cactctgtcg tctaatgtgc tctgtctaat gggatataaa gctctgcatg ctctgcaaga    65160
tgtttccatg catatagatg aatttcacaa actattagca atgctcacaa ggaaggattt    65220
ttccaacggt tatttgcata tataatctac ctgttttttc tattattaaa aaggaaaaag    65280
aatagccaaa gtgccatcca ggcaggtgtg attgtgcgcc tgctttatgc attcaacaca    65340
gttagtcagt gtgcatataa cttttctgctg gggtattttgc aaataacatg taaatatata    65400
ggttacatga aaaataccag caaacaacag atttaacctt gtttttttgc tgaccaaatt    65460
atatagcgtt gttttcacag gaagaaacat gggtaataaa ctacactttg gaaccacatg    65520
caagactgta ctaacaagaa cttaaagtga atatatttgt ggtcactaat cttatttgt    65580 aggcgtgatt gcttagaata ttaacactga catgaacatc aacccaaaca ccgtgcaagc    65640
atgtggaggg tgtagaacaa gatagtaaga aggaagacac cattttccac agagagacaa    65700
agcacgggga cgacagttac agacggatcc acgaggtcag gggagaggga aattggagag    65760
ttggaagcag tgggaccgct gtacctcggg tgccatcgcg gaaggccttg gagacatgct    65820
tgggtgtcca gcacaggccc tcatggcggt cgtcctcatc aagccccagc accagcgcgc    65880
accgttggct ccacggtgta gccccgtcac cgcggtgtcc cctgagagca tgtcgatgta    65940
gtcgttttgc tcatcatcat cgcatgcgga agcgacgacc gcgaggtggg cctgctcgag    66000
cgctcccatg gcggtagatg cacccatctc agaaacgata ttagatctcg attgatccct    66060
```

```
tggcaacttc gcgagccaat cagcagcttg gggaggagag agagtgcgta caggagagat    66120
gggggagagg agatggagcg aagcccgggt tccggtcgat gccgctagac tcgagatcga    66180
caaggacgag aacggcgggc gagatggtag gtgcgtatgg ggtatnnnnn nnnnnnnnnn    66240
nnnnngcgtt gcttgcgccg tcgccggccc ctggtcgtcg gccccacgct gaggttgtta    66300
cgaggatgag gggttgtgga tccccggcat cacggacgcg cgcagcgtgg ggggagcagg    66360
ggaggggagg gggctggggg gttgcggatc cccggcatca cggacgctcg cggcgtgggg    66420
ggagcagggg cgggacggca gctattgcgc aggggtttgc gtgcggcgtg ggggagcag    66480 gggcgggggc tggacggcag ctattgcgca ggggtttgcg gggcgtgggg attaggattt    66540
gagcgcgtac caaaacatgt ctgccgactt tgcgcatgc gacggcggat tgagctcggg     66600
gtttggggga ttgagctcag agccgggctt tggggtatgt ggcgaagtcg gagcgcgcgg    66660
cgcggcggta gcgctccgtc tgcccgagtg cggcgggtgc ggggattgt tggggacacc     66720 ccgattcgcg aaaggattgg tagggggcga gcgtggtagg ctgagctatt tgcggcggcg    66780
aggatcccgg agggtgggca gtcggagggc aggcgggggc ggtgtacgct ctgcggtgcg    66840
ggaggccgtt gtggggcgag atttcgctag cgcgtgcggg tagggagcgg gggcagtcta    66900
cactgccccc ttaatagtta gtacagattt ttagtttatc tattttattt tattttagtc    66960
attaatatat gttaaatata aaatattttt agtttccgta tttgataaat tagagactaa    67020
aataaaataa agagattaaa aattagtccc taaaaatcaa agaacccaaa atctgtccca    67080
aaaaatgtca gagctatcgg cgatcaggga tgcaaatcat gcatgaaaga gatgcatcaa    67140
aataaagccc catatgcgta cgtgctcgta aaaccaataa ctttagttat tccatcagac    67200
catcatggaa gtattcatcg atccatcatg gcggagattc ttcgatcagc ataggacgta    67260
aatgtccatc atgaaagtat tctcctgtat gcatgaccat gtccacaagc aatcatgcca    67320
attgctctta aattactttg agttttgacc cttcattcat tcaatctttg aataaaataa    67380
aaagtagaaa aaataaataa tatgtatatg tatccacttg tgctaataaa taaaatgcaa    67440
atattattta cgagctttaa gtcgttgtag aacatttata tatgttgcca tctgacatgc    67500
agtggatggc ctcgcaaaaa tagaatccac ataacttggt cccatgttcc tacatatgaa    67560
acactttacg agaaaataat tcatcatata atcaagcact accggacaca accgctttgc    67620
cgagtacttc ggacagtcga caaatctgta acacctcaaa tctcatttta gaagtttaat    67680
aaaattatct taaagatttt cggttaaaat ataatttca taagaattgt cttagctttc    67740
aacctacttt cccaaaaaca atgttttcaa aaaagaaag gatcttaata ataacttatt    67800
tgtccctttg gctgtggggg atagatatcc ccgggtccac taaagagtaa aagacctcac    67860
gaaaggccca agagcccaat aaatcataag gtcattcttt cgtgggcctg gggagagaca    67920
accagcagag cagatcgaca tgaggcagga ttgatgtaaa cctggacgac ccacaacgtc    67980
gagcgaatga ccacaacaga gatccgactt tcccgcgctg gggcccccat gcaacggagc    68040
catgcgagga taagtcggca ggattacacg gagataaact caagaagttc actatctttt    68100
agctactcgt tgttatcata tccacatgta ttgccccacg gtcgagtata tgaggcctag    68160 ggggcaccc ttcagaacga tcgaccctat tacttagcca cccacgtcaa ctctctgtat    68220
tctcaatcca gagagctctc ttgtaaccac attcaccaag catactcacc agaacgtagg    68280
gtgttacgca tctctaagcg gcccgaacct gtaaaccttg tccactgttc ctcgtgcaat    68340
cggcacgaac cattttgcta cagttgtcga caccgtccta ctcctaaaaa caccttgagg    68400
```

```
ggcaactccg ggtgtgcggt cggacccaaa acaccgacat tggcaaaata atatatttct   68460
aaatttgttc tcttaaggaa cttataaact agaattatct ttcttaaaat acatgttttt   68520
tgggtgtgca ttaagaaaac atttgcataa ataaatgaga tggtaaataa ataactatca   68580
taaattatat tgtgcatgct ggattttttt attgtgcatc aagtttaatc caaacacaga   68640
tttgaatttg aaatgaaata gaaatgcaaa atagggaaca gaaaatgaaa aaagagaga   68700 agaaataacc tgtgcctggg ccgaaccacc cagccgaccc atctcttcct ttcatctatg   68760
cggcccagaa tctccctcgc tcggcccatg tgcacctccc tagccagccc aacttcccca   68820
cctgcgcgcg tcgctgcacc caggtttcac cgacgcacgg gccccactac acaggcctac   68880
cgtgtattcc ccgtattttt tgcaatttcc ttttttttcaa aacaatttca catagacctc   68940
taaataactt aatgtcattt tgatccttta ctcggcgcca tgcctcatgg cgctgagata   69000
acacatctcg gcgccatggc ctatggcgcc gaggtaccta gtgagctggc aactaaggcc   69060
ctgtttggca cagcttattt tcagcttctt cacaaattta agcagaaggt ctgccaaaca   69120
gctagcttct gtagcagctt atcagttcag ctgcttctca aaatacacta aaagcagcca   69180
acaagcagaa gctactttc accagcttat cagataagct gcttttttcaa caagcagcag   69240 ctgtgccaaa cagggcctaa atacgagctg gtagctgatg tggcctagct cggcgccacg   69300
atttgtggcc ccgagctagg atatggcaag cctgtttagt tcgtggctaa ctgtgcacac   69360
tttgcctaaa cttagtcgtc cgaattgaaa aaccaaccct agtcagaaaa gttaggcaaa   69420
gtgtggcaag ttagtcagca aaccaaacat gaccggcgtc taccaccagc atacatgggc   69480
aactgggtgg ggcgatgtgc atccgtccac agatatagat gtccaaatgg gcgggtcgtg   69540
ccggcccggc ccgagcacgg ctaggctcgg cacggattag aaccgtgccg gtccggcccg   69600
gagtaggtag cgggccgtgc cgtgccggcc cacgggcccc aagtgaggcc caagcacagc   69660
ccgctaggtt aataatcatg ctgggccggc ccaaggcccg acgggcctaa cgggtccata   69720
acaatatata atgtttaaat gataaaaata tcctaaaaat atgcattttt aggatttaaa   69780
ccatatttat tagctctaaa catttattta cacccacata accaacaaaa acacatgttt   69840
cttgtgtttt atactatata ttcaagtata atatatgtat ttatatgaaa aaatagaaaa   69900
aaaataaaat cggaccgtgc tggacctagt ccgtcgtgcc acgccttcgg cctaggcacg   69960
acccggtgac cgggccggca cggccccggt tcactacgtg ccgtgccggg ttcgtgccgg   70020
accaaacccg tgccgggttt cggaccgttc gacaagctcg atccgtttgg acatctatag   70080
tcacagaaca gcgctacgtg cacgtcctat atagcattta tcttgatcac gtcctactcc   70140
tacacatgta cttaccaaag gctactgcta cctagtacaa aagacgtctg ctcgtaagga   70200
tccatacgct tttcagattg cagtatatac ttgcagcctt gtctgcatac ttaatactat   70260
aagtatacat gcatggtcac acatgccaac gtaagacgag atttggtata acaagaatca   70320
tacagcaaca caaagtacta gtacatgaa acactacacg cgtgggtatg gaagaagag   70380 caattactca aaaatttgcc tttcatttcg gttcttgttt tttattactt acgggtggtt   70440
tagttcagat atctgactct ttagcatggt actgagattt tactggcacc gtccacggtt   70500
cgttttcgtg cacccagcca cccataccat acatgcgttt ctttagttat cctatggatc   70560
gatcgtatag atagactagc cagttgcccg tgctttgcta cggttattat ctattactac   70620
tctataagga cgcaaggagg gcgtccacca cacaccacgc ctccgcccga ctctcctcgg   70680
ctcctcgccc gcgctcaggc tcaggcccg gctctcctcc ctcctcgcga ccgtgcaatc   70740
cccgcttgat gctttccatg gagagcagag tgtcagcctt ccgaaatctc cgcccaggac   70800
```

```
cccgccttct gctcccccac gcccgatcca cgcgaggccc acagtccctg tgccttccaa  70860
atcgccgcgc tgctagccgc atctcgtccg tgcatgccta acccacgcct cccaaatcgc  70920
cgccaactcc ccaagctcca cgagatctcg tgtcatctgg tattgcctcc cccgccgctg  70980
actactcctc ctagccagta gtctctccgc tgccccaccc ctcgatccca cccactttgt  71040
agctaatctt gtcgggatcg tagatctaga aggtagtatc ggatggctcc atagggaatg  71100
gaagcatgga tgcaggcgtt gacggggtgg cgaggatgaa ggcgattatg atgaggagga  71160
cattggacca ctgctcagct tcgatgagat gtttcacctc cacgcggcgt gcggcgtggc  71220
gcttccaggc gacatgatgg aggcaagccg gtgctgagga tcccacagtc gtggacatcg  71280
ccgggacgca gctgatgccg aaggaggagg cgctccagct ttgcaccggc tgtgtccact  71340
tctagacttc cttgcctcgc ctatcacctc caggaaggta cgtacgtgtc atccccaccc  71400 cacccctcc attgtccctt cgctatgaat ccccatcccc tcacttccac aatgccgcag  71460
tgatacctgc cttggaagaa tttggggatg aggatcccac gtcgcaacgt tccatagtgc  71520
ccctgcccca accgatgtcc acggccgtcg cgcccgggca tggcagtccg ctcccacgcg  71580
atgcaagtcc atccccaccg tcgcagctgc cgaggacccc ccttccgtag atgattttgc  71640
caccgcctac atcaaggagc actttgacga ggaggaagcc aaggcgtcgc gcccataatc  71700
gtcaccacaa aaccgcccgc cgcccagcga cgaccctggc cggctattcg tcggcaacat  71760
gaggtcatcg ggggaggccg atgaggccct cgacggcaac cgactcagtg gttgaagttg  71820
cggcctttga attgggcggc atcagtgcac ctctaggaag ccactcacgc tcggtcagcg  71880
gttatggcat tggagcggtt gtaggactgg gaggaggcag gccagtacca gttctacggt  71940
gacgtctagg cacgaccaga ggcatagtgg gaggaggcga tgtcggccag taccagctct  72000
acgacgaccg ccaggcgcga ctggaggcag acaccaccgg gatggccttt tcggtgagtc  72060
cctcatgctc ctgtgctcat gtcatgtgat gaccatgtgt gcctgccacc tgttgttgta  72120
ttggctcacc gaatgatcct gtttctatcg attataagag tgaatatcag atgggctgta  72180
ttatttccta ggcgttggag ctgatagcaa ggtgagaagt cacctatcac attcgctaat  72240
ggaatgtgaa actttacatg caaaaccggt tcaaatcatg ggtcaaagag aacttcctgt  72300
aactttgtgg agaagctgaa aggtcaaaga gaacttcctc gtcgtgcaag ttgtggactt  72360
gatctcttaa taatgtttat tgtcattttt ataattttct acttgtgtta gtgatgactt  72420
tgccaaatta gtgaacctgt tatatgttga gcagttctat tcaataactc atgcttgtgt  72480
tatatatgtc tgataactga tggctatatg tgaatgctat atgggttctg ttaccagtat  72540
agcatgaatg tcctaaattg ttctgtaacc cttgttggtt aatggacatt tatgttagct  72600
atcttaagac ttatgttacg cttatagctt aagactcatg gtaacagggt ttttacagtt  72660
attttcttac gtaaaagatt tattactaga tatttgaaat caatgatgta aaggcttgga  72720
catcaatgta aaggaagaac acatgttctg ttttcttctc aatttctatt gatgtaggaa  72780
ctcactacca ttgccaaatt ccatttattc attgccaact tttgtacaat ctttagactg  72840
caatctgcac ttattgtagc ttttgtataa catattgcag gaagatcaga aagtcataga  72900
aacatagctg atgatgcgcc aaaaagaact ccaaggtgaa gaagctaaaa tgagcagaaa  72960
acaaagcaga tattcttcta ccagaacggt aaccccaaca ataggagttg agtattgaga  73020
tatttgcagc acatccttttt caggttaaca ttggacataa ctaatatgct catttaataa  73080
tgctcaccta cacagccata tagccatgac ctctgtaatg ccatcgtatc agtgtactaa  73140
```

```
gcaaggaaat gattttggtt catctaaacc ttcatgctct agctaggcta acaggcgacc    73200
tttccattct atacacattc ggtacattca tgttatagtc gatacctaga tgttggagag    73260
tgtccaacct gaacatttat ttttttcatg taatcgttgt gctctaataa tttatcaaat    73320
aatttgtgtg tcatcgcaac gcatgtgcat tgtgtcgaat tcttgtaagg agactcgctc    73380
tcctcctaca ttttctaatg ttcaatgagg tctattactt ttcagttgga gaacctacaa    73440
atgtgctttt ggtcatttgg cacctcatga atattttagc ttgttcctgt catttagtct    73500
ttcatgcccg ccttggaaga gcattctgtt atgcgactct tttacctata tgttgaaatt    73560
tgtcgttgga tcgtatgcct gcagaacacc ggttaactgt aggttcaagt tgaaattctg    73620
taacagcttt ggtctcagtt aaatcagaga tcgacaaatt ttgcatggcg taccagtagc    73680
atccggtagg atacagatgt actgttttgg ttactattaa ttggaggaac aagttttttt    73740
cgtggttaaa agcacccact atgttccagc agatacatca acaagtatt ttctaaacac     73800 aaacttgcaa tgtattctaa atttgggggg agcaaacaag cttcagatat tatactcttt    73860
aaaatgctat taagcatcta ttactctatt agtgacagtt tgctagaaga taatagtgac    73920
actttgctag aagagtgtta tacctcttta aaatgctatt aagcgtctat tactctatta    73980
tgccattgaa attttagcaa ttccttattt gtaattgata atcacaaaat taaatttcag    74040
tggcatagag agttcaccca aggaatatta gcacaatgtc aaaatgtagt taagctgaat    74100
aacaattact cgcctgacat gatgttatca aacataaaag aaatgaattg gattaaagga    74160
taactacaaa tccaaaaaca taattaagtg ggtttatgag ttacgagttg atgttgttga    74220
acaactaaac aaaactggtt ttttctccta cacatggcaa ctttgcgggg catttgatta    74280
tctcttgaag ggaaagtcta aaatagaatt tgaatgtcat gtaccatttt gtatgctaat    74340
tttgataaat ttgtttagct gtaaagcaag ctcttcagac agagaaggca ccggcagcac    74400
taggccctaa ttctaaggcc atcaaagcaa ataatcttgt gtttgtttct ggagttcttg    74460
gcttaaatcc tgaggtttgc ttttgaactg ctgttctatt cacttgtttt tctacattgc    74520
ttgtattagt ttgctggttt ttccactttg gaacaaactg atcaccaggt tgtagctgaa    74580
gagacaacta atgtgccttt ttgttttcag acaaggaagt ttatctatgg tgtaagcaca    74640
cttctacgtt ctaatgactt gctagcatat aaagatgtca caacaaaggt tgttctatgg    74700
tgtaagtact ttatttcttt gtgatgttaa ccctttttaag taaggtaatc tatatctata    74760
tctatactaa tatattaaaa cctaatgtgg gcacctgtgc tacgaattca ccctccccat    74820
gcccagcacc cgcaaaaaat agtgcaaagc gagcactcga accacatcct tctactccag    74880
aaatttaggg ctaaccacta gaacacacgt attttagtgt ttagaaataa ataataatta    74940
tatttgcagc ctaggcaccg ctccccacgc cctcctctcc cgcctcgtgg caacgcacga    75000
gcacatacct tagttgaatc agtttttttg tttaacttca tgaaacttga caggtgatct    75060
acaaagccat gagcaatatc tttcatgtta attgaattac aaatattgca tttaacccctt   75120 tcacaaaaca taagtattgt tgctgggagg tggtctgttt ttgccaactg aatggtctct    75180
gttgtgtgct ccatggcact gcagctgtcc gttatatttt ggatctctgg aaattttgga    75240
tgtgatctgc cagctaactg cttgaacatt atatttgtga tagggtaata cgtgctactg    75300
gtttatgtgt ctggttatta ctatgaatca ttgtatgtgt aataaatatg tttaaagtga    75360
atatctgcgc gctcttatat ttttactttt caatatgggc tcttatcagt tgcttacata    75420
tgtgtgtatg caccaaaaca gctggatatt tgacaagtga ttcacgtgtg gtcgtcattt    75480
gtcgagatcg ctagcgctcg ctatatcttc aaaggaagcc tcacaacgcg ccatgggtaa    75540
```

```
tgtaatcatc cccgtcggtt caatctgtct aatctgttaa aaaatgttca gttagatttg   75600
ggtaacttat caaatgtgaa ttgattgttt agttcgattt gggtagtctt atcatagttg   75660
aagttttgca tattccatcc ttgcttttag tttcctcttc aatgcttcct gcacagtaaa   75720
atgaatcata tccttgagcc aatcagtttg cactatgata atgtatttac tatgtagtca   75780
tgacacaaaa tggcacacga gacccagttc aaacatgaga cgcataaatg attatctact   75840
acaacaagag caacaataat gtatgttgtg ccatggaact aatacccaga agccttgccc   75900
agaatttccg catgaccgat tggctagcct tgattgattc ttggacctgt ttagctttag   75960
ctttagcttt tgtagtgctt aggccttcca tagccttatc acattcctct gggtatgtct   76020
ctttttcttt tctattttga ttttgatccc cactcttcgt catcaatatc caacttaggt   76080
tgccctgcgg ttgtagttga tgatgcacga actgactgca gcaaagtcat tctttccaat   76140
tccataatat gatatagata tcccttgagc tggacatcgc agaaatctat tagcaagacc   76200
tgccaaattc ctattagtca aattcacaca gtattgctcc tgcaacaatt atttaggttt   76260
tattctttcc tcaacctttg ctgtacaatc cttcagtcac ttggtattgt tgttttttgta   76320 ttgatgtatt tgaacaactc gataaactga ttgttattag gtgtgtttat atgccatgga   76380
caatctagaa tgaacaatct tatcatgtga gtcttactat tatcctttga agaagttgcc   76440
aaactttgtt cagtttaagt aaaaacattt aggagaattg taactcgtta cataatcaaa   76500
tacagttatg tgccaaggga aaaaatagtt cactttcttg gtgtcactga acagatatgt   76560
gcattccact aagtgtcaac tctcaactac ctactcaagt tcttggtgtc actaaagttc   76620
ttggtgtcac aaaacatggc cgcataacct tcttggtgat tgcattattt ttgtatttta   76680
gatgcttttc cgcttttcga tccatcattt tttgctcttt tctgccaaat gtaatgaccc   76740
tttattagag tgtatgcttt aataatgtga gttttccact tatttgaaat tcatgttgta   76800
tctcggatac ttgaaccaag acctaacttt gacaatggtg agccattgag tcgctgtttt   76860
cagtgtttct agatatgacc tactgtagca cactctaatg ccatatgctc ttcatgtgca   76920
aactatgtgc ttggcatgat cttaagaatg ataagttaaa accaaggtta ttaaaacgac   76980
gaaacgttga aacgctcatg ggtgagtttt aacttttaaa cggtttaaac aaagtttaaa   77040
cgtagtttta aacaacatag ggaaatttca atatatcata attttaggca attatatcaa   77100
gtcaaatacc aaacaaccaa cataagttca cataataata atgtgcaaaa tgacatgtcc   77160
acaaccacat taccacaata acacaagttc aactaatagc aagtcgacaa ctgcaaacaa   77220
agtggaatga gatgtctaag gaggcgggag tgcgggacag gcggccgga cagcaagcga   77280 gcaacagcaa gccaaggag gcggggctgg cggcggccgg acagcgggag tgcgggacag   77340
ggcggccgga cagcaagcga gcaacaacaa gccaaggag gcgggatgg cgacggcccg   77400 gacagcaggg ctggcggcgg ccgaacagcg aggctggcag cggcggaca ggcagggttg   77460 agcggctaag cacgggggag ggaggaggct acataggga gggaggaggc tgcacggggg   77520
agaaggcggc ggcctagagc gcggcccggg gagggaggag gctgcacggg gagaaggagg   77580
cggcctggag ctcgaacacg gcctggagtg cgaccagaaa gcgccaaccc tagacttggg   77640
cggctgggct ggaattgggc tgggccaaat tctagcaggt ggcaaataaa acgcccaaaa   77700
cgcgacgttt cactctatac cgcgtttaaa cgacgtttta caagaatcg caaaacgttt   77760 tgtcgtttca gttctaacca gcgttttata gtttaaacga cgttttaacg tcgtttttaat   77820 aagcatggtt aaaaccgagg tgtaagtaga actgtcacac acataacaca atctgatggt   77880
```

```
tatatgtgtc gtgttagttg tttgttagga ataacactac acacaatgac acaaaactga   77940
ttgtgtgagc atgctgtcat tattgggttt gatgatgaca tgaaatgcac tctaggtatg   78000
aatctcccaa ctaattctct ctctttttg  ctttgatcat ttaaaggatg tatttatctt   78060
gttcaatcat attaatttgt gttgctttac agatcgtgac gaggggctcc aagtgttgca   78120
ttataaagtt gggcagaagt atgagctcac ttcgttcagg catgtatctt caaagaggaa   78180
gagacaaggt tatttgaaaa attgaaaaca taatagcaaa ctataccttc atacccatcg   78240
ttatgtgatt ttttacagaa gtttatcatg gctacattac tcggtggtat atcagtgttt   78300
ctatagcata atttctcaca tgctttaatg tttctaggt  tgtgccatca gatcaagcac   78360
acaaaataat aaaatataca acgccttgaa agagaaaggt ttgcctattg ctttggttga   78420
atatgaagga gagcaacatg ggtttcacaa agtcgttatc atacttatgt tttagatttt   78480
cagcaccctc cacactgtca acctgcacgg atttgtgact tctttctcga ttttgaacag   78540
gccgagaaca tcaagttcac attggagcaa catatggtgt tctttgcaag attagttggg   78600
aaatttgagg tgtaactcga ttatttgttc agtatattag ccgttgcagt gtcttttgg    78660 aatatgactt cattttattt ttggaggatt gatcgaaaac tcattttgct ttgtaacgaa   78720
tatgccattt ggaaaacaac atgcaatggt ccagatttta catatcatag tgatgtttgt   78780
tgttctgtat ctatgtttta tactattttt taattcttgt tcctgttttg ttttccttat   78840
gtattaattc cttaacttgt aatgcacatg atgttttcct tatgtattaa ttccttaact   78900
tttaaagcac atgatgaagg ctggttgtcg ggtaagttct cttaaacttt ggtaagctta   78960
cgtactagct atggatcttt tgaattaatt acaagataat tcatttaaaa atcgtagtaa   79020
cacacgtgta cctaaatatc atatataaaa gtctgtatgg tactgatggt tgcaatatag   79080
tggtgaaaca aatagattaa aataacaaaa tttgtgtatg gataggatca caaatgtatt   79140
aagaaacctt ttctcataac agtatcgcgg tattatatgt ttccgttgca acgcatgggc   79200
actcacctag tatatcaaat aaataggtat tgagatattt attcaaatat aattattgtt   79260
tatttctaaa cactaaggta cgtgtggttt ggtggttaac cccaattta  tgaagcagtg   79320 aggcgtgggt tcgagtgttt gctctgcact atttttttgtg tggtgtggta aatgcgcgct   79380
cggggtcagg tgctggctgc gcaggcgctg gggtccatag gacagtagct cagagagggt   79440
tgtgtgggct gatgtgggc  gtgtcagcgc ggagggtgaa gccgtgtacc accagatgcc   79500
cacattaggt tcttaataga gtagtataga ttgtactgga gaggacaaaa gtgctcgaga   79560 cacctttat  tcacaacatt gccctcaata gccgagcgcc acgacctatc aaagccatcc   79620
tacaattaca aagagcattt tggtgagtgc taagagcatc tccatttgtt ctctaaaaaa   79680
agctccctga actcatgttt ataaagttgc taaatagtta ttgagagtaa aaaaatagtt   79740
tggtctccaa caattcccga tatttagagg ctattttaat tttgaatcta gatttggtgg   79800 gtccatttc  tgcttttca  tgacacattg cagacactac agaaggttgt cccatgatgt   79860
agaccttagc ttgacatgtt tattttttat catatagttt gttgtcatat gcgaataaat   79920
agctactata atttagtgtg ataagaggct tccaatccta gctcagcttc ttggtctgaa   79980
taaaagaatg tctgatgcaa gcatacatag ataaaaacaa tcttgagtag tatctgatta   80040
atgtacaact tcagcacaaa gttctgatat tctggaggtg tgtgtaacag caagactctt   80100
gagtagtatc tggttggcac ggaagcggcc gaccacggga aagggaaaaa atcagagcga   80160
aaaatgtttt tatctagaga gcaaataaga ttacataata attaactaaa tttagcaagt   80220
ctttttagac aactattaga gaaacatttt cattcacttc ttaaatttaa tatttagaga   80280
```

```
gttgtttaga ggatgtggtt ggcaaatcta gagagcaaat agagttacat aacaattaac   80340
taaatttagc aagtctattt agagaactat tagagataca ttttttattc atttcttaaa   80400
tttaatattt agagggttgt ttagagaaca cagtctcgcc agcaagggga ttgaattata   80460
tggccctcaa tccccctccaa ttttcataca tccaaacaag cttagtgcat cttctaccaa   80520
gcccttagtc catctgctaa gttctaggac gttttagctg catccaaaaa tatggctttc   80580
cccaaacgtg agaaatctgt tcagcggtcg tatataccac aatacaaaat caaactttgt   80640
gttgatttaa cttatattca cttattagca gccgccgacc attgctgccc cacgcatggc   80700
atcaccggcc tatagccaca tctgactcta gcgcctcgcc tgctgcaccc actgcctaca   80760
cccctggagc tgagcaagtg caagacttta gacccatttg cctcgagaac tgcattgtga   80820
aatttatcta aaaaatccta tgtacacgtc taggatggaa ggggacatag catgggggtg   80880
aggatggaag gtagaggaga gcgacattca cggtggctag aaagggagcg cgatataggg   80940
gatcatgaca ttgtctccgg gcatgcgcga taggacgtg ggctggcaac gtgaggcgca   81000
cggttggtgg ggggggggn nnnnnnnnn nnnnnnnng gggcagagc ggggcattg   81060 ggagggtgtg gacgctgaca ctacattcat aatatagtaa tatagatata tgcttttgcg   81120
agcgaatgga atcctcatca accgttttg gctcgtgcgt ggtactggcg agcaacaggt   81180
agtaagcaca gcaccacgcc cctgggccat ggccatgact ctgtgagatt ctgcaccgga   81240
gggcgttact gcactgcacg acatcaatag gtactacagt ataatgccgg tcctcggctc   81300
gcgcgtccgg tcgcagagca gcagggcggt cccgtcgctc tgtctgcatg cttagacacg   81360
gctatggcgg atggccgcac gcgctatcag tgataggctg cacagcacag ctgctggcgt   81420
ggggtcgttg cgctctgact ttgatgagta cggcgggcat ggtgtgctgc acctgcgccg   81480
ctgcgtgctc agccttccgt ccgcccacga aacggccgac tccttccgag cttaagtcca   81540
gaattcctat tcctcatcct aggtgtatca tttgaatata ctaggctcca tatggaatgc   81600
gacaagacaa ttcttctcat gtccttcgag aatctcatta agtctctcct tgccagatag   81660
aatagaagca tgccttgctc ttttctctct ccctctatta ctaattaaat aaagagcagt   81720
ggataaattg ttcacgtgaa ggtaaaagtg caccaaaacc aaatgataca cctaggatga   81780
ggaataggaa ttctggacgt acgcaatgta aggctggaat caaattaaaa aatatatgat   81840
gaaaaaatgt ggtagctgca aagattgaac tggtgaattt ggagcataac catgagttca   81900
taactgacga agcagagaaa caacatctac gttgcaacaa aagtcaggat gcagaattca   81960
taaattttgt tgatgcaatg catgatagcc gagtgcccca gcattgcata gttgatttta   82020
tatcagacat gcatgatggg ccggagaacg taccggtaac tgctcaagtc tgaaaaacat   82080
gtaaggattt ttttgtgttg actatgtata tattgagtgc catagatatt actatagtaa   82140
atgtttggat ggtcattttt tgtacaaaaa ttgtaggagg gcagcaacga gacgagaaaa   82200
ttgcgcaaat gatgtagcca aactatgtc tttctttacg gaatgcaaga aacagaatcc   82260
acaatttttt tgtgtttttc agctagacaa ggatgagaaa atagtgagta ttttttggtc   82320
acacacaagt atgcaggggg aatatgcaga ttatggtgat gttgtgacct ttgatacaac   82380
acacaagacc aatatatatg ataaaccact aggcatgttt attggagcta acaaccatct   82440
gcaatgtact gtgtttggat ttgtgttgtt gggagatgaa atagttcaaa cttttgaatg   82500
ggttttcaat tcattcaaaa catgtatggg atgcgaggga ccgagagtta tgctaacagg   82560
tatgtggtat gtgaatttgt tatgctaacc cgtcaaataa tttattgtga tagtcaaata   82620
```

```
atgttttgtg agcaattgca gatcaagatc ctgcaatgcc aattgctctg caaattgtat    82680
ttccaaaaac aattcacaga atgtgtttat ggcatgttca gaacagattt atgccattct    82740
taaatgaatt atatgcaagg tttgctgata aagattttaa aacaaaattc ctatctatta    82800
tacatcatcc tttaactcct cgtgagtttg aatgtgcctg ggaaatgatg ccagaagaat    82860
acaatccgca tgaagatatg actctacgca agttatatga aataaggaaa gaatggatac    82920
tagccttttt taaaaatgac ttctgtgggg taatgatgtc tacacaacgc agtgagagca    82980
tgaacagatt agtgaagaaa tcacatgtag atgcgaacac ccctctgcat gagtttgcta    83040
aacaaatgat gaaaatgttg catagcagga aaatgaaaga atcaaaggag gcattgatga    83100
gcaaggtata tcgtgtttgt tatcaataat caatgtatac atgtttatgt aattatgtta    83160
tttaattatg acgttaacat cttataggga ccaaggacaa ccgatacgtt gtataggttc    83220
gaagtcaaag tctctagggc atacaccaga gctgttatga atatatttga gaatcaatga    83280
aatacgccac tgcatataga atattgaagg acacagacgg ttgtgataaa gattggatcg    83340
tacaacatac aaaaagatct aataaaattg tgtggggaca acatcaattc aagataacag    83400
cggacataga agctggagag tatacatgcg agtgcaaaca gtggaaacat acaggtttga    83460
acatcaaata attatactaa taaaagtaca tatttgatag ctttgttttt aattgttaaa    83520
tataataata tatatcatta acaatataat gattattctt catgattgca ggtctactat    83580
gtgttcatct tttaagagcc tttcatgcat ctacaagtag aaaagatacc ttcaaagtat    83640
atattgcaaa ggtacactgt ctcatcaaga caagatgtac cgttcgaaag aattgataag    83700
agcttcaggg gaaaggatgg agttactaaa tcatacagac ataaaatgtt gctaacgaaa    83760
acaatgaaag ttgttcgcca cgcgtgtatg tcaaaagcag ggtacgataa ggcaatggat    83820
gtgttgaatg agcttgatgg cgttctatgc cgattggagc catacattgg atgtaatgag    83880
tcatgtaatg ttattgatga tgaggaaaat caggtaataa aattcatttt ttgtaatgtt    83940
aaactaattg gaacatatga gtatgtatgg tcatatattt tttgtaacag gaaggagaaa    84000
taaataataa taaggatggg gagggaatgg atgaagctga caattcaatt acatgccaca    84060
caatagtatg taaaagataa atatataatc ttgcatgaaa tagtgtatgt aatgaatata    84120
tgaaatcact ggactcaaaa atattttata acgtaggatg atcataatat tatgaccgga    84180
tgtggaccta cgttaaaatt tttaacaact ggtaaacagg taaatataca aaatttggtg    84240
ttcatttata tataatgcaa tgatgtttat gctacattga aatgatgatt gatttgggtt    84300
atgctttata ggtggacaac atgaaaatac aacatgtgtt atgtgataca agttctccgt    84360
tacacgtatc acatgaccaa atggaacaga tgggtgcatc ctcagaagct aaaaaggtta    84420
gccttgataa ctggtttttc taagtggtac atatgtactg tttatttata tgtgtatagt    84480
aattaatatc gaatttgtat tatacagcgg ttgaattttta atgtggatgt tataaatctg    84540
ggtatgccgg atcgagcaag accaaaaggt cggataataa aaaatacaga agaaggatt    84600 atgaaactag gtgccaaagg agaaaaagaa gaagaatagg agatgccaat tgtgtggaat    84660
tgcagatgga cataacagca ggacgtgtct gtatgtggaa gagaacaagg caagactagc    84720
aagagtggct aatcgaaaga gaggacgacc ggcgggatca agactcaata gtaaaacaac    84780
tgctccacaa tggaatgaaa cctcgactgc taaaaacatt gtattgatga agaagtagac    84840
aatgaatcaa ccggtgaaca gatgggtttg ggtgaagaat tagatgtggg aaaatagaga    84900
ggttgacgta ttaaatattt gtaatagcac aatgacatct gtttgtttga ggtaatcaat    84960
attttgcatg aatgggttat ataatgcttg gatataacgg attgtgccag atcagtatgt    85020
```

```
aaaacaagtt tagaatgatt attacttatt atgatgtgaa catcataata agtagactgt    85080
attaacataa atatattgta taggtagcag tcattagttc caaagttata caatgataat    85140
ttagaaaaat gaacataatt gtatcgaata tatgaaacta taatatgttg cataacactt    85200
gaacattatg gaaaatatga aactagatat aagccaacaa ttggactgga acgattaaca    85260
gtgtgacaaa ctggacatga atggcataga cacttgggac acttgacata actaaacatt    85320
cagttaccac agcggtttta cacacttgac ataagactga tatgaagtag cataaacgct    85380
ggacatagta gacataagtg ccatgagaag tagcatacaa gtgtgcaaca cttgccataa    85440
gtgccttagg aagtaacata aacagttgt ggatcccata cggaatcttg ttcagctatg    85500
atatctaggt cctggctttt aaacaacgtc gtttccttgg aacatacttg aaaggcagca    85560
gttctgcagg aaggggtaa accctgttgt tgcgatgaaa ggtcaggtaa tgcagaacaa    85620
atgcatgttg gtccattggt tcatcctgta atagtcataa tagttgaatt aatgttaaga    85680
aatagtatga aaaagtaatt tatgcagtaa caaaaaagga atttagtaac gtactggtac    85740
aacaaattct gagacatcgc catcatcaaa gttgtagcat cgaatgaagc tagtgacaaa    85800
aaaaccacaa tcattggagc ctggtagcat ggttggacag ttgggaagaa gcccaatctt    85860
gtagttgcaa actttggtaa acaagaatct ggtcgagctt cgtgtaacgc caagctaagt    85920
cttttcatga ttaatctgga ccaaggtggt ttcgttacat ttatcatcac ttgatcattg    85980
tggatatgtt tctaggtagt gccaccaagt gatggcccat aaggatttga agctaaaatg    86040
tctattcggc gaagctggaa attgattgca tatagggtcc agtgactacg gcgtagcata    86100
ggaaccatga tatgttaaca tatatgtata tggtatgaat taacaatgat atggctgtag    86160
aaaaacagat aatatggact tggtaaacag ataataactt acaagaataa tgagtgaaca    86220
tccataaatt gttgtagtta tgtttgttct gttcctcttg tgccaacgac tggcagcatc    86280
acacagatca gtatatacta attgacacca atcaatctca gccatccggt ccatgtttgt    86340
tgtcattagg acctcgttgt tcgtaatacc ccatgaagca gatgggaata gaaggcgatt    86400
gaataaaatc agaaaaaaca tctgatggat aactcatcat cattcccaat aactagcttg    86460
tcctgtagct taacgacatc aaactcttct ttacaaatat tgagatctcg tctcagtttt    86520
gaagcagcgt caatttcacc ataccaataa gtgaaatccc tgccacctcc aacacttggc    86580
aatcccaata tgagacgaac cgtctctttt gtgatcttga gttctttacc agcccttggg    86640
cgtattgtca tgccgtctgg atccaactta tccaccaacc accttatgag agacctgctc    86700
tctaatgcat cgtgacgcaa atcaaatata ctttgaaatc ccaacctagc aacaacatca    86760
cgctgtcgat cactcattat ccaagttgac acaatgacat catacgggat gcaacggata    86820
ttcaatttct gctggaataa atgaataggt attaatacac aatgtatata tattgttaca    86880
actaaggata atatagttct acatataata tttattgtat ggttgtaaat aactatagtc    86940
taacaacact aacaaaaata aaaagcatac caaaataata atatataaaa tgtaacatttt    87000 gggtaataca acattgatta tgcaccaaaa ttaacaccta aacaaaaata aatatatgca    87060
tagtacctgg gattttttgg gtgtcctctg tttgggtgag cttgttttca taatgttctt    87120
tgacttgaca tcaatatcag actttgatct gcttgacaca atggagactt gtgggggtgg    87180
gatgtccatg ttcaatacac gagacttctt ctttgaacgg ttatttactg aagtggaggg    87240
tgcagctaat ctgaaattgc gcttcaatgt tggagtagcc atgaaatcat cgtcagacaa    87300
tgcggatgga gctgtaggct gattttttg acccgacaag ctagcgcctt tctacgaacc    87360
```

```
cgagtaactg gtaatggttg aggatcaatc tgctgctgtt tctagggatt atcagcatgt   87420
tgggctgagc tgctagatct tgtgtgtctt gaaatgtcaa cagaaaacac ctcctgactt   87480
gactcaatag ttaatctttt tacattagat ggtgggcgat caatagacct catgattcag   87540
caagcaatat aactgttgac aaaaatgatt ggatttaagt aaaataattt atgcataaat   87600
atatgccaaa aacaattcga atattgtata taattgtata caatgcatac tacataatac   87660
gaaatggagt tacgtatctt aaactacctt ttccggttat acgccataat attaatgaac   87720
catgtttata tacaagcata aatattaatt aactagttca tataattgca actagtgcat   87780
gataaaaaat tcctattttc atcgactaac tatacaaaat atttaaataa ctagttcata   87840
ttaatataca caatttgatg agattcaaac atggatattt aaataactag tgcatatata   87900
acagtaccgg tgtgcatata tatatatata tatatatata tatatatata tatatatata   87960
tatatatata aatatataat acaatgggta tgtaaaataa tatttcagat atcgggaaaa   88020
atacctatgt gcataaatat catgaccgat gttcataaat agcagtaccg ctgtgcataa   88080
acaacagtgt cgattgcata tatatcagta ctgatatgca tatatatata tattactacg   88140
ggtatgtaaa aataatctct gcaaactcgg gaagaaatac ctgaaccggc gacgttgcca   88200
aagtatttga agatcgagcg ataccaagga tctaaaagaa ctacagaggc tcttcaatcg   88260
gggctccaga atcaaagaga gatgcaatga gaggtttttt ttgtaagata acacacccga   88320
ttagagaaat gtgcaaacag attcaaatca aacacagctt ataactaagg gaaatatgca   88380
aaacgacttc aaatcgacaa aaataccctca acggcgaca gaaatctcga tgtgtttcaa   88440
gttggagcga taacctggaa cttcatggga agcaatgact cttcaatcgg ggctccaaaa   88500
tcgcagattg aatgagcgga gatggatgga agaggcggaa gtcgcctggc aagtcacctc   88560
agccgccggg attcaggggt ctccttttg ttcggcggat gcagatgcta gaaacccta   88620 tggacttggg tgggtttaac tcaagtgatt gcgcgaagac agttttggaa accgggaaac   88680
gggggagacg tgcgtggcta acggcgatca tgagtgggta tatgctgacc aggtttggtt   88740
caaccaaaag tgcatattga ctggtctgga cttcctctat tattagaagc ccagggctct   88800
ttatatatcc taaaccgtaa acggtcgatc atcctctgtt tagcgtttaa tcggactata   88860
tggacgttca aatggattat tatacgggat taaacgaatt aaacggccta aacggttagt   88920
tacagagtag catttaaatg gtctaaatgt ctgtttagga taaccgtgct atatacacga   88980
ggcttaccta gcagccttca tgttgggaga tgtgaactgg tgtggttagc gtgcttgatg   89040
ccttgtaatt gtaaatggag atgaggcagc caagacgaag gatatttat gtgggttttg   89100 ttaatgatta cttatgttgt gatgagtgaa attgtttcag attgcaagga atacatagat   89160
ttggacttgt ttgactggac tatgctagat ttatatcaat cagcagatca ttaccacaaa   89220
aatgattttt ggttaaaagg acgggcacat taacatatgt accacccatg taaaatgttt   89280
ctattttaat cgtcaatttt taaattaaag atggtatttt aagatgtatg tttctgaaaa   89340
ttattgtata attacaggcg tgggcatcta gcagtttcat ctaaaaggta attcataact   89400
tctctatatg gacatggatg cggacaatct gcaaaaagaa aaattatctg aaatcaccta   89460
atatcccaaa tataaacgtt agatttctca tgttttggag tacaaatttt cattttctt   89520 tcgaatgttc acgaacgaat gggtgctcat catccaaggg agggagaaag agatagatgt   89580
atcattttgg cacaattata aaagtgtttg ttataactat tagattttca ttcttcttc   89640 gaatgttcaa gaacgaatgg gtgctaatca gctcagggag ggaggaagag atatagatgg   89700
acatcggcgg tgctgttgca acgacgtaac tagagtcacg tgtagaaagt gatgtgtgtg   89760
```

```
cattgtttaa ttagtgacca cttaaaaatg atgggaccgg ccaatgtact tgacgacttc   89820
ttttaaacca attagaccac atgcatgggt aacacatgcc tcactaataa ttaattaatc   89880
acgcacgcgt tgtgtttgca ccagaagtca aagtaatcca tttcccctat atcatcagtt   89940
ttctatatat ggacacttgt tttgaatatg taggccaaag cagctgaatg tactctccga   90000
tcctccgcat ttgtacgtta tgactttaac agataacttt tatatattac ttctaaaaca   90060
atcgggtaca acaaaattgt acttctactg tttatacaag catgtttgct agggtagaca   90120
agcctgtttg ctggggttta attcgtactg acttatactg tttatacagt gtttcgtcta   90180
tagattatag ctgcagcggt ccaaacagat agctttaatc cgaagcgaat aagtggatta   90240
atagaaaaca accatgaact ctacaagaaa gcaatgccag ctggctgaca ataatgcgtc   90300
tagccgttta agtcttggac gtctaatctc cagccttttc ttatgcgcgt acagagtggc   90360
agctgccttt tcttaatagt gaattaagaa ccaatcatga ttcttatttt atgaaaacaa   90420
tgcaaaataa tattatagaa ataaattttt ttagcattt atttctaatt atccgtgtgg   90480
cggtcccgat gtctataggt gacatatcaa atcataacac cgtcacttaa aaataacctg   90540
aaaagaaaag aaatgtggaa aacggtcgga aaatcacctg taaatcataa ccacgttgct   90600
ggtcgtcctg catgaatatc ctgtataaag aagtgaattc aggatgctgt acacaatgtg   90660
aaaggctttg cgccgttctt ttttctttta gaaaaaatgt gcacgtggtt gtacttgtga   90720
ttctatatga tatgaacagg aaatattcat gaaagccttt gtacaatgca agatttagaa   90780
ctgaagtcag agctgtacac aatgtgaaaa tcatggatac tggtcctcct gcaggaatac   90840
cctagctaaa gaatagaatt caggacacta gacacaatgt gaaatgcgga ctgaatcagc   90900
gtagccctca acacacacta tatggccgca caagtttcta aagatgctcg ctctcaacag   90960
atgatcctgt tttctgcctt aaatttgacc gatttgcata tatatataga gatcagctga   91020
ccaaaatgta tcctaggctg agatgactgt gcatatatcg agatccatct gtagattaat   91080
tccactgaac aaaatacaac taattgaact gcccggggaa cgacccgggg caaaaaacaa   91140
aaaaaaagga aaaagagga cctgctaaac accaaggaga ccttaattag gaactcatat   91200
ggctaacttg aactggtcca cctcctcttt gacaataaat gcattttgta ggggatgaca   91260
cattaattgt tgaaaacttc ttctatttat gtccttccaa atattccacc ataaaccaac   91320
aaccaggcca tcaaagtctc ttctaacgga caactataat cctgcattta ctccaccatc   91380
tgataaggga ctcgccttaa atgatagctg gtaaatggtt aaggtcgaac cagctagcta   91440
gctgattcca aacttgtcct gagaaaccac attctttaca gagatgagtt ggtgtttcta   91500
gcgtaatgtt ataaagcttg cagattggat catgtggcca attcctttag tccaagttgt   91560
tagcagtcaa gattgttttc taaggagga tacaagcaaa gatcttacac tttggctccg   91620
atttagcttt ctagatcagt gcaagattga acattttaga tcttccaaca aattggattt   91680
gttatgcact aatattggaa tcattaccat tggatgtcca tttccacatt atttcatcct   91740
cggtggattc atctctattg atctcttgaa ttgcctccca caaggcaaca tatttctta   91800 tgaattgttg tgttgtgaac ccatgttggt gagaaaccta ggcattattc tgcagagctt   91860
tctgaacaat catgttcttc tgtctggatt tgctaaagac atgaggtgct aggtttttgg   91920
ggcttgtcca tttaaccatc ttgaatgcaa gaagagggct tgttgccaa taccaccagt   91980 aacaatcgtg gaagtgtgga ataagtctct atcgcttttg tcgcaaggga tatccatgtt   92040
tgatcagggc ctgtcactat gcttccattt aaaccaatac catcttagcc ttagtgccct   92100
```

```
agcgaactgc tcaaggtcta cgacgcctag tcccnctaag tcttttggtg tacatactgt  92160
tggcaactta ccaagcagcg accaccatta acattttcta tctccttgcc tttccacacg  92220
acacttctcc aatattgatc gattttcttg attaaccatt tttagttgag aaaacagtga  92280
gatggtagat aggtgcgctg aaaggactct cttcaccaaa gtttcacatc gtaccaatga  92340
aaggactatt ttcaataata atgctagtaa gtaaatagg gttaatccca cattaaaagt  92400
gcaagacttt agccaactta agaggtggac tttgtgtaca ccatctacaa agttagaaaa  92460
ggagactagt gtgtcccacg cgcttgctcg aggtgtcggg ccatgtcgtg ctgtgatgag  92520
ataaatgttt tgccattata taatttaatt aggtggagta actcataacg taaatggaat  92580
gataactact tgaccgttac atcctgtaac tgttgtcact tgatgttca tcaatgcaca   92640
tcagagagcg tataggttta gtgaatagag gtcctcttgc acctacacaa gagacatgca  92700
cccttctgc tctcttgact aagtcacaac taaggtcctg tttggaagca cctagttttt   92760
aagaaactag tttatagaaa ttgaggtggt tccaaacata ccagtttatg actcagttta  92820
tagaaattag attcagtttc ttaaaaacca agaagttggc ctctcctaac taaaagataa  92880
aaattggttt cttaaaaact aggttgcttc caaacaagac ctaactggta ttcctgcttt  92940
tatgagagct cttctttctc cctttgtgtg ttttcttcct tgctacatat tttgcatctc  93000
ccacagacct agaaagagta gacctctgaa gccctgtcac acagaagatt ctgctaggat  93060
aagtggagca acaagatttc tgtagagagt cttcacatga ctgctcattg tatgagtact  93120
tcctgaaagc catgaacgac tactttcaat caaccattcg acactaccgg aatctagctc  93180
tttaaagagt gctcggtgct ttaccgagtg cattttgtcg ggcactcgac aaagcattct  93240
ttgctgagtg ccactctcgg tgaaataaga ctcttggcaa tgacctcatt taccaagagt  93300
gagacgctcg acatagacgg acactcgaca aatcccccctt tgccgactat caaactctcg  93360
gtgaaacacg acgctcgaca aatggtcgtc agcaaccgtc tatagctaac ggtcgttaac  93420
tttgccgagc atcaggcgtt gacactcggc aaattcatat tttggtgagt gtctttcttg  93480
acactcggta aagtatattt tcaattttt tccttttct caccaaactt ttttgtggtg    93540
tgttcctaca ctatatagag ctacatgttt gattttagca caattataaa agtatttgct  93600
ataactatta gactttgttc gtttaattga atttcctcgg ataattcaga tttgaagttc  93660
tatgatttca tttaaaggac acttaggttt ctacactatg tagaaaccta gccgatctag  93720
attgaagttc tataatttca tgtgaaggac acttaggttt ctacacatag tgcgtgacaa  93780
ttttcttgaa acagtctcaa attttttatct taggctctac atatgatatc atgcatgtt   93840
gacaagtttc ataatttct gactttgttt gtgttttata caattttaaa ataactggat   93900
cacaagttca cggtcatgtt ttgtgagcat gatgctagaa aattctggca tgttcctgaa  93960
ataggccgta acttgtgcta aacaacatga atatcatttt gcattcattg tttacatttt  94020
tcgagtgact tgcagttcaa atctgaatta tccatataaa ttcaattaaa cgaactaaat  94080
ctgatagtta taacaaacac tttgataatt gtgtcaaaat taaatatgta ggtctacata  94140
ctgtaagaac acaccataaa aagtttggtg aaaaaaaga aaagaataaa aatatagttt  94200
gtcgtgtgtc aaaggaagac actcgacaaa acattatatg tcgattgtct gccagtggac  94260
gctcgacaaa gaacttttaa aaaaattaaa acaatctttg tcgatttctt atcagtggac  94320
actcggatcc agaacactca gcaaagtata ttttaaatt taaaaaaaat ccttgccaag   94380
tgccagaccg cgggcactcg gcaaagccgt cgaccatatt tctaattgtg ccttcaccgt  94440
tactgctcgc catcgtcgct cattacttgc cgacgtcggt ccccactatc cccgtctccg  94500
```

```
gccagacgtg ctcggctcgg cccctcgccg ccggccgtcc tcggcttcgg ctccgccacg   94560
gccatcgccc cctccctagc cgccgaccac caggcccttc cccggccatc ggccaccttc   94620
cccgtacgcc gtcggctctc tccatattca aggtttgtgt ttgtaattat ctgggtatta   94680
aatattcatt acacgattca ctgaaataaa tacaaaatta ttcacttcct cataaattac   94740
tatagtaaaa tgtagtggta agattgtttc atgcaaagcc tatgcctcca ttttaatttc   94800
taggcacaca ttctgagtta tttgtcttgg aatgattacc attactgtga ataaaatcat   94860
ataacaacac aaatctacat ataagttacc tacttatgct atctcggtaa atactatagt   94920
gatacttact tgagcggtgg ttttagggca ttctagtgaa tctgctatgt ttagtaaaat   94980
agtttctata tattgtgatg gtggatatgg atgccgatta gatgtgactg gcagccatcg   95040
tgccatttgt atatgtgcgt gtcagccatc ctgctgttac tttatttac aggatttgaa    95100 aacctccccg tgcaggggag gtgctgccga aatgttttgt tgacaggctt gtttatttt     95160 tcagaggtct tcctacccgt tgcgggtcta tcagcaccgt gtcgcgtcgc cactgcaccg   95220
acccgccaca gcctcgctag cctgactcca ttgtcaccat aggtataacc tctatttccg   95280
catcatggtc gtagatcatg taacctagct aggcatctcc cattcgaaag agatacgata   95340
tagatatgca gatctttgca tatctaaaaa tgtatttgtt tcaaattgtc catgtttttt   95400
ggacagcccg cagttgcgta gatggtgtta gtttccatgc tctactctag tccaagatag   95460
agtttcggcg tcacctcact gttgttctcc agacaataca ctctccgtgc caggatgtgt   95520
atccgaagaa cagtggggag gtgctgccga aactctctct cggatcggag tagagcatgg   95580
aaactaaccc tatttacgca accacgggtg ggagtaggac ctatcctcgc ctattagaag   95640
gtaggaacgt agtgtacata cattacatgt ttattaaact atactcggtt atatatgtta   95700
gagaatggag gaccgtgagt agatgtacat gggctgtgta ggaaggaatg atgtcacccc   95760
tgaatggatt agaaagacca attctttcat ggaacaagca tttggcaaag cttctaaagg   95820
agcgagtcta gtcccatgct cgtgcaacaa atgtgccaac atgaaaaaac aaagaaggcc   95880
atgataaaac atatttggaa gaatggattt acgccggact atactcggtg gatcttccat   95940
ggtgaagcac accgtacgag agaggaggtg gtgagacaac gtgtcgagga ttatgatgct   96000
aatgccgagg tagcagatat gttgaacaat tatcacgatg cacagtgagt acacatccat   96060
ggcacaagac gtccatgggc cagattacga tccgaggata gaggacatcg acagagatgc   96120
cctcatgagg gtcggaggag gcaagaggta tgtgcagtac tggattgccg acggggcaat   96180
agactcgtcg tccactccca ctctgtctca ggtgcgagca aggagcacga gcacgagccc   96240
atacatacga cctcggcagg acaactcaca tcgtcagata caacaactct aggttagtgc   96300
ttctgtaact cgtcattact tgagttatat atcttctctt tgagttatta taacattggg   96360
gtgaaatatt acaggcccaa ctagaagaag agaggagaga acggatggag atggaggcaa   96420
ggatgagggc ggagcgggtg gatcgcttag cagattagca gaggatggcg gaaatgttcc   96480
agtacatgca gagccttggc gccgcatagg gttttgctcc accacctccg ttgttccctc   96540
cagctgaccc tgctcaattc catactcctg tgagtatcaa aattctagtc ctgcatgatg   96600
tatatccatc tggtataaca catgtaatct cttgcaggga caatttgcgg catccaacta   96660
ccctcatgga tcgcccagcc catcgccgaa ccagtccaac cgcccacctc gctgatgttc   96720
ttctaaactt agttgtgaga catgtttatg ccatatattg gatgtttgtg gacttattta   96780
tgtgagtact tgttagtgat gtgaactatt ttgtgatact tgtgactttg tgaagaaaca   96840
```

```
tgtgatctttgtgagctatgtcgtgtgtttgatgtatgtgatgattcttgatatatgtga    96900
tgtatatgtgatgattttgtgatatacatttgtttgtttggatggaatagcaaaaacaa    96960
ataaaaaaggcattctggtcactttctcgagtgtaacactcggcaaagaggtactttgcc    97020
gagtgccataaccatagcgctcagtaaagaaggcaccccctgggaactggtaaagcttctt    97080
tgccgagtgttgtggcagcgagactcggcaaccaagcaacctttgccgagtgccacagtg    97140
acaaaggggaccatgaggtgcttctttgccgagggccggtacaaaaggcactcggcaaag    97200
agggagccttgccgatagtcatggtggcacacgacaaagtctccgtcactgtcacctggc    97260
gccgtgacggtgattttcttagtgagaactaaatggagtgcctgacaaaaagtacttg    97320
gcaaagaagctaaggccgatgtacatttcaccgatactgctttggcgactcgccgagta    97380
ttttctaggtttgccgagtgcttcagacactcggcaaaacaattgtgtccgatagtgcga    97440
gggaccgtatatagcatgaactcttcattgcaaccgtgtagcatggttactccagttggt    97500
aacggcgcatctggtgcctccaacactagctagccccgtcttagagtatatttggaattt    97560
attttggttcttattaattttgtttgttcattcttaaatgactgttaaatatgaacacatg    97620
tgcatcatgctatgcttgactcacaaaaaacatggtgattaattgtctatgtatgatata    97680
taaaatgtcattgccgagtagtaggttgactgatagagatatatcacagagtttcatct    97740
ccataaaactctctcatcttacattagatgaaactctcccataactctcctagttaaatt    97800
acatgtgatgtcatgcatattgtttgctaataatgtggcaatgtcattttttaataagaa    97860
tgaaactctcgtgaaacatctagtatactcctatatacagtatgtaacttgcagttggtg    97920
ctgggtgattcaggcaagtgtgagccggcgggcggacggtgaggtgagagggcagttccg    97980
gcggggccaagggcaacaacgcacgttatattcagcaaccaacagcgcgccatgcctgc    98040
atcaataatcatccgtgcatgcacgtcggacgtgtagaaaacatggaagaaaattgaaa    98100
aataagttggttataatagttggattgatatgtatatttttatgtgtagagagatatag    98160
ggaaatttataatgaggacgttgtgagaagagtgaatataaaagagaatcttgctga    98220
cgtggctgtcacaaatgtttccccgtcgcctcccctccctggtacaaaagcaaaagcacc    98280
aagtacaaaagcagaagccctgtgatcctgcctataaataccgtaccattgaagtcctgt    98340
catcatagttgagcacaagcagcaagtcgatcgtgagcagctcttccctgctcatcgtcg    98400
ccagctggtccaaaggaggagaagagatagatggacgtcgtcggctgtgctgctgctg    98460
gtggtggcgattcaaagcaggttcgtacgtacgttgccctttttcaattgcagtttttttt    98520
ccaactacagtgcattgttccgtacactaccggaatccgcgcctttgccgagtgtgaaa    98580
gtatttgtctgagtgcttttatcgggcactcggcaagagctctcggcacagggactgg    98640
cggtggggcccctggacctgttttttgccgagggccccacactcagcaaaattggtctc    98700
tttgccgagtgccacggacggcacttggcaaaggatccgtcaccgtcacttggcgcccgt    98760
gacggtgactttctttgccgagtgcccgacaaaaagtactcggcaaagagactgttgcc    98820
gatgtacagttcgccgagcgttctttgccgagtgttacactcggcaaaacctttgccgag    98880
tgtaaaatagccctttgccgtgtgtctcaggagctgattccggtagtggtatatatata    98940
tggagatgaagaactcattcatatatatatttatttcctctattttctagctcttggttg    99000
aaacagatggaacacacgcacgcttatttgaacaggccaaaaccagctgaatgtactct    99060
cccctgcaatggtacgtacacgttgtgactcaagatcgaggtcgcctgcagtattatac    99120
ttcattcatgtttgctgattaattcatgatagttgttgctcatgtcgttgcaggttaag    99180
ggactcctgagctgtttcactgcttatgtgaaagatgatgagttaagttgttgattatg    99240
```

```
aaggtatcta gctctcgtac cacacagatc gtttgaactg taataattga tcaatatttt   99300
acaagttttg atatcatcta taccaaagct gtagttttca acgcaacctg tgcaactttta   99360 gagttcacaa gttatagaat cgagagacat gtcagtctca actatacatt tcagaattcg   99420
tatttgtttt taatcttctt actatcttgg acgaagaatg catcctttag cataatatat   99480
tgttgagctc aatgacacct atataagcta cgcggtgaaa caattttaat ttggaatcat   99540
ataatttcag gtctaaaata ttcaccgcaa aattatgtaa tgtagtaaaa aagatatagt   99600
atcatgccat atatatgatt attctgcgca gctgtgctga tggtccttga tttaaccttc   99660
agagacactt ttttttggatt ttgtggaaat cgttaactga gggcctctta acacgacagc   99720
gtccatgaat ggcaatacta tacatgttgc atgcctttgt tagagtaagt atagtaacag   99780
agtataagaa gtctaaatgc tgtgttggag gacagagaag atgagacaga ggagaatcag   99840
actattatga tctcacaatc gatttagata cgagaacaaa aaaaaaacct gacgagagag   99900
acaagttaat catacattaa taataaagag ctaactatta tacaagtggt ggttgcaaca   99960
atcactgcag ctatcagttg gctatatcat tagccttgtc tctttgttga ttagcggagg  100020
ttgcggcctc agttaatgga ttaacaaagg tgggtagccg gcccaagaca ataatggatt  100080
aattttatct agtagatgaa attatttctc atttcttgtt ataagaactt ctaaaactta  100140
cacaataaca actataattt tactatctat aggaagctat atgtcgatct tatgtttgtc  100200
attgtattga tgtatcacat gttttcatcg agctatcaca tgttttcagg gttctggaag  100260
agcattttgt gctggaggtg atgttgttgc tggtgtccag acaataaata atggtacaca  100320
caccttgcat ccaaaaagaa tgtaatttca gaatttggac aattcagact ttttaatttt  100380
aatcacgttt atatgaaaaa acatcaatat ttatgtctct agttaggttt attatgaaaa  100440
tatattctat aatcaacata tacttattta gcatcataaa tcttccactt tttcataaat  100500
ttgttaaagt tgtttgactt attggtaatt aagagttgca ttcttttcag gatggaggac  100560
atctaacttt agctagcctc taccatttct attgtccaat tatgatttat ttagtatttt  100620
caatggctta tatcaccttta gtcaaaaccc atgttacata ttatatatag gtctaatgtt  100680
gttccacatg tttttttggct gtgttgtgtg cttatttgat aaattagaag gatggaaatt  100740
gggcgctgat ttcttccgag atcaatattt tttaaactac ataattgcaa catgcatcaa  100800
acctcaggtg accttcatct cttcatcata gtgattcaat gtaattattt gcttctctgc  100860
tcattgcatc taaatgatag acgatttaac tacaggtttc tcttcttgct ggaattgtca  100920
tgnnnnnnnn nnnnnnnnnn nngggggtgtt tgtttgggat tataatctac ctagattata  100980
taatccaata acttttggac taagagttag ttaaaaaatt attggattat ataatctagg  101040
tagattataa tcccaaacaa acacccactt aattatggta caaaccttt cgtgcgcttg  101100 atcggtgcca gtagttcttc ttctcatttg gaatatagag aatcttgcat tatttttcatt  101160 ggaaaaatca ttatattttg atatgccaaa atcaatgtta tcttggacac taaacgctaa  101220
atgaccactc gcccaccatt tattgtttag atagtttaga taatgactag atagtatgaa  101280
caccttacat tacagcagta aatatacata tgaattataa ttttttgtata aactttttta  101340 agtacagttt aatgcatgaa tatagttata aaagttgata taaacagtaa acaattatac  101400
ataaaggcat acacatggtc atatggacat catttaaaac ataagcattt gtgctccttc  101460
acacaagcct aatttcacaa aattaataaa gttcaccaac cacccaaaca ttcgtggctt  101520
atcacctata ttattgttta aacacatgtt ttctgtttac atctacttag ccatcattta  101580
```

-continued

```
aacaaatttt ctaaccagtt tgactgttta gacaccttta gtgtttaatt cagtgactag 101640
gacctaaact acacgtgaac acattattta gcgtttaagc acacatggac tgtcatttag 101700
acatgtttag gtggacaata accaaaatct gaatcattta ccttttgaat atccatgcag 101760
gtttttgcaa tgccagaaac atctcttggt ctttttcccg atgttgggc ctcatatttt 101820 ttgtctcgac ttcctgggtt ctatggttct ctaataccc cgatctttat ttagttgaaa 101880
tgcatgtagc taagtcattg caacatatat aatatttcaa tgttctgcta aacctcgagg 101940
gatattatgt atcattcttt agttttagtt ttataccatg tgattttatt cttagcaagt 102000
gtgattcttg cacaattgat ctatgcaatt acgtatttga ttatggtgat atattaatat 102060
aaagaaatga aaatgacaat ctttcttctt ttcaagttga tttattggtt ccattatgag 102120
gtagccatat agttggtggt aatgatagca ttggatatct tgttaaataa aacattactc 102180
taacattctg caggagagta tgttgctctt gttggtgcta gattggatgg tgctgaaatg 102240
cttgcatgtg gtctcgcaac tcattttgtc ccttcaaatg taggttcact agtaactcaa 102300
tttttaaatg agttgtcaat tttcttacag ttatgatgtt tggtgttata tttatggtta 102360
ctattattga gaatgttcta tgtataaaaa tcctagcctc atagcatttg cacatgggct 102420
ttgaagtttt gttctctagc atcattaagt ttatttatgt ggtatatctg ttgaaatagt 102480
tttgttttcc agagaatgct attgctggaa gaatccctta aaaaggtgga cacctcgaat 102540
agttttgttg tatgtagtac tatcgatcaa ttctgtcaac agccatcccc aaaacaaaaa 102600
agttccttaa ataggtaagg gcatttctaa ttaactcaaa gacatatgtt tggttcataa 102660
tatcactatt tttcattctt tggtgcacct taggttggaa atcatcaaca aatgcttttc 102720
taaaggaaca gttgaagaaa ttatatcctc tcttgtaagt ttgttatatt aattgtaggt 102780
ttctatgggt tcacttctta tattatgaaa aataataaat gcatatttgt tctgtcagga 102840
ggaagtggcc tcaaattcag caagcaaatg ggctgctcag acaattcaat atctgaaaaa 102900
ggcttctcct actagtctga aaatcacatt gagatcggta ttccttagaa accacacccc 102960
ataattgtac tattaatcta cgacatatat ttgtctcatt atatgttttc taacatggag 103020
ttcagataag agaagggaga acacaaaccg ttggggagtg cttgcaacgg gaatatagaa 103080
tggtttgcca tgtcgtacgt ggtgacttta gtcgagactt ttttgaagta attaaacatg 103140
gacatcacta atactttgct ctatactttg ttgtcattgt acatcaatgt atgtacctaa 103200
catccaactc cttttacagg gatgtagggc tatactagta gataaagata aaaatccaaa 103260
ggttcttata cttccatatt tagcacctct ccatcaaaat tcattacgac ttatttttatt 103320 tgatataacc attagatgat ggtgttcttt tttggggagc ttgcagtgga tgcctccaat 103380
gttggaacaa gtgcatgatg atgcagttga agagtatttc tctagggttg atgttccaga 103440
gtgggaagat ttggacctac ctgtcatgtg ttcaaatgga agaattatgg agtccaagct 103500
ttgaattaag cctttattga atagtttagt ggaacctcgg ttgtgcttag aataagaacc 103560
catcccatgt tcaaagagtc tatgtacact gaatacaatt gataaaataa aattgaatat 103620
gtggtgtata tacacttata ccatagaagg tactcattgt tattttttttg tagggatagg 103680 caatatcaac aagctagctg gttcctagct cgatctggct tatttagctc gtgagccacc 103740
atataatatg ctaccactat tggttaaatt gaaataataa tatgttatct attggtttca 103800
gaagtactaa aacaaataat gattgtgaac ctcttgaact gacacaaaaa atggttagca 103860
caaccagttt aagccactaa caggtagtgt tatgcactac ttattccaat aacaaatata 103920
tagtgttgag gtctatcttt agccgaaggt cctcaaaaca ttaactaacc agttatttt 103980
```

```
agcatgtttt aagtatcgat ggacaccttc atccaaatca gtaccggaat cgggcgcttt    104040
gccgagtgcc cgaagcactc gacaaagccc gataaacact cagcaaaaac tttgccgagt    104100
gtgacactca gcaaagagag ctcggcgaac agtacatcgg caacggcttc tttgccaagt    104160
acttttatcg agcactcgac aaagactttg tcgagtgtca ctcggtcctc agcaaagaaa    104220
agccgccatc acgacgtctg gtaacggaga cggtgcctgt gccgagtgtt ctaggtgaca    104280
ctcgacaaag aaattacctt tgtcgagcgt cacctaatac actcgacaaa gatattacct    104340
ctttgacgag tgtccaccag cctacacttg acaaagggtc caccagcgag gccatttgtc    104400
agtttgttta ccgagcgtca cctaatacac tcggcaaaga tgtgctttgc cgagtgttag    104460
ggccacaaca cttggcaaag aagctttacc ggtgcccagg tgtttcttct ctgccgagtg    104520
ctatggccct tacactcggc aaagcacctc tttgtcgagt gttacactcg acaaagtgac    104580
cagtatacac cttttaaatt tgtttttaat attccatcca aataaacaaa agatatcaca    104640
tatacatcac aaatatcaca tatacatcac atatctcaca acaccataa atcaaacaag    104700 ttctcacaac attaccaaca tgtttggaca caaacataag tatccaacac tcaagaacat    104760
aagtctcaag tatctcacaa agcattacca acatctaaca agttcagacc gggttatctt    104820
acaaagtatg aacaacacta agaaagataa tatctcatcg aggtgggcgg ctggactggt    104880
gcggcgatgg gctaggcgat ccatgagggt tgttggatgc caccccagat tgtccctgca    104940
tagagaagag attgcatgtg ttacaccaca tggaaaaccg tgaatgcaaa aacgatatcc    105000
atgttattta gcacaagtta caatcgattt caggaacaga ccggaatctt cgagcaccaa    105060
gctcactaaa catgatcgtg aacttgccat caagttgttt aaaaattgta taaaacacaa    105120
acaaagtcag aaaatcatga aacttgtcca catgtcatga tatcatatgt agaggttgtg    105180
ataaannnnn nnnnnnnnn nnnnnttcga gaaagttgtg acgcactacg tgtagaaacc    105240
taagtggcct acacatgaaa tcataaagtt ttaatgtaga ccggctaggt ttctacacgt    105300
agtgtgtcac aactttatcg aaacattctc aaatttttat cacatcctct acatatgata    105360
tcatgacatg tggacaagtt tcatgatttt ctgactttgt ttgtgtttta tacaattttt    105420
aaacaactgg atggcaagtt catggtcatg tttagtgagc atggtgctcg aagattccgg    105480
tttgctcctg aaatcaattg taacttgtgc taaataacat gcatatcatt tttgcatgca    105540
cggtttttca tgtttcgagt gaattgctgt tcaaatgtga attttccgaa gaaattcaaa    105600
taaacgaact aaatctaata gttatagaaa acacttttat aattatgcca aaatggtaca    105660
tgtaggtcta catagtgtag gaacatacca caaaagttt gattgggaaa agaaaaaat    105720 aaaaatatac tttgtcgagt gtccaagaat gacactcggc acagcatgct ctgccgagtg    105780
ttagatgtaa gacactcgac aaagaagctt ctttgccgag tgccaaatct cggcgctcgg    105840
caaagataac ggccgtcagc tgtagacggc tgctgacggc cctttgccga gcaccgccgt    105900
tcgccgagtg tttggcactc ggcaaagatt tctttgccga gtgtatttct gtgccgagag    105960
tcctgctctc gataaacgtg gtcgttaccg agagcaggac tttgctgagt gcccgacaaa    106020
aaacactcgg caaagcgtcg agcactcggc aaagagccgg attcagtagt gaatacaatg    106080
tacaccatca atataattgt agagatgaag ctaagagctt cgtaatatta atgcatgcac    106140
aaggtaaaga agctagccgg atcaagacga ggtcatcatg acttattcag caaggacaag    106200
ggaagaaaat acaacattat ccttagcctg ctcgttggta caaatgtata ggctgaagtg    106260
taaatgtaat tttgtcgaag atgtacctca cgcgtctata aatagaagaa caatgccata    106320
```

```
cattagacac gcttttttgg ccagagaaaa ttgattcgtt gtgcctacaa agttgtgttt    106380 tacctaccttt cattctataa ttccaaagag tcgaaagtac acctgtaatc ttttgttaga   106440
cagtaataag aaaaggaaat atattatctt ataaggctta atcatgtgct tcatcgttat    106500
attatgcata gtatggcctt aatgtccttt tctattccta tccatttcct acatcttcat    106560
cctttaatca acctcttctc ggaaagggga aggctaaaat gatgaagatg gggcataatt    106620
taattgtgtt gctttgtttt tgatatctca aaagaatcaa aagtgagtga ccaacacata    106680
gtaaattaaa aaaatgaaa ttaacaatgt tggttggttt gttgtgggac acaatagcaa     106740
agagccctca taatcaggtc aggacattaa aaactaactt aacctctctc gctctcgact    106800
gttacatcag atggacagtg gagctagctc accatggagt gactgaatat ggatgtaaac    106860
actcaccctc gtgtagctcg atcgcatatg gggccatgca gagttttcta tcatcagtgg    106920
gtatggtcgg atccaaaccg agcatcacgg ctggaactag gcctagctag caacatttgt    106980
gaagggcaca agggacgtga ggccctgagt tttctccgta cctcaactag tggatgccca    107040
tgtggaaata tgtcactttg ttcccatcta atccaaaaac tgaaaagata cctaaatgct    107100
aatgcatggt agatatgtga ttgtgtgtag atgagtgatt gttaagtgat gatcaagcta    107160
tagtttattg tattgatact aactatatat agccactact agcactaccg gaaatagctg    107220
ctttgtcgag tgtctgacgc actagacaaa gcctacaaaa cactcggtga aggctttccc    107280
gagtatgaca ctcggcaaaa aagctcggtg aactgtacat cggcaacggc ttctttgcca    107340 agtactttttt attgggcact cgacaaagac tttcccgagt gtcattaggt acttgacaaa   107400
gaaaagttgc cgtcacagcg tcaggtacgg gcgacggagc cgttgccgag tgccacacag    107460
tggcatttgg taaaggctca ctcttttccg agtgtccact aagtggctca ctcggcaaaa    107520
aagctccccg tggggcctta ctaggtccgt tgccgagcgt attaggtggc actcggcaaa    107580
ggctccctct ttgccgagtg cccgattact agcactcaga aaagggatca ccagcgggcc    107640
cctttgtcag ttactttgcc gagtgtattg gaaggcactc ggcaaagaat caatctttac    107700
cgagagccaa ggccacatca ctcggcaaag tggctttact ggtgcccagg tgtgccttct    107760
ttgccgaaaa taacccttta tgccaccgaa aatagcttat tttcggtggc ataagactta    107820
ttttcggtgg ttcctggccg tcgaaaatga cttcgttac tgtagtgata gtccacgtgg     107880
gcatcacaga tgacgagcca ttgacaattt taccattatt atttgtgggc ttcgtaatat    107940
gccattatgc tcataaatta tagacacaga tggtcccacc agtcatagac acggaataac    108000
ataataacat gaatcaaaaa cttagagtgg taaaattaca aatttatcac agatgacagc    108060
ttgctagttt cattcactag cctccgggac atagaaacga tgattacaaa agattacaga    108120
ttttccacaa ttccatggtg cttgcatgca ctgaaccgta tgtagttgaa gcaagccaaa    108180
ggtgagagaa cctgcgaagt catggctgct tggaagtagt agacccacga agaagacggg    108240
ggccgtgacc atccgagttc ccttgaagca gcatccagac tcggtgctca ctcggtgctc    108300
aggtacccga acactacagt aaaataacaa acatccgacg gtcacgttat cttcgacggc    108360
tgcctacgta gccgtcggac gtaaggttat gtccgacagt cacctctggc tcttggaaat    108420
agagccttat gtccgacgga cataaaccta cgtccgacgg ccgcgtccat agctgtcgga    108480
gataaggagt ttcaacgcgg acacagcctg cgcgcggttt tatttcacgc gcgctccttt    108540
ctctctgccc gaccgccgcc gccgccgtct caaccagccg tgccgtcgcc gcccgtcgtc    108600
gttcccgccg cccactgccc acagcccgt cgccgccccg gccgcccgc cgtcgacgac     108660 cgccgccagc cgcggccccg ctcgcgtcgg tcgcccagtc gcccacaccg ccggtgttgc    108720
```

```
cccgtcgccg ccggccacat ctccgcccgt gccggaatta tcccgcccgt cattctaagt   108780
aagtattttt agttttattt tgtatatatt aatattgttt tgtagtttcc attgttgtta   108840
ttaaataatt agcatgttaa ataatgttta tcttattata tacgatggcc gaaatttgat   108900
tatatggcga aatttgatta tgtaattaat ttagtttgtt ttcgtttact tagtggtgct   108960
tagataattt aaattttaaa tttccgaggg taattattat gccctcggaa ataaggtcat   109020
tttatatgat ttgtcacccg tgataatgtt atgtagtggt gtctatatag tttaaactat   109080
taatttccaa gggtaattat tatgccctcg gaaataaggt tattttatat gatttagggt   109140
cccgtgaaat tattttcctt gtattagtgt ggtttattag attagaggcg tgattaactt   109200
aactaatcaa gttaatatct catatctagt atggaggagg atcgtcgatg gatgtatgaa   109260
ggttggaaga aaagaggtgc tctatcaagt gagtgggttg ccaagactga cgtgtttctc   109320
gaccgtgctt ttgctcggtc agagactgga accgatgtta ggtgcccttg tagcaagtgt   109380
cagaatattt atttccttga caggaggact atgtcgatag atctttgcaa gaacggttat   109440
atgccaggct atgaggtgtg ggtgcaccac ggtgaggacc cacctcctcg tattgtatcg   109500
gaagttcagt cacatgaaga gggggactac gataggatgg aagagatgct tgacgatgta   109560
tgccatgagc ttctaaccgt cgattcggag aaccccggtc aacccaccga gtatgaggat   109620
ccagctacac ctgaggttca gaagttcttc gagctcctta aagctgccga agagccgttg   109680
catgagcaca caaaagtgac cgtccttgta tttgtgactc gacttatggc tattaagtct   109740
aagtttgcat tctcatacaa ctgttacaaa aagcttttga acttgatcag tgatgtactt   109800
ccggagaatc acaagatgcc aaaggacatg tatcagttca aaaagttgtt atctgggctc   109860
ggtatggact acaaaaaaat cgatgtctgt gacaataatt gtatgctttt ctggaaagag   109920
accgcgggtg agaagaagtg tactgtatgt ggtgagcgta gattcgttga ggttgaaaac   109980
gacgatggtt tgaccgtgac tacgaagatt gcacgtaagc agcttcgtta catgcctctt   110040
atacctcggt tgaaacgttt gttcatctcc aagaatacag ccagacacat gaggtggcac   110100
aaagaagggg tacgtgagaa tccaaatgtc atggtgcacc cagctgatac agatgcatgg   110160
aaggcactag atgcttttga ttccagcttt gctgatgaag tgcggaatgt ccgcttcggt   110220
ttggcaacag atggtttctc gccattcaat ctaactgcaa cgtcctactc atgttggccc   110280
gtctttgttg ttccatacaa ccttgcacca gctctttgca tgaaatatga atttatttc   110340
ttgtgtcttg taatacctgg ttcggatcat cctagaacaa agatcgatgt gacgatgaga   110400
cccctgattg aagaattgaa aattttgtgg gaaggagtcg aggcgtacga ttgttacaag   110460
aaacaaaagt tcaacctgag agccgcgttt ttgtggtcta ttcatgattt tatggcttat   110520
ggtatctttg ctggatggag ttgtcatggg attttgacat gtccgatatg cgttgaagac   110580
actttatgct ttcgactaaa gtttggtgga aagatatgtt acttcgattg ccatagatgt   110640
tttttgccag aggatcaccc gttcaggttt gataggaacg ctttttaaaaa ggacacgatt   110700
gtgatgaggg gaccatccaa gcgtctaagt ggtccagaga ttctcgcgag acttaatgat   110760
ttgaaactaa acggacatgg aaatcgtttt gaaggttatg gaaccgagca taattggact   110820
cacaaatgtg gtctatggga actccctat atgaaagcct tgattctaat gcataacatt   110880
gatgtcatgc accaggaacg aaatatgggt gaaagcatta tcagcacttg catgaatatc   110940
actgacaaaa caaagacaa ccctaaggct agaaaagact tggccttaat ctgtagaaga   111000
ccaactatgg agataggaga gaatcagaaa aagccacgtg ctcctttcag tattaaaacct   111060
```

```
ataaggaaga aacaattgat gaaatggttg aaaaacttaa agttcccaga tggttacgcc   111120
gcgagcttta gaaggtctgt gaatttgaag acgggcaagt tttctgggtt gaagagtcat   111180
gactaccaca taataatgga aagactcctt cctgttatgt ttcgtggttt tgtaaaaaat   111240
gatgtctgga aagcattagc ggagcaaagc tacttttata gacatctttg tgctaaagaa   111300
ataagaaag agatgatgga gaagcttgag cgacaaatac cgattttggt atgcaaactt   111360
gaaaaaatat ttccaccagg tttcttcaat ccgatgcaac gtctacttgt tcacctacca   111420
tacaaagcta aggtaggagg tcttgtgcaa tatagatgaa tgtatcacat cgaaaggaca   111480
ctaaagaagc tacgttcaat ggttggtaat aagagacgag ttgaagggtg catcgctgaa   111540
gaattcaaat ataaagagat agcatcgttc acgggcctgt actttgcaga ggaacacaat   111600
gtcaatgtcc ctacgttgcg gtatcatgtc gacgagccct ctatcagtga tattgaaatt   111660
tttcaatgga ggggcaaaac tgtaggaccc agcacaacat attgtttcac caacgacgaa   111720
tggaagactt ctttactcta catgtataac atggaagaga tgagtcagtt tctcctgtaa   111780
gtgtaaactt tattttagtc attgccgcta gaattttttct tgtgatacta aaaggtttgt   111840
ttccttgtac taacagggaa tttgattctc aaaattgcat ctctggctgt gaacgtgacc   111900
agatttgtcg agaggggaaa gatggggac ttaatttctt gtgttggttt cgagattatg   111960
tagataaaaa tgacaatata cacccggacc ttcgacaatt atccctagga gcagtaactg   112020
gcagacgtta tggtcggtat gatgtcaatg attttagatt ccgttccaca aggttcgaag   112080
atgatcatcc tctagcagcc acgacaaatt ccggagttgt aactagagct gttgatgatg   112140
aagggaaggt gactaattat tatggagtca ttaatgatat aatcgagtac aagttttttg   112200
gagataaaca actcaaagtg gtgttcttcg attgtgattg gttttctcca aatacaacgc   112260
gagaaaatca atatggcatg gtggaagtca acacaacga tagattaaaa agccatgaca   112320
ctataatcct tgcccaccaa tgcgagcagg tgtattatat gacatatcca tctaagaaaa   112380
agggtttggt tgattggagg gtagtgtaca aagttaatcc tcgtgaacga ctatatgctc   112440
ctggtgatgt tggttatgtt gaaagtcaaa tcgagcagga agtgggggtt gctgannnnn   112500
nnnnnnnnnn nnnngtttt aatttctaca ttgttttcta tttgcaggac ttggatcgac   112560
gactcgttca caagcacagg acactacagg caggtgaaca tggtccttgg taatcttgtt   112620
cgtctgcact ggcctggtct tgtgattttg cctactggcg agtttgtcct cgccaccact   112680
tgggagcatt atcgctatgg tgtctataca acgtttggca acacacaggc actagtttgg   112740
gatgcgttct gggtatgaat tgtttatact attttagtta ttccatatat ggttgctttt   112800
atgataacac taatttttttt tgcagaaacg gtacaagttg ccggacgatg gatcatatga   112860
tatgaacgct cgttacgtct ttgagtataa cgcgaacaat gtcgttgtaa atgcaatgta   112920
ctatgcacga attcaggcta ttaaggcatg gtacagagca aatgttgatg atcgaccgat   112980
gccaaatacc aaggccgagt ggtcatcaat ttacttgacg gaggagcaat acctagaggt   113040
aaacaggttg ttgcatctca tatcgcatga agccatgtat ttgcttgctt tatttaaaaa   113100
atttcatgta ggtgtcggtg ccgtggatgg ccacccgatc agacggttat cgggccttgt   113160
gcagatggt gtcttcccct gagtttcgtg ccatttttcga aaggaacagg ggaaaccgtg   113220
ggactgagtc gttccacaac tacgacggtg atggtcatgt gcgcttggct aagcgaatgg   113280
taagtcaaag tatgttgtaa ctttgaatta catagaaatg tgtcattgta acttttatgt   113340
acaggaagtc aaatccggtc gtacgcccac agacgtggag gtgtatatgc aagggcatag   113400
gggttctgat cctcagaatc ctgatgtgtt atgcactcag acggccaccg accgtctagt   113460
```

```
gagtttttgg tactctatta tgtgtttgat attgtttgca agggcataag ggttatgcac  113520
ctatatttga tattgtttgc ctccaggctt cgtatgggta ggagatggtt taacgccatg  113580
ggcaggagta cgattggagg agccagccaa tcgacccttg gcagcatat gctagcgcag  113640
taggacaagc ccatggacgg tgggattatt tgatttggat ttcaaaattg tcatcatatg  113700
cttgcgattc aactgagcca tgagttacta tactaagtgc atggttcact cttgtaggtt  113760
gggtattttt gattctacga ttgattccag agagctgaga cgctgtggac gacagtccac  113820
atcgtcgtct tcacaatcgt cccgttcaca agcatccgcc caggagatag agcttgcagt  113880
gttgcgtcaa caggcagagt accataaatc agtcttgagg gaacaattgg agtaccagag  113940
gcaacaatct gagtaccaga gacaacaagc cgagtaccag aagaagaggg acgagtatta  114000
tgcaaacctc cagacccaaa atcaagctct tctctcggta agttgaagta acattttgta  114060
gcttattttg caaaacacgt gatgtgtatc ttatttctc atcaatgact tgtatataat  114120
ttgtagcaac tagcccaaca agcgagcgtc tcgatgccca cctatgggat gtcgcctccg  114180
gactttgcac tctcgatgcc aatgcttgcg cctccacctc cgcctccgtc ataattccct  114240
acggtatgta cacatatgcg tgtgtgacat gttcatagat gtcttatgtg tttaaatgaa  114300
aaactgagtg gttacaattt tatgtgcgtg tgttataggg atttcagaca cccccgctt   114360
cagttgcagc accaggagat gggtctggtc aagacgacgc atcgcattct tgggtgaata  114420
acatttttcaa cacgcatagt ccagcaggag gaggtggcta ctcgaaccat ccaggcgatg  114480
gatatgattg atgtgtcgtg atgttaattt gtgaaacact ttgcaacact tgtttgcaac  114540
cgtgattaca acacttgttt gtgagacaca atgtcagttt gcaacaaccg tcggacctat  114600
atgttgatgt taaatttgtg aatgttaata tttatatgag aatatttgtg attgtgaata  114660
cttatgtgaa tgtgtatatt tgtgattgtg aatgtgtata tgtgcatgaa atctgttttt  114720
gttttgtaaa tgtcagattt ttaaaaaaat ggaattttgt gtaatttctg taatttatta  114780
tgtccgatgg cctagtctta gccgtcggac ataagggctc gttatgtccg atggctttag  114840
aaaccgtcga agatataaat cctttatgtc cgacggccgg cgctaggcc gtcggacata  114900
actctgtggg ccccacaggc tgaccggtaa acggttggt ctttattatt tccgacgggc  114960
agaggtggcc gtcggagata gcttatgtcc gacggctgcc atcggatata acgctatttc  115020
cgaccactag tacagagaag ctttatagtg gcgtgcgtaa acctatttt agtgccgttt  115080
ttcgtaaccc gccagtgcta gaggccagta aaaatcatca ttttacagg cgggtnnnnn  115140
nnnnnnnnn nnnnnattat ttttattatg ggggcctcag caaccccacc ccaccgtct   115200
cccccaagtc gcaagtcgcg acattttcg cgcaaaatc gcgcgctaca cagttgttag  115260
tactcgaacc gtcgacctca ccctcacgcg tactctccac taccactcca tttatgacat  115320
gcattgtgtc ttgtttgtag ttgtttgtc cacatattac aaccatttga gtgtaaattg  115380
cttatttgag actctaaacg aattcaaata aaaaaattgt caactacaaa gttgaataac  115440
ttttgaagtt ctacaacttt tattttgaca ctttttcatc cgaggtagtt tgcaaaatat  115500
gaattttaaa tttgacatac ttagattcat ttttttagaa ccgaaacgag ttcaaataaa  115560
aaagttgtca actacaaagt ttcataactt ttagaggtct ataactttta ttttggtggt  115620
tttgtcatac gaggttgttt gaaaaactca aaaaataag gataaaaatg atttctagtg  115680
gcggttcctt aagaaaactg tcattagaaa tcgatttcta caggcggctc cttaagaaat  115740
ccgccactag aaatcatgga tttttaagaa accgtctgta gaaatacgat ttctagtggc  115800
```

```
ggttttctta aggaaccgtc actaaaaata gcacagttgg ttgataaacg aatccgtcta   115860
taaaaatata tcgtcccgca aactgagttt ttttctacta gtggacgcct tacctccgac   115920
ggcttaaaac cgtcggagat aggttaatac catcgaacat aatcgatctc cgatggtgtg   115980
aatcttatat ccgacggctt tggccgtcgg aagttgttcc gtttactgta gtggaaggcg   116040
tagacgaagg acaggaaggt ggccgcgtac agcggcttgc tgctgaggtt gaaggcgcac   116100
aggaagcaga gggtgcacga cagcagcgtc cacaccgcaa ccgtgcgccc atgcacgccg   116160
atcactgaaa agcccaggtc ataaactcat aatgcatgca tggtttcgaa gctgaaaggg   116220
tagctagcta gcatcaggat cgagttccgg ccgccatagt ctcaaggtca gcagaacgta   116280
cgcaccctgt atctcggaga aggtggctga gcagagcgac ccggagccga agaagcacga   116340
ccaggtgaag gccaagcgga aggtgccgac agccatgagc cagcacccca gtgccggcat   116400
gccgcgcttc ttcgaagggc cagacatgga gaggcttggg tgttcggccg gggcaacgag   116460
acgaccaagc agtagaggcc tagagggaga gcgcgcgcga ggtccttcac gcaacgctgc   116520
gagccaccaa gttcctacaa aacgccacca gccctccatt tatagggtac caaaagtcta   116580
gagagctctg tagtttttat ttgttgctaa ttattggcta attaaccgaa tcgcagtcat   116640
cgtcatatga aactgagaag agttttgtta caaagatgag ggcaccgagt ggccattgag   116700
gatgggcccc gcaacagata gtgtaaaata gagcatttgc acggtaaatt acactatttg   116760
tatattaaaa tttaaaacag aagataagat agggtactag agacaactac tcgagtcatc   116820
cccctccatt gccatcgctg acatccacat tgaggacagc atgcatgcac ctccatgcct   116880
acatccatgg tcatcggctt cttgccttgc tagacagtgg ctcgatccat aacttcatca   116940
atatcggggt catgcatcat gtaagactag ggaccacaaa caaaactaaa atgcgggaca   117000
tggtggccaa tgctgatcgt ggtccctacg agggcgtgga aagtaacatg gccatgcaca   117060
tcggttagga ggattttacc atcagcccat cagctgcttg aacatccacc taggttggtt   117120
tggcctcgtc ctaggcatag aacaacgagc tcgagcggta gtgcactgcc atacccatcc   117180
ggacaagcac tgctccgttc ttgctctggt gcttcaagtc aagaaggcaa agggctgcta   117240
aaagttttgc attaactact gtgagctaaa tgacaagaca tccatggata agttctccat   117300
ctctatggtc gatgatctac tctatgagct ctatagtgtc aaatacgtca caaagctaga   117360
cttgccgttc ggctatcaac atgtggggat gcatcctatg gacatcagaa gacgaaatta   117420
tgtacccacc actaccactt caagttcctt gtcatgccct tcggtctctc caatgcatca   117480
gccatattcc agacactcat gaaggacatc ctccgaccct ttatctgttg attcatcatg   117540
gtccgagcac ttgcaacatg attgtctcgc ccttgaccca tgtaccacta ttgcaccatg   117600
ggtgggcatc tacatgcctc ggttcactat cttatttgga tggagtactg ctataatatt   117660
tcattccaca tggcgctcta caccacactc gaacccctcc ccgctgatt cttgcacaaa    117720 tcgcagggc agctcaaaca aaggcaatgg acgccctctt gtgtgaccag aacacccttta   117780 acttaaggcg ggtgctcgtc tccacgatgt atttcacatg gggattctca agccattcca   117840
tgggaccgcc tacgattaat gggatctaat ataaaatcct accatgtctg cataagttgt   117900
atggatagga gatcgatgac tggggtgtgt accctcgaca gagcacaaga gtcgttgttg   117960
cgcatagaaa agtaggcaag cgagaaagag acgtgggaga tgacctttaa ggccaagcaa   118020
gacaattgtc ttacttgatt agatttcaat atcttctcac tttatataga gagagagact   118080
tacttgatcc tacggaaact atttttttagt tttattgaaa ccttgtaatc aagaatcaat   118140
catggtctca gctctaaacc gtcgaacttg tgtaaaatta catacatgaa agcaatcccc   118200
```

```
aaaagcgtgc atgcctcacg tggcacattg tccgaaacaa tatggaacga taagaattat    118260
ccaagtgaat taaagatcgt gctggcgcgc gcagcatgcc tgtacaggag aattaccatg    118320
cctatatatg cagacccgct gccttttctt aactgaatga tatagctata tgcctatata    118380
cacgactaca cgaggctcat gttgggatgt taatagaata acaagttagg tgaactggtg    118440
tggtcttgat gccttgtaaa taaatgaggc cagccaagac caaggatatt ttatgggggt    118500
tttgttaatg attacttatg ttgtgatgag tgcaattgtt tcagattgca aggcttggac    118560
ttctttgatc ggactatgct agatttatat caatcagatc attaccacag aaatgatttt    118620
tggttaaaaa gacaggcaca ttaacatatg taccacccat gtaaaatgtt tctattaatc    118680 gttgatttttt aaagatgtgt attttaagat gcatgtttct gaaaatcgtt ataatgggct    118740
ttccctactt taagcagtag tttcatctaa aaggtaattc ataacttctc tatatggaca    118800
tgcatggatg cggacaatct gcaattttttt ttatttaagg tcacctaata tcccaaatat    118860
aaatttctca tgtttcgaaa ttcaaatttt cattttttctt tcgaatgatc acgatcgaat    118920
gggtgcccag ctcatccatg ggaggaagag atagatggac gtcggcggtg atgttccaac    118980
gacgtaacta cagtgacgtc tagaaagtga cgtatatatg tgcattgttt aattagtgac    119040
cacttaaaat gatgagaccg gccaattact tgacgacttc ttttaaccca aggccacatg    119100
catgggtaac acatggctta ctaattaatc acgcacgttg tgtgctcagc tcattttgct    119160
tcaacaattt gattgattcg cgtttgtttg caccagaagt caaagtaatt catttcccct    119220
atatcattag ttttcttcct tttggctaaa ggagatgccg atagataggg ttggatattg    119280
agcgagctcg atttagcttg ttcgagttca gactggctcg ttaagctaac gagttggatc    119340
gggagccact gagttagctt gactcggcta gtttacaagc tcgactggct cgtttagctc    119400
gcaagttaaa gcagaaaaaa caatatccag gctataacat caccaaagac tccacagggc    119460
tacactctct ctctaggctc tggttccacc tactcaacaa gattcaggct acaatgacag    119520
accatgaagt ggatggtcgt ctctgcaagt agctccatga tgcgactctt gggacaccac    119580
aacaaaccgt cgatgacttc ttattccatg gtaaggtgtc ttcgtgttag tgtagcatgg    119640
cttgtgctag taagtgcttg cattggccca taccactatc caagaggaga tatagaagac    119700
cctccaacga ttgtgtgtac atatctacat ccatggcgat caggcgctca tccaggacta    119760
cgtcgatacg tgcgtcatgt gtcaacataa taagacacta tacatatagt tagctagtct    119820
catataagca ctcgacatgt tgtcctaggt gtggctaaca tctcgcacca cagtttggag    119880
atataattct tgatgtgggc gctgctggta gaccactgca tgtgtctgca agccggccat    119940
catatttgtc taattatttt atgaactgaa gtaataattc aattgcaaat gtacctggtg    120000
cagctctgtg caatgacgca gaattatcat cgcctgcttc ttctcctctg tcgtcatcca    120060
ttgtaaacaa tgcaatacaa tcagccgcca cgttcctttt tatatgccct gagctaacca    120120
atcccgtgta caatgtttac gctattttgt tcggtcaatt acgtactata aagtttgttc    120180
ctgcatgcca ggagatattg tcggactggt gataacaact cgagaggatt tatcgtggtt    120240
tgttgaaaca gatttatatt tactgaagta catgcaacca gttacgccat tatatgtaca    120300
tatttatgcc tcgcgtttct gcttacgtgc atgtttgggcg atattttcgg gaggcttcag    120360
ttatcgttcg cgattttatc gcgtatatca ttttacgcta aaatacacaa gggtttacga    120420
tctgttggct tatgatttac gctgtggttc gactagacca taaaccgccg aacaaacctg    120480
cggtctgacc gattccgtct aattggctgg ggcttcccga tactaatgga agccctgggc    120540
```

-continued

```
ttccattagt tcgtccctat atatatatat atatatatat atatatatat atatatatat   120600
atatatatat agggcaggta taacgggagc cctgggcttc ggatattaaa ggaagcccaa   120660
gtcggttccc gagatctggt cgatggaaca ggcgcgcctg tgttttaacg tggggctgag   120720
aggcggcatg caggacagac ggcgccgtga cgcggttgtt tgaatggtaa gggaattgcg   120780
cggaattaaa gggaatagat gccacatgca aacgtgatta ctgtgatacg tgggcgcgta   120840
aattatggat cttgcatggt aagtattgtg cggaaggtaa aaaaaatgaa gcataagatg   120900
ttgaaagata tggcataaaa ccgaaacggc ataatagatg cataaacagt ataccgat    120960
tggcgtaaaa cgttgtgtca ttgtgcgtaa attttatatt atgaatttta gtttgacaaa   121020
tacgtcgcca taatatcggg acggtttcgg aaataatggg gagaccctgt aaacgtggat   121080
gcggttactt ttatagtatc cgagatttac tttcattcgg aaaaaagacc actaagcctg   121140
cataactaat cggagttgga gatggccggc tctggagggt cgccggtgat ggaaggagat   121200
ggcgttcgtc ttgatccaga gacagaggga ggagttggtg gtaactcact ggtgacacca   121260
cctcctgctc taatgggtcc tgagatcgcc gagatgagca taggggaaga aggagaacaa   121320
agggttcgac ctcctatgtc caatattagc tccagggaga tggatacgcc acagatactg   121380
cgttcacatg taagtccaat cgctgtattt gattattgat tgattatatt gttgtgaaca   121440
tattccatgg tacaaacaac aatgacaatg aaatagcagg caaaaaacat tgatccaact   121500
atagtgccaa cggtagggat gactttcaag gatgttgatg atgcatataa attctataaa   121560
aggtatgcat atgaagttgg atttccactg aagaaataca gagagaagac attcagtaag   121620
tggataaatt gttcacgtga aggtaaaagt gcagcaaaat caaatgatac acttaggatg   121680
aggaatagat catcagggcg tacgcaatgc aaagctgaaa taaaattaaa aaaaatatat   121740
gatgatgaaa acaaaatggt tgtagctaca aaaattgaac tggtaaactt ggagcataac   121800
catgagttca taactgacga agcagagaaa caacatttac attgcaacaa aattagggat   121860
gctgagttca taaattttgt ggatgcaatg catgatagcc gagtgccgca gcattgcata   121920
gttgatttta tatcagaaat gcatgatggg ccgaagaacg taccggtaac tgctcaagat   121980
ctgaaaaaca tgtaagcaat actttttttgt tacatgtgta tatatcaata gccatgaata   122040
ttaccatagt aaatgtgtgt gtaataattt tttgtgcaaa caaatgtagg agggcagcca   122100
ggagaagaga aaattgctca aatgatgtag ccaaactttt ggctttcttt agagaatgca   122160
agaaacagaa tccacaattt tttgtgattt ccagctagac gatgatggga aaatagttag   122220
tatttttggt cacacgcaag tatgcagggg gaatacgcag attatggtga tgctgtgaca   122280
tttgatacaa cacacaagac aaatatatat gataaaccac tgggcatgtt tgttggagct   122340
aacagccatc tgcagtgtac agtgtttgga tttgttttgt tgggagatga aactgtgcat   122400
acttttgaat gggctttcaa ttcattcaaa acatgtatgg gatgcgaggg tccaagagtt   122460
atgcttacag gtatgtgata tataaatttg ttatgcaaaa cagtgaatta atttattgtg   122520
aaaataactg aataatctgt gagcaattgc agatcaagat cctgcaatgc caattgctct   122580
gagaactgta tttccaaaaa cagttcatag actgtgctta tggcatgtac agaacagatt   122640
tatgccattc ctaaatgaga tatatgccag gtttgctgtt aaggatttta aaacaacatt   122700
ccagtctatt atacatcatc cattaactcc tcatgagttt gaatgtgcct gggaaatgat   122760
gctagaggag ttcaatcttc atgaagatat gactgtacgc aaattatatg aaataagaaa   122820
agaatggata cctgcatttt ttaaaaatga cttctgtggg gtaatggtat ctacacaacg   122880
aagtgagagc atgaacagat tagtgaagca atcacatgta gatgcgaaca ccccactgca   122940
```

```
tgagttcgct aaacaaatga tgaaaatgtt gcacagcagg aaaatgaaaa aaatcaaagg  123000
aggcattggt gagcaaggta tgtcgtgctt gttagcaata atggtttgca tacatttatg  123060
taaataattg ggaaatttgg atccatacca ttaaaagatc accactttgg atccatacca  123120
ttaatatctc acttacatgt gggtccacat gagtcaatga catgtggggt ccatggtata  123180
tatctaaagt ttggatcttt taatggtata gatctaattg ttcctaaata atttgtttaa  123240
ttatgataat aatgtgttat aggcaccaag gacaacagat acattatata ggttcgaagt  123300
gagagtctct agagcataca ccagagctgt tatgaataga tttgaggaat caatgaaata  123360
cgccactgca tacaaaatat taaaggaccc agacggatgt gataatgaat ggatcgtaca  123420
gcatacaaaa cggtctaata aaattgtgtg gggacaacat caattcaaga taacagcaaa  123480
catagaagtt ggggagtata catgcgagtg caaacagtgg gaacatacag gtttgtacgt  123540
attatgttgg ttagcataaa aaatttgcat actagagaat ttgatgattg tagtacaaat  123600
taatgtatat ttttgaaata atggttcgtt ttcatgtttt caggtctatt gtgtgttcat  123660
cttttaagag ccttcatgca tcttcaagtt gaaaagatac cttcaaagta tatattgcaa  123720
aggtacactg tctcatcaag aaaagatgtt ccgtttgaaa gaattgataa gagcttcagg  123780
gggaaggatg gagttactaa atcatacaga cagaaaatgt tgttaacgaa aacaatgaaa  123840
gtagttcgcc aggcgtgtat gtcaaaagca gggtatgata aggcgatgga tgtgttggat  123900
gagctcgatg tcgttctaag ccgattggag ccagatattg gatgtaatga gtcaacagat  123960
gttagtgata atgaggaaga caaggtaata atattgcaga tgttttagtg ttatactatt  124020
tgtaacataa attatgcata gtaacatgtt attttgtacc aggaagaaga gttgaataaa  124080
aataatgctg gcgatgggat ggaagatgac aatacaatta catgtcataa taaggtatgt  124140
aaaagatata tatataagct tgcatgaagt attgtacata atgaatatat aaaatcaatg  124200
taataagcaa ataatatttt gtaggattcg cataacacca ggactggatg tgaacatgcg  124260
ttaacaataa taacaactgg taaccaggta catattaaaa taatattgtt tatttgtcta  124320
aaatgaaaat atatatttat gctgcatgta aatgttgatg tatttgggtt gggctctaaa  124380
ggaggacaac atgagaattt cacatgaggt tggtgataca agttctctgt gtcacgtagc  124440
acataaacaa atggaacata ttgctgcatc ctcagaagct aaaaaggtga gcattgataa  124500
atgattttac tgattggtat aaatatatgt aaatatgtgt atactaaata gtaatgtcta  124560
ttattatgca gaggttgaat tttaacgtgg atgttataaa tctgagtatg ccggatcgtg  124620
caagaccaaa aggccggaca atcaaaaatt cagaagagag ggttatgaga ctaggtgcga  124680
aaggagagaa aaagaagaat aggagatgcc atttgtgtgg aatagcagat gggcataaca  124740
gcagaacatg tctgtctgtg gaagagaaca gggcaaggct agcaaaactg tctaatcgaa  124800
agagaggacg gccagccgga tcaagactaa acaataaaac aactgctcca cagtggaatg  124860
aaacatcgac tgcaaaaaaa cattgtattg atgaagaagt ggaaaatgaa gaagccgatg  124920
agcatatgga tttgggcgaa taatttgaag tgtgactaaa gagtggtcga tttagtagaa  124980
acttgtaata tcacaatgac ttatgcttta ttttgttgga aattcaatag tttgcatgaa  125040
agggttatat aatgcgttga tataaaacta taaaatgttg cgtaaatata gacaattaca  125100
caaattatgt aactgaatat gtacaacaaa ttggcattga acgtttagca atcggaaggt  125160
ctggacatta atggtatata aaactgtata cacttaacaa tactaatcaa atgggagtgc  125220
atacgtcggt ttcacacttc caatacaaca aacaggatat agcataaaca cttgttacaa  125280
```

```
ttagcataat tagcgtgaaa aatgtataaa agatgaacct agtgtatata aaataaggaa    125340
gtatatatta tgcataaaac ttgaatattg aaacaatatg ataatacaaa taagccaaac    125400
attggaagca aaatgattaa ccaactcaca aactggagat gaaaacagca tagaatttgt    125460
taacagataa cataaataga cattctggta acaattatgt ttgacacact tcaaataaaa    125520
actgatgcga agtagcatag acattagaca cattgaacat aagtggcaca cggagtatca    125580
aacacatgat cagaggcctg acataagtga cttaacaagt aacataaaca gttttgtgga    125640
tcccacaggg aatcatgttc agctatgcta tctaagtctt ggctttcaaa cagcggcgtc    125700
tccttggagc atacttgaaa ggcagcagtt ctgcaggaag gggggcaacc atgttgttgc    125760
gatgaaaggt aaggtaatgc agaacaaagg cacgttggtc taatggttca tcctgaaata    125820
gccataatat caaattaatg gtagaataaa atctgaagga gtaatatatg caagattaga    125880
agactaattt agtgacatac cggagtataa aattctgata agtcgccatc atcaaaatcg    125940
tagtagtgga ggaagtttgc gacaaaaaaa ccacaatcat ttgaccctgg tgtcatggtt    126000
ggacaattgg gaaggagccc aatcttgtag ttgccaaact ttggtacagt tgactcaggt    126060
cgagcttcat gtaaggcaat gctaagtctt ctcattatta atctggacca aggtatcttc    126120
gttccatgta tcatcatttg atcattatgg atttgtttcc atgtagtgcc tccaagcaat    126180
gtaccataag gatttgaatc taagatgtct attcgacaac gttcaaaatt gattgcataa    126240
agggtccagt ggcttcggcg tagcatagga accaggatct gttaaatata tatgtaaatt    126300
tatgaatgat ttatactatg catatgaaaa attaaaacta atacaacata aaactagtga    126360
ccaaaagaac attctaacat ttgtacaaat gaaactgatt agagctcacc aatttaatct    126420
ggttcagaac atcatctgaa ggaagggttg gttcaagttg ttctttaaga agtgatgttg    126480
tgaagggctg tggatttgaa ctgtgttgtt caaactcctc gatattcaaa acggtctgga    126540
caaagaaaat aaattgatta gtattatata tttatacagt aagtgttgca ataagataca    126600
aagttgtgga gaaaaaatta ccccaacgtt gacattcagt attagagtgt tgattacaga    126660
atctggattg tataatacat catcctgacg aatacagtcg ataaattcct gcatgaaagt    126720
attctcaaga catttgttgg gaccaaacga ctggacaaca tcaaggacag accctccaaa    126780
tcctccaaaa ttaatgatag gcctggggaa aaaactttga ttacaattct tctaattata    126840
cttaattgga atttgaataa ctaatacata catgctcgga tctagttttc ctgacaaaat    126900
gaacttaagc aggttgcgag cacagtcttc acgtgacacg tggggatgtt cagcgactgc    126960
agctttacag gaactatcct ttgcaaccag gtcagtagtt gcctaatatg tgaatatatg    127020
ttagtaaaca gttgcataaa tatgtatgtc ttagtgtata aataggaaaa atatgaaaat    127080
gacaacatgt cttacatctg tcagtggggt tttatcgaac agaggtgcac cagatacaag    127140
agtatcatgt gtaacagatt tttgtccttc ctgtaaccaa taaatttatt aatataaacg    127200
taatgaaaca tagggtataa ttaatattag cataatatga tgaaggtgta aatacttaca    127260
ctatttatat ctggtgttaa cttaggagca gcaggcttgt ctgttgtggg agcctgggga    127320
tttaaaaaaa ataaagcatg catatatatt aatgttactt gcatacattg taaatgaaat    127380
aataataatt gtgatataag gaagtcaaac attagatttt ggagtcttgt caaaaatagg    127440
ggcatccata acttcatctt ttttgcagac gttcccactg acaatctata atggaaacaa    127500
ctgagatttg agtaaacagt aacttgtatg cagaatagaa tatatgcatt gtatatatag    127560
tttgtatgag aaaacttaca tcatcttata cttttatatg atcagtagga acatggcttt    127620
cctgatcatg ttgctgttta tcaggtgttg gaacagttgg tgtggatact ggatcatttg    127680
```

```
ttggaggcat tgaggtagtg gggggttatc tacatttgga acatataata atatagtagt   127740
tgttactgaa atataactgc aatataaatg tatcgttata aaaaaatggt taaacataca   127800
catttgcaaa ctacatcagt atactatcag gatgcataaa taaaatacag ttttcaaaaa   127860
atgaaataca ctgaaaaaat atgttgctgc ttgtatgagt ataaattaat atataatttg   127920
tatatacaaa actgcatata ataaattatt tgagatcgta taagtatata ttattttcca   127980
ggaaataatt cgtgaacttg attagtttta aaaaataaac ataaatacta aaaccttctg   128040
gctgtgaatc gcgctgcgtt gcagctctca gaacttcatc gatcatttca ccaaatgttt   128100
cagagagttc aatctgcttc gaaacaatca tctgatggct cagctgaagg gaatcacagt   128160
atttatccac ctctttgtca tgagcatcaa acaatgattg aaacattgga cgctgctggg   128220
agggcaaaca ttgcaacttg ttgccaatca aattcttgat acgtggtaca tatatgttga   128280
aaacggcaga aacaggccat tctggagcaa tgacgtaaca cgtttctgaa cggctacgaa   128340
actgtagaaa gtaatataga acagttagca gtaataatat tttaacatct gcataacagg   128400
acaaaaagtt gtttatgtct aacctctgca tatccgaatg gttcaccagt tttacggggg   128460 ggggggnnnnn nnnnnnnnnn nnnnnggaat gcacaaaatat ataaaattag tacataacaa   128520
ctatttgcat atcatatata tgcacattaa acaaaaaaat acttaccaga acaatgagtg   128580
agcatccata tattgttgtt gtgatgtttg ttttgttcct tttatgccaa cgtgcggcag   128640
catcacacaa atccgtgtaa actagttgac accagtcaat atcagacatt cgggccatgt   128700
ttgaagtcat gagtacctca ttgtttgtaa tgccccaaga agcagaagga aaaagaagcc   128760
gattgaatag aatcagaaaa aaaacatcta attgatagct catcatcgtt gccaagcact   128820
atcttgtctt gaagcttgac aacatcaaat tcttctttac caacattgag atcacgtctc   128880
agttttgcag cagcatccac ttcaccatac caatcagtaa actccctgcc tcctccagca   128940
catggcaaac ccaaaatcag atgaaccgta tcttttgtta tcttcagttc cttgccagcc   129000
cctgggcgta tggtcatgtc atgtggatcc aatttatcca tcaaccacct gatgagtgat   129060
ctgctctcta aggcatcagt tcgcaaatca aatatgcttg aaaattccaa cctagcgaca   129120
gcatcgcgct gccgatcgct cattatccaa gatgatacaa taacatcata gggaatgcag   129180
cggatattca gtttctggaa gcataaatga atatgcatta atacacaaag aatatatata   129240
gttagaacta atgatacaat atttacaaac aagggataat tattacatgc ttgtaaataa   129300
ctagtctaca acaataaaaa aagtaaacac catatttgtt gataataata tacataaatt   129360
taaagtgggg gaaaatacaa acttgattgg acaccaaaat taacacatga ataaacataa   129420
atatatacat gttacctgtg attttctagg agtcttctgt ttaggagagt tttttttgta   129480
atgatattag actttggact tcttttcacg caaggaactt aaggaaaagg tacttttaac   129540
ttctttgcac tgatttgttc tgaaggagaa ggtgaggcag atctgaactg acgcttcaac   129600
gatggagcat ccatgaaatc gtcgtcggac agtgtggatg gagcaggagg ttttcttttt   129660
aaacgacaag ctaacgcctt tctgcgaaaa cgatggattg gggctggctg tggctcattc   129720
tgctcctgat tttggggaat atcatcttgg tgagctgagc tgctggatct tgtacgtctg   129780
gaaatgtcaa ttgaaaaaac ctcctgactg gattcaatgg ttaatctttt tggattactg   129840
ggtgggcgat caacagactt catgattaaa tactgaatag atctgtagaa aaaagaagtt   129900 gttttttaaat acattgattt atgcatgaat atatgccaaa aaaagaacta atttttacta   129960
taactatctg aaatgcatac tatataatgc taagtggaat tacataactt aaactacctt   130020
```

```
ttacatttat gcgatagcat ttaatgaaca atggttatat acaagcataa agattgattt    130080
aatatttcat ataattgtaa atggaccagg ataaaataag agccttttg catcaactaa      130140 ctatacaaca tattttaata actggttcat agtaataaaa acatttagct caaataacat    130200
gtatatttaa ataacatttg cttaaataac agtatttgta tgtatttata tataatgaac    130260
aggagtgtaa actaattatg caagtaaata gaacaattca aatatgctta atatattgcg    130320
aaatgttcat aaacttgtgt atgaatgagc atacacatta ctgccaatat gcatatatat    130380
caaatccaat gagtatattt tatatataat aaaacagatg tgtacacaaa tgatttaatt    130440
gaatgggcat aaaaagtact gaggatatgc atataaatga aatacaataa gcatattaga    130500
taattaaata gatgtgaaaa caaatcatta gagtaaatgt gcataaagaa tactgactat    130560
atgcatgtat aataaaacaa atgtgtaaac aaatgactca agtgaatgtg cataaacagt    130620
actgaggata tgcatatata tcaaatacaa ataagcatat ttgataataa aatagatgtg    130680
aaaacaaatc attaaagtaa atgtgcataa atagtactga ctatatgcat atataataaa    130740
acaaatgtgt aaacaaatga ctcaggtgaa tgtgcataaa cagtactgaa gatatgcata    130800
tatattacat acaaaaagca tatatgtgtt acttgggttg tataagagta ctctctgcta    130860
actcatcagt aaatacctaa tccacagcct ttgtctaaat ctatgaatgt cgggcgatag    130920
tgggaatata gaataaatac acatgcccta atatcggggc tcctaaacaa aaagagatg    130980 caatgcgcga tgcaatgacc cgattatagt gatgtctaag cggatacaaa tcacacattt    131040
agctggagaa taagggttac aatcaaatcc acttcaatcg accgataggc ttcaaaaaat    131100
cgacggcaaa ctcggtgtat ttcaatgttg gattacctgg aacttcttga atcgggctcc    131160
aatgctggga gattgaagga tgtaaggtgg aatagaaggg cgctggattg gagcggcggt    131220
ggattggcgc tgcgctggtt tggaggcgcg gaaatcgtct ggggagtcgc ctccgacgaa    131280
aggaaaatct gcgcggctgg ggttttcttc aaatcggcgc tggtttgtct ccgttgaatg    131340
cgcgactacg gttttagaaa catgaaacgt gggagaggtg gctggctgac ggaggtaacg    131400
gcgccgtgac taggacctgt tgattcggta tggttcaacc aaaatgccca tattgactag    131460
cctgggcttc ctctattatt ggaagcccaa ggctcttaat atataaacta tatatatata    131520
tatgccttcg gcctggtttg cctcggacat ggggaatgtg gacgacccac tgaagtttag    131580 attcttttc ggaatattta tttccttgat ttattttaat tctagagaaa tctagaatca    131640
atatttaaac catgaaaagt atcttgaagg tttcgaaaat tctaggaaac atccgaaagg    131700
tctattattt ggacatgagg aatatgaata aaatatctag agcctataaa aagatttag    131760 agccttctaa taaatatcta atagcagtag gagaacgaga ataattgcta gaaaaatttg    131820
gtaaattctt aggagaacct attcgataga taaacacttt ttgaaacatt tgaactcaaa    131880
gaaacccaat agcacacaca agcaagcaag caacacacac aagatcaatt aattttagaa    131940
aataaataat tgttttttt tcttacgtta agttccctg taaaataaat tagcttgcca      132000
aaatcttaaa attatgcgaa aaccgttgca tctaattatt cttttgtat tgacatgctg     132060 aaatttggga atccagggc gtgacaactg acaaccatct aacaccacaa taattacatg     132120
aaaacaataa aaataaaact acatttcgca atttataaca gtcgtcagaa ctagtaggca    132180
tgcatgtgca tacaaacact agtacaattt ggctctatac aagcggtagg attttacat     132240 cacaggcggt tcggttagaa aaccgcctgt gatgtcccag gcggtttagt acgcctgtga    132300
tgtaatagta tcacaagcgg ttttttgttaa ggaccgcctg tgatgctcta tccttttcac   132360
aagcggaccc taagacaaaa ccgcctgtga ttgtaaaaat atgaaaatac aatttaaata    132420
```

```
tgaaaataat tttaatttta acagaaatat gcaaatacaa tttaaatgaa ttaatattta    132480 attttaaca ataatatgca aatacaattt aaatgaatta taatagcaca catagataac    132540
tagagagatt ttaaattaat tggcaaccac aattcatagt cgatcataca tgataacaaa    132600
tacaatttga ttcatacaat tttcatgaa ctaccatttt tccgcatgta tggctttaag    132660
ttcttatcaa ttttcttttc cacacgcttg attctctctg gaccgttaaa gacgaacatc    132720
tcttcatact tattgtattc ctcatcttgg tctcccacat tctcaactcc aacaattttt    132780
tgctttccag aaataactac atgcatcttc tcatctgctg gatcgagtac atagaacact    132840
tgtgcaacac attcggcgag aacccacggg tcatctttat atcctacttt ctttaagtct    132900
accagtgtga gtctgtagtt atccactatc accccacgg gtccacctat agtccctagc    132960
atcgttggat ctgtgcaaga cttgaccaag taccctgtag acgatattgt tgaggacaag    133020
ccttgctttc ttcatattcc aatcaatcga tctgggacaa aaacaaagca agctgctact    133080
ggtttggtaa aaccaggact tgttaactac aaggacaatc ctgtcccgcc acactatgct    133140
gtggtccaag ttctagaaat cacagacaat ggttgtgaag attgggagat ggattttcca    133200
gttgagggga tcataacttt gcatgaggca attaacgagt tggtcctttg gcatcgacgc    133260
gacatcaagt ttggtgatga gccgaattca acaccaatgc aacaaaaagc tagttcgatc    133320
attccacacc ccatggtgca ggaagatatg acaccgacct ccaaaaaaat cgttgaaaca    133380
atcatatcgc ctcttgcgaa ggaactcgac gaggggacg tagacaaaat tgttcctcag    133440
aatgtcgacg tcaacataaa aaaggaacca aaggttggca ccaatgttga agggccaact    133500
atttcaaaga agattcataa gcgaatcgcc acagacgatg tcaagaaacc gtcagaatca    133560
gtggcacgct acctgcataa attgcagaga gttatgacta atcaatcaaa agcagtatca    133620
gcatctcatg gagtaggcac acggccggcc caaatagaca atttcgaaat atgggaagaa    133680
gatggaatga ttcatactcg agaatcatta cgtcttaaaa ccaatatctc ggtatacaag    133740
aaggaggatg ttcctcctaa atttgtgaat gggaggccgt tcttaacgac ggtgcaactt    133800
tctaagttgt cgactccgga gattagaatg cacgagtggt acatggtggc tagcaacaaa    133860
tacaaactcg aggaattcac attgttgtg ccagaagatg cattttggag caatgatcat    133920
ataaatcctg tgcggcattt attctttgat gatctctggt cgttgtacca ccgacaaagg    133980
atggaaacga actacttaac cctcttctgc ttgtaagtac ctctaaactt tcatatttgt    134040
tagttttgta cacgcacaca taaacgagag tctaacgatt aacactatta cacgtaggat    134100
gcaatacatg gatgataaga agaaacaact taagacaggg tttcttgacc cgttgatgat    134160
atcccaagct cgctacaaag tagttgctcg gaggcaagga gaagaataca aagacttgga    134220
cgatgctgaa tttgagaaag ccgtcaaaca gaatcagaga aagaaaatga aggtaatggc    134280
ggcatacatt ggacgagcca tgtataatca tgtacaacat ggcaaggact aataatagc    134340 tccgcaccac tttaagtaag ttatcgacat ggtttaattt tgaactataa attatggcaa    134400
tcgtgatatt aacatgtgtt ttcgtctatg tctatatagt gaccactaca tttgtatcat    134460
gatctgacca aaggatggta aagtcgtggt cttcgactca ctgagaatgg aaaaggctac    134520
gtataatgac ttcttgaaga ttttagagaa gtatgattat tattgcacac ttgtacttat    134580
tacaacttaa caaatgtatt cttaatctca caatgctatt cttatatgca gtgcataccg    134640
tttttattgg aaagatcttg gcggcgaaca tccagaggac aagcctaatt tgtcaatatc    134700
attatttcta tatggtgaca aacaacctcc gggtactgtc ctgtgcggtt attatgtatg    134760
```

```
cgaatggtgt cgtgtcacct tccattacat ggtcaatcgt gaggatgtaa gttcactatc    134820
attgtctata ttgcaattt tatgttatat tgttgctcat cacattactc ttagcaccga    134880
ttgatttttg ctttcattgc aggttcctaa atctaagatc aatgttgaat ggttagaaag    134940
agatatggtt tccaccggcg tggctaaggt tgtaagagac ttgctttact ttatgcgccg    135000
tgaagttctt catcaacaag ggctattcta caatgtaaat ggaaatttgc aaaaattccc    135060
agaactaagt ttgtacacaa tatcacacag tgtttaggtc tttagttagg aactttagat    135120
gtttagttgt ctatggaact ttgagatgtt gagttgttat gcaacttgat gtgtataaat    135180
ctgtgtatga tggaacttga tatatatgtg atgaatctg tgtatggaac ctgctatata    135240
tggggatgtt tgaatctttg tatgatgaat atgtgtttga atctgtgttt gaatcacagg    135300
ctgttattaa ttctgtttct gtatatgaat ctggaaaata tatatgaatc tgcttctgta    135360
tatgaatctg ggaaatacag gcggcttata attaaaaccg cctgtgatgt gtgactatca    135420
caggcggttc ttttaaactg gaccgcctgt gatgtgtgtc tatcacaggc ggttttgat    135480 tgaccgcatg tgatgttgtt ttacatcaca ggcgggtgca ccacaagcgg ttcctggaac    135540
cgcctgtgta gaggctattt cgaccgcctg tatagaggat acctgtagta gtgaaaatga    135600
ctcgacccgg tgccgtgcca gtgagggcaa atcatgatca tcgttttaat ttgtagcgtt    135660
cccgggcccc acaaaaaaca ccaataatag acgattccaa gtgcagaatt gtgaccgtat    135720
agaaactggg gagatcgata tatatcccgg ggctgaaaag taatgaacac tagtagagta    135780
tttagataag gagttgttcg tggggctcaa gataacggtt gcaagtgtgt ggtgcccgg    135840 cctttttatt gacagtatat ataaaccact gggcctcaac tagttgagca taaaattacc    135900
cacacacacc cagcagccag caccgatcga gaggaccaaa aacactccgg ccatcattaa    135960
ttaccgtatg tgctcttcct gctcttatta gctactacat atttatttgc agctttgctc    136020
ttattagtta cgaacatgcc agtgaagaag taaaccctgt ctgctgcttt tgtattaatt    136080
gcaggtaata atacgaaggc cgccatgatt gttgcagtag tagtactggc gctattgctg    136140
ttccacgccg actccctccc ccagaacagc acggacgaca tgctctccct gctcgacttc    136200
agaaaggaaa tcagcagtga tccaagaggt ttcctcacat cctggaacac taatagtagc    136260
gccgcccact actgcagctg gaatggcgtc acatgcagca gaacgcatcg agggcgggtc    136320
attgaactca aactcagcag ccaaagcttg caaggccgaa tctctccatc tctcggtaat    136380
ctaaccttcc ttagaacgct ggacctgtcc tcaaacagct tctttggcca gctgcccctt    136440
cttagtcgcc ttgtcaggct tcaggacctt gttctagaca acaaccagct gcagggtttg    136500
gctcctgacg cacttatcaa ctgctccagc ttgtactccg taacccttc atccaacatg    136560 ttagctgggc caataatacc agccagcata ggttccctct ctaaccttat gtacctttac    136620
cttgattcta acaacttcac tggagccttt ccatccagcc tgctcaacat gtctaaacta    136680
gaggagctcg acctttcttc aaacatgcta gctgggccaa tacatcctaa tatcggttcc    136740
ctctttaacc ttacacttct ctaccttgat tctaacaact tcactggagc catcccatcc    136800
agcctggtca acatctccaa actagaacag ctcatgctcc aggataatca gctcatagac    136860
aggatacctc aagttcttgg caatttatca aatatgaatc tattgttgct agcacataat    136920
atgctatcag gtagcatccc tgcaaccatt ctgaccaac attctcttga aattctggac    136980
ctcggaacca atttatacg tatggtgttg ccatccaata ttggcaaaac ccttccaaac    137040
ctcctcgggc tttccttgca caataacatg ttccatggtc caatcccagc atcgcttgga    137100
aacatttcgt tactccagat attagatttc acatctaaca gtttcactgg ccatgtacct    137160
```

```
agttccttgg gaaatctaac catcttgcgc ttcctaaaac tagaagagaa tagccttgaa   137220
gcaaaagaca atgagggctg ggaattcata gatgcgctgg gcaaatgtat gtacttgcaa   137280
cacctcttat tatctagcaa tcagctacaa ggagccatac cttagtaacc aagttcccgg   137340
atcgttggga tcgagaaatg gaaacgtggt acacggtacg ctactaaaat taggttttaa   137400
cactacggga acgagattgt tcccacgttc ctggaacaga acgaacgtta ccgtaatgag   137460
gaacgttggc catgttccta gttctcggtt actctatctc cagcagttta cccatactca   137520
tacctatatt caaacttcac tctgcgaaca gtacaatcta cagtacagaa caatacaaaa   137580
tagtgttttt attaggtaaa ctttgggtag actcctgcag acaccagaca acctaagagc   137640
cataccaact tcagttggga agttgtccaa tagcagtctt cagtacctat attatggcaa   137700
aaaataactt gtcgggagct gttccagaga gcatggcgaa ccttattgcc ttaaacgagt   137760
tagatctaga acaaaacaat ttgaacggtc cgattggatc atgggttgga aagttcaaca   137820
acttgaaaat attatctctc tctgacaata actttagtgg gccgatttca tcttccgttg   137880
gtagccttac taaggggggtg tttggtttct agggactaat gtttagtcct atcattttat   137940 tctatttag tttataaatt accaaatata gaaactaaaa taaagttta gtttctatat   138000 ttgacaattt tagaactaaa atggaataaa atgtagggac taaaaattag tccctagaaa   138060
ccaaacaccc cctaagttaa cacatctcca cctagagagc aacagatttg aaggtccaat   138120
acctcccagt ttgagtaaac ttcaaggttt actagaacta aatcttagtt ataacaatct   138180
ataaggcccc gttaatgaag agctttagtg ctacaccttc tttgaccaaa tgtgtgttgt   138240
cctataacaa tttagatggt ccaataccct cgcaggttag caaccttcag caactcactg   138300
aactagatct ttcgtcaaat aaacttgaag gggaaatgcc ttccacttta ggcgaatgtc   138360
gttagccaag tatactccaa atggactcca atttttctcat agggactcta cgtacaagct   138420
tgaacatgct caacctctca cacaatatgt tatcaggcat catccctgca gaactaggtg   138480
gtatgtcctc tcttacccag ctggatctat cttacctagt tgtggtggtc tgccagattt   138540
gcacttgtcc ccctgcccta ttgcctcaag ggaaaaagta gcacaatact acatcattag   138600
agtgttgatc ccaatatttg gcttcatatc actgttgatg ttgatatgtt tcgttcacac   138660
taagaaaagg tctgcacaac aatcatcaat atctcctctt ggtgaccaat tccaaatagt   138720
ttcttacaat gatttaattc aagctacaaa taccttctcc aattcaaatt gataggggaga   138780 ggaggttgtg gttctatata tagtgcgaat ttgatggaaa acaagctaaa ggtggctatt   138840
aaagttcttg acagtgacat gcatggcgtc gagaaaagtt tcttagcaga atgtgaagct   138900
ttgaggaaca tccgacaccg aaatctagtc cctatcaaaa caacatgctc aaggttagat   138960
atcaaaggca atgttttccaa agctcttgta tatgaattta tgccaaacgg gaatttggac   139020
tcatggttgc atcagcaagg cagtgggaat gtcagaaaac cttttggactt aaatcaaaga   139080 acaagcttag ctaccaactt agctgacgta cttgattatc tgcacaacaa atgtgggaaa   139140
acaattatcc attgtgatgt caagcccagt aacatactcc tcgatgatga catgaatgcc   139200
agtttgggag acttcggcat tgcaaaattc tgtattggtt ctatgtcaac atcaactgga   139260
gattcaaaat ctataaactc aaccggaatg aagggtacta tcggctacat acctccaggt   139320
acatattggc ttttgcaaaa ttccatcttt caattctagg tagctagtat acttcgagca   139380
tgcgctaatt caatgcatct ttagagtatg ctcgaggtgg acacgcatca acatgcgggg   139440
atgtttacag ttttggaata gtactgctag agatgcttac agggagaagg ccaactgatc   139500
```

```
atgtgtttgt ggacgaacta acattgtcga aattcgtgga gaggagcttc cctaataaaa 139560
tattggatgt gattgatggt tccttacgtg atgacttcaa gagtgcgcaa ataaacatgg 139620
taacagagag tgagacctac cgatgcttgt tttctctact ccaagtagca ctttcatgca 139680
cacgtgagat tcctggtgaa cgaacgacca tggaagaagc agctagcaga atttgttcaa 139740
tcaagaccac gtatgctaga gggattgaaa atgcaagcag gcaattgaat tgaaaccatc 139800
tctatgttga gcgaacgtac gtggggatgg acatcatccc aatatcgctt accatatggc 139860
agaaccgaca atgatgctcc gatggtgtcg ggaacaagta gtgaaattac cagttttcat 139920
atgaaatgtt acagaatgga agtgagagtc aatatcgact ttgtttgtag agcccatttc 139980
tatgccaacc aattgcgttt atagatttca gaaatacagt tctctttgga aactagaaaa 140040
tttatctgaa gcaagtgaca tgacgatgac atccatatgc actaccggaa tctgtggctt 140100
tgccgagtgc tcggcgcttt gtcgggtgct ttttgtcggg cactcggcaa agaaactttt 140160
tgccgagtac acatgaaatc atagagtttc aatgtagttc acctaggttt ctacacatag 140220
tgtctcacaa ctttctcgaa acattatcaa aattttatca cagcctctac atatgatatc 140280
atgacatgtg acaagtttc atgatttct gactttgttt atgttttata caattttaa 140340
acagctggat ggcaagttta cgaccatgtt cagtgagcat ggtgctcgaa gtttccggtc 140400
cgctcctgaa atcggtcgta acttgtgcta aatagcatgg atatcatttt tgcatgcacg 140460
gttttctaag tttcgagtga cttgcagttc aaatgtaatt ttttcgaaaa aattcaaata 140520
aacgaactaa atccagtagt tatagaaaat aatattataa ttgtcccaaa atggtacatg 140580
tatgtctaca tagtgtacga acataccata aaaagtttgg ttgggaaaag aaaaaataaa 140640
aaatatactt tgccgagtgt ccagaactga cactcggcaa agctttctct gccgagtgcc 140700
agctggtgga cactcggcaa agaagcatct ttgccgagtg tcccccttg gcgcttggca 140760
aaaaccctaa gtccagtttt tatcgagcgc ctgtcagtcg gcactcgaca aagacgtctt 140820
tgccgagtgc cagatctgtg gcactcgaca aaatatattt tttaattttt aaaaaatcct 140880
ttgccgagtg cccgcgatct ggcactcggc aaagccagtc aattttacac cggccgtctt 140940
cgtcttcttc tcttcactca ctctatctca attgcgcgcg cacccgctgc acccggcccg 141000
tgctccgccc taccgctcgc gcggccctg ccccgccgcg cgccgccgcc cctgtgccct 141060
gccgctcgtg cgctgccgcc cacgcacgtc gcccccatgc cccgccaccc ccatgcgctg 141120
tcgcccccgc gcgccgcgcc atctccgcca ctcccactct tgacccccatc aatctcgcgc 141180
catcctcccg ccaccaggcc gtacgaccat cgctacgacc aatttcaccg ggagcgtcgg 141240
gtatgaattt accgcgactc atggcccggt catgggtacg catccgcccc atcctactcg 141300
cctctctggt tttctaccta agcagtatta tccatatgag catgcacacg ataggaag 141360
cgtggttgtg cccctgtttg gaacagcttc tgggcggctt ctggccgcca gaagccgaac 141420
cacgacgcca aatgcacggc ttctcgccca gcttttcgtc gtcacgcttc ctaaagaagc 141480
cagcccgaaa gaagcccaag aagcgggcat caggccgcgt tggtagaaag cccccttgc 141540
ttcgttcgct cccctcctct ccatctggtc cattacgccg ccatcggtcc gcctcccctc 141600
catctttcat ctcatttgat ctggtgtagg tggtgctacg ggtggacacc gccgccgagg 141660
acttgtcgga tttgttagac atgagagacc gcgcaccact tcatctgcaa accagtggat 141720
ctagtaagca catgtacatc actcgggtat acctgatcca cgattcagtc gtcatgtctt 141780
cgatttctag gggcttgagt tctgcgcccc aaactgattc tttgttgttt catcacaggt 141840
ctgtgcccct gtcgtattac ctgtcccatt agaggttggt agacggcatg cgtctacagt 141900
```

-continued

```
ggttacatgc gtaaccatag ttggtgaatc ttcgacaagg ccgcggtctt cttatccatg    141960
tacacccgta tgcctgagcg gggtaggtac gcgcattgaa tgccgctgtc ccctgacggc    142020
ctttgggtga gcctcgttcc aggttttgtc cttgtcgtcc gaggtgggct caagcgaggt    142080
gaactttgct gtccagggat gtggggacct tggtccggac ggagattctt ccaagcacac    142140
gccccgtcca agatcgggct ccggcgaggc ggagttttgg gagaacccc tgagggagac    142200 ttcgggcgag acagagttct tgatcctttg accttgggga acgtactttg atgatgtcct    142260
taagttttaa tagcatttta ggggcgtaat ataggtgtcc ctaattatca tacccgatag    142320
tagctttcga gccttccaaa caagtgtttt gacaattgtt tggaggttct tctgtttttt    142380
gcgcgggtac gttgtccttc ctaaatgagt ggaaggtttt tgtttccgat gggtgcgcgc    142440
gagcgcaccc gtcgggtgta gcccccaagg ccccgaagga gtagttgact ctttcgagtt    142500 cttactttt acctctgtag gcatggttga cttcattcgt cacctgaccg tagccttggt    142560
gcgaacgaag cccctagcg tctacatcgg attgctggtg tttccaacaa gtttgccaca    142620
acgtgagttg caagggcacc cctgagcctc tggacgtggc gagagggcga tcgagggaca    142680
ccttgacttt ttttggttat acgcctcttc gttgcctttt cgcaaggagg aagagggga    142740 aagcgtcacg ctaccctcaa tgggcaatga gcatgacatc tccggtgagc tgtttaacgg    142800
gtaatccaag cgaaagcccg aactccatac gatagaagtc ggctagtggt ccggagacgt    142860
gccccaaaag tacatgcggg tgattcgcct ggtctcgaac ccgtttaatt gggtctgagg    142920
gctcgatgcc tccctacgat gggacaccat catgaatcac tcccgggggt ctcggatatg    142980
tcttaggata cctcgggatc gtggcccgac ccttggccat gtacgaacgt acccatagtc    143040
atccctgact ctatgctctg ggcaattgcc gaacccttct gaggggccaa ccttcgaacc    143100
cctgatcagt aacgaactcg aagcccacgt gtcctaaggc ggtttcccga accctgtcaa    143160
gggcccaacc ttcgaacctc tgaacagtat gtcgcctctc tcttttttcct tctcgaggaa    143220 ggcaccccga ggtgggggcg ccttcttccc gttatctcca agggaatgga aaaaggagag    143280
agaaagaggc acacctttg atgcgttagc ccgaggcggc gaagcggcgc ctgctgtctt    143340
acgtcagccc gacagggaga gggggaatta atgcgactgg atgcgttggc ccacaggccg    143400
accgatacag cgcgcgtgcg cggggaattc gaagcgacct agctcactcc cgactttgac    143460
tcacggtggc tcaacccatg tctcagtgac tctgtctgtc catataaatt cgcccgagat    143520
gggttcttcg attctttacc ttttgctctc gcttccctga cctagccgcc ttctgcctta    143580
gcagtaaaaa agctcatgcg ctctcttctc gtcttcatcc ttaggaacaa tggccgagaa    143640
actaagtgtc ctccctccct acgatccatg gctcattttc ttcgtcacca acgaagacat    143700
gcaggtgttg gtgtcctaga tcctacaccc acatccccgc cgccacctcc ccctcactca    143760
tgccaccacc actgtcgtca acccttcgc tcgcgcagtc gtcaatccct ccgctccaca    143820
gaatcgtatc attcactaca ggactcaact tcttgtcta gtgtcacaga cactaggtaa    143880
agcctctttt gcacttagca aatgctttgc ctagtgctac gctgcgaaaa aggtatcgac    143940
agaggacctt cgttgagtgt tatatgtcag gcactcgata aagactttct agtgctacgc    144000
gacactcggc aaagaaaagt catcataacg gtgggagaca cagtaacaat ggctttgcct    144060
agtgtagcac ttgccaaatg tttgcctagt gttgcacttg gcaaagattg cacctttgcc    144120
tagtgttacc ttcggcaaaa caaaaatcga accccctcca aaattatagc aaaaaattcc    144180
aaacaaaaca aaacattttt taaatggaac atgcacccac tagctgcgag catattttgc    144240
```

```
cttttttgcaa aggtgcttgg tattcagtgc accctcgcgt ggaaactgct ctaccactat 144300
cacatgtgtt tgcaagatgt ttttcttccc tcatattata ccaaaacgaa tgtaaattga 144360
ttgtttgagg aaatgaatga attcaaatga aaaggttgtc aactacaaag ttgtataact 144420
ttttgaatct ataactttca tattaataat ttcttcattc aaggtcgttt acaaaattta 144480
atatttcaaa cttgaaaact tcaaacgtat ttttctataa taggatgatt tcaaatcaaa 144540
aggttgtcaa ctacatagtt aaataacttt ttgataccta taactttcat tttggtggtt 144600
tttcaatccg aggtcatttg aaaattttga attttaaaat tcgaacatag ttttgcatga 144660
cacaatgatt tcaaataaaa aagttgtcaa ccataaagtt tcataacttt tcagaaacta 144720
caactatcat ttttgtgttt ttttatctga gatcatttga cagaaaatgt ttttaaaatt 144780
ttaaattcaa acacagtttt cgttgacaaa atgactacaa atcaaaaagt ttccaactac 144840
aaaatttttat aacttctgaa gatctacaaa gtttattttg gttgttggat catttttttca 144900
tccaacatgg tggtcctaac attcttcaca aatctatgta taagatttgt gaacaaattt 144960
tttttattgt catatgaaaa ataacccaaa aaattataca tcttgatgag ttatgcaaat 145020
ttgtagtttt tctttgccta gtgttcggca ctagacaaat cgtcttttta ccaagtattt 145080
tttgcctagt gtttttcttt gcctagtgtc cagcactaga caaatcgtct ttttgcccag 145140
tgttttttgt ctagtgtcca gtactcggcg aagtgcctct ttgcctagtg ttttttctttg 145200
cctattgcac taccggaatc tagctctttg cggagtgcca agtgatttgc caagtgattt 145260
tttcgggcac tcggtaaaga agcttttttac cgagtgtaaa aaacattcga caacacttct 145320
ttgccgagtg ccaagggatt tgccgagtgt tttttccggc actcagcaaa gaagcttttt 145380
gccgagtata aaaaaacact cgacaatgct tctttgccga gtgttatttt ttgacagtag 145440
acaaagataa tttttaaatc aaattttgaa gtagtaaatt aatttaaata aaaaattcaa 145500
ctacaaagtt gtataactca taagagatgta caatatttat tttagccatt tcttcatatg 145560
acaaggttaa agtaaatttg ttcacaaaac ttatatacct cttttgtaga tttgtgaaca 145620
atgttagagc caccatgttg gatgaataaa taatcaaaca accaaaataa aaattttata 145680
tcttacaaac ctatagggtt ttgtagtttg caacttttg atttgaggtc atcttgtcaa 145740
cataaactat ttctgaacta aaatttaaaa ttcgaatttg tgaaatgatg gaaaataac 145800
caaaatgata gttataggta ttaaaaagtt atgaaatttt gtagttcgaa tctcaccggc 145860
cacaaaacat gtgaattcca tttaagaaat ggtgaaaacg atagggtgat gggcagagca 145920
atggcgatgg ttggtgggtt gttcctctaa tttaaaaaaa tattgttttt cgggtttctt 145980
tggcgattct taatttgcgg caaaaaaact ctttactaat aaaatattta gctagtgtta 146040
tttgccgagt gcaaaagac tttgatttta ctgagtgtct aggacgcttg gcaaagaagg 146100
cgagtccgat agtggtgtag tactcggcaa gtgacacttt gactagtgcc cgtggatttg 146160
aactcggtaa agaatttagt ggttagtatg agctatatac tagtcatgta aatcttctag 146220
tacatataaa ttgacttgac ccgctgccgt gctagagagg gcaaatcata tggttgcagt 146280
gtttcacaca aaagacaata cagaggacac cactactatc gtaaggacca aactggatt 146340
ggacccagaa gaatcttgtt ccggtagacg attccatcag taggaatttt ggcggtcaag 146400
atacggtaag ctatgacgac gccacgcgcg tgtgtggacg taattccatt gtaatgccct 146460
ttttacattg tatataaaca accactgggc cttaactagt tgagcataca atttaactgg 146520
ataccacaaa agctcgccgc aggtgtatac atactctctc gccgatcgac cttaccttag 146580
gtgctcttct tcttcttcct cctctcttgt taattattac tacctctatt tttttacttg 146640
```

```
acgctagtta gtacaatttt acactaacta acgtaactat aaaaaaacgg agggagtagc  146700
ttgttattaa ttcctaccag gctaggaaca ttatttcatg tggacagacc ttagcttgct  146760
aggtagttcc tacgtacgaa catgcatgcc aatgaagtaa acctgcctgt tgctttgtat  146820
atatatatgt taatcgcagg tactatgaag tctgccatgg ttgctgctgt agtactagcc  146880
ctactgctgt tctatgggac tggaaacgcc aactgcgcaa cgctgcgtcc cagcagcagc  146940
aggagcagca cggacgacat gctctccctg ctcgatttca gaaggaaat cagcagtgat   147000
ccaggaggtt tcctcagatc ctggaacact agtggtagta gcgccgccga ctactgcagc  147060
tggaatggcg tcacatgcag cagaacgcac ccagggcggg tcacgagct caacctcagc   147120
agccaaagcc tgcaaggccg aatctctcca tctcttggta acctaacctt ccttcgaata  147180
ctggacctgt cctacaacag cttctttggc cagctgcccc ttcttagtcg ccccgttagg  147240
cttcaggacc tagttctgaa caacaaccag ctgcaaagtt tccccattga cgcacttacg  147300
aactgctcca gcttgcacgc tatagacctt tcgtccaaca tgtttactgg gccaatacca  147360
gccagcatcg gttctctccc taaccttacg tacttgtacc tttatgctaa tagcttcact  147420
ggagccatcc catcgagctt gctaaacatc tctaaactac aggagctcgt gctttcctca  147480
aacatgctag ctgggccaat accacctaat atcggttccc tcatgaacct tacacttctc  147540
taccttgatt ctaacaactt cactggagcc atcccatcca gcctgggaaa tatctccaaa  147600
ctacagcagc tcgtgctcca gaataatcag ctccatggca ccatacctca ggatcttggc  147660
aatttatcaa atctgaatat attggtgcta gggcataata gtctatcagg tcacatcccg  147720
acaacaattc tgaaccagcg ttcccttgga tttctgggct tggaagcgaa tttgctacgt  147780
atggcgttgc catctaatat tggtaatacc cttcctaaca tctacgcact taccttgtac  147840
aataacatgt tccatggtcc aatcccagct tcgctaggaa atgcttccca tctcacgata  147900
ttagatttcg catctaacca aactgaactt cctaagacta gaacagaaca accttgaagc  147960
aaaagataat gaaggctggg aattcataga tgcactaggc aattgtatgt ggctgaaata  148020
cctattatta tctgacaatc agctacaagg agccatacca gattcagttg gaagttgtc   148080
caatagcagc cttcagtacc tatattttgg cgaaaacaac ttgtcgggag ctgttccaga  148140
gagcatgggg aaccttattg ccttaaatac gttagttctt gaacaaaaca atttgaacgg  148200
tccgattgga tcatgggttg gaaagttcat caacttgaca gtattatctc tctcagacaa  148260
taacttcagt gggccgattc catcgtccat tggtagcctt actaagctaa cacatctcca  148320
cctacagagc aacaaatttg taggtccaat acctcccagt ttgggtaaac ttcaaggttt  148380
actagaacta aatcttagtt ataacaatct aacaagcttt gagtgaatgt cgtcagttga  148440
atgtactcca aatgggctcc aattttatca cagggaacat ttcgcctcta cgtagtctaa  148500
caagcttgaa catgatcaac ctctcacaca atatgttgtc agggatcatc cctgcagaac  148560
tgggtggkat gtcctctctt acccagctgg atctatctta taatgatcta caaggcaaaa  148620
ttccaatgga tggagtattt agaaatgctt cagctgtctc acttgttggc aactsgagac  148680
tctgtggtgg tctgtcagat ttgcacatgc ccccctgccc trttgcctta aaggaaaagg  148740
cagcacaata ctacaycatt agagtgttka tcccaatatt trgcttcatr tcactsttga  148800
tgttggtatg tttcgttctc actaagaaaa gractgcaca acaatcatca atatctcctc  148860
ttggtgacca attcccaata gtttcttata atgatttagt tcaagctaca aataccttct  148920
ccaattcaaa tctgataggg agaggaggtt gtggttctgt atayagaggg awwttgatgg  148980
```

```
aaaacaasct aaaggtggct attaaagttc ttgacagtga catgcstggc gtcgagaaaa 149040
gtttcttagc agaatgtgaa gctttgagga acatccgaca ccgaaatcta gtccctatca 149100
taacaacatg ctcaaggtta gatatcaaag gcaatgtttt caaagctctt gtatatgaat 149160
ttatgccaaa tgggaatttg gactcatggt tgcatcagca tggcagtggg aatgtcagga 149220
aacctttgga cttaaatcaa agaacaagct tagctaccaa catagctaac gtacttgatt 149280
atctgcacaa cgaatgtggg aaaacaatta tccattgtga tgtcaagccc agtaacatac 149340
tcctcgatga tgacatgaat gcccgtttgg gagacttcgg cattgcaaaa ttctgtattg 149400
gttctatgtc aacatcaatt ggagattcag aacctataaa ctcaaccggt atgaagggta 149460
ctatcggcta catgcctcca ggtacataac ggcttttgca aaattccatc tttcaattct 149520
aggtagtata cttcgagcat gcactaattc aatgcgtctt tagagtatgc tcgaggtgga 149580
catgcatcaa catgcgggga tgtttacagt tttggaatag acttctaga gatgcttaca 149640
gggagaaggc caattgatca tgtgtttgtg gacgaactaa acattgtcaa attcgtggag 149700
aggagcttcc ctgataaaat attggatgtg attgatgttt cattacgtga tgacttcaag 149760
agtgcccaaa taaacatggt aacagagagt gagacctacc gatgcttgtt ttctctactg 149820
caagtagcac tttcttgcac acgtgagatt cctggtgaac gaacgaccat ggaagaagca 149880
gctagcagaa ttggttcaat caagaccacg tatgctaaag gaattgaaaa cgcaagcagg 149940
cattgaattg aaaccacctc tatgttgagc gaacgtacgt ggggatggac atcatccaat 150000
aatatcgctt accatatgca gcgataagta gtcattggcg gctctagaag aaccgacaat 150060
gatgctccga tggtgtaggg agctagtagt gaaattacca gttttcatat gagatgttac 150120
ataatggaag tgagagtcag tatcgacctc tgcttgtaga gcccatttct atgccaacca 150180
attgcgtttg tagatttcag aaatacagta ctctttggaa agtagaaaat ttatccgaag 150240
caagtgacat gacgatgaca gccatatgga aggttcaagg ttgcaactca gtagcactgc 150300
ttcaaatcaa ttgtaaaata aactcagtaa ctcagcagct ctacagacac ccttcctgga 150360
agaggaaata aactctgtaa ttgcaagcct ctccaatggc aaggcaccgg gtccagatgg 150420
cttcaataca gatttcctaa aaaatgttgg ccggttatct cacaggattt ttatggtctt 150480
tgtaaaaatt tctacaaaga aaatgtttgt atacagagta ttaatgcatg gttcccacat 150540
taccctgctc ccgaagaaat caccccccccc cccctcacag tcagtgacta cagaccaatc 150600
tatttgctta acacgagtat caagttagtg acaaagattc tagctaatag gctccagaaa 150660
gttatcacca acctcatcca cgaaaaccaa tatgggttca tcaaacggcg taccatccaa 150720
gattgtttgg cttgggcctt tgaaaatatt tatatgaagt caaatggtta ttctaaagtt 150780
tgactttgaa aaaacttttg ataaaataga acacagtgct attatggata tacttcgcca 150840
caagggcttt ggggccaaat ggtggaagtg gatggatatg atcatgtact cggggacatc 150900
ttcagttctg ttaaatggag taccagggaa aaacgtttca ctgcaaaaga ggatacgcta 150960
ggaggacctg tgggaaacag tcagcgtaag atgggagggt gaattacgac ttctaaaaac 151020
tatctctaaa caaggccacg aattaatccc tagaacaaaa catatgcaaa taagcaaact 151080
agaatatgca aagtaggttt tgtctaaatg tttctatctc taccgcaaaa tgagtttgt 151140
aacctaagtt ccaatcctaa atattctaac tagaaaggag agattgactt aagtacttaa 151200
tggaaatacg aaagattaaa gagctagtag agaaagcaaa ctctcgtgga tgacgtcggt 151260
attcttatcg aggtatctgg aaccacgtaa ggtcccaact aattctcgtt ggtgcctctt 151320
catagggtag cccacgagag gccaagcacc acggtcgagt aactctgtag agagctacgg 151380
```

```
gccttctaca cacacaagtg gtgctccact tccagctcct ctcgaatgca ccccgtcgtc   151440
tccactatcg agcttccggc cgaaacaccg tgtgtcttgt tctctccgga cacaaactcg   151500
gttgtcacgg tctcgcaaga ctctcgtcac actcagtaca atattaaaac ggcttgcaca   151560
agagtcgagg ggttatgtga gttttttcta aactcactca actaattagg gatctcttag   151620
caagcgcatg agcggtctaa ctaacctaaa ctaatcactg cgtgatttta ttaagcactt   151680
ggatgtttga gcaattgaaa atgtctataa catatgttgg tatgtttctt gggctcccac   151740
atgccttcaa atgatcagtt gggtcaagta taccagacag tccggtggta ggcaccagac   151800
agtctggtgc tatgtccggt gccctatagc cgttggatat atctgttgca ttcaaccgtt   151860
agcactgtgc agccttacac cggacagtct ggtggctttc ctccgcccac tgtgtctcac   151920
attgctcgta gagaagtcca catttacaga ttactgacgt gtcgagatga tcatcagaga   151980
ggcgcgttca tcagcaggga ggaacgctaa ggtatgacgc taccaaacct aacgtacatg   152040
caatatctgc aatacaatga cgaccgagga ccgcatctct caagcctttg tcatgtcagt   152100
cgcgtcaata atttgtatat ataagcatat gctgatgtgc aggctaatta gaggaggcga   152160
cttaacatca aaaaaattag acgagctagg cgacttcaag tcattccttt tttctgaccc   152220
cagattatta tgaacaatat tatccacctt tattcattgg tcaataattc aaatacaaac   152280
aatattatct atgaaaataa aacaatatta tctatgatgt gccatttcgt ctttatgccg   152340
tatctacatc atcctgttgc ttctatatag gagtacctaa ttgagaatat atactaactt   152400
tttgttcagg actagaccgt acatcgtctc tctcgtttat ctacaatgca gtctccattc   152460
gatctgttca gagagtgcca aaacttgcat gacgtcacca gggccgttca gccgttcctg   152520
agttttatgg ggctggggac tgagattata aaccgaggtc ccaatattat taggccccgt   152580
tcgtttgttc cgtatcgaag acagacatgt ttttattcta ggaccaaata gggtgaatcc   152640
ggatatttca ctcaacattg gccaggaaaa aatctagctc tggaataaaa actggtgcta   152700
cagtgaaggt tgttcgcttt gacaggtttg ttggttgctg ctcagtttcg gccagcatag   152760
ctgctgccta gtccagtttt agtcaggata actgctcagc tttgtttcta atgtacttgc   152820
acatacatac acatattaac aactaaaaaa caatggtgta catatataca tacaaagata   152880
catttcggtt gttgtgttca tggagaggag atgatggtgt acgaatacat gcccaacaag   152940
agtctggact catttatttt cagtaagttt tcagctacct gcagccctga ttctatacag   153000
atactctata cagtgagcca gcaaacgaaa attttcctat ggacagttaa cacttcctat   153060
cgaaatttcg agacgaaagt aagaggctcg tgttaggctg gagactgcaa tacaagatca   153120
tatcagcact gcagccagca gccccggaga ggagggtgcc gtgcacgaat gatggcggcc   153180
gtgcaaacgg aggcgaggat ccatggatgc catctacgcg cgcgcgtgcg agggactggc   153240
cggcgaacgg aggcgccacg gagctctgag cgagtgcctt ccacgcaacg tacgccacgg   153300
atcgatctgc atctgcgcac ggcgcggtgc tcattcgcat tccccagccc cactgcatct   153360
gcgccgcggg ccatccatgg atttgccttc ctgagctctc cgctacacga acttccaggg   153420
agcctcctcg tacgaaggca agagctcaga tgcagatgca gtggagaaga tgcagataca   153480
gtggaaggca aggaaacaa cgcatatgca gatgcagtgg ggaccgacag cactcaagga   153540
cgaggcagcg caggtgcgtt tggggaagag agggcattgg ttaccggtga gaatgcaacg   153600
aggagagtta tcgtcatcgc tgcgttgtgt cgtcaagccg tcacttcgcg ccgccgtctc   153660
ctcgcctcgt tcgtcgccag cgttgcccag tgcccgttcc tccaagattg gatccggagg   153720
```

```
gcagcacacc cggatttcta ccgggccacg gtgttcagaa aaactctaaa ccagatcctt   153780 ctcattttt gattcagacc caaacgaaca gaattcagac aagcggccca atttcaatcc   153840
aagtcatttt tttccaccta aaaccaggcc cggaatggac caaaccagcc taaccgaacg   153900
ggcccttagg aagtcccagc cgtccactcg accgcgcaca caacggcct atgcggtcag   153960 tcaagctgac ggtccatcac ctaaccctgg taaaaccttc cgacacgcgt cgttcaaaca   154020 cccaacccc acgtgggaca cacgtcaatc gtggttttat ttattttta cgcaaataac   154080 ataaatagtt cacagaaata gcgtaaataa ttaatagaga tatcataaaa cctcagtcca   154140
accactggac cacgtccaca ggcgcagacg tatacatgca aatcctattt ttatggtaga   154200
gatccgataa ttatgacaaa tcatgagagt ttccattgta tgtgcgcaaa ttttggatga   154260
cattttcgtt ttcattgcat gtgcgcaaaa attggatgac tccataaata taggatcgct   154320
caaacaacca tgcagctagg ctcgttagaa ccgatttatg atatatagtg atactaatta   154380
tgttatacgg tgtaggtaaa aatatgtttc ctgctacatg cacacaaatt taggatggca   154440
cgaatgtgca ataaaaggaa atgaattggc atgtatgaaa acaaaaaatc ttatataaat   154500
gctttattta ctacataaga gcattccac agccatgtag ttaggctcgt tacaaccagt   154560
ttatgatata tactgatact aattatgcta caaggtgtgg gtatttatgc aatgttgtac   154620
acttcgtaaa agtttggcat gcggttcagt ggtggacgta tatccatatt tgagcgtaaa   154680
aacattcaat tttgagcgta aaacccata gttataagcg taaatactga tccaacatga   154740
aagctgttga aaacttcttg atgttggcat aaatatatat acaaagtgac ataaaaatat   154800
atacgcgatt gtatatgtca ctccaccagg aacatgcaca ttcaggcaca tcccccacca   154860
gatgaacgca tgatgtccta tttgtattgt agatctaaaa aatatggcaa ccataggca   154920 catgtatgcg attctagttt ttatacaggt ccaaaaatta tggcaggtcg tggggattc   154980 cattgcatgc acacaaattt tgaatgacat tttcgttcca acaacataca tgcaaaatt   155040 ggatggctga gattgcacaa agcataaatt gttatagaaa gttgcataaa tatctacatc   155100
gtacatcata attaataaaa aatctagtaa gggctcaacc aacagtcgca tgcataaata   155160
aaggattgga ggaggtcatc gctagattgg aggagttggt catcgaagga cgctcgaacc   155220
atcatgcaga ccaccgaacc tcgcagccca cgccttgtgc gaccttcgtc acagtcgcag   155280
ccacccgcgc cttgtgcggc cgatgtagcc actagagcca cccgcgcctc gcgtgtccac   155340
tcccactgga gacggcctca cgaccgcagg tttggaagag gtcctcgtcg aaggacgcac   155400
gagtaacgct ggattggagg atgtcacgtg cggccgtcgt cgaagtcaac cgtggtcttg   155460
agtggccgac gccaccccgc atccgatact cgccgcatta cagaccgatg accatcgcag   155520
ccctcagcca tcgctcgtga ctcgagggcg tagtcgccgc atgcgtctcg aggacgtcgc   155580
cgccgcacac gccccctag tccctcgcgc ctggggttgt ttttatagac gtctgaccct   155640
ggtgtggctg aaccggatga caccgttggg ccaggacttc ctctagttat tggaagccca   155700
gtgacttaga tatggaacta agattgttgc ctcaaatata ttgtagggat caccttaaaa   155760 tgactttaa catttctaaa tgcaaaatca tcaatgatgg cttgaatatt aataacatct   155820
aacaattttg tctcaacaca tgaagttgct atcctattta atctttattg aggcattata   155880
aaccttaaat aattctttaa taattttagc tttgagaagc tcctttaagc tgatgtcata   155940 gttttggta ttgtaaataa tatcgataag caacaaatat attaggatag caatctattt   156000
ctctaataac taaaaaaat tcataacaaa cattgatcta tctgacagtg tcatttgcaa   156060
tattcttaac tctaatatta gatcatttgt gtttgattgt gtgtaggcta tggcctggct   156120
```

```
ggctgatcgc tagaccgagt ttctgtatgc actaagatgg gccctgggaa gtggaggtct 156180
aggtcggtcg acctcttcga ctcccctctt gcacaaccct ggacatcgct caccctaggt 156240
ataaaagccg aaaccaaaga ccgaacgaac cagagagaaa cctagagcga aagtaaaaat 156300
cccaaaaccc aaagcccaaa tacaattttt gggtatgtaa tgtgaaaacc caatcaagtt 156360
ttgggtctgt tccggtacta tgttgtgata cccgaatttt ccgagcatcc taaaatactc 156420
acgacggggt caacgttggt cactgagtgc tcacggtcac cacctaattc tctaactccc 156480
ttcggcctat aggtgtccag gcctccatgg accatggtcc agcgttgctt gcccacaggt 156540
acacatgcat cccatcccca agcctcaacc ctaggagtaa ctacaaccaa gcaaggcatc 156600
gcaccaccac ccactgcaag ttgtagtcgc tcgacagttg ccacgatgcc acccccacac 156660
ggacaaggcc caaggggacc atatatagcg accaagcgac gacacaaact aaggcacgat 156720
aggcaacaac tggcgaccaa gacgacatga gcctttctca agcttctgct ccatgcttgc 156780
ttcctactta gttcccttt gaaactagta gatgaaagat tcatgtactt ggttatcttt 156840
tttggggttt ttttgtatag atggttgtcg atgatatctt gatagtaaat ttgtatgtgg 156900
gcattcacaa gatcttagaa ctaagagtaa tggcacatga gacggaaaaa ttatactaat 156960
tcagactctc ttgagagata ataccctaag tctagtttga cggtggctat gcttatgatc 157020
gtgatgtcgc tgccctctca ggggacctca acccccccatt atagtcgaag aagtgagttg 157080
gttacaagga aaggaactcg tccataacaa actaggactc ttatatgtgt tacaatatca 157140
tcttatccat atctctatgt gttaactcgc atttatatca tgtactactg ttacaatgaa 157200
gatatgcaaa taatggaatc ttactgttga ccagatcccc tcctgatgtg agatccaggt 157260
ttcctaatat tcaatctgtg tgtgagtcct ttgcggaatc cgagttgcga ggaccgagtt 157320
gggcccacaa actgaccact caaagataag catacttagg gtactcctga cacatctcct 157380
gtacagttgc ccctgagctt aacatagctg agttgtcttc ttgagtaggt tgagctcaaa 157440
catatctcaa tattttctgg tagtcgaatt attcatacta gatgaaactc ctgattccta 157500
gaactcggtc actttattgt tcataactcc gtctgaggat gtcgggccac ttgttgtttc 157560
aacttccaag cataagtttg aaactccctg aaggttataa aaaaggccat tggttttag 157620 ggttacacaa ttttgtttct ccgcccttgc tttctcagta caattgccaa cttcttagag 157680
tgatgatctt tgtccatacc gccctttcac tccaaattct agcacgcaac ttcctttaca 157740
gtctcacttc gaccatggtc gcctcccatc ctcacgagtt cgagaaatct accatcagaa 157800
caaaagatct agaagccttg atggcgatga agcgtttact tgagagggat attatttagg 157860
ggaagtttct gggtaagaac aaaatcttcc ccatgcccga tattgaccaa atcttaattt 157920
tctagcacca tttccttcat aggataggaa ttctggcttc ggtcttactg agggatctgg 157980
agtattataa aattgacata gttcacttga atcctaactc catccatcat attgccattt 158040
tttctctttt atgcgaggat tttttagga ctcctccgtc cttacctttg ttccagtatt 158100
attatatcct tttgttctcg ccgatccggg gatgaaaacg gtcggaaacg gtatttattt 158160
ggtaatcagt tttttggtcg tttttctttg attgcgaaca aataggatat agaatataca 158220
atacaaattt gtattcttgt tttaacatcc agcttgttaa gattcataaa aggtaaatct 158280
caaattcagc ctatattttc tcaaataata gatataaact tcggtatgta ttcggaaaca 158340
aattcggtaa tttttttcaac ttttttgtgtt gtagggagca ataatacat aaaacaattt 158400 atgtaatatt ttattcatat ttgtactaat gtgcttgata acataagaaa agatcaacat 158460
```

```
caaattttac acatatctat tttaaaatat taaatttatt ctaacagttc ggattaccac   158520
tttcatccct agatccgggc accaataact acgatgagaa ctggcagcgg tgctctctgg   158580
ggaagcgcgg acgtctgcg gccaagggcc agacggtccg tgacctggcg cagagggtag   158640
ggttcctgcc tgacgagctg gatggtccac gcctgatggg cggacggtct gcacgtgcgc   158700
aggggcgata gagtgcgccg acggcgcctg gatctcaatc ccgggaggga cccgtcggg    158760
gaggagagat cctaggtgtg tcttgggatc gataggccat ccaagacacc tctaaatgat   158820
gtagagctag agagaggtga agattagaga gagaaatcta aattactgcc taccoctagg   158880
gcaaaatgta aagaactagt ggtatattga ttgattgatc gattgttggt ttcttcgatc   158940
ggtcatacco cttcaaatat ataagggggg gggggggtct agactcgttc ctaggcatcc   159000
tccaacaaat cctatcgcgg accgtccgca cctatcggta gaccatccac gggatggacc   159060
gtcctggcct aatgtcggac cattcggcca tgcccagtgc cacaaatggt gctcaataca   159120
tgtgatacco agtttgcaaa gaagagaagt tggagtttat tctttcgttg tttcttttt    159180
ccttctttct ttcgggtggt acgctttttgg ggttgggaat ttttgggaa gcattcacca   159240
gtaaactagt agaattttgg ttagactcat gcgctagggg gggtcggggg ttgaggtgtg   159300
aacgagttgg gtcgtggttc ttgatccggc ccactagttc ccctaaccct agccgcccct   159360
cccttaatcc cttgggatt tttttcagcca cgcccctccc cttttctctt gtgcagccgc    159420
ccccctctct ctaggcttgg aggacgcccc tctcactcct ccaccatttt gcagccgcca   159480
ccccacctcc cccatcaaac cctagccgcc ccctcctcaa gcccttctct ccaaggtgcc   159540
attccttttcc cgctcggatc tacgtcgcgt tggtgcatgt ctccaattgg attttggtgg   159600
agggaagaag aagggaggaa agggggagga ttcaaggtga ttttgagatt gtatcttgtt   159660
taattgtgtt gtaatctaat tgattatatg tttacctatt cgaatcggta gaggtgttgt   159720
cctgaaattt tgtgggtggg cgaacaacag tagttctagg gatttctggg aattttacgt    159780
gggtaattag tggagatcag tgggtgaatc atgtagagct ttgtcatacc tttccaacgg   159840
gtacttatgc gctcgattcg gagttataat ttaggagata tcgttgtttg aatccggtta   159900
tgttgctgtc caaaaaaaca gattttcagg tgggtgaaca gcagtagtat tagcagtttc   159960
tgggcatttt tcgtgggtaa ttagtgttaa ctagtatgat aataatgtag ggctttgtct   160020
tatgtttcca atgagtactt atgcgcttga tttggaatta tattttaaaa gatatcgctg   160080
tttgaatccg ggtatgtcgc tgtccaaaag acaaaaaaaa aacagattac cgggttcatc   160140
ttgtggactg ttttgggcta attagatgtt ggaatttaat tataaattgt gtacaaaact   160200
tgtggggaat tttatgtaga tgcctctgga gtttttgttt gttaccactg ctgtcataat   160260
tttaaagtta tgaaattatt aaacagcccc gctgcagttt ggtgggtgtg gggagagatg   160320
taacccgcag cggggtttga gtttgtgcgt aggtgcggcg tcgcttatga gcctgattat   160380
gtgaaatggt gcactaagtt gtgtgtcaaa acaggtggt ggacttccgg atcgtactta    160440
gggatttgcc cgaacttccg gtaaaggcaa gtaaatacag tggtggttgc taccgtttgg   160500
tttgcatcct attccctgtc attgggtatg cataagtttt aattatgtta atcattgaat   160560
tctatgatga agtttatttg tttggaagta ttaattctca attgtctaat attgtggatg   160620
atcataattt gttaatgata tatgtggttg attcccatct tggatgaagt tgaagtatct   160680
ttttgaatca cgttatatga agtgttgtag gcatgacatg cacatcgcat catccatctt   160740
gcattttgaa gttatgtcgt gatcttatgg tccgaccgta ccggtacatt attagcatcg   160800
tacgttgccc gaggaggggt acgatgcggc ttcatatcct tggaggtatg aaggcagaag   160860
```

```
tcattcttgc atttgcagac atttgcactc atgaggtata tatatatgaa gtgtgacatt   160920
actatgttac tattgtggtt tctacctgcg aggtgtggtg actaggtgtg ttgtacgttg   160980
tatacgtgct gcaccttcgt aataagaagg ttgtggaatc aagtggtggt aaaacaatgt   161040
tcttatatgg ttaaacagtt tgatattatt ttacttgctg agatgtgtca tctcactctt   161100
gcattactca atgcaggtac ttgatacatg ttgggaatga ggggagtagc agcacgtcca   161160 cttcactct cacaatagcg ctgccgaggt gcatctatga tttaattaga aagttagctt   161220
attgggccgt aggaagttca ctctcacaaa caatgtcact ttcactctca caattcttgc   161280
atttgtaatg ttggtcaaat taactttcta gaggcttatt gggccgtagg aagttagcta   161340
gctaacttcc taggggctat agtcagccgt agaaagctaa cttcctaggg gctacagtca   161400
gccatagaaa gttagtcgta ggaagttaat cagctgacgg cgctgacggc gtgaagctac   161460
taacttccga gaacctacta acttccgaga ggcttctttg gctgtaggaa gttagctaac   161520
ttcctagagg gctctaggaa gttaagctaa cttccgacaa aaaatttccg agagccaaac   161580
ttccgacggg atggcttaac tttcgagagt ttagctaact tcctagagtt tagggctaac   161640
ttcctagggt ttaggctcta ggaagtttat tattttggtg tagtgcaagc ttcttctcgt   161700
cgtcgatgag caacgccaac gcgagcgcct cctgccagtg gtgtttgttc ggggtttcca   161760
tgtaagaaac atggattcat ctttggcatt ggtttatgaa aatgacttac amatyaratc   161820
catggaaaaa atattatgga gaataaatat cacgcatata aaaaggaat ttaagttgaa    161880 aatattataa aacaatcgtc aaatattata aaacggcgtc gcagcggtga tcgcgagggc   161940
ttggatggtg atcgggacga catggcgacg acggagaact ggctttgata ccaaatgaca   162000
gagtcccggt ctacgatgac acacacaagc acatgtaaaa gacacgagag gtattttggt   162060
gctgcaaagc cacttacttg cttgtgttgt ttagctattg ctatataaag gaaatacacg   162120
cagttataca tggttaccca atcccggcat aatcgtgctc gatgattgcc atcccaatca   162180
cctggggtat gccgcaatct gggcagatat tcttctaatg gcgctagggg ccctctgctt   162240
tctatagtta gcagctagga tttattcaaa cagtggtcgc aggggcgccg ccgtgtaagt   162300
gccgaagatg gtgggcttga cgacggattc cgctcgacgt tcccgctcga ggagtttgtt   162360
gacacacgcc acctcctcga cccgcttgac gagatcgggc cgccattgct cgaggtcggt   162420
gcgcttcccc tccaacgcaa tgccatgttc gtcactgcag agtgcagcga catcgacctg   162480
ctcctggatc ttctcgcacc gcactgtgaa gagtgcaggg agtcgcaccg cacctccacg   162540
cgccgctcga cgctgtcgca gcgtccggtg aacttctcgg agaggccgga ggcgtgcttc   162600
catcaagcat atctggcggt tggtcggcgt gctccatagc agacgtggtt gcacgagtac   162660
gccatggaca gatgccgctc gaatcgagtg tgtctgattc tgataccaga ttgttagcac   162720
tcgggaggga attgatgagc aggaagaaag ggggttcggg aaaaacagcg acggcgctgc   162780
cgctcgtagt tttactgttt tgttcatcga cggttcgttc tctggtgatg aggctactta   162840
tacctcacct attacagccc agcccaatgg ctcttacacg gcccactccg gcccacacac   162900
acgcacggtg tcgacgtggt cgtgcccctgg cgccttgctc catcgcactt gctgcatctt   162960
cctcggcttg gcctccgtct tcacctggtg tagctgtgct gacatgttgt tcatcccat    163020 gtccgcttgg tgaggcaaac atagaccggt gcttgtgcta acacagagat ggtttcaatt   163080
caatgtttgc ttgtgttttc aattccaatc ctctgctata cggggtcttg atttgaacca   163140
attctactgc tagatagctg cttcttccat ggtcgttcat tcaccaggaa tttcacgcac   163200
```

```
gtgtgcaaga aagtgctact tgcagtgtac tagaaaacaa gcatcggtag gcctagctca   163260
ctcgatctct attaccaact aatggactat ggaatgggcc cactgaagtt attgtctgaa   163320
agagataatc ttaccaagtt gttcaacttt ccaacccatg atccaatcag accgttcaaa   163380
ttgttttgtt ctagatctaa cgtatttaag gcaataaggt tccccatgct ctccggaaca   163440
gctcccgaca agttgtttct gccgaatcgt aggtactgaa ggctgttgtt ggataacttc   163500
ccaactgaat ttggtatggc tcctcctagc tgattgtaag ataataagag ttttttccagg  163560 aactgacatt tgcgcaatgc atctatgaat tcccatccct cattatcatt tgctttgagg   163620
ttgttctgtt ctagttgtag gagggatagg taggttagat ttcccaaaga actaggtaca   163680
tgtccagtga aactgttagc tgtcaagtct aatatcatga gaattgaagc gtttcctagc   163740
gatgctggga ttggaccgta gaacatgtta ttgtacaggg aaagcgcacc gagttgagga   163800
agggtatggc caatatcaga tggcaacatc atacgtagag aattctcacc caggtccaga   163860
atcctaaggt tacgttgctt cagaatggtt gtcgggatgc tacctgatag actattatgc   163920
cctaacaaca attcgtacag atttgataac ttgccaagat cttgaggtat ggtccctatg   163980
agctgattat cctggagcag gagcagttct agtttggaga tgttgcccag gctggacggg   164040
atggctccag tgaagttgtt agaatcaagg tcgagaattt taaggtgaaa gagggaaccg   164100
atattaggcg gtattggccc agctagcatg ttggaggaca ggtccagtat tctaaggaag   164160
gttaggttac cgagagatgg agagattagg ccttgcaagc tttggctgct gaggttgagt   164220
tcaatgaccc gccctgggtg ctttctgctg catgtgacgc cattccagcc gcagtagtcg   164280
gcggcgctac tattattagt gttccaggat gtgaggaaac ctcctggatc actgctgatt   164340
tcctttctga agtcgagcag ggagagcatg tcgtccgtgc tgttctgggg gagggagtcg   164400
gcgtgtccag ccccgtagaa cagcaatagc gccagtacta ctgcaagaat catggcggcc   164460
ttcgtattat tacctgcaat taatacaaaa gcagcaggaa ggggacctgt tgtttcggc    164520 ttctggcagc ttatgccac caaaagctgc tgcagactgc caaacgctca gcttttcagc    164580
cagcttctat aaaattcgtt gggggcaaaa accatccaaa atcaacataa acacataatc   164640
ggttgagtcg ttgtaatagt aggaatccgt cactttctag atcctgagcc ctatgaacaa   164700 atttatttc ctccacacgt aatcgtaatg atactcagat ttttcccaca gccagattct    164760
ccgcatagcc agatcttcag aaaaactggt cagaaaaaag ctgaaccaaa caggcccagg   164820
gtttacttct tcactggcat gttcgtaact aataagagca aagctgcaaa gaaataagta   164880
gcagctaata agagcaggaa gagcacatac ggtaattaag gatgactcga tcggtgctgg   164940
ctgctgggtg tgtgggtaat tttatgctca actagttgag gcccagtggt ttatatatac   165000
tgtcaataaa aaggccgggg caccacacac ttgcaaccgt tatcttgcaa ccgttatctt   165060
gagccccacg aacaactcct tatctaaata ctctactagt attcattact tttcagcccc   165120
gggatatcga tctccccagt ttctatacgg tcacaattct gcacttggaa tcgtctatta   165180
ttggtgtttt ttgtggggac cgggaacgct aaaaattaaa acgatgatca tgatttgtcc   165240
tcactagcac ggcaccggat cgagtcattt tgtatgcaca tgcgtgcact actactttc    165300 agccccggga tatcgatctc cccagttct atacggtcac aattctgcac atggaatcgt    165360
ctattattgg tgttttttgt ggggaccggg attccgggaa cgctacaaaa cgatgatcat   165420
gatttgccct cactggcacg gcaccgggtc gagtcatttt gtatgcacat gcatgcacta   165480
ctagttctga cgactgttat atataaattg cgaaatgtag ttttatttt  atttttca     165540 tgtaattatt gtggtgttag atggttgtca gttgtcacgc cctggaattc ccaaatttca   165600
```

```
ggatgtcaat agaatgaata attagatgca agcataattt taagattttg gcaagctaat    165660
ttattttaca gggaatttta acgtaaaaaa acaattattt attttctaaa attaattgat    165720
cttgtgtgtg ctgcttgctt gcttgtgtgt gctattgggt ttctttgagt tcaaatgttt    165780
caaaaagtgt ttatctatcg aataggttct cctcgaaatc tactaaattt ttctagcaat    165840
tattctcgtt ctcctactgc tattagatat ttattagaag gctctaaaat cttttatag    165900
gctctagata ttttattcat attcctcatg tccaaataat agacctttcg gatgtttcct    165960
agaattttcg aaacgtccaa gatatacttt tcgtggttta aatattgatt ctagacttct    166020
ctagaattaa aataaatcaa ggaaataaat attctgaaaa aaaattctaa acttcggtgg    166080
gacgtccact ttccccatgc ccgaggcaaa ccggaccgaa ggcgtaatct gtgatctgtt    166140
ttttacctca agattgcgcc cacgcatgtg gactctcaat cacacctagt gactgacgcg    166200
tagaacccac ccaacttttt ttttgctttt tggcctattt tacaaaagat tttcacaaat    166260
acatctaacc tggtttgaat tcagaaaatg gatctttacc tcggcgccat cattattggc    166320
gccaaggtca aacatctcga tgtcaatata gatggcgcca aaatctcgtt tacatcgctg    166380
agttggcgct tacgtgtgag ggggttggcg ctgtaagcat tggcgccgac ccccccattta    166440
tttactcgta tgatcgacct gcctcctgct ggtatggcag ctttgccacg actctagctt    166500
catttttaat tttctatctt actatttact catgtactac tcgtccattt tcaatggtga    166560
ctcttacagc aaactgtcca gagtgatttg acgtgaggtg cggtcacaat gacgatggca    166620
aacgtctcgc ttcatgcacg aaagcagccg gcaaggtgta ctgcacctcc caatgcaagg    166680
atggagctcg atctgacacc tgtatcgcta ctctaaaata tgtatacacg aataattgat    166740
aaaataaaaa tataataatg tttgaataaa tatattacat tgaagtaaga tctacctata    166800
tgatatatag aaaccataac aatgtacgtt tagctaacca ttaaacatta atatccatta    166860
aacattaata ttgtttacat aattatagcc aaaccttagt ttaattgact tagtgacttc    166920
tattagaatt atatttttag aatgcctccc gcatctatct tatcttattc cctattttaa    166980
actccacttt agaaatatta ttattaacag tacaaattat ctattttaca caatctactg    167040
aacctttata attcgagccc gccatagccc atagatgcat atgcatgcac gcatatcagc    167100
atatgccacc attggggctg caagcagagc attgatacat gtgtacagta cagttgtact    167160
cgtactgggt agctagttgg tcgggattgg ataggcaata atgacggcga cgagcatgga    167220
tacatgtgta cagtacagta caaaacattt atattggcgc cgagctctag ccacgtaacg    167280
tgtaacctcg gcgccaataa tgatggcgcc gaggtaaggg tccatttct gaattcaaac     167340
cagaaagggc gtagttgtga aaatctttca taaaagtgt caaaaagcaa aaagttggt      167400
agaacccact catcatactc atctcctacc tagagtctct ggactcagtc gtcgtgattt    167460
ttcgaaggtc taatatgagg accccaaaag tacaaatatg acaagatgt tattggaata     167520
gaagagacaa gttagagtcc taaacataca tgacaaaatc acaacataca aggcagagtc    167580
ctaagatata agataggatc ctaacggata aggaagcata attgtgatta tatagagttg    167640
gactcccata cgactaggtt accagattag atctgttagt gtttcgaacc tcactccgat    167700
aagtaaattt attatgcacg ttccgggatc cggagggcgt gcgcggtggg tgcaaggttt    167760
atactggttc agacagaacg tccccacatc cagtcatcag tggcttgcgc taccgacaca    167820
aagctcatag taggggttac aagcaaggcg agagagggag gagaggctcc caagtctctt    167880
tttcatggtc cagatgatta caaggtgaag tcctagctaa gtattggctt ggcaacagga    167940
```

```
ctccgacctc caagtcacct cctatacgtc ggtcttctcg gtgttgtctt ccttgggttc 168000
atccttgcat tgtctgcccg agccaaagaa catattgagc ctaggggccg acctcctcct 168060
tttataggct aaggagggag gtcgcccgtg atgtcttcct caagaaggag ccaccaggtg 168120
atggtaaaac tgggcgtcct accttggggt aaatccacgt acgacggttg cttggctatc 168180
ccgtattctt tattatagac agcataggca acgtgggttg gagtgccatg agttgggctt 168240
tgccgaccct gggcctacat agcctgaggc tcggcacgac tcatcatgtt gtaccctgcc 168300
agcggcccat gcactcaagc attgtcccaa taggccatga gtgtgccgct ggattggaga 168360
cacgtaggcc ataaatgcac catagtctga ggggaaggac gacaccattg ttaccgggtg 168420
ggactcgaag tagtgtcgta gatttcgcta agctaggact actgtgtaca acagttttgg 168480
acttgtgggt agcggatctt catttcggac aatacctcgc tgatgaagta gactagcctt 168540
tgaacaggca aggtatgtcc ttcctctcgc atttccatta caaccgtgac gctgaccacc 168600
tgggtggttg cggtgacgta gagcaagagg ggttcccctt cgacagggc accaaaatgg 168660
gtgtgttggt aaggatcctc ttaaggttct cgagggcttc ttcgtcctca ggggtccaaa 168720
tgaaacgctc ggtcttcctc aagagtcggt acaagggcat gcccttctcg tcgaggcatg 168780
aaaatgaaaca actcagggct gcaaggcatc ccatgaccca ttgaactccc ttaattaaca 168840
tcttctatcg tcccatgttt gtgattgcca agaccttttc taggttggct tcgatacctc 168900
gttccgacac gatgaaccct agaagcatgc attggggaac atcgaaaaca cacttctcgg 168960
ggttgagtct aacgctcgtg gcccggaggc aagcgaaggt tgttttgaga tcggagacga 169020
ggtcacaagc tttccttatc ttgactatga tgtcatcgat gtaggcttcg atcgtcacgc 169080
caatgtggtt gacgaacatg tggttcatgc aacgtagata cgtggcagcg gcgttacgca 169140
acccgaaggg catggttgta taacaataca tgccctgggg tgatgaaaga gggcgcgagc 169200
tggtcggact ctttcatccg aatttgatgg taaccggagt aggcatcaag taaggataga 169260
gtttcacatc ctgtagtgga gtcaacgatt tgatcgatct gaggcagggg tagggaactt 169320
ttggacatgc tttatttaaa ccagcgtagt gtacacaaat cctccatttc cctcccttt 169380
tcttgactaa tacgggtttt gccaaccact cgggatggaa aacttccttg atgaacccgg 169440
ccgccaagag cttgtgtacc tcctccccga tgcccatgca cttctcctcg ttgaatcggc 169500
gcaggtgttg cctcaccggt ttggagccag cacagatgtc caaggagtgc tcggcgacct 169560
ccctcggtat atctgacatg tccgagggac tccacgcaaa tatatcggca tttgcgcgga 169620
ggaagtcggc gaacaccact tccaatttgg gctcgagttg ggagctaatc cacaacgtcc 169680
tctcaccgga gacaccgggg tcgaggagga cggtcttcgt gtcttccaca ggctcaaagc 169740
tgtcggcatg cttcttgggg gtttggaacc tctccgggga ggttctccaa gtcagcgatg 169800
agcgcctcgg attctatgag tgcctcggcg tattctacgc actcgacgtt gcactcgtag 169860
gtgtggcggt acgtggggcc gatagtgatg acgcctgttg gtccaggcat ctttagcttc 169920
aggtatgtat agttcgggat gaccatgaac ttggcgtaac atggcctccc gagcacggtg 169980
tggtaggtgc cttagaaccc taccacctcg aaggtgagga cttctctctt gaagttggca 170040
agggtcccga gtagacgaa taggtcgatc tgcctgaggg ggtgcactct cttgctgagg 170100
gtgatgccat gaaatggcgc ggccccagct cgatcctagg actggcctat ccccatgagg 170160
cccgaggtgt cagcatagat gatgttgagg ctgctggctg catccatgag caccttggtg 170220
aggcgagtgt tggcgatgat ggggtcaacg tcgagcgggt acttcccact cttagccttg 170280
cgcaaagaaa aataacatca gcgatttgtt tgtaacatct ctcacgagga actgaagaaa 170340
```

```
aaggagatta acaaatcaaa attacacatt agccttccgc aaagaaaaag aagtacacat    170400
tacattgttc gaagatctga aacatgactt ttttgaggta aaaactatag ggagattcct    170460
acggtaaatt ttccattaag aaaggatgtg aaatgtacaa agaattatat agagtgtata    170520
ttgtgattgt tgaagccaga gcctaatata gaagacgagc cacgtctctt ttttgatttt    170580
ttgcagctca aaatagttgg aggcaggggc ggagccaaag ggggcccggc aggggccatg    170640
gctcctccta aggctgtgac acagacaaga gaatatctat atagtctaaa ttttatgtgt    170700
ctaaatatat atactctaaa ttttgtacaa aataaattt gtttataaaa cctatatctc     170760
tctcgtagtt tatgaaacta cgagagagat gtataagatt tgtgcatatt gttagaacca    170820
tcatgtgaga tgaacaaatg accaaacaac caaaataaac tttgtagatc ttgagaagtt    170880
atagaatttt gtagttgaca acttttcat ttcaagtcat cttgttaaca aaaactatgt      170940
ctgaatttta aaaattaaa atttgaattt tgaaacgac ctcgaaagaa aaaaaccac        171000 caacatgaaa gttgtaggta ctgaagagtt atgaaacttt gtagttgcca ctgttttggt     171060
ttgaaatcat cttgtcatgc aaaactatgt ttgaatttta aatttgaat ttttcaaact      171120 acctcagatg gaaaaaccag caaaataaaa gttgtaggtc ttaaaatgaa tgaaactttg    171180
taattggcaa ttttttttatt tgaaatcatc ttatcattga aaaattcgtg tgaagttttc   171240
gaatttgaaa tttaaatttt gtaaacggcc tcatatatag aaactatcaa atagaacctt    171300
gtagatcttg aaaagttatg caactttata gttgatcatg ttttcaaatg aattcattta    171360
gtgccttaaa taatcaaatt actctcgaat tgttatagta catgaggaat gaaaacgtaa    171420
tatagacata attgatgtag tagtgtagtg gtagagaatg gtatgcacga gagagaggct    171480
atgagttcga atctcaccat tcacaaaaca tgtaaattta attcaaaaaa ataatagtga    171540
aaaatgatag ggcgatgggt atggtaatga gtagtggctg gagagttgtt cctataatt     171600 aaaaaatgtt tgttgtact ttttaggttt tttcgattct taatttgtcg agtgctttta      171660
tttgccgagt gtccgaaaaa agtactcggc aaagagttgg ctggagagtt gttcctataa    171720
tttaaaaata ttttgttgta tttttgagtt ttttcgattc ttaatttggc gagtgtccga    171780
aaaaagtact cggcaaaaaa ccttttgccg ataaaatgtt tgccgagtgt aaaatggcct    171840
ttgccgagtt cttagacact cggtaaagaa tgcgattccg gtagtgcttt attattttgg    171900
tattgttctt gcgtcataac tttaattcaa tatatcaatt agctagaaaa tagactcatg    171960
aactaagata atatattaaa atttagaatt ctaacttaat aacattatat aatatttttt    172020
atcgtatagc ggccctttta tatagtaatc cttgctctgc ccatggttgg aggtatgttt    172080
ttgaaaaccc acccttact gcactttcac tttcagatgc acaataatat cactatgact      172140
atttccaggc tccggctttg ttgatctgaa acgggcttcc atcggtactc cattcaagca    172200
gaaacaaaca ggttacaggc atacattata ctgttcgcca acagttccct cgggtcgctc    172260 catttctttta ctgacacgtg aaattggcaa acaatggaga aaaaaactaa gtgcaggaaa   172320
ttaattatac tgatttctca cacctggaga agaataagtt cccaacgatc gtagtaatag    172380
gaacagaaag atcagaaact aatttgggcg ccctacgtac agttcagacg tttagtatca    172440
gactctaaaa gtgtagctag accaaacatg catgtaaaca caacgataaa cttttgagta    172500
caaatagctt acaaatagca tgtataagca gttggactgt atctgatctg tgttcattat    172560
ttgatagtat catggtgtta ctggattatt aggagcacac ccggccggcc ctatgaagag    172620
cagctgaggt acgtaaccga gctggaccat aggcctattg tatagctttt caaccagagg    172680
```

```
cctgcattct agtagcagag gcctgatcac aacatcgacg ggagaagaaa aaaataaaaa    172740
tgataaatta gtcactgaac tgagtacgca cctgatgaag aacagtccac ctagctgacc    172800
tagatttta  gcacaagaga aggctaaact accagctctg aaccaagacc tgcaattcca    172860
ccatcatgca tggaaacgaa gacgggaagg aaaaaaaaac acaagactgg cggaagaggg    172920
agaagacagc aactgcacta gcggacaaag cgagcctcac gcaacgagtg gaacgaagag    172980
gaggggggga agtagcacaa ccaaagctgg tagatatagg gaggagtggg tgcacaggcc    173040
ggtcaatgac gctaagcaca actgcttgca gggcgcaatg gaagagagaa gccttgtcag    173100
accaacaaca aaaggcatgg gcgctatact tggtgttagt tctatgcagt ggcggagatc    173160
agtgtattaa atcgcgggct aagaggttta gcggctgggt tccagaacag ctaagtccag    173220
ctataaccgg ctatagcgga agctaaacat ttttgcggat ttgcaaaaaa atagagtata    173280
aatttgacac agatgaatag atgaatagac gacaaatttg atagtcatac atattgccat    173340
acatatagga gttcagctct atacatgact gccgtaaaat gtctgagcag cttaacttaa    173400
aacaaaatgt ctgagctcag cttaacttaa aacaaaatgt ctaagctcca agacattgag    173460
atcattagtt tagttcacag ttcacccaaa atgactgtcc acaaggtcaa atataacatt    173520
gtaatctagc atcaatcaga atcaaaggca tgtggagact tatcagattc agagaattcc    173580
attgcaatgt caccatcttc tgaatccgat gaggactgct gcacttgaac ttaaacatca    173640
cgcatcagag actggaggct tcttaacttc tttctaggct tcatagacct cttctttttt    173700
gcttgtactt gaacttgtgc ttgtgatgtt tgttctccct gtgatcttcc atcttgcgct    173760
ggttcaacaa catcattcgg aagaggtaca ataccagtaa tgaattcatt gtcatcatca    173820
ccaacaacat catctacttc cctctctaaa ggatctctgt ctattctctc cttctttccc    173880
cttagcttgg agttaaattt aacaaacaca aggtctctca tcctatcatg aagtagcctg    173940
tttctccttt ttgtatgaac ctatgagtga aatagtgaac ataagataac atgtttgaaa    174000
caagatttga aacagtacaa taaatatggt tttctatgca tttggatagt agagcttgca    174060
gttttactac taaaaatatt cacaagtggc caaacagatc ccacataagt gtatttacct    174120
gttcaaatac ggaccaattt ctctcacaag ctgaggaact acatgttaga tttagaattt    174180
ttgaagccaa tatcctcaga ttaggtgtgt ttgtaccatg gtttagccac cactttgctg    174240
cataaacaag ttaataatta cataattgtg aaagaggcaa gaaacaaatt gaattctgaa    174300
accatgtatt caaaatagaa tcacctggat taaagttctt gtttctcctt tgccttatgg    174360
caatttcatg tccaaataaa tgtcccttgt tgatcttggt acatgtagag ttcttcaatt    174420
atttttgtctt gtgtttcttc atcaccaatc atctttgtaa tgcaattaat cactccagct    174480
ctaaaggatc catcatgctc aatttcagac ttctttggat aataaaagta aggattcaag    174540
tagtacccag ctaagtgaag cggagttttg agcttgctat cccaccgctt atcaataata    174600
tcccaagcaa ctttgtagcg gctctcatca ttgtcaaacc tctcagaaat ttctttcttt    174660
gcctcaagca ttaatccatg aaagaatccc attgccggta catcactgtc cagtctcctc    174720
aacacatttg ccaatggttc aaaaaaattt acagctatat caacattttt cgaaaaggtt    174780
tcagatctca aactttatt  ggctttcttt cccttgtcct ttttcaagta acccaactca    174840
ttaagttcat ctgatctgaa caaccttgtc aattcttct  tgttatcaag caagcttttc    174900
aagttcaagt aggcagtagc aaatctagta atcccagatc tcaccaagtc tttcttcaga    174960
aactttctca tcaaatctaa caccccttgtg tgagcataca agaaattagt gatctgcctt    175020
gcacttgtga tagtttgctc cactggctca agcttcccaa gatcctctag catgagatct    175080
```

```
aggcaatgag cagcacatcc cattccaaaa tattgagggc ctctttgctg tcaataggct    175140
tgctgctgct gtattgacac tagcattatc agtcaccact tggacaacat ttgcctcccc    175200
aatctcctct atgcatttgt ccacaaggtc aaatatgtac ttaccatctt ttctctcacc    175260
cgagcagtcc actgaatcta agaagcaaac tccatgagca ctatggacga ctaaattcat    175320 cactcccta cccttcctat ctgtccatgc atctgtcatg attgtacatc ctgtttgctc     175380
ccatgattcc ttgtggttct tgaaaccatc caataccttt tgtttccttt tctgcaagaa    175440
tggtccactc atctcataag gactaggccc tctcaaacct ttaccaaatt gcccaatggc    175500
ctcaagcata agtgcaaagc taggaagggt gactgtgttg tgtgcaatac tagcttcata    175560
gaaaaactga catatgtact cacaagcctt atcccttctc tcttctcttt tctgagttga    175620
caatgttgtt tgaaccttgt tgctaaggtt aattccttta tgcatcattt gaacaaattc    175680
ttcaatagta gaaggtttat aaaatctgtc aatagtgcca ccacgtacca ctgttctaca    175740
gctaaggcta ctagaaccct tgttggctt ttgcttcacc acaaggactt cattcccaag     175800
atcaatatcc acttgctcac aactttcatc ttctcagatg tctaagttaa tttcatctct    175860
ctctttcctt ttcttttgct ttatggtcct tttcttctgt attctttgta agcaaagcaa    175920
tcatatcttc tttcacatca cttggaacct tcaaacactt tgtaacatta ttccctttaa    175980
taccagcaag gtgccactta attcttgtaa tcccagcttt gcatagcttg tcacagtact    176040
tgcacttcag ccaatgcttc ttgtttgcat ctgggcaaaa acaatgagcc caagctacat    176100
catctgagtt gataatagct tgtggtgctg ctgcatttga tacagaggca gaggcgacac    176160
ttgatggaat aactacacaa tttgaagaca cataatgcat aatattagga aatgaaaag    176220 ctttaaacag atgaacatct attgaagaat gtgttgcggc ctaccgccta catcaatgga    176280
actactacaa ctattttaat cacgtataaa gcaagatact gataagaaat ttaattgtca    176340
ttacaacatt gcttgccact acgacgtacg ttctgtcatg tgaaaccttg acttcttcaa    176400
aaatacgagt tgcaatattg cttgtattca ggtttcaaag tatattcgtg ttggaaatcc    176460
ataaaaagcc gttagcgcta accaaatgtt catcaagctt gtgagctaga gtatggatca    176520
ataacgaaac aaaaaaaata agtaaaaata catttgtcag caagaacatt tcttcacgtt    176580
agcaccatcc taaattatag ttcagctgtt gaccaggttt aggtacatgg tacacggaga    176640
agtcaataaa attgttttaa aaaaggtatc aatagagtgt ctagattgtt aatctatttg    176700
caatatcaaa tgcaccatcg cagctacact ttttttgca gtgtctatac ttttatatat     176760
atccaccatt gaatatttg gattaaagtt catcggaaag aaataggatg atactcaagt     176820
gaatgatatg gtaaaacaat cataactaca agtcaatgtg ttgcagccta ccgcctacat    176880
caatggaact actacaacta ttttaatcac caaaaaaatg ctgcagaaaa catagctaca    176940
agggactaca ctacacgtca catgaacatc tattgaaaaa tacatgcctg tttgcttctc    177000
ttgctgagac atggtgccgg ttcaactgga caacaattgg aggttggaga gtggagaaa     177060 tactattgga gtgctgcctt gattgttgct acttgcttca ttgcttaccg ccagcaggga    177120
accaacgtgt tgaacttgaa ctgttgaagc cagccgccgc catcaggttg aagccagccg    177180
ccagtgcctt ttgaaaatga gagtctgagc tagggttcgc agttttgcac aagaaaaggc    177240
agagggagat aatgggctgg gtcggacgcg cgcaagaaaa tgggccaggt tgatttagc    177300 tgccgctaga agatggccca tttaacggat ttcaccggct aatagcggct aatagcggtc   177360
agcaagcaat agcggcagaa ttgtaatctc ctagcggcat tgtttgccag aagcgatctc    177420
```

```
cggcgatagc ggcagcgatc tccggtgatt taaaacattg gcggagatag gcctatggct 177480
agtagggcct gtgtcttact tttggaccaa atagtctcta aaggtccata tactggcaag 177540
tatggttagc tgtgactgtt gtccaaagag ctagtttttg gtgtctaaag gtctatacat 177600
cgttttcagt gttatattcg gccctatact taaagagatt ctaactccgc cactggttct 177660
atgggatctt tgctgggtca cacttagtcg atctgaggtt acttgaatga acagtagtga 177720
atctacgcgt gtgctctcac tgtgaacaca taaacagagg tgattaggac gacatattgt 177780
tgccttacag tggtggagat ggattcaatc ctctccacca cctcctccat tcctgctaga 177840
ggtggctcag tcgtcgagat tcgaggccgc cattagagtt gtcgttcttc cagtcactcc 177900
aacgcctagg cgatagggtc ctgtctgtgg atttgggttt agggcaagat actagtgttg 177960
gctttaattt cctacgaccc ttaatccttt atatagcgtc gtgtgacagg tggctccaac 178020
cgaggttagc gtggaccctc caaatcaagg gcctgattaa ggagatggac gattgggtta 178080
atccaaatcc agtcactgat gactgggtgt agaggacaca cccaacaatc tctcctttgt 178140
tctctacatt cctatactc aacttttggg attccatccc ttgacaagtt tacacataga 178200
gaccaatgtg tgacaatgac cgattaagta tcaccacact caatgactac aacatgatcc 178260
cctgcttcag aacgaaaaga tactttatta ggttgcaatt tgtagcccct gtgaatcaag 178320
atcatatgca ctcccttaaa cccatgtcgg ctacatgttg tcttaacacg ttgggtggaa 178380
ggccttttgt gagcgatccg ctaacattgc tatcttctat tatgctcaac ttttatggtt 178440
tgatcctgaa ttttctcctt aacaacataa cactaaatga caaagaactt gacttgttgt 178500
tataggagta aaataccgta ggctcattat cgcagtaaat tctcagtgat cgctctatgc 178560
tatcaaccac tcttaattcg ggtacgaatt tcttcatcca taatgcctgc ccatttgcct 178620
catatatggc tacaaactca gcgtccatta tcgacgatga tctcgttgtc tgtttgcaac 178680
ttttctaaga aataactccc ctagagagtg tacatacccc aaagtagact tcagtctatc 178740
tttacaacct catcagtcgg catctgcaca accaactatt cataggaac tacatctttt 178800 gtatgttagc atgagacctt ttagtacctt gcacgtactt tagagccttc ttaattgttt 178860
acagtgttct atgcctgtgt tgattttata tctcccaagc aactcggtag taaattctaa 178920
gttaggcgaa tatatatttg agcatacata atgcttccaa tagtagaaac atatggtact 178980
gacttcatct gatcttttctg acactgattc tagggacatt gataattccc aaacttatca 179040
cccttgacta ttggcgcagg cgtggcctta cactgatgca tactgtaatt ctttattact 179100
tttctatata tgacttctgt gagagttcta atactccctt atgtctatct ctgtgaaatt 179160
ctatttctag aacttaagag gcttctccca tatctttcat atcaaagttc gaggaaagaa 179220
acatgtctgt ttccgccagt atatcattat cactactacc taaaagtatg tcatcggcat 179280
atagaacaag gaattttcct ttcttaaact ttgcataaat gcaattgtct tcctcgtttt 179340
ccttgaaaac caaactttct gatagtctga tcaaacttga tgtaccacag tctagaggct 179400
tgttttaatc cataaatgga cctccttagg tgacatccca tatgttcttt accgcgcatg 179460
acgaaaccct ttggttgtgc catgaaaacg ttttctact aactctctat ataagaatgt 179520
tatttttaca tccatctggt ggagatctag atcaaaatgg tccactaatg ccataatgat 179580
ccggaatgaa tctttcgttg atacaggtga gaaggtttca tggtagtcaa tgtattctct 179640
ctgtgtgaac ccccttggcca caagtctagc cttgtacctt tctacattcc ctttggcgtc 179700
acgtttggtc ttgtagaccc acttacagcc tactattttg gctctttagg gaatgacctc 179760
taagtcccaa actttgttta ttctcatgga ttccaattca tcttccatgt ctaaaaacca 179820
```

```
tttggttgaa ttttcactta tcatagcttc ttcatatgta gtgggatcac cttctacatc   179880
aatgtcctcg ctcatataaa tctcatcaca ttctgtttct acactttcgt aaacttcata   179940
gtcgtcagga atcacagatc gtctggacca tagagacctt tttagacttg gttctagttc   180000
tggtttgttc tggggctcct acaatagtgt gtcacttggc gcaacactac cactgtcttg   180060
tgaactctcc tgtgcgaccg actcagaagg gccaggctac gcagaaggtg aagaaacttg   180120
ctctatagta gctgcactgg gtgatgcaac atttgcaata ggggtttcac ctcatcgtta   180180
caaccattgg tggaaccaca ataggtatcg agaagtatgg tttttttaacc attagaatcg   180240 gtacatacgt cctcttttcgt aaaggtcaac ctctctgagt accttgctcc ccttgatcat   180300
gtcaccctct agaaaaatgg catgtatggt ttctataaac ttggtttgtc tacctagaca   180360
gtagaatctg taacctttg atctctcagg gtagccaata aaatgaaagc tagtggttct   180420
atcatctagc ttttctgtc caggattaaa tattctagct tctgctggac aaccccatat   180480
gtgaaagtag ttgagcgtgg gctttctgtc attccacaac tcatatggag ttttggatac   180540
tgatttacta gggactatgt tgagtatatg gatagtgatt ttaaagcctc catctgtggt   180600
agaacctccc aagttattgg gcccacatgc acctgtccgt gtctcaaaga cctcagacgg   180660
ctatgcatgt gcaccagata acttaacagg atatgtccga gtgtcccaag gacctcggat   180720
aaaccactta caaccaggat cacaagatta agtaaacaca aatcacacac caataatttg   180780
cagcagaaat cttattacca aattttacaa gttacgtcaa gtttacattg tacatgatcg   180840
gagtgattac aaaagtgact caaagaaata actttgaact gttataaatt atttgtagtt   180900
ttgaaatata tgctagctca agtgaccatt ctcaataaga agtatagaag agttacttag   180960
acttataaga aggtcgtgcc caccggcgct taacaccaat cacaatcaag tgactcgaaa   181020
cctacagcaa caatgggtaa aaccctaagt acgcaagtac tcagcaagac ttacccgact   181080
aaagaaaaga cttttcaaggg tatgctggtt ttaaaaggat tcaagataag acttgtcaag   181140
aatcaaggac tcaattttttg cagaagagct tactagtagt ggatccttat gccaaacttt   181200
tacttcacaa gttaagtact tttcctgaat ctagatttgc ctaatctaga gcattcactt   181260
gtcctacact agcttccttt taaccaaatc acaatcatgt ttcacttatt aaactacgat   181320
gcagggcagt gatccagtct tcatatccga gaagtctggc gatccgaatc gattaatacc   181380
cagctgggga tctccaacca cacgacatat gcttccctta actcttttgc acatgtctac   181440
cattcccacg aatcctccac cacatgaaca ggtccgcgcc acccgagagc acaccacccc   181500
ttttaggtgg tccgttgcca agagggtatg tgtcactctc gccatctctc cactcccagt   181560
gtgcgattgt cttttcatgt ttggaatagc tgggttcagg cttacccatg atgaggtatg   181620
tggccagtta aagggtccta gatcagcagg ccaacaatcg gtacgatcct taatcgacac   181680
agacgggcga ccttgtctgc tcagcacctg gtctagattt attcaaacca ttttcccatt   181740
tttggtacct gacaggggta ctcttttcca atgatgagcc cactctggcc aaagtggagt   181800
catcacctta gtttgctttg attttttgaat caaaagctc ataaccattg ttctgcaatc   181860 attcttttttg aaaacaaatg atttttcagt ttcaagcag ggctaagcat tatcagttct   181920
ttttataaaa cagggattaa ggagtttcca aggaatggta atgcatcaat tgtttatcac   181980
acaacttcta tcaacctaat gcatcatatc aggtgataaa gtatttaaaa cacaaggaat   182040
gggcaaatgc accggagctt gcctgggtaa cactaggtta gtgttgttag acgacgacca   182100
cttgacgatc atccttgtcc tagcacttga tcaggcaggt tcgtccatca gtatcaccat   182160
```

```
gcggagtagc tcgcgcttgg ggtcgacttg gctcgtcttc cgcatcacat ggttaattta    182220
cgtacctgaa tgaaatgcat tatgcacatg aatgcatata taacatatat atttcaaaag    182280
cctagtaaaa cctggactcc ctagtattaa atgccaacga cttaaaatag ttataagaac    182340
aatctaatca acatctttaa accgtgcgtc ttaattaacc taaattacag acttaactaa    182400
atcgaacatc acaatatacg tatgctaaat caataacaat taccgcgacc aacaattata    182460
tttaatctaa ttatatacct agttgactgg aataacgaat caacttaccc tcattaaatt    182520
cgacttgaaa ccacgaaatc acgacgcctt tcagctctag catttcacca aacacatggt    182580
gagtgctgca tcgaatcgcg tttcttctcc atccacatag agaatcctcc ggtcgcgtac    182640
tgatttattt ccttcggcgc caaatcttct cggattttg gcgtgaacac aagtgggagg    182700
cgtcacgtag gagccagcat cggggcaagg cgacggatcg ataacaagca ccaagagggg    182760
ataggcgacg ttgttgtaga ctcggaaagg ggacgaacga cgatgtcgat gtgtcggcac    182820
cacgattccc gatcgacgaa gacgatggta tgacgactta tcggagctga ggcgaacgcg    182880
atctaggtac catagcagca cgccgataag tccatgacaa caccacgagg tagacgcgac    182940
aacgcacggc ccaacggaca aaggagtgcg acggctggcg agctgactga ggaagtcggc    183000
gccgagctgt tgctgctcca ccgatggaga ggacccaaaa aaatgacgag gaaagagagg    183060
aagctctagc cgagcgctgg ccgagcgctc cagcagcaag gagaaactca ctgggttcac    183120
gcgatggaga ggacacagtg agcaagaagc ttcaggagtt tgagcctttg ggaagggacg    183180
acgtgcttgg gtaggagtag gaagtatgtg agggagataa ccatatgtgc tggcctgatt    183240
tggatcaggg aggcgacgtg gtggcgtctg gtgatgtcca gggacaagaa ctaatgggag    183300
ggagccagca catgatgggg ataggattaa agatatagag gacagtgatg ataagtgaga    183360
agatgttttt ttattataat cattctcttc acctattggt ttttttaacg caattactat    183420
tcctagattc actctcaaaa cataattata gtttagactc aaaactagtg gaaaaattcg    183480
tttttgcctc aattcaaaat gacacaaggg gaacatagct ccggcgtgat ctttctgctc    183540
caaaactgat ccaggttttc agtcacctga aacttcaagt cagattttca ctccttttcc    183600
catgctgctg gcttgataca tctccttact aggagttgat ctcctataat cactctccaa    183660 cttgcttta atgggtacca actaccaact aagattcaac agatttcagg ttagggagct    183720
ccaaggttgg gtcaacacca ccgaactgca caactcagcg aactgaattt aactcagcac    183780
acctctgtct gatagagcga gtttgagaac cttttcgct caattcgaag taaggacagg    183840 aagatcctc ctcataaaaa gtattccgtt acaatagatc tccagatttc ccataatacc    183900
cacggatcac aggcgcaagg attaaaagct aaacagtgtt aaacctgaga ggaactcact    183960
gcctttctga aattcagcaa actgaattga gtccgattgt accatgcctc tttgctaacc    184020
cacctaaatc tcatgatttc aaataataac aggccgacct caattaataa aacttgttca    184080
taaaacataa ctctacaaac ttgctacagc taccctaggt caaaaattta tggatcaaaa    184140
gttatagtgc tccaaagtgg ggtgaaaact ctaaaattca gctgcatcta actgaatcaa    184200
aaactgaaca cacatgcctg acagagaatt gttgggcaca atttactcca tttttgtgca    184260
gcaccaacca aaccttctt aaggaaactt gctcaccatt atttgttctt caacttttct    184320
atagatacaa accccagaat tccatggatc aggcacaaag aagctccaaa gttgcgccaa    184380
aaacactaaa attcagattt agttagctgc acaagtctga aatccaaatc tgtgagctcc    184440
actttggacc acctttttctc caagttccaa gtagctttag gggtatgagc tttaactaaa    184500
cttgcacacc aacatacgtt cttatacttt ggtacacaaa ctttagcccc tagctgtatg    184560
```

```
gatcagccac caacaagctc ccaaagttgc ttcagaatat aaattgttca ggttcagaga   184620
ttacactaag tctgaaactc cacatgtatt acaacctcat tttggaccag ttttacaccc   184680
agttgcatat ggttttaggg gcaggttgcc taagcaaatg tgtactccta gtgtagctct   184740
acaactttgt tacattgtcc accttcaaac tgtttatga tcaaaagtta taaaggacca   184800
aaaacagcta gttgatatta ttttcagcaa acttcaaatc tgaatcagaa ctgaatttag   184860
aattttactc caacttttcc tataaaactt ggacatctcc acacatggaa gttgttcaac   184920
tttccacgct ttaccatttt ggtatatgga cttttggcaa cttctcacta gatcttaaat   184980 tccactttc gggctagttt agggtttcaa ttgaaatttt ggacctaata aaatgtattc   185040
taggtgtatc aagcaagatg atgctaatgc atatgatgac atgccacaat tttagttctc   185100
gtaacaccag tggtgttaca ccatctacag acccaatggt aagctagagt aactaagcat   185160
actccttacc atgtccatta gcgttatgtt tcgcctttcg gctaccccat tctgtcggag   185220
ttcaccaggt gtcgaatatt gggcaactat gtcattttct tattgggaac ctcacaaaag   185280
tcccttggac ttgtccatac tctgtatggc gcacgtagta ctcccctgt tctgatttga    185340 caatatttat cttcaaattg tgttgatttt ctatctcggt cttgaactat ttaaactctt   185400
ctaaagcttg tgatatttgc ttaataggat aactataata gtagcgagag tattcatcta   185460
tgaaggttat gaacgaattg aactcatcta ttgtcctaac tagaaaagaa ccacatatat   185520
ttgtacgaat aatttctaac actctcgtat tgtgcttatc atttttctta atatgcttcg   185580
taaatttacc gttgatgcaa tctctgcatt gctctaagtc tatagtgtct aagggatgga   185640
gaatctcttc cttaatgata cactctattc tcccctcga aatatggccc atacaatagt    185700
gccataattt cgatgatgtc ttgaaagtgc atccatccct tttgtgggtt ttggtgattt   185760
ggataacaac acatttaaag ctctaaaaat tttgctacgt gttgaacaag aaattcagta   185820
tgatgaacat acttgaatag tgtataatga tcagtgaaca aaagttcaca aggttaaata   185880
accaatgaga caatgtaaat ggatataata tggtctctat attggtttga atataaggac   185940
aagacctaag aaatcactat gcataaatat gatcataata gagtttgaag tgattaagag   186000
gattggtcaa gccaaagtga ataagatatg aggaatcatg aattggcttg accatattac   186060
tattagtcca tatatgcttc tatgagaatc aaactagagc ttgattgatc ttagcattta   186120
tatgtagatg acattcaagc aaggttcaca atattgacga aatgattctc tcaatgatg    186180 ctcaatatta tgtgactcaa gaatggctcg ataggtgaa gatagcaagg aaagggcttc    186240
gagggactaa gcgaaggtga aggccaagcg acagattgtg gactaaggta ccatggctaa   186300
ggtgaagaag agaatacttg cactaagtcg atgaactaat cagctatgaa gagttatatt   186360
gtgttgatgc attagtaagg tgacttgaag ccatgatttg aacttatata tggtgaaata   186420
gttcaagtca caaggcttga tttgtgtttg ctacaaaagg tgagacaaag atgtttgtga   186480
tccttatgaa aaaacgtcat ggagaaatca cgcatgagac accaattact caatgagttt   186540
acttaattac attttattta acttgagtat aggaatcatc gtactatcaa ggagtccaaa   186600
aagaaggttg gtgtttgcca aagcttaatc ctctaaattc aaaagctatt ttgtaaacca   186660
atttcttcgg acactatgtg agttcgactg atgttaggtt tgagagatgg agagtcttcc   186720
cattgagaag cagctgaact ttctttcaga aaagttgaac ttgactttag ctgagttgaa   186780
cttgacttca gctgagttga acttttcttc aaatgagttg aacttgactt cagctgagtt   186840
gagcttttct tcaactgagt tgaacttgac ttctgctgag ttaagctttt cttcagctga   186900
```

```
gttgagcctt tcttcagttg agttgaactt gacttcggct gagttgagct tttcttcagc    186960
tgagttgaac ttgactttag ctaagttgaa cttgacttca gttgagttga actggacttc    187020
agctgaggtg aacttgactt caactaagaa actctctcgt caaaaccggt tgaaccgacc    187080
ctgggagagg ttcaatcagt gtcagggttt gactaactat tatgacctct gtctaccagt    187140
ctgactagaa gattgtagga caggtggttg aaccggcctt gaggggcagt tcaaccgttt    187200
tttgcgcaaa aagtcccaaa cggctagttt tggagcccta cctatatata ctcactccta    187260
cctctctccc ccacaaaaga gcacgccttg aactccattt ctaacctaag aaacactccc    187320
cactctctct cacacgtctc ttgcctctct catttcaaat cttgggaggg aaatcttagt    187380
gtgggattaa agagttgcgg ggttttgtgc tttatcttca aatccttctt gttttcttg     187440
attcgaactt tgatacttca ttgagttctt tgtggattca ttactttgg aacttctagc     187500
tcctagtcga ctaggtgtcg cttgtgagtc tccaaatatt gttgaagatc acaagaaagt    187560
ttgtattacc cgctcgtttg agcaaagatt agtgtgtggg cttgaccttt gtggtcggcg    187620
aagggaggat taggggttgaa agagacccag ctctttgtgg gcgcctcaac gaggaagtag   187680
gacacctttg tggtgtgacc aaacctcggg ataaatctta tatcttttgt gttcttgctc    187740
attgtgtttg ttcgcgttct tcgttctctc atcattctgt ggaatgattg ttcttatctt    187800
tttggtgtgt ggattttgag aagtgtcctt ctctgatcta ctacttttaa ccctatggat    187860
catctaggac atcccatttg caaagttaac ttggtgaatt ttgagatcaa ttcatttta    187920
tatctcattc tttagttgag ctcgttcaaa ccggttgaac cagttttgac acctattgaa    187980
ccgattttac tcagtttatt tctagttttt gttgaaaata tttctgcttg cctattcacc    188040
cccctctag gcaactttca attggtagca gagtctaatc cttgttttaa cgcttaacca    188100
cacgaggaaa aatcatgcaa ggggactaat aaatgaaagt gcttctaagc ttgaagaagt    188160
tgaggttgcc tcaacttcac cctttggtgc agatgttgat tctagggcaa tagaccttgc    188220
catgagaatc gccgagaaga tgttcctcaa aataaggaa gatgaggcaa agaacaatat     188280
tgaagaagaa aatgatcgat ggagaccaaa cgaggaatcc acctcttcac aaggtttgta    188340
tttcaatgcc acttctcata tgtgcttgt cgctaatggg aatgacagtg aaagtgaaag     188400
tgaggatgag gagaaatatg aaagtgataa tgaagatgag gataatctta aacaattctt    188460
cactcaacta gcaagaaga accaaatgat cttgctcaaa ttgatgaaaa gagcaaaga     188520
acaacaataa atgtttcata agcaagaaga cattctcatc aacaagacca aaagactgga    188580
tgagttgacc aaagaacatg aggagctaaa atgctctcat gatgatttgg tccaaaggta    188640
tcgagcaatg tcaattgagc gaactagaat tataaactct ttatcatgtg ttgctcaatt    188700
agaagatgaa aattatatgc ttaagaacat agtagaaaag ctaaaaattg aaatctagc     188760
tttgcaagaa aacatgatat gttgttatgc acacatgaaa agtttataaa tgaacatatc    188820
acgctagaca ttgctcatga ggttgtgctc aatagtctaa atacatatct acctcacaaa    188880
tgcacatgta ctcaaataga aactatatta tcatgtgcta acaaatgttg ctctcaagaa    188940
agccaatctt ccattgagct agaatttca ggaacaagta atgtttccta tgcaaaagaa     189000
aacaatgagc tcaaggaaga aaatgagagg ctaagaagga gcttgactca attgaaagga    189060
aagtgtcatg ctcaaccttt tcaagataac catgataaca tggtgaaaaa gcttgagaag    189120
gggacaaccg tagtatgcac aaaacccctt caaaagaata ccaagctttc caagaaggac    189180
atgagcaaga cttaaggtga gaaaattaat gatcatatta tatgctctaa taatgttcat    189240
atgtgcttca acaaagtaag attaagggga agcgatagaa tggggtatgg atgcaaggag    189300
```

```
aagggtcatg aaattagttc atgcccccac atgaagaacc aataccttgc accatcaaaa 189360
taactaacca taaacaaaca tgtaacaagc aaaaggcaaa taccttgcaa gaataagcaa 189420
catataccwc ttcggatggt tagtccctgg atgaagagaa cggctctaat tccaattgag 189480
agcacctaga gggggtgaa taggtgatcc agtaaaaata gctcaacaaa acaaacttg 189540 gtctacaatt ggtttagtaa gatcagaaac caagtttgaa tgaagagtat gagaggagag 189600
aacttcttca cttaattgct ctcataaggt aagtattaaa cttagagcaa tattgtaagt 189660
gaagtgaaat gctagaaagg gtgaaatctc aataaggtaa agtagacagg tgacacatcg 189720
tttttatctc gtggttcggt caagcgtaaa atgcttgcct actccacgtt gtggcgtccc 189780
aatggacgag ggttgcactc aacccctctc aagtgatcca atgattaact tgagtaccac 189840
agttatcttt cttatctcaa gtttttcatg ttatgaggaa tctccacaat ttggagtctc 189900
tcatgcctta cacagttgat ctccaataat ccacaagaat aaggtagggg aagtcaagac 189960
acacataaga gacaaacttg cagcaacaca cgcacacgag tcgagagaga gagcacaaaa 190020
cagcacagcg gaattacaac tcaaaagaag tgctcaaatc ttagtctagc aaagcaaagg 190080
cgtggatgcg atgtctcggc gttgtagaat gttcaatggg agcttggtat tatgctccaa 190140
gcacctaggg gtcccttta tagcaccaag gacctaatag ccattggagc tcaatttggc 190200
aggctctggt tgccttctgt ccacgggtgc accggacaat gaacactaca atggcagaga 190260 atcccctga ttggctactt tctgcttcag ggggcaccgg accgtccggt gcaccacttg 190320
accgttggtc cgtggccgat gtggccacta gccgttggct agctggcaca cctgactgcc 190380
tggcgctcca cgcagatggt ccaatgaatt atagctaacg taggttgaaa ttctcgagag 190440
cagctagtac ggcggaccgt gcaccggact gtccggtggg tggcaccgta ccgtctggtg 190500
caatgcagtc cagcccactt ttctcattt tcaatcttat tccctttgc tccttctgg 190560 cttgacttca taaagtccct agcacttaga caaatatgat tagtacccaa aacaattgac 190620
tgagtgtcca gagcttgcct ttttcactta gtctcatata gatttgtatt tttccttctc 190680
ccaagctcaa tttacttta agtacatgtg cttacttctc acattagatg gtgttagtct 190740
aaacaaaatg tgttgagcat ctaatcacca aaactatata gaaatggccc aagggcacat 190800 ttcccttca gtctgcctac gccaatacac accctaggat tctcctcccc gacgaggtcc 190860
ctccttagag gccagatcta ggtctgctat gaagaagacg acgttctgca ccatcgcgga 190920
ccgtccaagc ccgaggcacg aaccgtccgg acgtacgcag aggagaagtc gctcctgcgc 190980
ccaggtcacg atcgtctggc cctgcgtcgt ggaccatcca cgcctccgta gagagcaccg 191040
tcaggtggac ctttctagtg aggcacctct ttcatttcac acatctatgt gtattctcca 191100
ctccctacca tggatgatgc actaacggaa tcaattgctt tgtcgagtgt ctaaaacact 191160
tgttaaagcc taaaaacact ctgcagaggc tttgccgagt gtaacactcg gcaaagaaag 191220
ctcggtgaac tatacatcgg caatggcttc tttgctgagt acttctcatc aggcactcgg 191280
caaagaaaag tcaccgtcat ggcggtaggt aacggcgacg aagactgtgc cgagtgtcac 191340
ggagtgacac tcggcaaagg ctcactcttt gtcgtgtgtc cactatacgg acactcggta 191400
aagaagcccc ctgtgggccc ctttaccagg gcctttgcag agcgtattag gtggcactcg 191460
gcaaaggctc catctttgct gagtgcccgc cggactagca ctcggcaaag ggatcaccaa 191520 cgggccccctt tgtcagttcc tttgtcgagt gctctaggag gcactcggta aagcttgctt 191580
ctttgtcgag tgccaaggcc acagcactcg acaaagaggc tttatcggtg cccaggtgtg 191640
```

```
ccttctttgc cgagtgctat gacattgaca ctcggcaaag tacctctttg ccaagtgtaa    191700
cactcagcaa agtgaccaga ttacccccctt ttttatttgt ttttgctatt gcatccaaac   191760
aaacaaaata tatatcatat aatcatcacc tatacatcac agatatcaca taatcatcac    191820
atacataata gataccacat atttcacaaa aaaacccaaa tctcacaagt ttttcacaaa    191880
catgtctatg ttcataccaa gatccaccaa cataagtatc acagaactct aaaacagaag    191940
tttttcacaa acataagttc aggacaagtt tatcacacaa gctaagagaa gatcatgagc    192000
gaggtgggcg gctggactag tgcggcgacg ggctgggcga tccataaggg ttgttggatg    192060
ccgacccaga ttgtccctac acagagaaga gattgtctat gttataccag ataaatatat    192120
atcatgcaag actacaattt tgatactcac atgagtatgg aactgagcag ggtcaactgg    192180
aggggaacaa cggaggtggt ggagcaaaac cctgtgcggc gccaaggctc tggatgtact    192240
ggaacatctt cgtcatcctc agttgatctc ctaagcgagc ctcccgctct gccatcatcc    192300
tcgcctcaat ttcatgatgt tccctcctct cttcttctag ctaggcctat aatacttcaa    192360
cccaatatta taataactca aagagaaggt atataactca aggaatgacg agttacagaa    192420
gcactaacct ggagttgttg tatctgatga tgtgagatgt cctaccgagg tcatatggct    192480
gggctcgagc tcgtggtcct tgctcgcacc tgagattgag tgggagtgga cgacgagtcg    192540
attgccccgt tggcaatcca gtaccgccca tgcctcctgc ctcctccgac cctcatgagg    192600
acatctccgt cgatgtcctc gatcctcgga tcgtaatcta gcccatggac ctcatgtgcc    192660
atggcagtgt actcacttag gcggtttaga cgacgaggtt gctatacgca tcgggcccat    192720
catccgggtt ataggtgaca tcggacgtcg ccatgccctt atgggccata gcataagccg    192780
agaagatgga gcatggctgg ccattgatgc cgactgcaat aaaaccattg agatagttag    192840
aaataatatc taaaccagtg ttatatacct aaataaaaaa gaggttgtac acatgcttct    192900
gcatatttgt cgaggttgtg gctgccttgg tggtgggagg gaccttgcat catcaaacgt    192960
cgttcccagc tagcgttgtg tgcctcgtcc cactcaagcg agcaccacct atccaccatc    193020
tgctcccagc actgaggatg cgcgacgcac caataaggaa tcatctacaa agtaaaacaa    193080
gtacactgca tatcagaaga taaaattaag taaattttct catgaatatt aaagtgatgt    193140
atttacctgc aagtattggt ccctagtcaa tgacatggtt cgggcctcct gcttggtcac    193200
cttctcccca aggacggagt catggtagct gacgatggcc tggattcgca cctcgtagtg    193260
catgtccacg atgagcttct tatagctcat ggtggccacc acatccgccc ttgcctcgta    193320
tccagcctcg catctgaaga aatcttgcat acaaagacga tgtatccata cattatttca    193380
agtatgtgca acgaatgcga catattttac aatatagtaa gacttactca tagctcttgc    193440
ttcacccgct tcaccttgtt gttaaattcc ctgtcatccc ggtctactgt atctggggcg    193500
acggcgtaga ggtcgaaggt gtaggctggg cccgtcgctc tggcgtactc aaccagtcca    193560
gggaagtgtt ccctgcatag aaggctgagg atgccattgg ggttgcggtc gtgacccccc t 193620 acattctcca ccaccttcta agaactgtcc aagtgataag taaaaatatt agtttatatt    193680
atgaatttga acacataata tgaacaaaca gcgagaacat aaagttacat gcctctcccc    193740
atctggccga atcagtggct gcctgtctcg atgtatggga cgctatggga gactcgcggg    193800
acctcgcagg tagacgttcc tcgaacctaa ggcaccagaa cctgaggtgt tttgctgagc    193860
atcatcgtcg tcctgctgcg ccgcatcgac agcggcctgc tgttccacct gctgttggac    193920
atcattgtcc tagtgtgccc cctcyattgt cctaccggtg ctcctcctcc cccttctcg    193980 tcctcatccc accgcccacc atctttgtcc aataacctgc actaaagagt aagcaaataa    194040
```

```
gcacatatag aaaagatgta ttcagaaata ggtgcgaaat aaaaaatata gcattacatc   194100
aattaaaaat aatcttcata tgtgtcgggg ttagccggat cataagtgtc atcatcacta   194160
tcaaccattt catagtcaac accatctaaa ggcgcaagtt cgtcattaat gtccatcact   194220
aggcaacttc atctcttggt ttggtctatc acataatgct gccagatcca ctcttgcctt   194280
tacgttatcc tttgacttat caggaatgtc cataattgtt gcccaaagtg cctcgtcggg   194340
agccaagtca agcccgactt atgtgtccac atatgctgct caccatatcc cacaaatcta   194400
ccttctggat tggccacgag cctatctatc atttgacgaa ttttggcacc agtcatcatt   194460
gcaggtgggt ggtctatcac tatgacacct ttcgaacgat gaatattttc cacccttctt   194520
caaccaaatg aacctaagag cttccttgca aactgggtat gggaacttat cgtgaacaca   194580
ttaggtgcag aatagcccat acgttgataa gtcatgcatg gagtactggt accaaacatg   194640
cattttgatg tttgtcttcg tagctcggtc atacgtccat accccttcct cccaagcacg   194700
caccaattca tcaaacaaag gctccatata cacgtctatt ttattcatcg ggtgtccggg   194760
aattatcaac gacacgaata tattctgcct ttgaaagcat acaccggggg ggagattgat   194820
tgggataaca aacacggacc aacatgtgta cggggcagcg ctcgttccat agggattgaa   194880
cccatctgtg gccagctatc acacccgggt tttaggggtc caaacccgg gcacgaaata   194940 aacaccaggt gtgctaggac caggtctcac acatatgacg aatagtggta cagaaacgaa   195000
tgtcacatct ttactatatt atgggagttc tgtacaaaat aaataaataa ttacatcgta   195060
aggagaccat gatccagcaa cccaaagttg actgggagac gacggcctag acctctcacg   195120
aactcatcac agcatcctcc atacgcctca tcctgtggta cctgttcttg acctgtgtgg   195180
gggtgtgaga cagcaagagt gagctcacat acgttcatag ctcaacaagt tgtggggaat   195240
aatgtgcatg aactcgccaa aggtgggagc tcatgaagtg taaggcttac caaagaggat   195300
ggttgtagct gagcattgcg tttaaagttg gtcaaaattt tattagcaat tactaagtat   195360
aagtaaatac caacccaatt aagtagtaga acagaagtaa taacaacacc tgcgatgcaa   195420
tgcatatgac aaaattgaatt tagttccata aattaatcat gtgagtgtcc gagctgctca   195480
tgaccataag cacagctagt ataccagttt tacactctgc agaggttgcg catctttacc   195540
cacaagtcat gttacccatc tgccaagaga aggccaatcc catacacctc taccgaggag   195600
gcgaggcagg gtaacactac gaggccttta caaagttcca ctagcttcag aaaacccgct   195660
acagtttcta ggaagctcca atgcagggat cccttgcctg accgtcattg cagcaaaatc   195720
aacccaagga cctccctaca ctgaccactc ccctactgcc cttgtccctt cgggtaaggg   195780
tagctgtcga agttttagat cgacaatgca ccacggggta taccacgtga tgcttttgtg   195840
agttggcaac atcaactgta gctcgatggt tcgcttcgag gcacgacaaa acacaagatt   195900
tatacaggtt cgggccgcgg gatgcgtaat accctacatc ctgtttgcag cgggttgtat   195960
tgctttgata tctagaggtt acaatgaggg ctagggtttg gatgtttgat gagagagcga   196020
gggcgtgtat gagatcagat ccctctaaga tctgccttgg gagggatccc tagctcgcct   196080
tatataatcc ggcgtggctt gggttacaag tcagttacct tatatatctc ctagacggtt   196140
tagattacaa tagagtcctt gtttcgtgcg ctaagtttgt ttagcccatt ggcctcgggc   196200
ccgagtcggt cggtcggccc atgtagataa tacgtctcat ttggacccag gggatatcca   196260
tcccccacaa gccctcgagc ttcaagttga cttgagaaac aatcagcttg aagatccaaa   196320
ttctgctttc tgaagatttt tccttgtagt cttcaaaagt ttttttgat ggtatcctcc   196380
```

```
attcgaggat caagcaactt actccttcaa gtggtcttgg tgaggtggga agcagcaccc    196440
gagctgacaa agtggtcgac gaggtgcgtc gtaacgcaac cctgagctga tgaggcggtg    196500
gcgtggcctc ccggagtcga cgaagcagcg aatcggcgag gcgggcgatg acccagccct    196560
cgagtcgccg aagtagcgag tcggcgaggg aggygatggc ctagctccca aaccggtgaa    196620
gcagcgtgtc ggcgaggcgg gcgatgtccc agccttcgag ccggtgaagt agtgagtcga    196680
cgaggcaagc aatagcctag ccctcgagct gtcgaagtag tgactcggca aggcgggcga    196740
cgacccagcc cccgagctgt cgaagtagcg agtcggcgag gcgggcgaca aaccagcccc    196800
cgagctgtcg atgtagcgag tcggcgaggc agagaacagc ccagccccg agctgtcgaa    196860 gtagcgagtc ggcgaggcgg gcgacaaccc agcccccgag ctgtcgatgt agcgagtygg    196920
cgaggcggac aacgacccag ccctcgagct gtcgaagtag cgagtcggcg aggcgggcga    196980
cgacccagcc cccgagctga cgatgagtca aggaggctgc gcggcggaca acgacccagc    197040
cctcgagctg tcgaagtagc gagtcggcga ggcgggcgac gacccagccc tcgagctgtc    197100
gaagtagcga gtcggcgagg cggacaacra cctagccctc gagctgtcga agtagcgagt    197160
cggcgaggcg gacaacgacc cagccctcga gctgttgaag tagcgagtcg gcgaggcggg    197220
cgacgaccca gccctcgagc tgtcgaagta gcgagtcggc gaggcggaca acaacccagc    197280
cctcgagctg tcgaagtagc gagtcggcga ggcgggcgac aaaccagcct ccgagctgtc    197340
gaagtagcga gtcggcgagg cgggcgacaa accagcctcc gagctgtcga tgtagtgagc    197400
cggcgaggca ggcgacaacc cagccctcga gctgtcgaag tagcgagtcg gcgaggcggg    197460
cgacgaccca gcccttgagc tgtcgaagta gcaagtcagc gaggcgggcg acgacctagc    197520
cctcgagctg tcgaagtaat gagtcggcga ggcaggcgac aacccagccc caagctgtc     197580 gaagtagcga gtcggtgagg cggacaacga cccagccctc gagctgtcga agtagcgagt    197640
cggcgaggcg ggcgacgacc yagccctcga gctgtcgaag tagcgagtcg gcgaggcggg    197700
cgacgaccta gccctcgagc tgtcgaagta gcgagtcggc gaggcggaca acggcccagc    197760
ccccgagctg acgatgagtc aaggaggctg cgcggtggtg acgcagcccc gtgtgacgga    197820
gaggcagcga agctgtgtga tgacggcata acccttgagc taacgaggat gtcttaggat    197880
agcccgtgag tcggctacta tggaaatccg acatctgagt ctgcaccttg agaacatgaa    197940
tttatgagga cgtgagggca ggtaacgccc gtgggaaagg ggagagaggc acccttcact    198000
gagtaagcga catgcatgta gcgtcggcgg gccaggccga ctgcatgtat gaagggtcta    198060
gagttacgct gtcgagattt tgcgtgggca tgtagcacca aacttgagtc ggcgacacga    198120
ctcaagccga ttgcctcacg aggtagggcc tgagttcacc ctgcaagagc tgacgaaggc    198180
atgtaacacc acccataagt cgaagggtga cttaaggtga ttgcctcgtg taagtaaggg    198240
cttagagatc acccatgagt caagtgaggc atgtagcacc ggcgggccag accgattgcc    198300
tcgttttaac cgtggtcata tagggttcat gacgccagtt acataaggat gcagagatga    198360
tctgagtgcg ccgaggtacg taatgcacag tttgaatgtc tagaaataat ttgagtaata    198420
tgaaaccctg agtgatcctg aaataacagg aataatctag aaataatgat cctaaaatta    198480
atatgaatga tctgaaacaa tgtgagtaat tcagagttga ttcgagtaat ttcgatgatc    198540
tagaaataag ctgagtgatc tggagttttg ggtaatccaa aaataatatg aatatatctg    198600
tagtcgggtg atccaaagac aatacgagtg atccaatgcc ctgagtaatc ccaaaataat    198660
tcaattgatc tagaaataag ctgagtaatc tgacatcctg agtgatatag taacaatcca    198720
actagaaacc gctaaaagtt tacgcgaagt cgaaacaatt ttttccagaaa taatgatgcc    198780
```

```
gaagtaatat gaatgatcca ggaataaatga tccagtataa ataatccaga aatgatccga   198840
aatcccgagt gatctagaaa taatatagac aatccgagtg atccatgaat aatcctcact   198900
ccatgaataa tccgattgat ccaataactc gaatacttca gaaataaaat aattgggatc   198960
caatagctag atgattcaga aataattcag catatcagta gcccggagac tagaagttga   199020
gcgaacagcc ccccgagttg atgaattagt cggcgaggac gtttagtcgg cgaggatgtc   199080
cgagcgtttg ggagttaagt aatgcagccc ttgagtttcg ggctggtaga aatataaaac   199140
cctccagcag actacaaaat agacaatgcg aatattatgt agcatgatgc aaaatataga   199200
atatatattt aatcaaccga agtattttgt aaaattgtcc catgtatctc ttctacggga   199260
ctaaacaaga gaagatgtag gaaacggatt ttttgaaaag acaataataa ttaaataaat   199320
gcacaaaata aatattagag aaacttagct ctgtatgttg ccgattagtt tggaccagat   199380
ctgagtgacg gctggtttga tccaagtccg atgcggaaga catgctgctt cttctttatc   199440 tctggtatttt ttctttgagt aaagaaacga ctcggactat ggtagcactt ccttgaaccg   199500
tacgtaacac ggcctctgca attgcctact tgctcctcgt gaggacagga tgcctccgtt   199560
gattggactt cagtttgcat gcgaatcatg aatgtgactc gaattatgat agcaggaacc   199620
aagaaggact tcagatcggc attaacagga ggacaggagc agatggatct tttctgtagg   199680
agaggcgtca aacccaagca ccaggaagaa cagatgtatc ccgctgcctc gggaacagca   199740
acaaatatgt aggacacgcg cggatggcgg cgatgcgatg aacatcgtcg gcgatggtga   199800
tatcaacagg gactgaaacc ctaatttttt aatctcctga tgttgatgac gttggcagag   199860
atgatggcca tggagctagc taatgtcggt gtcgccttcc ccacggtggg cgccagctgt   199920
cgaagtttta gatcgacaat gcaccacggg gtataccacg tgatgctttt gtgagttggc   199980
aacatcaact gtagctcgat ggttcgcttc gaggcacgac aaaacacaag atttatacag   200040
gttcgggccg cgggatgcgt aatacctac atcctgtttg cagcgggttg tattgctttg   200100
atatctagag gttacaatga gggctagggt ttggatgttt gatgagagag cgaggcgtg   200160 tatgagatca gatccctcta agatctgcct tgggagggat ccctagctcg ccttatataa   200220
tccggcgtgg cttgggttac aagtcagtta ccttatatat ctcctagacg gtttagatta   200280
caatagagtc cttgttttgt gcgctaagtt tgtttagccc attggcctcg ggcccgagtc   200340
ggtcggtcgg cccatgtaga taatacgtct catttggacc caggggatat ccatccccca   200400
cagtagtcct ccactagctt tcctaattag tcagccaagg gcgtcccata ccaccccttgt   200460 ggtagcactg ttttcccggg tggttctcaa tgttccaatt aacataatga tcttaacatg   200520
aacagtaaat aacaactgat aataaaagta taatcatgaa tagtgtgtrt ctctataccc   200580
aaaaccacat atagcaatag caggtactac ccaaaaattc agtggtaaac aagatataaa   200640
gatagtcaaa ctagggtaac ctattgggtc ccatcaaaat taacctatgc agatcattat   200700
gattaatcag aacatgactg ggtaaaaaga agtgatcaag gcacaacttt gcctgggact   200760
tgagattcca ggtaccaact tgctcttcag atgacacgtg tcctcactgc taaacgtagc   200820
aatacagaca aacatgatat aggcaaaatt aacatcacat caaacataag aataaactgt   200880
gtaataataa tctatgcgtc gctacgaaat cgtgggttcg agaattacta aagtcggagt   200940
tgtggttaag gagttatgat ttgtggaaga taaatatgat ttaaatgttg ccactgcgca   201000
gacaataatt ttatgaagct aacgcaattt gaatggatca aatcggagtt acggttctca   201060
agttacgatt tttctgaagt cattaaatac ttaatataga ataaatcgag tggataattt   201120
```

```
tttttatcta ggtttcatga caaaacatgg ttactagatg ataaacaata ttattataaa  201180
attttttgcaa ctggaatgga ttaaaaagga gccaagatga atttttctatg aattatataa  201240
gttctggaat tattttttata ttcaaaatcg atttctaaat cttttttcctg ttttctttaa  201300
ttcctggact gcgcgcacaa atactgagta gctcggggtc ggatctgcaa aaatccccaa  201360
gactcaggat tcccccatat ggatggcggg ttattttctg ataagtgcag ggtctcttac  201420
gcaaagttac atggccgaag gggtacgggg ttgtcccagc cgtcggatca gattttaacg  201480
gcacagatta gaatttatct ttaccgaacc ggtacgcaat tctggctatc agatccgaga  201540
tctatggtct aggttttatt aacgcgtgat ctaaccacat ccgtccaccc acggatcaac  201600
gcttcccatg caatcccctg gatagggcgc ccaccatctg atttcgctgc gttcgattat  201660
gatccaacgg ccagggccgt ttcttcttcc ctacacagyg gctggccacg ccagcccccc  201720
acggcggcgc aacgccggcg agccaccctg ccagacgatc gaacgcgcaa acgcacaaag  201780
tgaaagacgc acgtttacgg ggaaccacag gagttgtttc ttacccgcat tccgagcatc  201840
acagcgaccg atcgacgtat gtggcgaaag gtgcgcaacg cggtgaccgc caggaggaag  201900
aagacgaagg ccccccctgga gcggcgagtg ggtcttgagc atgcgcgcca cggtgtggga  201960
gtccccgggt ggtgcggatt tcggccatgg cgacgtcgac atgccttggt ttctcccgcc  202020
gtgacgccca ccacatcgcg cccggtgccc tgttccgagc tcccatcgtg gtctggtaga  202080
aatcgatgga ggaagaggga gaggggctcg gaggttggtt ttatagttgt ggagggtgaa  202140
caattggttc cggaatcctc ggtcggctac ggcggacgag ggcgaatccg gcggggtttg  202200
ttgagcgcga aagagagct tggacaaggg agagtctaac gcatgggccc acacgtagtg  202260
gcacagggtg agaccacgcc agaacgagga aggtcaggag tgtgggcccg cgtgttagta  202320
acctgatgcg cacgcagaac agggttggcg ggggaaagaa atttgggccg cgaggaaaca  202380
attttgaagg tgagccggtt ctaggcgatt tggcccaggc gccaactgac tccatttttta  202440
tattttttca atttatttta agatttctta ttttgaatac ccatttaaat ctgaatttaa  202500
aaaattcaaa ttcatatgca caagtacaac aaaactccag catgtgatgt tagtattgtt  202560
ttaccaatta tctcaccccta ttatttgtga cattatttca aatatgcaat tgttggagac  202620
tttgttctca aatgctatga attaagaaca aggcaacata aaatgttaaa tatcaaagcc  202680
cttcgtcgtt cgaagcatta ttttcccttg gatataatgg atttcggacg aaggttatga  202740
aggtcacacc ttcataatca tgataaaaga taagaaaaga tttatgcata aaatacggaa  202800
aataacatga ttactttgaa cattattatt aatttatttc tatttatttt acttatataa  202860
ataataacaa attacaaatg taccttcggc ttgaaggaaa ataagggtac aagcgagatg  202920
ccaatgccca ctacaggaaa cgcctaaatt ttcgtgggcc gagatatttt cgtcggctgg  202980
cccacgaaaa tactgacgtt attttttgtcg gtccctaggc cgacgaaaat aatgcgtatt  203040
ttcgtgggcc catcaatatg ttcgtcggca ggcccatgaa aatacagaaa cgtattttcg  203100
tcggtcacta ggccgacgaa aataacgcgt attttcgtgg gtcgaggcca aaccgacgaa  203160
aataygtcat taaccgtcct ctattttcgt cggcctagtg aggccgacga aaatagwggc  203220
ccaacatcgt tgtcctcggc ctcgctcgtt tcaatcgcgc gtcactcgtt tcaatccgac  203280
gtcgcctcgc cgcgacgccg ccccacgccc gcccgctcca tcgcgaaggt ctcccagctg  203340
cgccgtcgcc cgcctcgact cgttcgcatt tttcgccatc aggcaagtat aattgccgag  203400
gctccgaggt cattaattta tattagtcat cttgtcgtgt tgtgattagt ttaactgttt  203460
attgctttaa ttcaaattca tatttgtctc cgagttatgt tttaatgttt agagtttagt  203520
```

```
tttaatcgtt aaccgtagcg aaccgtatgc gtcacccgtt cgggaacggc aaacgtcaca  203580
ttggcttgtg aggttcgccg ctccggaatt gtccacgtat tttggacagc ctgagagtgt  203640
aggccgatgc ttgtgatttg tcatatgtgc cttacgattt acgcggaatt tcggttgtgt  203700
aactcagttg ttctccaaca caccatgttc aggcgtgtgc ttggagagca gcagggttat  203760
gctgccgaaa tttctcggca atcgtaggct acacatcaca aatcacaagc atcggtctac  203820
actcttgggt gggtttagga cctttaccta atagggagtt cacctaagcc acggacgatc  203880
gttgatgttc tttgtctttc gtttagcctt tgaaatgaac ggtgatcgga gggtgatgta  203940
tgacgggtgg agaaaggatg gggcacattc gaatgaatgg atggttgtaa caaaggcttt  204000
tcttgggcac gctttcaaag atgcaactgg tcgtctagtg aagtgtcctt gcaatcgctg  204060
cgagaacaag tggcctcaga agaaggaaga aatggagaaa cacctttgca aaagtgggtt  204120
tatgccgaac taccttgtat ggtaacggca tggagagtct attagtcacg ttgacgcgga  204180
ggtggaactt gatgacgatc atgataggat ggacgacatg ttgcatgatc ttggtaggga  204240
tgttgaaatg aacgctgagg agccggggca gcttccacgc gatgctcagg aattcttccg  204300
gctactcgcc gcgggagaag agagactgca cgagcacact cagatgtcag ttcttgggac  204360
tctcacaaga ctaatggcga taaagtcgaa gcacaacatt tcaaacagtg cttacaacga  204420
catcgtccaa ctgatgggcg aggttctccc ggagaatcat aagttgccaa agaacatgta  204480
cttcgcaaag aagatgttgg ttggtcttgg gatgacatat gagaagatcg acgtgtgtcc  204540
caacagttgc atgctattct ttgaggagga tgacaagctg gacagttgta agcattgcga  204600
agcttctaga tatgtcgagg tgacaaatga tgagggtgaa ttggtagtta cgaaggtcgc  204660
agctaagcaa cttcgtcggt tgcccatcat tcctcggctt tcaaggttgt tcctcaacaa  204720
ggaaatagct ctgcatatga cgtggccaaa gaatggtgta cgtctcgtca ctgatccaga  204780
cataatggtc catccgtcgg acggtgatgc gtggaaggca tttgatgagt ttgatcccga  204840
atttgcaaac gaccctagga gtgtacggct tggtctatcg acagacggat tcacacctttt  204900
caataccagt gcaagccctt actcgtgttg gcctgtcttc attgtgccat ataatcttcc  204960
tcctgagttg gtcaataaag aagagttcat gttccttgca ctagtcatcc caggccctga  205020
gcatccaggg ccaaagctga atatgtttgt tcgccctttta attgaagagc tgaaacaatt  205080
gtggagaggt gtgaaggctt atgacagcca tactgaaaag gagtttacca tgcgcgctgc  205140
ttatttgtgg tcagtgcatg atctgctggc gtatggagat tggtctggat ggtgtgttca  205200
tggtcggttg tgctgtccca tatgtatgaa tgatacggat gcattcagat tgaagcatgg  205260
tgggaaagtg tcattctttg atgctcatcg acgttggact ccattcaagc atgatttcag  205320
gaattcgctt actgcattca gaagtggagc caaaatcata aatgggccac caagaggca  205380
aactgcaccg cagataatgg catggcatgc ttgtctgaag caaggagaaa atgataggtt  205440
tcaaggctac ggggaggacc acaactggac ccatattcca tcaatatggg agctttcgta  205500
tgcaaaagcc ttgatcatgc cgcacaacat agacttgatg caccaagagc gtaacgttgc  205560
tgaaagcatc ataagcacat gtttcgatgt gactgataaa acgaaagata atatgaaggc  205620
aagaaaagac atggctgaaa tttctaagag accgatgctc gagttgaaag taagcgataa  205680
agggcatgag agtaggccgc gagctgatta ctgcctcaag ccagatgaaa ggaaagaaat  205740
atttaagtgg ttgaagaatc tgaaatttcc aaatcgatat gcggcaaatc tgaaacggac  205800
agtcaatctg aagaccggta aattgatcgg tttgaaaagc catgactacc atattattat  205860
```

```
ggagaggctg atgctcgtga tgtttcgagg ctatttaag gatgagcttt ggagcatatt 205920
tgcagagctg agttacttct atagggaagt atgcgcaaag acggtatcga agaggttgat 205980
gcagaaattt gagaaagaaa ttccaattct tatttgtaaa tttgaaaagg ttttcccgcc 206040
aggattcttc aatgtgatgc aacatctaat tgtgcatttg ccttgggaag ctttggtagg 206100
cggaccagtg aaattcaggt ggatgtatcc tatagaaagg gcgttgaaaa agctcagggc 206160
gtctgttcgc aacaaggcta gagtcgaagg gtctattgcg gaggcttttg cccttaagga 206220
gatatctcaa ttctcaacca ggtatttcgc tcgagccaac aatgtgtttg ctccttcaat 206280
gcgacttcat gtcgaaaatg aatcgcccca aagcacccct caaattttg cgaatccggg 206340
taaagcagtt ggaaaaggga gtgtacgtca cattgaagga tccgatttga acacgctaat 206400
gctatatatg tatagcaata ttgacagcac acaggaggcg ttcgagtaag ttttcctcat 206460
agttacttcc attttctcat ctcataattt ctatagtgtg taatctccat gtttctaata 206520
tgtccagcat gtttgatgaa gaatgttgga aatctactag taaacctacg gccatccaat 206580
tagaaaatct tcgacgtgat gggttgaaag gtggaccaaa cttcgtgcag tggtttcgta 206640
attatgttag taattgtcgt tctctcattg tccatactta atctttgaat tttggacttg 206700
gaagatataa tgcatatact aattccttat ataggtttca aaaaactctg tgcacccgga 206760
cttgcagcaa atggcacata cctctgtgtc cgtccggaac tatactcgct atgatgtaaa 206820
tggatatcgc ttccgaaccg cgaaattgga gaagagtcga ccattggcag ccaccaccaa 206880
tagtggtgtg ttggcaagtt catatgttga cgatgacaaa gtagtggact attacggtgt 206940
tcttcaaaac attatagagt tgattttcga tggccccaag gaacttaaag tcatgttttt 207000
tgagtgcgac tggtttgatg ctcatagtgg gactcgtgtc gacaagtatg gtaatgtcga 207060
ggtgaagcat agctctagga ttccgagcag tatgagcgat gttgtccttg caaatcaggc 207120
aaaacaggtg tactacctgc catatcctca cccaagcctt agggcttggt gggttgcaat 207180
caaagtcaac ccacaagtcg tcgctccaga gagtgctgac tacgtgaata cgagcaggga 207240
caacgatgac gctattttc aactagaagc ggcgtcgaat caagacatag ctcaccgatt 207300
tccatgtgac caatggagaa ggcccttgaa aatctctgtt gcaattcaag cgacttaatt 207360
gaagaaccta ggtcaaagcg caaacgacct gtcgtcgtta aagatcagt aaggatccaa 207420
cgaaatcaag agcgtatgaa taaacaacga gccgaagaag catcatcgga tgcggatgac 207480
ttttgattag tatgtttctt ttagttaatc aattaagcta tgtattccaa tttccacatt 207540
attaattttc atattatttg tttcatatac tgtggtttga cattaattta tctacagttg 207600
aacatgttca agcataggag atcgaggagg agtggggca gcgcggccag cgaggacagc 207660
tcgggcagtg ggcttttca gggcacctca gagccgacag aggcagcagc aacttctcga 207720
ctgtctagac gaagtgcagg gtgaggaggg tgagcaggag actcctcagc aggatgctca 207780
tgtgcagggt gaggagggtg agcaggatga ggaggttgac ccaatggggg caggcagcgc 207840
gggcgacgcg tcagatggtt ctacgtcctt caggtattat tatgcatatt agtttaattg 207900
atattagttt ttaatcattt catcatattg aatttacttg tatacttagg tataagaaga 207960
gcaatgcgct tggtccgaga cctgccgaga ggaggctcat ccggacgcat ggagaatggt 208020
ggggcttatt tctgttgtgt taatttttta atgtgaacgt gattgcactg gtttacttgt 208080
tttattaatt tttgtaggtc atgrgaagac ttgacttggg acggtacagg cagacgtccc 208140
aaggtgaacg aggtgttggg tagcctctgt cgcttctact accctggcat ggtggagctc 208200
aatggcgaga ggttcgcggc tatgcagtgg gctgactggg gtctaaagga ctatgtcgag 208260
```

```
ccagggagt caggggaaag cagtagcgga gggggaagtt cgggaaaaaa atgaaggact   208320
tgtcaggtgg ctgtgtggga cgagttctgg gtgagtttac tttcgtatat aagcaattca   208380
ctgaattatt gcttctccta atcttacttt aacttaactt ctccattgat atgtagggga   208440
ggttccaatt gccggatgac atcgaggagg atcaggctca gtggacacgt gtgaagaggc   208500
actttcggaa gtgcgctgat aagataatca aggatgccat gtacaatgct cgcatcgcgg   208560
ccgtcaacta ctactacaag aagataaagg gcagaaaat gagcaaagca ttaggggcca   208620
atgagatcta cctcacagag gagcagtacc tggagagcat tgtggattgg ctggcgaagg   208680
acatggaagc ctgaggtgg ttggctaaga gatgggcgtc gcctgagtgg attgcagagt   208740
ccaacaagca ccgtgccaac cgtggcactg aaggaccggg gcacaggtac ggcgccgatg   208800
gacaccttga taccgcacgc cgcatggtaa gtatataaat caaacttgta tgttacatct   208860
atgaaaatta tatggtttaa ctcttctttt tcatgcagga agctgaaagt ggagttgctc   208920
caagttttat ggaggtttac gtccgtggtc accgtggccc tgatccggcg aaccctgatg   208980
tgctatgcag cgaggcggca agggagaaaa tggtaaacaa gtttgtattt acgaattaaa   209040
ttgcatgttt tgtgtctaac tccaactcta actttctttg cagaatgcat atggggagga   209100
aatgactcaa cgccatgggc ctgacttcga ctggatgcat tcagacttag atgcctcggc   209160
gttgtaccac agtggtgggg gtagaaagca tggcaggtga ggtgtttgtg tttgattcga   209220 cgattcatt aacaagaatg tgtccactta atggctcaac tatgtgtatc atgcaggttt   209280
gcctttggca ccggcgttgt ggaatataac aggacaatag gtcaagggaa ggcatcgtct   209340
tcgggaggga gttctcgctc ctccaggtct gctcgagagg ctcggctgga ggaggagact   209400
cgggcagcac aggagcaggc tcgagcagca caggagcagg ctcgagcagc gtaggagcag   209460
gttggacagc tgacgcaata tatggcttct tattttcagg taatccgtct atctcatcac   209520
gtgtcgtcat tgaattcaaa gtataatgtt gtgattctaa cgttgcatcc atttgcagga   209580
aatgactact cgactcggcc ctgatatgaa cttgcccgct tttcgccctc cccaggtaac   209640
actatctgaa cacttcaatt ccatagcaac tcttttttta ttatcaaaaa tggctcgcag   209700
gcacaaggat ggggacagtg gccaggacaa gctccagcgt cgcagccaca gtggaccggt   209760
gttgggtgga cgcaggcacc tccaggcact tggatgcctc caccacccca aggatcgcag   209820
ccagtcccgg gatgggtgcc accggtctcc cagccaccgg cgggctctca gccatttcaa   209880
gcgtggatgg caccgccacc gacggggtgg gtgccaccac ctctggggtg gccagcacaa   209940
cagtacacgt ggatgcatgc acaacctcct cctcaccatg gatcacaggt gacgttccat   210000
gtttagtttt atgcaaatat tgaccaaaca cagcaatgta taggtatatg gatagcaaaa   210060
tacaaccttc tttgaatgat tgatgaattg cagggttcag cgtcacatgc tcatggatcg   210120
gagggtggtg tcaacgtcca agacttcctc gtccatggtg ctggagggag tggccaccct   210180
cctggtggca gaggagggag tggccaaaac tcccacagcc cgccggagtg aggagtgagt   210240
agtgagtagt gagtagctag tgagtgtgtt ttgtgaattg tgtatttgaa tggacaatgg   210300
acttatggac ttatggactc tggacttatt tgaatggact atggactatt tatgtatatg   210360
tgaatgtgtt ttgtgaatta tgtattaggc ttgtgaatct gtatatgtga attgtgatat   210420
tgtgtatttt gctgtgaatt attaataggt gtagaaaaat ctgttttagg gggggaacca   210480
tcaattttyg tcggcctckg tggtggccga craaaatatg ttcccaggct attttcgtcg   210540
gccaccaccg aggccgamra aaaawascct gayacgtatt ttcgtckgcc acsatcsggg   210600
```

```
ccgamgaaaa tagtcagtcg accatttatt ttcgtcggcc ttgggaaagc ccgacgaaaa 210660
taggttattt tcgtcggtac cgacgaaaat aggtgcctat tttcgtcgaa cttattttcg 210720
gcggctattt tcgtcggttt aggcttattt tcgtgggttt ttggcccacg aaaatttagg 210780
tgtttcctgt agtggccaag tcagcgtgaa cagtacggga gtactgttca tctatttata 210840
ggcacgggac gtagcccatg taaaattaca ttaatgccct ttgcttttat cactaactct 210900
atagtaattc tctgaggtct aatttggctt ttcatcttta agtcggttcc ccttttctgc 210960
tgtcatgccg aagcttttct gtacatagct tcgtgatcgt ttcatccttc gtcacgatcg 211020
tcttccattt cagtcaagct tcatcttgac catgcttttg tatatctgca acctgattyc 211080
gaagatacct gctcgcatac ttggaaaaca ttgtcaaatt atgttttga ggaccttcgg 211140 aagccgaagg cccccaacag tagcccctcg caatattaat ttgctgtaat gataaattca 211200
tattgcgata tggacgaagg ccttaagccg aaggtccgaa aaacaccctt ctctttgcta 211260
gaatagcaac agtctttgac aagcgggacc ctccagtttt caacgcactg ggtgtataaa 211320
taagagctca tcccgagttt atttggcacg ctctcttgcc aactgctttt actcacccaa 211380
ctattagcct gcgcgcaaca acacttgctt ggccttttgg attttttaagc ttcggtttcg 211440 agagcacttt ctcagcgttt gcaaggatgt ctgaggataa aaaagttgt tagtgattcg 211500 aagctaagtc tttcttagga gatgcatctg ggctttcttc aatcaatgtc gaagactaat 211560
acagagaaga ttactaaaga aattttggag ggtttgtctg aagatactgg tgacagtgac 211620
agttatgatg tagaaagtgg gggcgaagac tcagaagatc gaccgtggcg accgagtcac 211680
acagtcttcg gcaaatcgag cattaagcag agtcatcttg ataccatgaa ggaaggtat 211740 tttcgagaca tgtctattgt gagggtggat attggggaga aaattgtgcc tactcccgaa 211800
gaaaatgaag tcatggtatt ccgaagcttc ttgaaagctg gactacgatt tcccttaagc 211860
agttttgttg tggaagtact gaaggttttt gaagtctacc ttccaccaact cactcccgaa 211920 tcaatcataa ggatgggcat cttcgtctgg gccgtgagga gccaaggttt ggaaccaaat 211980
gctaaaagtt tttgcaacat acatgatttg ttgtacgaga cgaaaccttg gggcaaagag 212040
cagtatcaca acaattttgg ctgctacagc ttcggcgccc gatctgggtc aagttgcccc 212100
gtgccaacct ttcggaaaag atggcccggc aactggatga cagaatggtt ttatgtgaaa 212160
aataatttaa aaatccggga agatattaaa ggtatcatta tgcgccctgt ttggcaacgc 212220
ttcggccttc ggaggccgaa ggtggtgatg gatgaaacag ccgaagaatg cyaaagagcc 212280
ttcggcgcag tgtgctcttt tattgggaca agagatttaa tgcaagaaca tattgccttc 212340
agagtatggc cacttgcaca taactgggaa atgccgaagg aaaccgttaa agaacctgac 212400
gaaggtggac tagtcaggct aaaatacaca ttcaagtacg gagataaatt cgttgagcca 212460
gatgatgact ggctaaaaag cattgagact gtaagtgatg aactgcttgg ggtatactca 212520
aaggccgaag atactgcatt atcagcagcc ttcggaggcc gaaagaaaaa aaggctcaac 212580
cgagtatttg acgcaattgg gtttgtctac cccgactacc attatcccgt gcggggtcaa 212640
aaaagaaaga atacttcctc tgcgaaggaa actacttcag ccgctcctag tgagccggcg 212700
tcgaagagga aagggtaaa ggttctcaca caccggccac gttatattga actggccata 212760
gtacctgagt tcgccggtga gacctcttcg gccaccgaag ctaaagaatc aacactgctg 212820
ccagaaatcg aagagttggc cgaagtgcca gcaacagaaa agatagaaga accaaggact 212880
gaagaagcaa aaacattaga agtttttaagt ccttcagcaa aaattgagac aggaaaaagc 212940
cagaagggtc caacagtgac cctgttgggt ctatgcttcg acgccgaagg tcttatagaa 213000
```

```
agaagtgatc ctcggatgaa gctgttcgta caagatagcc gaaggtacct tttcgtagag 213060
cttcggcatt accaatcgac ttaaagatag aatgacattt tagtccataa aggtctgagt 213120
caatgttgta agttcttata aggggcatac ttgtaattcc tcacaggctg cgtcctgtgc 213180
ctataaatag tgaacagtat tccgttactg ttcacgcatt ctggtatttg caaccgcatc 213240
tctcggaata caacctttgt caaggcatag gtatcattgt atttgatgat tcaatatatt 213300
aagtgaatat gatataatac atctgtgaat catttactca tttttatatc ttttactttg 213360
cattatctta caatatttat taaaagttta ttacgaaggt tcaacttcgt aataagactc 213420
ttatcaacct tcgtccaagg ttcattatcc ccaaaggaat aatgcttcac ggacgaagga 213480
cagtatcatt taacattttt atgttgcctt gttcttaatt catagcattt gagaacaagt 213540
ccacaacatt ggcgcccacc tccggtgaac tcacttccac tttttgagct gatggcttcg 213600
ttcaacaacc aagctggagc tgcttcggac ccgaagctgg tgctcccgat cacaggtggc 213660
tcgtcctcag agccagctaa caagaaacag aagaaggaag cacagagaag ggtacagcat 213720
gttggggtgc aaggacccctt catcaagtca agatggtctc acattcctat taccttctcc 213780
caagaggacc ttcagctcaa agattaccca cacaacgatg ctatggttat ctcttgtgtt 213840
atcaaaggat ttctggtcca caatgtcttg gttgatacag gcagtgcagc tgacatcatc 213900
tttgctaagg ccttcagaca aatgcaagag ccagaagata agattcatga tgctacacat 213960
cctctttgtg gcttcggagg aagacagatc gtagcactgg gtaagatcac catgtcagtg 214020
accttcgggt tcatcaacaa cactagaacc gagcaagttg tgtttgatat tgttgacatg 214080
gaatacccctt acaatgcaat tattggtcgt ggtactctta atgccttcga agcaatcctt 214140
catcctgctt atctttgcat gaagataccct tcggatcagg gacccattgc tatccatgga 214200
agtcaggaag ctgcaagaag ggccgaaggc aattggactg actcaaaagc aatccataac 214260
atagatggag ctgaagcttg tgagcagtac aagttcagga gggagaaagc agcttcagca 214320
gaccagccga agcctatgct cttatgtgag gacatagcag agcagaaggt gctgttagga 214380
tctcagttat ccgaagagca aaagaaaacc ttgataaggt ttttgttcaa taacaaggat 214440
gtttttgcat ggtcagccaa tgatctttgt ggagttaata gagatgttat cgagcactcg 214500
ctcaatgtcg atccatcctt cagacccaga aagcaaaggc ttcggaaaat gtcagatgat 214560
aaggccgaag gtgctcgcaa cgaagtcaaa agactcctca gtgcaggagt tattagagag 214620
gtgaagtacc cagaatggct ggctaacact gttatggtaa aaaaggccaa tggcaagtgg 214680
cgaatgtgca tcgattttac agatcttaac aaggcttgtc cgaaggatga attcccacta 214740
ccaaggatag actctttagt tgatgcagca gcttcgtcag agctcatgag tctgttagac 214800
tgctattcag gctatcacca aatttggatg aagaaggaag atgagccgaa gactagcttc 214860
atcactccaa gtggcacata ttgctatctt cggatgcctg aggggctcaa aaacgctgga 214920
ggaagtttca gccgaatgac tgcgaaggtt cttcaatctc aaataggcag aaatgtgcta 214980
acttatgttg atgacatcat tgtcaaaagc acgaagcagg agaatcatat tgctgatctg 215040
caggagacct tcgccagttt caggcaagct ggcttaaagt taaatccaga aaaatgtgtc 215100
ttcgagtga agaaggggaa atttcttgga tgcttggttt caacaaaggg aattgaagcc 215160
aatccaagta aaattgaagc tatacttcgg atggagccac caactacaaa gaaggggggct 215220
caaagattga caggaagatt ggcatctctc aatagattca tatccagatc agcagagaga 215280
aatttaccat tcttcgaagt gctgaagtcg gccgaagtct ttcaatgggg accaatccag 215340
```

```
cagaaggctt tcgaagaact gaaacagtat ttgatagatc taacaacact gactccacca 215400
atgccagggg ctcctttatt attatatgtg gcagcttcgc actcagcggt aagtgcagcg 215460
cttgtccaag agaagcttga tggtcaagtc agaaggcagg ccccaatata ttttgtttcc 215520
gaagtcctta gtttatcaaa gaaaaactat acagagttgg agaagatact gtatgctgtc 215580
ttgatggcct ccaggaagct tcggcactat tttcaagctt acaacataat tgttccttca 215640
tcacaacctc tgaaggatat tatgaggaac cgagaagcta ctggaaggat tggaaaatgg 215700
gctgcagagc tcaatgaatt ttgtattgaa tatgttcata gatcttcgat tcagtcacag 215760
gcactggcag actttattgc tgattggacg ccagggggctc aggaggagga aacaaataaa 215820
gacaacgaag cctggacagt gttttgtgat ggatcttggg gaaccttcgg agcaggagcg 215880
gctgctgtgt tggtttcacc ttccaaagtc aaaacttgtt atgcagcaaa gcttgatttt 215940
aattgcacaa acaacattgc tgagtacgaa gcattgattc taggtcttcg aaagttaaaa 216000
ggaatgggaa tcagaagagc catacttaaa actgattccc aggttgtttc gggtcatatt 216060
gacaaaagtt gcaaggctaa ggatccgaag cttgaaaaat atctggatat ggttcgaaga 216120
gttgaagctt cyttcgaagg gttttctgtc aaaaatatcc ctagaggaca aaatgagcat 216180
gctgatttgc tagctaagtc agcagcacaa gggctgcctt taccttcgga tgtatttttc 216240
gaaacaataa aagcaccttc ggtggaactt cttgaaagag cagttcttaa tatatctcct 216300
gtttttagcg aagattggag aaccgagatc atctcttacc ttcagggtaa atttctttca 216360
gatgacgaag cttataacaa gagaatagaa gcaagagctc gtccatatgt cataatagaa 216420
ggggaattgt ataaacatgg agtttgtgct ccgctgctca aatgcttatc cagaaccgaa 216480
ggtatagagt taatgaaaga aatacatgca ggcctgtgtg gatctcacat tggatctagg 216540
ccgttactcg gaaaaatttt ccgtcaaggg ttttattggc cgaaggcagc ttcggatgca 216600
gcagaattgg ttcaaaagtg cgaaggttgt cagaaatgtg caagagatca aaaacaacct 216660
tcgtccttga cacagcttat acaacccact tggccattgc aaaggtgggg ccttgacttg 216720
ttaggtccgt taccaccggc ccaagggaac ctgagatatg ttgtggtagc tgtggaatat 216780
ttttctaaat ggattgaggc gaagccttta gccacaataa cttcggctac catccaaaaa 216840
tttttctggc agaatattgt ttgtcgtttc ggggtgccaa aggctatcac tgtggacaat 216900
ggaacacagt ttgactccga agctttcagg gatttctrtg accaaattgg tacgaagatc 216960
catttcgcat cagtcaggca cccggagtca aatggactcg ttgaaagagc caacggcatt 217020
ataatgacag gaataatgaa gctaatcttc aatcaaccta gaggaaaatg gccagatcag 217080
ctaaccaaag tggtgtggag ccacaacacg acaacatcaa ggtctacagg cttcactcca 217140
tttaagttgt tattcggtga cgaagcaata actccagagg aagctaaagc cggatcaata 217200
aggatagtag cttcggcaga atcagattcc gaagctgctt attctataga aaaagatgct 217260
ttagaaggga tcagactaca agccgtggag aatattaata aatatcaagc tgaaacagtc 217320
aaatggcggg atagaaaggt tcggttaaaa aatattgagc cagggcactt ggtgcttcgg 217380
agggtggcca acccggaagc agtgggcaaa ttgcagttga atgggacgg cctttctta 217440 gtagcatctt cgtcaaggcc cggttcatac agattgaaag atatgacgg caatgacatt 217500 cctagatctt ggaatgcgga tgagcttcgg cgatactatg tataattcga tgtaattttt 217560 catatttta tttttctttt catggcaccc ttttccttc caaggggga gaaggttttt 217620 taatggggcc agtatatgta atttcctttt ttagttttat aagagcaaaa tcccccaaag 217680
aatgtaaatg taaaagctga gagtgcacca tcgagtgccc aaaaagtaaa aacgaagaag 217740
```

```
ctccaaagac gttcctaagg gaatgcagag cttacagcga aaagtcaacg ctgattccrc 217800
caaaagtaaa ggcgaagaag ctccaaagac gttcctaagg gaatgcagag cttacagcga 217860
aaagtcaacg ctgattccgc caaaagtaaa ggcgaagaag ctccaaagtc gttcctaagg 217920
gaatgcagag ctgaggtgtg attgttttta agaaactaat ggttatgaat atggcttcgg 217980
atacgtgttt ggccattcat ttgcacatca cattgcatca tagcatttgc attcataaac 218040
attcatctag gcatatgtag gataatcatt ttcatcgcat aaaatggttg cttcggcaag 218100
aagagaaaaa agaaaggaaa aaaaaatgtt gttttccatg aaggagtgct tcggaaaaaa 218160
ggaaaatgtt gttttttatg cttcgttgcg tacgaaaaga agggaaggtg ttttttcgcc 218220
ttcggctcaa aaaggaaat ttcgtccaca tcaaagcatt tcacatacat cagtgaaagg 218280
ttaaggatat attacaaggt atgaacagca tacattaaaa acaagttttg tttacattca 218340
caaaagttat ctcaaaagtt ttttaagtac tgtctgcagt ttactatcta aatctccaag 218400
gagcttcggc ttcggcatta tctttggtca tcagcttcgg cttcatcatt ctacacgaat 218460
aaggtcgttg gaagtcaaaa tcaagtttac agaaaaaggt aagcacaagg tatgatttct 218520
tactggatca aggtggcttc gagcttcgtc tccagctttc tctcgaccac cttttgtcca 218580
tatcattttt atgaatcgat ttgagatgct tcgggcgaga tcaggatgt catccaggat 218640 tgatggtgat aaagtgaaat ttggcctgtt gacaattttc ccatgatcac agccagcctt 218700
caggaatgct gcagcagtcc ctcgagaagc cacccaggca caaagtcgc catgcccagc 218760 tatgacttcg tcgagctcgt caatctcccc ctcaatgtgt tcgaaggttt ttggtagatc 218820
ttcagctgag ggggtaaatt tttcgctgct ggctccaact gagtgaaaaa tcttccttag 218880
tcgttgaata cacttgttgc taaattcaag gcattttct tgaagatttg tcagtagttt 218940
tctcaaatcc gaattttgct gagcttcggc ttcaagtttt gcattaagat cttgttttc 219000 ttgttcgaac tgctcagact ggcggagaag cttcgtgttc agttctgata ttttttgcttc 219060 agcttccgcc agtaaacctt cggccgcctg gagctcaaag ttcttttttct caaaagcatt 219120 tgattgctct tttattttgt tttccaaatt tccaattata acttcatgct tttttatcttc 219180 aagatcttgc tgcatttgca aggctttgct caatagcata ctctacataa acacaaccttt 219240 cgtcagacat gttttttacta gaagcaataa aagttaaggg acaagtcatt caccttgaag 219300
ttggagaaaa ataaactacc aacgacatgt tgtcgtcggt agcggctgat atctgttttct 219360 agcttcggga atccaatact cctggacaga gtgctgatga ctttggcccc tgtttggtcc 219420
cgaatacact ctaatttctc atcatcaacg cctccgaaga ggagtgcccc aggtttgtat 219480
ccacaggatt gggcatactc tttaagctct tctatttcag cttttgttag atgttctcca 219540 actaagttttt tgaacgcaaa gacttcgttt tccgaagctt catcagcaat ttcttttcct 219600
ttctttgacg ctgcggtcac agcttcttcg gcagcagtgg cagcttcctc tgcagccatg 219660
tctagcagca tttggtcaat atgttcaatt gtgctctcta aattcaaatc ttcagctgag 219720
gtaacttcgg cggctgcggc ctccgaaggt gcaatttcaa tatctgcccc ctctgctgct 219780
gcttgtgttt tttgggccga agctcttggc ggcgttttgt caattacctc tgtcacggta 219840
atgattcttt gtttctttcc cttgattgtt ttcctcaatt tctcaggctc cttgtccttc 219900
tgaaaaaact tagtcagttg aggacccagt ggacttagct tcgcaggtaa ggattcagtc 219960
attaccttca gaatttcttc aacaacagca gcagaaggtg atgcgggggt ttcttctgct 220020
tcggatattt gttgcttcgg agaagaaggt tccttttttct ttgaaatttt cttctttact 220080
```

```
ggctcttttt caccctcatc taaggcttca gtcgcccttt ccttttttg ccctctggca   220140 cctttgttca gatcttcgta gtctgggtat tcgaaaccca aggcgtccaa tactcgattt   220200
agccttcgtt tcggacgggt gccgaaggct gcggtcatca attgatcttc ttttttttgaa  220260 taattaccaa gtatctcgtt gcacatcact tcaatcgtat ccagccactc ttggcaagga   220320
gttttaaaat attttttaaa tttgaagtag taaggcaaac gtacaagttc accttttttc   220380
ttctccccct tcaacttcgg catttcccay tcttttacac taggaaaaac cttgaaggcc   220440
aagaattcct ggaccaggtc ccttgtacta atattctctg caattatttt gaattcaaac   220500 attgctttt gagttggacc ctctggtagc atgtggcact gggggggcgag tttctccgaa   220560 ggtcagttcc agtggactct gcacaagctt ttctttatca tcatcaacct taacatagaa   220620
ccattctgat ttccaccctg ctgcccattt gcttcggtag ctgatcacag gatacttcgt   220680
agttttccga taagcaaaat tataacaacc aaaattctca tgtaaaccat cctttctagc   220740
ctttgtctga tagtgcagtt cgtgaactcg acagaagctg tcagcaaatg gttccaccgc   220800
ctggcttcgg agtgcccaga tataaacatt aagcctaacg atagcgttag gagttagctg   220860
gtgaaaatag attccaaaat ttttcaatat ctctgcaata atcccatgaa gggggaatct   220920
taatccagcc tttaggaagc tcttaaaaat aacaatttca tctttctccg gcttcggggt   220980
agtctcttct cccccgaagc gtaatagctt cttttgattt tcagtaaaat agcctgattt   221040
taccatcttg gacagatcag ccttcgaaac agtagatttc ccgaagtcca agtgactggg   221100
tttgcttggc gtggcaaggt gataatcatc ttcggggtca gtttccccag catcttctcc   221160
ttctgcttca gcgacagctt gttccgcatc atcaccaaga atcttctccg aagtcactaa   221220
cccggatcgt tgcatggctt cggagatagg gacagtctct gaagcttcag tttcgtcccc   221280
ctcacgctca accctagcgg tagaacggac tctggccatt taactatgaa cttgtgaaac   221340
tttaatactt ttttctccga agcaggcttc aagatggagc ttcgttcaat tctcacaaac   221400
aagcttcggc gatggttaaa attttggcag caaaacagtg caaatagcag taaatgctgt   221460
ggtaatttca cacctactcg tctgtttata tagtgccgca ggtaagaagg cgaagcgcca   221520
ggagttttac accaggcgaa cacccgctcg cactcgctgt acggtggacc gcagtgaccg   221580
aacagtaact ctgcaaggtg gggccgctgc gcgcagggaa atcgaatcgt ttctcgacaa   221640
cgagctcagg gaaggtgttt tttgagacct tcggcgctcc gaagcttaag aaacttttt   221700 cacggatcaa gctcgttacg aaaaacgatc tagcaccgcg aaaggggcta ctgttgggtc   221760
tatgcttcga cgccgaaggt cttatagaaa gaagtgatcc tcggatgaag ctgttcgtac   221820
aagatagccg aaggtaccttt ttcgtagagc ttcggcatta ccaaccgact taaagataga   221880
atgacatttt agtccataaa ggtctgagtc aatgttgtaa gttcttataa ggggcatact   221940
tgtaattcct cacaggctgc gtcctgtgcc tataaatagt gaacagtatt ccgttactgt   222000
tcactcattc tggtatttgc aaccgcatct ctcggaatac aacctttgtc aaggcatagg   222060
tatcattgta tttgatgatt caatatatta agtgaatatg atataataca tctgtgaatc   222120
atttactcat ttttatatct tttactttgc attatcttac aatatttatt aaaagtttat   222180
tacgaaggtt caacttcgta ataagactct tatcaacctt cgtccaaggt tcattatccc   222240
caaaggaata atgcttcacg gacgaaggac agtatcattt aacattttta tgttgccttg   222300
ttcttaattc atagcatttg agaacaagtc cacaacagac cccgaaaaga aaaggatgg    222360 ttaatgtgtt agatgttttg gagacaatta aatcttcaag cataactcca aagaaaactg   222420
ttgaaacttc tgaagtgtct actgaagcct tgttgttgt agcttcgaag caacaatttg    222480
```

```
aaactgaagt tgggccttca gagcccacca aggtaaaacc tttggaaacc gaagaaacaa   222540
aaattacaaa ggcagctttg gaagccgaaa aaataaaaat gtcagagcca attttggttg   222600
aagaaattga cactgctgcc cccgaagcac cttccaaaat atgcgattat attgtgcgac   222660
atgcttcggg gaagaaatta tctgaagaag atattttttga agctaatcac tatgccgagag 222720 aactgaaata tccgaagggg gcactagtgt tcaatgggac agacgaagat gacttcctat   222780
actgcctccc tgacaacaaa gaattatctg tctgccggga gatggctaga agtatggggt   222840
ttccgaagct tgaagctgga ctctacgcta tgacgaagga cgatcttgcg gatagccttg   222900
catataatag tctgaaggtg tgagaattgt atatttggaa atttacaatt tttgaatcat   222960
tcttttattc ttatactaat tcttttttcat atagggtttt aatactgagc aacgctttga   223020
gagcgcaaaa agaatgccga agacgagagc tataatattg ctttcaacaa cctacgagca   223080
gaggttatca agcttgagga acgaagcttt ggaaaaagat aaaattctgc ttacactagt   223140
ggataaaata aaggaagacg aagctacctc taaggctcaa gctgaagccc aaaagtgtga   223200
aattcaggat cttcagaaac aactggccag agttaaagaa gaacgcatac tagaagaaac   223260
aaaacgagaa cttagtgatc aatgggcaaa tcatttggaa ataaatgctg aagagcttcg   223320
tgcttccaag aaaaggtact atgataaatc catagagtgt gttaagaaga taaaatccag   223380
cttcgccagc gttggcgcat tctctagcga agaaaatttc acaagggggga atccagaagg   223440 ctcgattgag tggatcagtc acgaagctga ggccttcgag gaaatcttga atagccgcgg   223500
agacatatgt gcttttttcag gcgccagggg gattgctact gttttggaaa gaaaggttgt   223560
aatcatgtga aatctttagc gcaatctgaa actgccttgt cttccgaaga tataaaggac   223620
ccctcggtcg aagcaagcct ggttggtgga aaaaatttca ccgacatttg gacaatggc    223680 ggccgagaaa tggctcaaga aatcattcaa agaagcgaaa aaggcatcca tgatgctagg   223740
aagatagcag aggctgctga gaaaaacgca gagcccgaag ggcaaatagg tattaactag   223800 tggttttat tctgttgtaa ttttttgattt cagactttgt tcgtggtttg taatagtaat    223860
atagccgtat cttctcctcc ctcagaacct gctgaggcat ctccgggccc ccacccgaag   223920
ggggacgacg aaattagaaa aatggtcgaa gccatcatgg acaaggttgt cgatcagcta   223980
ctgaacgaag ctgcagaagt agttcttagg gaagattaga tgctattgtt aaaatatttg   224040
gaatgtaaca tgtgtaatac attgtaactt tgaatgtaat atataatcta tttatagttc   224100
aattctttac gatgcatgaa attttgcata cataccgttt tttgagcctt cggcgaaaaa   224160
acaccttccc ttcttttcat gcttcgtgaa gaaaatcttt tatatatcac aagaatttcc   224220
atacttctct gatgaggaat atccaagctt cgtgaaaata ttctctgaag ctataaaaag   224280
ttttatgttg tctctctaat gaagctacac ttctcaattt atcttgtgcc ttagcacgat   224340
tttctctttt tcaaaacatt ctccgaagat caatactgta tccccttctt gttccacatg   224400
caatatgatg tatgatgctt atgttatgca aaatgatgtg atgatgttat gttatgcaaa   224460
atgatatttg tgccaaagat acacacatcc ctgcaataga gcacacaatc ttttatatc     224520 agcgctgact tttcgctgta agcctcccct aggagcttct tcgccttta ctttcagcgg    224580 aatcagcgtt tattttttcgt tgtaagcctc ccttaggagc ttcttcgcct tttactttca   224640
gcggaatcag cgtttatttt tcgctgtaag cctcccttag gagcttcttc gccttttact   224700
ttcggtggaa tcagcgctta ttttttcgttg taggctcaga aaacttacac tgctctccct   224760
taggaacgac ttttttactgc ttcgaataaa ttgcactgtg tcccttagaa caaattttg    224820
```

```
ataattcaaa ggtccttcgt gccaccataa attcgtatgc ttcggcaact caagcctatg   224880
gagaagatat atttcatta tggcaaaaga cgaaactatt acaagaaatt gacaaacgat    224940
aaaaaacact tagacttccc ataattgttc cttattaaca aaaaaagtaa tattgaatgt   225000
aaaaatgcga aaaaactgtt gtcgaggtag gatatttgtc agtaaatgtg cttcgactct   225060
ggcacagtgc tattgactgt gcgagcttcg gactcctctc tgaagtccct ctgaaggtga   225120
gtgtgttgac tcccttctgg ctgctgtcct cgctgcgttg gtggtggcgg tggaggttga   225180
tgccaagatg cttggggttg acttgccgaa gcaacagaag ttgcagagtg attgcctaca   225240
tattctggaa tgtaaggcga atggtacgaa gcagtgtgca tgacctgctt tggctgactc   225300
tgttgtgcta cagcttctgc tatctcattt tgcttctgga tggtgacgtg gcacatcctg   225360
gtggtatggc cctgtcttc accacagaat agacagtaaa ttcttcttgg ctgatcccca    225420
aatcttcccc cgaagcccct ggcgcctctg ccccttggcg ctggcggccg aacagagctt   225480
tgttgttgcc ccgaagcttg cgaagagtat tgtggccttt gttgttggct ccctctatca   225540
tcactttggg tggagttatg aattgaccta acgtgcctcg gatgaaatct tcctccgaag   225600
cccctggtca tttcagagaa cctgaatgcc tcctcccttc tttggcggaa gtcattgtca   225660
gctcggatat actcgtccat cttctggagc agcttctcca aagtttgtgg tggcttcctg   225720
gcaaagtatt gcgctgaagg ttccggccga agtcccttaa tcatggcctc aatgacaatt   225780
tcattgggca ctgttggcgc ctgtgccctc agacgcagaa accttcggac atacgcctgg   225840
aggtattctt cgtggtcctg ggtacactgg aataaagctt gagcagtaac tggcttcgtc   225900 tgaaccctt ggaagctggt tatcaacata tccttcagct tctgccaaga ggtgattgtc    225960
cctggccgaa gagaggagta ccaggtttga gcgacactct tgacggccat gacaaaagac   226020
tttgccatga ctgcagtatt gccaccatac gaagatatgg ttgcttcata gctcatcaag   226080
aattgcttcg ggtctgtatg accgttgtac atggggagct ggggtggctt gtaagactgg   226140
ggccatggtg tagcctgcaa ttctgttgat agaggagaag catcatcaaa agcaagattt   226200
ccatgatgga aatcttcata ccagtcgtcc tcattgtaga agccttcctg atgaagctct   226260
ctgcgcggag gccttcggtt ctggtcatct tgaacaagat gacgaacctc ttccgaagct   226320
tcatctatct gtctctgaag gtcagctaaa cgagccatct tctccttctt tcgttgcacc   226380
tgttgctgaa ggatctccag gttttggatc tcctgatcca agttgtcctc cggaggcgtt   226440
ggactagtgg ccttcctctt cttgcttcgg gcctccctaa gagaaaggac gtcctgattg   226500
gggtccaacg gctgcagagt ggcagcccct gtcgctgaag cttttttcgg cggcatgacg   226560
aaggtgatgc ttgccgaagg tgttcaaagc tcaagaaatg gaagtgagtt caccggaggt   226620
gggcgccaat gttggagact ttgttctcaa atgctatgaa ttaagaacaa ggcaacataa   226680
aatgttaaat atcaaatccc ttcgtccttc gaaggcatta tttcccttg gatataatgg    226740 atttcggacg aaggttatga aggtcacacc ttcataatca tgataaaaga taagaaaaga   226800
tttatgcata aaatatggaa aataacatga ttactttgaa cattattatt aatttatttc   226860
tatttatttt acttatataa ataataacaa attacaaatg taccttcggc ttgaaggaaa   226920
gtaagggtac aagcgagatg ccaatgccaa gtcagcgtga acagtacggg agtactgttc   226980
atctatttat aggcacgaga cgcagcccat gtaaaattac attaatgccc tttgctttta   227040
tcactaactc tatagtaatt ctctgaggtc taatttggct tttcatcttt aagtcggttc   227100
cccttttctg ctgtcatgcc gaagcttttc tgtacatagc ttcgtgatcg tttcatcctt   227160
cgtcacgatt gtcttccatt tcagtcaagc ttcgtcttga ccatgctttt gtatatccgc   227220
```

```
aacctgattc cgaagataca tgctcgcata cttggaaaac attgtcaaat tatgttttg    227280
aggaccttcg gaagccaaag gcccccaaca gcaatgtacc catgaaatgt tttaaggaaa   227340
tatggtgtta ggtattgtag ttaaaatttc atttaaaggt gaatattcat tacttaatta   227400
ttttaggaga aaatattgta tatttatttg ctatcatgag tcactttacc acataaagga   227460
atattttata tatagcctta gaaggggtta atctattcta ataaattgaa gctatcctca   227520
ttatttctta aaatttataa ctgaacttat tatttcaact gtcataaaaa atccatttta   227580
taattattta ttaggacact ttcctttgat ttcttttact aatttcaaaa atcataattt   227640
tggggtgtta caccagcaac acgtatatta cgagcctctt cggctttctc acggtgaatg   227700
gcatcacagt gtttccatgc ttcaccrtcg gatgtgtgca ccatcttgtc aggattgtat   227760
tgtttgccat ttttgtgtca tgtcatctgt ttcgtggatt cctcggtcat gtgtagacgc   227820
tggaccctcg gtatgaacgg aaggtggcgt aggattgtca cggggatgtc gagctgcctc   227880
ttctgtccat caccagagta tacctccatg aacctaaacg atttacactt cggacagtac   227940
tttgccttcg catattcttt cctaaatagc acgcaaccct tcggacaagt atgtatctgc   228000
tcatacgtca tcttgagtgc acgaaggagt ttcagtgcct cgtacatgct ctttggcaga   228060
acgtggtcct ctagaagcag gctaccaata actatcaaca agccatcgaa tgtgtctcga   228120
ctcatgttgt aatgtaactt gaacgtcatt acacgctcaa tggcatccag ttaagaaacc   228180
tttgtttggc cgtgaaggag cttctgtgtc gcgtcaaaca tgtcgtagaa cgcctttgcg   228240
gtcggctcta gctcgtccta tgtacatcct tcggtgaact gtgcctcatg atagtcgttt   228300
aacatatccg ctaccccggc atcagcatca taatcctcga cacatttatc tcaccacctc   228360
ctctctcgta tgatgcaaag atctgcatat gtacatcgta tctctttcga gccggagatg   228420
ccttactggt tgatgtgatc tacgacgatg atgcggaaat agaggttata cctagggtga   228480
tggtgcaatt aggctagcgg ggttgtggcg gttcggtgca gtggcgacgc gtcgcggtgc   228540
aggcagaccc gcaacagcta ggaaggcctc tgcaaaaaaa gaacaaaaat atgtcaacaa   228600
aaaaatcgac agcacctccc ctacaccgcg aggtttccaa aacctacaaa taaaactaac   228660
agcacgatgg ctgacattca cacacatacc aacggcatga tgaccgaaaa tcacatatac   228720
atcagtaaat gtaccataaa agacaatatg atcaaggcac atgttcatgg taagggccaa   228780
tgccatgact gaaaaatatg gactgctatt ttgttgacaa acctcactc gcaaagcaac    228840
ataaactagc agaaccatat gatccaacta attattagca catcataata aattacatcg   228900
acgacatatt tcatccatgc atttttttgtt agctaagtag ttggtcttag cttcatccac   228960
tattctaact gtacgtatat ttcatccacg catgcatata ttaataagat catataaacg   229020
gagacaatga aatgtatacc ttagtggagc tccgacgaga gggatggtcg gagccaggga   229080
cgagagggat ggtcgagagg gcggtgggt tggtcgggtg gcagggctgg acggcggcgg    229140
ttggccagcg gtggggatgg atggccggtg gtggggatgg atggcggcgg cgattggccg   229200
ggcggtgggc cggggttggc cgggcggcgt gggttggacg gcggtgggg ttggacggcg     229260
gtggcaggtg ggttggacag cagtggatgg ctacggcgtg gagaagagaa agaaaaatga   229320
agagaagaag aaggccagtt aagactatgt aaacagactt gtcgagtgt cgcgatctag     229380
cagtcggcaa agttattttt taatttaaaa atatactttg ccgagtgtcc tcgatctrac   229440
actcggcaaa gctgtctttg tcgagtgccc tttgataagc acttgacaaa gattgtttta   229500
ttttttttta aatacgttgt cgagtgttcc acggcaggca ctcggcaaag aatgttttac   229560
```

```
ggagtgtctt attttgacac tcgacaaagt ttattttat tcttttcttt tttccaacca  229620 aatttttgt ggtttgttcc tacaccatgt atacatacat gttcagtttt ggcacaatta  229680
taatagtgtt tgctagttat ttgatttagt ttgtttaatt gaattttcg gatgattcag  229740 atttgaattg caagtcactc gaaaaataga aacggtgaat gcaaaaatga tatgaatgtt  229800
attgagcaca agttacggcc tatttcagga acagaccgga attttcgagc accatcctca  229860
cgaaacatga ttgtgaactt gccacacagt tgtttaaaaa ttgtataaaa cacaaacaag  229920
tcagaaaatc atgaaacttg tagacatgtc atgatttcat atgtagagcc tatgataaaa  229980
ttttgagaat gtttcgtgat atgtgtagaa accaaagagt cctaaacatg aaatcataga  230040
acttcaattt aaatctgcta ggtttctaca catagtatgt gataatttc acaaaacatt  230100 ctcaaatttt tatcatatgc tctacatatg atatcatgac atgtcgacaa gtttcatgat  230160
tttctgactt tgtttgtgtt ttatacaatt tttaaataac tggatggcaa atttactgtc  230220
atgtttagtg agcatggtgc tcgaaaattc cagtctgctc cttaaatcgg atgtaacttg  230280
tgttaaataa catggatacc attttacat tcatgatttt acattttcg agtgacttgt  230340 tgttcaaatc tgaattatct gagtaaattc gattaaacga acaaaatcta atagttatag  230400
caaacacttt ttgtaattgt gccaaaatga atatgtaag tctacatagt gtaagaacat  230460
agtagaaaat gtttgattga gaaagaaaa ataataaaa atatactttg tcgagtgtcc  230520
aaggtagaca ctcgtcaaaa catagtttac cgagtgtcag tctagagaca ctcggcaaag  230580
aagcttcttt ggcgtgtcga gtgccaaagg ccggcgctcg gcaaagttaa cggtcgtcgg  230640
ctatagacgg ttgctgacgg cccttgacg agcgtctcga ttcgccgagt gtttagcact  230700
cgggcaaagt ggtctttgcc gagtgtcttc ctgtgccgat gctctcgata aacgtggctg  230760
ttaccgaggg taggattttg ccgagtacgg atctttgcga agcgccgagc actcgacaaa  230820
gagccggatt cctgtagtga tgtgacatcg aatctgcaca agcacatgca tgttcatcaa  230880 tattttgcg acataaaaaa ctagttttgt gatttgtcaa acaactacta gctaccttca  230940
taaagatggc gtcgccactg tgacttgatc gagcatgagc atgttcccgc ccacgtgctc  231000
cacgcctgca tcgatcatcc gcagaataga accatcatgc gccgtgtttg ttagtagcca  231060
aatctcgaaa caaatttagc tagctatcga cagacccaat cgaattcaga cgggtattat  231120
ttggcttcgc ctgagcgacg acgtaagtca gagggcgaag ttgatgccgc tgatgtgctt  231180
gtacctagag gtgatcatgc ccaggacggt gccgcgttgc cgcagaccat gtcaacgacg  231240
gtgcggatgg cgcgtcgccg tcgaagccgg tgcaccgctg ggagagtagc tggagcaact  231300
tgtcgcaggc cagcgccgag atctgggaca tggcctggtt gtactgccgg ctcacctgag  231360
ggttcttctt ctccatgtag tcgaacggcg gccatatcga acgcgccgca gccgtccagc  231420
acagcctccg ccatatgctg cctttgcatt gttgacgtca ttttatgtcg tcgttttcac  231480
ttttagacaa agcgtttcat cagatttata caatacaata ataatatttc cgtgactgtc  231540
gtttattaag agcatctcca agaggaaatg caaaaaaaaa atccccaaaa actgattatg  231600
gagggcatat tgaacgtttt gtaggggtga ataaatggt aactccaaca gtttcctcaa  231660
aataaaaaac tgaaataaaa ctgggctaac ttttaaaaat tgctgcccca ttttgcctaa  231720
atcgcatccc atttgttgca tacggcatat agttggtttt gacttttacg ctgcaactct  231780
ctgggagctg tactcagccg ccaccagccg ttaccaggtg ccagccgcgt gggatttcat  231840
gcgcgatcga caaatcattg catcacgaca gcaagttttc aagtatggtt ttttctctcc  231900
accgtgatat aagttttgc atcttagctt gaccgtaatc aggaattta taaataaaac  231960
```

```
aattgtttga cgtctagatt ggttatggct cgactaagcc tttcaatgca actagtattg  232020
gaatcatcat tagatgagga agatgatgat tattttctcg ctgtaacgca tgtggccacg  232080
aatacgaatg aatctgatga tgacaagaaa tatcgtggtt ctattcaagg gcatcgagtc  232140
cttcggcgag acagaatagc aggggcatca taggctatat caaaattatt tttcagagaa  232200
tcctacatac ggacattgct attttcgaca tcggtatgta tatattacac atattttttt  232260 gcatttttt taaaaactag tgtacgcatg cgtcttataa tctttaaatg caggtttcga  232320
atgaggcgta cattgtttga acgcttatgg aaagaggtag aacaacacca tatttttta  232380 tctctctgac attacataat ttttatatt aatttatgta gtatatatat agttagtttg  232440
tgggtcagca tcaccattca ttttgcgtag gtggtattgc tggaccagag ctagccacga  232500
cgtacacaaa atttagatca ttatttgtgc tgtgtgtacc aaagaataga cctggaaaat  232560
tccatttttt ggtaatgatg aattaaattt tacttctgag ggctgaggaa atatggtggc  232620
cacttttttt ttagtaagat tactcttgga ggatcggaat ggaagctttt gttcctttag  232680
ccttttaatt tcggtatgta attaagcttc catagtacca tcgtgtgtga gttgtgttac  232740
tatcagtggc ggacgcagga taaaattata ggtggagcga cattataaaa agctaaatca  232800
ctagaccaga tcacaactca caagataaaa ctagttttgt gatgacaatc tagagactaa  232860
gtaataataa taatagaaat gtttcataat aacatgcata ccgaaatttc tctcttaatc  232920
tgcagtgcgg caccaaaatc accaacaaaa atccaatcta cagttagaaa agatgtatat  232980
tagatgaaca tcaatacaag aaaagtacat tgatgtaaat agtacagtga atataccact  233040
aagttgtcaa tcttgtagtt gtgactcgag gcaattgcat tcttctagtt ttaagacgct  233100
ggaatcttct agtaatagtc tcatcatcaa gggatttgaa tatctctttc tccgtatagc  233160
aaaccatcaa atcattcatc caatcatctt caattttgtt acgcaattct ctcttaatga  233220
tgttcattgc caaaaatatt ctctcaacac ttgctgttga cacgggtaat aacaaggcca  233280
actcaattag cttgaaaacc aaagggaaca caagatgctt tttagtttca accatcttca  233340
tagatagaga tgcaatatct tcacaagtac caaaagcagc atgccttcgc acgtggacaa  233400
tgtatgtctc aagttgctct cttaacattg cacattcaat aactgaaaaa tccttatcat  233460
atagagtacc aagtcgaaca agtttctcta tatcaaaacc gcaaaataag ttctttggat  233520
cgaggcaaga aaagcaaaca agcaactcgc tagaaacttc attaaagcga tggcataact  233580
cagtgttgat tttatcaaga acaacaaaga atatctcggt gcggtagtag tgaaggtttg  233640
tgattgtgaa gccatctcgc cttgaacggc ctctaatagg cacttcttca tccatatcta  233700
ccacaggaat acccttttga gcacagaatt cttttcacgct ttgaaagaat gactcccaac  233760
cactatctgt cctcattgta gccattcggg ttttcacaac atcaagcaac tccatagcat  233820
gaacaatgtt ggcattcttc ctttgcaagg tttgagagag ctcatttgtg attgcaagca  233880
ttttcaacat caattttaaa atgaaaacaa atttgaagct ctccattttt tcaatcaacc  233940
ccgctgcctg tgttggtaca cggccatctt catgcacaat ggtaagaaca tgcaatactg  234000
agtcccacat tgtctctaat cgaagcaatg ttaaataatg tgaacccat cttgtgtcac  234060 caggtctagc aaggttagtt tcttgattca cacctctacc agataaaatt tcacccctttt  234120 ctagttttc taaaatattc tggtggtgtt tttcttttag agcatccctt ctcttgcaag  234180
atgagcttgt ggtggtgaca attaagtgga tgtactcaaa gaagtcatga actgattggc  234240
aacaagcact actagcaata gaaaccacca caagttgaag ttgatgtgca aaacaatgaa  234300
```

```
cataataggc atgtggatta atatcaaata tctttctttg taagccatta aattcacctc   234360
gcatattcga tgctccatca tatccttgcc ccctgatctt ggatatagat aatccatggt   234420
gatcaagaag gccaaaaata gcttccttca aggcttctga tgtagtatcc ttgacatgct   234480
tgagcgcaag aaaccgttcc atcacatggc cttgattatt cacatatcta tcttacaaaa   234540
aattagttag ctaggcaaca cgacatgaaa ataaaatatg aaactacaat atgcaaataa   234600
aatatgaaag tactattacc ttaatatcac cgccatttgt tctttaacag aaacatcacg   234660
tgattcatca ataagaatag agaagtttct atctcctatt tctcctagga tgttctctgt   234720
gatctgttga gcgcaacact ttgcaagatc tttttgaata tgtggtgata tcataatgca   234780
atttcttgga gcacgctcaa aagcatctct cacttattta attttatctt tcatccaata   234840
aatcaattct agaaaatttc ccttatttag cgaactagat gattcatcat gaccacgaaa   234900
agccaaacct tgcatcaaaa gaaatctgga acaagccaat gaagaagtca aacgaatttt   234960
ataaaggtct tcagcctcac gactggcact agacatgata gttgatatgc tttgtctttg   235020
gttgttaaaa tcatcaaaat gtaacctagc attgttgtgg atactgttaa caccaccaac   235080
atgtgatttc aaccttcaa ctgcatcttt ccaattatta tacccaactt tagtgaaagc   235140
ttcatattta tcacctttca ctgcttgctt aaaaagaaag caataaaagc aatacactgc   235200
atcttttgat tcaatatact ccaaccaatc atacttgtca taccattcct ctttaaaagg   235260
ccttaaactt tgttcatact gtctatgagg gaaatctaaa ccctttggtt ggcatggacc   235320
atttagaaca tatgcccttc tcacttggtt ttggacatct ttatcatatt cataaatttg   235380
cctccttaaa gcgggatctg caactatgtc atccggattg aacgtccctc caacagttgg   235440
tgtgttattc acattattat tagcactagt gccagagcct cttgaaagtg gctggaaaaa   235500
ccttctcatt tgcttcaccc aatgtttctg tgaggtttaa aggcctaaaa aatcatagaa   235560
acaatatcca ataaaacaca tcagttgaca aattattaac ttgaattcta tgggctggag   235620
cattttgccg aacaccttgc gctcaccaat ggacttatgg actgttgccc caaattggct   235680
ctataaatct aaatcaataa actgctatct aaatcactaa actgctttgt tgcaaagctg   235740
ctataggacc aagcgaccaa gcggcgtgcg cagaggtaga tcaagcggcg agcgcaaagg   235800
cagatctagg catggaacag aacggaagga ccaaaggatt taccgctcgg tggctgggtc   235860
ctgggctcct ggcctcgacg gcggggccgc tggtcgaacg gcggaagaag aacgccggc   235920
tgactgggcg cctgggcgaa cggcggagct tgcggctgtt ggcgcctggt gggccgctgc   235980
ggttttggtt tcctggcgaa tggctggatg gcgactcgct cctattccta tatcatatta   236040
tgaagattat aaaatttgag gtggggccat ggcccacctt gccctcactg tggatccgtc   236100
gctggttact atgaatctag ttctattgcg cagacgtttt gagggactca aatttctaag   236160
caacactagt cgattgcctg tacgttgcga cgacttacaa caatatccac gtaaactatc   236220
cacaaaacaa attcaagatt ttttttattga ttgtctcccc tctctgtata atatttttt   236280
gatttggcta actgatgtta ttgtttactt catgcaatat gtcatggtac aacacgacca   236340
atgaagtgag cgattagaag aaagttcaca acgactgact gaacgaacag agattataaa   236400
atgacataat tccatcatac atagaccaaa taagagaaag cttgtgagct caagtttcta   236460
aaataagtca catgaactca aacttataaa aaagatggat caaaatatga agtgattgct   236520
aaagtcaggc atcaataaaa actggatgcg cttcatataa attatgctac tttgtagcaa   236580
ttactgacgt ttaaaaccaa caaataacct ttcattttac tgttagtgtg acaaatcatt   236640
attgctctat ccaattcagc aacctcaaac accatggagt ccattgcgtc aatgtggtct   236700
```

```
cagaaacgac ctaatacttg caagagccaa gaacttcgtg tcgtgcttgg gctgtagcct 236760
cggcccgtag tgctgaccgg cccgacatga ttatattttt tattttacaa aaaaacgtat 236820
atacatatat acaatttata ttcaatattt aaaacatctg agcataatgt tctactggtt 236880
agacagcttc acacagtgtc ccccgccctt cttccatcag ggtatgggtt tgaaccccac 236940
cttctgcact gttttttaac attttacgct gatttaatta aatggatcga cgggctaacg 237000
tgctggatcg gcatagtctg caggccggca tgacgtgtct gggccagagt tgtggcccgt 237060
gggtgtctcg cccgtgccgg gccgctgttt ggccatctat aggcgtgcaa cgattaattt 237120
aaaatacttg tgatgggtta tttgtaaaaa gatgatgcgg gacgactatt aaaactggtg 237180
ttttaagtat agtatagatt atggcaaaac caaatttatg ctgcagggtg gtgggaaagt 237240
tgttcattgt aacaatgttg gggataaagg gttgtagacc tcggtttagg ggggtgataa 237300
tgacaacttg agagtattat gaccaccgta tgttctgcag aaacaaggta agggagatca 237360
caataatgct agtgattggg cttacgagtt atttatgtcc ttcttgattg agataatcaa 237420
cggtcctttt aaaaaaaatc gaaaaggtta agtttaagct aggtctaagt gtcaatagag 237480
ttgtcggagg cttaaagtag tgataaaacc tttattttca tttagttgta aaataaaaga 237540
tgacatgaga cgagtaactt aatctaggtg tgtttagtta ggtgtaatgg tgcacactag 237600
taaaactagt gccagttaca tccaaaaaag cccacaaaaa gtttaaaaga aacccactg 237660 aaaaaacgat tgaaacaagt gagttgaaga gcatacactt gcatcagatg tatccagtga 237720
ctcaccagat aaaacacaag atggagagtg ccctgtcggt gtgtcttgtg tgcaccaagt 237780
ttggtgcatc aaacaaggca ctcagacaat gcgcaaaagt ggcatcataa aatgcacaaa 237840
atagacaata ccctttttact tatgaacaat tcggttcaaa gatttacgtt cttaaaattc 237900
ccatgccagt atagaattag caattagggt gccaattgag gacgcaacat aatagatgat 237960
actgtttaac attgtttgca aagtgaagtt taaaatagag tataaggctg gtgccaatgg 238020
aggcggcagc gagggtggga ggaagccggt gccgcctgaa cacgggcgag agaggggccc 238080
caggcgacgc agctcgtgcc tagcgagagc gagcggtatc gtctcgctct cgcggtctcg 238140
cccgcgctgt agcgtgcacc cgggcgagag gtgggccaga gcgaggcgct ggtcgggcgg 238200
atgcgcgggc gagagcgagc tggcgcgatt tgattggtcc acatggcgcc atatgtgcta 238260
gccgttgcaa ctagtagttt tttaccgttt ggagtccaaa aaatcaaaga aaattgcaaa 238320
aaaacacaaa tttcatcccc caatccctct ataaataccc ctaccccggt ggagctcatt 238380
ccacacacca tttcatctca tttttctctt caaaactccc ctctcttcac acaatgtcgg 238440
gttggtccta gatttgaaca ccttcacgga tctcttgtag tccgatggat cacctacaac 238500
ccttccgttt gatgagtctt ctccactaca tcgtcgctcc aatgtttcag cctcagaccc 238560
cgtgcattat ttccggctgc gcgtccacca ccacacccctt atccctgtca tttatcatat 238620
ggtcaacctc tagcttccca agccataatt taagcttcat tcccagtacg tccgtatgcc 238680
cctccccacc tgctacggat ggaagtcaag aggtacctcc gtacgcccct cctccatatg 238740
ctccaccttc gtatggagta cctccttatg ctctatatgc tccaccttcg tatgtgatag 238800
ggcaaaggcg gttgcgcgaa agacaaaaat gaaggggaaa gggaaggaag gcacgagcag 238860
cagatcaaca agtgaagcat tcaaaatgaa gagcttgtgg ggtggattag tgaaggacaa 238920
tctgttgaag caatggaaca tcctaaaggg tcgatcaacc agggatatgg acccggctga 238980
aagacgtacc catgctaggg tcgtaaagat ggtccaaaaa gaacttggtc tgatagatga 239040
```

```
cgaaaagagg aaccggaact ggaacgtgaa gaggaggaag atgaggtcga ggagtctaat 239100
tagagtcatg taattttatt ttaattatta tgcactttgt agtttttaat gcaataaaaa 239160
tattatgttt tgtggtttcc gagtgttgaa ataaatccac atgaattact taattctgaa 239220
atagaaaaga tgatatggct atatgatgag gttgtactct actgtagttt gtgtgcacta 239280
gagtggtagg ggcgagagtg gagtcgatat agctgatgtg gcagggacga gagggaagct 239340
atacatcaga accagtagga gattggataa gacctccttt gtaacatagg aattttatag 239400
aaatcataaa gaaattttat aggaatcagc ttattttcac atgaaacagg aaattttcgc 239460
ttatttcaaa gaaggcctga gagctgctgg atacagcctt acagtcgact atatatacgt 239520
ggatgttctg cagttctggc gtgtacgact ttagattcgt tagatccgag tcataggacg 239580
gtcaaagtgg caaccagatc gattacgata acagctggcc ggcacaatct gttgaagct 239640 ggaacactcc aatcaattta ttcccacttt atttatttat ttgtaataca cggcagtaca 239700
agttgttaca gttaagtata catgcagcag cacactagct agcaagagtg aaattgaagc 239760
tgctgcagga aagcccgatt gcgttgagga aagtggtgaa tccgagctgc ttcttgtcca 239820
cgtcgagcag cagcaggtgg ttctccagct ggaacccacc gatgacggcc gccggcgctt 239880
gcccaggcgc ctggacgaag ccgaggcagg ccgtgttggc gttcacctgc accatggagt 239940
tgccgccgag caccgtgaag ttctgcccgc cctccagcat cacgtcgatc tgcggcacgg 240000
cgtagccgag cagactctgc gggagcttgg tggagtcgta gcaccggtcg aacgcgcca 240060 ccgcggcgac cctggacatc caggggaagt tgggcccggc cgccgccgcg tcgaacgcct 240120
tgacgaacgg agcgtacacg tcgggccgga gcgccgtgta cggaccgtg gagctcagcg 240180 ccacgacgag cgccccgcgg gggccgccca cgcgggcctg ctccacggcg atgccggtgg 240240
aggagacgta gtacccgggg gcaccggctc cggctccggc gtggagcggc gccgtgccgg 240300
ccagcatcgt ggtgaagtcg ccgcggtccg gcgggacgaa gaacagcggg ccgccgccga 240360
agatggccac gccgacgctg tcgcccgacg tggacctgcc gtcgctgggc aggcacagcg 240420
cgaccttgtc ggcgaccttc tgcgtgcgcg ccacctgcgc cgggagcgac tgctggctgc 240480
tggaggaggg cgcgagcccc gcgacgccga cggcgccggc gccggcgggc agcttggacg 240540
acggcgcgca cgtggccacc gccgagaagg agaccgggaa cagcgggttc tggccgtcgg 240600
tggcgttggc ggatagcgtg gcggtgagcg tgccgttgtt gttcttggag gagctggcgc 240660
acgtggccag cgagatgacc gggctagtga ggtcgaggac gagcgggtgg ccgtccttga 240720
gcggcgccgt gtagagggag gtggacgcgt ccttggtgac ggcggtgacc aggggcttgc 240780
cgcccagctg accggctgcc gtgcatggcc atggcgacga cgacaacgcc gagatgcaga 240840
gtagtgaggt gaccagggct tgttgaggt tccacattcg tgatggcatt gtgtgttgtt 240900
gttgctggtt ttgctagtag tatatatata gatggatagg gcattgcatt gcatgtggac 240960
ttgtcgatag acaaacggtc tctagtagga agttgcttga gatttgttga gtgccacgac 241020
tcattttcaa gtcaaacatg gcaactcctc cacgtgctta ttagcatgtt cgttttcttt 241080
atctgaattt tgatcaattc gaatatatcy aycatatmca tagaatacta gtacatactt 241140
attcttcatt aattacccca agtcgggagg ccctatcatc gttgaaatst ctwatgccaa 241200
caatatgttt gtttggcatt attattaaak tatamgakat amswsrtawt wmktwtywwc 241260
gawcgataat cctaagccat ctatagttcg gcggccagtg caccgacggt gcgtatagat 241320
aagatggtga cacaccccaa ttattccacg atgcatgcat gcatgcatgg gtggtgttac 241380
gatggcacag attatttatt gtgatckrrk rackgatrrc ttctaaaatc ggactgggat 241440
```

```
ctactagcaa aactgggctt ctaaaatcta gmcacggcac cctcgcgtgt acatggacct 241500
catctcgtgt cctcgaacgt ctcgcacacg actacgccaa cgctgggcag gatcgagcac 241560
ctggctcgcg tgcctcgcgc atggctgcgt cgcccgtcgc catgcaggcc attttctccc 241620
taaatctttt tgatttgagg atttctctcc ggcgtccat tgcagacgtg cttctcctct 241680
gtgtacgcgc acgagcaagc gcgcagcacg caaggcttct atgcttggcg tccgctcaac 241740
ggctaaggct tctactgcat atatggccgc gggcacttgg acgtcacacc agtggccatg 241800
gatggaacac attactcaga aggtgactcg gtttcctaat taaaagtgtt atttgtgtct 241860
ttgataggaa aatatattct cagaaaaatg aagtgtaacc caaaaagaca tcatctaaag 241920
tttttggtcc aattttgttt tttaattaat ggtatggtga cgtttgccaa ataaccacat 241980
gtacgcaaat atgaaataga ttgttctatc ccttctaacc ttcatataga gttatctcat 242040
tgttctttgt gggaattctt tttaatacat gattcattgt tggagtgaca tccccaccat 242100
gccttagcta gataaatatg tagggcctgt ttggtgtggc accgaagctg ccacaccctg 242160
cctaagcagc ggcgctcgat ttggctgcca caacgacgac gacaaatttg tggcgcgttg 242220
tggcgtgggc ggcggccaac caaacaggcc cgtagtatcc aacatagcat taatcaggcc 242280
agtaatattg tggttctttc ttttggcgac cctgattgat tagggcaagt agagagaagt 242340
tccctcatgt atgactccat ttttagtgca aaattgagag caatcattta ataaatactc 242400
tccaccttga tctaacgatg aacttttgat tcttttatcc aattgattct caaccttagt 242460
cttacattag gtgaaaaaga gctatgttga tttggatgca ccatcctttg cctgagcctt 242520
ttcttcctcg tcaagagatg ctaatagatt cttagtagat atgttttcct cctacgtttc 242580
agagacaggc aaaatccttc taattttgag ataatttggc aatgacgccc cctgccacaa 242640
atgcatgagg taacatatgt ccaagttgtt ggagctcgtc aacaatgagt tatatctcat 242700
gagattgctc aaccatagag cagttgtcaa tcatcttgta gccatgataa tgacaatatt 242760
cactgcatgt tgcattatag tttgctgcag caactcgaac acatcttttt cagtcatgtc 242820
gatgtccgag ctagacaaag acatcgcaac aacgctttgc tcgaatttaa caagagtgag 242880
atgaatatga tgagtcagaa gagaaatttc aagtgtgagt tttgtgagtt agctcaaacc 242940
accccctcta tttatagttt ggatttagag ggttcaactt tgggtggggg cagcagggtt 243000
cgaattcaaa taggaaaaat agcgccaaca aatcagatca cgccatatca gctacaacca 243060
gacgatatcg accattgtca gtcgataaca acctcgaccc gactggtcga tatcgaccgg 243120
cctagcccca ttgtggcccc catattgact agcccgatta tatggtgcac taattaattg 243180
ataggatttg cttcttggtg aagacaaaa atcgtcata gttccgtatt tcaatagcca 243240
ccataaacac acgacaaaaa ataagctttt catgcacctt cttaggcctt gttcggttac 243300
aaaggaataa atcccaccat gaatttaatc cgggtctaga ttgggtgaat ccatatgtca 243360
caatcaatcc tatggtggga ttaaatccat catttaatcc atgtatctct caaagctagc 243420
tattcttttg attcatggat tctaatataa acttgtacaa tatcttcatg gatttgttcc 243480
atacctaatg agctatagat agaatccatg tcttccatag tttaaaaaat tctcaaatca 243540
ttgtgttata atccatgatg gaccgaataa aaaaattgag taggcttaga ttattttgga 243600
gcgtgaattg tggcataaat ttaatttcaa ttcatgctaa tccagagctg gattggtgta 243660
aacgaacaat gacttgttga gaatgtaagg agctcaatgg ctgagaatac cattgttagc 243720
gtccacttca aacacagcat gcacatacat gtgtacatgt aagaaaagtt aaagagttat 243780
```

```
tcgtttacag aaggaaaatc gataaacggc ataggtacac aggaatagac aatgtagcta 243840
aatcaatatg ttgcatctcc gagaaacaag ggtaagctaa actattcaaa ctgaggatac 243900
aagggtaagc taaactattc aaactgagga tatgcctcgt aacctttgag ttccgcaaag 243960
aagaatattg ttcccaactc aaataattgt tcgattcgta caataatttt aaaaaaaaaa 244020
tactcaatgg agctcaattc agcaacatag tagcaagcat gctgagtaga ttggcatcaa 244080
ctcatcatac tcatcgtgct cggcggagcc aaaacatgta aaaacttctc caataacaat 244140
gctacattat tttgtatcta gcatctgagc gagaactgaa agaagcctaa ggatataatc 244200
atgtaactga gccacatatt tatgccttat ctcctcaagt tctactcagc gcaaatgatg 244260
ttgaagccaa ttttcttct agaggtgtca agagacggac tacaagtaca caacaatgaa 244320
ctgtggtgtc taacggaatg ctgaaataga agtgacaacc tttctacacc accaccaaaa 244380
ctgagtacat tccaggtatc agaaactgca tgatagaggc acagacaata tcagaaaaat 244440
actaaaagca aatggtttca gtggagcgag agaaaaaatg atgccatctg aaattatata 244500
tgactagttg attacagatc attattgtca ttaacaagat gtaaaacaca gaacaatatt 244560
aaaattaatt tttggggagc aaaatgcatt tttgccttca gggacagtat atctacctca 244620
aacgaaggca gcaagccatc tcatctctgc accatttcca tttgataagt agtatatctt 244680
tttccatttc tcttctgaaa aattctcgcg ccgaatgatc ttttgcctgg tcaagtgttt 244740
tgccgatttt catcaattga gttagcaatt aatatgccag agtcaaacat gcagattat 244800 caaacactat gaacagagag aaatatgcca aatttctggg agaaaaaata cctcatataa 244860
tagtgacata cagtctcagc ttcatctaag gtgtaacgtg gaaagatcaa acgagcatca 244920
gaaggaacat ctggcagctc ctgccgtagt ttgccaactg ctgttgagtg tgaaaaagcc 244980
cccaccatca tatcattgtg cagcattgat ctataagcat tgacctgttt atagtgcaag 245040
tgaaacatta aatgtgtatg tccagggaac tgattactag tgttaaaaaa agcgctcgga 245100
ttaaagccgg ctgtttggac tgctgcagct gcaatcaata gagacaaaaa cattgtgaaa 245160
gtagtagaag ccggtacgga ttaaagccaa acgaacagat gatgctaggc atcgtacatc 245220
ttacacatgt cccaagatct ccaccaagca gtaaaaaagg ctaatacaga ttcatatgtt 245280
tatctttaca aaaatataag tcgctcagaa actgtatatt tacttattag gcaacaaaac 245340
agagtccatg aaatgttaca caacacaaga taattaacgc atagaaaagt gtaaggaacg 245400
taacaatttt tactacatca caaccaaaaa atacatgcaa ataagcagaa tgggtgtgca 245460
aatatttgtt acttcaaag taggtttctg aaggacataa aagaatgtgt tgcttgaaca 245520
aggtgaagta tctcagtgca acaaaccatt gtaagctctt ttgcatggat cgatcgacag 245580
gatcggacag ttacaggttc ctggaagtca ctgaatgtga accagctatt gtactgcaaa 245640
gaaaaaataa tcttttaatg tgtttcacat taatgggaaa ttttacaca taacacatca 245700 aacatggaag tggcagcagc caattaagtt atggtttcaa tgctctgacg tacctgatca 245760
atggcaaata gtacaggcac gtctttaaca agggacagct ccttccttaa gcgaaccata 245820
acaccaactg aagcatgtgt ttgagttatc ccagtttgaa tgagatcata taatgtggac 245880
ccttcaggca tttccattgt gtcaacccct ttcatcattc caacaccagc accttctccc 245940
aggggaatag gctcaaaaat ttggcatggt aactgttgta aacgtgtttc attgtacttc 246000
aaaaaattct gaagcagcaa cagaaacaaa tttagagaaa atggtgaaac caatatata 246060 tgttaccata catcacaagt ttaagatgta ctgcctccaa gtaaaactga tgtagtgcaa 246120
gtgtagagca tgcagcattt tacattttgg cacaatatct tttaaaatat gtacattcga 246180
```

```
ttcaaaaatt cataagtgca taattgtcct aaaattactt taataacttt taataggttc 246240
tacaaatatg ttgcagcaca aattagtggt gagatttgta ttttaaaaga tgtcacagat 246300
tacctgcttc ctagcaatgg atgtgtatgt ttaatagagt atcaatggac ccaagtgtaa 246360
caaaggaaat atatacaaat aaacaagcat aagtttacat tactagttta ctactaactt 246420
attatcaaat atcaatatac aactgggatt agagaaaccc agtttgcata cagtatggag 246480
tatgaactga tgatacaaaa taacacaagt gagatgtatt taaaatatca atctttagca 246540
aatatgtaac cctatcagat attagatttc acgatgacaa tttgaaaaca gaaaaggctc 246600
caccagtacc aaataagatt caatgttaat caatatatgc atgaccatcg tccacctatc 246660
aacacatagt attcttataa tcgttgccac ttgatggtta ctatatcatc acatacatca 246720
agctagcatt atttggagcg tgtaggcaga ttacacaaat aaaacaaaga aaatagatga 246780
tggtgcattc tatctgcatc catatatact gagaaaagaa aagaggaata tggaagatag 246840
tctatttgaa gcaactggaa catacaaaat cacaaagatt agcacctgca agatattggc 246900
agcctgtact ggtgtatcga aaaaatcact gtatgtgttt ctatagaaga atcctccatg 246960
agtccaatcc ttcccttgtg gaacataaaa taccagccat ccttcagtac gcgcccaatg 247020
gacaagcatc gcaagtgcaa tgcttttacc acaactccgt gggccatcca agacaatttg 247080
ttttctggta tctgtataca aacaagcagg aaaaatgctt gagatcttga gatacagtgt 247140
tgaggcagat atatgtgtac atatgcaatc acattgtatt gaatatgttt tgcaatggca 247200
atgtgttcag agaaaaacaa gttaaaaata tggattctca taaatatggc ttaattgtag 247260
tgcaaactat gaaactaaac agcttaactc tagcaacaca tgaaatataa tgaggcacat 247320
tatacacttc taaatgtgta attatttgca tggttatata ttaatggtac tgtggttctt 247380
tctgcaacaa cagcatcaat ttggaacttg tttcagaaag ttgagacaag gaaagaaga 247440 gttacgtttt tttactatta atcttgccag gcgaaaaatc atgttccttc catcccataa 247500
tataaggtgg acacacaatt aaaaatttga actccttaaa tctttcacca acaattagta 247560
taacacatta tgaaaacttt ggatacaaat ttacaaatac tttctgataa tcaaactttt 247620
gttgccatga atgatatttc ccccattcca aattataaga cgttttggct tctctagaca 247680
cattgcttta gacatagtgt acatctaagt gcatagcaac agctatgtat ctaaaaaagc 247740
caaaatgtct tataatttgg aatgtaggga ctatattata agagaaatta gcagccgaag 247800
tgtgatatta aagaccctgc caaaccaaac cacctttat atttttggat ggagtggtta 247860
tcaccgtttt tagaattaag aaacctactt actcagtcac cctttctttt cttttgctct 247920
gatagtatgc cttaaagact ccgaaatgaa gtaatgaact aatgctaaat catgggcata 247980
ttaccttaat tttcaacatg aattttgaga agttgacat gtcagcacat cagttcaatc 248040
aaaccacaaa tacgatgtgt gttaagtgga gcagcatttg cttgacagtt gacaccataa 248100
aagattagca tgatggtgat gatgcaatca acagcaaatg tcttcactat aatctgaagg 248160
aatcaaggaa cacaaatcat ccatgctaac atatgactta agcagtgcaa acacaagaac 248220
tgtacacaaa gcatcaattg acagtgcacc atatatcatc tgagactaac acatctcata 248280
gtgttaataa cagcgagcat cccagaatcc attatgcaca ggcaaatcaa cacattacac 248340
acctttgagg tttgttgtaa cagctggatc aacaatccta cggaagttat cccggagatc 248400
taggaagctt ttcctcacca tcacagcaca ccgtcttgtc tcctgaaact ctttcatcat 248460
ccctgctggc agcccttctg gtaacatggc attccattca tccaaactga aaatatgcaa 248520
```

```
caagacagag gaataaaaga aaattcgacg ttccaaaaga atctcccact ggcatccaag    248580
aaattcaaac tgaacaatat tctgtctcct ggttggagct taatgtacga aatgaattct    248640
cttttatatg taacgagagg agatactaca aaatatagta tattgagtgg acttataaca    248700
tggcaaaagt taacatttca ctattagtca tacacattaa gaaaacaaa tacaattaga    248760 catacacgaa atacagtatg tccctaaact cagatgagga aaacatcaaa cggacttgaa    248820
gttagcaaaa agaaaaaaaa cacaaaaact ggacatatcc atagagcgtc tagataaaat    248880
caacccgcct ccatcgttat atctctacta tgctagttag agatgaagcg acacaaagat    248940
aaattatgag cagaaaaaat acaaggaata aaccctactt gattgaaatg gtattataac    249000
caaatcccaa acaatctact agataaaatt ccgataccgt gattgcgacc tacaactgtt    249060
aatgtggcca gagagatcgc tgcaatgccc ttcaacgtcc acgcaaattg ggaaataatc    249120 gagaggggg agggtgccta cgtgaagtcg acatagatgt tcgcgtcacg gtgggcgaag    249180
gacccgaacg tgtcagtgaa agcgaagagc gggcggccgc cggggccgac gtcgagagct    249240
ggatcatatg taggggcag cgggtcggtg ggcagctcga actcggtgtc aatgtcgtcg    249300
cccccacctc cggcggagaa ttcggctccc gcggcatcat cggccgacgc caccccgcgc    249360
gggtccttgg cgcggacctt gccgcggttt gacgtggacg acgccggctt gccccgcccc    249420
ttggccttcg cgtaggatcg ggaggcgagg aaaagggagg cgagagcggc aggcgggtcg    249480
gggagtgcta tggcgcgagc cccgttagag gataccgcgg cggcggcggc ggcgccgcgg    249540
cggaggaaag ggcggaggag catttcggcg gcagggttta daccgtcgga ggggagaagg    249600
gttaggagcc tgattggact cttcctgggt cgtctcgggt cgcgatcgcg agttgactaa    249660
gtgggctttc agttttttaac gggctgggct tgtagggtca cgtaggtttt tctcgacaaa    249720
taaaggtttt ctcgataaat gaatttcggg taactattca gtgactcctt gaccaacaaa    249780
aagaaatact cccacgattt tatttacatg ttgaattagc tttattcaaa tttaaatatt    249840
tggttttttc ataatttaag aaaaattata taaattcatg acaattcata tttttaaaca    249900 tactttata atgtatagtt catattttat tgtttttgtt gtttcttttt aaatagatgg    249960
ttacaaatat aaatatttga tatagggtag agccaatgtg atttacaaaa tagagagtac    250020
accactaaat ataatgtgca ttcaactagg tacactcttg ctcagcatct aggtcacttt    250080
tttctcttaa gtagtattta tttgaaaaaa aaacttggta gaatgagaac tcatttatct    250140
tgtaacagtg ttaccgtaat aacttcatag tagtattacc agatcaagtt caaaatccca    250200
gaacttagat acctcatgtt aaagatatat atcaggata ttcgagaccg aatttgtgaa    250260
caagaccgtg acaggtgggt ttaagggctc gatcatgatg cccaagggct caacccacat    250320
gtcaacaaaa tatcgtacct gcaagaaagt atcaataaga tagagatggt aaatatccta    250380
tcaaattaaa agataagatt gatgcctatg tatacatgtc acctagaaga ttagggcaaa    250440
aatgcatgta gagatagaga taggttaccg atagctcagg atatagtcga ctaggcttgg    250500
tcgctatcat tatccggtga tcggtctata ttgttttcct aacatccttc tatactacta    250560
taaagcaccg tcgttcaatg gtcgtcgtgt gtcacccagt gccggccctg gcggggtcg    250620 agcagtgccc ccgaccaggc cccccaaatt aatgggacct cactttagtt actaaataac    250680
agtatatata tacagccata tagcgtatat tgtgtatata tatatatctg ttagctctac    250740 aaaacttta aagacataat tataagtaaa caacacggca acaacaagca aggagaatta    250800
gacgtaaccc attaatctta atttctatat tctagtagta gtatttctta gtctcaggct    250860
catctgccta ggctctcagt cgcaaacaga caggcggtcg tgccctctcc tctcggtagc    250920
```

```
caacacacga cattgggtac gacaacgctt ttgtctttcc ctacatagcg aacacgaaac  250980
taacatgaca taatcgattg atctcacaac gtattacatc tatttgatca ttgttcgagg  251040
taaccttctt ttgagtcatc tggacacata tataccctat ttttctacga gatgttatgt  251100
tatattttag ttactttgta tttaatatga acaacgtttt caaatataca taaatattta  251160
ttaacaatat atatatgcac tataattatg tgtaataatt aatattatca agggcctcca  251220
ttataagtct tgccccgggc ctctaaaatg tcaggaccgg cactggtgtc accctgctcc  251280
cccgtattta aatgataaaa aactaaaaat atacgcgcat ggggatttaa atcatggttg  251340
ttggctccaa gcctatattt gcacccacct agccaataga acaaacatgt ctatgtgttt  251400
tatactctat actcagcata aatgaaaacg tagcaatata tatgcatcta acttgtagag  251460
ttaaaaggag ggtcaggaca ctctaagagg gaagatcatt tgatcacatt tcatagaaaa  251520
aagacaccaa cgcaaaaaca ggacatagga tgttatctta cattgagtcc aacacatgca  251580
taagagcttc tttggtacac gtgaattagt taaaaaacac agaaaaaaca caggattcag  251640
gaatttatcc tttgttccaa aggatgccta aatctttaag gacatgtttg gttgcctagg  251700
aacggtcgcc taaatatcat atgattctat ttcaaaacct tttttacttg ttcatatgaa  251760
actaagatcg aaaggatgat ttttaggatt atagaagcca gacactcata catacaaatg  251820
agggattgct caaaaagcag acactttttt tctaaatcca tgcacagatt atgtcgcaaa  251880
ccctcgacga gggctgtatg agaaaacttg agagggaggt cttttatgat agtcattagg  251940
atatgttaat aaaatttttt gccgacttta atacgatatt agaatcgtag gtttctatgc  252000
attttcaatg aactcgtaga actcgatatt taattgtaac atcacatata tagtatgaaa  252060
aataaagcta tgatatattt atatgtaatc ttcatgcttt agggtcgaag ttaaaaaaat  252120
tgttaagatt gtattttaat ttgatagaga tttaatagga cattgtcact tgttgtcatc  252180
ataaaataaa atataacctt tatattttac agtgagggta aaatatagca tatttgctag  252240
ttttctgtaa aagcaaacat aggtgttggc ccgttgttac gagaagctat agaagagaag  252300
aagaaaaaaa atggtaccat gtcacgtggt gatgggctga cagtctgtct gcatatgatt  252360
cgtgggccgt tctgggcata tatgctggat gaatactttc cacaagatag ataagcgagg  252420
cctcttcgtt cacctctgtc tcgctttcct ttcccgttca ccccaagccc ccaacctgcg  252480
agctgcgaca agttcgtctc tctcgtggcc acgactggcc gccgccccg cctcgtccc    252540
ctcgcagatt cccaggtctt cgccgctccc ttcgccgcca aagagcaccc actaggcatg  252600
cctacccctt ctcttctctt cctgctgtgc gaaacgagaa cccaaaacct aatttcagct  252660
atttggatat ttgtattcgg atctgatcta ctactagtgt atacatgtct gcgcctaca   252720
agtttcgatt ttttttgcag aagttattgg gtgtacactg tttttagaca tgtcctttac  252780
tggttccgcc cctttcttgg cttaagcgca aaaatcatac tggattttag atttctgtac  252840
tgttttatt ggctaaattc tactgtatgc ttatttgttt tctgcggttc acttgcccct   252900
ttagctacaa tttgcctcaa aattatgttt caggttaaat ccgccagggg gaaatctcca  252960
tcaagtggct cgtgctaatt atgcgatctt catgggctga ctcagttgcg aacgccgagg  253020
aatcggcgcc cgcgactgct gctgctaatg gctctgttgc aactcatagc acctcgcgcc  253080
ctacgcgcag ctcctacgtg cctccacatc ttcgtggccg ctcagctggt gctgctgttg  253140
aagctcaagc aggcttagta gcaccagcac aaggtggacc actgccattg gctgctgcac  253200
aaccttctgg tcagggtgct gctgttggtg gccctcgctg ggctggcatt gtgaatggtg  253260
```

```
gtggtggtgg tggcagcatt ggtgctcctc gccagggcca tggtggcgga ggcgggggcc    253320
gtgctgcttg gaactcccgt cctggtggtt gggaccgcag agaccgggag ccagatccgt    253380
ttgcgaaagc cgaggctgaa gaaattgatt tcgacggcca ggagaatact ggcatcaatt    253440
ttgatgccta tgaagacatc cctgttgaga ccagtggcca tgatgtgcct gcaccagtca    253500
acacatttgc agagattgat ttgggtgatg cattgaatga caatatccgg aggtgcaagt    253560
atgtgaaacc aacaccagtg cagcgttacg ccatcccaat ctccattgct gggcgggatc    253620
tcatggcctg cgcacagact ggatccggaa aaaccgccgc attctgtttt ccaatcatca    253680
gtgggatctt gaagtcacca aagccacacc agaggtcacg gagtacaagg accgcttgcc    253740
ctctagctct gatcttatca cccactcgtg agctttcagt ccaagtatgt caaaccaata    253800
aacatttatt cagtagtgct ttctttaaat ctttctgatt tttactgttt tctcttctaa    253860
ctattgatgt cttagatcca tgaagaagca aggaagtttg cataccagac tggtgtcaga    253920
gttgtggttg catatggtgg cgcaccaata actaaccagg tacccatttt gttgttgatg    253980
tgtttctatt gtgattcctg gtattttaat tgctgcctat atcttcacct attttatgtt    254040
tggtaattat tgtggttcct tccagtttaa attatcaatg atgttttcc actttggaat     254100 atctactgct gtaaactttg ttttttacat tcgtattcta ctgtaagaat aaagtgaaat    254160
ttatatggca cttagtgtaa aatactgcag ctgtattgta cctcaaggaa gaaaagttg     254220 ccttgactct caaattgcta ttggagagtc aacactggtt gttctggtgt aacaaaatta    254280
gatactgagt actcttttgc tagtctcctt gccacaaagt atatagatat ctggatatga    254340
aagcaaacat gtcttgaatc attaatccaa tcattatttt tatgtataaa atgttgtgg     254400 tgccattgag ttatagaatt ttggtctata gcacttatgc attgtgaaaa tcatcgtatt    254460
ttaatgtatt tcttgaaaca ttgcagctga gggagttaga gagaggtgtg gaaatcctgg    254520
tggcaactcc tggtcgcttg atggatctgt tggagagggc tagagtctca cttcaaatga    254580 taaagtatt agctcttgat gaagctgatc ggatgcttga tatgggtttt gagccacaga    254640
tacgtaaaat tgttgagggc atggacatgc ctcaacgtgg tgagaggcag acaatgttgt    254700
tcagtgcaac attcccaaaa gagatacagg tttgtttctt tcctgttttt gtttcaccct    254760
tcaagtaaat gtcatgtatt ctgttgtgtc tattgttatg gtttcatgca cttgaagcaa    254820
ctaatcgata tgcagtgtct acactgtatg agtgcatgtg tagttgttta tcttgtgatt    254880
tctttcatca acatgattgt gtacttgata cacaaaaaat gtgttaatgg tcagctctaa    254940
tgcgatcaat catggtttaa tcagaaaatt gtcaatttat ggaagatgga ccctatttt     255000 tttctatttc tggcatagtg tgttttttga attggggtct gactaattgt tttagagcta    255060
tggaggctat ttttgcattt gctgagtttc acaactatgt aagggccacc ataaatgtag    255120
gcttttgtcg aaaatatgtg ttccttttca ttttctacat aaatcttttg ttatgaagaa    255180
gctgtaaaga aaatgaacat acattctgtc cttatttacc tctcccatat acttccaaaa    255240
cttctctagt actatcgtgc tttatttgt cttggagaag tgcaacacag ttgattgatg     255300
gtagcggaaa atggtatgat ggccatgcct caaatacgcg gactatagtc tatatgaact    255360
tggttacccc ctgcaggtcg aggtttttt tttcgtatg gactgaatta ctatgtagta     255420
gtgtttgcta aagcattttg tggaatgagg attttttactt actcattaga gactgtttat    255480
ttctgctatt ataggatctt tatcacaagt tgtttgctgt agaatagttt agttttataa    255540
aaattgtatg ctgaatagtt catatattgt tgtgcagagg atggccgcag atttccttgc    255600
tgattacatc tttcttgctg ttgggagagt tggttcaagc accgatttga ttgttcagag    255660
```

```
ggtggagttt gtcctcgatt cagacaaacg aagctacctc atggatcttc tgcatgcaca 255720
aaaggctaat ggcacacatg gaaaggtcct atatttttca ggatttgtta tgttcctaag 255780
tcgaacctga ttgggttgaa agtttctact attttgtatc ttgtcatttc ctaacttgtt 255840
cacagttttc atgacacttt atctttttt ttgttggatg cagcacgctc ttacattggt 255900
ctttgtggag acaaagaggg gggctgatgc cctggaggac tggcttttta gaaatggatt 255960
tcctgcaact agcattcatg gagacaggac acaacaggta gattggaggt ttcatggtta 256020
ctaatagcac aagtgcatgc ttaagataga atagtgtata gtgcaaattg gatttgtttt 256080
aatcatattt ttgtaagata ataatatgag taatcgattg tgcaatttga tttgttatta 256140
atgtaatatc attagaaaag agtacatata tcagaagcaa ttttgttacc tatgtttttt 256200
tgacattatt atgtatctgc taaatgaata aagctcaaaa atcaaaatct gagcatccaa 256260
taagtaaact caaactctca agtttgcatt ttttatgttt cttcagtacg ttaaaaggtg 256320
ccattgatgt gtacatttga aatttaaatt gttatttta ttggacagtg ttattacggt 256380
gttgattaca tctagcaatt ggaatacaaa agaacacatc ttatggccct tttatttcat 256440
ttaccaaaaa aaaacactgt tttctttggt gctcctggat tgagaattaa tcgttccagt 256500
acaattcatg agcagaaaga taatgagttg catatttaga taagaaattc acttttcatc 256560
cacatggaca gctgtatttg ttttaattct atggctatta tgtaatccta atgttcgtga 256620
ttccttgaga tatttggttg accatagcac tgtttgttct ttatacagga aagggagcat 256680
gcccttaggt ccttcaagag cggagcaact cccatccttg tgtgacatac cacatgttgc 256740
ccatgtgatt aattttgacc tccctaatga tatagatgac tatgttcatc ggattggaag 256800
gactggacgt gctgggaaat ctggtcttgc gactgcattc ttcaacgaga gcaacactac 256860
gcttgcaagg ccgttgagtg atctcatgaa agaggccaac caggaggttc ctaagtggct 256920
tgagggatac gctgcccgat cagcctacgg aggtggaggt ggtagaaacc gcagacaagg 256980
tagcagtgcc agatttggtg gccgtgattt ccggcgagat aggggcagtg gtggaggata 257040
tggtggtggt tcctacgagg gaggtggtgg tggtggatat gggggatcat caggatacgg 257100
tggtgcctat ggtggcggtg gcagcggcgg cggcggctat ggtggtggtc agagtacgag 257160
ttcttgggac tgaactgaac tctgattaga agtgaaaaat gggccaacct tttgggcgtg 257220
aaaaatgggt caaccgttat cgattagtcc ctgttggatg gagcgaatgc ttgaaatttg 257280
ttgcttgaca tacgattaat cttgcgttgt gttgtgctaa gggattggct tatgttatta 257340
tctggattgg tggttttct acgcctcatg cttgtgctgt ctcgtttcac aaaatatctt 257400
ttttgcttat gtcatagata taatttcatc taggtctgtc atttatatca acttctgact 257460
ttgaccatta tcgtgtcaaa tcttcttgca catactctgt gtaaggtaat atattttgt 257520 agatagtccc aaacaggttt aaggtagatt agagttaaat tcaatagaag tcataaatca 257580
aagtttatac gtgtgaataa ttataagtct tgagtgaaag ttatggtaga ctagagttga 257640
aaattcaaca aaagttacaa atcgaagttc agacatagat aattatgatg cacagaatta 257700
agaatcaggt acatgaataa ttgtgaataa ttatgttgga atgatctaca tttgtgatga 257760
gaggaaagtg ttcagatgtt tactgtaggg attatatttg tgattgttca gggtatttat 257820 attttaacc ggagaagttg atattattga ggtagctcag cttagttctt acttttctgt 257880
caatctctgt ctaaaaaatg tggggggaca ccgactttgc atttgctacg agtgtgacat 257940
tggcaatttg ttgttgacgt tattcattgg tattcggatc aatattaata tattatatct 258000
```

```
tattctgaga aataatgtga gcacccactt ttggtttgtg gatataaata tggtacaaga 258060
gcttcgtttt tttatatttt gtaattagat taatatagac gtgcacgaat catatataat 258120
tacctctgta agactgtctt cagtcagtcg atatggtaaa atagagaagg taaagttgta 258180
aatgatattg tttaatgctg tttatataga gtgaagttta aaaatagaga atagatatat 258240
tatgggatag aagttctgct aaagatagcc taaatacaca ttgagctcta taaatacaca 258300
aaactatatc tctaaaaata ctttcttaag aaacttacga aacacacact tgttataata 258360
ctggaccgac aatttcgtaa gacaagattg ataaagtcat ataagtgtct tgttgtcgat 258420
ggtttgattt cagggagagt tacatccaaa acgtgtgttg ttattaagga tcatatatat 258480
ggctgtgcaa aacaccactc tcacttttca aattagtatt cgttttaggt attaattttc 258540
atatctatat tcaaattaat aatgataaat gatgaatcta gacacatata aaaacacac 258600
acatcaatta tagtataaaa ttattaaaaa taagtcacaa atgtcaacaa ttactttcat 258660
tatatacata atgcagtcaa tattttttgtt taatgagttg ctaaatggtt gtcaaatgta 258720
gatatgaaat gaggttagat gagaacttta taaatttagg aagttcattt agagaactgt 258780
tgaagaggag ttttttatatt aactacctaa attattgatt taggaagtct tttagagaac 258840
tactctagtt gctcctacta caagcactga gcaacaaggt atcggtagca cgagccgtcg 258900
aatactggat acagtggcgt tctgcttgaa ccagtataaa ttttgtgcat actgagcaca 258960
ccaatcggat ccataacgca cacacataaa tttacttgtc ggagctggtt cgaaacatga 259020
cactcatgaa aggccataga ggtttactaa tatgctctaa ccatatgaaa tacttttggt 259080
aacctagtac cagtaaagaa cttttgcaaa acttattttg cataaaacta ccaatttaag 259140
gcatagttcg ttgttagttg tgaagaagtg taatctctat tctaggtgta tgtttaactt 259200
aatagtcttt attgaaacat aattatatca aatgactgac aggtaggaac acttcatatg 259260
ttccctagaa cttagtggag attgttagat ttaatatgag attgcaccat atttaattta 259320
atttaataaa tcccaaaccc atattaaatt atggtgcatt atagttttga ttatgggtat 259380
aatttttatt acttgttgac tcaacataaa tagacgaaat atgtgtgcac ctattaaaaa 259440
gaagagagag gctaaggaca tgcaacacga gcacatgcgc cgtcgttagg gtgtggcatg 259500
cagggattta aatcccgctc ggaattcggc gaaacccgcc attttctgt tcccgctgtt 259560
tggtggaatc gaaatccgtt ggactttttt cgaaaaatcg atttgaattt caaaaaaaaa 259620
aatcaaaaac tataaaaccg aatttcggtg ttttttaggca gttttgactg aattttggtg 259680
tttatagcct aatttcgccg aaaattcgtt gaaaaacgaa aaaatcattt ttaaatttaa 259740
aattccatct tgagcgggtt tgggtgaatt tcagcgaaaa tcgctccaaa tttcgttttc 259800
ggtgtattac gaggtttaca ttttcgtcgt ggtggcatgg catggcatat atcgtgttat 259860
acgatgagat ggggatgaac tgactagcga ctgccttact tcactgattg agtctttctg 259920
gtatagaggg agcctcctat gacagaacct cccaagttat taggcccacc tacagttgtc 259980
cttgtccatc ggacttcgga caaccctgta gatgcacctg atcacttgat aagttcggta 260040
tctgaattct ttaccttgcc taagagcgtt tcacccgtca tgcagatatt acaacatatc 260100
agaggaacga gtatgcggaa gtagttatag caacttattt tatattaaag tatagaaaga 260160
gtagtattat tacagaccag taaaatataa gagtgctgga gtaatattat tacaaccttg 260220
ggaggcacaa ttgaaaggga aatgtgccct tgggccattt ctaagtattt tggtgattaa 260280
gtgaccaaca caagtgctta agtgttaaat tatgccaagt aatggacaaa gtgcaaataa 260340
agagtaaagg tatgtttcta agacttagta cattgttttg aagactaatg tattgtgtct 260400
```

```
aagtgctaga aacaggaaaa gaccaatttg gaaaagattt ggctgaccag ccaagactct 260460
gcgcagtctg ggtgcaccgg acagtgtccg gtgcgccagg ctggctctgg tgaaaaggcc 260520
gctctcggga tttcgtcggc ggcgtacaac taaaattcac cggactgtcc ggtgtgcacc 260580
agactatccg gtgagccaac agtcggacag gccaatggtc ggccgcgtaa ccgcgcgcg 260640 acgcgtggca gagccaacgg ttagaagggg gcaccagact gtccggtgtg caccagacag 260700
tgtccggtgc gccaacggct ctgaatctcc aacggttggc ttcgccaaag aaggaaagaa 260760
atccgcaccg gactgtccgg tgcgccaggc gacagaaggc aagaattgcc tttctggaat 260820
gctctcaacg gctcctagct gccttgtggc tataaaaggg accctaggc gcatggagga 260880 gtacaccaag cattctctaa gcattcctaa gcaccaagac tccaatttcg cgcattcgat 260940
tctttgtgat agcaactaga gctccatttg agtagagaac tctttgggtt gtgttgtgag 261000
ctcgagttgt gacttgtgtg cgtatttgtg ctctgatttt gtgtcttgtg tgtgttgctc 261060
attccatcct tacttccgtg cttctttgtg aacatcaaat tgtaagggcg agagactcca 261120
aattgtggag attcctcgca acgggatat agtaaacaaa gcagaacacc gtggtattca 261180
agtgggtctt tggaccgctt gagagggggtt gattgcaacc ctcgtccgtt gggacgccac 261240
aacgtggagt aggcaagtgt tgaacttggc cgaaccacgg gataaaccac tgtgcctatc 261300
tatgttgatc ttcttgtggt tatcgtgtct tgcaagaact cctctctagc cacttggctt 261360
tattgtgcta actcctaatc aagttttgtg gcattaagtt tcaagttttt acaggatcac 261420
ctattcaccc cccctctagg tgctctcaat tggtatcaga gttgttctct tcacgtaagg 261480
gactaatcac ccgaagagat ggatcctaag ggcaaggga tggtggtcaa tgataaggag 261540
aaggagtcct tcgtcaatga tccaaaagat gacaagccta ctgactcggg ctcgagccac 261600
ataagaaaag acgggaagag gaagaaaaca aggcgcatca aggagatcgt ctactacgac 261660
gacagcgacg agtcctcttc ttcccaaaag gacgacgaca actatgagaa aaagaaaacg 261720
gtcaattcaa actttctctt tgattattct cgtattccgc aaagtacaaa tgctcattta 261780
ctctccattc cacttagtaa acctcctcac tttgatggag aggactacgg attttggagt 261840
cacaaaatgc atagtcactt gttctctctc catccaagca tatgggagat agtagagagt 261900
ggaatgcaat ttgatagtac tgatagtccc atatttatca atgagcaaat tcacaaaaat 261960
gcacaagcta ctactgttct tctagcatca ttgtgcaggg atgaatacca taaggtgagc 262020
ggcttggata acgccaagca gatctgggac accctcaaga tctcacatga ggggaacgac 262080
gtcaccatgc tcaccaagat ggagttggtg gagggcgaac ttgggagatt cgcaatgatc 262140
aggggcgagg agccaaccca aacgtacaac cggctcaaga ccctcgtcaa caaaataagg 262200
agctatggaa gcacacgatg gagggaccac gacgttgtcc gcctaatgct aaggtccttc 262260
actgtccttg atccacatct tgtaaacaat attcgtgaaa atcctaggta taccaagatg 262320
tcgcccgaag aaatacttgg aaagttcgta agcgggcgga tgatgatcaa ggaggcaaga 262380
tacattgatg atgcgttgaa tggtccaatc cacgagcctc aaaccgttgc tctcaaagca 262440
acgaggagca aggaagtgct acctagcaag gtggcacaag ttgaggcggc gaggctcaat 262500
gaggaagaga tgcccctcat catcaagcgt ttcaagacgg cgctaagggg tcgcaaggag 262560
catcccaaca agaacaagat aaagggggaag cgctcatgct tcaaatgtgg taagattggt 262620
cattttatcg ctaattgtcc cgataatggt agtgaccagg aacaagagaa gaagagggaa 262680
aagaagaagg cttacaagaa ggctaaaggc gaggcacacc ttggcaagga gtgggactca 262740
```

```
gattgttcat cgtccgactc cgacaacgaa ggactcgccg cctcggcctt taacaaatcg  262800
tcccttttcc ccaacgagca tcacacttgc atcatggcaa aagagaagaa ggtaaacact  262860
cgaaagacta cttatgcttc ttctagtgat gatgaatcta gcgatgatga aatagattat  262920
tctagtttgt tcaagggctt ataaagaact aagattgata agattaatga attaatcgat  262980
gccttgaatg ataagaatag attgttagaa aagcaagagg atcttttgta tgaagaacat  263040
gataaatttg tagaagcaca aaaatctctt gctttagaag ttaaaagaaa tgaaatgctt  263100
tcttgtgaac tatctacttg ccacgagacc atttctagtt taaaggtgt  taatgatgat  263160 ttaaatgcta aactagaagt agcaaataga tctaactctt gtgtagaaaa tgttgtgatt  263220
tgcaataggt gtaaagattt taatgttgat gtttgtagtg aacacctagt ttctattgca  263280
aagttaaatg atgaagtggc tagtcttaat gctcaactta aatctagcaa aaatgatttg  263340
ataaactaaa atttgcaaga gatgcctaca cggttggtag acaccctca  attaaggatg  263400 ggcttggctt caagagggaa gtcaagaact tgacaagtca taaggctccc atctccgcca  263460
aggagaaagg gaaggcccct atggcaaata gtattcaaaa gaacaatgct ttcctatatc  263520
atgataggag atattctagg aatgttcatc atgatagaag ttgcaatgat gttgtttcac  263580
atgcttatga ttcaaatgca atgttcgctt caagttctat tatgcatgat agaagtttgg  263640
ctaggaaaaa tgtcattcat catgtgccta ggagaaatgc tcatgtacct aggaaaacaa  263700
gtaatgaacc ttctacaatt tatcatgctt gcaatgcttc ctttgcaatt tgtagaaagg  263760
ataagaaggt gattgctagg aaattagggg caaaatgcaa gggagataaa acttgtattt  263820
gggtccctaa gaccattgtt actaaccttg taggacccaa caagagttgg gtacctaaga  263880
cccaagccta aattgccgtg caagtttatg catccggggg atcaagctgg attatcgaca  263940
gcggatgcac aaaccacatg acgggggaga agaagatgtt cacctcctac gtcaagaaca  264000
aagattccca agactcaatc atattcggtg acgggaatca aggcaaggtg aaagggttag  264060
taaagattgc tatttcatcc aagcactcca tttctaatgt attttagtt gagtcgcttg  264120 gatataactt gttgtctgtt agtcaacttt gtaatatggg atataattgc ttattcacaa  264180
atgtagatgt gtccgtcttt agaaggattg atggttcatt agcttttaag ggtgtattag  264240
acgacaaact ctacttagtt gattttgcta agaggaggc  cggtctagat gcatgcttaa  264300
ttgctaagac tagcatgggc tggttgtggc atcgccgttt agcacatgtg gggatgaaga  264360
accttcacaa acttttaaag ggagaacacg tgataggtct aacaaacgta accttcgaaa  264420
aagatagacc ttgtgcagct tgtcaagcag gtaaacaggt gggaagctct catcatacca  264480
aaaatgtgat gaccacatca agacctttgg agctgcttca tatggacctc ttcggacccg  264540
tcgcctatct aagcatagga ggaagtaagt atggtcttgt tatagttgat gatttttccc  264600
gcttcacttg ggtattcttt ttgcaggata aatctgaaac ccaagggacc ctcaagcgct  264660
tcctaaggag agctcaaaat gagtttgagc tcaaggtgaa gaagataagg agcgacaacg  264720
ggtccgagtt caagaacctt caagtggagg agtaccttga ggaggaaggg atcaagcacg  264780
agttctccgc tccctacaca ccacaacaaa acggtgtggt agagaggaag aacaggacac  264840
tcatagacat ggcgaggaca atgcttggag aattcaagac acccgagcgg ttctggtcgg  264900
aagccgtgaa cacggcttgc cacgccataa accgggtgta ccttcatcgc ctcctcaaga  264960
agacttcgta tgagcttctg accggtaaca aacccaatgt ttcatacttt cgtgtatttg  265020
ggagcaaatg ttatattcta gtaaagaaag gtagaaatta aagtttgct cccaaagttg  265080 tagaagggtt tttgttaggt tatgactcaa atacaaaggc atataggagtc ttcaacaaat  265140
```

-continued

```
catcgggttt ggttgaagtc tctagcgacg ttgtatttga tgagactaat ggctctccaa    265200
gagagcaagt tgttgatctt gatgatgtag atgaagaaga cgttccaacg gccgcaatac    265260
gcaccatggt gattggagac gtgcggccac tggaacaaaa ggagcaagat caaccttctt    265320
cctcaacaat ggtgcatacc ccaactctag acgttgaaca agttcatcaa gaggaggcat    265380
gtgatcaagc ggagcacaag atgatcatgt aatggaggaa gaagcacaac cggcacctcc    265440
aactcaagtt cgagcgacga ttcaaaggaa tcatcccgtc gaccaaattt tgggtgatat    265500
tagcaaggga gtaactactc gctctagatt agttaatttt tgtgagcatt actcttttgt    265560
ctcttctatt gagcctttca gggtagaaga ggccttgcta gatccggact ggatgttggc    265620
catgcaggaa gagctcaaca acttcaagag aaatgaagtt tggacactgg tgcctcgtcc    265680
caagcaaaac gttgtgggaa ccaagtgggt gttccgcaac aaacaagaca agcacgaggt    265740
ggtgacaagg aacaaggcac gacttgtggc aaaaggttat gcccaagtcg caggtttgga    265800 cttttgaggag acttttgctc ctgtggctag gctagagtca attcgcatat tgttagccta    265860
tgctgctcac cattctttca ggttgttcca aatggatgtg aagagcgctt tcctcaacgg    265920
accaatcaag gaggaggtgt acgtggagca acccctggct tcgaggatga acgatacccc    265980
gaccacgtgt gtaagctctc taaggcgctc tatggactta agcaagcccc aagagcatgg    266040
tatgaatgcc ttagagactt tttaattgct aatgctttca aggttgggaa agtcgatcca    266100
actttgttca ctaagacttg tgatggtgat cttttttgtgt gccaaatcta tgtcgatgac    266160
ataatatttg gttctactaa ccaaaagtct tgtgaagagt ttagcagggt gatgactcag    266220
aaattcgaga tgtcgatgat gggcgagttg aactacttcc ttgggttcca agtgaagcaa    266280
ctcaaggatg gcaccttcat ctcacaaacg aagtatacac aagatgtgct caagaggttt    266340
gggatgacgg acgccaagcc cgcaaagact ccaatgggaa ccgacagaca catcgacctc    266400
aacaaaggag gtaagtccgt tgatcaaaag gcataccggt ctatgatagg gtctttactt    266460
tatttatgtg ctagtagacc agatattatg cttagtgtat gcatgtgtgc tagatttcaa    266520
tccaatccaa gggagtgtca cttagtggcc gtgaagcaaa ttcttagata tttagtcgct    266580
acgccttgct tcgggatctg gtatccaaag gggtctacct ttgacttgat tggatattca    266640
gactccgatt atgctggatg taaggtcgat aggaaaagta catcagggac gtgccaattc    266700
ttaggaaggt ccctggtgtc ttggagctct aagaaacaaa ctttttgttgc cctatccacc    266760 gctgaggccg agtatgttgc cgcaggacag tgttgcgcgc aactactttg gatgaggcaa    266820
accctcaggg actttggcta caatctgagc aaagtcccac tcctatgtga taatgagagt    266880
gctatccgca tggcggataa tcctgttgaa cacaaccgca taaagcactt agacatctgg    266940
catcactttt tgagagacca ccagcaaaag ggggatatcg aagtgtttta tgttagcacc    267000
gagaaccagc tagccgatat cttttaccaag cctttagatg agaagaacctt ttgcaggctg    267060 tggagtgagc taaatgtctt agattcgcga aacttggatt gatttatagc atacatgtgt    267120
tttatgcctt gatcatattc ctctatgcat attgtgttta ttaatggtgc tcaagttgta    267180
ttcatgatcc ccggacctca caagtccatt tgcaagtgat gcacttattt aggggggaggc    267240 atgctacaac ttgaccccctt gagactaact gtgtgcttga gtttgcttga tttagtctca    267300
aaggtgaatt gaaaggaaaa aggtggactt ggaccatgca agacttccgc tgcactccga    267360
tgagagggta acttattcca agttcatctc catgctctta ttgcctttttt actcttaatt    267420 gaagattttg gtgaggcaat ggggtttaag ggccaagatt gatcccgttt tggtgcttga    267480
```

```
tgccaaaggg ggagaaaata aggccaaagc aacaaatgga tcagctacca cttgagaatt   267540
ttgaaaatag tagaatagag cttttggttt gtcaaaaatc tcttattgtc tcttttgtca   267600
aaagttggcc tcttgtgggg agaatggttg attatgggaa aaaggggag tttttgaaat    267660 ctttgatcaa tttctcttgg aacaactctc tttatgtctc aacaagtatg tttgacttag   267720
agataggaaa ttgaggttga tttacaaaaa caaaaccaag tggtggcaaa gaatgataca   267780
aatatgccaa atttgaatta aagcaaattt gtgttctcat ttgaattgat gttgcacttc   267840
ttttagttgc cttttgttgt gttggcataa atcaccaaaa aggggagatt gaaagggaaa   267900
tgtgcccttg ggccatttct aagtattttg gtgattaagt gaccaacaca agtgcttaag   267960
tgttaaatta tgccaagtaa tggacaaagt gcaaatcaag agtaaaggta tgtttctaag   268020
acttagtaca ttgttttgaa gactaatgta ttgtgtctaa gtgctagaaa caggaaaaga   268080
ccaatttgga aaagacttgg ctgagcagcc aagactctgc gcagtctggg tgcaccggat   268140
agtgtccggt gcgccaggct ggctctggtg aaaaggctgc tctcgggatt tcgtcgacgg   268200
cgtacggcta aaattcaccg gactgtccgg tgtgcaccgg actatccggt gagccaacaa   268260
tcggccaggc caacggtcgg ccgcgtaatc cgcgcgcgac acgtggcaga gccaacggtc   268320 agaaggggc accagactgt ccggtgtgca ccggacagtg tccggtgcgc caacggctct   268380
gaatctccaa cggtcggctt cgccaaagaa ggaaagaaat ctgcaccgga cagtgtccgg   268440
tggtgcaccg gactgtccgg tgcgccaggc gatagaaggc aagaattgcc ttcctggaat   268500
gctctcaacg gctcctagct gccttggggc tataaaaggg accctaggc gcatggagga    268560 gtacaccaag cattctctaa gcattcctaa gcaccaagac tccaatttcg tgcattcgat   268620
tctttgtgat agcaactaga gctccatttg agtagagaac tctttggggt gtgttgtgag   268680
ctcgagttgt gacttgtgtg cgtattggtg ctctgatttt gtgtcttgtg tgcgttgctc   268740
atcccatcct tacttccgtg cttctttgtg aacatcaaat tgtaagggcg agaggctcca   268800
aattgtggag attcctcgca aacgggatat agtaaacaaa gcaaaatact gtggtattca   268860
agtgggtctt tggaccgctt gagagggtt gattgcaacc cttgtccgtt gggacgccac    268920
aacgtggagt aggcaagtgt tgaacttggc cgaaccacgg gataaaccac tgtgcctatc   268980
tgtgttgatc ttcttgtggt tatcgtgcct tgcaagaact cctctctagc cacttggctt   269040
tattgtgcta actcctaatc aagttttgtg gcattaagtt tcaagttttt acaggatcac    269100
ctattcaccc ccctctagg tgctctcaaa aatcccctcc cgattaacag taaaaagttt     269160
ttaaaggagg acacttcctc ccaaggcttt aatcctggtt ttcttcctta ggcaccacct   269220
tggaacaaaa gcaacaaaaa tttgctgctt cctcacctac aacaacatgg gttcgaaaac   269280
cctgagtacg gagtgtactt tcgcaagtct tacccgtcaa aataaaagac tctcaaggat   269340
atgcgtgtta tcttattctg gtattagtct gcccgaggca aagcttaccc atgatgaggc   269400
atgtgaccag ttaaaaggtc ctcgatcagc aagcctacat caacaaggtc cttaatcgac   269460
tcagacggag acactacacc aagactccct tctcgtgcaa gtcacccgcc cggtctcagc   269520
tttatctttt aacccaaagt ttggtacctg acagaggtac atcttttcca atgttgaacc   269580
catcatggcc atgatggatc caccatcaag ttttattttg aaaacatccc atcccatttg   269640
aagcatcatc ttttgtcaaa acaaaacatt ttattttttct atagcaaggc taagcataag   269700
aaaaaccttt ttgtaaaata ggggatcaag gaaaggtaat caaattcaca aggaaggaaa   269760
tgcagcaatt tgtttagcac acaactccta tcacctaatg catcaagcaa gtgagaaaga   269820
ttttaaaata gcaaggaggt ggcaaatgca ccggggcttg ccttgtgtta tagggagtc    269880
```

```
gggctctgct ccacaaatgt caaaatcaaa gcagttcccg gccggtgggt cttcaggtgg    269940
tggtggtgta gctcttgctt cttcaacttc tatttcttcc tcgttttcta tatataacca    270000
tatataatct tgaatgctca tgtaatgctt atgaaaatgt aaagataata aagtatatt     270060 atcttaggtc ttgaatacaa ttttccttca cgggactcta ggaaactaag gttttttggag   270120 tcagaattga agttcctagg gcaggtatca ctagaagact agggttttgg ggtttaatca    270180
tcaaacattg tccaaatcat accaaacttt acccaaggct tctaaataac atttaaagct    270240
tatccaacaa ttttaatgat ttttggagtt attgatcaat ttctaaaatt ccaggagtat    270300
aagttttggc tattttaaat actccataat tccctattta gactaaaaat catactacta    270360
tttttatata atactataga aaattaggaa cctagaaaaa ttgatcttgt atttttagca    270420
tttttctacc attttctat                                                  270439

<210> SEQ ID NO 26
<211> LENGTH: 1119
<212> TYPE: DNA
<213> ORGANISM: Zea mays

<400> SEQUENCE: 26
atgccatcac gaatgtggaa cctcaacaaa gccctggtca cctcactact ctgcatctcg      60
gcgttgtcgt cgtcgccatg gccatgcacg gcagccggtc agctgggcgg caagcccctg     120
gtcaccgccg tcaccaagga cgcgtccacc tccctctaca cggcgccgct caaggacggc     180
cacccgctcg tcctcgacct cactagcccg gtcatctcgc tggccacgtg cgccagctcc     240
tccaagaaca caacggcac gctcaccgcc acgctatccg ccaacgccac cgacggccag     300
aacccgctgt tccgggtctc cttctcggcg gtggccacgt gcgcgccgtc gtcgaggctg     360
cccgccggcg ccgtcggcgt cgcggggctc gcgccctcct ccagcagcca gcagtcgctc     420
ccggcgcagg tggcgcgcac gcagaaggtc gccgacaagg tcgcgctgtg cctgcccagc     480
gacggcaggt ccacgtcggg cgacagcgtc ggcgtggcca tcttcggcgg cggcccgctg     540
ttcttcgtcc ccccggaccg cggcgacttc accacgatgc tggccggcac ggcgccgctc     600
cacgccggag ccggagccgg tgcccccggg tactacgtct cctccaccgg catcgccgtg     660
gagcaggccc gcgtgggcgg ccccgccggg gcgctcgtcg tggcgctgag ctccacggtc     720
ccgtacacgg cgctccggcc cgacgtgtac gctccgttcg tcaaggcgtt cgacgcggcg     780
gcggccgggc ccaacttccc ctggatgtcc agggtcgccg cggtggcgcc gttcgaccgt     840
ctgctcggct acgccgtgcc gcagatcgac gtgatgctgg agggcgggca gaacttcacg     900
gtgctcggcg gcaactccat ggtgcaggtg aacgccaaca cggcttgcct cggcttcgtc     960
caggcgccgg ggcaagcgcc ggcggccgtc atcggtgggt ccagctggaa gaaccacctg    1020
ctgctgctcg acgtggacaa gaagcagctc ggattcacca cttttcctcaa cgcaatcggg   1080 ctttcctgca gcagcttcaa tttcactctt gctagctag                           1119

<210> SEQ ID NO 27
<211> LENGTH: 372
<212> TYPE: PRT
<213> ORGANISM: Zea mays

<400> SEQUENCE: 27

Met Pro Ser Arg Met Trp Asn Leu Asn Lys Ala Leu Val Thr Ser Leu
1               5                   10                  15

Leu Cys Ile Ser Ala Leu Ser Ser Ser Pro Trp Pro Cys Thr Ala Ala
```

```
                  20                  25                  30
Gly Gln Leu Gly Gly Lys Pro Leu Val Thr Ala Val Thr Lys Asp Ala
             35                  40                  45
Ser Thr Ser Leu Tyr Thr Ala Pro Leu Lys Asp Gly His Pro Leu Val
     50                  55                  60
Leu Asp Leu Thr Ser Pro Val Ile Ser Leu Ala Thr Cys Ala Ser Ser
 65                  70                  75                  80
Ser Lys Asn Asn Asn Gly Thr Leu Thr Ala Thr Leu Ser Ala Asn Ala
                 85                  90                  95
Thr Asp Gly Gln Asn Pro Leu Phe Pro Val Ser Phe Ser Ala Val Ala
            100                 105                 110
Thr Cys Ala Pro Ser Ser Arg Leu Pro Ala Gly Ala Val Gly Val Ala
            115                 120                 125
Gly Leu Ala Pro Ser Ser Ser Gln Gln Ser Leu Pro Ala Gln Val
            130                 135                 140
Ala Arg Thr Gln Lys Val Ala Asp Lys Val Ala Leu Cys Leu Pro Ser
145                 150                 155                 160
Asp Gly Arg Ser Thr Ser Gly Asp Ser Val Gly Val Ala Ile Phe Gly
                165                 170                 175
Gly Gly Pro Leu Phe Phe Val Pro Pro Asp Arg Gly Asp Phe Thr Thr
            180                 185                 190
Met Leu Ala Gly Thr Ala Pro Leu His Ala Gly Ala Gly Ala Gly Ala
            195                 200                 205
Pro Gly Tyr Tyr Val Ser Ser Thr Gly Ile Ala Val Glu Gln Ala Arg
            210                 215                 220
Val Gly Gly Pro Ala Gly Ala Leu Val Val Ala Leu Ser Ser Thr Val
225                 230                 235                 240
Pro Tyr Thr Ala Leu Arg Pro Asp Val Tyr Ala Pro Phe Val Lys Ala
                245                 250                 255
Phe Asp Ala Ala Ala Gly Pro Asn Phe Pro Trp Met Ser Arg Val
            260                 265                 270
Ala Ala Val Ala Pro Phe Asp Arg Leu Leu Gly Tyr Ala Val Pro Gln
            275                 280                 285
Ile Asp Val Met Leu Glu Gly Gly Gln Asn Phe Thr Val Leu Gly Gly
            290                 295                 300
Asn Ser Met Val Gln Val Asn Ala Asn Thr Ala Cys Leu Gly Phe Val
305                 310                 315                 320
Gln Ala Pro Gly Gln Ala Pro Ala Ala Val Ile Gly Gly Phe Gln Leu
                325                 330                 335
Glu Asn His Leu Leu Leu Leu Asp Val Asp Lys Lys Gln Leu Gly Phe
            340                 345                 350
Thr Thr Phe Leu Asn Ala Ile Gly Leu Ser Cys Ser Ser Phe Asn Phe
            355                 360                 365
Thr Leu Ala Ser
    370

<210> SEQ ID NO 28
<211> LENGTH: 1155
<212> TYPE: DNA
<213> ORGANISM: Zea mays

<400> SEQUENCE: 28
atgccatcac gaatgtggaa cctcaacaaa gccctggtca cctcactact ctgcatctcg      60
gcgttgtcgt cgtcgccatg gccatgcacg gcagccggtc agctgggcgg caagcccctg     120
```

```
gtcaccgccg tcaccaagga cgcgtccacc tccctctaca cggcgccgct caaggacggc    180
cacccgctcg tcctcgacct cactagcccg gtcatctcgc tggccacgtg cgccagctcc    240
tccaagaaca acaacggcac gctcaccgcc acgctatccg ccaacgccac cgacggccag    300
aacccgctgt tccggtctc cttctcgggc gtggccacgt gcgcgccgtc gtccaagctg    360
cccgccggcg ccggcgccgt cggcgtcgcg gggctcgcgc cctcctccag cagccagcag    420
tcgctcccgg cgcaggtggc cgcacgcag aaggtcgccg acaaggtcgc gctgtgcctg    480
cccagcgacg gcaggtccac gtcgggcgac agcgtcggcg tggccatctt cggcggcggc    540
ccgctgttct tcgtcccgcc ggaccgcggc gacttcacca cgatgctggc cggcacggcg    600
ccgctccacg ccggagccgg agccggtgcc cccgggtact acgtctcctc caccggcatc    660
gccgtggagc aggcccgcgt gggcggcccc cgcggggcgc tcgtcgtggc gctgagctcc    720
acggtcccgt acacggcgct ccggcccgac gtgtacgctc cgttcgtcaa ggcgttcgac    780
gcggcggcgg ccgggcccaa cttcccctgg atgtccaggg tcgccgcggt ggcgccgttc    840
gaccggtgct acgactccac caagctcccg cagagtctgc tcggctacgc cgtgccgcag    900
atcgacgtga tgctggaggg cgggcagaac ttcacggtgc tcggcggcaa ctccatggtg    960
caggtgaacg ccaacacggc ctgcctcggc ttcgtccagg cgcctgggca agcgccggcg   1020
gccgtcatcg gtgggttcca gctggagaac cacctgctgc tgctcgacgt ggacaagaag   1080
cagctcggat tcaccacttt cctcaacgca atcgggcttt cctgcagcag cttcaatttc   1140
actcttgcta gctag                                                   1155
```

<210> SEQ ID NO 29
<211> LENGTH: 384
<212> TYPE: PRT
<213> ORGANISM: Zea mays

<400> SEQUENCE: 29

```
Met Pro Ser Arg Met Trp Asn Leu Asn Lys Ala Leu Val Thr Ser Leu
1               5                   10                  15

Leu Cys Ile Ser Ala Leu Ser Ser Ser Pro Trp Pro Cys Thr Ala Ala
            20                  25                  30

Gly Gln Leu Gly Gly Lys Pro Leu Val Thr Ala Val Thr Lys Asp Ala
        35                  40                  45

Ser Thr Ser Leu Tyr Thr Ala Pro Leu Lys Asp Gly His Pro Leu Val
    50                  55                  60

Leu Asp Leu Thr Ser Pro Val Ile Ser Leu Ala Thr Cys Ala Ser Ser
65                  70                  75                  80

Ser Lys Asn Asn Asn Gly Thr Leu Thr Ala Thr Leu Ser Ala Asn Ala
                85                  90                  95

Thr Asp Gly Gln Asn Pro Leu Phe Pro Val Ser Phe Ser Ala Val Ala
            100                 105                 110

Thr Cys Ala Pro Ser Ser Lys Leu Pro Ala Gly Ala Gly Ala Val Gly
        115                 120                 125

Val Ala Gly Leu Ala Pro Ser Ser Ser Gln Gln Ser Leu Pro Ala
    130                 135                 140

Gln Val Ala Arg Thr Gln Lys Val Ala Asp Lys Val Ala Leu Cys Leu
145                 150                 155                 160

Pro Ser Asp Gly Arg Ser Thr Ser Gly Asp Ser Val Gly Val Ala Ile
                165                 170                 175

Phe Gly Gly Gly Pro Leu Phe Phe Val Pro Pro Asp Arg Gly Asp Phe
```

|   | 180 |   |   |   | 185 |   |   |   | 190 |   |   |
|---|---|---|---|---|---|---|---|---|---|---|---|
| Thr | Thr | Met | Leu | Ala | Gly | Thr | Ala | Pro | Leu | His | Ala | Gly | Ala | Gly | Ala |
|   |   | 195 |   |   |   |   | 200 |   |   |   |   | 205 |   |   |   |

Thr Thr Met Leu Ala Gly Thr Ala Pro Leu His Ala Gly Ala Gly Ala
            195                     200                 205

Gly Ala Pro Gly Tyr Tyr Val Ser Ser Thr Gly Ile Ala Val Glu Gln
    210                 215                 220

Ala Arg Val Gly Gly Pro Arg Gly Ala Leu Val Val Ala Leu Ser Ser
225             230                 235                     240

Thr Val Pro Tyr Thr Ala Leu Arg Pro Asp Val Tyr Ala Pro Phe Val
            245                 250                 255

Lys Ala Phe Asp Ala Ala Ala Gly Pro Asn Phe Pro Trp Met Ser
            260                 265                 270

Arg Val Ala Ala Val Ala Pro Phe Asp Arg Cys Tyr Asp Ser Thr Lys
            275                 280                 285

Leu Pro Gln Ser Leu Leu Gly Tyr Ala Val Pro Gln Ile Asp Val Met
            290                 295                 300

Leu Glu Gly Gly Gln Asn Phe Thr Val Leu Gly Gly Asn Ser Met Val
305                 310                 315                 320

Gln Val Asn Ala Asn Thr Ala Cys Leu Gly Phe Val Gln Ala Pro Gly
                325                 330                 335

Gln Ala Pro Ala Ala Val Ile Gly Gly Phe Gln Leu Glu Asn His Leu
            340                 345                 350

Leu Leu Leu Asp Val Asp Lys Lys Gln Leu Gly Phe Thr Phe Leu
            355                 360                 365

Asn Ala Ile Gly Leu Ser Cys Ser Ser Phe Asn Phe Thr Leu Ala Ser
370                 375                 380

<210> SEQ ID NO 30
<211> LENGTH: 3549
<212> TYPE: DNA
<213> ORGANISM: Zea mays

<400> SEQUENCE: 30

```
aaccgaacaa ggcctaagaa ggtgcatgaa aagcttattt ttgtccgtgt gtttatggtg      60
gctattgaaa tacggaacta tgacgatttt ttgtcttcca ccaagaagca aatcctatca     120
attaattagt gcaccatata atcgggctag tcaatatggg ggccacaatg gggctaggcc     180
ggtcgatatc gaccagtcgg gtcgaggttg ttatcgactg acaatggtcg atatcgtctg     240
gttgtagctg atatggcgtg atctgatttg ttggcgctat ttttcctatt tgaattcgaa     300
ccctgctgcc cccacccaaa gttgaaccct ctaaatccaa actataaata gaggggtgg      360
tttgagctaa ctcacaaaac tcacacttga aatttctctt ctgactcatc atattcatct     420
cactcttgtt aaattcgagc aaagcgttgt tgcgatgtct ttgtctagct cggacatcga     480
catgactgaa aaagatgtgt tcgagttgct gcagcaaact ataatgcaac atgcagtgaa     540
tattgtcatt atcatggcta caagatgatt gacaactgct ctatggttga gcaatctcat     600
gagatataac tcattgttga cgagctccaa caacttggac atatgttacc tcatgcattt     660
gtggcagggg gcgtcattgc caaattatct caaaattaga aggattttgc ctgtctctga     720
aacgtaggag gaaacatat ctactaagaa tctattagca tctcttgacg aggaagaaaa     780
ggctcaggca aaggatggtg catccaaatc aacatagctc ttttcaccct aatgtaagac     840
taaggttgag aatcaattgg ataaaagaat caaaagttca tcgttagatc aaggtggaga     900
gtatttatta aatgattgct ctcaattttg cactaaaaat ggagtcatac atgagggaac     960
ttctctctac ttgcctaat caatcagggt cgccaaaaga aagaaccaca atattactgg    1020
```

```
cctgattaat gctatgttgg atactacggg cctgtttggt tggccgccgc ccacgccaca    1080
acgcgccaca aatttgtcgt cgtcgttgtg gcagccaaat cgagcgccgc tgcttaggca    1140
gggtgtggca gcttcggtgc cacaccaaac aggccctaca tatttatcta gctaaggcat    1200
ggtggggatg tcactccaac aatgaatcat gtattaaaaa gaattcccac aaagaacaat    1260
gagataactc tatatgaagg ttagaaggga tagaacaatc tatttcatat ttgcgtacat    1320
gtggttattt ggcaaacgtc accataccat taattaaaaa acaaaattgg accaaaaact    1380
ttagatgatg tcttttttggg ttacacttca tttttctgag aatatatttt cctatcaaag    1440
acacaaataa cacttttaat taggaaaccg agtcaccttc tgagtaatgt gttccatcca    1500
tggccactgg tgtgacgtcc aagtgcccgc ggccatatat gcagtagaag ccttagccgt    1560
tgagcggacg ccaagcatag aagccttgcg tgctgcgcgc ttgctcgtgc gcgtacacag    1620
aggagaagca cgtctgcaat gggacgccgg agagaaatcc tcaaatcaaa aagatttagg    1680
gagaaaatgg cctgcatggc gacgggcgac gcagccatgc gcgaggcacg cgagccaggt    1740
gctcgatcct gcccagcgtt ggcgtagtcg tgtgcgagac gttcgaggac acgagatgag    1800
gtccatgtac acgcgagggt gccgtgtcta gattttagaa gcccagtttt gctagtagat    1860
cccagtccga ttttagaagc tagtcatccg atcacaataa ataatctgtg ccatcgtaac    1920
accacccatg catgcatgca tgcatcgtgg aataattggg gtgtgtcacc atcttatcta    1980
tacgcaccgt cggtgcactg gccgccgaac tatagatggc taggattatc gatcgttgaa    2040
aattaatacg agttatctcg tatactttaa taataatgcc aaacaaacat attgttggca    2100
taagacattt caacgatgat agggcctccc gacttggggt aattaatgaa gaataatatg    2160
tactattcta tgtatatggt agatatattc gaattgatca aattcagata aagaaaacga    2220
acatgctaat aagcacgtgg aggagttgcc atgtttgact tgaaaatgag tcgtggcact    2280
caacaaatct caagcaactt cctactagag accgtttgtc tatcgacaag tccacatgca    2340
atgcaatgcc ctatccatct atatatatac tactagcaaa accagcaaca acaacacaca    2400
atgccatcac gaatgtggaa cctcaacaaa gccctggtca cctcactact ctgcatctcg    2460
gcgttgtcgt cgtcgccatg gccatgcacg gcagccggtc agctgggcgg caagcccctg    2520
gtcaccgccg tcaccaagga cgcgtccacc tccctctaca cggcgccgct caaggacggc    2580
cacccgctcg tcctcgacct cactagcccg gtcatctcgc tggccacgtg cgccagctcc    2640
tccaagaaca caacggcac gctcaccgcc acgctatccg ccaacgccac cgacggccag    2700
aacccgctgt tccggtctc cttctcggcg gtggccacgt gcgcgccgtc gtcgaggctg    2760
cccgccggcg ccgtcggcgt cgcggggctc gcgccctcct ccagcagcca gcagtcgctc    2820
ccggcgcagg tggcgcgcac gcagaaggtc gccgacaagg tcgcgctgtg cctgcccagc    2880
gacggcaggt ccacgtcggg cgacagcgtc ggcgtggcca tcttcggcgg cggcccgctg    2940
ttcttcgtcc ccccggaccg cggcgacttc accacgatgc tggccggcac ggcgccgctc    3000
cacgccggag ccggagccgg tgcccccggg tactacgtct cctccaccgg catcgccgtg    3060
gagcaggccc gcgtgggcgg ccccgccggg gcgctcgtcg tggcgctgag ctccacggtc    3120
ccgtacacgg cgctccggcc cgacgtgtac gctccgttcg tcaaggcgtt cgacgcggcg    3180
gcggccgggc caacttccc ctggatgtcc agggtcgccg cggtggcgcc gttcgaccgg    3240
tgatacgact ccaccaagct cccgcagagt ctgctcggct acgccgtgcc gcagatcgac    3300
gtgatgctgg agggcgggca gaacttcacg gtgctcggcg gcaactccat ggtgcaggtg    3360
```

```
aacgccaaca cggcttgcct cggcttcgtc caggcgccgg ggcaagcgcc ggcggccgtc    3420
atcggtgggt tccagctgga gaaccacctg ctgctgctcg acgtggacaa gaagcagctc    3480
ggattcacca ctttcctcaa cgcaatcggg ctttcctgca gcagcttcaa tttcactctt    3540
gctagctag                                                            3549
```

<210> SEQ ID NO 31
<211> LENGTH: 2193
<212> TYPE: DNA
<213> ORGANISM: Zea mays

<400> SEQUENCE: 31

```
atgtcatcac tcctgttgcg agtgctgctc atccagcttg cagcagtgga gtgcctctcc      60
gccgcgattc caggctgcct aacgcaatgt ggaggcgtag agatacccta tccattcggc     120
gtcggcacca actgctcccg caaagggttc cggatcaagt gcatcaacgg cagcgcgggc     180
gaggagattc cagtgctgct acctactacg cgctaccaga acatccgggt gctgaacctg     240
tccgtgtcgc cgttgccgga ggctcgagtg cttcttccgg tggcatggca gtgcttcaac     300
gccgccgggg gcgtcactgg gatctactcg ggagatgtgg acttcaaccc agagggcgta     360
taccgcatct ccaacacaca gaacgagctc ttcgtcctcg gctgcgacac ctatgcgttc     420
accaaaggcg tgagggtgca caacgttaac gcacgcttcc cttacagata cttcacgggg     480
tgtatcaccc tcagtgtaga cgagaaggac ccgcgcgacg tgcctgcgc gggcctcggc      540 tgctgccgcg tcgacatccc gccaggcatc acggacacca gcatgacctt ctcgtctacc     600
tggacgcgtg ccaaccagac cttctgcccc tgcgactacg ccttcatcgt ggagaagggc     660
aactacacct tcaaggcatc cgaccttgtg tcgcacacac ccgacaaccg tctgcctttg     720
gactggtgga ccatgccact gcgtctcgac tgggccatcc gcgacaacaa cggcgactcc     780
atgacttcca tctcctgcgc ccaggcaccc aacgaacctg actatggctg ccgcagcaag     840
catagcgagt gcactaattc aaccaatggc cctggctact tctgcaagtg tgcccatggc     900
tacgacggaa accctatgt ccagagtgat ggtgaatgca cgaatatcaa cgagtgccaa      960
gatccaaagt cacataattg ttcaagtggc agcaaatgca ttgacacaga cggaggctat    1020
tattgtcaat gcaatttctt ccgaagaggg cagcaatgtg atcccttaat tcctatggct    1080
gccgttgcac tgttaacaac atttgctgcc gtcgtccttg gatgtgtcgc aattgttttg    1140
cttcagactc taaacaacag gaaaagattc aacagaaatg gaggtaaact actgaatgcc    1200
cagggcataa ccacctacac caaaagggag ctgaagaaga taactaatgg ctacagcaaa    1260
cgccttggag gagggcactt tggcaatgtt tacgagggca ccatcgtcga cggcagaaag    1320
gtcgccgtca atgtcccttt gcggacaagg gtgtcgtcgc accgctgcca ttggaagaat    1380
ttgattcgac ctcgccgtgt accgctaccg caacagaggg tggaggaaga tgggtcgttc    1440
atgaacgaga tcaggttcca gttcgaagtc agtcgtcaca agaacttggt ccagctcctg    1500
ggatgctgcc tagagaccga cattccgatc ctagtcttcg agtttgtcgc caatggaagc    1560
ctggaggaca tacttcatag tgccaagaaa ccatgtaccc tctcgctgcc ggagcggctg    1620
gacatcgcca ttggctccgc ggaagctatc gcctacatgc actcccttga caatcaaaag    1680
cgtgtccatg agagacatca agccttccaa catcctcctt gacgatgacct caatccaaaa    1740 gtctctgact ttggttcctc caagctcctg gcaatccata gctactacgt tagggcagtg    1800
gctgcagata taggctacat ggacccatta tatatgaaga ccgagcactt cacattggag    1860
tgcgatgtct acagcttcgg cgtggtgctt ctggagctca tcacgaggag aagggccagc    1920
```

-continued

```
tggtatgaac aagatcagca agggaacaag atcctcccca tcgagttcgt caagtgcttc    1980
aaggaccacg gtagcggatg tgcgatgtat gatagcagac ttgatttctc aggcgaggat    2040
actcaatctc gatgcaacaa gcgttgcctc gacatgattg gcatgttggc cgtccgatgc    2100
ctcaaggaag acaagaggga gaggccaacc atggcagagg ttgtcgagga gcttaagcga    2160
gtgaaggtac tactgctggg tacacatata taa                                2193
```

<210> SEQ ID NO 32
<211> LENGTH: 730
<212> TYPE: PRT
<213> ORGANISM: Zea mays

<400> SEQUENCE: 32

```
Met Ser Ser Leu Leu Leu Arg Val Leu Leu Ile Gln Leu Ala Ala Val
1               5                   10                  15

Glu Cys Leu Ser Ala Ala Ile Pro Gly Cys Leu Thr Gln Cys Gly Gly
            20                  25                  30

Val Glu Ile Pro Tyr Pro Phe Gly Val Gly Thr Asn Cys Ser Arg Lys
        35                  40                  45

Gly Phe Arg Ile Lys Cys Ile Asn Gly Ser Ala Gly Glu Glu Ile Pro
    50                  55                  60

Val Leu Leu Pro Thr Thr Arg Tyr Gln Asn Ile Arg Val Leu Asn Leu
65                  70                  75                  80

Ser Val Ser Pro Leu Pro Glu Ala Arg Val Leu Leu Pro Val Ala Trp
                85                  90                  95

Gln Cys Phe Asn Ala Ala Gly Gly Val Thr Gly Ile Tyr Ser Gly Asp
            100                 105                 110

Val Asp Phe Asn Pro Glu Gly Val Tyr Arg Ile Ser Asn Thr Gln Asn
        115                 120                 125

Glu Leu Phe Val Leu Gly Cys Asp Thr Tyr Ala Phe Thr Lys Gly Val
    130                 135                 140

Arg Val His Asn Val Asn Ala Arg Phe Pro Tyr Arg Tyr Phe Thr Gly
145                 150                 155                 160

Cys Ile Thr Val Ser Val Asp Glu Lys Asp Pro Arg Asp Gly Ala Cys
                165                 170                 175

Ala Gly Leu Gly Cys Cys Arg Val Asp Ile Pro Pro Gly Ile Thr Asp
            180                 185                 190

Thr Ser Met Thr Phe Ser Ser Thr Trp Thr Arg Ala Asn Gln Thr Phe
        195                 200                 205

Cys Pro Cys Asp Tyr Ala Phe Ile Val Glu Lys Gly Asn Tyr Thr Phe
    210                 215                 220

Lys Ala Ser Asp Leu Val Ser His Thr Pro Asn Arg Leu Pro Leu
225                 230                 235                 240

Asp Trp Trp Thr Met Pro Leu Arg Leu Asp Trp Ala Ile Arg Asp Asn
                245                 250                 255

Asn Gly Asp Ser Met Thr Ser Ile Ser Cys Ala Gln Ala Pro Asn Glu
            260                 265                 270

Pro Asp Tyr Gly Cys Arg Ser Lys His Ser Glu Cys Thr Asn Ser Thr
        275                 280                 285

Asn Gly Pro Gly Tyr Phe Cys Lys Cys Ala His Gly Tyr Asp Gly Asn
    290                 295                 300

Pro Tyr Val Gln Ser Asp Gly Glu Cys Thr Asn Ile Asn Glu Cys Gln
305                 310                 315                 320
```

-continued

Asp Pro Lys Ser His Asn Cys Ser Ser Gly Ser Lys Cys Ile Asp Thr
            325                 330                 335

Asp Gly Gly Tyr Tyr Cys Gln Cys Asn Phe Phe Arg Arg Gly Gln Gln
            340                 345                 350

Cys Asp Pro Leu Ile Pro Met Ala Ala Val Ala Leu Leu Thr Thr Phe
            355                 360                 365

Ala Ala Val Val Leu Gly Cys Val Ala Ile Val Leu Leu Gln Thr Leu
370                 375                 380

Asn Asn Arg Lys Arg Phe Asn Arg Asn Gly Lys Leu Leu Asn Ala
385                 390                 395                 400

Gln Gly Ile Thr Thr Tyr Thr Lys Arg Glu Leu Lys Lys Ile Thr Asn
            405                 410                 415

Gly Tyr Ser Lys Arg Leu Gly Gly His Phe Gly Asn Val Tyr Glu
            420                 425                 430

Gly Thr Ile Val Asp Gly Arg Lys Val Ala Val Lys Cys Pro Leu Arg
            435                 440                 445

Thr Arg Val Ser Ser His Arg Cys His Trp Lys Asn Leu Ile Arg Pro
450                 455                 460

Arg Arg Val Pro Leu Pro Gln Gln Arg Val Glu Glu Asp Gly Ser Phe
465                 470                 475                 480

Met Asn Glu Ile Arg Phe Gln Phe Glu Val Ser Arg His Lys Asn Leu
            485                 490                 495

Val Gln Leu Leu Gly Cys Cys Leu Glu Thr Asp Ile Pro Ile Leu Val
            500                 505                 510

Phe Glu Phe Val Ala Asn Gly Ser Leu Glu Asp Ile Leu His Ser Ala
            515                 520                 525

Lys Lys Pro Cys Thr Leu Ser Leu Pro Glu Arg Leu Asp Ile Ala Ile
            530                 535                 540

Gly Ser Ala Glu Ala Ile Ala Tyr Met His Ser Leu Asp Asn Gln Lys
545                 550                 555                 560

Arg Val His Gly Asp Ile Lys Pro Ser Asn Ile Leu Leu Asp Asp Asp
            565                 570                 575

Leu Asn Pro Lys Val Ser Asp Phe Gly Ser Ser Lys Leu Leu Ala Ile
            580                 585                 590

His Ser Tyr Tyr Val Arg Ala Val Ala Ala Asp Ile Gly Tyr Met Asp
            595                 600                 605

Pro Leu Tyr Met Lys Thr Glu His Phe Thr Leu Glu Cys Asp Val Tyr
            610                 615                 620

Ser Phe Gly Val Val Leu Leu Glu Leu Ile Thr Arg Arg Arg Ala Ser
625                 630                 635                 640

Trp Tyr Glu Gln Asp Gln Gln Gly Asn Lys Ile Leu Pro Ile Glu Phe
            645                 650                 655

Val Lys Cys Phe Lys Asp His Gly Ser Gly Cys Ala Met Tyr Asp Ser
            660                 665                 670

Arg Leu Asp Phe Ser Gly Glu Asp Thr Gln Ser Arg Cys Asn Lys Arg
            675                 680                 685

Cys Leu Asp Met Ile Gly Met Leu Ala Val Arg Cys Leu Lys Glu Asp
            690                 695                 700

Lys Arg Glu Arg Pro Thr Met Ala Glu Val Glu Glu Leu Lys Arg
705                 710                 715                 720

Val Lys Val Leu Leu Leu Gly Thr His Ile
            725                 730

```
<210> SEQ ID NO 33
<211> LENGTH: 6000
<212> TYPE: DNA
<213> ORGANISM: Zea mays

<400> SEQUENCE: 33
atgtcatcac tcctgttgcg agtgctgctc atccagcttg cagcagtgga gtgcctctcc     60
gccgcgattc caggctgcct aacgcaatgt ggaggcgtag agatacccta tccattcggc    120
gtcggcacca actgctcccg caaagggttc cggatcaagt gcatcaacgg cagcgcgggc    180
gaggagattc cagtgctgct acctactacg cgctaccaga acatccgggt gctgaacctg    240
tccgtgtcgc cgttgccgga ggctcgagtg cttcttccgg tggcatggca gtgcttcaac    300
gccgccgggg gcgtcactgg gatctactcg ggagatgtgg acttcaaccc agagggcgta    360
taccgcatct ccaacacaca gaacgagctc ttcgtcctcg gctgcgacac ctatgcgttc    420
accaaaggcg tgagggtgca caacgttaac gcacgcttcc cttacagata cttcacgggg    480
tgtatcaccg tcagtgtaga cgagaaggac ccgcgcgacg tgcctgcgc gggcctcggc    540 tgctgccgcg tcgacatccc gccaggcatc acggacacca gcatgacctt ctcgtctacc    600
tggacgcgtg ccaaccagac cttctgcccc tgcgactacg ccttcatcgt ggagaagggc    660
aactacacct tcaaggcatc cgaccttgtg tcgcacacac ccgacaaccg tctgcctttg    720
gactggtgga ccatgccact gcgtctcgac tgggccatcc gcgacaacaa cggcgactcc    780
atgacttcca tctcctgcgc ccaggcaccc aacgaacctg actatggctg ccgcagcaag    840
catagcgagt gcactaattc aaccaatggc cctggctact tctgcaagtg tgcccatggc    900
tacgacggaa accctatgt ccagagtgat ggtgaatgca cgagtaagta gtataattcc    960
cttcttctca atctataagt ggttttattt ggttattta aatacatcac ttttattatt   1020
aactatatgt atcccgatat atatatatct acctcattgc aattttgccc gtaccttgtt   1080
tgtgatggca aatgtcctaa tcacttctat atgtctttca gatgtaattt ttctatcctt   1140
tcatgctatc gtcagtggca caaaaggata agtacatgtg atttttcttac cctttacgt   1200 cactgacgag agcatgaaaa ggtaagaaat tgcatccgag tgacatagaa gagtttagga   1260
tgtactggac aaaattgcgg tgacatacgt agaattttct ctatatatct agtaatgcat   1320
ctagaaaaac taaattggca taatttggag caggactggt gtatattctc aaggcacggt   1380
gccatactat actcattatt taatatatac catgtaggat agaaagctga tgtgacattt   1440
gagtaaagaa ggaagaaaat aaaacaatat cttgagggag atgccactta gacacgggat   1500
cataggcatt gaaacctaaa acaactaaat gaccacaatt cattctctca tacacaatta   1560
tcgttaaatt gtcttatgtg tggcactatc ggaattcggc tttttgccgg gtgccaaata   1620
ttttgccgag tgttttctt caggcactcg tcaagaagt ttttaccaa gtgccagaca   1680 aaaaagcctc ggtaaataaa acactcggca acaagatct tgccgagtg ttttattttt   1740 tacactcggc aaagacaatt ttaaatcaca ttttaaagca gtaaattaat tcaaataaaa   1800
aaatttcaac tacaaatttg tatcactcat catgatgtac aatttatatt ttgaacattt   1860
cttcatatga caaatataa gtaaatttat ttataaaatc tatatctctc tcgtagttta   1920
taaaactacg agagagatgt attagatttg tgcatattgt tagaaccatc atgtgagatg   1980
aacaaatgac caaaccaccg aaataaactt tgtagatctt gagaagttat agaagtttat   2040
agttgacaac ttttcatt gaagtcatct tgtcaactaa aactacgtct gaattttaaa   2100
aatttaaaat ttgaattttg aaaacgacct cgaaaaaaac caccaacatg aaaattgtag   2160
```

```
gtattgaagg gttatgaaac tttatagttg acaatatttt ggtttgaaat catcttgtca    2220
tgcaaaacta tgattaaatt ttaaaatttg aattttaaa  actacctcga atggaaaaac    2280
caccaaaata aaagttgtag gtcttgaaat gtaataaaac tttgtaattg acaaattttt    2340
tattttaaat catcttacca tttaaaattt cgtgtgaagt tttaaaattt gaaattgaag    2400
ttttgtaaac aatctcgtat gtagaaacta tcaaaataga acttgtagat cttgaaaagt    2460
tatacaactt tatagttgtt cacattttca aatgaattca tttagtgtct caaataatca    2520
aattactctc ggggttgttat agtatatggg aatgaaaacg taatatagac ataattgatg    2580
tagtagtgta gtgcgcgaga gaggttgcaa gttcgaatct cactattcat aaaacatgta    2640 aatttattc  aaaataatag tgaaaaatga taggataatg gggtatggta ttgggtagtg    2700
gttggagagt tgttcatata atttagaaaa tgttttgcta tttttttaggg ttttttttg     2760 cgattcctaa tttaccgagt gttttcgac  acttgacaaa gtctttgttg agtatccgaa    2820
aaaatatact cgacaaaaac cctttaccga taaaatattt gtcaagtgta aaatggcctt    2880
tgccgagccg agtgttttag acactcggca agaacgtga  gtccggtagt gtggactatg    2940
aaacaacgta tggtaatata cacgggataa ctatatagaa tcttcaataa taacatatga    3000
gacgacaact ttgaatactt tgacaagaaa tagtggtttg gaaatgggct aagccatcca    3060
gtccgtgaga gggcacaagt tgtcggacta gtgtcgttga taataacgga gatagttggt    3120
ctgatgtcac tgtccagaaa tccatatgat catggaatta ttatcaacga caaatttgta    3180
tggccacaca tcacatccat acagattcct ttgtctactt cctattcgtt gacaagaaat    3240
tgtgatagca ctcgcattat tgttatgtcc cgtttagatc attggaattg aattccattc    3300
taataacagt aattaggtat atactaatta actaattcga ttttatgtaa aatatatttg    3360
tatactgtta ttaacaaggt atcggagata tttatgtgct acattttac  tatcgagaag    3420 tgagttgaaa atcgtcttgt aagttagaga gtcgaaacaa attatattga ttcataaaat    3480
catttccaat cttccatctc atgaatttga gatagactta tatctgaacc ttaaaaagtg    3540
gtagaatgtt aaattccaag gtaaatgggt tactttattg actgaattct agttccacta    3600
aaatgaaggt atatatccaa acgcacaaaa gcgacaaagt agcaatgact tcaacctttt    3660
aaaaaagggt gcctttaaaa aaaacaaaag agcaggaatc tgtttattaa gattaatttt    3720
ccgaaccgtg tgttggattc ttttgagttc tcacatctca aaagatcgct ccttgctttc    3780
ataaattatt ggcaaacgac tgactctctt ttgtgactat ttgaatgctc acaaaattaa    3840
taattaatta tatacagata tcaacgagtg ccaagatcca aagtcacata attgttcaag    3900
tggcagcaaa tgcattgaca cagacggagg ctattattgt caatgcaatt tcttccgaag    3960
agggcagcaa tgtgatccct taattcctat ggctgccgtt gcactgttaa gtaagcacaa    4020
aattctatta acaccttgtt acattacatc attctcttta atttgcactt agcttgttga    4080
tccttaatta tcatgttctg tttcgtccta aaagtgacta aaacgacaaa acttttgcac    4140
cattttagtc attttttagct ctttgtactt ggacctttag ctaccgggat aaagtggcca    4200
agggagaaaa atgtaaggct atgagtcgcc ttgagttgtg atttgcgaca acacgggcgt    4260
gagcctatct agcgacttag cgaggtttct ccatgaattt tttggtgatg ttagcctggt    4320
ttataattta aaaaaatcat ttatagtggt agttttatta ataaaactgc tattattgta    4380
aacctagtgt ctgagaatgt aaatatttat agtggcggtt tttaaccaat gtctggcctt    4440
gcacacgtac gggcggttaa agaaaccatc aataagggc  agtttgagaa ctccattttc    4500
tcatggaatt tctattttc  cattgtaaaa tgaactaatt tttcttggaa aaatgaaaat    4560
```

```
ccattgggaa aattaggttt ccaaactagc cctaaagatc agttttctac cgtaggtaaa    4620
agtcttttgt gtagtgttct gataatttct taaacattca attacacaaa tagaagaact    4680
aagagcgttg cctaggcctt aaaaaattct aaaaatgaat aaaagaaaca agaagcatta    4740
tgattttgag ttagcaaaaa aaaagatagc agcaaccgac tagatcaaaa tttgaaaaac    4800
tcaaatatag attcacgggg atagatatgc aataagattc atgctatgtt ctgttagttg    4860
aatggttgaa catgcatgta tctttcttga attctgtctg cagcaacatt tgctgccgtc    4920
gtccttggat gtgtcgcaat tgttttgctt cagactctaa acaacaggaa aagattcaac    4980
agaaatggag gtaaactact gaatgcccag ggcataacca cctacaccaa aagggagctg    5040
aagaagataa ctaatggcta cagcaaacgc cttggaggag ggcactttgg caatgtttac    5100
gagggcacca tcgtcgacgg cagaaaggtc gccgtcaaat gtcctttgcg gacaagggtg    5160
tcgtcgcacc gctgccattg gaagaatttg attcgacctc gccgtgtacc gctaccgcaa    5220
cagagggtgg aggaagatgg gtcgttcatg aacgagatca ggttccagtt cgaagtcagt    5280
cgtcacaaga acttggtcca gctcctggga tgctgcctag agaccgacat tccgatccta    5340
gtcttcgagt ttgtcgccaa tggaagcctg gaggacatac ttcatagtgc caagaaacca    5400
tgtaccctct cgctgccgga gcggctggac atcgccattg gctccgcgga agctatcgcc    5460
tacatgcact cccttgacaa tcaaaagcgt gtccatggag acatcaagcc ttccaacatc    5520
ctccttgacg atgacctcaa tccaaaagtc tctgactttg gttcctccaa gctcctggca    5580
atccatagct actacgttag ggcagtggct gcagatatag gctacatgga cccattatat    5640
atgaagaccg agcacttcac attggagtgc gatgtctaca gcttcggcgt ggtgcttctg    5700
gagctcatca cgaggagaag ggccagctgg tatgaacaag atcagcaagg gaacaagatc    5760
ctccccatcg agttcgtcaa gtgcttcaag gaccacggta gcggatgtgc gatgtatgat    5820
agcagacttg atttctcagg cgaggatact caatctcgat gcaacaagcg ttgcctcgac    5880
atgattggca tgttggccgt ccgatgcctc aaggaagaca agagggagag gccaaccatg    5940
gcagaggttg tcgaggagct taagcgagtg aaggtactac tgctgggtac acatatataa    6000
```

<210> SEQ ID NO 34
<211> LENGTH: 2220
<212> TYPE: DNA
<213> ORGANISM: Zea mays

<400> SEQUENCE: 34

```
atgagaaggt ttttccagcc actttcaaga ggctctggca ctagtgctaa taataatgtg      60
aataacacac caactgttgg agggacgttc aatccggatg acatagttgc agatcccgct     120
ttaaggaggc aaatttatga atatgataaa gatgtccaaa accaagtgag aagggcatat     180
gttctaaatg gtccatgcca accaaagggt ttagatttcc ctcatagaca gtatgaacaa     240
agtttaaggc cttttaaaga ggaatggtat gacaagtatg attggttgga gtatattgaa     300
tcaaaagatg cagtgtattg cttttattgc tttcttttta agcaagcagt gaaaggtgat     360
aaatatgaag ctttcactaa agttgggtat aataattgga agatgcagt tgaaaggttg     420 aaatcacatg ttggtggtgt taacagtatc cacaacaatg ctaggttaca ttttgatgat     480
tttaacaacc aaagacaaag catatcaact atcatgtcta gtgccagtcg tgaggctgaa     540
gacctttata aaattcgttt gacttcttca ttggcttgtt ccagattttct tttgatgcaa     600 gatcttgcaa agtgttgcgc tcaacagatc acagagaaca tcctaggaga aataggagat     660
```

```
agaaacttct ctattcttat tgatgaatca cgtgatgttt ctgttaaaga acaaatggcg    720
gtgatattaa gatatgtgaa taatcaaggc catgtgatgg aacggtttct tgcgctcaag    780
catgtcaagg atactacatc agaagccttg aaggaagcta ttttggcct tcttgatcac     840
catggattat ctatatccaa gatcagggg caaggatatg atggagcatc gaatatgcga     900
ggtgaattta atggcttaca agaaagata tttgatatta atccacatgc ctattatgtt     960
cattgttttg cacatcaact tcaacttgtg gtggtttcta ttgctagtag tgcttgttgc    1020
caatcagttc atgacttctt tgagtacatc cacttaattg tcaccaccac aagctcatct    1080
tgcaagagaa gggatgctct aaagaaaaaa caccaccaga atattttaga aaaactagaa    1140
agggtgaaa ttttatctgg tagaggtgtg aatcaagaaa ctaaccttgc tagacctggt     1200
gacacaagat ggggttcaca ttatttaaca ttgcttcgat tagagacaat gtgggactca    1260
gtattgcatg ttcttaccat tgtgcatgaa gatggccgtg taccaacaca ggcagcgggg    1320
ttgattgaaa aaatggagag cttcaaattt gttttcattt taaaattgat gttgaaaatg    1380
cttgcaatca caaatgagct ctctcaaacc ttgcaaagga agaatgccaa cattgttcat    1440
gctatggagt tgcttgatgt tgtgaaaacc cgaatggcta caatgaggac agatagtggt    1500
tgggagtcat tctttcaaag cgtgaaagaa ttctgtgctc aaaagggtat tcctgtggta    1560
gatatggatg aagaagtgcc tattagaggc cgttcaaggc gagatggctt cacaatcaca    1620
aaccttcact actaccgcac cgagatattc tttgttgttc ttgataaaat caacactgag    1680
ttatgccatc gctttaatga agtttctagc gagttgcttg tttgcttttc ttgcctcgat    1740
ccaaagaact tattttgcgg ttttgatata gagaaacttg ttcgacttgg tactctatat    1800
gataaggatt tttcagttat tgaatgtgca atgttaagag agcaacttga gacatacatt    1860
gtccacgtgc gaaggcatgc tgcttttggt acttgtgaag atattgcatc tctatctatg    1920
aagatggttg aaactaaaaa gcatcttgtg ttcccttgg ttttcaagct aattgagttg      1980
gccttgttat tacccgtctc aacagcaagt gttgagagaa tattttggc aatgaacatc     2040
attaagagag aattgcgtaa caaaattgaa gatgattgga tgaatgattt gatggtttgc    2100
tatacggaga aagagatatt caaatcccctt gatgatgaga ctattactag aagattccag    2160
cgtcttaaaa ctagaagaat gcaattgcct cgagtcacaa ctacaagatt gacaacttag    2220
```

<210> SEQ ID NO 35  
<211> LENGTH: 739  
<212> TYPE: PRT  
<213> ORGANISM: Zea mays

<400> SEQUENCE: 35

```
Met Arg Arg Phe Phe Gln Pro Leu Ser Arg Gly Ser Gly Thr Ser Ala
1               5                  10                 15

Asn Asn Asn Val Asn Asn Thr Pro Thr Val Gly Gly Thr Phe Asn Pro
            20                 25                  30

Asp Asp Ile Val Ala Asp Pro Ala Leu Arg Arg Gln Ile Tyr Glu Tyr
        35                 40                  45

Asp Lys Asp Val Gln Asn Gln Val Arg Arg Ala Tyr Val Leu Asn Gly
    50                  55                  60

Pro Cys Gln Pro Lys Gly Leu Asp Phe Pro His Arg Gln Tyr Glu Gln
65                  70                  75                  80

Ser Leu Arg Pro Phe Lys Glu Glu Trp Tyr Asp Lys Tyr Asp Trp Leu
                85                  90                  95

Glu Tyr Ile Glu Ser Lys Asp Ala Val Tyr Cys Phe Tyr Cys Phe Leu
```

-continued

```
                100             105             110
Phe Lys Gln Ala Val Lys Gly Asp Lys Tyr Glu Ala Phe Thr Lys Val
            115                 120                 125
Gly Tyr Asn Asn Trp Lys Asp Ala Val Glu Arg Leu Lys Ser His Val
        130                 135                 140
Gly Gly Val Asn Ser Ile His Asn Asn Ala Arg Leu His Phe Asp Asp
145                 150                 155                 160
Phe Asn Asn Gln Arg Gln Ser Ile Ser Thr Ile Met Ser Ser Ala Ser
                165                 170                 175
Arg Glu Ala Glu Asp Leu Tyr Lys Ile Arg Leu Thr Ser Ser Leu Ala
            180                 185                 190
Cys Ser Arg Phe Leu Leu Met Gln Asp Leu Ala Lys Cys Cys Ala Gln
        195                 200                 205
Gln Ile Thr Glu Asn Ile Leu Gly Glu Ile Gly Asp Arg Asn Phe Ser
    210                 215                 220
Ile Leu Ile Asp Glu Ser Arg Asp Val Ser Val Lys Glu Gln Met Ala
225                 230                 235                 240
Val Ile Leu Arg Tyr Val Asn Asn Gln Gly His Val Met Glu Arg Phe
                245                 250                 255
Leu Ala Leu Lys His Val Lys Asp Thr Thr Ser Glu Ala Leu Lys Glu
            260                 265                 270
Ala Ile Phe Gly Leu Leu Asp His His Gly Leu Ser Ile Ser Lys Ile
        275                 280                 285
Arg Gly Gln Gly Tyr Asp Gly Ala Ser Asn Met Arg Gly Glu Phe Asn
    290                 295                 300
Gly Leu Gln Arg Lys Ile Phe Asp Ile Asn Pro His Ala Tyr Tyr Val
305                 310                 315                 320
His Cys Phe Ala His Gln Leu Gln Leu Val Val Val Ser Ile Ala Ser
                325                 330                 335
Ser Ala Cys Cys Gln Ser Val His Asp Phe Phe Glu Tyr Ile His Leu
            340                 345                 350
Ile Val Thr Thr Thr Ser Ser Ser Cys Lys Arg Arg Asp Ala Leu Lys
        355                 360                 365
Glu Lys His His Gln Asn Ile Leu Glu Lys Leu Glu Arg Gly Glu Ile
    370                 375                 380
Leu Ser Gly Arg Gly Val Asn Gln Glu Thr Asn Leu Ala Arg Pro Gly
385                 390                 395                 400
Asp Thr Arg Trp Gly Ser His Tyr Leu Thr Leu Leu Arg Leu Glu Thr
                405                 410                 415
Met Trp Asp Ser Val Leu His Val Leu Thr Ile Val His Glu Asp Gly
            420                 425                 430
Arg Val Pro Thr Gln Ala Ala Gly Leu Ile Glu Lys Met Glu Ser Phe
        435                 440                 445
Lys Phe Val Phe Ile Leu Lys Leu Met Leu Lys Met Leu Ala Ile Thr
    450                 455                 460
Asn Glu Leu Ser Gln Thr Leu Gln Arg Lys Asn Ala Asn Ile Val His
465                 470                 475                 480
Ala Met Glu Leu Leu Asp Val Val Lys Thr Arg Met Ala Thr Met Arg
                485                 490                 495
Thr Asp Ser Gly Trp Glu Ser Phe Phe Gln Ser Val Lys Glu Phe Cys
            500                 505                 510
Ala Gln Lys Gly Ile Pro Val Val Asp Met Asp Glu Glu Val Pro Ile
        515                 520                 525
```

```
Arg Gly Arg Ser Arg Arg Asp Gly Phe Thr Ile Thr Asn Leu His Tyr
            530                 535                 540

Tyr Arg Thr Glu Ile Phe Phe Val Val Leu Asp Lys Ile Asn Thr Glu
545                 550                 555                 560

Leu Cys His Arg Phe Asn Glu Val Ser Ser Glu Leu Leu Val Cys Phe
                565                 570                 575

Ser Cys Leu Asp Pro Lys Asn Leu Phe Cys Gly Phe Asp Ile Glu Lys
            580                 585                 590

Leu Val Arg Leu Gly Thr Leu Tyr Asp Lys Asp Phe Ser Val Ile Glu
            595                 600                 605

Cys Ala Met Leu Arg Glu Gln Leu Glu Thr Tyr Ile Val His Val Arg
            610                 615                 620

Arg His Ala Ala Phe Gly Thr Cys Glu Asp Ile Ala Ser Leu Ser Met
625                 630                 635                 640

Lys Met Val Glu Thr Lys Lys His Leu Val Phe Pro Leu Val Phe Lys
                645                 650                 655

Leu Ile Glu Leu Ala Leu Leu Leu Pro Val Ser Thr Ala Ser Val Glu
            660                 665                 670

Arg Ile Phe Leu Ala Met Asn Ile Ile Lys Arg Glu Leu Arg Asn Lys
            675                 680                 685

Ile Glu Asp Asp Trp Met Asn Asp Leu Met Val Cys Tyr Thr Glu Lys
690                 695                 700

Glu Ile Phe Lys Ser Leu Asp Asp Glu Thr Ile Thr Arg Arg Phe Gln
705                 710                 715                 720

Arg Leu Lys Thr Arg Arg Met Gln Leu Pro Arg Val Thr Thr Thr Arg
                725                 730                 735

Leu Thr Thr

<210> SEQ ID NO 36
<211> LENGTH: 6046
<212> TYPE: DNA
<213> ORGANISM: Zea mays

<400> SEQUENCE: 36
tcatcttcct cctcttcacg ttccagttcc ggttcctctt ttcgtcatct atcagaccaa    60 gttcttttg gaccatcttt acgaccctag catgggtacg tctttcagcc gggtccatat    120
ccctggttga tcgaccctttt aggatgttcc attgcttcaa cagattgtcc ttcactaatc    180
caccccacaa gctcttcatt ttgaatgctt cacttgttga tctgctgctc gtgccttcct    240 tcccttttccc cttcattttt gtctttcgcg caaccgcctt tgccctatca catacgaagg    300
tggagcatat agagcataag gaggtactcc atacgaaggt ggagcatatg gaggaggggc    360
gtacggaggt acctcttgac ttccatccgt agcaggtggg gagggcata cggacgtact    420 gggaatgaag cttaaattat ggcttgggaa gctagaggtt gaccatatga taaatgacag    480
ggataagggt gtggtggtgg acgcgcagcc ggaaataatg cacgggtct gaggctgaaa    540 cattggagcg acgatgtagt ggagaagact catcaaacgg aagggttgta ggtgatccat    600
cggactacaa gagatccgtg aaggtgttca aatctaggac caacccgaca ttgtgtgaag    660
agaggggagt tttgaagaga aaaatgagat gaaatggtgt gtggaatgag ctccacccgg    720
gtaggggtat ttatagaggg attgggggat gaaatttgtg ttttttttgca attttctttg    780 atttttttgga ctccaaacgg taaaaaacta ctagttgcaa cggctagcac atatggcgcc    840
atgtggacca atcaaatcgc gccagctcgc tctcgcccgc gcatccgccc gaccagcgcc    900
```

```
tcgctctggc ccacctctcg cccgggtgca cgctacagcg cggggcgagac cgcgagagcg      960
agacgatacc gctcgctctc gctaggcacg agctgcgtcg cctggggccc ctctctcgcc     1020
cgtgttcagg cggcaccggc ttcctcccac cctcgctgcc gcctccattg gcaccagcct     1080
tatactctat tttaaacttc actttgcaaa caatgttaaa cagtatcatc tattatgttg     1140
cgtcctcaat tggcacccta attgctaatt ctatactggc atgggaattt taagaacgta     1200
aatctttgaa ccgaattgtt cataagtaaa agggtattgt ctattttgtg cattttatga     1260
tgccactttt gcgcattgtc tgagtgcctt gtttgatgca ccaaacttgg tgcacacaag     1320
acacaccgac agggcactct ccatcttgtg ttttatctgg tgagtcactg gatacatctg     1380
atgcaagtgt atgctcttca actcacttgt ttcaatcgtt ttttcagtgg gttttctttt     1440
aaacttttg tgggcttttt tggatgtaac tggcactagt tttactagtg tgcaccatta     1500
cacctaacta aacacaccta gattaagtta ctcgtctcat gtcatctttt attttacaac     1560
taaatgaaaa taaggttttt atcactactt taagcctccg acaactctat tgacacttag     1620
acctagctta aacttaacct tttcgatttt ttttaaaagg accgttgatt atctcaatca     1680
agaaggacat aaataactcg taagcccaat cactagcatt attgtgatct cccttacctt     1740
gtttctgcag aacatacggt ggtcataata ctctcaagtt gtcattatca ccccctaaa     1800
ccgaggtcta caacccttta tccccaacat tgttacaatg aacaactttc ccaccaccct     1860
gcagcataaa tttggttttg ccataatcta tactatactt aaaacaccag ttttaatagt     1920
cgtcccgcat catcttttta caaataaccc atcacaagta ttttaaatta atcgttgcac     1980
gcctatagat ggccaaacag cggcccggca cgggcgagac acccgcgggc cacaactctg     2040
gcccagacac gtcatgccgg cctgcagact atgccgatcc agcacgttag cccgtcgatc     2100
catttaatta aatcagcgta aaatgttaaa aaacagtgca gaaggtgggg ttcaaaccca     2160
taccctgatg gaagaagggc gggggacact gtgtgaagct gtctaaccag tagaacatta     2220
tgctcagatg ttttaaatat tgaatataaa ttgtatatat gtatatacgt ttttttgtaa     2280
aataaaaaat ataatcatgt cgggccggtc agcactacgg gccgaggcta cagcccaagc     2340
acgacacgaa gttcttggct cttgcaagta ttaggtcgtt tctgagacca cattgacgca     2400
atggactcca tggtgtttga ggttgctgaa ttggatagag caataatgat tgtcacact     2460
aacagtaaaa tgaaaggtta tttgttggtt ttaaacgtca gtaattgcta caaagtagca     2520
taatttatat gaagcgcatc cagttttat tgatgcctga ctttagcaat cacttcatat     2580
tttgatccat ctttttata agtttgagtt catgtgactt attttagaaa cttgagctca     2640
caagctttct cttatttggt ctatgtatga tggaattatg tcattttata atctctgttc     2700
gttcagtcag tcgttgtgaa ctttcttcta atcgctcact tcattggtcg tgttgtacca     2760
tgacatattg catgaagtaa acaataacat cagttagcca aatcaaaaaa atattataca     2820
gagaggggag acaatcaata aaaaaatctt gaatttgttt tgtggatagt ttacgtggat     2880
attgttgtaa gtcgtcgcaa cgtacaggca atcgactagt gttgcttaga aatttgagtc     2940
cctcaaaacg tctgcgcaat agaactagat tcatagtaac cagcgacgga tccacagtga     3000
gggcaaggtg ggccatggcc ccacctcaaa ttttataatc ttcataatat gatataggaa     3060
taggagcgag tcgccatcca gccattcgcc aggaaaccaa aaccgcagcg gcccaccagg     3120
cgccaacagc cgcaagctcc gccgttcgcc caggcgccca gtcagccggc cgttcttctt     3180
ccgccgttcg accagcggcc ccgccgtcga ggccaggagc ccaggaccca gccaccgagc     3240
```

```
ggtaaatcct ttggtccttc cgttctgttc catgcctaga tctgcctttg cgctcgccgc    3300
ttgatctacc tctgcgcacg ccgcttggtc gcttggtcct atagcagctt tgcaacaaag    3360
cagtttagtg atttagatag cagtttattg atttagattt atagagccaa tttggggcaa    3420
cagtccataa gtccattggt gagcgcaagg tgttcggcaa aatgctccag cccatagaat    3480
tcaagttaat aatttgtcaa ctgatgtgtt ttattggata ttgtttctat gatttttag     3540
gcctttaaac ctcacagaaa cattgggtga agcaaatgag aaggttttc cagccacttt     3600
caagaggctc tggcactagt gctaataata atgtgaataa cacaccaact gttggaggga    3660
cgttcaatcc ggatgacata gttgcagatc ccgctttaag gaggcaaatt tatgaatatg    3720
ataaagatgt ccaaaaccaa gtgagaaggg catatgttct aaatggtcca tgccaaccaa    3780
agggtttaga tttccctcat agacagtatg aacaaagttt aaggcctttt aaagaggaat    3840
ggtatgacaa gtatgattgg ttggagtata ttgaatcaaa agatgcagtg tattgctttt    3900
attgctttct ttttaagcaa gcagtgaaag gtgataaata tgaagctttc actaaagttg    3960
ggtataataa ttggaaagat gcagttgaaa ggttgaaatc acatgttggt ggtgttaaca    4020
gtatccacaa caatgctagg ttacattttg atgattttaa caaccaaaga caaagcatat    4080
caactatcat gtctagtgcc agtcgtgagg ctgaagacct ttataaaatt cgtttgactt    4140
cttcattggc ttgttccaga tttcttttga tgcaaggttt ggcttttcgt ggtcatgatg    4200
aatcatctag ttcgctaaat aagggaaatt ttctagaatt gatttattgg atgaaagata    4260
aaattaaata agtgagagat gcttttgagc gtgctccaag aaattgcatt atgatatcac    4320
cacatattca aaaagatctt gcaaagtgtt gcgctcaaca gatcacagag aacatcctag    4380
gagaaatagg agatagaaac ttctctattc ttattgatga atcacgtgat gtttctgtta    4440
aagaacaaat ggcggtgata ttaaggtaat agtactttca tattttattt gcatattgta    4500
gtttcatatt ttattttcat gtcgtgttgc ctagctaact aattttttgt aagatagata    4560
tgtgaataat caaggccatg tgatggaacg gtttcttgcg ctcaagcatg tcaaggatac    4620
tacatcagaa gccttgaagg aagctatttt tggccttctt gatcaccatg gattatctat    4680
atccaagatc aggggcaag gatatgatgg agcatcgaat atgcgaggtg aatttaatgg     4740
cttacaaaga aagatatttg atattaatcc acatgcctat tatgttcatt gttttgcaca    4800
tcaacttcaa cttgtggtgg tttctattgc tagtagtgct tgttgccaat cagttcatga    4860
cttctttgag tacatccact taattgtcac caccacaagc tcatcttgca agagaaggga    4920
tgctctaaaa gaaaacacc accagaatat tttagaaaaa ctagaaaggg gtgaaatttt     4980
atctggtaga ggtgtgaatc aagaaactaa ccttgctaga cctggtgaca aagatgggg     5040
ttcacattat ttaacattgc ttcgattaga gacaatgtgg gactcagtat tgcatgttct    5100
taccattgtg catgaagatg gccgtgtacc aacacaggca gcggggttga ttgaaaaaat    5160
ggagagcttc aaatttgttt tcatttaaa attgatgttg aaaatgcttg caatcacaaa     5220
tgagctctct caaaccttgc aaaggaagaa tgccaacatt gttcatgcta tggagttgct    5280
tgatgttgtg aaaacccgaa tggctacaat gaggacagat agtggttggg agtcattctt    5340
tcaaagcgtg aaagaattct gtgctcaaaa gggtattcct gtggtagata tggatgaaga    5400
agtgcctatt agaggccgtt caaggcgaga tggcttcaca atcacaaacc ttcactacta    5460
ccgcaccgag atattctttg ttgttcttga taaaatcaac actgagttat gccatcgctt    5520
taatgaagtt tctagcgagt tgcttgtttg cttttcttgc ctcgatccaa gaacttatt    5580
ttgcggtttt gatatagaga aacttgttcg acttggtact ctatatgata aggattttc    5640
```

-continued

| | |
|---|---|
| agttattgaa tgtgcaatgt taagagagca acttgagaca tacattgtcc acgtgcgaag | 5700 |
| gcatgctgct tttggtactt gtgaagatat tgcatctcta tctatgaaga tggttgaaac | 5760 |
| taaaaagcat cttgtgttcc ctttggtttt caagctaatt gagttggcct tgttattacc | 5820 |
| cgtctcaaca gcaagtgttg agagaatatt tttggcaatg aacatcatta agagagaatt | 5880 |
| gcgtaacaaa attgaagatg attggatgaa tgatttgatg gtttgctata cggagaaaga | 5940 |
| gatattcaaa tcccttgatg atgagactat tactagaaga ttccagcgtc ttaaaactag | 6000 |
| aagaatgcaa ttgcctcgag tcacaactac aagattgaca acttag | 6046 |

<210> SEQ ID NO 37
<211> LENGTH: 1920
<212> TYPE: DNA
<213> ORGANISM: Zea mays

<400> SEQUENCE: 37

| | |
|---|---|
| atggcggcgg ctggcttcaa cagttcaagt tcaacacgtt ggttccctgc tggcgttatt | 60 |
| ccatcaagtg tcgcctctgc ctctgtatca aatgcagcag caccacaagc tattatcaac | 120 |
| tcagatgatg tagcttgggc tcattgtttt tgcccagatg caaacaagaa gcattggctg | 180 |
| aagtgcaagt actgtgacaa gctatgcaaa gctgggatta caagaattaa gtggcacctt | 240 |
| gctgtccttg tggtgaagca aaagccaaca aaaggttcta gtagccttag ctgtagaaca | 300 |
| gtggtacgtg gtggcactat tgacagattt tataaaacctt ctactattga agaatttgtt | 360 |
| caaatgatgc ataaaggaat taaccttagc aacaaggttc aaacaacatt gtcaactcag | 420 |
| aaaagagaag agagaaggga taaggcttgt gagtacatat gtcagttttt ctatgaagct | 480 |
| agtattgcac acaacacagt caccccttcct agctttgcac ttatgcttga ggccattggg | 540 |
| caatttggta aggtttgag agggcctagt ccttatgaga tgagtggacc attcttgcag | 600 |
| aaaaggaaac aaaaggtatt ggatggtttc aagaaccaca aggaatcatg ggagcaaaca | 660 |
| ggatgtacaa tcatgacaga tgcatggaca gataggaagg gtaggggagt gatgaattta | 720 |
| gtcgtccata gtgctcatgg agtttgcttc ttagattcag tggactgctc gggtgagaga | 780 |
| aaagatgatc tcatgctaga ggatcttggg aagcttgagc cagtggagca aactatcaca | 840 |
| agtgcaaggc agatcactaa tttcttgtat gctcacacaa gggtgttaga tttgatgaga | 900 |
| aagtttctga agaaagactt ggtgagatct gggattacta gatttgctac tgcctacttg | 960 |
| aacttgaaaa gcttgcttga taacaagaaa gaattgacaa ggttgttcag atcagatgaa | 1020 |
| cttaatgagt tgggttactt gaaaaaggac aagggaaaga aagccaataa agttgtgaga | 1080 |
| tctgaaaccct tttcgaaaaa tgttgatata gctgtaaatt ttttttgaacc attggcaaat | 1140 |
| gtgttgagga gactggacag tgatgtaccg gcaatgggat tctttcatgg attaatgctt | 1200 |
| gaggcaaaga aagaaatttc tgagaggttt gacaatgatg agagccgcta caagttgct | 1260 |
| tgggatatta ttgataagcg gtgggatagc aagctcaaaa ctccgcttca cttagctggg | 1320 |
| tactacttga atccttactt ttattatcca aagaagtctg aaattgagca tgatggatcc | 1380 |
| tttagagctg gagtgattaa ttgcattaca aagatgattg gtgatgaaga aacacaagac | 1440 |
| aaaataattg aagaactcta catttcctca gcttgtgaga gaaattggtc cgtatttgaa | 1500 |
| caggttcata caaaaaggag aaacaggcta cttcatgata ggatgagaga ccttgtgttt | 1560 |
| gttaaattta actccaagct aagggggaaag aaggagagaa tagacagaga tcctttagag | 1620 |
| agggaagtag atgatgttgt tggtgatgat gacaatgaat tcattactgg tattgtacct | 1680 |

-continued

```
cttccgaatg atgttgttga accagcgcaa gatggaagat cacagggaga acaaacatca   1740
caagcacaag ttcaagtaca agcaaaaaga aagaggtctt ggttcagagc tggtagttta    1800
gccttctctt gtgctaaaaa tctaggtcag ctaggtggac tgttcttcat cagggcgccc   1860
aaattagttt ctgatctttc tgttcctatt actacgatcg ttgggaactt attcttctcc   1920
```

```
<210> SEQ ID NO 38
<211> LENGTH: 640
<212> TYPE: PRT
<213> ORGANISM: Zea mays

<400> SEQUENCE: 38

Met Ala Ala Ala Gly Phe Asn Ser Ser Ser Thr Arg Trp Phe Pro
1               5                   10                  15

Ala Gly Val Ile Pro Ser Ser Val Ala Ser Ala Ser Val Ser Asn Ala
            20                  25                  30

Ala Ala Pro Gln Ala Ile Ile Asn Ser Asp Asp Val Ala Trp Ala His
        35                  40                  45

Cys Phe Cys Pro Asp Ala Asn Lys Lys His Trp Leu Lys Cys Lys Tyr
    50                  55                  60

Cys Asp Lys Leu Cys Lys Ala Gly Ile Thr Arg Ile Lys Trp His Leu
65                  70                  75                  80

Ala Val Leu Val Lys Gln Lys Pro Thr Lys Gly Ser Ser Ser Leu
                85                  90                  95

Ser Cys Arg Thr Val Val Arg Gly Gly Thr Ile Asp Arg Phe Tyr Lys
            100                 105                 110

Pro Ser Thr Ile Glu Glu Phe Val Gln Met Met His Lys Gly Ile Asn
        115                 120                 125

Leu Ser Asn Lys Val Gln Thr Thr Leu Ser Thr Gln Lys Arg Glu Glu
    130                 135                 140

Arg Arg Asp Lys Ala Cys Glu Tyr Ile Cys Gln Phe Phe Tyr Glu Ala
145                 150                 155                 160

Ser Ile Ala His Asn Thr Val Thr Leu Pro Ser Phe Ala Leu Met Leu
                165                 170                 175

Glu Ala Ile Gly Gln Phe Gly Lys Gly Leu Arg Gly Pro Ser Pro Tyr
            180                 185                 190

Glu Met Ser Gly Pro Phe Leu Gln Lys Arg Lys Gln Lys Val Leu Asp
        195                 200                 205

Gly Phe Lys Asn His Lys Glu Ser Trp Glu Gln Thr Gly Cys Thr Ile
    210                 215                 220

Met Thr Asp Ala Trp Thr Asp Arg Lys Gly Arg Gly Val Met Asn Leu
225                 230                 235                 240

Val Val His Ser Ala His Gly Val Cys Phe Leu Asp Ser Val Asp Cys
                245                 250                 255

Ser Gly Glu Arg Lys Asp Asp Leu Met Leu Glu Asp Leu Gly Lys Leu
            260                 265                 270

Glu Pro Val Glu Gln Thr Ile Thr Ser Ala Arg Gln Ile Thr Asn Phe
        275                 280                 285

Leu Tyr Ala His Thr Arg Val Leu Asp Leu Met Arg Lys Phe Leu Lys
    290                 295                 300

Lys Asp Leu Val Arg Ser Gly Ile Thr Arg Phe Ala Thr Ala Tyr Leu
305                 310                 315                 320

Asn Leu Lys Ser Leu Leu Asp Asn Lys Lys Glu Leu Thr Arg Leu Phe
                325                 330                 335
```

Arg Ser Asp Glu Leu Asn Glu Leu Gly Tyr Leu Lys Lys Asp Lys Gly
                340                 345                 350

Lys Lys Ala Asn Lys Val Val Arg Ser Glu Thr Phe Ser Lys Asn Val
            355                 360                 365

Asp Ile Ala Val Asn Phe Phe Glu Pro Leu Ala Asn Val Leu Arg Arg
        370                 375                 380

Leu Asp Ser Asp Val Pro Ala Met Gly Phe Phe His Gly Leu Met Leu
385                 390                 395                 400

Glu Ala Lys Lys Glu Ile Ser Glu Arg Phe Asp Asn Asp Glu Ser Arg
                405                 410                 415

Tyr Lys Val Ala Trp Asp Ile Ile Asp Lys Arg Trp Asp Ser Lys Leu
            420                 425                 430

Lys Thr Pro Leu His Leu Ala Gly Tyr Tyr Leu Asn Pro Tyr Phe Tyr
        435                 440                 445

Tyr Pro Lys Lys Ser Glu Ile Glu His Asp Gly Ser Phe Arg Ala Gly
        450                 455                 460

Val Ile Asn Cys Ile Thr Lys Met Ile Gly Asp Glu Thr Gln Asp
465                 470                 475                 480

Lys Ile Ile Glu Glu Leu Tyr Ile Ser Ser Ala Cys Glu Arg Asn Trp
                485                 490                 495

Ser Val Phe Glu Gln Val His Thr Lys Arg Arg Asn Arg Leu Leu His
            500                 505                 510

Asp Arg Met Arg Asp Leu Val Phe Val Lys Phe Asn Ser Lys Leu Arg
        515                 520                 525

Gly Lys Lys Glu Arg Ile Asp Arg Asp Pro Leu Glu Arg Glu Val Asp
530                 535                 540

Asp Val Val Gly Asp Asp Asp Asn Glu Phe Ile Thr Gly Ile Val Pro
545                 550                 555                 560

Leu Pro Asn Asp Val Val Glu Pro Ala Gln Asp Gly Arg Ser Gln Gly
                565                 570                 575

Glu Gln Thr Ser Gln Ala Gln Val Gln Val Ala Lys Arg Lys Arg
            580                 585                 590

Ser Trp Phe Arg Ala Gly Ser Leu Ala Phe Ser Cys Ala Lys Asn Leu
        595                 600                 605

Gly Gln Leu Gly Gly Leu Phe Phe Ile Arg Ala Pro Lys Leu Val Ser
        610                 615                 620

Asp Leu Ser Val Pro Ile Thr Thr Ile Val Gly Asn Leu Phe Phe Ser
625                 630                 635                 640

<210> SEQ ID NO 39
<211> LENGTH: 7239
<212> TYPE: DNA
<213> ORGANISM: Zea mays

<400> SEQUENCE: 39
ggaccatttt gatctagatc tccaccagat ggatgtaaaa ataacattct tatatagaga      60
gttagtagaa aaacgttttc atggcacaac caaagggttt cgtcatgcgc ggtaaagaac     120
atatgggatg tcacctaagg aggtccattt atggattaaa acaagcctct agactgtggt     180
acatcaagtt tgatcagact atcagaaagt ttggttttca aggaaaacga ggaagacaat     240
tgcatttatg caaagtttaa gaaggaaaa ttccttgttc tatatgccga tgacatactt      300
ttaggtagta gtgataatga tatactggcg gaaacagaca tgtttctttc ctcgaacttt     360
gatatgaaag atatgggaga agcctcttaa gttctagaaa tagaatttca cagagataga     420

-continued

| | | |
|---|---|---|
| cataagggag tattagaact ctcacagaag tcatatatag aaaagtaata aagaattaca | 480 | |
| gtatgcatca gtgtaaggcc acgcctgcgc caatagtcaa gggtgataag tttgggaatt | 540 | |
| atcaatgtcc ctagaatcag tgtcagaaag atcagatgaa gtcagtacca tatgtttcta | 600 | |
| ctattggaag cattatgtat gctcaaatat atattcgcct aacttagaat ttactaccga | 660 | |
| gttgcttggg agatataaaa tcaacacagg catagaacac tgtaaacaat taagaaggct | 720 | |
| ctaaagtacg tgcaaggtac taaaaggtct catgctaaca tacaaaagat gtagttccct | 780 | |
| atgaatagtt ggttgtgcag atgccgactg atgaggttgt aaagatagac tgaagtctac | 840 | |
| tttagggtat gtacactctc tagggagtt atttcttaga aaagttgcaa acagacaacg | 900 | |
| agatcatcgt cgataatgga cgctgagttt gtagccatat atgaggcaaa tgggcaggca | 960 | |
| ttatggatga agaaattcgt acccgaatta agagtggttg atagcataga gcgatcactg | 1020 | |
| agaatttact gcgataatga gcctacggta ttttactcct ataacaacaa gtcaagttct | 1080 | |
| ttgtcattta gtgttatgtt gttaaggaga aaattcagga tcaaaccata aaagttgagc | 1140 | |
| ataatagaag atagcaatgt tagcggatcg ctcacaaaag gccttccacc caacgtgtta | 1200 | |
| agacaacatg tagccgacat gggtttaagg gagtgcatat gatcttgatt cacaggggct | 1260 | |
| acaaattgca acctaataaa gtatcttttc gttctgaagc aggggatcat gttgtagtca | 1320 | |
| ttgagtgtgg tgatacttaa tcggtcattg tcacacattg gtctctatgt gtaaacttgt | 1380 | |
| caagggatgg aatcccaaaa gttgagtata aggaatgtag agaacaaagg agagattgtt | 1440 | |
| gggtgtgtcc tctacaccca gtcatcagtg actggatttg gattaaccca atcgtccatc | 1500 | |
| tccttaatca ggcccttgat ttggagggtc cacgctaacc tcggttggag ccacctgtca | 1560 | |
| cacgacgcta tataaaggat taagggtcgt aggaaattaa agccaacact agtatcttgc | 1620 | |
| cctaaaccca aatccacaga caggacccta tcgcctaggc gttggagtga ctggaagaac | 1680 | |
| gacaactcta atggcggcct cgaatctcga cgactgagcc acctctagca ggaatggagg | 1740 | |
| aggtggtgga gaggattgaa tccatctcca ccactgtaag gcaacaatat gtcgtcctaa | 1800 | |
| tcacctctgt ttatgtgttc acagtgagag cacacgcgta gattcactac tgttcattca | 1860 | |
| agtaacctca gatcgactaa gtgtgaccca gcaaagatcc catagaacca gtggcggagt | 1920 | |
| tagaatctct ttaagtatag ggccgaatat aacactgaaa acgatgtata gacctttaga | 1980 | |
| caccaaaaac tagctctttg gacaacagtc acagctaacc atacttgcca gtatatggac | 2040 | |
| ctttagagac tatttggtcc aaaagtaaga cacaggccct actagccata ggcctatctc | 2100 | |
| cgccaatgtt ttaaatcacc ggagatcgct gccgctatcg ccggagatcg cttctggcaa | 2160 | |
| acaatgccgc taggagatta caattctgcc gctattgctt gctgaccgct attagccgct | 2220 | |
| attagccggt gaaatccgtt aaatgggcca tcttctagcg gcagctaaat caaacctggg | 2280 | |
| ccattttctt gcgcgcgtcc gacccagccc attatctccc tctgcctttt cttgtgcaaa | 2340 | |
| actgcgaacc ctagctcaga ctctcatttc caaaaggcac tggcggctgg cttcaacctg | 2400 | |
| atggcggcgg ctggcttcaa cagttcaagt tcaacacgtt ggttccctgc tggcggtaag | 2460 | |
| caatgaagca agtagcaaca atcaaggcag cactccaata gtattctctc cactctccaa | 2520 | |
| cctccaattg ttgtccagtt gaaccggcac catgtctcag caagagaagc aaacaggcat | 2580 | |
| gtatttttca atagatgttc atgtgacgtg tagtgtagtc ccttgtagct atgttttctg | 2640 | |
| cagcattttt ttggtgatta aaatagttgt agtagttcca ttgatgtagg cggtaggctg | 2700 | |
| caacacattg acttgtagtt atgattgttt taccatatca ttcacttgag tatcatccta | 2760 | |
| tttctttccg atgaacttta atccaaaata ttcaatggtg gatatatata aaagtataga | 2820 | |

```
cactgcaaaa aaaagtgtag ctgcgatggt gcatttgata ttgcaaatag attaacaatc    2880
tagacactct attgatacct tttttaaaac aattttattg acttctccgt gtaccatgta    2940
cctaaacctg gtcaacagct gaactataat ttaggatggt gctaacgtga agaaatgttc    3000
ttgctgacaa atgtattttt acttatttttt tttgtttcgt tattgatcca tactctagct    3060
cacaagcttg atgaacattt ggttagcgct aacggctttt tatggatttc aacacgaat     3120 atactttgaa acctgaatac aagcaatatt gcaactcgta ttttttgaaga agtcaaggtt   3180 tcacatgaca gaacgtacgt cgtagtggca agcaatgttg taatgacaat taaatttctt   3240
atcagtatct tgctttatac gtgattaaaa tagttgtagt agttccattg atgtaggcgg    3300
taggccgcaa cacattcttc aatagatgtt catctgttta aagcttttca ttttcctaat    3360
attatgcatt atgtgtcttc aaattgtgta gttattccat caagtgtcgc ctctgcctct    3420
gtatcaaatg cagcagcacc acaagctatt atcaactcag atgatgtagc ttgggctcat    3480 tgttttttgcc cagatgcaaa caagaagcat tggctgaagt gcaagtactg tgacaagcta   3540
tgcaaagctg ggattacaag aattaagtgg caccttgctg gtattaaagg gaataatgtt    3600
acaaagtgtt tgaaggttcc aagtgatgtg aagaagata tgattgcttt gcttacaaag    3660
aatacagaag aaaaggacca taaagcaaaa gaaaaggaaa gagagagatg aaattaactt    3720
agacatctga gaagatgaaa gttgtgagca agtggatatt gatcttggga atgaagtcct    3780
tgtggtgaag caaaagccaa caaaaggttc tagtagcctt agctgtagaa cagtggtacg    3840
tggtggcact attgacagat tttataaacc ttctactatt gaagaatttg ttcaaatgat    3900
gcataaagga attaacctta gcaacaaggt tcaaacaaca ttgtcaactc agaaaagaga   3960
agagagaagg gataaggctt gtgagtacat atgtcagttt ttctatgaag ctagtattgc    4020
acacaacaca gtcacccttc ctagctttgc acttatgctt gaggccattg gcaatttgg     4080 taaaggtttg agagggccta gtccttatga gatgagtgga ccattcttgc agaaaaggaa   4140
acaaaaggta ttggatggtt tcaagaacca caaggaatca tgggagcaaa caggatgtac    4200
aatcatgaca gatgcatgga cagataggaa gggtagggga gtgatgaatt tagtcgtcca    4260
tagtgctcat ggagtttgct tcttagattc agtggactgc tcgggtgaga gaaaagatgg    4320
taagtacata tttgaccttg tggacaaatg catagaggag attggggagg caaatgttgt    4380
ccaagtggtg actgataatg ctagtgtcaa tacagcagca gcaagcctat tgacagcaaa    4440
gaggccctca atattttgga atgggatgtg ctgctcattg cctagatctc atgctagagg    4500
atcttgggaa gcttgagcca gtggagcaaa ctatcacaag tgcaaggcag atcactaatt    4560
tcttgtatgc tcacacaagg gtgttagatt tgatgagaaa gtttctgaag aaagacttgg    4620
tgagatctgg gattactaga tttgctactg cctacttgaa cttgaaaagc ttgcttgata    4680
acaagaaaga attgacaagg ttgttcagat cagatgaact taatgagttg ggttacttga    4740
aaaaggacaa gggaaagaaa gccaataaag ttgtgagatc tgaaaccttt tcgaaaaatg    4800
ttgatatagc tgtaaatttt tttgaaccat ggcaaatgt gttgaggaga ctggacagtg     4860
atgtaccggc aatgggattc tttcatggat taatgcttga ggcaagaaa gaaatttctg    4920 agaggtttga caatgatgag agccgctaca agttgcttg gatattatt gataagcggt      4980 gggatagcaa gctcaaaact ccgcttcact tagctgggta ctacttgaat ccttactttt    5040
attatccaaa gaagtctgaa attgagcatg atggatcctt tagagctgga gtgattaatt    5100
gcattacaaa gatgattggt gatgaagaaa cacaagacaa ataattgaa gaactctaca    5160
```

| | |
|---|---:|
| tgtaccaaga tcaacaaggg acatttattt ggacatgaaa ttgccataag gcaaaggaga | 5220 |
| aacaagaact ttaatccagg tgattctatt ttgaatacat ggtttcagaa ttcaatttgt | 5280 |
| ttcttgcctc tttcacaatt atgtaattat taacttgttt atgcagcaaa gtggtggcta | 5340 |
| aaccatggta caaacacacc taatctgagg atattggctt caaaaattct aaatctaaca | 5400 |
| tgtagttcct cagcttgtga gagaaattgg tccgtatttg aacaggtaaa tacacttatg | 5460 |
| tgggatctgt ttggccactt tgtgaatattt ttagtagtaa aactgcaagc tctactatcc | 5520 |
| aaatgcatag aaaaccatat ttattgtact gtttcaaatc ttgtttcaaa catgttatct | 5580 |
| tatgttcact atttcactca taggttcata caaaaaggag aaacaggcta cttcatgata | 5640 |
| ggatgagaga ccttgtgttt gttaaattta actccaagct aaggggaaag aaggagagaa | 5700 |
| tagacagaga tcctttagag agggaagtag atgatgttgt tggtgatgat gacaatgaat | 5760 |
| tcattactgg tattgtacct cttccgaatg atgttgttga accagcgcaa gatggaagat | 5820 |
| cacagggaga acaaacatca caagcacaag ttcaagtaca agcaaaaaga aagaggtcta | 5880 |
| tgaagcctag aaagaagtta agaagcctcc agtctctgat gcgtgatgtt taagttcaag | 5940 |
| tgcagcagtc ctcatcggat tcagaagatg gtgacattgc aatggaattc tctgaatctg | 6000 |
| ataagtctcc acatgccttt gattctgatt gatgctagat tacaatgtta tatttgacct | 6060 |
| tgtggacagt cattttgggt gaactgtgaa ctaaactaat gatctcaatg tcttggagct | 6120 |
| tagacatttt gttttaagtt aagctgagct cagacatttt gttttaagtt aagctgctca | 6180 |
| gacattttac ggcagtcatg tatagagctg aactcctata tgtatggcaa tatgtatgac | 6240 |
| tatcaaattt gtcgtctatt catctattca tctgtgtcaa atttatactc tatttttttg | 6300 |
| caaatccgca aaaatgttta gcttccgcta tagccggtta tagctggact tagctgttct | 6360 |
| ggaacccagc cgctaaacct cttagcccgc gatttaatac actgatctcc gccactgcat | 6420 |
| agaactaaca ccaagtatag cgcccatgcc ttttgttgtt ggtctgacaa ggcttctctc | 6480 |
| ttccattgcg ccctgcaagc agttgtgctt agcgtcattg accggcctgt gcacccactc | 6540 |
| ctccctatat ctaccagctt tggttgtgct acttccccccc ctcctcttcg ttccactcgt | 6600 |
| tgcgtgaggc tcgctttgtc cgctagtgca gttgctgtct tctccctctt ccgccagtct | 6660 |
| tgtgtttttt tttccttccc gtcttcgttt ccatgcatga tggtggaatt gcaggtcttg | 6720 |
| gttcagagct ggtagtttag ccttctcttg tgctaaaaat ctaggtcagc taggtggact | 6780 |
| gttcttcatc aggtgcgtac tcagttcagt gactaattta tcatttttat ttttttcttc | 6840 |
| tcccgtcgat gttgtgatca ggcctctgct actagaatgc aggcctctgg ttgaaaagct | 6900 |
| atacaatagg cctatggtcc agctcggtta cgtacctcag ctgctcttca tagggccggc | 6960 |
| cgggtgtgct cctaataatc cagtaacacc atgatactat caaataatga acacagatca | 7020 |
| gatacagtcc aactgcttat acatgctatt tgtaagctat ttgtactcaa aagtttatcg | 7080 |
| ttgtgtttac atgcatgttt ggtctagcta cacttttaga gtctgatact aaacgtctga | 7140 |
| actgtacgta gggcgcccaa attagtttct gatctttctg ttcctattac tacgatcgtt | 7200 |
| gggaacttat tcttctccag gtgtgagaaa tcagtataa | 7239 |

<210> SEQ ID NO 40
<211> LENGTH: 963
<212> TYPE: DNA
<213> ORGANISM: Zea mays

<400> SEQUENCE: 40

| | |
|---|---:|
| atggacgaat tcgagatgct actgcaggcg gccatcaaag gcagagccca agaactggag | 60 |

```
cagctggtgc aagacaagcc tgaggtgcta ccaaacaa ctgaagcagg gaacacctgc    120
ctccacatcg ccgctctctg cggccacggg gatttctgca gcaaggtcct cgccctccgc    180
ctgacgcagg agccgagtct cccgtcgtct ctgctctcca ccgccaacga cgacggggag    240
acgccgctgc tcgtcgctgt gaagagcggc cgcgtctccc tggcccttga cctgctcgag    300
cagcactcga ggcacgagct gctggacgag caccttctga agcgagacag gcacggatgc    360
aacgtcctgc accacgccat ccgcaacggc tacgacgagg gcctcgcgct gcgactgatc    420
ggccggcagc ctgcgctctc ggagtcccgc agcgggcgcg gcgagtcgcc catgttcatc    480
gcggttctca aaggtttcag gagcgtctac atggcgctgc tgagcaacga gaggtcggaa    540
tacagcgggg ccaatggctc caacgccttg cacgctgctg tcaagtacgg acaccaagac    600
cgaggccacg tagcttttgc tcgagcgctt ctggagcact gtccagatgc gcctaccac    660
gacgagcagg gcaggacatg tctccacgaa gctgtagaca aggaccgggc ggagtttgtt    720
gagttcatcc ttgacgacaa ctccaagctc cggaaacttg tcaacatgct agatagcgtt    780
gatgacagtg ctctgcatct cgcggttcag aagaacaacc cgaggatggt ccgtgctttg    840
ctggatcacc ctgacatcga catcaccgtt gtcaaccagc gtaattgcac agcgatctgg    900
aatctgtacc atgatgggga ctacgtcaag actataaact ggatggtgcc taactttttt    960
tga                                                                   963

<210> SEQ ID NO 41
<211> LENGTH: 300
<212> TYPE: PRT
<213> ORGANISM: Zea mays

<400> SEQUENCE: 41

Met Asp Glu Phe Glu Met Leu Leu Gln Ala Ala Ile Lys Gly Arg Ala
1               5                   10                  15

Gln Glu Leu Glu Gln Leu Val Gln Asp Lys Pro Glu Val Leu Tyr Gln
            20                  25                  30

Thr Thr Glu Ala Gly Asn Thr Cys Leu His Ile Ala Ala Leu Cys Gly
        35                  40                  45

His Gly Asp Phe Cys Ser Lys Val Leu Ala Leu Arg Leu Thr Gln Glu
    50                  55                  60

Pro Ser Leu Pro Ser Ser Leu Leu Ser Thr Ala Asn Asp Asp Gly Glu
65                  70                  75                  80

Thr Pro Leu Leu Val Ala Val Lys Ser Gly Arg Val Ser Leu Ala Leu
                85                  90                  95

Asp Leu Leu Glu Gln His Ser Arg His Glu Leu Leu Asp Glu His Leu
            100                 105                 110

Leu Lys Arg Asp Arg His Gly Cys Asn Val Leu His His Ala Ile Arg
        115                 120                 125

Asn Gly Tyr Asp Glu Gly Leu Ala Leu Arg Leu Ile Gly Arg Gln Pro
    130                 135                 140

Ala Leu Ser Glu Ser Arg Ser Gly Arg Gly Glu Ser Pro Met Phe Ile
145                 150                 155                 160

Ala Val Leu Lys Gly Phe Arg Ser Val Tyr Met Ala Leu Leu Ser Asn
                165                 170                 175

Glu Arg Ser Glu Tyr Ser Gly Ala Asn Gly Ser Asn Ala Leu His Ala
            180                 185                 190

Ala Val Lys Tyr Gly His Gln Asp Arg Gly His Val Ala Phe Ala Arg
        195                 200                 205
```

```
Ala Leu Leu Glu His Cys Pro Asp Ala Pro Tyr His Asp Glu Gln Gly
    210                 215                 220

Arg Thr Cys Leu His Glu Ala Val Asp Lys Asp Arg Ala Glu Phe Val
225                 230                 235                 240

Glu Phe Ile Leu Asp Asp Asn Ser Lys Leu Arg Lys Leu Val Asn Met
                245                 250                 255

Leu Asp Ser Val Asp Ser Ala Leu His Leu Ala Val Gln Lys Asn
                260                 265                 270

Asn Pro Arg Met Val Arg Ala Leu Leu Asp His Pro Asp Ile Asp Ile
        275                 280                 285

Thr Val Val Asn Gln Arg Asn Cys Thr Ala Ile Trp
    290                 295                 300

<210> SEQ ID NO 42
<211> LENGTH: 4324
<212> TYPE: DNA
<213> ORGANISM: Zea mays

<400> SEQUENCE: 42
aggttcacat ctttcctgcc agagggagga ggtcaacagc atcggcgaga cgacgataac     60
gacgatggag gaccttatcc cctagcgtga ctgggctaat caagaaagta aggagtaaga    120
aaatgataga ctactttatt tttcaaacat ttacaacctt ttgacataga tatttcttca    180
atcttgatac aaataaccaa ctcattcact gatatgttta tgtcaacaac cctttttaaat   240
aactattttt tcctacctaa atacgcaaca taaccagtta tatctatttta accaatcaac   300
tatttcctga tacccttaaa gcaaattcaa acggctgtga ctttcaaatc aatcatgtat    360
gtctttcttt tcactgatga cacctgcaac cagctcttca tctacgatgc acagttttt    420
ctttggttac tgaagcactt cgcacctaca tcctcaattt gttcatatcc tattttttcta  480
tgtacaatat gtcaaatttg ttattgcact gacgtgtaca gctaggatgc atactcctgc   540
acgtttgtat ttggaaaaca tgtacatact aaaaaatgtg tacgaacgca cacacattac   600
tttgatacat ctcaaatatt ccaaaaaaaa aaaagtata acgacaatac tccagtataa    660
cacctctatt cgttcattgt ttttcttatt tgatttacct taatactacc actttatcta   720
tacattgcct cctcacatta acatcgcgcg gtttatttac cgatacatta ttatgcactt   780
actaacgtat tttctgcttg actatacatg ctgcaacgaa aatgtgacca ccacgaaaaa    840
agagaggtaa caatacatca ccagacccct tttgtcccct tattgttttt tctatttaac   900
ctacctcacc actgccagct tctctataca ttagtttctc acaagagcct tttgctatgc   960
acgataaacc atcaattacc aaaactcttc atctcgcaac ggttcgcaaa caaccagaga  1020
acaacaattt aataattcta tctgcaagta caaacgggta tagctactaa tgcacaacca  1080
acaactacta atgcatgaac cgatatattt tgctgctaat ttttaacgaa agcaactatg  1140
cacaatctga aagtctcttt tttcaattcg tatacacttt aaagaaagaa atattttaaa  1200
tgttgcctgt cagattataa attacataca taactttact ttcctgttta tatatatata  1260
tatatatata tatatacaca gctgaccttc atttttaaat tcttgatgtt gcaggtatct  1320
tcgatacttc aaattggtta cccaaatttt caaataacac tagatttcat gttcttttga  1380
atcagttcca tgctaaaaaa aactaattaa tctagccagc ggtcatatat ttactgtaaa  1440
taaataaatt actacacatg caaataacta acttacaata aaatggtatt cataatactt  1500
aaattacgaa atgtttcgta cgcgtgcaac gcgcgccagt cactagttat tacaatcagt  1560
```

```
agtgtccagt taaattttcc ttggcatatt tgaattccgt ttctagattt catttgttta    1620
ttttggaagg agatgcccag gttcagcatg cttagtgttt tggcatgtat atatgagagt    1680
tttattggtg ttcaagtagc atttcctttg tggatagatg gacgacgaat tcgagaggct    1740
actgcagcct gcaggcggcc atcaaaggca gagcccaaga actgcaggct cccatttacc    1800
cctctccacc ggttcttcac tctaactagc cgttggaccc aagtcaaatg cttacattag    1860
tcccgtcccg tgctcaactc tactccctca cgtgtcccgt tgttgtcat tttggataag     1920
atttaaatca aagttataaa ctctttatta taaataacta ttttattatg tagttttaaa    1980
acataatgtt tatatacacc gatttatctt aacaagttct tttacaaaag tataaatata    2040
ttaagagttt atttatattt aaaaaatatt ggttaaattt atattttga gaccatatcg     2100
ctgttctaaa cgacaactaa tagtacactc aaagggagta atcattacta aaccaaagg     2160
ctcactagcg aaacctcgta agcttgtgta ttttttaatg cgcacaaggg gaacggccgg    2220
accggttggg gtggttttga aactctctcc ccagagttgc aggagaaaca tccatctttc    2280
agttgggtca ccagattcac cgttacaatc ttaattttcc ttcatagtat tatttgaata    2340
agtgagcgtc taggtttcat ttctctagtc tctctgtggc agtgttcaaa gtgtagctag    2400
atggacgaat tcgagatgct actgcaggcg gccatcaaag gcagagccca agaactggag    2460
cagctggtgc aagacaagcc tgaggtgcta taccaaacaa ctgaagcagg gaacacctgc    2520
ctccacatcg ccgctctctg cggccacggg gatttctgca gcaaggtcct cgccctccgc    2580
ctgacgcagg agccgagtct cccgtcgtct ctgctctcca ccgccaacga cgacggggag    2640
acgccgctgc tcgtcgctgt gaagagcggc gcgtctccc tggcccttga cctgctcgag     2700
cagcactcga ggcacgagct gctggacgag caccttctga agcgagacag gcacggatgc    2760
aacgtcctgc accacgccat ccgcaacggc tacgacgagg gcctcgcgct gcgactgatc    2820
ggccggcagc ctgcgctctc ggagtcccgc agcgggcgcg gcgagtcgcc catgttcatc    2880
gcggttctca aaggtttcag gagcgtctac atggcgctgc tgagcaacga gaggtcggaa    2940
tacagcgggg ccaatggctc caacgccttg cacgctgctg tcaagtacgg acaccaaggt    3000
acctgctgca gatgcttgct cttcatgcat ttttttttccc tcttcgtctc ttgcttaaaa    3060
gccaaaaccg cgaaactaac ttgtttttc agatttcgtt gaacaacttg tggacaagca     3120
tcccgagaag gccaaagtgc tggcgagaca agcggacagt aaaagggaca ctccaatgca    3180
tctcactgcg catttcaaca gggataggat tctaacgctg atgctgagat gtgatcggtc    3240
cttggggtac gtgctgcacg aggaacactc cacgcctctt ctttccatcg ccgcagaccg    3300
aggccacgta gcttttgctc gagcgcttct ggagcactgt ccagatgcgc cctaccacga    3360
cgagcagggc aggacatgtc tccacgaagc tgtagacaag gaccgggcgg agtttgttga    3420
gttcatcctt gacgacaact ccaagctccg gaaacttgtc aacatgctag atagcgttga    3480
tgacagtgct ctgcatctcg cggttcagaa gaacaacccg aggatggtcc gtgctttgct    3540
ggatcaccct gacatcgaca tcaccgttgt caaccagcgt aattgcacag cgatctggaa    3600
tctgtaccat gatggggact acgtcaagac tataaactgg gtatgtatgt atttctgtat    3660
gtaatgtatg agattgcttc attaattcag atggtgccta actttttttg attgaatcca    3720
tgcatatatg cagaacaaaa tctgctgcct catactgaat gcggatcgta gagctgaaac    3780
tgacatctac aatttccaag aggagatcag gaacaaagta atcgatacaa caaggaaaga    3840
tgccaagtct ctgatccaaa catacacaag caacacgtcc ttagtggcta tcctcatagc    3900
gacgattacc ttcgctgcag cttcacatt gccaggaggg tacagcagtg atgctggaag     3960
```

```
cgagggctc ccaatcatgg ctaggaaggt cgcgttccag gcgttcttga tcttcgacac    4020
ctcggcgatg tgcgcctccc tcgtcgttgc cttcatatgc gtcatagcaa ggtggatgga    4080 cttttgagttc ttgctgcact acaggtccgt cacgacgaag ctcatgtggt tcgcgtacat   4140
ggcaaccacc cttgcatttg cgactggtct gtacacggtt ctggaagatc gccttccttg    4200
gctggccatt gcgatctgcg ttctgtccgt gctgctgccc gttcttacga tgctggtcgg    4260
caaatggccc atattgaagc tcagaattcg atacggtagg tctgatttcc ttgacatggt    4320
ctag                                                                 4324

<210> SEQ ID NO 43
<211> LENGTH: 1875
<212> TYPE: DNA
<213> ORGANISM: Zea mays

<400> SEQUENCE: 43
atggttgctg ctgtagtact agccctactg ctgttctatg ggactggaaa cgccaactgc      60
gcaacgctgc gtcccagcag cagcaggagc agcacggacg acatgctctc cctgctcgat     120
ttcagaaagg aaatcagcag tgatccagga ggtttcctca gatcctggaa cactagtggt     180
agtagcgccg ccgactactg cagctggaat ggcgtcacat gcagcagaac gcacccaggg     240
cgggtcacgg agctcaacct cagcagccaa agcctgcaag ccgaatctc tccatctctt      300 ggtaacctaa ccttccttcg aatactggac ctgtcctaca acagcttctt tggccagctg     360
ccccttctta gtcgcccgt taggcttcag gacctagttc tgaacaacaa ccagctgcaa      420
agtttcccca ttgacgcact tacgaactgc tccagcttgc acgctataga cctttcgtcc    480
aacatgttta ctgggccaat accagccagc atcggttctc tccctaaccct tacgtacttg   540 tacctttatg ctaatagctt cactggagcc atcccatcga gcttgctaaa catctctaaa     600
ctacaggagc tcgtgctttc ctcaaacatg ctagctgggc aataccacc taatatcgt       660 tccctcatga accttacact tctctacctt gattctaaca acttcactgg agccatccca     720
tccagcctgg gaaatatctc caaactcag cagctcgtgc tccagaataa tcagctccat      780
ggcaccatac ctcaggatct tggcaattta tcaaatctga atatattggt gctagggcat     840
aatagtctat caggtcacat cccgacaaca attctgaacc agcgttccct tggatttctg    900
ggcttggaag cgaatttgct acgtatggcg ttgccatcta atattgggat catccctgca    960
gaactgggtg gcatgtcctc tcttaccccag ctggatctat cttataatga tctacaaggc   1020
aaaattccaa tggatggagt atttagaaat gcttcagctg tctcacttgt tggcaactcg    1080
agactctgtg gtggtctgtc agatttgcac atgcccccct gccctcttgc cttaaaggaa    1140
aaggcagcac aatactacac cattagagtg ttcatcccaa tatttcgctt catctcactc    1200
ttgatgttgc atggcagtgg gaatgtcagg aaacctttgg acttaaatca agaacaagc     1260 ttagctacca acatagctaa cgtacttgat tatctgcaca acgaatgtgg gaaaacaatt    1320
atccattgtg atgtcaagcc cagtaacata ctcctcgatg atgacatgaa tgcccgtttg    1380
ggagacttcg gcattgcaaa attctgtatt ggttctatgt caacatcaat tggagattca    1440
gaacctataa actcaaccgg tatgaagggt actatcggct acatgcctcc agagtatgct    1500
cgaggtggac atgcatcaac atgcggggat gtttacagtt ttggaatagt acttctagag    1560
atgcttacag ggagaaggcc aattgatcat gtgtttgtgg acgaactaaa cattgtcaaa    1620 ttcgtgggaga ggagcttccc tgataaaata ttggatgtga ttgatgtttc attacgtgat   1680
```

| | | |
|---|---|---|
| gacttcaaga gtgcccaaat aaacatggta acagagagtg agacctaccg atgcttgttt | 1740 | |
| tctctactgc aagtagcact ttcttgcaca cgtgagattc ctggtgaacg aacgaccatg | 1800 | |
| gaagaagcag ctagcagaat tggttcaatc aagaccacgt atgctaaagg aattgaaaac | 1860 | |
| gcaagcaggc attga | 1875 | |

<210> SEQ ID NO 44
<211> LENGTH: 624
<212> TYPE: PRT
<213> ORGANISM: Zea mays

<400> SEQUENCE: 44

```
Met Val Ala Ala Val Val Leu Ala Leu Leu Leu Phe Tyr Gly Thr Gly
1               5                   10                  15

Asn Ala Asn Cys Ala Thr Leu Arg Pro Ser Ser Arg Ser Ser Thr
            20                  25                  30

Asp Asp Met Leu Ser Leu Leu Asp Phe Arg Lys Glu Ile Ser Ser Asp
        35                  40                  45

Pro Gly Gly Phe Leu Arg Ser Trp Asn Thr Ser Gly Ser Ser Ala Ala
    50                  55                  60

Asp Tyr Cys Ser Trp Asn Gly Val Thr Cys Ser Arg Thr His Pro Gly
65                  70                  75                  80

Arg Val Thr Glu Leu Asn Leu Ser Ser Gln Ser Leu Gln Gly Arg Ile
                85                  90                  95

Ser Pro Ser Leu Gly Asn Leu Thr Phe Leu Arg Ile Leu Asp Leu Ser
            100                 105                 110

Tyr Asn Ser Phe Phe Gly Gln Leu Pro Leu Leu Ser Arg Pro Val Arg
        115                 120                 125

Leu Gln Asp Leu Val Leu Asn Asn Asn Gln Leu Gln Ser Phe Pro Ile
    130                 135                 140

Asp Ala Leu Thr Asn Cys Ser Ser Leu His Ala Ile Asp Leu Ser Ser
145                 150                 155                 160

Asn Met Phe Thr Gly Pro Ile Pro Ala Ser Ile Gly Ser Leu Pro Asn
                165                 170                 175

Leu Thr Tyr Leu Tyr Leu Tyr Ala Asn Ser Phe Thr Gly Ala Ile Pro
            180                 185                 190

Ser Ser Leu Leu Asn Ile Ser Lys Leu Gln Glu Leu Val Leu Ser Ser
        195                 200                 205

Asn Met Leu Ala Gly Pro Ile Pro Pro Asn Ile Gly Ser Leu Met Asn
    210                 215                 220

Leu Thr Leu Leu Tyr Leu Asp Ser Asn Asn Phe Thr Gly Ala Ile Pro
225                 230                 235                 240

Ser Ser Leu Gly Asn Ile Ser Lys Leu Gln Gln Leu Val Leu Gln Asn
                245                 250                 255

Asn Gln Leu His Gly Thr Ile Pro Gln Asp Leu Gly Asn Leu Ser Asn
            260                 265                 270

Leu Asn Ile Leu Val Leu Gly His Asn Ser Leu Ser Gly His Ile Pro
        275                 280                 285

Thr Thr Ile Leu Asn Gln Arg Ser Leu Gly Phe Leu Gly Leu Glu Ala
    290                 295                 300

Asn Leu Leu Arg Met Ala Leu Pro Ser Asn Ile Gly Ile Ile Pro Ala
305                 310                 315                 320

Glu Leu Gly Gly Met Ser Ser Leu Thr Gln Leu Asp Leu Ser Tyr Asn
                325                 330                 335
```

```
Asp Leu Gln Gly Lys Ile Pro Met Asp Val Phe Arg Asn Ala Ser
            340                 345                 350

Ala Val Ser Leu Val Gly Asn Ser Arg Leu Cys Gly Gly Leu Ser Asp
        355                 360                 365

Leu His Met Pro Pro Cys Pro Leu Ala Leu Lys Glu Lys Ala Ala Gln
    370                 375                 380

Tyr Tyr Thr Ile Arg Val Phe Ile Pro Ile Phe Arg Phe Ile Ser Leu
385                 390                 395                 400

Leu Met Leu His Gly Ser Gly Asn Val Arg Lys Pro Leu Asp Leu Asn
                405                 410                 415

Gln Arg Thr Ser Leu Ala Thr Asn Ile Ala Asn Val Leu Asp Tyr Leu
            420                 425                 430

His Asn Glu Cys Gly Lys Thr Ile Ile His Cys Asp Val Lys Pro Ser
        435                 440                 445

Asn Ile Leu Leu Asp Asp Met Asn Ala Arg Leu Gly Asp Phe Gly
    450                 455                 460

Ile Ala Lys Phe Cys Ile Gly Ser Met Ser Thr Ser Ile Gly Asp Ser
465                 470                 475                 480

Glu Pro Ile Asn Ser Thr Gly Met Lys Gly Thr Ile Gly Tyr Met Pro
                485                 490                 495

Pro Glu Tyr Ala Arg Gly Gly His Ala Ser Thr Cys Gly Asp Val Tyr
            500                 505                 510

Ser Phe Gly Ile Val Leu Leu Glu Met Leu Thr Gly Arg Arg Pro Ile
        515                 520                 525

Asp His Val Phe Val Asp Glu Leu Asn Ile Val Lys Phe Val Glu Arg
    530                 535                 540

Ser Phe Pro Asp Lys Ile Leu Asp Val Ile Asp Val Ser Leu Arg Asp
545                 550                 555                 560

Asp Phe Lys Ser Ala Gln Ile Asn Met Val Thr Glu Ser Glu Thr Tyr
                565                 570                 575

Arg Cys Leu Phe Ser Leu Leu Gln Val Ala Leu Ser Cys Thr Arg Glu
            580                 585                 590

Ile Pro Gly Glu Arg Thr Thr Met Glu Glu Ala Ala Ser Arg Ile Gly
        595                 600                 605

Ser Ile Lys Thr Thr Tyr Ala Lys Gly Ile Glu Asn Ala Ser Arg His
    610                 615                 620

<210> SEQ ID NO 45
<211> LENGTH: 5490
<212> TYPE: DNA
<213> ORGANISM: Zea mays
<220> FEATURE:
<221> NAME/KEY: misc_feature
<222> LOCATION: (4112)..(4112)
<223> OTHER INFORMATION: n is a, c, g, or t
<220> FEATURE:
<221> NAME/KEY: misc_feature
<222> LOCATION: (4219)..(4219)
<223> OTHER INFORMATION: n is a, c, g, or t
<220> FEATURE:
<221> NAME/KEY: misc_feature
<222> LOCATION: (4266)..(4266)
<223> OTHER INFORMATION: n is a, c, g, or t
<220> FEATURE:
<221> NAME/KEY: misc_feature
<222> LOCATION: (4300)..(4300)
<223> OTHER INFORMATION: n is a, c, g, or t
<220> FEATURE:
<221> NAME/KEY: misc_feature
<222> LOCATION: (4313)..(4313)
<223> OTHER INFORMATION: n is a, c, g, or t
```

```
<220> FEATURE:
<221> NAME/KEY: misc_feature
<222> LOCATION: (4326)..(4326)
<223> OTHER INFORMATION: n is a, c, g, or t
<220> FEATURE:
<221> NAME/KEY: misc_feature
<222> LOCATION: (4334)..(4334)
<223> OTHER INFORMATION: n is a, c, g, or t
<220> FEATURE:
<221> NAME/KEY: misc_feature
<222> LOCATION: (4340)..(4340)
<223> OTHER INFORMATION: n is a, c, g, or t
<220> FEATURE:
<221> NAME/KEY: misc_feature
<222> LOCATION: (4376)..(4376)
<223> OTHER INFORMATION: n is a, c, g, or t
<220> FEATURE:
<221> NAME/KEY: misc_feature
<222> LOCATION: (4508)..(4508)
<223> OTHER INFORMATION: n is a, c, g, or t
<220> FEATURE:
<221> NAME/KEY: misc_feature
<222> LOCATION: (4516)..(4517)
<223> OTHER INFORMATION: n is a, c, g, or t
<220> FEATURE:
<221> NAME/KEY: misc_feature
<222> LOCATION: (4532)..(4532)
<223> OTHER INFORMATION: n is a, c, g, or t
<220> FEATURE:
<221> NAME/KEY: misc_feature
<222> LOCATION: (4570)..(4570)
<223> OTHER INFORMATION: n is a, c, g, or t

<400> SEQUENCE: 45
attcaaggtc gtttacaaaa tttaatattt caaacttgaa aacttcaaac gtatttttct      60
ataataggat gatttcaaat caaaaggttg tcaactacat agttaaataa cttttttgata   120 cctataactt tcattttggt ggttttttcaa tccgaggtca tttgaaaatt ttgaattta    180 aaattcgaac atagttttgc atgacacaat gatttcaaat aaaaaagttg tcaaccataa   240
agtttcataa cttttcagaa actacaacta tcattttttgt gttttttttat ctgagatcat  300 ttgacagaaa atgttttttaa aatttttaaat tcaaacacag ttttcgttga caaaatgact  360
acaaatcaaa aagtttccaa ctacaaaatt ttataacttc tgaagatcta caaagtttat   420
tttggttgtt ggatcatttt ttcatccaac atggtggtcc taacattctt cacaaatcta   480
tgtataagat ttgtgaacaa ttttttttta ttgtcatatg aaaaataacc caaaaaatta   540
tacatcttga tgagttatgc aaatttgtag ttttttcttg cctagtgttc ggcactagac   600
aaatcgtctt tttaccaagt attttttgcc tagtgttttt ctttgcctag tgtccagcac   660
tagacaaatc gtcttttttgc ccagtgtttt ttgtctagtg tccagtactc ggcgaagtgc  720
ctctttgcct agtgttttttc tttgcctatt gcactaccgg aatctagctc tttgcggagt  780
gccaagtgat tgccaagtg attttttttcgg gcactcggta aagaagcttt ttaccgagtg  840
taaaaaacat tcgacaacac ttctttgccg agtgccaagg gatttgccga gtgttttttc   900
cggcactcag caaagaagct ttttgccgag tataaaaaaa cactcgacaa tgcttctttg  960
ccgagtgtta tttttttgaca gtagacaaag ataattttta aatcaaattt tgaagtagta  1020
aattaattta ataaaaaaat tcaactacaa agttgtataa ctcataaaga tgtacaatat  1080
ttattttagc catttcttca tatgacaagg ttaaagtaaa tttgttcaca aaacttatat  1140
acctcttttg tagatttgtg aacaatgtta gagccaccat gttggatgaa taaataatca  1200
aacaaccaaa ataaaaattt tatatcttac aaacctatag ggtttttgtag tttgcaactt  1260 tttgatttga ggtcatcttg tcaacataaa ctatttctga actaaaattt aaaattcgaa  1320
```

-continued

```
tttgtgaaat gatggaaaaa taaccaaaat gatagttata ggtattaaaa agttatgaaa    1380
ttttgtagtt cgaatctcac cggccacaaa acatgtgaat tccatttaag aaatggtgaa    1440
aacgataggg tgatgggcag agcaatggcg atggttggtg ggttgttcct ctaatttaaa    1500
aaaatattgt ttttcgggtt tctttggcga ttcttaattt gcggcaaaaa aactctttac    1560
taataaaata tttagctagt gttatttgcc gagtgcaaaa agactttgat tttactgagt    1620
gtctaggacg cttggcaaag aaggcgagtc cgatagtggt gtagtactcg gcaagtgaca    1680
cttttgactag tgcccgtgga tttgaactcg gtaaagaatt tagtggttag tatgagctat    1740
atactagtca tgtaaatctt ctagtacata taaattgact tgacccgctg ccgtgctaga    1800
gagggcaaat catatggttg cagtgtttca cacaaaagac aatacagagg acaccactac    1860
tatcgtaagg accaaactgg atttggaccc agaagaatct tgttccggta gacgattcca    1920
tcagtaggaa ttttggcggt caagatacgg taagctatga cgacgccacg cgcgtgtgtg    1980
gacgtaattc cattgtaatg ccctttttac attgtatata aacaaccact gggccttaac    2040
tagttgagca tacaatttaa ctggatacca caaaagctcg ccgcaggtgt atacatactc    2100
tctcgccgat cgaccttacc ttaggtgctc ttcttcttct tcctcctctc ttgttaatta    2160
ttactacctc tattttttta cttgacgcta gttagtacaa ttttacacta actaacgtaa    2220
ctataaaaaa acggagggag tagcttgtta ttaattccta ccaggctagg aacattattt    2280
catgtggaca gaccttagct tgctaggtag ttcctacgta cgaacatgca tgccaatgaa    2340
gtaaacctgc ctgttgcttt gtatatatat atgttaatcg caggtactat gaagtctgcc    2400
atggttgctg ctgtagtact agccctactg ctgttctatg ggactggaaa cgccaactgc    2460
gcaacgctgc gtcccagcag cagcaggagc agcacggacg acatgctctc cctgctcgat    2520
ttcagaaagg aaatcagcag tgatccagga ggtttcctca gatcctggaa cactagtggt    2580
agtagcgccg ccgactactg cagctggaat ggcgtcacat gcagcagaac gcacccaggg    2640
cgggtcacga agctcaacct cagcagccaa agcctgcaag gccgaatctc tccatctctt    2700
ggtaacctaa ccttccttcg aatactggac ctgtcctaca acagcttctt tggccagctg    2760
ccccttctta gtcgcccgt aggcttcag gacctagttc tgaacaacaa ccagctgcaa    2820
agtttcccca ttgacgcact tacgaactgc tccagcttgc acgctataga cctttcgtcc    2880
aacatgttta ctgggccaat accagccagc atcggttctc tccctaacct tacgtacttg    2940
tacctttatg ctaatagctt cactggagcc atcccatcga gcttgctaaa catctctaaa    3000
ctacaggagc tcgtgctttc ctcaaacatg ctagctgggc caataccacc taatatcggt    3060
tccctcatga accttacact tctctacctt gattctaaca acttcactgg agccatccca    3120
tccagcctgg gaaatatctc caaactacag cagctcgtgc tccagaataa tcagctccat    3180
ggcaccatac ctcaggatct tggcaattta tcaaatctga atatattggt gctagggcat    3240
aatagtctat caggtcacat cccgacaaca attctgaacc agcgttccct tggatttctg    3300
ggcttggaag cgaatttgct acgtatggcg ttgccatcta atattggtaa tacccttcct    3360
aacatctacg cacttacctt gtacaataac atgttccatg gtccaatccc agcttcgcta    3420
ggaaatgctt cccatctcac gatattagat ttcgcatcta accaaactga acttcctaag    3480
actagaacag aacaaccttg aagcaaaaga taatgaaggc tgggaattca tagatgcact    3540
aggcaattgt atgtggctga atacctatt attatctgac aatcagctac aaggagccat    3600
accagattca gttgggaagt tgtccaatag cagccttcag tacctatatt ttggcgaaaa    3660
caacttgtcg ggagctgttc cagagagcat ggggaacctt attgccttaa atacgttagt    3720
```

```
tcttgaacaa aacaatttga acggtccgat tggatcatgg gttggaaagt tcatcaactt    3780
gacagtatta tctctctcag acaataactt cagtgggccg attccatcgt ccattggtag    3840
ccttactaag ctaacacatc tccacctaca gagcaacaaa tttgtaggtc caatacctcc    3900
cagtttgggt aaacttcaag gtttactaga actaaatctt agttataaca atctaacaag    3960
ctttgagtga atgtcgtcag ttgaatgtac tccaaatggg ctccaatttt atcacaggga    4020
acatttcgcc tctacgtagt ctaacaagct tgaacatgat caacctctca cacaatatgt    4080
tgtcagggat catccctgca gaactgggtg gnatgtcctc tcttacccag ctggatctat    4140
cttataatga tctacaaggc aaaattccaa tggatggagt atttagaaat gcttcagctg    4200
tctcacttgt tggcaactng agactctgtg gtggtctgtc agatttgcac atgccccct     4260 gccctnttgc cttaaaggaa aaggcagcac aatactacan cattagagtg ttnatcccaa    4320
tatttngctt catntcactn ttgatgttgg tatgtttcgt tctcactaag aaaagnactg    4380
cacaacaatc atcaatatct cctcttggtg accaattccc aatagtttct tataatgatt    4440
tagttcaagc tacaaatacc ttctccaatt caaatctgat agggagagga ggttgtggtt    4500
ctgtatanag agggannttg atggaaaaca anctaaaggt ggctattaaa gttcttgaca    4560
gtgacatgcn tggcgtcgag aaaagtttct tagcagaatg tgaagctttg aggaacatcc    4620
gacaccgaaa tctagtccct atcataacaa catgctcaag gttagatatc aaaggcaatg    4680
ttttcaaagc tcttgtatat gaatttatgc caaatgggaa tttggactca tggttgcatc    4740
agcatggcag tgggaatgtc aggaaaacctt tggacttaaa tcaaagaaca agcttagcta    4800
ccaacatagc taacgtactt gattatctgc acaacgaatg tgggaaaaca attatccatt    4860
gtgatgtcaa gcccagtaac atactcctcg atgatgacat gaatgcccgt ttgggagact    4920
tcggcattgc aaaattctgt attggttcta tgtcaacatc aattggagat tcagaaccta    4980
taaactcaac cggtatgaag ggtactatcg gctacatgcc tccaggtaca taacggcttt    5040
tgcaaaattc catcttttcaa ttctaggtag tatacttcga gcatgcacta attcaatgcg    5100
tctttagagt atgctcgagg tggacatgca tcaacatgcg gggatgttta cagttttgga    5160
atagtacttc tagagatgct tacagggaga aggccaattg atcatgtgtt tgtggacgaa    5220
ctaaacattg tcaaattcgt ggagaggagc ttccctgata aaatattgga tgtgattgat    5280
gtttcattac gtgatgactt caagagtgcc caaataaaca tggtaacaga gagtgagacc    5340
taccgatgct tgttttctct actgcaagta gcactttctt gcacacgtga gattcctggt    5400
gaacgaacga ccatggaaga agcagctagc agaattggtt caatcaagac cacgtatgct    5460
aaaggaattg aaaacgcaag caggcattga                                     5490
```

<210> SEQ ID NO 46
<211> LENGTH: 1870
<212> TYPE: DNA
<213> ORGANISM: Zea mays

<400> SEQUENCE: 46

```
tccataagcg ttcaaacaat gtacgcctca ttcgaaacct gcatttaaag attataagac      60
gcatgcgtac actagttttt aaaaaaaatg caaaaaaata tgtgtaatat atacataccg     120
atgtcgaaaa tagcaatgtc cgtatgtagg attctctgaa aaataatttt gatatagcct     180
atgatgccct gctattctgt ctcgccgaag gactcgatgc ccttgaatag aaccacgata     240
tttcttgtca tcatcagatt cattcgtatt cgtggccaca tgcgttacag cgagaaaata     300
```

| | | |
|---|---|---|
| atcatcatct tcctcatcta atgatgattc caatactagt tgcattgaaa ggcttagtcg | 360 | |
| agccataacc aatctagacg tcaaacaatt gttttattta taaaattcct gattacggtc | 420 | |
| aagctaagat gcaaaaactt atatcacggt ggagagaaaa aaccatactt gaaaacttgc | 480 | |
| tgtcgtgatg caatgatttg tcgatcgcgc atgaaatccc acgcggctgg cacctggtaa | 540 | |
| cggctggtgg cggctgagta cagctcccag agagttgcag cgtaaaagtc aaaaccaact | 600 | |
| atatgccgta tgcaacaaat gggatgcgat ttaggcaaaa tgggccagca attttttaaaa | 660 | |
| gttagcccag ttttatttca gttttttatt ttgaggaaac tgttggagtt accatttatt | 720 | |
| tcacccctac aaaacgttca atatgccctc cataatcagt ttttggggat tttttttttg | 780 | |
| catttcctct tggagatgct cttaataaac gacagtcacg gaaatattat tattgtattg | 840 | |
| tataaatctg atgaaacgct ttgtctaaaa gtgaaaacga cgacataaaa tgacgtcaac | 900 | |
| aatgcaaagg cagcatatgg cggaggctgt gctggacggc tgcggcgcgt tcgatatggc | 960 | |
| cgccgttcga ctacatggag aagaagaacc ctcaggtgag ccggcagtac aaccaggcca | 1020 | |
| tgtcccagat ctcggcgctg gcctgcgaca agttgctcca gctactctcc cagcggtgca | 1080 | |
| ccggcttcga cggcgacgcg ccatccgcac cgtcgttgac atggtctgcg gcaacgcggc | 1140 | |
| accgtcctgg gcatgatcac ctctaggtac aagcacatca gcggcatcaa cttcgccctc | 1200 | |
| tgacttacgt cgtcgctcag gcgaagccaa ataatacccg tctgaattcg attgggtctg | 1260 | |
| tcgatagcta gctaaatttg tttcgagatt tggctactaa caaacacggc gcatgatggt | 1320 | |
| tctattctgc ggatgatcga tgcaggcgtg gagcacgtgg gcgggaacat gctcatgctc | 1380 | |
| gatcaagtca cagtggcgac gccatcttta tgaaggtagc tagtagttgt ttgacaaatc | 1440 | |
| acaaaactag tttttatgt cgcaaaaata ttgatgaaca tgcatgtgct tgtgcagatt | 1500 | |
| cgatgtcaca tcactacagg aatccggctc tttgtcgagt gctcggcgct tcgcaaagat | 1560 | |
| ccgtactcgg caaaatccta ccctcggtaa cagccacgtt tatcgagagc atcggcacag | 1620 | |
| gaagacactc ggcaaagacc actttgcccg agtgctaaac actcggcgaa tcgagacgct | 1680 | |
| cgtcaaaggg ccgtcagcaa ccgtctatag ccgacgaccg ttaactttgc cgagcgccgg | 1740 | |
| cctttggcac tcgacacgcc aaagaagctt ctttgccgag tgtctctaga ctgacactcg | 1800 | |
| gtaaactatg ttttgacgag tgtctacctt ggacactcga caaagtatat ttttatttat | 1860 | |
| ttttcttttc | 1870 | |

<210> SEQ ID NO 47
<211> LENGTH: 325
<212> TYPE: DNA
<213> ORGANISM: Zea mays

<400> SEQUENCE: 47

| | | |
|---|---|---|
| gtatttctac cagcgtggcc ttcaccgatg ttggatggcc gacggagaca aaaccttggc | 60 | |
| acatgaactg ccctttaaca tcttcatata ccgccttggc aagtgtagtc tttcccaaac | 120 | |
| cttcctgacc taggatagac accccttca gctccttttg cccgtccatc atgagctctc | 180 | |
| taacttcaga cttgggaacc tcgagacctt tcacagcagc atcagcagaa caaaattcca | 240 | |
| gtacttgctt ggaaagctcg tacctttcac agcggcgcat agcttcctgg atctgctcct | 300 | |
| tgaattcttc gatctgcagc ttgtc | 325 | |

<210> SEQ ID NO 48
<211> LENGTH: 325
<212> TYPE: DNA
<213> ORGANISM: Zea mays

```
<400> SEQUENCE: 48
gtatttctac cagcgtggcc ttcaccgatg ttggatggcc gacggagaca aaaccttggc    60
acatgaactg ccctttaaca tcttcatata ccgccttggc aagtgtagtc tttcccaaac   120
cttcctgacc taggatagac accccttca gctccttttg cccgtccatc atgacctctc    180
taacttcaga cttgggaacc tcgagacctt tcacagcagc atcagcagaa caaaattcca   240
gtacttgctt ggaaagctcg tacctttcac agcggcgcat agcttcctgg atctgctcct   300
tgaattcttc gatctgcagc ttgtc                                        325

<210> SEQ ID NO 49
<211> LENGTH: 132
<212> TYPE: DNA
<213> ORGANISM: Zea mays

<400> SEQUENCE: 49
cttccatcgg tactccattc aagttccctc gggtcgctcc atttctttac tgacacgtga    60
aattggcaaa caatggagaa aaaaaaacta agcgcaggaa attaattata ctgatttctc   120
acacctgggg aa                                                      132

<210> SEQ ID NO 50
<211> LENGTH: 21
<212> TYPE: DNA
<213> ORGANISM: Artificial Sequence
<220> FEATURE:
<223> OTHER INFORMATION: primer MZA6393L

<400> SEQUENCE: 50
gtatttctac cagcgtggcc t                                             21

<210> SEQ ID NO 51
<211> LENGTH: 20
<212> TYPE: DNA
<213> ORGANISM: Artificial Sequence
<220> FEATURE:
<223> OTHER INFORMATION: primer MZA6393R

<400> SEQUENCE: 51
gacaagctgc agatcgaaga                                               20

<210> SEQ ID NO 52
<211> LENGTH: 20
<212> TYPE: DNA
<213> ORGANISM: Artificial Sequence
<220> FEATURE:
<223> OTHER INFORMATION: primer 1M2-9L

<400> SEQUENCE: 52
tcgtgacgga cctgtagtgc                                               20

<210> SEQ ID NO 53
<211> LENGTH: 20
<212> TYPE: DNA
<213> ORGANISM: Artificial Sequence
<220> FEATURE:
<223> OTHER INFORMATION: primer 1M2-9R

<400> SEQUENCE: 53
tcgcggttca gaagaacaac                                               20

<210> SEQ ID NO 54
```

<211> LENGTH: 618
<212> TYPE: DNA
<213> ORGANISM: Zea mays

<400> SEQUENCE: 54

```
tcgtgacgga cctgtagtgc agcaagaact caaagtccat ccaccttgct atgacgcata    60
tgaaggcaac gacgagggag gcgcacatcg ccgaggtgtc gaagatcaag aacgcctgga   120
acgcgacctt cctagccatg attgggagcc cctcgcttcc agcatcactg ctgtaccctc   180
ctggcaatgt gaaagctgca gcgaaggtaa tcgtcgctat gaggatagcc actaaggacg   240
tgttgcttgt gtatgtttgg atcagagact tggcatcttt ccttgttgta tcgattactt   300
tgttcctgat ctcctcttgg aaattgtaga tgtcagtttc agctctacga tccgcattca   360
gtatgaggca gcagattttg ttctgcatat atgcatggat tcaatcaaaa aaagttaggc   420
accatctgaa ttaatgaagc aatctcatac attacataca gaaatacata catacccagt   480
ttatagtctt gacgtagtcc ccatcatggt acagattcca gatcgctgtg caattacgct   540
ggttgacaac ggtgatgtcg atgtcagggt gatccagcaa agcacggacc atcctcgggt   600
tgttcttctg aaccgcga                                                 618
```

<210> SEQ ID NO 55
<211> LENGTH: 759
<212> TYPE: DNA
<213> ORGANISM: Zea mays

<400> SEQUENCE: 55

```
tcgtgacgga cctgtagtgc agcaagaact caaagtccat ccaccttgct atgacgcata    60
tgaaggcaac gacgagggag gcgcacatcg ccgaggtgtc gaagatcaag aacgcctgga   120
acgcgacctt cctagccatg attgggagcc cctcgcttcc agcatcactg ctgtaccctc   180
ctggcaatgt gaaagctgca gcgaaggtaa tcgtcgctat gaggatagcc actaaggacg   240
tgttgcttgt gtatgtttgg atcagagact tggcatcttt ccttgttgta tcgattactt   300
tgttcctgat ctcctcttgg aaattgtaga tgtcagtttc agctctacga tccgcattca   360
gtatgaggca gcagattttg ttctgcatat atgcatggat tcaatcaaaa aaagttaggc   420
accatctgaa ttaatgaagc aatctcatac attacataca gaaatacata catacccagt   480
ttagggcttg ttcggttagc tctcaatcca tgtggattga gcgggattgg atgggtttga   540
atcccaaaca agtcaaactt cttcacaatt ttttccaatc ccatccaatc catgtgtatt   600
gggaataacc gaacaagccc ttatagtctt gacgtagtcc cccatcatgg tacagattcc   660
agatcgctgt gcaattacgc tggctgacaa cggtgatgtc gatgtcaggg tgatccagca   720
aagcacggac catcctcggg ttgttcttct gaaccgcga                          759
```

<210> SEQ ID NO 56
<211> LENGTH: 20
<212> TYPE: DNA
<213> ORGANISM: Artificial Sequence
<220> FEATURE:
<223> OTHER INFORMATION: primer E6765-3L

<400> SEQUENCE: 56

```
catgtgccga ccgaccattc                                                20
```

<210> SEQ ID NO 57
<211> LENGTH: 20
<212> TYPE: DNA
<213> ORGANISM: Artificial Sequence

```
<220> FEATURE:
<223> OTHER INFORMATION: primer E6765-3R

<400> SEQUENCE: 57
ggagtgcgat gtctacagct                                                    20

<210> SEQ ID NO 58
<211> LENGTH: 426
<212> TYPE: DNA
<213> ORGANISM: Zea mays

<400> SEQUENCE: 58
catgtgccga ccgaccattc ttattgcttg cttcgcttcc attcatctgc gtgcttcgaa        60
ctcgcttgag agctgcagag gccattattt tatatatgtg tacccagcag tagtaccttc       120
actcgcttaa gctcctcgac aacctctgcc atggttggcc tctccctctt gtcttccttg       180
aggcatcgga cggccaacat gccaatcatg tcgaggcaac gcttgttgca tcgagattga       240
gtatcctcgc ctgagaaatc aagtctgcta tcatacatcg cacatccgct accgtggtcc       300
ttgaagcact tgacgaactc gatggggagg atcttgttcc cttgctgatc ttgttcatac       360
cagctggccc ttctcctcgt gatgagctcc agaagcacca cgccgaagct gtagacatcg       420
cactcc                                                                  426

<210> SEQ ID NO 59
<211> LENGTH: 20
<212> TYPE: DNA
<213> ORGANISM: Artificial Sequence
<220> FEATURE:
<223> OTHER INFORMATION: primer 2M4-1L

<400> SEQUENCE: 59
cacgttgtga ctcaagatcg                                                    20

<210> SEQ ID NO 60
<211> LENGTH: 20
<212> TYPE: DNA
<213> ORGANISM: Artificial Sequence
<220> FEATURE:
<223> OTHER INFORMATION: primer 2M4-1R

<400> SEQUENCE: 60
atcaaggacc atcagcacag                                                    20

<210> SEQ ID NO 61
<211> LENGTH: 573
<212> TYPE: DNA
<213> ORGANISM: Zea mays

<400> SEQUENCE: 61
cacgttgtga ctcaagatcg agggtcgcct gcagtattat acttcattca tgtttgctga        60
ttaattcatg atagttgttg cttcatgtcg ttgcaggtta agggactcct gagctgtttc       120
actgcttatg tgaaagatga tggagttaag ttgttgatta tgaaggtatc tagctctcgt       180
accacacaga tcgtttgaac tgtaataatt gatcaatatt ttacaagttt tgatatcatc       240
tataccaaag ctgtagtttt caacgcaacc tgtgcaactt tagagttcac aagttataga       300
atcgagagac atgtcagtct caactataca tttcagaatt cgtatttgtt tttaatcttc       360
ttactatctt ggacgaagaa tgcatccttt agcataatat attgttgagc tcaatgacac       420
ctatataagc tacgcggtga aacaatttta atttggaatc atataatttc aggtctaaaa       480
```

```
tattcaccgc aaaattatgt aatgtagtaa aaaagatata gtatcatgcc atatatatga    540
ttattctgcg cagctgtgct gatggtcctt gat                                573

<210> SEQ ID NO 62
<211> LENGTH: 20
<212> TYPE: DNA
<213> ORGANISM: Artificial Sequence
<220> FEATURE:
<223> OTHER INFORMATION: primer 2M10-5L

<400> SEQUENCE: 62
cctcctctcc atctggtcca                                                20

<210> SEQ ID NO 63
<211> LENGTH: 20
<212> TYPE: DNA
<213> ORGANISM: Artificial Sequence
<220> FEATURE:
<223> OTHER INFORMATION: primer 2M10-5R

<400> SEQUENCE: 63
cgtgtgcttg gaagaatctc                                                20

<210> SEQ ID NO 64
<211> LENGTH: 589
<212> TYPE: DNA
<213> ORGANISM: Zea mays

<400> SEQUENCE: 64
cctcctctcc atctggtcca ttacgccgcc atcggtccgc ctcccctcca tctttcatct    60
catttgatct ggtgtaggtg gtgctacggg tggacaccgc cgccgaggac ttgtcggatt   120
tgttagacat gagagaccgc gcaccacttc atctgcaaac cagtggatct agtaagcaca   180
tgtacatcac tcgggtatac ctgatccacg attcagtcgt catgtcttcg atttctaggg   240
gcttgagttc tgcgcccaa actgattctt tgttgtttca tcacaggtct gtgcccctgt    300
cgtattacct gtcccattag aggttggtag acggcatgcg tctacagtgg ttacatgcgt   360
aaccatagtt ggtgaatctt cgacaaggcc gcggtcttct tatccatgta cacccgtatg   420
cctgagcggg gtaggtacgc gcattgaatg ccgctgtccc ctgacggcct ttgggtgagc   480
ctcgttccag gttttgtcct tgtcgtccga ggtgggctca agcgaggtga actttgctgt   540
ccagggatgt ggggaccttg gtccggacgg agattcttcc aagcacacg               589

<210> SEQ ID NO 65
<211> LENGTH: 20
<212> TYPE: DNA
<213> ORGANISM: Artificial Sequence
<220> FEATURE:
<223> OTHER INFORMATION: primer 2M11-3L

<400> SEQUENCE: 65
tggacagacc ttagcttgct                                                20

<210> SEQ ID NO 66
<211> LENGTH: 20
<212> TYPE: DNA
<213> ORGANISM: Artificial Sequence
<220> FEATURE:
<223> OTHER INFORMATION: primer 2M11-3R

<400> SEQUENCE: 66
gttcgtaagt gcgtcaatgg                                                20
```

<210> SEQ ID NO 67
<211> LENGTH: 563
<212> TYPE: DNA
<213> ORGANISM: Zea mays

<400> SEQUENCE: 67

```
tggacagacc ttagcttgct aggtagttcc tacgtacgaa catgcatgcc aatgaagtaa      60
acctgcctgt tgctttgtat atatatatgt taatcgcagg tactatgaag tctgccatgg     120
ttgctgctgt agtactagcc ctactgctgt tctatgggac tggaaacgcc aactgcgcaa     180
cgctgcgtcc cagcagcagc aggagcagca cggacgacat gctctccctg ctcgatttca     240
gaaaggaaat cagcagtgat ccaggaggtt cctcagatc ctggaacact agtggtagta      300
gcgccgccga ctactgcagc tggaatggcg tcacatgcag cagaacgcac ccagggcggg     360
tcacggagct caacctcagc agccaaagcc tgcaaggccg aatctctcca tctcttggta     420
acctaacctt cctttcgaata ctggacctgt cctacaacag cttctttggc cagctgcccc    480
ttcttagtcg ccccgttagg cttcaggacc tagttctgaa caacaaccag ctgcaaagtt     540
tccccattga cgcacttacg aac                                              563
```

<210> SEQ ID NO 68
<211> LENGTH: 20
<212> TYPE: DNA
<213> ORGANISM: Artificial Sequence
<220> FEATURE:
<223> OTHER INFORMATION: primer 3M1-25L

<400> SEQUENCE: 68

```
gctagatagc tgcttcttcc                                                   20
```

<210> SEQ ID NO 69
<211> LENGTH: 20
<212> TYPE: DNA
<213> ORGANISM: Artificial Sequence
<220> FEATURE:
<223> OTHER INFORMATION: primer 3M1-25R

<400> SEQUENCE: 69

```
gtacctacga ttcggcagaa                                                   20
```

<210> SEQ ID NO 70
<211> LENGTH: 328
<212> TYPE: DNA
<213> ORGANISM: Zea mays

<400> SEQUENCE: 70

```
gctagatagc tgcttcttcc atggtcgttc attcaccagg aatttcacgc acgtgtgcaa      60
gaaagtgcta cttgcagtgt actagaaaac aagcatcggt aggcctagct cactcgatct     120
ctattaccaa ctaatggact atggaatggg cccactgaag ttattgtctg aaagagataa     180
tcttaccaag ttgttcaact ttccaaccca tgatccaatc agaccgttca aattgttttg     240
ttctagatct aacgtattta aggcaataag gttccccatg ctctccggaa cagctcccga     300
caagttgttt ctgccgaatc gtaggtac                                         328
```

<210> SEQ ID NO 71
<211> LENGTH: 468
<212> TYPE: DNA
<213> ORGANISM: Zea mays

<400> SEQUENCE: 71

```
gctagatagc tgcttcttcc atggtcgttc attcaccagg aatttcacgc acgtgtgcaa    60
gaaagtgcta cttgcagtgt actagaaaac aagcatcggt aggcctagct cactcgatct   120
ctattaccaa ctaatggact atggaatggg cccactgaag ttattgtctg aaagagataa   180
tcttaccaag ttgttcaact ttccaaccca tgatccaatc agaccgttca gggcttgttc   240
ggttagctct caatccatgt ggattgagcg ggattggatg ggtttgaatc ccaaacagct   300
caaacttctt cacaattttt tccaatctca tccaatccat gtgtattggg aataaccgaa   360
caagccctca aattgttttg ttctagatct aacgtattta aggcaataag gttccccatg   420
ctctccggaa cagctcccga caagttgttt ctgccgaatc gtaggtac                468
```

<210> SEQ ID NO 72
<211> LENGTH: 20
<212> TYPE: DNA
<213> ORGANISM: Artificial Sequence
<220> FEATURE:
<223> OTHER INFORMATION: primer STS148-1L

<400> SEQUENCE: 72

```
cttccatcgg tactccattc                                                20
```

<210> SEQ ID NO 73
<211> LENGTH: 20
<212> TYPE: DNA
<213> ORGANISM: Artificial Sequence
<220> FEATURE:
<223> OTHER INFORMATION: primer STS148-1R

<400> SEQUENCE: 73

```
ttctccaggt gtgagaaatc                                                20
```

<210> SEQ ID NO 74
<211> LENGTH: 21
<212> TYPE: DNA
<213> ORGANISM: Artificial Sequence
<220> FEATURE:
<223> OTHER INFORMATION: primer MZA15839-4-L

<400> SEQUENCE: 74

```
gatgcaatgg aagaattcgt g                                              21
```

<210> SEQ ID NO 75
<211> LENGTH: 22
<212> TYPE: DNA
<213> ORGANISM: Artificial Sequence
<220> FEATURE:
<223> OTHER INFORMATION: primer MZA15839-4-R

<400> SEQUENCE: 75

```
tgaactcagc tttggatacc aa                                             22
```

<210> SEQ ID NO 76
<211> LENGTH: 21
<212> TYPE: DNA
<213> ORGANISM: Artificial Sequence
<220> FEATURE:
<223> OTHER INFORMATION: primer MZA18530-16-L

<400> SEQUENCE: 76

```
gtttcctcat ggcactactc t                                              21
```

```
<210> SEQ ID NO 77
<211> LENGTH: 22
<212> TYPE: DNA
<213> ORGANISM: Artificial Sequence
<220> FEATURE:
<223> OTHER INFORMATION: primer MZA18530-16-R

<400> SEQUENCE: 77
agtaaagcca cacatcttat tc                                              22

<210> SEQ ID NO 78
<211> LENGTH: 20
<212> TYPE: DNA
<213> ORGANISM: Artificial Sequence
<220> FEATURE:
<223> OTHER INFORMATION: primer MZA5473-801-L

<400> SEQUENCE: 78
cccatgatgg ctacattctg                                                 20

<210> SEQ ID NO 79
<211> LENGTH: 20
<212> TYPE: DNA
<213> ORGANISM: Artificial Sequence
<220> FEATURE:
<223> OTHER INFORMATION: primer MZA5473-801-R

<400> SEQUENCE: 79
cagaggcttg cgttaacaac                                                 20

<210> SEQ ID NO 80
<211> LENGTH: 20
<212> TYPE: DNA
<213> ORGANISM: Artificial Sequence
<220> FEATURE:
<223> OTHER INFORMATION: primer MZA16870-15-L

<400> SEQUENCE: 80
atttcagcgt ttgcggtgtc                                                 20

<210> SEQ ID NO 81
<211> LENGTH: 22
<212> TYPE: DNA
<213> ORGANISM: Artificial Sequence
<220> FEATURE:
<223> OTHER INFORMATION: primer MZA16870-15-R

<400> SEQUENCE: 81
ataatgaagt tgacctaagt cc                                              22

<210> SEQ ID NO 82
<211> LENGTH: 20
<212> TYPE: DNA
<213> ORGANISM: Artificial Sequence
<220> FEATURE:
<223> OTHER INFORMATION: primer MZA4087-19-L

<400> SEQUENCE: 82
agctaaacag cggatgactg                                                 20

<210> SEQ ID NO 83
<211> LENGTH: 22
<212> TYPE: DNA
<213> ORGANISM: Artificial Sequence
<220> FEATURE:
<223> OTHER INFORMATION: primer MZA4087-19-R
```

```
<400> SEQUENCE: 83
caaacatgca aagaatgagg tt                                              22

<210> SEQ ID NO 84
<211> LENGTH: 18
<212> TYPE: DNA
<213> ORGANISM: Artificial Sequence
<220> FEATURE:
<223> OTHER INFORMATION: primer MZA158-30-L

<400> SEQUENCE: 84
ccaccaccgg ccccagta                                                   18

<210> SEQ ID NO 85
<211> LENGTH: 22
<212> TYPE: DNA
<213> ORGANISM: Artificial Sequence
<220> FEATURE:
<223> OTHER INFORMATION: primer MZA158-30-R

<400> SEQUENCE: 85
aaagtgatac ataaggcaca ca                                              22

<210> SEQ ID NO 86
<211> LENGTH: 21
<212> TYPE: DNA
<213> ORGANISM: Artificial Sequence
<220> FEATURE:
<223> OTHER INFORMATION: primer MZA15493-15-L

<400> SEQUENCE: 86
gataattggg aatgggcaga t                                               21

<210> SEQ ID NO 87
<211> LENGTH: 22
<212> TYPE: DNA
<213> ORGANISM: Artificial Sequence
<220> FEATURE:
<223> OTHER INFORMATION: primer MZA15493-15-R

<400> SEQUENCE: 87
agaaatatcc tcatcctcaa tg                                              22

<210> SEQ ID NO 88
<211> LENGTH: 20
<212> TYPE: DNA
<213> ORGANISM: Artificial Sequence
<220> FEATURE:
<223> OTHER INFORMATION: primer MZA9967-11-L

<400> SEQUENCE: 88
tttccggttt tggtggacga                                                 20

<210> SEQ ID NO 89
<211> LENGTH: 21
<212> TYPE: DNA
<213> ORGANISM: Artificial Sequence
<220> FEATURE:
<223> OTHER INFORMATION: primer MZA9967-11-R

<400> SEQUENCE: 89
cgtccgactc attatacatc a                                               21

<210> SEQ ID NO 90
<211> LENGTH: 18
```

```
<212> TYPE: DNA
<213> ORGANISM: Artificial Sequence
<220> FEATURE:
<223> OTHER INFORMATION: primer MZA1556-23-L

<400> SEQUENCE: 90
tgtgctccct ggtccgcc                                                 18

<210> SEQ ID NO 91
<211> LENGTH: 19
<212> TYPE: DNA
<213> ORGANISM: Artificial Sequence
<220> FEATURE:
<223> OTHER INFORMATION: primer MZA1556-23-R

<400> SEQUENCE: 91
tcaagtgccc ctagctcct                                                19

<210> SEQ ID NO 92
<211> LENGTH: 18
<212> TYPE: DNA
<213> ORGANISM: Artificial Sequence
<220> FEATURE:
<223> OTHER INFORMATION: primer MZA1556-801-L

<400> SEQUENCE: 92
tgtgctccct ggtccgcc                                                 18

<210> SEQ ID NO 93
<211> LENGTH: 19
<212> TYPE: DNA
<213> ORGANISM: Artificial Sequence
<220> FEATURE:
<223> OTHER INFORMATION: primer MZA1556-801-R

<400> SEQUENCE: 93
tcaagtgccc ctagctcct                                                19

<210> SEQ ID NO 94
<211> LENGTH: 19
<212> TYPE: DNA
<213> ORGANISM: Artificial Sequence
<220> FEATURE:
<223> OTHER INFORMATION: primer MZA17365-10-L

<400> SEQUENCE: 94
cctatggctg gttgctctt                                                19

<210> SEQ ID NO 95
<211> LENGTH: 21
<212> TYPE: DNA
<213> ORGANISM: Artificial Sequence
<220> FEATURE:
<223> OTHER INFORMATION: primer MZA17365-10-R

<400> SEQUENCE: 95
gccaacaagt caacatccta a                                             21

<210> SEQ ID NO 96
<211> LENGTH: 19
<212> TYPE: DNA
<213> ORGANISM: Artificial Sequence
<220> FEATURE:
<223> OTHER INFORMATION: primer MZA17365-801-L

<400> SEQUENCE: 96
```
cctatggctg gttgctctt                                        19

<210> SEQ ID NO 97
<211> LENGTH: 21
<212> TYPE: DNA
<213> ORGANISM: Artificial Sequence
<220> FEATURE:
<223> OTHER INFORMATION: primer MZA17365-801-R

<400> SEQUENCE: 97
gccaacaagt caacatccta a                                     21

<210> SEQ ID NO 98
<211> LENGTH: 20
<212> TYPE: DNA
<213> ORGANISM: Artificial Sequence
<220> FEATURE:
<223> OTHER INFORMATION: primer MZA14192-8-L

<400> SEQUENCE: 98
tcctggaacg ccatggtact                                       20

<210> SEQ ID NO 99
<211> LENGTH: 18
<212> TYPE: DNA
<213> ORGANISM: Artificial Sequence
<220> FEATURE:
<223> OTHER INFORMATION: primer MZA14192-8-R

<400> SEQUENCE: 99
cagggacatc aagcgcca                                         18

<210> SEQ ID NO 100
<211> LENGTH: 20
<212> TYPE: DNA
<213> ORGANISM: Artificial Sequence
<220> FEATURE:
<223> OTHER INFORMATION: primer MZA15554-13-L

<400> SEQUENCE: 100
acttccgagg cgtcgcagtt                                       20

<210> SEQ ID NO 101
<211> LENGTH: 21
<212> TYPE: DNA
<213> ORGANISM: Artificial Sequence
<220> FEATURE:
<223> OTHER INFORMATION: primer MZA15554-13-R

<400> SEQUENCE: 101
atgaacactc actcactcct c                                     21

<210> SEQ ID NO 102
<211> LENGTH: 20
<212> TYPE: DNA
<213> ORGANISM: Artificial Sequence
<220> FEATURE:
<223> OTHER INFORMATION: primer MZA4454-14-L

<400> SEQUENCE: 102
atgagggttt ggaggcgtat                                       20

<210> SEQ ID NO 103
<211> LENGTH: 21
<212> TYPE: DNA
<213> ORGANISM: Artificial Sequence

```
<220> FEATURE:
<223> OTHER INFORMATION: primer MZA4454-14-R

<400> SEQUENCE: 103
ttacctcaac taagggcatc c                                                    21

<210> SEQ ID NO 104
<211> LENGTH: 1737
<212> TYPE: DNA
<213> ORGANISM: Zea mays

<400> SEQUENCE: 104
atggacgaat tcgagatgct actgcaggcg gccatcaaag gcagagccca agaactggag          60
cagctggtgc aagacaagcc tgaggtgcta taccaaacaa ctgaagcagg gaacacctgc         120
ctccacatcg ccgctctctg cggccacggg gatttctgca gcaaggtcct cgccctccgc         180
ctgacgcagg agccgagtct cccgtcgtct ctgctctcca ccgccaacga cgacggggag         240
acgccgctgc tcgtcgctgt gaagagcggc gcgtctccc tggcccttga cctgctcgag          300
cagcactcga ggcacgagct gctggacgag caccttctga agcgagacag gcacggatgc         360
aacgtcctgc accacgccat ccgcaacggc tacgacgagg cctcgcgct gcgactgatc          420 ggccggcagc ctgcgctctc ggagtcccgc agcgggcgcg gcgagtcgcc catgttcatc         480
gcggttctca aaggtttcag gagcgtctac atggcgctgc tgagcaacga gaggtcggaa         540
tacagcgggg ccaatggctc caacgccttg cacgctgctg tcaagtacgg acaccaagat         600
ttcgttgaac aacttgtgga caagcatccc gagaaggcca agtgctggc gagacaagcg          660 gacagtaaaa gggacactcc aatgcatctc actgcgcatt caacaggga taggattcta          720 acgctgatgc tgagatgtga tcggtccttg gggtacgtgc tgcacgagga cactccacg          780 cctcttcttt ccatcgccgc agaccgaggc cacgtagctt ttgctcgagc gcttctggag         840
cactgtccag atgcgcccta ccacgacgag cagggcagga catgtctcca cgaagctgta         900
gacaaggacc gggcggagtt tgttgagttc atccttgacg acaactccaa gctccggaaa         960
cttgtcaaca tgctagatag cgttgatgac agtgctctgc atctcgcggt tcagaagaac        1020
aacccgagga tggtccgtgc tttgctggat cacccctgaca tcgacatcac cgttgtcaac       1080
cagcgtaatt gcacagcgat ctggaatctg taccatgatg gggactacgt caagactata        1140
aactggaaca aaatctgctg cctcatactg aatgcggatc gtagagctga aactgacatc        1200 tacaattt cc aagaggagat caggaacaaa gtaatcgata caacaaggaa agatgccaag       1260
tctctgatcc aaacatacac aagcaacacg tccttagtgg ctatcctcat agcgacgatt        1320
accttcgctg cagctttcac attgccagga gggtacagca gtgatgctgg aagcgagggg       1380
ctcccaatca tggctaggaa ggtcgcgttc caggcgttct tgatcttcga cacctcggcg       1440
atgtgcgcct ccctcgtcgt tgccttcata tgcgtcatag caaggtggat ggactttgag      1500
ttcttgctgc actacaggtc cgtcacgacg aagctcatgt ggttcgcgta catggcaacc       1560
acccttgcat ttgcgactgg tctgtacacg gttctggaag atcgccttcc ttggctggcc      1620
attgcgatct gcgttctgtc cgtgctgctg cccgttctta cgatgctggt cggcaaatgg     1680
cccatattga agctcagaat tcgatacggt aggtctgatt tccttgacat ggtctag         1737

<210> SEQ ID NO 105
<211> LENGTH: 578
<212> TYPE: PRT
<213> ORGANISM: Zea mays
```

<400> SEQUENCE: 105

```
Met Asp Glu Phe Glu Met Leu Leu Gln Ala Ala Ile Lys Gly Arg Ala
1               5                   10                  15
Gln Glu Leu Glu Gln Leu Val Gln Asp Lys Pro Glu Val Leu Tyr Gln
            20                  25                  30
Thr Thr Glu Ala Gly Asn Thr Cys Leu His Ile Ala Ala Leu Cys Gly
        35                  40                  45
His Gly Asp Phe Cys Ser Lys Val Leu Ala Leu Arg Leu Thr Gln Glu
    50                  55                  60
Pro Ser Leu Pro Ser Ser Leu Leu Ser Thr Ala Asn Asp Asp Gly Glu
65                  70                  75                  80
Thr Pro Leu Leu Val Ala Val Lys Ser Gly Arg Val Ser Leu Ala Leu
                85                  90                  95
Asp Leu Leu Glu Gln His Ser Arg His Glu Leu Leu Asp Glu His Leu
            100                 105                 110
Leu Lys Arg Asp Arg His Gly Cys Asn Val Leu His His Ala Ile Arg
        115                 120                 125
Asn Gly Tyr Asp Glu Gly Leu Ala Leu Arg Leu Ile Gly Arg Gln Pro
    130                 135                 140
Ala Leu Ser Glu Ser Arg Ser Gly Arg Gly Glu Ser Pro Met Phe Ile
145                 150                 155                 160
Ala Val Leu Lys Gly Phe Arg Ser Val Tyr Met Ala Leu Leu Ser Asn
                165                 170                 175
Glu Arg Ser Glu Tyr Ser Gly Ala Asn Gly Ser Asn Ala Leu His Ala
            180                 185                 190
Ala Val Lys Tyr Gly His Gln Asp Phe Val Glu Gln Leu Val Asp Lys
        195                 200                 205
His Pro Glu Lys Ala Lys Val Leu Ala Arg Gln Ala Asp Ser Lys Arg
    210                 215                 220
Asp Thr Pro Met His Leu Thr Ala His Phe Asn Arg Asp Arg Ile Leu
225                 230                 235                 240
Thr Leu Met Leu Arg Cys Asp Arg Ser Leu Gly Tyr Val Leu His Glu
                245                 250                 255
Glu His Ser Thr Pro Leu Leu Ser Ile Ala Ala Asp Arg Gly His Val
            260                 265                 270
Ala Phe Ala Arg Ala Leu Leu Glu His Cys Pro Asp Ala Pro Tyr His
        275                 280                 285
Asp Glu Gln Gly Arg Thr Cys Leu His Glu Ala Val Asp Lys Asp Arg
    290                 295                 300
Ala Glu Phe Val Glu Phe Ile Leu Asp Asp Asn Ser Lys Leu Arg Lys
305                 310                 315                 320
Leu Val Asn Met Leu Asp Ser Val Asp Ser Ala Leu His Leu Ala
                325                 330                 335
Val Gln Lys Asn Asn Pro Arg Met Val Arg Ala Leu Leu Asp His Pro
            340                 345                 350
Asp Ile Asp Ile Thr Val Val Asn Gln Arg Asn Cys Thr Ala Ile Trp
        355                 360                 365
Asn Leu Tyr His Asp Gly Asp Tyr Val Lys Thr Ile Asn Trp Asn Lys
    370                 375                 380
Ile Cys Cys Leu Ile Leu Asn Ala Asp Arg Arg Ala Glu Thr Asp Ile
385                 390                 395                 400
Tyr Asn Phe Gln Glu Glu Ile Arg Asn Lys Val Ile Asp Thr Thr Arg
                405                 410                 415
```

Lys Asp Ala Lys Ser Leu Ile Gln Thr Tyr Thr Ser Asn Thr Ser Leu
            420                 425                 430

Val Ala Ile Leu Ile Ala Thr Ile Thr Phe Ala Ala Ala Phe Thr Leu
        435                 440                 445

Pro Gly Gly Tyr Ser Ser Asp Ala Gly Ser Glu Gly Leu Pro Ile Met
    450                 455                 460

Ala Arg Lys Val Ala Phe Gln Ala Phe Leu Ile Phe Asp Thr Ser Ala
465                 470                 475                 480

Met Cys Ala Ser Leu Val Val Ala Phe Ile Cys Val Ile Ala Arg Trp
                485                 490                 495

Met Asp Phe Glu Phe Leu Leu His Tyr Arg Ser Val Thr Thr Lys Leu
            500                 505                 510

Met Trp Phe Ala Tyr Met Ala Thr Thr Leu Ala Phe Ala Thr Gly Leu
        515                 520                 525

Tyr Thr Val Leu Glu Asp Arg Leu Pro Trp Leu Ala Ile Ala Ile Cys
    530                 535                 540

Val Leu Ser Val Leu Leu Pro Val Leu Thr Met Leu Val Gly Lys Trp
545                 550                 555                 560

Pro Ile Leu Lys Leu Arg Ile Arg Tyr Gly Arg Ser Asp Phe Leu Asp
                565                 570                 575

Met Val

<210> SEQ ID NO 106
<211> LENGTH: 1924
<212> TYPE: DNA
<213> ORGANISM: Zea mays

<400> SEQUENCE: 106

| | | |
|---|---|---|
| atggacgaat tcgagatgct actgcaggcg gccatcaaag gcagagccca agaactggag | 60 |
| cagctggtgc aagacaagcc tgaggtgcta taccaaacaa ctgaagcagg gaacacctgc | 120 |
| ctccacatcg ccgctctctg cggccacggg gatttctgca gcaaggtcct cgccctccgc | 180 |
| ctgacgcagg agccgagtct cccgtcgtct ctgctctcca ccgccaacga cgacggggag | 240 |
| acgccgctgc tcgtcgctgt gaagagcggc cgcgtctccc tggcccttga cctgctcgag | 300 |
| cagcactcga ggcacgagct gctggacgag caccttctga agcgagacag gcacggatgc | 360 |
| aacgtcctgc accacgccat ccgcaacggc tacgacgagg gcctcgcgct gcgactgatc | 420 |
| ggccggcagc ctgcgctctc ggagtcccga gcgggcgcg gcgagtcgcc catgttcatc | 480 |
| gcggttctca aggtttcag gagcgtctac atggcgctgc tgagcaacga gaggtcggaa | 540 |
| tacagcgggg ccaatggctc caacgccttg cacgctgctg tcaagtacgg acaccaaggt | 600 |
| acctgctgca gatgcttgct cttcatgcat tttttttccc tcttcgtctc ttgcttaaaa | 660 |
| gccaaaaccg cgaaactaac ttgttttttc agatttcgtt gaacaacttg tggacaagca | 720 |
| tcccgagaag gccaaagtgc tggcgagaca agcggacagt aaaagggaca ctccaatgca | 780 |
| tctcactgcg catttcaaca gggataggat tctaacgctg atgctgagat gtgatcggtc | 840 |
| cttggggtac gtgctgcacg aggaacactc cacgcctctt ctttccatcg ccgcagaccg | 900 |
| aggccacgta gcttttgctc gagcgcttct ggagcactgt ccagatgcgc cctaccacga | 960 |
| cgagcagggc aggacatgtc tccacgaagc tgtagacaag gaccgggcgg agtttgttga | 1020 |
| gttcatcctt gacgacaact ccaagctccg gaaacttgtc aacatgctag atagcgttga | 1080 |
| tgacagtgct ctgcatctcg cggttcagaa gaacaaccgg aggatggtcc gtgctttgct | 1140 |

-continued

```
ggatcaccct gacatcgaca tcaccgttgt caaccagcgt aattgcacag cgatctggaa      1200
tctgtaccat gatggggact acgtcaagac tataaactgg gtatgtatgt atttctgtat      1260
gtaatgtatg agattgcttc attaattcag atggtgccta actttttttg attgaatcca      1320
tgcatatatg cagaacaaaa tctgctgcct catactgaat gcggatcgta gagctgaaac      1380
tgacatctac aatttccaag aggagatcag gaacaaagta atcgatacaa caaggaaaga      1440
tgccaagtct ctgatccaaa catacacaag caacacgtcc ttagtggcta tcctcatagc      1500
gacgattacc ttcgctgcag cttttcacatt gccaggaggg tacagcagtg atgctggaag      1560
cgaggggctc ccaatcatgg ctaggaaggt cgcgttccag cgttcttga tcttcgacac       1620 ctcggcgatg tgcgcctccc tcgtcgttgc cttcatatgc gtcatagcaa ggtggatgga      1680 cttttgagttc ttgctgcact acaggtccgt cacgacgaag ctcatgtggt tcgcgtacat     1740
ggcaaccacc cttgcatttg cgactggtct gtacacggtt ctggaagatc gccttccttg      1800
gctggccatt gcgatctgcg ttctgtccgt gctgctgccc gttcttacga tgctggtcgg      1860
caaatggccc atattgaagc tcagaattcg atacggtagg tctgatttcc ttgacatggt      1920
ctag                                                                   1924
```

<210> SEQ ID NO 107
<211> LENGTH: 627
<212> TYPE: DNA
<213> ORGANISM: Zea mays

<400> SEQUENCE: 107

```
atggacgtcg tcggctgtgc tgctgctggt ggtggcgatt caaagcagct cttggttgaa       60
acagatggga acacacgcac gcttattttg aacaggccaa accagctgaa tgtactctcc      120
cctgcaatgg ttaagggact cctgagctgt ttcactgctt atgtgaaaga tgatggagtt      180
aagttgttga ttatgaaggg ttctggaaga gcattttgtg ctggaggtga tgttgttgct      240
ggtgtccaga caataaataa tggagagtat gttgctcttg ttggtgctag attggatggt      300
gctgaaatgc ttgcatgtgg tctcgcaact cattttgtcc cttcaaatga ggaagtggcc      360
tcaaattcag caagcaaatg ggctgctcag acaattcaat atctgaaaaa ggcttctcct      420
actagtctga aaatcacatt gagatcggga tgtagggcta tctagtaga taaagataaa      480 aatccaaagt ggatgcctcc aatgttggaa caagtgcatg atgatgcagt tgaagagtat      540
ttctctaggg ttgatgttcc agagtgggaa gatttggacc tacctgtcat gtgttcaaat      600
ggaagaatta tggagtccaa gctttga                                         627
```

<210> SEQ ID NO 108
<211> LENGTH: 208
<212> TYPE: PRT
<213> ORGANISM: Zea mays

<400> SEQUENCE: 108

```
Met Asp Val Val Gly Cys Ala Ala Ala Gly Gly Gly Asp Ser Lys Gln
1               5                   10                  15

Leu Leu Val Glu Thr Asp Gly Asn Thr Arg Thr Leu Ile Leu Asn Arg
            20                  25                  30

Pro Asn Gln Leu Asn Val Leu Ser Pro Ala Met Val Lys Gly Leu Leu
        35                  40                  45

Ser Cys Phe Thr Ala Tyr Val Lys Asp Asp Gly Val Lys Leu Leu Ile
    50                  55                  60

Met Lys Gly Ser Gly Arg Ala Phe Cys Ala Gly Gly Asp Val Val Ala
```

```
                65                  70                  75                  80
Gly Val Gln Thr Ile Asn Asn Gly Glu Tyr Val Ala Leu Val Gly Ala
                    85                  90                  95

Arg Leu Asp Gly Ala Glu Met Leu Ala Cys Gly Leu Ala Thr His Phe
                100                 105                 110

Val Pro Ser Asn Glu Glu Val Ala Ser Asn Ser Ala Ser Lys Trp Ala
                115                 120                 125

Ala Gln Thr Ile Gln Tyr Leu Lys Lys Ala Ser Pro Thr Ser Leu Lys
            130                 135                 140

Ile Thr Leu Arg Ser Gly Cys Arg Ala Ile Leu Val Asp Lys Asp Lys
145                 150                 155                 160

Asn Pro Lys Trp Met Pro Pro Met Leu Glu Gln Val His Asp Asp Ala
                165                 170                 175

Val Glu Glu Tyr Phe Ser Arg Val Asp Val Pro Glu Trp Glu Asp Leu
                180                 185                 190

Asp Leu Pro Val Met Cys Ser Asn Gly Arg Ile Met Glu Ser Lys Leu
                195                 200                 205

<210> SEQ ID NO 109
<211> LENGTH: 5072
<212> TYPE: DNA
<213> ORGANISM: Zea mays
<220> FEATURE:
<221> NAME/KEY: misc_feature
<222> LOCATION: (2491)..(2510)
<223> OTHER INFORMATION: n is a, c, g, or t

<400> SEQUENCE: 109
atggacgtcg tcggctgtgc tgctgctggt ggtggcgatt caaagcaggt tcgtacgtac      60 gttgccccctt tcaattgcag ttttttttcc aactacaggt gcattgttcc gtacactacc     120
ggaatccgcg cctttgccga gtgtgaaagt atttgtctga gtgcttttta tcgggcactc     180
ggcaaagagc tctcggcaca gggactggcg gtggggcccc ctggacctgt tttttgccga     240
gggccccaca ctcagcaaaa ttggtctctt tgccgagtgc acggacggc acttggcaaa      300 ggatccgtca ccgtcacttg gcgcccgtga cggtgacttt tctttgccga gtgcccgaca     360
aaaagtactc ggcaaagaga ctgttgccga tgtacagttc gccgagcgtt ctttgccgag     420
tgttacactc ggcaaaacct tgccgagtg taaaatagcc tttgccgtgt gtctcaggag     480
ctgattccgg tagtggtata tatatatatg gagatgaaga actcattcat atatatattt      540
atttcctcta ttttctagct cttggttgaa acagatggga acacacgcac gcttattttg     600
aacaggccaa accagctgaa tgtactctcc cctgcaatgg tacgtacacg ttgtgactca     660
agatcgaggg tcgcctgcag tattatactt cattcatgtt tgctgattaa ttcatgatag     720
ttgttgcttc atgtcgttgc aggttaaggg actcctgagc tgtttcactg cttatgtgaa     780
agatgatgga gttaagttgt tgattatgaa ggtatctagc tctcgtacca cacagatcgt     840
ttgaactgta ataattgatc aatattttac aagtttgat atcatctata ccaaagctgt      900
agttttcaac gcaacctgtg caactttaga gttcacaagt tatagaatcg agagacatgt     960
cagtctcaac tatacatttc agaattcgta tttgttttta atcttcttac tatcttggac    1020
gaagaatgca tcctttagca taatatattg ttgagctcaa tgacacctat ataagctacg    1080
cggtgaaaca ttttaatttt ggaatcatat aatttcaggt ctaaaatatt caccgcaaaa    1140
ttatgtaatg tagtaaaaaa gatatagtat catgccatat atatgattat tctgcgcagc    1200
tgtgctgatg gtccttgatt taaccttcag agacactttt tttggatttt gtggaaatcg    1260
```

```
ttaactgagg gcctcttaac acgacagcgt ccatgaatgg caatactata catgttgcat    1320
gcctttgtta gagtaagtat agtaacagag tataagaagt ctaaatgctg tgttggagga    1380
cagagaagat gagacagagg agaatcagac tattatgatc tcacaatcga tttagatacg    1440
agaacaaaaa aaaaacctga cgagagagac aagttaatca tacattaata ataaagagct    1500
aactattata caagtggtgg ttgcaacaat cactgcagct atcagttggc tatatcatta    1560
gcctttgctc tttgttgatt agcggaggtt gcggcctcag ttaatggatt aacaaaggtg    1620
ggtagccggc ccaagacaat aatggattaa ttttatctag tagatgaaat tatttctcat    1680
ttcttgttat aagaacttct aaaacttaca caataacaac tataatttta ctatctatag    1740
gaagctatat gtcgatctta tgtttgtcat tgtattgatg tatcacatgt tttcatcgag    1800
ctatcacatg ttttcagggt tctggaagag cattttgtgc tggaggtgat gttgttgctg    1860
gtgtccagac aataaataat ggtacacaca ccttgcatcc aaaagaatg taatttcaga    1920 atttggacaa ttcagacttt ttaattttaa tcacgtttat atgaaaaaac atcaatattt    1980
atgtctctag ttaggtttat tatgaaaata tattctataa tcaacatata cttatttagc    2040
atcataaatc ttccactttt tcataaattt gttaaagttg tttgacttat tggtaattaa    2100
gagttgcatt cttttcagga tggaggacat ctaactttag ctagcctcta ccatttctat    2160
tgtccaatta tgatttattt agtattttca atggcttata tcaccttagt caaaacccat    2220
gttacatatt atatataggt ctaatgttgt tccacatgtt ttttggctgt gttgtgtgct    2280
tatttgataa attagaagga tggaaattgg gcgctgattt cttccgagat caatattttt    2340
taaactacat aattgcaaca tgcatcaaac ctcaggtgac cttcatctct tcatcatagt    2400
gattcaatgt aattatttgc ttctctgctc attgcatcta aatgatagac gatttaacta    2460
caggtttctc ttcttgctgg aattgtcatg nnnnnnnnnn nnnnnnnnnn ggggtgtttg    2520
tttgggatta taatctacct agattatata atccaataac ttttggacta agagttagtt    2580
aaaaaattat tggattatat aatctaggta gattataatc ccaaacaaac acccacttaa    2640
ttatggtaca aaccttttcg tgcgcttgat cggtgccagt agttcttctt ctcatttgga    2700
atatagagaa tcttgcatta ttttcattgg aaaaatcatt atattttgat atgccaaaat    2760
caatgttatc ttggacacta aacgctaaat gaccactcgc ccaccattta ttgtttagat    2820
agtttagata atgactagat agtatgaaca ccttacatta cagcagtaaa tatacatatg    2880
aattataatt tttgtataaa ctttttttaag tacagtttaa tgcatgaata tagttataaa    2940
agttgatata aacagtaaac aattatacat aaaggcatac acatggtcat atggacatca    3000
tttaaaacat aagcatttgt gctccttcac acaagcctaa tttcacaaaa ttaataaagt    3060
tcaccaacca cccaaacatt cgtggcttat cacctatatt attgtttaaa cacatgtttt    3120
ctgtttacat ctacttagcc atcatttaaa caaattttct aaccagtttg actgtttaga    3180 caccttagt gttaattca gtgactagga cctaaactac acgtgaacac attatttagc    3240
gtttaagcac acatggactg tcatttagac atgtttaggt ggacaataac caaaatctga    3300
atcatttacc ttttgaatat ccatgcaggt ttttgcaatg ccagaaacat ctcttggtct    3360
ttttcccgat gttgggggcct catatttttt gtctcgactt cctgggttct atggttctct    3420
aatacccccg atctttattt agttgaaatg catgtagcta agtcattgca acatatataa    3480
tatttcaatg ttctgctaaa cctcgaggga tattatgtat cattctttag ttttagtttt    3540
ataccatgtg atttttattct tagcaagtgt gattcttgca caattgatct atgcaattac    3600
```

| | |
|---|---|
| gtatttgatt atggtgatat attaatataa agaaatgaaa atgacaatct tcttcttttt | 3660 |
| caagttgatt tattggttcc attatgaggt agccatatag ttggtggtaa tgatagcatt | 3720 |
| ggatatcttg ttaaataaaa cattactcta acattctgca ggagagtatg ttgctcttgt | 3780 |
| tggtgctaga ttggatggtg ctgaaatgct tgcatgtggt ctcgcaactc attttgtccc | 3840 |
| ttcaaatgta ggttcactag taactcaatt tttaaatgag ttgtcaattt tcttacagtt | 3900 |
| atgatgtttg gtgttatatt tatgttact attattgaga atgttctatg tataaaaatc | 3960 |
| ctagcctcat agcatttgca catgggcttt gaagttttgt tctctagcat cattaagttt | 4020 |
| atttatgtgg tatatctgtt gaaatagttt tgttttccag agaatgctat tgctggaaga | 4080 |
| atcccttaaa aaggtggaca cctcgaatag ttttgttgta tgtagtacta tcgatcaatt | 4140 |
| ctgtcaacag ccatccccaa aacaaaaaag ttccttaaat aggtaagggc atttctaatt | 4200 |
| aactcaaaga catatgtttg gttcataata tcactatttt tcattctttg gtgcaccta | 4260 |
| ggttggaaat catcaacaaa tgcttttcta aggaacagt tgaagaaatt atatcctctc | 4320 |
| ttgtaagttt gttatattaa ttgtaggttt ctatgggttc acttcttata ttatgaaaaa | 4380 |
| taataaatgc atatttgttc tgtcaggagg aagtggcctc aaattcagca agcaaatggg | 4440 |
| ctgctcagac aattcaatat ctgaaaaagg cttctcctac tagtctgaaa atcacattga | 4500 |
| gatcggtatt ccttagaaac cacaccccat aattgtacta ttaatctacg acatatattt | 4560 |
| gtctcattat atgttttcta acatggagtt cagataagag aagggagaac acaaaccgtt | 4620 |
| ggggagtgct tgcaacggga atatagaatg gtttgccatg tcgtacgtgg tgactttagt | 4680 |
| cgagactttt ttgaagtaat taaacatgga catcactaat actttgctct atactttgtt | 4740 |
| gtcattgtac atcaatgtat gtacctaaca tccaactcct tttacaggga tgtagggcta | 4800 |
| tactagtaga taaagataaa aatccaaagg ttccttatact tccatattta gcacctctcc | 4860 |
| atcaaaattc attacgactt attttatttg atataaccat tagatgatgg tgttctttt | 4920 |
| tggggagctt gcagtggatg cctccaatgt tggaacaagt gcatgatgat gcagttgaag | 4980 |
| agtatttctc tagggttgat gttccagagt gggaagattt ggacctacct gtcatgtgtt | 5040 |
| caaatggaag aattatggag tccaagcttt ga | 5072 |

<210> SEQ ID NO 110
<211> LENGTH: 1920
<212> TYPE: DNA
<213> ORGANISM: Zea mays

<400> SEQUENCE: 110

| | |
|---|---|
| atgattgttg cagtagtagt actggcgcta ttgctgttcc acgccgactc cctcccccag | 60 |
| aacagcacgg acgacatgct ctccctgctc gacttcagaa aggaaatcag cagtgatcca | 120 |
| agaggtttcc tcacatcctg gaacactaat agtagcgccg cccactactg cagctggaat | 180 |
| ggcgtcacat gcagcagaac gcatcgaggg cgggtcattg aactcaaact cagcagccaa | 240 |
| agcttgcaag gccgaatctc tccatctctc ggtaatctaa ccttccttag aacgctggac | 300 |
| ctgtcctcaa acagcttctt tggccagctg ccccttctta gtcgccttgt caggcttcag | 360 |
| gaccttgttc tagacaacaa ccagctgcag ggtttggctc ctgacgcact tatcaactgc | 420 |
| tccagcttgt actccgtaac ccttcatcc aacatgttag ctgggccaat aataccagcc | 480 |
| agcataggtt ccctctctaa ccttatgtac ctttaccttg attctaacaa cttcactgga | 540 |
| gcctttccat ccagcctgct caacatgtct aaactagagg agctcgacct tcttcaaac | 600 |
| atgctagctg ggccaataca tcctaatatc ggttccctct ttaaccttac acttctctac | 660 |

```
cttgattcta acaacttcac tggagccatc ccatccagcc tggtcaacat ctccaaacta    720
gaacagctca tgctccagga taatcagctc atagacagga tacctcaagt tcttggcaat    780
ttatcaaata tgaatctatt gttgctagca cataatatgc tatcaggtag catccctgca    840
accattctga accaacattc tcttgaaatt ctggacctcg gaaccaattt tatacgtatg    900
gtgttgccat ccaatattgg caaaacccctt ccaaacctcc tcgggctttc cttgcacaat    960
aacatgttcc atggtccaat cccagcatcg cttggaaaca tttcgttact ccagatatta    1020
gatttcacat ctaacagttt cactggccat gtacctagtt ccttgggaaa tctaaccatc    1080
ttgcgcttcc taaaactaga agagaatagc cttgaagcaa aagacaatga gggctgggaa    1140
ttcatagatg cgctgggcaa atggagagga ggttgtggtt ctatatatag tgcgaatttg    1200
atggaaaaca agctaaaggt ggctattaaa gttcttgaca gtgacatgca tggcgtcgag    1260
aaaagtttct tagcagaatg tgaagctttg aggaacatcc gacaccgaaa tctagtccct    1320
atcaaaacaa catgctcaag gttagatatc aaaggcaatg tttccaaagc tcttgtatat    1380
gaatttatgc caaacgggaa tttggactca tggttgcatc agcaaggcag tgggaatgtc    1440
agaaaacctt tggacttaaa tcaaagaaca agcttagcta ccaacttagc tgacgtactt    1500
gattatctgc acaacaaatg tgggaaaaca attatccatt gtgatgtcaa gcccagtaac    1560
atactcctcg atgatgacat gaatgccagt ttgggagact tcggcattgc aaaattctgt    1620
attggttcta tgtcaacatc aactggagat tcaaaatcta taaactcaac cggaatgaag    1680
ggtactatcg gctacatacc tccagagtat gctcgaggtg acacgcatc aacatgcggg    1740 gatgtttaca gttttggaat agtactgcta gagatgctta cagggagaag gccaactgat    1800
catgtgtttg tggacgaact aaacattgtc aaattcgtgg agaggagctt ccctaataaa    1860
atattggatg tgattgatgg ttccttacgt gatgacttca gagtgcgca aataaacatg    1920
```

<210> SEQ ID NO 111
<211> LENGTH: 640
<212> TYPE: PRT
<213> ORGANISM: Zea mays

<400> SEQUENCE: 111

```
Met Ile Val Ala Val Val Leu Ala Leu Leu Leu Phe His Ala Asp
1               5                   10                  15

Ser Leu Pro Gln Asn Ser Thr Asp Asp Met Leu Ser Leu Leu Asp Phe
            20                  25                  30

Arg Lys Glu Ile Ser Ser Asp Pro Arg Gly Phe Leu Thr Ser Trp Asn
        35                  40                  45

Thr Asn Ser Ser Ala Ala His Tyr Cys Ser Trp Asn Gly Val Thr Cys
    50                  55                  60

Ser Arg Thr His Arg Gly Arg Val Ile Glu Leu Lys Leu Ser Ser Gln
65                  70                  75                  80

Ser Leu Gln Gly Arg Ile Ser Pro Ser Leu Gly Asn Leu Thr Phe Leu
                85                  90                  95

Arg Thr Leu Asp Leu Ser Ser Asn Ser Phe Phe Gly Gln Leu Pro Leu
            100                 105                 110

Leu Ser Arg Leu Val Arg Leu Gln Asp Leu Val Leu Asp Asn Asn Gln
        115                 120                 125

Leu Gln Gly Leu Ala Pro Asp Ala Leu Ile Asn Cys Ser Ser Leu Tyr
    130                 135                 140

Ser Val Thr Leu Ser Ser Asn Met Leu Ala Gly Pro Ile Ile Pro Ala
```

```
                145                 150                 155                 160
        Ser Ile Gly Ser Leu Ser Asn Leu Met Tyr Leu Tyr Leu Asp Ser Asn
                        165                 170                 175
        Asn Phe Thr Gly Ala Phe Pro Ser Ser Leu Leu Asn Met Ser Lys Leu
                        180                 185                 190
        Glu Glu Leu Asp Leu Ser Ser Asn Met Leu Ala Gly Pro Ile His Pro
                        195                 200                 205
        Asn Ile Gly Ser Leu Phe Asn Leu Thr Leu Leu Tyr Leu Asp Ser Asn
                        210                 215                 220
        Asn Phe Thr Gly Ala Ile Pro Ser Ser Leu Val Asn Ile Ser Lys Leu
        225                 230                 235                 240
        Glu Gln Leu Met Leu Gln Asp Asn Gln Leu Ile Asp Arg Ile Pro Gln
                        245                 250                 255
        Val Leu Gly Asn Leu Ser Asn Met Asn Leu Leu Leu Ala His Asn
                        260                 265                 270
        Met Leu Ser Gly Ser Ile Pro Ala Thr Ile Leu Asn Gln His Ser Leu
                        275                 280                 285
        Glu Ile Leu Asp Leu Gly Thr Asn Phe Ile Arg Met Val Leu Pro Ser
                        290                 295                 300
        Asn Ile Gly Lys Thr Leu Pro Asn Leu Leu Gly Leu Ser Leu His Asn
        305                 310                 315                 320
        Asn Met Phe His Gly Pro Ile Pro Ala Ser Leu Gly Asn Ile Ser Leu
                        325                 330                 335
        Leu Gln Ile Leu Asp Phe Thr Ser Asn Ser Phe Thr Gly His Val Pro
                        340                 345                 350
        Ser Ser Leu Gly Asn Leu Thr Ile Leu Arg Phe Leu Lys Leu Glu Glu
                        355                 360                 365
        Asn Ser Leu Glu Ala Lys Asp Asn Glu Gly Trp Glu Phe Ile Asp Ala
                        370                 375                 380
        Leu Gly Lys Trp Arg Gly Gly Cys Gly Ser Ile Tyr Ser Ala Asn Leu
        385                 390                 395                 400
        Met Glu Asn Lys Leu Lys Val Ala Ile Lys Val Leu Asp Ser Asp Met
                        405                 410                 415
        His Gly Val Glu Lys Ser Phe Leu Ala Glu Cys Glu Ala Leu Arg Asn
                        420                 425                 430
        Ile Arg His Arg Asn Leu Val Pro Ile Lys Thr Thr Cys Ser Arg Leu
                        435                 440                 445
        Asp Ile Lys Gly Asn Val Ser Lys Ala Leu Val Tyr Glu Phe Met Pro
        450                 455                 460
        Asn Gly Asn Leu Asp Ser Trp Leu His Gln Gln Gly Ser Gly Asn Val
        465                 470                 475                 480
        Arg Lys Pro Leu Asp Leu Asn Gln Arg Thr Ser Leu Ala Thr Asn Leu
                        485                 490                 495
        Ala Asp Val Leu Asp Tyr Leu His Asn Lys Cys Gly Lys Thr Ile Ile
                        500                 505                 510
        His Cys Asp Val Lys Pro Ser Asn Ile Leu Leu Asp Asp Met Asn
                        515                 520                 525
        Ala Ser Leu Gly Asp Phe Gly Ile Ala Lys Phe Cys Ile Gly Ser Met
                        530                 535                 540
        Ser Thr Ser Thr Gly Asp Ser Lys Ser Ile Asn Ser Thr Gly Met Lys
        545                 550                 555                 560
        Gly Thr Ile Gly Tyr Ile Pro Pro Glu Tyr Ala Arg Gly Gly His Ala
                        565                 570                 575
```

Ser Thr Cys Gly Asp Val Tyr Ser Phe Gly Ile Val Leu Leu Glu Met
            580                 585                 590

Leu Thr Gly Arg Arg Pro Thr Asp His Val Phe Val Asp Glu Leu Asn
        595                 600                 605

Ile Val Lys Phe Val Glu Arg Ser Phe Pro Asn Lys Ile Leu Asp Val
    610                 615                 620

Ile Asp Gly Ser Leu Arg Asp Asp Phe Lys Ser Ala Gln Ile Asn Met
625                 630                 635                 640

<210> SEQ ID NO 112
<211> LENGTH: 1875
<212> TYPE: DNA
<213> ORGANISM: Zea mays
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1186)..(1186)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t

<400> SEQUENCE: 112
atggttgctg ctgtagtact agccctactg ctgttctatg ggactggaaa cgccaactgc     60
gcaacgctgc gtcccagcag cagcaggagc agcacggacg acatgctctc cctgctcgat    120
ttcagaaagg aaatcagcag tgatccagga ggtttcctca gatcctggaa cactagtggt    180
agtagcgccg ccgactactg cagctggaat ggcgtcacat gcagcagaac gcacccaggg    240
cgggtcacga agctcaacct cagcagccaa agctgcaag gccgaatctc tccatctctt     300
ggtaacctaa ccttccttcg aatactggac ctgtcctaca acagcttctt tggccagctg    360
ccccttctta gtcgccccgt taggcttcag gacctagttc tgaacaacaa ccagctgcaa    420
agtttcccca ttgacgcact tacgaactgc tccagcttgc acgctataga cctttcgtcc    480
aacatgttta ctgggccaat accagccagc atcggttctc tccctaacct tacgtacttg    540
tacctttatg ctaatagctt cactggagcc atcccatcga gcttgctaaa catctctaaa    600
ctacaggagc tcgtgctttc ctcaaacatg ctagctgggc aataccacc taatatcggt     660 tccctcatga accttacact tctctacctt gattctaaca acttcactgg agccatccca    720
tccagcctgg gaaatatctc caaactacag cagctcgtgc tccagaataa tcagctccat    780

```
ggcaccatac ctcaggatct tggcaattta tcaaatctga atatattggt gctagggcat       840
aatagtctat caggtcacat cccgacaaca attctgaacc agcgttccct tggatttctg       900
ggcttggaag cgaatttgct acgtatggcg ttgccatcta atattgggat catccctgca       960
gaactgggtg gnatgtcctc tcttacccag ctggatctat cttataatga tctacaaggc      1020
aaaattccaa tggatggagt atttagaaat gcttcagctg tctcacttgt tggcaactng      1080
agactctgtg gtggtctgtc agatttgcac atgccccct gccctnttgc cttaaaggaa      1140
aaggcagcac aatactacan cattagagtg ttnatcccaa tatttngctt catntcactn      1200
ttgatgttgc atggcagtgg gaatgtcagg aaacctttgg acttaaatca agaacaagc       1260 ttagctacca acatagctaa cgtacttgat tatctgcaca acgaatgtgg gaaaacaatt      1320
atccattgtg atgtcaagcc cagtaacata ctcctcgatg atgacatgaa tgcccgtttg      1380
ggagacttcg gcattgcaaa attctgtatt ggttctatgt caacatcaat ggagattca       1440 gaacctataa actcaaccgg tatgaagggt actatcggct acatgcctcc agagtatgct      1500
cgaggtggac atgcatcaac atgcggggat gtttacagtt ttggaatagt acttctagag      1560
atgcttacag ggagaaggcc aattgatcat gtgtttgtgg acgaactaaa cattgtcaaa      1620
ttcgtggaga ggagcttccc tgataaaata ttggatgtga ttgatgtttc attacgtgat      1680
gacttcaaga gtgcccaaat aaacatggta acagagagtg agacctaccg atgcttgttt      1740
tctctactgc aagtagcact ttcttgcaca cgtgagattc ctggtgaacg aacgaccatg      1800
gaagaagcag ctagcagaat tggttcaatc aagaccacgt atgctaaagg aattgaaaac      1860
gcaagcaggc attga                                                      1875

<210> SEQ ID NO 113
<211> LENGTH: 624
<212> TYPE: PRT
<213> ORGANISM: Zea mays
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid

<400> SEQUENCE: 113

Met Val Ala Ala Val Val Leu Ala Leu Leu Leu Phe Tyr Gly Thr Gly
1               5                   10                  15

Asn Ala Asn Cys Ala Thr Leu Arg Pro Ser Ser Arg Ser Ser Thr
            20                  25                  30

Asp Asp Met Leu Ser Leu Leu Asp Phe Arg Lys Glu Ile Ser Ser Asp
        35                  40                  45
```

```
Pro Gly Gly Phe Leu Arg Ser Trp Asn Thr Ser Gly Ser Ser Ala Ala
    50                  55                  60
Asp Tyr Cys Ser Trp Asn Gly Val Thr Cys Ser Arg Thr His Pro Gly
65                  70                  75                  80
Arg Val Thr Glu Leu Asn Leu Ser Ser Gln Ser Leu Gln Gly Arg Ile
                85                  90                  95
Ser Pro Ser Leu Gly Asn Leu Thr Phe Leu Arg Ile Leu Asp Leu Ser
            100                 105                 110
Tyr Asn Ser Phe Phe Gly Gln Leu Pro Leu Leu Ser Arg Pro Val Arg
            115                 120                 125
Leu Gln Asp Leu Val Leu Asn Asn Gln Leu Gln Ser Phe Pro Ile
    130                 135                 140
Asp Ala Leu Thr Asn Cys Ser Ser Leu His Ala Ile Asp Leu Ser Ser
145                 150                 155                 160
Asn Met Phe Thr Gly Pro Ile Pro Ala Ser Ile Gly Ser Leu Pro Asn
                165                 170                 175
Leu Thr Tyr Leu Tyr Leu Tyr Ala Asn Ser Phe Thr Gly Ala Ile Pro
            180                 185                 190
Ser Ser Leu Leu Asn Ile Ser Lys Leu Gln Glu Leu Val Leu Ser Ser
            195                 200                 205
Asn Met Leu Ala Gly Pro Ile Pro Asn Ile Gly Ser Leu Met Asn
    210                 215                 220
Leu Thr Leu Leu Tyr Leu Asp Ser Asn Asn Phe Thr Gly Ala Ile Pro
225                 230                 235                 240
Ser Ser Leu Gly Asn Ile Ser Lys Leu Gln Gln Leu Val Leu Gln Asn
                245                 250                 255
Asn Gln Leu His Gly Thr Ile Pro Gln Asp Leu Gly Asn Leu Ser Asn
            260                 265                 270
Leu Asn Ile Leu Val Leu Gly His Asn Ser Leu Ser Gly His Ile Pro
            275                 280                 285
Thr Thr Ile Leu Asn Gln Arg Ser Leu Gly Phe Leu Gly Leu Glu Ala
    290                 295                 300
Asn Leu Leu Arg Met Ala Leu Pro Ser Asn Ile Gly Ile Ile Pro Ala
305                 310                 315                 320
Glu Leu Gly Gly Met Ser Ser Leu Thr Gln Leu Asp Leu Ser Tyr Asn
                325                 330                 335
Asp Leu Gln Gly Lys Ile Pro Met Asp Gly Val Phe Arg Asn Ala Ser
            340                 345                 350
Ala Val Ser Leu Val Gly Asn Xaa Arg Leu Cys Gly Gly Leu Ser Asp
            355                 360                 365
Leu His Met Pro Pro Cys Pro Xaa Ala Leu Lys Glu Lys Ala Ala Gln
    370                 375                 380
Tyr Tyr Xaa Ile Arg Val Xaa Ile Pro Ile Phe Xaa Phe Xaa Ser Leu
385                 390                 395                 400
Leu Met Leu His Gly Ser Gly Asn Val Arg Lys Pro Leu Asp Leu Asn
                405                 410                 415
Gln Arg Thr Ser Leu Ala Thr Asn Ile Ala Asn Val Leu Asp Tyr Leu
            420                 425                 430
His Asn Glu Cys Gly Lys Thr Ile His Cys Asp Val Lys Pro Ser
            435                 440                 445
Asn Ile Leu Leu Asp Asp Met Asn Ala Arg Leu Gly Asp Phe Gly
    450                 455                 460
Ile Ala Lys Phe Cys Ile Gly Ser Met Ser Thr Ser Ile Gly Asp Ser
```

```
                465                 470                 475                 480
Glu Pro Ile Asn Ser Thr Gly Met Lys Gly Thr Ile Gly Tyr Met Pro
                    485                 490                 495

Pro Glu Tyr Ala Arg Gly Gly His Ala Ser Thr Cys Gly Asp Val Tyr
            500                 505                 510

Ser Phe Gly Ile Val Leu Leu Glu Met Leu Thr Gly Arg Arg Pro Ile
        515                 520                 525

Asp His Val Phe Val Asp Glu Leu Asn Ile Val Lys Phe Val Glu Arg
    530                 535                 540

Ser Phe Pro Asp Lys Ile Leu Asp Val Ile Asp Val Ser Leu Arg Asp
545                 550                 555                 560

Asp Phe Lys Ser Ala Gln Ile Asn Met Val Thr Glu Ser Glu Thr Tyr
                565                 570                 575

Arg Cys Leu Phe Ser Leu Leu Gln Val Ala Leu Ser Cys Thr Arg Glu
            580                 585                 590

Ile Pro Gly Glu Arg Thr Thr Met Glu Glu Ala Ala Ser Arg Ile Gly
        595                 600                 605

Ser Ile Lys Thr Thr Tyr Ala Lys Gly Ile Glu Asn Ala Ser Arg His
    610                 615                 620

<210> SEQ ID NO 114
<211> LENGTH: 3090
<212> TYPE: DNA
<213> ORGANISM: Zea mays
<220> FEATURE:
<221> NAME/KEY: misc_feature
<222> LOCATION: (1712)..(1712)
<223> OTHER INFORMATION: n is a, c, g, or t
<220> FEATURE:
<221> NAME/KEY: misc_feature
<222> LOCATION: (1819)..(1819)
<223> OTHER INFORMATION: n is a, c, g, or t
<220> FEATURE:
<221> NAME/KEY: misc_feature
<222> LOCATION: (1866)..(1866)
<223> OTHER INFORMATION: n is a, c, g, or t
<220> FEATURE:
<221> NAME/KEY: misc_feature
<222> LOCATION: (1900)..(1900)
<223> OTHER INFORMATION: n is a, c, g, or t
<220> FEATURE:
<221> NAME/KEY: misc_feature
<222> LOCATION: (1913)..(1913)
<223> OTHER INFORMATION: n is a, c, g, or t
<220> FEATURE:
<221> NAME/KEY: misc_feature
<222> LOCATION: (1926)..(1926)
<223> OTHER INFORMATION: n is a, c, g, or t
<220> FEATURE:
<221> NAME/KEY: misc_feature
<222> LOCATION: (1934)..(1934)
<223> OTHER INFORMATION: n is a, c, g, or t
<220> FEATURE:
<221> NAME/KEY: misc_feature
<222> LOCATION: (1940)..(1940)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (2108)..(2108)
<223> OTHER INFORMATION: n is a, c, g, or t
<220> FEATURE:
<221> NAME/KEY: misc_feature
<222> LOCATION: (2116)..(2117)
<223> OTHER INFORMATION: n is a, c, g, or t
<220> FEATURE:
```

```
<221> NAME/KEY: misc_feature
<222> LOCATION: (2132)..(2132)
<223> OTHER INFORMATION: n is a, c, g, or t
<220> FEATURE:
<221> NAME/KEY: misc_feature
<222> LOCATION: (2170)..(2170)
<223> OTHER INFORMATION: n is a, c, g, or t

<400> SEQUENCE: 114
```

| | | | | | |
|---|---|---|---|---|---|
| atggttgctg | ctgtagtact | agccctactg | ctgttctatg | ggactggaaa | cgccaactgc      60 |
| gcaacgctgc | gtcccagcag | cagcaggagc | agcacggacg | acatgctctc | cctgctcgat     120 |
| ttcagaaagg | aaatcagcag | tgatccagga | ggtttcctca | gatcctggaa | cactagtggt     180 |
| agtagcgccg | ccgactactg | cagctggaat | ggcgtcacat | gcagcagaac | gcacccaggg     240 |
| cgggtcacgg | agctcaacct | cagcagccaa | agcctgcaag | gccgaatctc | tccatctctt     300 |
| ggtaacctaa | ccttccttcg | aatactggac | ctgtcctaca | acagcttctt | tggccagctg     360 |
| ccccttctta | gtcgcccccgt | taggcttcag | gacctagttc | tgaacaacaa | ccagctgcaa     420 |
| agtttcccca | ttgacgcact | tacgaactgc | tccagcttgc | acgctataga | cctttcgtcc     480 |
| aacatgttta | ctgggccaat | accagccagc | atcggttctc | tccctaacct | tacgtacttg     540 |
| tacctttatg | ctaatagctt | cactggagcc | atcccatcga | gcttgctaaa | catctctaaa     600 |
| ctacaggagc | tcgtgctttc | ctcaaacatg | ctagctgggc | caataccacc | taatatcggt     660 |
| tccctcatga | accttacact | tctctacctt | gattctaaca | acttcactgg | agccatccca     720 |
| tccagcctgg | gaaatatctc | caaactacag | cagctcgtgc | tccagaataa | tcagctccat     780 |
| ggcaccatac | ctcaggatct | tggcaattta | tcaaatctga | atatattggt | gctagggcat     840 |
| aatagtctat | caggtcacat | cccgacaaca | attctgaacc | agcgttccct | tggatttctg     900 |
| ggcttggaag | cgaatttgct | acgtatggcg | ttgccatcta | atattggtaa | tacccttcct     960 |
| aacatctacg | cacttacctt | gtacaataac | atgttccatg | gtccaatccc | agcttcgcta    1020 |
| ggaaatgctt | cccatctcac | gatattagat | ttcgcatcta | accaaactga | acttcctaag    1080 |
| actagaacag | aacaaccttg | aagcaaaaga | taatgaaggc | tgggaattca | tagatgcact    1140 |
| aggcaattgt | atgtggctga | ataccctatt | attatctgac | aatcagctac | aaggagccat    1200 |
| accagattca | gttgggaagt | tgtccaatag | cagccttcag | tacctatatt | ttggcgaaaa    1260 |
| caacttgtcg | ggagctgttc | cagagagcat | ggggaacctt | attgccttaa | atacgttagt    1320 |
| tcttgaacaa | aacaatttga | acggtccgat | tggatcatgg | gttggaaagt | tcatcaactt    1380 |
| gacagtatta | tctctctcag | acaataactt | cagtgggccg | attccatcgt | ccattggtag    1440 |
| ccttactaag | ctaacacatc | tccacctaca | gagcaacaaa | tttgtaggtc | caatacctcc    1500 |
| cagtttgggt | aaacttcaag | gtttactaga | actaaatctt | agttataaca | atctaacaag    1560 |
| ctttgagtga | atgtcgtcag | ttgaatgtac | tccaaatggg | ctccaatttt | atcacaggga    1620 |
| acatttcgcc | tctacgtagt | ctaacaagct | tgaacatgat | caacctctca | cacaatatgt    1680 |
| tgtcagggat | catccctgca | gaactgggtg | gnatgtcctc | tcttacccag | ctggatctat    1740 |
| cttataatga | tctacaaggc | aaaattccaa | tggatggagt | atttagaaat | gcttcagctg    1800 |
| tctcacttgt | tggcaactng | agactctgtg | gtggtctgtc | agatttgcac | atgcccccct    1860 |
| gccctnttgc | cttaaaggaa | aaggcagcac | aatactacan | cattagagtg | ttnatcccaa    1920 |
| tatttngctt | catntcactn | ttgatgttgg | tatgtttcgt | tctcactaag | aaaagnactg    1980 |
| cacaacaatc | atcaatatct | cctcttggtg | accaattccc | aatagtttct | tataatgatt    2040 |
| tagttcaagc | tacaaatacc | ttctccaatt | caaatctgat | agggagagga | ggttgtggtt    2100 |

```
ctgtatanag agggannttg atggaaaaca anctaaaggt ggctattaaa gttcttgaca      2160
gtgacatgcn tggcgtcgag aaaagtttct tagcagaatg tgaagctttg aggaacatcc      2220
gacaccgaaa tctagtccct atcataacaa catgctcaag gttagatatc aaaggcaatg      2280
ttttcaaagc tcttgtatat gaatttatgc caaatgggaa tttggactca tggttgcatc      2340
agcatggcag tgggaatgtc aggaaacctt tggacttaaa tcaaagaaca agcttagcta      2400
ccaacatagc taacgtactt gattatctgc acaacgaatg tgggaaaaca attatccatt      2460
gtgatgtcaa gcccagtaac atactcctcg atgatgacat gaatgcccgt ttgggagact      2520
tcggcattgc aaaattctgt attggttcta tgtcaacatc aattggagat tcagaaccta      2580
taaactcaac cggtatgaag ggtactatcg gctacatgcc tccaggtaca taacggcttt      2640
tgcaaaattc catcttttcaa ttctaggtag tatacttcga gcatgcacta attcaatgcg      2700
tctttagagt atgctcgagg tggacatgca tcaacatgcg gggatgttta cagttttgga      2760
atagtacttc tagagatgct tacagggaga aggccaattg atcatgtgtt tgtggacgaa      2820
ctaaacattg tcaaattcgt ggagaggagc ttccctgata aaatattgga tgtgattgat      2880
gtttcattac gtgatgactt caagagtgcc caaataaaca tggtaacaga gagtgagacc      2940
taccgatgct tgttttctct actgcaagta gcactttctt gcacacgtga gattcctggt      3000
gaacgaacga ccatggaaga agcagctagc agaattggtt caatcaagac cacgtatgct      3060
aaaggaattg aaaacgcaag caggcattga                                       3090

<210> SEQ ID NO 115
<211> LENGTH: 1557
<212> TYPE: DNA
<213> ORGANISM: Zea mays

<400> SEQUENCE: 115
atgattcttg cagtagtact ggcgctattg ctgttctacg gggctggaca cgccgactcc        60
ctcccccaga acagcacgga cgacatgctc tccctgctcg acttcagaaa ggaaatcagc       120
agtgatccag gaggtttcct cacatcctgg aacactaata atagtagcgc cgccgactac       180
tgcggctgga atggcgtcac atgcagcaga aagcacccag ggcgggtcat tgaactcaac       240
ctcagcagcc aaagcttgca aggcctaatc tctccatctc tcggtaacct aaccttcctt       300
agaatactgg acctgtcctc caacatgcta gctgggccaa taccgcctaa tatcggttcc       360
ctctttcacc ttaaaattct cgaccttgat tctaacaact tcactggagc catcccgtcc       420
agcctgggca acatctccaa actagaactg ctcctgctcc aggataatca gctcataggg       480 accataccctc aagatcttgg caagttatca aatctgtacg aattgttgtt agggcataat       540
agtctatcag gtagcatccc gacaaccatt ctgaagcaac gtaaccttag gattctggac       600
ctgggtgaga attctctacg tatgatgttg ccatctgata ttggccatac ccttcctcaa       660
ctcggtgcgc tttccctgta caataacatg ttctacggtc caatcccagc atcgctagga       720
aacgcttcaa ttctcatgat attagacttg acagctaaca gtttcactgg acatgtacct       780
agttctttgg gaaatctaac ctacctatcc ctcctacaac tagaacagaa caacctcaaa       840
gcaaatgata atgagggatg ggaattcata gatgcattgc gcaaatgtca gttcctggaa       900
aaactcttat tatcttacaa tcagctagga ggagccatac caaattcagt tgggaagtta       960
tccaacaaca gccttcagta cctacgattc ggcagaaaca acttgtcggg agctgttccg      1020
gagagcatgg ggaaccttat tgccttaaat acgttagatc tagaacaaaa caatttgaac      1080
```

```
ggtctgattg gatcatgggt tggaaagttg aacaacttga atcagacaca ctcgattcga    1140
gcggcatctg tccatggcgt actcgtgcaa ccacgtctgc tatggagcac gccgaccaac    1200
cgccagatat gcttgatgga agcacgcctc cggcctctcc gagaagttca ccggacgctg    1260
cgacagcgtc gagcggcgcg tggaggtgcg gtgcgactcc ctgcactctt cacagtgcgg    1320
tgcgagaaga tccaggagca ggtcgatgtc gctgcactct gcagtgacga acatggcatt    1380
gcgttggagg ggaagcgcac cgacctcgag caatggcggc ccgatctcgt caagcgggtc    1440
gaggaggtgg cgtgtgtcaa caaactcctc gagcgggaac gtcgagcgga atccgtcgtc    1500
aagcccacca tcttcggcac ttacacggcg gcgcccctgc gaccactgtt tgaataa       1557
```

<210> SEQ ID NO 116
<211> LENGTH: 518
<212> TYPE: PRT
<213> ORGANISM: Zea mays

<400> SEQUENCE: 116

```
Met Ile Leu Ala Val Val Leu Ala Leu Leu Leu Phe Tyr Gly Ala Gly
 1               5                  10                  15

His Ala Asp Ser Leu Pro Gln Asn Ser Thr Asp Asp Met Leu Ser Leu
            20                  25                  30

Leu Asp Phe Arg Lys Glu Ile Ser Ser Asp Pro Gly Gly Phe Leu Thr
        35                  40                  45

Ser Trp Asn Thr Asn Asn Ser Ser Ala Ala Asp Tyr Cys Gly Trp Asn
    50                  55                  60

Gly Val Thr Cys Ser Arg Lys His Pro Gly Arg Val Ile Glu Leu Asn
65                  70                  75                  80

Leu Ser Ser Gln Ser Leu Gln Gly Leu Ile Ser Pro Ser Leu Gly Asn
                85                  90                  95

Leu Thr Phe Leu Arg Ile Leu Asp Leu Ser Ser Asn Met Leu Ala Gly
            100                 105                 110

Pro Ile Pro Pro Asn Ile Gly Ser Leu Phe His Leu Lys Ile Leu Asp
        115                 120                 125

Leu Asp Ser Asn Asn Phe Thr Gly Ala Ile Pro Ser Ser Leu Gly Asn
    130                 135                 140

Ile Ser Lys Leu Glu Leu Leu Leu Gln Asp Asn Gln Leu Ile Gly
145                 150                 155                 160

Thr Ile Pro Gln Asp Leu Gly Lys Leu Ser Asn Leu Tyr Glu Leu Leu
                165                 170                 175

Leu Gly His Asn Ser Leu Ser Gly Ser Ile Pro Thr Thr Ile Leu Lys
            180                 185                 190

Gln Arg Asn Leu Arg Ile Leu Asp Leu Gly Glu Asn Ser Leu Arg Met
        195                 200                 205

Met Leu Pro Ser Asp Ile Gly His Thr Leu Pro Gln Leu Gly Ala Leu
    210                 215                 220

Ser Leu Tyr Asn Asn Met Phe Tyr Gly Pro Ile Pro Ala Ser Leu Gly
225                 230                 235                 240

Asn Ala Ser Ile Leu Met Ile Leu Asp Leu Thr Ala Asn Ser Phe Thr
                245                 250                 255

Gly His Val Pro Ser Ser Leu Gly Asn Leu Thr Tyr Leu Ser Leu Leu
            260                 265                 270

Gln Leu Glu Gln Asn Asn Leu Lys Ala Asn Asp Asn Glu Gly Trp Glu
        275                 280                 285

Phe Ile Asp Ala Leu Arg Lys Cys Gln Phe Leu Glu Lys Leu Leu Leu
```

```
Ser Tyr Asn Gln Leu Gly Gly Ala Ile Pro Asn Ser Val Gly Lys Leu
305                 310                 315                 320

Ser Asn Asn Ser Leu Gln Tyr Leu Arg Phe Gly Arg Asn Asn Leu Ser
            325                 330                 335

Gly Ala Val Pro Glu Ser Met Gly Asn Leu Ile Ala Leu Asn Thr Leu
        340                 345                 350

Asp Leu Glu Gln Asn Asn Leu Asn Gly Leu Ile Gly Ser Trp Val Gly
    355                 360                 365

Lys Leu Asn Asn Leu Asn Gln Thr His Ser Ile Arg Ala Ala Ser Val
370                 375                 380

His Gly Val Leu Val Gln Pro Arg Leu Leu Trp Ser Thr Pro Thr Asn
385                 390                 395                 400

Arg Gln Ile Cys Leu Met Glu Ala Arg Leu Arg Pro Leu Arg Glu Val
                405                 410                 415

His Arg Thr Leu Arg Gln Arg Ala Ala Arg Gly Gly Ala Val Arg
            420                 425                 430

Leu Pro Ala Leu Phe Thr Val Arg Cys Glu Lys Ile Gln Glu Gln Val
                435                 440                 445

Asp Val Ala Ala Leu Cys Ser Asp Glu His Gly Ile Ala Leu Glu Gly
        450                 455                 460

Lys Arg Thr Asp Leu Glu Gln Trp Arg Pro Asp Leu Val Lys Arg Val
465                 470                 475                 480

Glu Glu Val Ala Cys Val Asn Lys Leu Leu Glu Arg Glu Arg Arg Ala
            485                 490                 495

Glu Ser Val Val Lys Pro Thr Ile Phe Gly Thr Tyr Thr Ala Ala Pro
        500                 505                 510

Leu Arg Pro Leu Phe Glu
        515

<210> SEQ ID NO 117
<211> LENGTH: 2192
<212> TYPE: DNA
<213> ORGANISM: Zea mays

<400> SEQUENCE: 117
atgattcttg cagtagtact ggcgctattg ctgttctacg ggctggaca cgccgactcc    60 ctcccccaga cagcacgga cgacatgctc tccctgctcg acttcagaaa ggaaatcagc   120
agtgatccag gaggtttcct cacatcctgg aacactaata atagtagcgc cgccgactac   180
tgcggctgga atggcgtcac atgcagcaga aagcacccag gcgggtcat tgaactcaac   240 ctcagcagcc aaagcttgca aggcctaatc tctccatctc tcggtaacct aaccttcctt   300
agaatactgg acctgtcctc caacatgcta gctgggccaa taccgcctaa tatcggttcc   360
ctctttcacc ttaaaattct cgaccttgat tctaacaact tcactggagc catcccgtcc   420
agcctgggca acatctccaa actagaactg ctcctgctcc aggataatca gctcataggg   480
accataccct caagatcttgg caagttatca aatctgtacg aattgttgtt agggcataat   540
agtctatcag gtagcatccc gacaaccatt ctgaagcaac gtaaccttag gattctggac   600
ctgggtgaga attctctacg tatgatgttg ccatctgata ttggccatac ccttcctcaa   660
ctcggtgcgc tttccctgta caataacatg ttctacggtc caatcccagc atcgctagga   720
aacgcttcaa ttctcatgat attagacttg acagctaaca gtttcactgg acatgtacct   780 agttcttttgg gaaatctaac ctacctatcc ctcctacaac tagaacagaa caacctcaaa   840
```

```
gcaaatgata atgagggatg ggaattcata gatgcattgc gcaaatgtca gttcctggaa    900
aaactcttat tatcttacaa tcagctagga ggagccatac caaattcagt tgggaagtta    960
tccaacaaca gccttcagta cctacgattc ggcagaaaca acttgtcggg agctgttccg   1020
gagagcatgg ggaaccttat tgccttaaat acgttagatc tagaacaaaa caatttgaac   1080
ggtctgattg gatcatgggt tggaaagttg aacaacttgg taagattatc tctttcagac   1140
aataacttca gtgggcccat tccatagtcc attagttggt aatagagatc gagtgagcta   1200
ggcctaccga tgcttgtttt ctagtacact gcaagtagca ctttcttgca cacgtgcgtg   1260
aaattcctgg tgaatgaacg accatggaag aagcagctat ctagcagtag aattggttca   1320
aatcaagacc ccgtatagca gaggattgga attgaaaaca caagcaaaca ttgaattgaa   1380
accatctctg tgttagcaca agcaccggtc tatgtttgcc tcaccaagcg gacatgggga   1440
tgaacaacat gtcagcacag ctacaccagg tgaagacgga ggccaagccg aggaagatgc   1500
agcaagtgcg atggagcaag gcgccagggc acgaccacgt cgacaccgtg cgtgtgtgtg   1560
ggccggagtg ggccgtgtaa gagccattgg gctgggctgt aataggtgag gtataagtag   1620
cctcatcacc agagaacgaa ccgtcgatga acaaaacagt aaaactacga gcggcagcgc   1680
cgtcgctgtt tttcccgaac ccccttctt cctgctcatc aattccctcc cgagtgctaa    1740
caatctggta tcagaatcag acacactcga ttcgagcggc atctgtccat ggcgtactcg   1800
tgcaaccacg tctgctatgg agcacgccga ccaaccgcca gatatgcttg atggaagcac   1860
gcctccggcc tctccgagaa gttcaccgga cgctgcgaca gcgtcgagcg gcgcgtggag   1920
gtgcggtgcg actccctgca ctcttcacag tgcggtgcga gaagatccag gagcaggtcg   1980
atgtcgctgc actctgcagt gacgaacatg gcattgcgtt ggaggggaag cgcaccgacc   2040
tcgagcaatg gcggcccgat ctcgtcaagc gggtcgagga ggtggcgtgt gtcaacaaac   2100
tcctcgagcg ggaacgtcga gcggaatccg tcgtcaagcc caccatcttc ggcacttaca   2160
cggcggcgcc cctgcgacca ctgtttgaat aa                                 2192
```

GENETIC LOCI ASSOCIATED WITH HEAD SMUT RESISTANCE IN MAIZE

This application claims the benefit of U.S. Provisional Application No. 61/090,704, filed Aug. 21, 2008, the contents of which are hereby incorporated by reference.

FIELD OF THE INVENTION

The present disclosure relates to compositions and methods useful in enhancing resistance to head smut in maize.

BACKGROUND OF THE INVENTION

Head smut is a soil-borne and systemic disease in maize (Frederiksen 1977) caused by the host-specific fungus *Sphacelotheca reiliana* (Kühn) Clint. The teliospores from sori buried in soil are the primary source of infection, and can survive three years in soil without loss of any infection capacity (Wu et al. 1981). The fungus infects seedlings through roots or coleoptiles during and after seed emergence (Krüger 1962). In an infection of a susceptible variety the plants continue normal vegetative growth, but some may be stunted (Matyac and Kommedahl 1985a). At maturity sori replace ears or tassels of the infected plants, resulting in nearly no maize yield for the plant. The proportion of infected plants in an infected field could amount to 80% (Frederiksen 1977). Jin (2000) reported the incidence of this disease varied from 7.0% to 35.0%, some even reaching 62.0%, resulting from the cultivation of susceptible cultivars. In Northern China, head smut causes yield loss of up to 0.3 million tons annually (Bai et al. 1994). It was reported that maize in Southern Europe, North America, and Asia also seriously suffer from this disease (Xu et al. 1999). Considering both economic and ecological elements, cultivation of resistant varieties is an effective way to control epidemics of head smut. Breeding for multiple resistant genes/QTLs against head smut into elite maize varieties would be a promising way to improve the resistance against this disease.

To date, many researches have studied genetic models conferring resistance against head smut. Mei et al. (1982) reported that resistance against head smut was controlled by partially dominant nuclear genes with no difference being found in reciprocal crosses. Ma et al. (1983) reported maize resistance to head smut was a quantitative trait, affected by partial resistance genes and their non-allelic interactions. Stromberg et al. (1984) discovered that $F_1$ population showed an intermediate disease incidence between resistant and susceptible parents. Ali and Baggett (1990) reported additive and dominant genetic actions were preponderant under different treatments. Bernardo et al. (1992) studied genetic effect of resistance gene(s) by using generation mean analysis, suggesting that additive effect is decisive, while the dominant and epistatic effects are weak. Shi et al. (2005) reported that apart from additive effect, over-dominance also plays a key role in resistance against head smut. It is obvious that resistance against head smut in maize may involve in a number of genetic elements and act in a complex way.

SUMMARY OF THE INVENTION

Compositions and methods for identifying and selecting maize plants with increased resistance to head smut are provided.

In a first embodiment, the invention concerns an isolated polynucleotide comprising a polynucleotide selected from the group consisting of:

(a) at least one nucleotide sequence encoding a polypeptide conferring or improving resistance to head smut selected from the group consisting of SEQ ID NOs:27, 32, 35, 38, 41, 44, 105, 108, 111, 113, and 116;

(b) at least one nucleotide sequence capable of encoding a polypeptide conferring or enhancing resistance to head smut selected from the group consisting of SEQ ID NOs:25, 26, 30, 31, 34, 36, 37, 39, 40, 42, 43, 45, 104, 106, 107, 109, 110, 112, 114, 115, and 117; and (c) a complement of the nucleotide sequence of part (a) or (b), wherein the complement and the nucleotide sequence consist of the same number of nucleotides and are 100% complementary.

In a second embodiment, the invention concerns a vector comprising the claimed isolated polynucleotide.

In a third embodiment, the invention concerns a recombinant DNA construct comprising the isolated polynucleotide of the invention operably linked to at least one regulatory sequence.

In a fourth embodiment, the invention concerns a maize cell comprising the recombinant DNA construct or the isolated polynucleotide of the invention.

In a fifth embodiment, the invention concerns a process for producing a maize plant comprising transforming a plant cell with the recombinant DNA construct of the invention and regenerating a plant from the transformed plant cell.

In a sixth embodiment, the invention concerns a maize plant comprising the recombinant DNA construct of the invention.

In a seventh embodiment, the invention concerns a maize seed comprising the recombinant DNA construct of the invention.

In an eighth embodiment, the invention concerns a process of conferring or improving resistance to head smut, comprising transforming a plant with the recombinant DNA construct of the invention, thereby conferring or improving resistance to head smut.

In a ninth embodiment, the invention concerns a process of determining the presence or absence of the polynucleotide of the invention in a maize plant, comprising at least one of:

(a) isolating nucleic acid molecules from said maize plant and amplifying sequences homologous to the polynucleotide of the invention, or (b) isolating nucleic acid molecules from said maize plants and performing a Southern hybridization, or (c) isolating proteins from said maize plant and performing a western blot using antibodies to the protein, or (d) isolating proteins from said maize plant and performing an ELISA assay using antibodies to the protein, or (e) demonstrating the presence of mRNA sequences derived from the mRNA transcript and unique to the head smut resistance locus, thereby determining the presence of the polynucleotide of the invention in said maize plant.

In a tenth embodiment, the invention concerns a process of determining the presence or absence of the head smut resistance locus in a maize plant, comprising at least one of:

(a) isolating nucleic acid molecules from said maize plant and amplifying sequences unique to the polynucleotide of the invention, or (b) isolating proteins from said maize plant and performing a western blot using antibodies to the protein, or (c) isolating proteins from said maize plant and performing an ELISA assay using antibodies to the protein, or (d) demonstrating the presence of mRNA sequences derived from the mRNA transcript and unique to the head smut resistance locus, thereby determining the presence of the head smut resistance locus in said maize plant.

In an eleventh embodiment, the invention concerns a process of altering the level of expression of a protein capable of conferring resistance to head smut a maize cell comprising:

(a) transforming a maize cell with the recombinant DNA construct of the invention and (b) growing the transformed maize cell under conditions that are suitable for expression of the recombinant DNA construct wherein expression of the recombinant DNA construct results in production of altered levels of a protein capable of conferring resistance to head smut in the transformed maize cell when compared to levels of expression in a wild-type maize plant having resistance to head smut.

In a twelfth embodiment, the invention concerns a process of altering the level of expression of a protein capable of conferring resistance to head smut in a maize cell comprising:

(a) transforming a maize cell with the recombinant DNA construct of the invention; and (b) growing the transformed maize cell under conditions that are suitable for expression of the recombinant DNA construct wherein expression of the recombinant DNA construct results in production of altered levels of a protein capable of conferring resistance to head smut in the transformed maize cell when compared to levels of expression in a wild-type maize plant having resistance to head smut.

In a thirteenth embodiment, the invention concerns a process of altering the level of expression of a protein capable of conferring resistance to head smut in a maize plant comprising:

(a) transforming a maize plant cell with the recombinant DNA construct of the invention; and (b) regenerating a transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to head smut in the transformed maize plant when compared to levels of expression in a wild-type maize plant having resistance to head smut.

In a fourteenth embodiment, the invention concerns a process of altering the level of expression of a protein capable of conferring resistance to head smut in a maize plant comprising:

(a) transforming a maize plant cell with the recombinant DNA construct of the invention; and (b) regenerating the transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to head smut in the transformed maize plant when compared to levels of expression in a wild-type maize plant having resistance to head smut.

In a fifteenth embodiment, the invention concerns a method of identifying a maize plant that displays head smut resistance, the method comprising detecting in a maize plant a genetic marker locus wherein:

(a) a genetic marker probe comprising all or a portion of the genetic marker locus, or complement thereof, hybridizes under stringent conditions to bacm.pk071.j12, bacm.pk007.18, and bacm2.pk166.h1; and (b) said genetic marker locus comprises at least one allele that is associated with head smut resistance.

In a sixteenth embodiment, the invention concerns a method of identifying a maize plant that displays head smut resistance, the method comprising detecting in the germplasm of the maize plant at least one allele of a marker locus wherein:

(a) the marker locus is within 7 cM of SSR148152, CAPS25082, STS171, SNP661, and STS1944; and (b) at least one allele is associated with head smut resistance.

In a seventeenth embodiment, the invention concerns a method of identifying a maize plant that displays head smut resistance, the method comprising detecting in the germplasm of the maize plant at least one allele of a marker locus wherein:

(a) the marker locus is located within a chromosomal interval comprising and flanked by umc1736 and umc2184 or within a chromosomal interval comprising and flanked by SSR148152/SNP661; and (b) at least one allele is associated with head smut resistance.

In an eighteenth embodiment, the invention concerns a method of marker assisted selection comprising:

(a) obtaining a first maize plant having at least one allele of a marker locus, wherein the marker locus is located within 7 cM of SSR148152, CAPS25082, STS171, SNP661, and STS1944 on a public IBM genetic map and the allele is associated with increased resistance to head smut;

(b) crossing said first maize plant to a second maize plant;

(c) evaluating the progeny for at least said allele; and (d) selecting progeny maize plants that possess at least said allele.

In a nineteenth embodiment, the invention concerns a method of marker assisted selection comprising:

(a) obtaining a first maize plant having at least one allele of a marker locus, wherein the marker locus is located within a chromosomal interval comprising and flanked by umc1736 and umc2184 and the allele is associated with increased resistance to head smut;

(b) crossing said first maize plant to a second maize plant;

(c) evaluating the progeny for at least said allele; and (d) selecting progeny maize plants that possess at least said allele. In a nineteenth embodiment, the invention concerns a method of detecting a head smut resistance locus comprising detecting the presence of at least one marker allele selected from the group consisting of: MZA6393, 1M2-9, E6765-3, 2M4-1, 2M10-5, 2M11-3, 3M1-25, and STS148-1.

It is also clear that in any of the aforementioned methods, any of the described marker alleles associated head smut resistance may be linked to any second marker allele. Such a second marker allele would also be associated with head smut resistance, and would be useful in the ways described above.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1. Development of a SNP marker (SNP140313) for AZM4_140313 (assembled *Zea mays* sequence from TIGR) and its application in genotyping BC populations.

Figure 2:
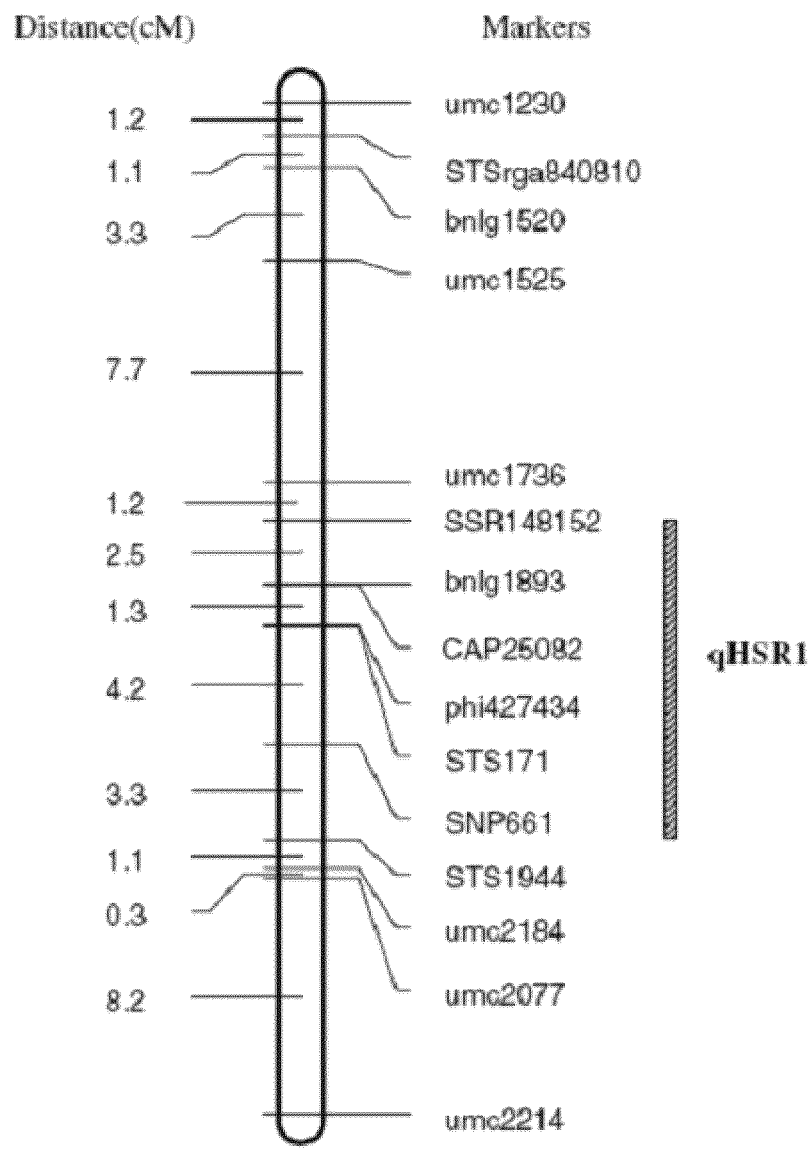

FIG. 2. Genetic-mapping of the newly-developed markers in the bin2.09 region.

FIG. 3. Alignment of the xylanase inhibitor gene from Mo17 and B73. The Mo17 sequence is found in qHSR1, the locus that confers head smut resistance in maize. B73 is a head smut sensitive variety of maize.

Figure 4:
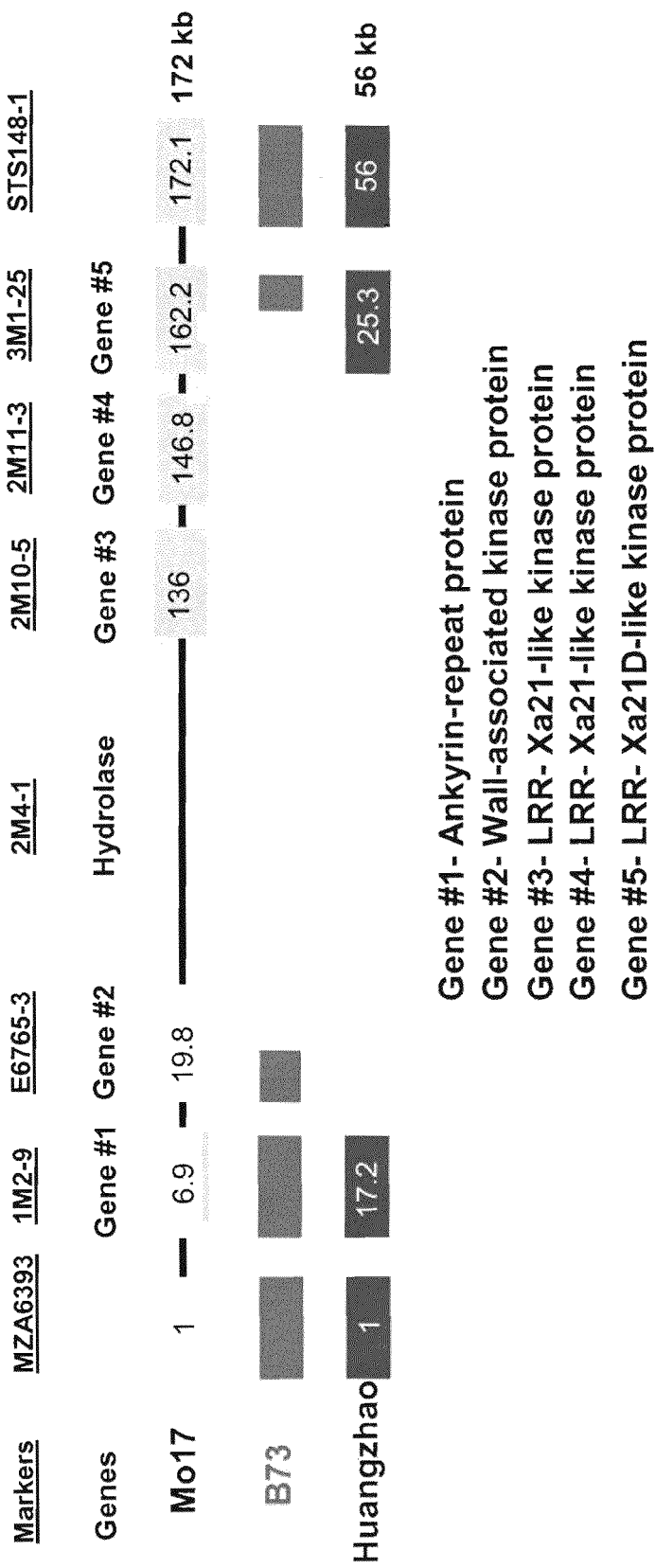

FIG. 4. A comparative drawing of Mo17, B73, and Huangzhao genomic structure in the qHSR region. B73 and Huangzhao both have deletions in the region when compared to Mo17. The markers mentioned in the current invention are shown at the top. Six genes of interest are noted, a hydrolase gene that is unique to Mo17; Gene 1, and ankyrin-repeat protein, is found in all three lines; Gene 2 a cell wall-associated kinase, is found in Mo17 and B73; Gene 3 and Gene 4 are related LRR-Xa21-like kinases that are unique to Mo17; and Gene 5 is a third LRR-Xa21 D-like kinase wholly or partly found in all three lines. Mo17 is 172 kb in length in this region, and Huangzhao is 56 kb in length.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

SEQ ID NO:1 is amplification primer CAPS25082-L.
SEQ ID NO:2 is amplification primer CAPS25082-R.
SEQ ID NO:3 is amplification primer SNP140313-L.
SEQ ID NO:4 is amplification primer SNP140313-R.
SEQ ID NO:5 is amplification primer SNP140313-snpL.
SEQ ID NO:6 is amplification primer SNP140313-snpR.
SEQ ID NO:7 is amplification primer SNP661-L.
SEQ ID NO:8 is amplification primer SNP661-R.
SEQ ID NO:9 is amplification primer SNP661-snpL.
SEQ ID NO:10 is amplification primer SNP661-snpR.
SEQ ID NO:11 is amplification primer STS1944-L.
SEQ ID NO:12 is amplification primer STS1944-R.
SEQ ID NO:13 is amplification primer STS171-L.
SEQ ID NO:14 is amplification primer STS171-R.
SEQ ID NO:15 is amplification primer SSR148152-L.
SEQ ID NO:16 is amplification primer SSR148152-R.
SEQ ID NO:17 is amplification primer STSrga3195-L.
SEQ ID NO:18 is amplification primer STSrga3195-R.
SEQ ID NO:19 is amplification primer STSrga840810-L.
SEQ ID NO:20 is amplification primer STSrga840810-R.
SEQ ID NO:21 is amplification primer STSsyn1-L.
SEQ ID NO:22 is amplification primer STSsyn1-R.
SEQ ID NO:23 is MZA6393 marker (from bacm.pk071.j12.f) that defines one end of the BAC contig covering the qHSR1 locus. The Huangzhao and B73 versions of this marker region are found in SEQ ID NOs:47 and 48 respectively.
SEQ ID NO:24 is ST148-1 the marker from the Mo17 version of ZMMBBc0478L09f that defines one end of the BAC contig covering the qHSR1 locus. The Huangzhao version of this marker region can be found in SEQ ID NOs:49.
SEQ ID NO:25 is the BAC contig comprised of overlapping clones bacm.pk071.j12, bacm.pk007.18, and bacm2.pk166.h1 that cover the qHSR1 locus.

SEQ ID NO:26 is the nucleic acid sequence from Mo17 representing the gene coding region for a xylanase inhibitor gene contained within the qHRS1 locus.
SEQ ID NO:27 is the translation product of SEQ ID NO:26.
SEQ ID NO:28 is the nucleic acid sequence from B73 representing the gene coding region for a xylanase inhibitor gene contained within the region of the B73 genome that is syntenic to the qHRS1 locus.
SEQ ID NO:29 is the translation product of SEQ ID NO:28.
SEQ ID NO:30 is the genomic DNA region from Mo17 encoding the xylanase inhibitor of SEQ ID NO:26/27 and 3 kb upstream of the coding region.
SEQ ID NO:31 is the nucleic acid sequence from Mo17 representing the gene coding region for a cell wall associated protein kinase gene contained within the qHRS1 locus.
SEQ ID NO:32 is the translation product of SEQ ID NO:31.
SEQ ID NO:33 is the genomic DNA region from Mo17 encoding the cell wall associated protein kinase of SEQ ID NO:31/32 and 2.4 kb upstream of the coding region.
SEQ ID NO:34 is the nucleic acid sequence from Mo17 representing the gene coding region for a HAT family dimerization protein gene (PCO662117) contained within the qHRS1 locus.
SEQ ID NO:35 is the translation product of SEQ ID NO:34.
SEQ ID NO:36 is the genomic DNA region from Mo17 encoding the HAT family dimerization protein gene of SEQ ID NO:34/35 and 2.4 kb upstream of the coding region.
SEQ ID NO:37 is the nucleic acid sequence from Mo17 representing the gene coding region for a HAT family dimerization protein gene (PCO66 2162/PCO548849/PCO523172) contained within the qHRS1 locus.
SEQ ID NO:38 is the translation product of SEQ ID NO:37.
SEQ ID NO:39 is the genomic DNA region from Mo17 encoding the HAT family dimerization protein gene of SEQ ID NO:37/38 and 2.4 kb upstream of the coding region.
SEQ ID NO:40 is the nucleic acid sequence from Mo17 representing the gene coding region for an uncharacterized protein gene (PCO648231) contained within the qHRS1 locus.
SEQ ID NO:41 is the translation product of SEQ ID NO:40.
SEQ ID NO:42 is the genomic DNA region from Mo17 encoding the uncharacterized protein gene of SEQ ID NO:40/41 and 2.4 kb upstream of the coding region.
SEQ ID NO:43 is the nucleic acid sequence from Mo17 representing the gene coding region for an uncharacterized protein gene (61_24) contained within the qHRS1 locus.
SEQ ID NO:44 is the translation product of SEQ ID NO:43.
SEQ ID NO:45 is the genomic DNA region from Mo17 encoding the uncharacterized protein gene of SEQ ID NO:43/44 and 2.4 kb upstream of the coding region.
SEQ ID NO:46 is nucleic acid sequence encoding a single EST sequence from Mo17 contained within the qHRS1 locus.
SEQ ID NO:47 is MZA6393 marker covering the qHSR1 locus from Huangzhao.
SEQ ID NO:48 is MZA6393 marker covering the qHSR1 locus from B73.
SEQ ID NO:49 is ST148-1 marker from Huangzhao4.
SEQ ID NO:47 is MZA6393 marker from Huangzhao4.
SEQ ID NO:48 is MZA6393 marker from B73.
SEQ ID NO:49 is STS148-1 marker from Huangzhao4.

SEQ ID NO:50 is amplification primer MZA6393L.
SEQ ID NO:51 is amplification primer MZA6393R.
SEQ ID NO:52 is amplification primer 1M2-9L.
SEQ ID NO:53 is amplification primer 1M2-9R.
SEQ ID NO:54 is 1M2-9 marker from Mo17.
SEQ ID NO:55 is 1M2-9 marker from Huangzhao4.
SEQ ID NO:56 is amplification primer E6765-3L.
SEQ ID NO:57 is amplification primer E6765-3R.
SEQ ID NO:58 is E6765-3 marker from Mo17.
SEQ ID NO:59 is amplification primer 2M4-1 L.
SEQ ID NO:60 is amplification primer 2M4-1R.
SEQ ID NO:61 is 2M4-1 marker from Mo17.
SEQ ID NO:62 is amplification primer 2M10-5L.
SEQ ID NO:63 is amplification primer 2M10-5R.
SEQ ID NO:64 is 2M10-5 marker from Mo17.
SEQ ID NO:65 is amplification primer 2M11-3L.
SEQ ID NO:66 is amplification primer 2M1'-3R.
SEQ ID NO:67 is 2M11-3 marker from Mo17.
SEQ ID NO:68 is amplification primer 3M1-25L.
SEQ ID NO:69 is amplification primer 3M1-25R.
SEQ ID NO:70 is 3M1-25 marker from Mo17.
SEQ ID NO:71 is 3M1-25 marker from Huangzhao4
SEQ ID NO:72 is amplification primer STS148-1L.
SEQ ID NO:73 is amplification primer STS148-1R.
SEQ ID NO:74 is amplification primer MZA15839-4-L.
SEQ ID NO:75 is amplification primer MZA15839-4-R.
SEQ ID NO:76 is amplification primer MZA18530-16-L.
SEQ ID NO:77 is amplification primer MZA18530-16-R.
SEQ ID NO:78 is amplification primer MZA5473-801-L.
SEQ ID NO:79 is amplification primer MZA5473-801-R.
SEQ ID NO:80 is amplification primer MZA16870-15-L.
SEQ ID NO:81 is amplification primer MZA16870-15-R.
SEQ ID NO:82 is amplification primer MZA4087-19-L.
SEQ ID NO:83 is amplification primer MZA4087-19-R.
SEQ ID NO:84 is amplification primer MZA158-30-L.
SEQ ID NO:85 is amplification primer MZA158-30-R.
SEQ ID NO:86 is amplification primer MZA15493-15-L.
SEQ ID NO:87 is amplification primer MZA15493-15-R.
SEQ ID NO:88 is amplification primer MZA9967-11-L.
SEQ ID NO:89 is amplification primer MZA9967-11-R.
SEQ ID NO:90 is amplification primer MZA1556-23-L.
SEQ ID NO:91 is amplification primer MZA1556-23-R.
SEQ ID NO:92 is amplification primer MZA1556-801-L.
SEQ ID NO:93 is amplification primer MZA1556-801-R.
SEQ ID NO:94 is amplification primer MZA17365-10-L.
SEQ ID NO:95 is amplification primer MZA17365-10-R.
SEQ ID NO:96 is amplification primer MZA17365-801-L.
SEQ ID NO:97 is amplification primer MZA17365-801-R.
SEQ ID NO:98 is amplification primer MZA14192-8-L.
SEQ ID NO:99 is amplification primer MZA14192-8-R.
SEQ ID NO:100 is amplification primer MZA15554-13-L.
SEQ ID NO:101 is amplification primer MZA15554-13-R.
SEQ ID NO:102 is amplification primer MZA4454-14-L.
SEQ ID NO:103 is amplification primer MZA4454-14-R.
SEQ ID NO:104 is the nucleic acid sequence from Mo17 representing the gene coding region for ankyrin-repeat protein (Gene 1 FIG. 4).
SEQ ID NO:105 is the translation product of SEQ ID NO:104.
SEQ ID NO:106 is the genomic DNA region from Mo17 encoding ankyrin repeat protein.
SEQ ID NO:107 is the nucleic acid sequence from Mo17 representing the gene coding region for hydrolase.
SEQ ID NO:108 is the translation product of SEQ ID NO:107.
SEQ ID NO:109 is the genomic DNA region from Mo17 encoding hydrolase.
SEQ ID NO:110 is the nucleic acid sequence from Mo17 representing the gene coding region for LRR-Xa21-like kinase (Gene 3, FIG. 4) coding region
SEQ ID NO:111 is the translation product of SEQ ID NO: 110.
SEQ ID NO:112 is the nucleic acid sequence from Mo17 representing the gene coding region for LRR-Xa21-like kinase (Gene 4, FIG. 4) coding region
SEQ ID NO:113 is the translation product of SEQ ID NO:112.
SEQ ID NO:114 is the genomic DNA region from Mo17 encoding LRR-Xa21-like kinase (Gene 4, FIG. 4).
SEQ ID NO:115 is the nucleic acid sequence from Mo17 representing the gene coding region for LRR-Xa21 D-like kinase (Gene 5, FIG. 4).
SEQ ID NO:116 is the translation product of SEQ ID NO:115.
SEQ ID NO:117 is the genomic DNA region from Mo17 encoding LRR-Xa21 D-like kinase (Gene 5, FIG. 4).

DETAILED DESCRIPTION

The present invention provides allelic compositions in maize and methods for identifying and for selecting maize plants with increased head smut resistance. Also within the scope of this invention are allelic compositions and methods used to identify and to counter-select maize plants that have decreased head smut resistance. The following definitions are provided as an aid to understand this invention.

The mapping of the head smut resistance locus is outlined in a manuscript "Identification and fine-mapping of a major QTL conferring resistance against head smut in maize" by Yongsheng Chen, Qing Chao, Guoqing Tan, Jing Zhao, Meijing Zhang, Qing Ji, and Mingliang Xu. The manuscript is attached as an appendix to the specification.

The term "allele" refers to one of two or more different nucleotide sequences that occur at a specific locus. A "favorable allele" is the allele at a particular locus that confers, or contributes to, an agronomically desirable phenotype, e.g., increased head smut resistance, or alternatively, is an allele that allows the identification of plants with decreased head smut resistance that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele is "positively" associated with a trait when it is linked to it and when the presence of the allele is an indicator that the desired trait or trait form will occur in a plant comprising the allele. An allele is "negatively" associated with a trait when it is linked to it and when the presence of the allele is an indicator that a desired trait or trait form will not occur in a plant comprising the allele.

An individual is "homozygous" at a locus if the individual has only one type of allele at that locus (e.g., a diploid organism has a copy of the same allele at a locus for each of two homologous chromosomes). An organism is "heterozygous" at a locus if more than one allele type is present at that locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo recombination at a frequency of less than or equal to 20% or 10%.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). A "topcross test" is a progeny test derived by crossing each parent with the same tester, usually a homozygous line. The parent being tested can be an open-pollinated variety, a cross, or an inbred line.

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. If two different markers have the same genetic map location, the two markers are in such close proximity to each other that recombination occurs between them with such low frequency that it is undetectable.

The order and genetic distances between genetic markers can differ from one genetic map to another. This is because each genetic map is a product of the mapping population, types of markers used, and the polymorphic potential of each marker between different populations. For example, 10 cM on the internally derived genetic map (also referred to herein as "PHB" for Pioneer Hi-Bred) is roughly equivalent to 25-30 cM on the IBM2 2005 neighbors frame public map (a high resolution map available on maizeGDB). However, information can be correlated from one map to another using a general framework of common markers. One of ordinary skill in the art can use the framework of common markers to identify the positions of genetic markers and QTLs on each individual genetic map. A comparison of marker positions between the internally derived genetic map and the IBM2 neighbors genetic map can be seen in Table 3.

"Genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

"Hybridization" or "nucleic acid hybridization" refers to the pairing of complementary RNA and DNA strands as well as the pairing of complementary DNA single strands. "Stringency" refers to the conditions with regard to temperature, ionic strength, and the presence of certain organic solvents, such as formamide, under which nucleic acid hybridizations are carried out. Under high stringency conditions (high temperature and low salt), two nucleic acid fragments will pair, or "hybridize", only if there is a high frequency of complementary base sequences between them.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite strain" is an agronomically superior line that has resulted from many cycles of breeding and selection for superior agronomic performance. Numerous elite lines are available and known to those of skill in the art of maize breeding. An "elite population" is an assortment of elite individuals or lines that can be used to represent the state of the art in terms of agronomically superior genotypes of a given crop species, such as maize. Similarly, an "elite germplasm" or elite strain of germplasm is an agronomically superior germplasm, typically derived from and/or capable of giving rise to a plant with superior agronomic performance, such as an existing or newly developed elite line of maize.

A "public IBM genetic map" refers to any of following maps: IBM, IBM2, IBM2 neighbors, IBM2 FPC0507, IBM2 2004 neighbors, IBM2 2005 neighbors, or IBM2 2005 neighbors frame. All of the IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps.

In contrast, an "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

As used herein, the term "linkage" is used to describe the degree with which one marker locus is "associated with" another marker locus or some other locus (for example, a head smut resistance locus). The linkage relationship between a molecular marker and a phenotype is given as a "probability" or "adjusted probability". The probability value (also known as p-value) is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

In interval mapping, linkage between two marker loci can be calculated using odds ratios (i.e. the ratio of linkage versus no linkage). This ratio is more conveniently expressed as the logarithm of the ratios and is called a logarithm of odds (LOD) value or LOD score (Risch, Science 255:803-804 (1992)). A LOD value of 3 between two markers indicates that linkage is 1000 times more likely than no linkage. Lower LOD values, such as 2.0 or 2.5, may be used to detect a greater level of linkage.

"Linked loci" are located in close proximity such that meiotic recombination between homologous chromosome pairs does not occur with high frequency (frequency of equal to or less than 10%) between the two loci, e.g., linked loci co-segregate at least about 90% of the time, e.g., 91%, 92%, 93%, 94%, 95%, 96%, 97%, 98%, 99%, 99.5%, 99.75%, or more of the time. Marker loci are especially useful when they demonstrate a significant probability of co-segregation (linkage) with a desired trait (e.g., increased head smut resistance). For example, in some aspects, these markers can be termed "linked QTL markers".

Linkage can be expressed as a desired limit or range. For example, in some embodiments, any marker is linked (genetically and physically) to any other marker when the markers are separated by less than 50, 40, 30, 25, 20, or 15 map units (or cM). Further linkage can be described by separations of 14, 13, 12, 11, 10, 9, 8, 7, 6, 5, 4, 3, 2, 1 map units (or cM). In some aspects, it is advantageous to define a bracketed range of linkage, for example, between 10 and 20 cM, between 10 and 30 cM, or between 10 and 40 cM.

The more closely a marker is linked to a second locus, the better an indicator for the second locus that marker becomes. Thus, "closely linked loci" such as a marker locus and a second locus display an inter-locus recombination frequency of 10% or less, or about 9% or less, or about 8% or less, or about 7% or less, or about 6% or less, or about 5% or less, or about 4% or less, or about 3% or less, and or about 2% or less. In other embodiments, the relevant loci display a recombination frequency of about 1% or less, e.g., about 0.75% or less, or about 0.5% or less, or about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two genetic markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5, 0.25, 0.1, 0.075, 0.05, 0.025, or 0.01 cM or less from each other.

When referring to the relationship between two genetic elements, such as a genetic element contributing to increased head smut resistance and a proximal marker, "coupling" phase linkage indicates the state where the "favorable" allele at the stalk strength locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a phenotype. A marker locus can be "associated with" (linked to) a trait, e.g., head smut resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. Values for $r^2$ above 1/3 indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a chromosomal region where a gene or marker is located. For example, a "gene locus" is a specific chromosome location in the genome of a species where a specific gene can be found.

"Maize" and "corn" are used interchangeably herein.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus. Nucleic acids are "complementary" when they specifically "hybridize", or pair, in solution, e.g., according to Watson-Crick base pairing rules.

The markers with the designation PHM represent a set of primers that amplify a specific piece of DNA, herein referred to as an "amplicon". The nucleotide sequences of the amplicons from multiple maize lines are compared, and polymorphisms, or variations, are identified. The polymorphisms include single nucleotide polymorphisms (SNPs), simple sequence repeats (SSRs), insertion/deletions (indels), etc.

A "marker allele", alternatively an "allele of a marker locus", can refer to one of a plurality of polymorphic nucleotide sequences found at a marker locus in a population that is polymorphic for the marker locus. Alternatively, marker alleles designated with a number represent the specific combination of alleles, also referred to as a "haplotype", at informative polymorphic sites of that specific marker locus. In some aspects, marker loci correlating with head smut resistance in maize are provided.

A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus.

"Genetic markers" are nucleic acids that are polymorphic in a population, and the marker alleles can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Head smut resistance" refers to the ability of a maize plant to withstand infection by the host-specific fungus *Sphacelotheca reiliana* (Kühn) Clint. This includes, but is not limited to, reduced sori production, improved plant vigor, improved tassel function, and improved corn yield when compared to maize plants lacking the resistance locus described herein.

The nucleic acids and polypeptides of the embodiments find use in methods for conferring or enhancing fungal resistance to a plant. The source of the resistance can be a naturally occurring genetic resistance locus that is introgressed via breeding into a sensitive maize population lacking the resistance locus, or alternatively, the genes conferring the resistance can be ectopically expressed as transgenes which confer resistance when expressed in the sensitive population. Accordingly, the compositions and methods disclosed herein are useful in protecting plants from fungal pathogens. "Pathogen resistance," "fungal resistance," and "disease resistance" are intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from pathogen attack.

Hence, the methods of the embodiments can be utilized to protect plants from disease, particularly those diseases that are caused by plant fungal pathogens. As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the invention also will enhance or improve fungal plant pathogen resistance, such that the resistance of the plant to a fungal pathogen or pathogens will increase. The term "enhance" refers to improve, increase, amplify, multiply, elevate, raise, and the like. Herein, plants of the invention are described as being resistant to infection by *Sphacelotheca reiliana* (Kühn) Clint or having 'enhanced resistance' to infection by *Sphacelotheca reiliana* (Kühn) Clint as a result of the head smut resistance locus of the invention. Accordingly, they typically exhibit increased resistance to the disease when compared to equivalent plants that are susceptible to infection by *Sphacelotheca reiliana* (Kühn) Clint because they lack the head smut resistance locus.

In particular aspects, methods for conferring or enhancing fungal resistance in a plant comprise introducing into a plant at least one expression cassette, wherein the expression cassette comprises a nucleotide sequence encoding an antifungal polypeptide of the embodiments operably linked to a promoter that drives expression in the plant. The plant expresses the polypeptide, thereby conferring fungal resistance upon the plant, or improving the plant's inherent level of resistance. In particular embodiments, the gene confers resistance to the fungal pathogen, *Sphacelotheca reiliana* (Kühn) Clint.

Expression of an antifungal polypeptide of the embodiments may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The embodiments of the invention encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have the ability to confer fungal resistance upon a plant. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments. Fragments of a nucleotide sequence that are useful as hybridization probes or PCR primers generally need not encode a biologically active portion of a protein.

As used herein, "full-length sequence," in reference to a specified polynucleotide, means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an antipathogenic polypeptide can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 3 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant fungal pathogen resistance as described herein. Such variants may result, for example, from genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the embodiments include both naturally occurring sequences as well as mutant forms. Likewise, the proteins of the embodiments encompass both naturally occurring proteins as well as variations and modified forms thereof. Such variants will continue to possess the desired ability to confer or enhance plant fungal pathogen resistance. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the ability of the plant to resist fungal pathogenic attack.

Variant polynucleotides and proteins also encompass sequences and proteins derived from mutagenic or recombinogenic procedures, including and not limited to procedures such as DNA shuffling. One of skill in the art could envision modifications that would alter the range of pathogens to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant fungal pathogen resistance. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances fungal plant pathogen resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the embodiments can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al, *Cloning Vectors: A Laboratory Manual,* 1985, supp. 1987; Weissbach and Weissbach, *Methods for Plant Molecular Biology, Academic Press,* 1989; and Flevin et al., *Plant Molecular Biology Manual*, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the embodiments. Screening to obtain lines displaying the desired expression level and pattern of the polynucleotides or of the Rcg1 locus may be accomplished by amplification, Southern analysis of DNA, northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, expression cassettes comprising a promoter operably linked to a heterologous nucleotide sequence of the embodiments are further provided. The expression cassettes of the embodiments find use in generating transformed plants, plant cells, and microorganisms and in practicing the methods for inducing plant fungal pathogen resistance disclosed herein. The expression cassette will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); PEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

It may sometimes be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, and are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the polypeptides of the embodiments within a particular plant tissue. For example, a tissue-preferred promoter may be used to express a polypeptide in a plant tissue where disease resistance is particularly important, such as, for example, the roots, the stalk or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, and are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of a polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al.

(1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, and are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, and are not limited to, bean β-phaseolin, napin, β-conglycinin, soybean lectin, cruciferin, and the like. For monocots, seed-specific promoters include, and are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes may additionally contain 5' leader sequences. Such leader sequences can act to enhance translation. Translation leaders are known in the art and include:

picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) *Ph.D. Thesis*, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) *Ph.D. Thesis*, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing Rcg1 with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® (a grain production system) methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al, 1987, *Meth. Enzymol.* 143:277) and particle-accelerated or "gene gun" transformation technology (Klein et al, 1987, *Nature* (London) 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055- and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, an expression cassette of the embodiments, stably incorporated into their genome.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant calli, plant clumps, and plant seeds. A plant cell is a cell of a plant, either taken directly from a seed or plant, or derived through culture from a cell taken from a plant. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance fungal plant pathogen resistance or protect from fungal pathogen attack in plants, especially corn (*Zea mays*). It will protect different parts of the plant from attack by pathogens, including and not limited to stalks, ears, leaves, roots and tassels. Other plant species may also be of interest in practicing the embodiments of the invention, including, and not limited to, The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

In maize, a number of BACs, or bacterial artificial chromosomes, each containing a large insert of maize genomic DNA, have been assembled into contigs (overlapping contiguous genetic fragments, or "contiguous DNA"). A BAC can assemble to a contig based on sequence alignment, if the BAC is sequenced, or via the alignment of its BAC fingerprint to the fingerprints of other BACs in a contig. The assemblies are available to the public using the genome Maize Genome Browser, which is publicly available on the internet.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "maize plant" includes whole maize plants, maize plant cells, maize plant protoplast, maize plant cell or maize tissue culture from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips and the like.

The term "quantitative trait locus" or "QTL" refers to a region of DNA that is associated with the differential expression of a phenotypic trait in at least one genetic background, e.g., in at least one breeding population. QTLs are closely linked to the gene or genes that underlie the trait in question.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Methods for identifying maize plants with increased head smut resistance through the genotyping of associated marker loci are provided. Head smut resistance in maize is an agronomically important trait, as head smut infection lowers yield.

It has been recognized for quite some time that specific chromosomal loci (or intervals) can be mapped in an organism's genome that correlate with particular quantitative phenotypes, such as head smut resistance. Such loci are termed quantitative trait loci, or QTL. The plant breeder can advantageously use molecular markers to identify desired individuals by identifying marker alleles that show a statistically significant probability of co-segregation with a desired phenotype, manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a quantitative trait such as head smut resistance. The basic idea underlying all of these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect QTLs are: 1) Population-based structured association analysis and 2) Pedigree-based association analysis. In a population-based structured association analysis, lines are obtained from pre-existing populations with multiple founders, e.g. elite breeding lines. Population-based association analyses rely on the decay of linkage disequilibrium (LD) and the idea that in an unstructured population, only correlations between QTL and markers closely linked to the QTL will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait. In pedigree-based association analyses, LD is generated by creating a population from a small number of founders.

For example, in an interval mapping approach (Lander and Botstein, Genetics 121:185-199 (1989), each of many positions along the genetic map (say at 1 cM intervals) is tested for the likelihood that a QTL is located at that position. The genotype/phenotype data are used to calculate for each test position a LOD score (log of likelihood ratio). When the LOD score exceeds a critical threshold value (herein equal to 2.5), there is significant evidence for the location of a QTL at that position on the genetic map (which will fall between two particular marker loci).

Markers associated with the head smut resistance trait are identified herein, as are marker alleles associated with either increased or decreased head smut resistance. The methods involve detecting the presence of at least one marker allele associated with either the increased or decreased head smut resistance in the germplasm of a maize plant.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in maize, 1 cM correlates, on average, to about 2,140,000 base pairs (2.14 Mbp).

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the QTL markers can be used to predict the state of the head smut resistance in a maize plant. This includes any marker within 50 cM of the genetic locus. The closer a marker is to a QTL marker, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM, 0.25 cM, 0.1 cM, 0.075 cM, 0.05 cM, 0.025 cM, or 0.01 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, 0.1%, 0.075%, 0.05%, 0.025%, or 0.01% or less) are said to be "proximal to" each other.

Although particular marker alleles can show co-segregation with the head smut resistance phenotype, it is important to note that the marker locus is not necessarily part of the QTL locus responsible for the expression of the head smut resistance phenotype. For example, it is not a requirement that the marker polynucleotide sequence be part of a gene that imparts increased head smut resistance (for example, be part of the gene open reading frame). The association between a specific marker allele with either the increased or decreased head smut resistance phenotype is due to the original "coupling" linkage phase between the marker allele and the QTL allele in the ancestral maize line from which the QTL allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the genetic marker can be used to monitor segregation of the phenotype. It only changes which marker allele is considered favorable in a given segregating population.

A variety of methods well known in the art are available for identifying chromosome intervals. The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for head smut resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

Methods for marker assisted selection (MAS), in which phenotypes are selected based on marker genotypes, are also provided. To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. The procedures used to detect marker alleles are known to one of ordinary skill in the art. After the presence (or absence) of a particular marker allele in the biological sample is verified, the plant is selected and is crossed to a second plant, preferably a maize plant from an elite line. The progeny plants produced by the cross can be evaluated for that specific marker allele, and only those progeny plants that have the desired marker allele will be chosen.

Maize plant breeders desire combinations of desired genetic loci, such as those marker alleles associated with increased resistance to head smut, with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to head smut resistance loci, provide an effective method for selecting varieties with head smut resistance in breeding programs. For example, one advantage of marker-assisted selection over field evaluations for head smut resistance is that MAS can be done at any time of year, regardless of the growing season. Moreover, environmental effects are largely irrelevant to marker-assisted selection.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable head smut resistance marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because plants may be otherwise undesirable, e.g., due to low yield, low fecundity, or the like. In contrast, strains which are the result of intensive breeding programs may have excellent yield, fecundity or the like, merely being deficient in one desired trait such as head smut resistance.

One application of MAS is to use the markers to increase the efficiency of an introgression or backcrossing effort aimed at introducing an increased resistance to head smut QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

The most preferred QTL markers (or marker alleles) for MAS are those that have the strongest association with the head smut resistance trait.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Plant Materials

Two inbred lines, 'Ji1037' (donor parent) and 'Huangzhao4' (recurrent parent), which differ wildly in resistance to the host-specific fungus *Sphacelotheca reiliana* Clint were used as parental lines to develop all mapping populations in this study. All plant materials tested in the present study were artificially inoculated with *S. reiliana* Clint. 'Ji1037' shows fully resistant to head smut and no any susceptible individual has ever been observed in the field; while, 'Huangzhao4', an elite Chinese inbred line, is highly susceptible to head smut with ~75% susceptible individuals in the field. In 2004, a $BC_1$ population consisting of 314 individuals along with two parents was grown in the experimental farm of the Jilin Academy of Agricultural Sciences, Gongzhulin. Each $BC_1$ individual was evaluated for its resistance against head smut. Resistant $BC_1$ individuals were backcrossed to 'Huangzhao4' to generate $BC_{1:2}$ families ($BC_2$ population). In 2005, ~20 plants from each $BC_{1:2}$ family were grown in a single plot to evaluate their resistances to head smut. Recombinant individuals from $BC_2$ population were identified and backcrossed to 'Huangzhao4' to generate $BC_{2:3}$ families or self-pollinated to produce $BC_2F_2$ families. In 2006, approximately 80 individuals from each of the 59 $BC_{2:3}$ and nine $BC_2F2$ families were grown in the experimental farm of the Jilin Academy of Agricultural Sciences for investigating their resistances to head smut.

Example 2

Artificial Inoculation and Resistant Scoring in the Field

The sori containing teliospores of *S. reliana* were collected from the field in the previous growing season and stored in cloth bag in a dry and well ventilated environment. Before planting, spores were removed from the sori, filtered, and then mixed with soil at a ratio of 1:1000. The mixture of soil and teliospores were used to cover maize kernels when sowing seeds to conduct artificial inoculation. Plants at maturity stage were scored for the presence/absence of sorus in either ear or tassels as an indicator for susceptibility/resistance.

DNA Extraction

Leaf tissues from one-month-old plants were harvested and ground to a powder in liquid nitrogen. Genomic DNA was extracted followed the method described by Murray and Thompson (1980).

Genotyping at SSR Markers and Linkage Map Construction

SSR markers were firstly employed to check their polymorphisms between two parents 'Ji1037' and 'Huangzhao4'. Only those SSR markers that showed unambiguously polymorphic bands and evenly distributed across ten chromosomes were used to genotype segregating populations. PCR reactions were performed as follows: denaturation at 94° C. for 2 minutes, followed by 35 cycles of denaturation at 94° C. for 30 seconds, annealing at 58° C. for 30 seconds, extension at 72° C. for 30 seconds, and with a final extension step at 72° C. for 10 minutes. The PCR products were subjected to electrophoresis on 6% polyacrylamide gel, followed by sliver-staining for visualization.

A total of 94 $BC_1$ individuals were randomly selected from the $BC_1$ generation and assayed for their genotypes at the 113 polymorphic SSR markers. A PCR band was marked as '2' if it is the same as that of the donor parent, and scored as '1' if it is identical to that of the recurrent parent. The ratio of homozygotes (1/1) to heterozygotes (1/2) in the $BC_1$ backcross population was analyzed for its consistency of 1:1 at each SSR marker by $x^2$ test. The genetic distances between SSR markers were estimated by MAPMAKER/Exp version 3.0b (Lincoln et al. 1992). By the way, some markers on chromosome 2 were genotyped in different scales of populations, and their genetic positions were adjusted with the integration data in the JoinMap software.

Data Analysis and QTL/Gene Mapping

Putative QTLs conferring resistance to head smut were identified according to design III of Trait-Based Analysis (Lebowitz et al. 1987). Briefly, $BC_1$ individuals with the resistance QTL are expected to be more resistant to head smut than those without the resistance QTL. Consequently, a marker allele adjacent to the resistance QTL in coupling would show higher frequency in the resistant group than that in the susceptible group. A tetrad grids $x^2$ test (SAS® 8.2 version) was used to test allele frequencies at all markers between the resistant and susceptible groups to scan putative QTL across whole genome. Thereafter, a number of methods were employed to confirm the major QTL region and its effectiveness in resistance to head smut. First, the SSR markers in the putative major QTL region were used to genotype all $BC_1$ individuals to confirm the presence of the major QTL. Second, infection percentages of $BC_1$ individuals were estimated based on their $BC_{1:2}$ progenies to confirm the putative major QTL by single-factor analysis of variance. Third, putative QTL was identified across the ten chromosomes by the composite interval mapping method (Windows QTL Cartographer Version 2.0 software). Finally, the major QTL was further confirmed by estimating its genetic effect in reducing disease incidence.

Example 3

Development of the Region-Specific Markers

Sequences available in the major resistance QTL region, including the anchored EST, IDP, RGA, BAC, and BAC-end sequences, were used to develop high-density markers. These sequences were compared to NCBI and MAGI databases via tBLASTn to obtain possible longer sequences. Primer was designed using the PRIMER5.0 software in accordance with the following parameters: 20 nucleotides in length, GC content of 40% to 60%, no secondary structure, and no consecutive tracts of a single nucleotide.

Primer pairs were used to amplify the corresponding segments from both parents. The cycling parameters were set up the same as those described above except for the annealing temperature that was adjusted according to different primer pairs. Only those amplicons with the same or bigger than predicted were cut down from gel and purified with Gel Extraction Kit (Qiagen GmbH, Hilden, Germany). The purified PCR products were then cloned into the vector PGEM® (Promega, Madison, USA). Normally, three to five positive clones for each amplicon were selected for sequencing to avoid any contamination or mismatch. The amplicon sequence was firstly compared with the original one from which it was derived to make sure the right one was obtained, and then comparison was conducted to search for sequence divergence between two parents by using DNAMAN software. The InDels were amenable for developing sequence-tagged site (STS) markers; while single nuclear polymorphism (SNP) can be used to develop either SNP marker or CAPS marker (cleaved-amplified polymorphic sequence). A CAPS marker is developed if the SNP is related to a given restriction site. In developing SNP marker, a SNPpicker program of SeqVISTA software was used to see if it was possible to create a specific restriction site by introducing a mismatch base pair into primer to alter a 'half-site' to a 'full-site' for a specific restriction site, following the method described by Niu and Hu (2004).

The primer pairs were used to amplify the two parents to develop high-density markers. For STS markers, polymorphic PCR bands should appear after electrophoresis on agarose or polyacrylamide gel. For those CAPS and SNP markers, polymorphic bands could be observed on agarose or polyacrylamide gel after digestion with certain restriction endonucleases.

Example 4

Fine Mapping

Recombinant individuals from the $BC_2$ population were screened out with the SSR markers in the major QTL region. Due to partial penetrance for head smut resistance, it would be at high risk to judge whether or not a $BC_2$ recombinant carries the resistance gene based on performance of a single individual. Hence, we adopted a more robust method to judge the presence/absence of the resistance gene for a single $BC_2$ recombinant based on both genotypes and phenotypes of its progeny. If there is no resistance gene in the donor region for a certain $BC_2$ recombinant, its progeny with donor regions would show no difference with those without donor regions in resistance to head smut. On the contrary, if the donor region harbors the resistance gene, the progeny with the donor regions would show significantly higher resistant than those without the donor regions. By comparing the insert sizes of the 'resistant' and 'non-resistant' donor regions, we could fix on an interval where the resistance gene resides on. With an application of the newly-developed high-density markers, we could definitely define the donor regions harboring the resistance gene and therefore narrow down the resistance region into a very short interval. In all comparisons, significant differences were estimated on SAS® software using $x^2$ test.

Example 5

Construction of the SSR Linkage Map

A total of 700 SSR markers were checked for their polymorphisms between 'Ji1037' and 'Huangzhao4'. Among the 347 polymorphic SSR markers, 113 markers evenly distributed across ten chromosomes were selected to genotype the $BC_1$ mapping population. Of these 113 markers, 33 (29.2%) showed distortion segregation at P<0.05 or at p<0.01. Generally, markers showing genetic distortion had no negative impact on QTL detection. Therefore, a linkage map was constructed using all 113 SSR markers. The map was ~1753.4 cM in length with one marker in every 14.6 cM averagely.

Example 6

Mapping Putative QTLs

According to the Design III of TB analysis (Lebowitz et al. 1987), each of the 113 SSR markers was tested for its frequency at 1/2 (heterozygote) and 1/1 (homozygote) in both the resistant and susceptible groups. The significant biases at frequencies between the resistant and susceptible groups were observed for those markers located on the four chromosomal regions (bins 1.02/3, 2.08/9, 6.07, and 10.03/4), suggesting the presence of four putative QTLs (Table 1). For instance, the markers on bin 2.09 showed no distortion from 1:1 ratios of heterozygote to homozygote in the whole $BC_1$ population. However, percentages of heterozygote at these markers significantly differ between the resistant and susceptible groups with the P values<0.0001 (Table 1). The result strongly indicated the presence of a major QTL (named as qHSR1) in this region. Markers on both bin 10.03/4 and bin 1.02/3 had the P values<0.01 (Table 1), implying the presence of putative QTLs with less effects in these two regions. Markers on bin 6.07 also showed skew with the P values<0.05 (Table 1), suggesting the presence of a possible minor QTL. In addition, only one marker on bin 4.01 or bin 5.03 was found to show frequency skew between the resistant and susceptible groups (Table 1), it was, therefore, difficult to judge whether or not a QTL was actually present in these two bins.

TABLE 1

Scanning putative QTL across the whole genome via a tetrad grids χ2 test at the 113 SSR markers

| | | Percentage of heterozygote (%) | | | P | putative |
|---|---|---|---|---|---|---|
| bins | Markers | In R group | In S group | χ2 | values | QTL |
| 1.02 | bnlg1614 | 48.65 | 71.43 | 4.93 | 0.0265 | Yes |
| 1.02 | bnlg1083 | 50.00 | 72.73 | 5.00 | 0.0253 | |
| 1.03 | umc1403 | 44.74 | 76.36 | 9.69 | 0.0019 | |

TABLE 1-continued

Scanning putative QTL across the whole genome via a tetrad grids χ2 test at the 113 SSR markers

| bins | Markers | Percentage of heterozygote (%) | | χ2 | P values | putative QTL |
|---|---|---|---|---|---|---|
| | | In R group | In S group | | | |
| 2.08 | bnlg1141 | 65.63 | 36.36 | 6.95 | 0.0084 | Yes |
| 2.08/09 | umc1230 | 68.57 | 40.38 | 6.66 | 0.0099 | |
| 2.09 | bnlg1520 | 72.22 | 36.36 | 11.19 | 0.0008 | |
| 2.09 | umc1525 | 81.08 | 33.93 | 19.87 | <0.0001 | |
| 2.09 | umc1736 | 86.11 | 30.00 | 26.49 | <0.0001 | |
| 2.09 | bnlg1893 | 91.67 | 26.00 | 36.28 | <0.0001 | |
| 2.09 | umc1207 | 91.67 | 26.53 | 35.46 | <0.0001 | |
| 2.09 | phi427434 | 91.43 | 29.63 | 32.64 | <0.0001 | |
| 2.09 | umc2184 | 94.74 | 30.19 | 37.65 | <0.0001 | |
| 2.09 | umc2077 | 94.59 | 28.85 | 37.96 | <0.0001 | |
| 2.09 | umc2214 | 92.11 | 34.55 | 30.58 | <0.0001 | |
| 4.01 | umc1164 | 60.00 | 37.21 | 4.02 | 0.045 | ? |
| 5.03 | umc1447 | 56.76 | 34.00 | 4.48 | 0.0344 | ? |
| 6.07 | umc1063 | 34.21 | 57.14 | 4.78 | 0.0289 | Yes |
| 6.07 | phi299852 | 33.33 | 56.36 | 4.638 | 0.0314 | |
| 10.03 | umc1938 | 76.47 | 34.69 | 14.038 | 0.0002 | Yes |
| 10.04 | phi062 | 72.97 | 41.07 | 9.128 | 0.0025 | |

SSR markers on each bin are ordered according to their positions on the genetic linkage map of the present study.
R group: resistant group;
S group: susceptible group;
P value: probability of H0 hypothesis that is independent between genotype and trait.

Percentages of heterozygote (1/2) in bin 2.09 and bin 10.03/4 were significant higher in the resistant group than those in the susceptible group, suggesting the resistance alleles were derived from the donor parent 'Ji1037'. On the contrary, heterozygotes (1/2) in bin 1.02/3 and bin 6.07 had lower percentages in the resistant group compared with those in the susceptible group, indicating that the resistance alleles were derived from the susceptible parent 'Huangzhao 4'.

Comparisons of the four putative QTLs in the present study with those detected by other groups resulted in two common QTLs. The QTL in bin 1.02/3 in this study was also reported by Shi et al. (2005) and Lu and Brewbaker (1999). The major QTL in bin 2.09 in our study was also detected in Shi's study, in which the mapping population was derived from the cross of 'Huangzhao4'×'Mo17' (Shi et al. 2005). Interestingly, the same susceptible line 'Huangzhao4' and a closely-related resistant line 'Ji1037' ('Ji1037' was developed from the cross of 'Mo17'/'Suwan') were used to prepare the mapping population in the present study. This may explain why the same major QTL with similar genetic effect was detected in bin 2.09 in both studies. The major QTL in bin 2.09 is, therefore, the best choice for the resistance gene cloning and marker-assisted selection to improve maize resistance to head smut.

Example 7

Confirmation of the Major QTL

To confirm the presence of the major QTL (qHSR1) in bin 2.09 and its genetic effect on resistance to head smut, it is necessary to utilize markers to genotype all $BC_1$ individuals. The eight SSR markers in bin2.09, including bnlg1520, umc1736, bnlg1893, umc1207, phi427-434, umc2184, umc2077, and umc2214, were used to genotype the 118 resistant and 158 susceptible $BC_1$ plants. Of the 118 resistant individuals, 107 (90.7%) were heterozygotes/recombinants and only 11 (9.3%) were homozygotes at the eight markers. Of the 158 susceptible individuals, however, only 60 (38%) were heterozygotes/recombinants and as many as 98 (62%) were homozygotes. These results showed that the donor region in bin 2.09 could significantly enhance maize resistance to head smut, strongly supporting the presence of the major QTL in bin2.09. It should be noted that head smut was very serious in 2004 due to drought during the seedling stage. The susceptible 'Huangzhao4' had 86% susceptible individuals, compared with ~75% in normal year.

In addition, a total of 97 $BC_{1:2}$ families were produced from the resistant $BC_1$ individuals. These $BC_{1:2}$ families ranged from 5.9%~88.3% in disease incidences. Single factor analysis of variance was performed by analyzing both disease incidence and genotype at each of the eight SSR markers on bin 2.09 region. The results showed that these eight SSR markers strongly linked to qHSR1 (Table 2).

TABLE 2

Single factor analysis of variance of the $BC_{1:2}$ families

| SSR markers | b0 | b1 | LR | F(1, n-2) | pf(F) |
|---|---|---|---|---|---|
| umc2214 | 3.8321 | −4.5175 | 18.6152 | 20.0983 | **0.0000 |
| umc2077 | 3.8506 | −4.5464 | 18.7612 | 20.2716 | **0.0000 |
| umc2184 | 3.8534 | −4.5509 | 18.7920 | 20.3082 | **0.0000 |
| phi427434 | 3.8583 | −4.5828 | 19.0426 | 20.6065 | **0.0000 |
| umc1207 | 3.8574 | −4.5890 | 19.0812 | 20.6525 | **0.0000 |
| bnlg1893 | 3.8566 | −4.5941 | 19.1175 | 20.6959 | **0.0000 |
| umc1736 | 3.8411 | −4.7083 | 20.0836 | 21.8536 | **0.0000 |
| bnlg1520 | 3.7321 | −4.4259 | 18.1954 | 19.6013 | **0.0000 | y = b0 + b1x + e;
LR = −2log(L0/L1);
**significant at 0.01% level

Furthermore, the WinQtlCart 2.0 software (Statistical Genetics, North Carolina State University, USA) was used to scan the putative QTLs across the whole genome with the Composite Interval Mapping (CIM). A major QTL with the LOD value of 11.8 was detected on bin 2.09, bordered by SSR markers umc1736 and umc2184. The QTL could explain ~30% of phenotypic variation.

Example 8

Developing New Markers on Bin 2.09 Region

In our study, a total of 30 primer pairs were designed based on the sequences available in bin 2.09 to amplify parental lines. Three of the 30 primer pairs have been directly developed into polymorphic STS/SSR markers. Two STS markers, STS1944 and STSrga3195, were developed from the IDP1944 and RGA3195 (ZmtucO3-0811.3195), respectively. The SSR marker SSR148152 was developed from the BAC clone AC148152 (Table 3). Of the remaining 27 primer pairs, 20 gave rise to unambiguous amplicons, which were then cloned and sequenced. Sequence alignments between two parental lines revealed varying degrees of nucleotide variations with regard to different amplicons. No polymorphism was found between two parental lines for those amplicons corresponding to two anchored ESTs. Three SNPs were observed for the amplicons corresponding to three maize sequences (a total length of 2,056 bp) retrieved from the TIGR website. Amplicons corresponding to BAC-end sequences revealed higher divergences with a total of 18

SNPs in the cumulative length of 1,251 bp sequence. Sequence alignment for the four RGA-based amplicons resulted in five InDels and 26 SNPs in a cumulated 3,711 bp sequence. Sequence alignment for five IDP-based amplicons revealed one InDel and 15 SNPs in 2,814 bp. The synteny sequence in rice was also used to develop markers and revealed only one InDel in 2,088 bp. Taken together, seven InDels and 62 SNPs were obtained, resulting in about one InDel per 1,800 bp and one SNP per 200 bp in the qHSR1 region. Based on above polymorphisms, additional six markers have been finally developed, including two SNP markers (SNP140313 and SNP661, developed from the AZM4_140313 and IDP661, respectively), one CAPS marker (CAPS25082, developed from IDP25082), and three STS markers (STS171, STSrga840810, and STSsyn1, developed from IDP171, RGA BG840810, and a syntenic rice gene LOC_Os07g07050, respectively) (Table 3 and FIG. 1).

Example 9

Phenotypic Evaluation of the $BC_2$ Recombinants and Fine-Mapping of the Major Resistance QTL Based on genotypes of parental $BC_2$ recombinants, we used markers STS171 and/or STS1944 to genotype all progeny of the $BC_2$ recombinants. The percentage of heterozygote was tested for its difference between the resistant and susceptible groups by $x^2$ test. The Probability value≤0.05 (here we set up the threshold at p=0.05) indicates the significant correlation between phenotype (resistance) and genotype (heterozygote), and the parental $BC_2$ recombinant was then deduced to carry the resistant donor region (Table 4). For example, $BC_{2-64}$ was inferred to harbor qHSR1 due to the low P value (<0.05) at the STS1944 locus. For BC2-50, both STS1944 and STS171 loci showed the very low P values, indicating that the parental BC2-50 must harbor qHSR1. On the contrary, no significant difference (as shown by the high P

TABLE 3

The names, original sequences, and primer sequences for nine newly-developed markers

| Markers | Original sequences | Types | Enzymes | Primer pairs (5'→3') [SEQ ID NO:] |
|---|---|---|---|---|
| CAPS25082 | IDP25082 | CAPS | TaqI | L: AAGTCCTTCACGGTCTACCA [1]<br>R: CGGTTAGGACGATGTCAGAA [2] |
| SNP140313 | AZM4_140313<br>from TIGR | SNP | HhaI | L: CAGAGGCATTGAACAGGAAG [3]<br>R: CTGCTATTCCACGAAGTGCT [4]<br>snpL: CTCTTCCACCGAGAATAGCG [5]<br>snpR: CTGCTATTCCACGAAGTGCT [6] |
| SNP661 | IDP661 | SNP | TaqI | L: CTTCTGTTCTGTGCCAGGTA [7]<br>R: CAAGAACGTAGCAACTCAGC [8]<br>snpL: ATTGTCCCTGAGATGATTCG [9]<br>snpR: CAAGAACGTAGCAACTCAGC [10] |
| STS1944 | IDP1944 | STS | | L: CATTGGCAACAGGACAAGTG [11]<br>R: GACATCAGCCTCAACATTGG [12] |
| STS171 | IDP171 | STS | | L: CCAGAGACTTGCGTGAAGAT [13]<br>R: AACAGACTGGTTGTACGTGC [14] |
| SSR148152 | BAC clone AC148152 | SSR | | L: GTAGGAAGACTGCCGGAGAC [15]<br>R: GACGCTAGAATGACTGAACC [16] |
| STSrga3195 | ZMTUC03-0811.3195<br>(RGA) | STS | | L: CTAGAGGTTCAGGCATATGGCG [17]<br>R: AGCTCCACAGGAATTCGTTGAG [18] |
| STSrga840810 | BG840810(RGA) | STS | | L: GCGTCAGGCAGTTCAACTTC [19]<br>R: TGTTCTTGCACTCGCACTTG [20] |
| STSsyn1 | LOC_Os07g07050<br>from rice | STS | | L: GGCACATGGACGTACAAGAT [21]<br>R: GCACAGAGGAAGCTAGGAGA [22] |

L: left primer; R: right primer.
For SNP markers, a pair of 'L' and 'R' primers was firstly used to amplify genomic DNA and then a pair of 'snpL' (mismatch primer) and 'snpR' primers was used to amplify diluted PCR products from the first step to alter a 'half-site' to 'full-site' for a specific restriction site. Polymorphic bands could be observed after digestion of second-round PCR products with a certain enzyme and subjected to electropherosis on polyacrylamide gel.

Of the nine newly-developed markers, SNP140313 and STSrga3195 were mapped on chr. 1, and STSsyn1 was mapped on chr. 5. The remaining six markers were authentically mapped on bin 2.09 with five markers (SSR148152, CAPS25082, STS171, SNP661, and STS1944) in and one marker (STSrga840810) out of the resistance qHSR1 region. The newly-developed markers would greatly facilitate MAS and fine mapping of the resistance gene (FIG. 2).

value) was observed in percentages of heterozygote between the resistant and susceptible groups for $BC_{2-25}$, indicating the absence of qHSR1 in the donor region. Taken together, 11 $BC_2$ recombinants (BC2-64, BC2-50, BC2-65, BC2-27, BC2-19, BC2-46, BC2-66, BC2-60, BC2-43, BC2-37, and BC2-69) were inferred to carry qHSR1 and regarded as the resistant $BC_2$ recombinants; whereas, five $BC_2$ recombinants (BC2-67, BC2-68, BC2-49, BC2-25, and BC2-45) were inferred to harbor no qHSR1 and considered to be the susceptible $BC_2$ recombinants (Table 4).

TABLE 4

Parental BC2 recombinants, their genotypes at the qHSR1 region, $\chi^2$ test in progenies, and deduced BC2 phenotypes

| | Genotypes at SSR markers for the parental BC2 recombinants | | | | | |
|---|---|---|---|---|---|---|
| Parental BC2 recombinants | SSR148152 | bnlg1893 | phi427434/ STS171 | SNP661 | STS1944 | umc2184 |
| BC2-50 | 1/2 | 1/2 | 1/2 | 1/2 | 1/2 | 1/2 |
| BC2-65 | 1/1 | 1/2 | 1/2 | 1/2 | 1/2 | 1/2 |
| BC2-27 | 1/1 | 1/2 | 1/2 | 1/2 | 1/2 | 1/2 |
| BC2-64 | 1/1 | 1/2 | 1/2 | 1/2 | 1/2 | 1/2 |
| BC2-67 | 1/1 | 1/1 | 1/1 | 1/2 | 1/2 | 1/2 |
| BC2-68 | 1/1 | 1/1 | 1/1 | 1/2 | 1/2 | 1/2 |
| BC2-49 | 1/1 | 1/1 | 1/1 | 1/2 | 1/2 | 1/2 |
| BC2-25 | 1/1 | 1/1 | 1/1 | 1/1 | 1/2 | 1/2 |
| BC2-45 | 1/1 | 1/1 | 1/1 | 1/1 | 1/2 | 1/2 |
| BC2-19 | 1/2 | 1/2 | 1/2 | 1/2 | 1/2 | 1/1 |
| BC2-46 | 1/2 | 1/2 | 1/2 | 1/2 | 1/2 | 1/1 |
| BC2-66 | 1/1 | 1/2 | 1/2 | 1/2 | 1/2 | 1/1 |
| BC2-60 | 1/2 | 1/2 | 1/2 | 1/2 | 1/2 | 1/1 |
| BC2-43 | 1/2 | 1/2 | 1/2 | 1/2 | 1/1 | 1/1 |
| BC2-37 | 1/2 | 1/2 | 1/2 | 1/1 | 1/1 | / |
| BC2-69 | 1/2 | 1/2 | 1/2 | 1/1 | 1/1 | 1/1 |

| Parental BC2 recombinants | $\chi^2$ test in progenies | | Deduced BC2 Phenotypes |
|---|---|---|---|
| | Markers | P Values | |
| BC2-50 | STS171 | 0.003 | Resistant |
| | STS1944 | 0.0002 | |
| BC2-65 | STS171 | 0.042 | Resistant |
| | STS1944 | 0.051 | |
| BC2-27 | STS171 | 0.006 | Resistant |
| BC2-64 | STS1944 | 0.022 | Resistant |
| BC2-67 | STS1944 | 0.273 | Susceptible |
| BC2-68 | STS1944 | 0.384 | Susceptible |
| BC2-49 | STS1944 | 0.805 | Susceptible |
| BC2-25 | STS1944 | 0.478 | Susceptible |
| BC2-45 | STS1944 | 0.730 | Susceptible |
| BC2-19 | STS171 | 0.033 | Resistant |
| BC2-46 | STS171 | <0.0001 | Resistant |
| | STS1944 | 0.0107 | |
| BC2-66 | STS1944 | 0.026 | Resistant |
| BC2-60 | STS1944 | 0.020 | Resistant |
| BC2-43 | STS171 | 0.033 | Resistant |
| BC2-37 | STS171 | 0.018 | Resistant |
| BC2-69 | STS171 | 0.004 | Resistant |

Based on the deduced phenotypes, the major resistance QTL region could be narrowed down by comparing the donor regions amongst all BC$_2$ recombinants (Table 4). BC2-50 had a heterogenous genotype in the qHSR1 region and showed high resistance to head smut with the P value<0.01. On the left side, three BC$_2$ recombinants (BC2-64 and BC2-65, and BC2-27) with their crossover points upstream of bnlg1893 showed resistance to head smut; while, the other five BC$_2$ recombinants with their crossover points downstream of STS171 (BC2-67, BC2-68, and BC2-49) or SNP 661 (BC2-25 and BC2-45) displayed susceptibility to head smut. On the right side, all seven BC$_2$ recombinants showed resistance to head smut and they had crossover points downstream of STS1944 (BC2-19, BC2-46, BC2-66, and BC2-60) or SNP661 (BC2-43) or STS171 (BC2-37 and BC$_2$-69). Interestingly, one resistant BC$_2$ recombinant, BC2-66, had the shortest donor region between SSR148152 and umc2184 and this donor region was assumed to cover qHSR1. It could be concluded from the above analysis that the major resistance QTL (qHSR1) was located in an interval of SSR148152/SNP661, which was estimated to be ~2 Mb based on the physical map available at the University of Arizona.

Example 10

Estimation of the Genetic Effect of the Major QTL

Theoretically, 93.75% of the genetic background in the BC$_{2:3}$ progeny was reverted to the recurrent parent 'Huangzhao4'. Due to the low background noise in BC$_{2:3}$ progeny, the genetic effect of qHSR1 could be definitely estimated by comparison of disease incidences between two groups with/without qHSR1 within the same BC$_{2:3}$ family. A total of 1,524 individuals from 24 BC$_{2:3}$ families were checked for the presence/absence of qHSR1 with markers STS171 and STS1944. The disease incidences were estimated for two groups with/without qHSR1 in each BC$_{2:3}$ family. As a consequence, the group without qHSR1 showed more susceptible than the group with qHSR1 in each BC$_{2:3}$ family with an average difference of 28.6%±10.8%. In other word, a single resistance qHSR1 could reduce disease incidence by 28.6%±10.8% (FIG. 2).

Apart from BC$_{2:3}$ progeny, BC$_2$F$_2$ progeny was also employed to estimate the genetic effect of qHSR1 in the present study. The BC$_2$ population was firstly genotyped at two markers bnlg1893 and umc2184, resulting in 73 BC$_2$ plants with qHSR1 and another 31 BC$_2$ plants without qHSR1. All these BC$_2$ plants were self-pollinated to produce corresponding BC$_2$F$_2$ families. As expected, the BC$_2$F$_2$ progeny derived from BC$_2$ plants with qHSR1 showed more resistant than those derived from BC$_2$ plants without qHSR1. Of the 529 BC$_2$F$_2$ individuals derived from 31 BC$_2$ plants without qHSR1, 204 (38.7%) were found to be susceptible. Whereas, 262 (19.3%) of 1,358 BC$_2$F$_2$ individuals derived from 73 BC$_2$ plants with qHSR1 were susceptible. In the BC$_2$F$_2$ progeny derived from BC$_2$ plants with qHSR1, segregation occurred at the qHSR1 locus, resulting in one-fourth BC$_2$F$_2$ individuals without qHSR1. These BC$_2$F$_2$ individuals without qHSR1 are expected to have the same disease incidence as that estimated from the 31 BC$_2$F$_2$ families without qHSR1 (38.7%). For the other three-fourth BC$_2$F$_2$ individuals with qHSR1 (one-fourth homozygotes and a half heterozygotes), we needed to estimate its disease incidence. Based on above explanations, we could draw an equation as $\frac{3}{4}X\% + \frac{1}{4} * 38.7\% = 19.3\%$; here, 'X' represents infection percentage for those BC$_2$F$_2$ individuals with qHSR1. The 'X' is calculated to be 12.8%. In summary, the qHSR1 locus could reduce disease incidence by 25.9% in the BC$_2$F$_2$ progeny, from 38.7% (individuals without qHSR1) to 12.8% (individuals with qHSR1).

Example 11

Characterization of Genomic Sequence of qHSR1

In order to isolate the gene responsible for the phenotype conferred by the qHSR1 locus, BACs containing the region between the markers MZA6393 (from bacm.pk071.j12.f SEQ ID NO:23) and marker ST148-1 the Mo17 version of ZMMBBc0478L09f (SEQ ID NO:24) were isolated from a BAC library prepared from the resistant Mo17 line. This library was prepared using standard techniques for the preparation of genomic DNA (Zhang et al. (1995) *Plant Journal* 7:175-184) followed by partial digestion with HindIII and ligation of size selected fragments into a modified form of the commercially available vector pCC1 BAC™ (Epicentre, Madison, USA). After transformation into EPI300™ *E. coli* cells following the vendors instructions (Epicentre, Madison, USA), 125,184 recombinant clones were arrayed into 326 384-well microtiter dishes. These clones were then gridded onto nylon filters (Hybond N+, Amersham Biosciences, Piscataway, USA). Three overlapping clones (bacm.pk071.j12, bacm.pk007.18, and bacm2.pk166.h1) were identified and characterized.

The library was probed with overlapping oligonucleotide probes (overgo probes; Ross et al. (1999) *Screening large-insert libraries by hybridization*, p. 5.6.1-5.6.52, In A. Boyl, ed. Current Protocols in Human Genetics. Wiley, New York) designed on the basis of sequences found in the BAC sequences. BLAST search analyses were done to screen out repeated sequences and identify unique sequences for probe design. The position and interspacing of the probes along the contig was verified by PCR. For each probe two 24-mer oligos self-complementary over 8 bp were designed. Their annealing resulted in a 40 bp overgo, whose two 16 bp overhangs were filled in. The exact sequences are different as they were to be used as overgo probes rather than just PCR primers. Probes for hybridization were prepared as described (Ross et al. (1999) supra), and the filters prepared by the gridding of the BAC library were hybridized and washed as described by (Ross et al. (1999) supra). Phosphorimager analysis was used for detection of hybridization signals. Thereafter, the membranes were stripped of probes by placing them in a just-boiled solution of 0.1×SSC and 0.1% SDS and allowing them to cool to room temperature in the solution overnight.

BACs that gave a positive signal were isolated from the plates. Restriction mapping, PCR experiments with primers corresponding to the markers previously used and sequences obtained from the ends of each BAC were used to determine the order of the BACs covering the region of interest. Three BACs that spanned the entire region (bacm.pk071.j1 2, bacm.pk007.18, and bacm2.pk166.h1) were selected for sequencing. These BACs were sequenced using standard shotgun sequencing techniques and the sequences assembled using the Phred/Phrap/Consed software package (Ewing et al. (1998) *Genome Research*, 8:175-185). The assembled sequence of the BAC clones is shown in SEQ ID NO:25.

After assembly, the sequences thought to be in the region closest to the locus on the basis of the mapping data were annotated, meaning that possible gene-encoding regions and regions representing repetitive elements were deduced. Gene encoding (genic) regions were sought using the fGenesH software package (Softberry, Mount Kisco, N.Y., USA). fGenesH predicted a portion of a protein, that when BLASTed (BLASTx/nr), displayed partial homology at the amino acid level to a portion of a rice protein that was annotated as encoding for a protein that confers disease resistance in rice. The portion of the maize sequence that displayed homology to this protein fell at the end of a contiguous stretch of BAC consensus sequence and appeared to be truncated. In order to obtain the full representation of the gene in the maize BAC, the rice amino acid sequence was used in a tBLASTn analysis against all other consensus sequences from the same maize BAC clone. This resulted in the identification of a consensus sequence representing the 3' end of the maize gene. However, the center portion of the gene was not represented in the sequences so obtained. PCR primers were designed based on the 5' and 3' regions of the putative gene and used in a PCR experiment with DNA from the original maize BAC as a template. The sequence of the resulting PCR product contained sequence bridging the 5' and 3' fragments previously isolated.

Several open reading frames were detected in SEQ ID NO:25 including a xylanase inhibitor gene (SEQ ID NO:26/27), a cell wall associated protein kinase (SEQ ID NO:31/32), two HAT family protein dimerization genes (SEQ ID NO:34/35 and SEQ ID NO:37/38), and two uncharacterized proteins (SEQ ID NO:40/41 and SEQ ID NO:43/44). The xylanase inhibitor gene shows a polymorphic difference when compared to the ortholog found in B73. The Mo17 gene is 97.8% identical, by Clustal V alignment, to the B73 gene, and contains two deletions of 2 and 10 amino acids (see FIG. 3.) The genomic DNA region including 2.4 kb upstream of the ORFs from SEQ ID NOs:43/44 is shown in SEQ ID NO:45. The nucleic acid sequence encoding an additional EST fragment from the qHSR region is shown in SEQ ID NO:46.

Any one, any combination, or all, of these genes may confer, or contribute to, head smut resistance at the qHSR1 locus. It is expected that polymorphisms associated with Mo17, which is resistant to head smut, will be diagnostic of sequences that define qHSR1.

Example 12

Backcrossing of the qHSR1 Locus into Susceptible Lines

A qHSR1 locus introgression of inbred lines are made to confirm that the qHSR1 locus could be successfully backcrossed into inbreds, and that hybrids produced with the inbred lines with the qHSR1 locus would have enhanced or conferred head smut resistance.

MO17 is an inbred line with strong resistance to head smut, but its weak agronomic characteristics make it a poor donor parent in the absence of the use of the marker assisted breeding methods described herein. To demonstrate the phenotypic value of the qHSR1 locus, the locus is introgressed into 10 elite inbred lines, with an additional 25 inbreds added in the second through to the BC3 stage as follows. The F1 population derived from the cross between MO17 and the elite inbred lines are backcrossed once more to the recurrent parents (the elite inbreds), resulting in a BC1 population. Seedlings are planted out, genotyped with markers across the genome, selected (with the qHSR1 locus and minimal MO17 background) and backcrossed again to recurrent inbred lines to develop a BC2 population. BC2 families are genotyping and selected again for the presence of the MO17 qHSR1 region. Positive plants are backcrossed to recurrent parental inbreds once more to develop BC3 populations. Seeds from these BC3 populations are planted and plants are genotyped. BC3 plants with or without the region of interest are selfed to make BC3S1 families. These families were used for phenotypic comparison (BC3S1 with or without the region of interest).

In order to observe the performance of the qHSR1 gene in a heterozygous situation such as would be found in a commercial hybrid, appropriate testcrosses are made. Specifically, individual BC3S1 plants homozygous for the qHSR1 gene as well as plants homozygous for the susceptible allele are used to make testcrosses with selected inbreds.

In the case of both the BC3S1 lines and the hybrids, the expected phenotypic differences indicate significant improvement for head smut resistance in lines and hybrids containing the region carrying qHSR1. The data clearly demonstrate that using crossing techniques to move the gene of the embodiments into other lines genetically competent to use the gene result in enhanced resistance to head smut.

As a result of fine mapping the location of the qHSR1 gene, one may utilize any two flanking markers that are genetically linked with the qHSR1 gene to select for a small chromosomal region with crossovers both north and south of the qHSR1 gene. This has the benefit of reducing linkage drag, which can be a confounding factor when trying to introgress a specific gene from non-adapted germplasm, such as MO17, into elite germplasm. It is advantageous to have closely linked flanking markers for selection of a gene, and highly advantageous to have markers within the gene itself. This is an improvement over the use of a single marker or distant flanking markers, since with a single marker or with distant flanking markers the linkage associated with qHSR1 may be broken, and by selecting for such markers one is more likely to inadvertently select for plants without the qHSR1 gene. Since marker assisted selection is often used instead of phenotypic selection once the marker-trait association has been confirmed, the unfortunate result of such a mistake would be to select plants that are not resistant to head smut and to discard plants that are resistant to head smut. In this regard, markers within the qHSR1 gene are particularly useful, since they will, by definition, remain linked with resistance to head smut as enhanced or conferred by the gene. Further, markers within the qHSR1 locus are just as useful for a similar reason. Due to their very close proximity to the qHSR1 gene they are highly likely to remain linked with the qHSR1 gene. Once introgressed with the qHSR1 gene, such elite inbreds may be used both for hybrid seed production and as a donor source for further introgression of the qHSR1 gene into other inbred lines.

Thus, the data shows that inbred progeny converted by using MO17 as a donor source retain the truncated MO17 chromosomal interval. The inbreds comprising the truncated MO17 chromosomal interval are very useful as donor sources themselves, and there is no need to revert to MO17 as a donor source. By using marker assisted breeding as described herein, the truncated MO17 chromosomal interval can be further reduced in size as necessary without concern for losing the linkage between the markers and the qHSR1 gene.

Example 13

Use of qHSR1 as a Transgene to Create Resistant Corn Plants

The qHSR1 gene can be expressed as a transgene as well, allowing modulation of its expression in different circumstances. The following examples show how the qHSR1 gene could be expressed in different ways to combat different diseases or protect different portions of the plant, or simply to move the qHSR1 gene into different corn lines as a transgene, as an alternative to the method described in Example 12.

Example 13a

In this example, the qHSR1 candidate gene (xylanase inhibitor and other annotated genes in the QTL interval, as defined in Example 11) is expressed using its own promoter.

In order to transform the complete qHSR1 genes, including the promoter and protein encoding regions, DNA fragments containing the complete coding region and approximately 2 kb upstream region are amplified by PCR using the BAC clone as template DNA. To enable cloning using the GATEWAY® Technology (Invitrogen) Carlsbad, USA), attB sites are incorporated into the PCR primers, and the amplified product is cloned into PDONR™221 vector by GATEWAY® BP recombination reaction. The resulting fragment, flanked by attL sites, is moved by the GATEWAY® LR recombination reaction into a binary vector. The construct DNA is then used for corn transformation as described in Example 14.

Example 13b

In order to express the qHSR1 genes (xylanase inhibitor and other annotated genes in the QTL interval, as defined in Example 11) throughout the plant at a low level, the coding region of the genes and their terminators are placed behind the promoters of either a rice actin gene (U.S. Pat. Nos. 5,641,876 and 5,684,239) or the F3.7 gene (U.S. Pat. No. 5,850,018). To enable cloning using the GATEWAY® Technology (Invitrogen, Carlsbad, USA), attB sites are incorporated into PCR primers that are used to amplify the qHSR1 genes starting 35 bp upstream from its initiation codon. A NotI site is added to the attB1 primer. The amplified qHSR1 product is cloned into PDONR™221 vector by GATEWAY® BP recombination reaction (Invitrogen, Carlsbad, USA). After cloning, the resulting qHSR1 gene is flanked by attL sites and has a unique NotI site at 35 bp upstream the initiation codon. Thereafter, promoter fragments are PCR amplified using primers that contain NotI sites. Each promoter is fused to the NotI site of qHSR1. In the final step, the chimeric gene construct is moved by GATEWAY® LR recombination reaction (Invitrogen, Carlsbad, USA) into the binary vector PHP20622. This is used for corn transformation as described in Example 14.

Example 13c

In order to express the qHSR1 genes (xylanase inhibitor and other annotated genes in the QTL interval, as defined in Example 11) throughout the plant at a high level, the coding region of the genes and their terminators are placed behind the promoter, 5' untranslated region and an intron of a maize ubiquitin gene (Christensen et al. (1989) *Plant Mol. Biol.* 12:619-632; Christensen et al. (1992) *Plant Mol. Biol.* 18:675-689). To enable cloning using the GATEWAY® Technology (Invitrogen, Carlsbad, USA), attB sites are incorporated into PCR primers that are used to amplify the qHSR1 gene starting at 142 bp upstream of the initiation codon. The amplified product is cloned into PDONR™221 (Invitrogen, Carlsbad, USA) using a GATEWAY® BP recombination reaction (Invitrogen, Carlsbad, USA). After cloning, the resulting qHSR1 gene is flanked by attL sites. In the final step, the qHSR1 clone is moved by GATEWAY® LR recombination reaction (Invitrogen, Carlsbad, USA) into a vector which contained the maize ubiquitin promoter, 5' untranslated region and first intron of the ubiquitin gene as described by Christensen et al. (supra) followed by GATEWAY® ATTR1 and R2 sites for insertion of the qHSR1 gene, behind the ubiquitin expression cassette. The vector also contained a marker gene suitable for corn transformation, so the resulting plasmid, carrying the chimeric gene (maize ubiquitin promoter-ubiquitin 5' untranslated region-ubiquitin intron 1-qHSR1), is suitable for corn transformation as described in Example 14.

Example 13d

In order to express the qHSR1 genes (xylanase inhibitor and other annotated genes in the QTL interval, as defined in Example 11) at a root-preferred, low level of expression, the coding region of the genes and their terminators are placed behind a root preferred promoter such as but not limited to, maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664). The fragment described in Example 13b containing the qHSR1 coding region flanked by attL sites and containing a unique NotI site 35 bp upstream of the qHSR1 initiation codon is used to enable cloning using the GATEWAY® Technology (Invitrogen, Carlsbad, USA). Promoter fragment is PCR amplified using primers that contain NotI sites. Each promoter is fused to the NotI site of qHSR1. In the final step, the chimeric gene construct is moved by GATEWAY® LR recombination reaction (Invitrogen, Carlsbad, USA) into the binary vector PHP20622. This is used for corn transformation as described in Example 14.

Example 14

*Agrobacterium*-Mediated Transformation of Maize and Regeneration of Transgenic Plants The recombinant DNA constructs prepared in Example 6a-6d were used to prepare transgenic maize plants as follows.

Maize is transformed with selected polynucleotide constructs described in Example 13a and 13c using the method of Zhao (U.S. Pat. No. 5,981,840, and PCT patent publication WO98/32326). Briefly, immature embryos were isolated from maize and the embryos contacted with a suspension of *Agrobacterium*, where the bacteria were capable of transferring the polynucleotide construct to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent, and growing transformed callus is recovered (step 4: the selection step). The callus is then regenerated into plants (step 5: the regeneration step), and calli grown on selective medium were cultured on solid medium to regenerate the plants.

Example 15

Transgenic Plant Evaluation

Transgenic plants are made as described in Example 14 using the constructs described in Examples 13a to 13d, respectively. They are evaluated with protocols described in Example 9 for improvement in head smut resistance.

Example 16

Analysis of qHSR1 Gene Distribution Across Germplasm and Identification of qHSR1 Sequence Variants Following the identification, sequencing and fine mapping of qHSR1, other lines are screened for the qHSR1 gene. To determine the presence of the qHSR1 gene in other maize germplasm, gene specific primers combinations are used to amplify genomic DNA from a diverse panel of maize inbred lines by polymerase chain reaction. Inbred lines with qHSR1 (MO17 allele) are identified. Thus, in addition to using MO17 as the donor source, other sources containing the qHSR1 gene can also be used as a donor source.

Variants of the qHSR1 gene are also identified and analyzed for single nucleotide polymorphisms (SNPs). Not all of the allelic variants of the qHSR1 gene indicated a resistant phenotype. Inbred lines with distinct haplotypes or alleles are evaluated for their head smut resistance, and putative resistant allelic variants are identified. Their efficacy in head smut resistance is validated in segregating populations (e.g. F2 population). The SNPs can be used as markers to precisely identify and track the qHSR1 sequence in a plant breeding program, and to distinguish between resistant and susceptible allelic variants. Further, these SNPs indicate that there are variant sequences that show a resistant phenotype and can be used in the methods and products disclosed herein.

Example 17

Further Analysis of qHSR1 Gene Distribution Across Germplasm and Identification of qHSR1 Sequence Variants The qHSR1 region has been further defined as an 172-kb interval in the resistant parental line Ji1037 and a 56-kb interval in the susceptible parental line Huangzhao4. The size discrepancy is due to a deletion (116 kb) in Huangzhao4 compared with Ji1037. The key recombinants which were used for fine-mapping have been repeatedly investigated for their resistances to head smut in Gongzhuling in Jilin Province and in the winter nursery on Hainan Island, and show consistent resistance to head smut.

Positive Mo17 BAC clones have been selected based on the characterization of the qHSR1 region. In addition, markers in the qHSR1 region were used to screen a Huangzhao4 BAC library. The minimal tiling positive BAC clones were subjected to sequencing to get a broad view in the qHSR1 region. The comparative view among the Mo17, B73, and Huangzhao4 inbred lines is shown in the FIG. 4. A total of six additional putative genes have been identified, an ankyrin-repeat protein (SEQ ID NO:104-106, the coding sequence, protein translation, and genomic DNA, respectively) is found in all three inbred lines, a gene coding a Wall-associated kinase protein (SEQ ID NOs:31-33) is missing in Huangzhao4, a gene coding hydrolase (SEQ ID NO:107-109) is missing in B73 and Huangzhao4, two of the three Xa21-like kinase proteins (SEQ ID NOs: 110-115) are missing in Huangzhao 4, and the third Xa21-like kinase protein (SEQ ID NOs:115-117) is present in at least Mo17 and Huangzhao4.

Example 18

Characterization of Candidate Resistance Genes in the qHSR1 Region

Three approaches are being taken to validate the candidate resistance genes: 1) a complementarity test, since both Mo17 and B73 show some resistance to head smut, the three shared genes (Ankyrin-repeat protein, Wall-associated kinase protein, and Xa21 D kinase), are likely to be candidate genes contributing to the phenotype, all these three genes are subcloned from the positive BAC clones into an expression vector, followed by transformation into susceptible inbred lines; 2) RNAi technique, RNAi vectors are constructed for all six putative genes in the 172-kb region and then are transformed into Mo17 to knock out putative genes one by one, this allows for the identification of those genes involved in resistance to head smut; 3) overexpression of candidate genes in susceptible lines, overexpression constructs with each of the six individual candidate genes linked to strong promoters are constructed and introduced into susceptible lines to determine if any of the individual candidate genes in the qHSR1 region is sufficient to confer resistance to head smut.

Example 19

Development of Markers in the qHSR1 Region Useful for Marker-Assisted Selection

The BAC sequences, especially those coding sequences were further used to develop high-density markers. In total, eight markers have been developed in the 172-kb region (Ji1037 qHSR1 which is equivalent to Mo17) (Table 5). These markers were used to integrate the resistance qHSR1 into other susceptible inbred lines via marker-assisted selection.

TABLE 5

Markers in the 172 kb interval covering the qHSR1 region

| Marker position | name | primer | Sequence [SEQ ID NO:] | PCR product (Ji1037/Huangzhao4) [SEQ ID NO:] | maker type |
|---|---|---|---|---|---|
| 0 | MZA6393 | MZA6393L | 5'-GTATTTCTACCAGCGTGGCCT-3' [50] | 412 bp/325 bp [23/47] | codominant |
|  |  | MZA6393R | 5'-GACAAGCTGCAGATCGAAGA-3' [51] |  |  |
| 7.27kb | 1M2-9 | 1M2-9L | 5'-TCGTGACGGACCTGTAGTGC-3' [52] | 618 bp/759 bp [54/55] | codominant |
|  |  | 1M2-9R | 5'-TCGCGGTTCAGAAGAACAAC-3' [53] |  |  |
| 26.4kb | E6765-3 | E6765-3L | 5'-CATGTGCCGACCGACCATTC-3' [56] | 426 bp [58] | dominant |
|  |  | E6765-3R | 5'-GGAGTGCGATGTCTACAGCT-3' [57] |  |  |
| 99kb | 2M4-1 | 2M4-1L | 5'-CACGTTGTGACTCAAGATCG-3' [59] | 573 bp [61] | dominant |
|  |  | 2M4-1R | 5'-ATCAAGGACCATCAGCACAG-3' [60] |  |  |
| 141.5kb | 2M10-5 | 2M10-5L | 5'-CCTCCTCTCCATCTGGTCCA-3' [62] | 589 bp [64] | dominant |
|  |  | 2M10-5R | 5'-CGTGTGCTTGGAAGAATCTC-3' [63] |  |  |
| 148kb | 2M11-3 | 2M11-3L | 5'-TGGACAGACCTTAGCTTGCT-3' [65] | 563 bp [67] | dominant |
|  |  | 2M11-3R | 5'-GTTCGTAAGTGCGTCAATGG-3' [66] |  |  |

TABLE 5-continued

Markers in the 172 kb interval covering the qHSR1 region

| Marker position | name | primer | Sequence [SEQ ID NO:] | PCR product (Ji1037/Huangzhao4) [SEQ ID NO:] | maker type |
|---|---|---|---|---|---|
| 163kb | 3M1-25 | 3M1-25L | 5'-GCTAGATAGCTGCTTCTTCC-3' [68] | 328 bp/468 bp [70/71] | codominant |
|  |  | 3M1-25R | 5'-GTACCTACGATTCGGCAGAA-3' [69] |  |  |
| 172.1kb | STS148-1 | STS148-1L | 5'-CTTCCATCGGTACTCCATTC-3' [72] | 177 bp/132 bp [24/49] | codominant |
|  |  | STS148-1R | 5'-TTCTCCAGGTGTGAGAAATC-3' [73] |  |  |

The genetic effect of the qHSR1 region in resistance to head smut was tested using eleven BC4 populations. The Mo17 inbred line was crossed to Ji853, 444, 4287, 98107, 99094, Chang7-2, V022, V4, 982, 8903, and 8902. The qHSR1 region was then backcrossed for four generations, using markers, such as MZA6393, 2M10-5, STS148-1, STS661 and E148-4, to select the plants with the qHSR1 region. These BC4 populations were phenotyped in the winter nursery in Hainan Island. These BC4 populations contained plants both with and without the qHSR1 (Table 6A and B.) The plants without the qHSR1 region were considered controls to tell the baseline resistance of the different genetic backgrounds. The individual plants within the BC4 populations were scored for resistance to head smut, and the percentage of resistant plants was calculated, for the groups both with and without the qHSR1 region. The qHSR1 region conferred an increase of approximately 25% in resistance index. The inbred line '4287' itself has the qHSR1 region and shows resistance to head smut, this is why the integration of the qHSR1 region in '4287' genetic background has minimal effect on resistance to head smut.

TABLE 6A

The genetic effects of the qHSR1 region in resistance to head smut

| Genetic backgrounds | Size of the population | | Markers following the R region |
|---|---|---|---|
|  | Without qHSR1 | With qHSR1 |  |
| Ji853 | 353 | 28 | MZA6393, 2M10-5, STS148-1 |
| 444 | 118 | 29 | MZA6393, 2M10-5, STS148-1 |
| 4287 | 226 | 64 | MZA6393, STS661 |
| 98107 | 81 | 27 | MZA6393, 2M10-5, STS661 |
| 99094 | 17 | 46 | MZA6393, 2M10-5, STS661 |
| Chang7-2 | 176 | 86 | MZA6393, 2M10-5, STS148-1 |
| V022 | 148 | 91 | MZA6393, 2M10-5, STS148-1 |
| V4 | 69 | 134 | MZA6393, 2M10-5, STS148-1 |
| 982 | 99 | 83 | MZA6393, 2M10-5, STS661 |
| 8903 | 201 | 143 | MZA6393, 2M10-5, E148-4 |
| 8902 | 67 | 118 | MZA6393, 2M10-5, E148-4 |

TABLE 6B

| Genetic back-grounds | Percentage of the resistant plants in backcross populations | | Difference | P-value |
|---|---|---|---|---|
|  | Without qHSR1 | With qHSR1 |  |  |
| Ji853 | 20.54% | 52.60% | 32.06% | 5.27E-09 |
| 444 | 35.37% | 59.53% | 24.16% | 0.0012 |

TABLE 6B-continued

| Genetic back-grounds | Percentage of the resistant plants in backcross populations | | Difference | P-value |
|---|---|---|---|---|
|  | Without qHSR1 | With qHSR1 |  |  |
| 4287 | 84.67% | 84.31% | -0.36% |  |
| 98107 | 18.22% | 42.22% | 24.00% | 0.0004 |
| 99094 | 0 | 33.93% | 33.93% | 0.01253 |
| Chang7-2 | 12.48% | 38.63% | 26.15% | 7.52E-08 |
| V022 | 44.41% | 71.82% | 27.41% | 1.71E-06 |
| V4 | 21.29% | 49.97% | 28.68% | 5.24E-05 |
| 982 | 16.83% | 29.91% | 13.08% | 3.30E-05 |
| 8903 | 23.96% | 40.34% | 16.38% | 2.79E-09 |
| 8902 | 18.41% | 38.26% | 19.85% | 9.19E-06 |

Example 20

Additional Development of Markers in the qHSR1 Region Useful for Marker-Assisted Selection Introgression lines for qHSR1 are being created for breeding material and the evaluation of qHSR1 efficacy in Western North America, Mexico, and China. Thirty-five Pioneer inbred lines (CN3K7 is the donor line; GRB1M, HNA9B, HN4CV, HNVS3, HNN4B, HNH9H, HNGFT, GR0RA, HFTWK, and GRVNS are non-stiff-stalk lines for China; GR0P2, HEF3D, HF0SV, HFHHN, HN05F, HN088, HN0E1, HN8T0, HNNWJ, and HNW4C are non-stiff-stalk lines for Western North America; EDGJ4, EDW1N, EDVNA, EDVS9, and EDV9Z are stiff-stalk lines for China; and 2HC5H, 2H071, 4F1FM, 4F1VJ, 4FJNE, 7T9HV, 1ARMJ, 1AY0M, 1AGFC, and 1A1V3 are stiff-stalk lines for Mexico) were crossed with Mo17 to create the F1. SNP markers, such as MZA15839-4, MZA18530-16, MZA5473-801, MZA16870-15, MZA4087-19, MZA158-30, MZA15493-15, MZA9967-11, MZA1556-23, MZA1556-801, MZA17365-10, MZA17365-801, MZA14192-8, MZA15554-13 and MZA4454-14, are being used to select for the qHSR1 region during subsequent backcrosses. Between 39 and 65 SNP markers on unlinked chromosomal regions were used in the BC1 generation to select against the background.

The lines are being backcrossed to a BC1, BC2, BC3, or BC4 generation, and then selfed. The plants homozygous for the qHSR1 region are identified in the selfed generation, and then crossed to an appropriate Test Cross Inbred, such as EF6WC or EF890 for NSS introgressions. The Test Cross BC lines are then evaluated for efficacy at the location appropriate for the inbred line, such as Western North America, Mexico, or China. At each location, a sufficient number of reps and population size are used to evaluate the qHSR1 efficacy. The equivalent hybrid without the head smut QTL was also grown for comparison. If high disease pressure is not expected, the experiment will be artificially inoculated with the head smut pathogen to insure high disease pressure.

Markers that are useful for marker assisted breeding to develop introgression lines are shown in Table 7. Eight of these markers (MZA6393, 1M2-9, E6765-3, 2M4-1, 2M10-5, 2M11-3, 3M1-25, and STS148-1) are located within the qHSR region. The markers in Table 7 that are outside of the qHSR region have been developed to be specific for Mo17, and therefore are linked to the qHSR region. These markers, although exemplary, are not intended to be a complete listing of all useful markers. Many markers that are specific for the qHSR region can be developed. In addition, any marker that is linked or associated with one of these specific markers could be useful in marker assisted selection.

TABLE 7

Markers in the qHSR Region

| Marker | Marker Type | Chromsome | Genetic Position | Physical Position (bp)* | Mo17 SNP |
|---|---|---|---|---|---|
| MZA15839-4 | SNP | 2 | 220.22 | | T |
| MZA18530-16 | SNP | 2 | 220.34 | | G |
| MZA5473-801 | SNP | 2 | 225.11 | | G |
| MZA16870-15 | SNP | 2 | 226.92 | | G |
| MZA4087-19 | SNP | 2 | 228.58 | | C |
| MZA158-30 | SNP | 2 | 228.58 | | T |
| MZA15493-15 | SNP | 2 | 230.55 | | G |
| MZA9967-11 | SNP | 2 | 231.1 | | T |
| MZA6393 | codominant | 2 | x | 0 | x |
| 1M2-9 | codominant | 2 | x | 7.27 | x |
| E6765-3 | dominant | 2 | x | 26.4 | x |
| 2M4-1 | dominant | 2 | x | 99 | x |
| 2M10-5 | dominant | 2 | x | 141.5 | x |
| 2M11-3 | dominant | 2 | x | 148 | x |
| 3M1-25 | codominant | 2 | x | 163 | x |
| STS148-1 | codominant | 2 | x | 172.1 | x |
| MZA1556-23 | SNP | 2 | 235.32 | | A |
| MZA1556-801 | SNP | 2 | 235.32 | | C |
| MZA17365-10 | SNP | 2 | 235.68 | | G |
| MZA17365-801 | SNP | 2 | 235.68 | | D |
| MZA14192-8 | SNP | 2 | 235.8 | | G |
| MZA15554-13 | SNP | 2 | 244.27 | | G |
| MZA4454-14 | SNP | 2 | 245.91 | | C |

| Marker | Forward Primer [SEQ ID NO:] | Reverse Primer [SEQ ID NO:] | Size (Ji1037/Huangzhao4) [SEQ ID NO:] |
|---|---|---|---|
| MZA15839-4 | gatgcaatggaagaattcgtg [74] | tgaactcagctttggataccaa [75] | |
| MZA18530-16 | gtttcctcatggcactactct [76] | agtaaagccacacatcttattc [77] | |
| MZA5473-801 | cccatgatggctacattctg [78] | cagaggcttgcgttaacaac [79] | |
| MZA16870-15 | atttcagcgtttgcggtgtc [80] | ataatgaagttgacctaagtcc [81] | |

TABLE 7-continued

Markers in the qHSR Region

| MZA4087-19 | agctaaacagcggatgactg [82] | caaacatgcaaagaatgaggtt [83] | |
| --- | --- | --- | --- |
| MZA158-30 | ccaccaccggccccagta [84] | aaagtgatacataaggcacaca [85] | |
| MZA15493-15 | gataattgggaatgggcagat [86] | agaaatatcctcatcctcaatg [87] | |
| MZA9967-11 | tttccggttttggtggacga [88] | cgtccgactcattatacatca [89] | |
| MZA6393 | gtatttctaccagcgtggcct [50] | gacaagctgcagatcgaaga [51] | 412/325 [23/47] |
| 1M2-9 | tcgtgacggacctgtagtgc [52] | tcgcggttcagaagaacaac [53] | 618/759 [54/55] |
| E6765-3 | catgtgccgaccgaccattc [56] | ggagtgcgatgtctacagct [57] | 426 [58] |
| 2M4-1 | cacgttgtgactcaagatcg [59] | atcaaggaccatcagcacag [60] | 573 [61] |
| 2M10-5 | cctcctctccatctggtcca [62] | cgtgtgcttggaagaatctc [63] | 589 [64] |
| 2M11-3 | tggacagaccttagcttgct [65] | gttcgtaagtgcgtcaatgg [66] | 563 [67] |
| 3M1-25 | gctagatagctgcttcttcc [68] | gtacctacgattcggcagaa [69] | 328/468 [70/71] |
| STS148-1 | cttccatcggtactccattc [72] | ttctccaggtgtgagaaatc [73] | 176/132 [24/49] |
| MZA1556-23 | tgtgctccctggtccgcc [90] | tcaagtgccctagctcct [91] | |
| MZA1556-801 | tgtgctccctggtccgcc [92] | tcaagtgccctagctcct [93] | |
| MZA17365-10 | cctatggctggttgctctt [94] | gccaacaagtcaacatcctaa [95] | |
| MZA17365-801 | cctatggctggttgctctt [96] | gccaacaagtcaacatcctaa [97] | |
| MZA14192-8 | tcctggaacgccatggtact [98] | cagggacatcaagcgcca [99] | |
| MZA15554-13 | acttccgaggcgtcgcagtt [100] | atgaacactcactcactcctc [101] | |
| MZA4454-14 | atgagggtttggaggcgtat [102] | ttacctcaactaagggcatcc [103] | |

What is claimed is:

1. A method of identifying a maize plant that displays head smut resistance, the method comprising:
   A. isolating nucleic acid molecules from a maize plant;
   B. analyzing the isolated nucleic acid molecules for the presence of a QTL allele that is associated with head smut resistance, wherein the presence of said QTL allele is determined by detecting in the germplasm of the maize plant at least one allele of a marker locus wherein:
   (a) the marker locus is located within a chromosomal interval comprising and flanked by umc1736 and umc2184; and
   (b) the at least one allele is associated with head smut resistance; and
   C. selecting said maize plant if said QTL allele is detected, wherein the selected plant displays head smut resistance.

2. The method of claim 1, wherein the marker locus is located within a chromosomal interval comprising and flanked by SSR148152 and SNP661.

3. A method of marker assisted selection of a maize plant that displays head smut resistance comprising:
   (a) obtaining a first maize plant having at least one marker allele selected from the group consisting of:
   (i) the sequence set forth in SEQ ID NO:23;
   (ii) the sequence set forth in SEQ ID NO:54;
   (iii) the sequence set forth in SEQ ID NO:58;
   (iv) the sequence set forth in SEQ ID NO:61;
   (v) the sequence set forth in SEQ ID NO:64;
   (vi) the sequence set forth in SEQ ID NO:67;
   (vii) the sequence set forth in SEQ ID NO:70; and
   (viii) the sequence set forth in SEQ ID NO:24;
   (b) crossing said first maize plant to a second maize plant;
   (c) detecting the presence of the marker allele in the progeny of the crossing; and
   (d) selecting a progeny maize plant that possesses the at least one marker allele detected, wherein the selected progeny maize plant displays head smut resistance.

4. A method of detecting a head smut resistance locus in a maize plant comprising:
   A. isolating nucleic acid molecules from a maize plant;
   B. analyzing the isolated nucleic acid molecules for the presence of a QTL allele that is associated with head smut resistance, wherein the presence of said QTL allele is determined by detecting the presence in the maize plant of:
   a) the sequence set forth in SEQ ID NO:23,
   b) the sequence set forth in SEQ ID NO:54,
   c) the sequence set forth in SEQ ID NO:58, d) the sequence set forth in SEQ ID NO:61,
e) the sequence set forth in SEQ ID NO:64,
f) the sequence set forth in SEQ ID NO:67,
g) the sequence set forth in SEQ ID NO:70, or
h) the sequence set forth in SEQ ID NO:24; and
C. selecting said maize plant if said QTL allele is detected, wherein the selected maize plant displays head smut resistance.

\* \* \* \* \*